United States Patent
Shoemaker et al.

(10) Patent No.: US 9,770,170 B2
(45) Date of Patent: Sep. 26, 2017

(54) METHODS FOR DIAGNOSING, TREATING, AND MONITORING CHRONIC INFLAMMATORY RESPONSE SYNDROME

(71) Applicants: Ritchie Shoemaker, Pocomoke City, MD (US); Jimmy Ryan, Vero Beach, FL (US)

(72) Inventors: Ritchie Shoemaker, Pocomoke City, MD (US); Jimmy Ryan, Vero Beach, FL (US)

( * ) Notice: Subject to any disclaimer, the term of this patent is extended or adjusted under 35 U.S.C. 154(b) by 668 days.

(21) Appl. No.: 13/961,642

(22) Filed: Aug. 7, 2013

(65) Prior Publication Data
US 2014/0046143 A1    Feb. 13, 2014

Related U.S. Application Data

(60) Provisional application No. 61/680,613, filed on Aug. 7, 2012.

(51) Int. Cl.
| | |
|---|---|
| *A61K 38/16* | (2006.01) |
| *A61B 5/00* | (2006.01) |
| *G01N 33/68* | (2006.01) |
| *A61K 31/785* | (2006.01) |
| *A61K 38/22* | (2006.01) |
| *C12Q 1/68* | (2006.01) |
| *C07K 14/475* | (2006.01) |

(52) U.S. Cl.
CPC .............. *A61B 5/00* (2013.01); *A61K 31/785* (2013.01); *A61K 38/2278* (2013.01); *C12Q 1/6883* (2013.01); *G01N 33/6893* (2013.01); *A61B 5/4064* (2013.01); *C12Q 2600/158* (2013.01); *C12Q 2600/178* (2013.01); *G01N 2800/60* (2013.01); *G01N 2800/7095* (2013.01)

(58) Field of Classification Search
None
See application file for complete search history.

(56) References Cited

U.S. PATENT DOCUMENTS

2003/0219400 A1* 11/2003 Shoemaker ............ A61K 31/12
424/78.1

OTHER PUBLICATIONS

Ryan et al. BMC Medical Genomics (2015) 8:15. "Transcriptomic signatures in whole blood of patients who acquire a chronic inflammatory response syndrome (CIRS) following an exposure to the marine toxin ciguatoxin".*
R.C. Shoemaker et al., Neurotoxicology and Teratology 28 (2006) 573-588. "Sick building syndrome (SBS) and exposure to water-damaged buildings: Time series study, clinical trial and mechanisms".*
6th International Scientific Conference on Bioaerosols, Fungi, Bacteria, Mycotoxins in Indoor and Outdoor Environments and Human Health, Sep. 6-9, 2011, pp. 1-124.
Shoemaker et al., "Vasoactive intestinal polypeptide (VIP) corrects chronic inflammatory response syndrome (CIRS) acquired following exposure to water-damaged buildings," Health, vol. 5(3), 2013, pp. 396-401.

* cited by examiner

*Primary Examiner* — Lorraine Spector

(57) ABSTRACT

The present invention relates generally to the diagnosis, treatment, and monitoring of Chronic Inflammatory Response Syndrome (CIRS), kits for use in the methods, and pharmaceutical compositions for use in the methods of treatment. The invention specifically relates to the diagnosis, treatment and monitoring of CIRS through a comprehensive approach comprising an assessment of a subject for case definition parameters and a proteogenomic analysis. The proteogenomic analysis for the diagnosis, treatment, and monitoring of CIRS is based on identifying proteins and/or genes that are differentially expressed in subjects suffering from CIRS compared to healthy subjects.

12 Claims, 3 Drawing Sheets
(1 of 3 Drawing Sheet(s) Filed in Color)

METHODS FOR DIAGNOSING, TREATING, AND MONITORING CHRONIC INFLAMMATORY RESPONSE SYNDROME

RELATED APPLICATION DATA

This application claims priority to Provisional Application No. 61/680,613, filed on Aug. 7, 2012, the disclosure of which is hereby incorporated by reference herein in its entirety.

FIELD OF THE INVENTION

The present invention relates generally to the diagnosis, treatment, and monitoring of Chronic Inflammatory Response Syndrome (CIRS), kits for use in the methods, and pharmaceutical compositions for use in the methods of treatment. The invention specifically relates to the diagnosis, treatment and monitoring of CIRS through a comprehensive approach comprising an assessment of a subject for case definition parameters and a proteogenomic analysis. The proteogenomic analysis for the diagnosis, treatment, and monitoring of CIRS is based on identifying proteins and/or genes that are differentially expressed in subjects suffering from CIRS compared to healthy subjects.

BACKGROUND OF THE INVENTION

CIRS is a form of Systemic Inflammatory Response Syndrome (SIRS) and is characterized by (1) lack of regulation of host inflammatory response as evidenced by deficiency of alpha melanocyte stimulating hormone (MSH) and/or vasoactive intestinal polypeptide (VIP); (2) presence of more than one of Th1 responses (pro-inflammatory); Th2 responses (anti-inflammatory); Th17 responses (tied to transforming growth factor beta-1 (TGF-β1)); coagulation abnormalities, especially abnormalities in von Willebrand's profile; activation of complement split products; activation of elements under regulation of hypoxia inducible factor including vascular endothelial growth factor (VEGF) and erythropoietin; abnormal regulation of ACTH responses to cortisol and ADH responses to osmolality. CIRS may be acquired through different mechanisms, for example, an exposure to toxins or inflammagens that may include, but are not limited to, environmental biotoxins, and chronic illness from Lyme disease present even after treatment with antibiotics. The exposure to environmental sources of biotoxins includes a chronic exposure to the interior environment of water-damaged buildings (WDB), or ingestion of fish contaminated with the toxins of marine dinoflagellates, such as ciguatoxins. Other environmental sources of biotoxins that can lead to CIRS include certain compounds made by dinoflagellates, cyanobacteria, fungi, actinomycetes, bacteria, mycobacteria, etc. When CIRS is acquired because of an exposure to a WDB, it is termed CIRS-WDB (Expert Treating Physicians Consensus, 2010).

According to a report released by the World Health Organization in 2009, in a WDB, people are chronically exposed to different microbes and/or compounds of microbial or other origin that are present in the indoor air of a WDB. These compounds initiate an innate immune inflammatory response in the human host. These microbes and compounds include but are not limited to fungi, bacteria, actinomycetes, and mycobacteria and their toxins; as well as inflammagens from fragments of fungal structures; and beta glucans, mannans, hemolysins, proteinases, spirocyclic drimanes and volatile organic compounds (VOCs). An ongoing exposure to the above microbes and/or compounds can result in a recurrent activation of immune responses, leading to exaggerated immune responses and prolonged production of inflammatory mediators, especially in the absence of regulation of inflammation by neuropeptides MSH or VIP.

Some of the organisms that make biotoxins that can cause CIRS include dinoflagellates (*Pfiesteria, Gambierdiscus* (ciguatera), *Karenia* (and other species that produce brevetoxins) cyanobacteria (*Microcystis, Cylindrospermopsis, Lyngbya wollei*); fungi (*Wallemia, Stachybotrys, Chaetomium, Trichoderma, Aspergillus versicolor, Aspergillus versicolor* and others); actinomycetes (*Streptomyces* and others); apicomplexans (*Babesia, Sarcocystis, Eimeria*), and spirochetes (*Borrelia* spp *burgdorferi* and (likely) *B. lonestari*). Organisms such as commensal multiple-antibiotic resistant coagulase negative staphylococci (MARCoNS), including methicillin resistant *Staphylococcus epidermidis*, may also contribute to CIRS.

Two examples of inflammagens that may cause CIRS are beta-glucans and mannans made by fungi that activate specific C-type lectin receptors, namely dectin-1 and dectin-2 receptors.

Patients with CIRS are often misdiagnosed as having depression, stress, allergy, fibromyalgia, post traumatic stress disorder, Chronic Fatigue Syndrome or somatization, etc., and are treated with various therapies, some of them being potentially toxic, which have not yet been shown to be effective, and are often costly. One reason that CIRS may be misdiagnosed is because there are no biomarkers that have been identified yet for CIRS or for those commonly-misdiagnosed illnesses, which would allow for a confirmatory diagnosis. Treating CIRS patients for the above conditions does not improve their symptoms of CIRS. With proper detection, diagnosis, and documentation of the objective basis of illness pathophysiology, CIRS may be treated effectively to improve symptoms and decrease the recurrence of uncontrolled inflammatory responses. Therefore, there exists a need for accurate diagnosing of CIRS in order to effectively treat patients with CIRS.

SUMMARY OF THE INVENTION

The present invention relates to the diagnosis, prognosis, prevention and/or treatment of CIRS. In particular, the invention is directed to the differential diagnosis of CIRS in a subject suspected of having CIRS, including differential diagnosis based on a detailed medical history and optional visual contrast sensitivity testing (VCS), and also identifying a panel of proteogenomic markers that are differentially expressed in subjects with CIRS relative to reference levels of expression of these markers either in disease-free healthy subjects or in subjects with CIRS prior to receiving the treatment for CIRS.

The term "a subject suspected of having CIRS" refers to, but is not limited to, individuals who are exposed to CIRS etiological factors such as environmental sources of toxins, including WDB, ciguatoxins, or other toxic components originating from dinoflagellates, cyanobacteria, fungi, actinomycetes, bacteria, mycobacteria, etc., or chronic illness from Lyme disease.

The term "differential diagnosis" as used herein refers to obtaining medical history and objective parameters from a subject, determining whether the subject has been exposed to any potential CIRS etiological factors, optionally performing visual contrast sensitivity (VCS) testing on the subject, and making a determination as to whether the subject is suspected of having CIRS or not having CIRS based on the medical history, laboratory testing, and the results of VCS testing, if performed.

The term "proteogenomic markers" as used herein refers to a combination of one or more genomic markers and/or one or more proteomic markers that are used in order to make a determination of whether a subject is suspected of having CIRS or not having CIRS. The proteogenomic markers may include any one of the markers set forth in Tables 3-4 and Appendices A-D, any combination of markers set forth in Tables 3-4 and Appendices A-D, or all of the markers set forth in Tables 3-4 and Appendices A-D.

The present invention also includes methods for testing trigger mechanisms of CIRS, such as an Environmental Relative Moldiness Index (ERMI) and its derivative, Health Roster of Type Specific formers of Mycotoxins and Inflammagens, second iteration (HERTSMI-2); testing for the presence of fungi in the built environment; testing for *Lyme borreliosis*; or an assessment of intoxication with ciguatoxins.

The treatment methods of the invention may also include removing the subject from the source of the toxins and/or inflammagens, and/or removing the toxins and/or inflammagens from the subject or the environment surrounding the subject. Such toxins or inflammagens may include, but are not limited to, environmental biotoxins, such as those found in the interior environment of water-damaged buildings (WDB), in fish contaminated with the toxins of marine dinoflagellates (e.g., ciguatoxins), as well as certain compounds produced by dinoflagellates, cyanobacteria, fungi, actinomycetes, bacteria, mycobacteria, etc. The toxins may also be present in the subject as a result of chronic illness from Lyme disease present even after treatment with antibiotics, for example.

In one embodiment, the method of diagnosing Chronic Inflammatory Response Syndrome (CIRS) in a subject suspected of having CIRS, comprises a) obtaining at least the case definition parameters listed in Table 1 for the subject; and b) diagnosing the subject as having CIRS if the subject shows the presence of one or more, two or more, three or more, four or more, five or more, six or more, seven or more eight or more, nine or more, or all ten of the case definition parameters listed in Table 1. Preferably, the presence of at least three of these parameters is detected; more preferably, the presence of at least four parameters is detected; most preferably, the presence of at least five parameters is detected. The step of obtaining case definition parameters may comprise i) obtaining medical history of the subject; ii) optionally performing a visual contrast sensitivity testing on the subject; iii) determining levels of one or more protein markers listed in Tables 3 and 4 in a biological sample obtained from the subject; iv) determining levels of one or more mRNA markers selected from Appendices A, B and/or C in the biological sample; v) determining levels of one or more micro-RNA markers listed in Appendix D in the biological sample.

In one embodiment, the step of obtaining medical history is followed by differential diagnosis to diagnose the subject as suspected of having CIRS or not having CIRS. The differential diagnosis is then confirmed by determining the levels of one or more proteogenomic markers.

In another embodiment, the method of diagnosing CIRS comprises diagnosing CIRS based on the expression levels of one or more protein markers. According to this embodiment, the method of diagnosing chronic inflammatory response syndrome (CIRS) in a subject suspected of having CIRS comprises a) determining levels of one or more protein markers listed in Table 3 in a biological sample obtained from the subject; b) diagnosing the subject as having CIRS if the levels of the one or more protein markers are statistically significantly different from reference levels for the one or more protein markers.

In yet another embodiment, the method of diagnosing CIRS comprises diagnosing CIRS based on the expression levels of one or more mRNA markers. According to this embodiment, the method of diagnosing chronic inflammatory response syndrome (CIRS) in a subject suspected of having CIRS comprises a) determining levels of one or more mRNA markers selected from Appendices A, B and/or C in a biological sample obtained from the subject; b) diagnosing the subject as having CIRS if the levels of the one or more mRNA markers are statistically significantly different from reference levels for the one or more mRNA markers.

In yet another embodiment, the method of diagnosing CIRS comprises diagnosing CIRS based on the expression levels of one or more micro-RNA markers. According to this embodiment, the method of diagnosing chronic inflammatory response syndrome (CIRS) in a subject suspected of having CIRS comprises a) determining levels of one or more micro-RNA markers listed in Appendix D in a biological sample obtained from the subject; b) diagnosing the subject as having CIRS if the levels of the one or more micro-RNA markers are statistically significantly different from reference levels for the one or more micro-RNA markers.

According to the invention, it has been found that subjects with CIRS may also exhibit brain abnormalities. Specifically, it has been found that subjects with CIRS may exhibit structural brain volumes abnormalities including, but not limited to, an increase in forebrain parenchyma, an increase in cortical gray area, an increase in the volume of the hippocampus, a decrease in the volume of caudate, and/or an increase in the volume of pallidum. These structural brain abnormalities have been identified, for example, in subjects suffering from CIRS-WDB. Accordingly, in another embodiment, the method of diagnosing CIRS may further comprise detecting brain abnormalities in a subject suspected of having CIRS using known or as-yet undeveloped methods for detecting brain abnormalities. The methods of monitoring treatment of CIRS may also further comprise detecting brain abnormalities in a subject being treated for CIRS at a first time period prior to treatment, and comparing the abnormalities with brain abnormalities detected at a second time period after treatment has been initiated, and determining whether improvement in brain abnormalities is observed. Methods known in the art for detecting brain abnormalities may include, but are not limited to, CT scans, MRI scans, PET scans, brain volume measurement (i.e., FreeSurfer, Martinos Center for Biomedical Imaging, Charlestown, Mass.), and NeuroQuant® (CorTechs Labs, La Jolla, Calif.).

The present invention also provides methods of treating chronic inflammatory response syndrome (CIRS). In one embodiment, a method of treating CIRS in a subject, comprises: a) obtaining case definition parameters listed in Table 1 for the subject; b) diagnosing the subject as having CIRS if the subject shows the presence of at least five of the case definition parameters listed in Table 1; c) administering cholestyramine to the subject. The methods may also optionally include removing or reducing the amount of any toxins and/or inflammagens that are suspected of causing CIRS in the subject. When cholestyramine is administered to the subject, dosage amounts and schedules are within the ability of the skilled practitioner to determine, and may be, for example, in the range of 1 to 40 grams per day, preferably 8 to 36 grams per day, more preferably 16 to 24 grams per day. The doses may be provided from 1 to 6 times per day, preferably 2 to 4 times per day. The doses are preferably administered orally. Cholestyramine may be administered for any period of time necessary to achieve relief from CIRS. However, it should be noted that the present invention is not limited by the dosage amount, administration route, or length of administration.

In another embodiment, a method of treating CIRS in a subject comprises: a) obtaining case definition parameters listed in Table 1 for the subject; b) diagnosing the subject as having CIRS if the subject shows the presence of at least five of the case definition parameters listed in Table 1; c) administering vasoactive intestinal peptide (VIP) to the subject. The methods may also optionally include removing or reducing the amount of any toxins and/or inflammagens that are suspected of causing CIRS in the subject. When VIP (aviptadil) is administered to the subject, dosage amounts and schedules are within the ability of the skilled practitioner to determine, and may be, for example, in the range of 5 to 200 micrograms, preferably 10 to 100 micrograms, more preferably 25 to 75 micrograms. According to one embodiment, a dose of 50 micrograms is administered. The doses may be provided from 1 to 4 times per day, preferably 1 time per day. The doses may be administered nasally or injected, although nasal instillation is a preferred method of administration. VIP may be administered for any period of time necessary to achieve relief from CIRS. However, it should be noted that the present invention is not limited by the dosage amount, administration route, or length of administration.

In yet another embodiment, a method of treating CIRS in a subject comprises sequential therapeutic intervention shown in FIG. 2. According to this embodiment, a method of treating CIRS in a subject comprises: a) obtaining case definition parameters listed in Table 1 for the subject including performing differential diagnosis; b) diagnosing the subject as having CIRS if the subject shows the presence of at least five of the case definition parameters listed in Table 1; c) administering a therapeutically effective dose of cholestyramine to the subject; d) treating the subject to eliminate MARCoNS infection if the subject has MARCoNS infection; e) correcting or restoring levels of antigliadin, androgens, ADH/osmolality, MMP9, VEGF, C3a, C4a, TGF-β1; and f) administering a therapeutically effective dose of VIP to the subject.

In one embodiment, the method of treating chronic inflammatory response syndrome (CIRS) in a subject comprises a) determining levels of: one or more protein markers listed in Table 3 and/or one or more mRNA markers selected from Appendices A, B and/or C and/or one or more micro-RNA markers listed in Appendix D in a biological sample obtained from the subject; b) diagnosing the subject as having CIRS if the levels of the one or more protein markers and/or the one or more mRNA markers and/or the one or more micro-RNA markers are statistically significantly different from reference levels for corresponding markers; c) administering a therapeutically effective dose of cholestyramine to the subject.

In another embodiment, the method of treating chronic inflammatory response syndrome (CIRS) in a subject comprises a) obtaining case definition parameters listed in Table 1 for the subject, including performing differential diagnosis, at a first time; b) diagnosing the subject as having CIRS if the subject shows the presence of at least five of the case definition parameters listed in Table 1; c) administering a therapeutically effective dose of cholestyramine to the subject; d) treating the subject to eliminate MARCoNS infection if the subject has MARCoNS infection; e) correcting or restoring levels of antigliadin, androgens, ADH/osmolality, MMP9, VEGF, C3a, C4a, TGF-β1; f) administering a therapeutically effective dose of VIP to the subject; g) obtaining case definition parameters listed in Table 1 for the subject at a second time for monitoring the status of CIRS in the subject, wherein the second time is later than the first time; h) diagnosing the subject as showing an improvement of CIRS if, at the second time, the subject shows the presence of fewer health symptoms or the presence of less than five case definition parameters listed in Table 1 or diagnosing the subject as not showing an improvement if the subject shows the presence of at least five of the case definition parameters listed in Table 1; i) repeating steps d) to g), until resolution of CIRS is obtained.

The present invention also provides a method for monitoring CIRS in a subject comprising: a) obtaining case definition parameters listed in Table 1 for the subject at a first time; b) diagnosing the subject as having CIRS if the subject shows the presence of at least five of the case definition parameters listed in Table 1; c) administering a dose of cholestyramine to the subject; d) obtaining case definition parameters listed in Table 1 for the subject at a second time for monitoring the status of CIRS in the subject, wherein the second time is later than the first time; e) diagnosing the subject as showing an improvement of CIRS if the subject shows the presence of less than five case definition parameters listed in Table 1 or diagnosing the subject as not showing an improvement if the subject shows the presence of at least five of the case definition parameters listed in Table 1; f) adjusting the dose of cholestyramine, if required based on the diagnosis in step e); g) administering the adjusted or the same dose of cholestyramine to the subject; h) repeating steps d) to g) until resolution of CIRS is obtained.

In one aspect, the method for diagnosing or monitoring CIRS in a subject according to the invention further comprises a step of detecting, in a biological sample of the subject, a level of regulatory T lymphocytes (Treg cells) as an indirect indicator of the status of tissue-based inflammation in the subject.

In another aspect, the method for diagnosing or monitoring CIRS in a subject according to the invention further comprises determining the presence of unusual staphylococci such as coagulase negative staphylococci, staphylococci which are resistant in Kirby-Bauer susceptibility testing to at least two classes of antibiotics (MARCoNS), and methicillin resistant staphylococci (MRCoNS) in the subject by obtaining an aerobic culture using the API-STAPH or similar technique from deep nasal spaces from the subject. These organisms invariably form biofilm, providing a mechanism to continue to colonize deep nasal spaces without causing overt invasive symptoms such as headache or sinus congestion. In one aspect, the method for diagnosing or monitoring CIRS in a subject according to the invention comprises determining diagnostic parameters that are not altered in CIRS compared to other diseases or disorders the symptoms of which may overlap with CIRS. Such diagnostic parameters include, but are not limited to, erythrocyte sedimentation rate (ESR), C-reactive protein (CRP), etc.

The methods of diagnosing, treating, and monitoring CIRS according to the invention may comprise various permutations and combinations of the methods disclosed herein.

According to the invention, it has been found that subjects with CIRS may show a distinct and specific pattern or profile of expression for a set of genes (for example, set X)

compared to healthy subjects or subjects with illnesses that have symptoms similar to CIRS. For example, in one aspect of the invention, subjects with CIRS may show a distinct and specific pattern of expression for one or more mRNA markers selected from Appendices A, B and/or C and/or one or more micro RNA markers selected from Appendix D. It has also been found that the expression profile of a set of genes (for example, set Y) may vary between the subjects with CIRS based on the etiology of CIRS. For example, a subject that has acquired CIRS because of an exposure to WDB may show a gene expression pattern different from the gene expression pattern of a subject that has acquired CIRS because of chronic illness from Lyme disease. According to one aspect of the invention, set Y is a subset of set X. Accordingly, the present invention is also directed to predicting the causative agent of CIRS.

In one aspect of the invention, the diagnosis of CIRS is carried out by detecting levels of one or more genes that are differentially expressed between the subjects with CIRS and disease-free healthy subjects. The differential expression of CIRS genes may be measured at the gene level, transcript level and/or polypeptide level. The term "transcript" as used herein encompasses all RNA products produced from the genome, including sense and antisense products, coding RNAs such as messenger RNAs (mRNAs) as well as non-coding RNAs such as Long Intergenic Non-Coding (linc) RNAs as well as regulatory RNAs such as micro-RNAs. Micro-RNAs are a class of small, non-coding RNAs that control gene expression by hybridizing to and triggering either translational repression or, more frequently, degradation of a messenger RNA (mRNA) target. linc RNAs are in general considered as non-protein coding transcripts longer than 200 nucleotides.

The term "differential expression" as used herein means either an over-expression or under-expression of one or more CIRS genes, transcripts or proteins relative to reference levels of expression of corresponding genes, transcripts or proteins. That is, in an embodiment, certain genes, transcripts, and/or proteins are down-regulated while certain other genes, transcripts, and/or proteins are up-regulated compared to reference levels of corresponding genes, transcripts, and/or proteins. In one example, a gene, transcript, and/or protein for vasoactive intestinal peptide (VIP) may be under-expressed while a gene, transcript, and/or protein for anaphylatoxin C4a may be over-expressed. The term CIRS gene, transcript or protein means a gene, transcript or protein that is differentially expressed in CIRS subjects compared to healthy subjects.

In one embodiment, reference levels of expression are the expression levels of genes, transcripts or proteins in a healthy subject. In another embodiment, reference levels of expression are the expression levels of genes, transcripts or proteins in a subject with CIRS prior to the treatment of CIRS. In another embodiment, reference levels of expression are the expression levels of genes, transcripts or proteins in a subject with CIRS at various stages during the course of treatment for CIRS.

The term "statistically significantly different" means the p-value of the differential expression for each selected CIRS gene, transcript or protein is no more than 0.05. In one embodiment, the difference in the expression levels of CIRS genes, transcripts or proteins compared to the reference levels of expression of corresponding genes, transcripts or proteins is at least 1.3-, 2-, 3-, 4-, 5-, 10-, 20-fold or more. In another embodiment, the expression level is indicative of CIRS if it is found in at least 70%, at least 75%, at least 80%, at least 85%, at least 90%, at least 95%, at least 97%, at least 98%, at least 99%, or more in subjects with CIRS and is found in less than 20%, less than 10%, less than 8%, less than 5%, less than 2.5%, or less than 1% of subjects who do not have CIRS.

In yet another embodiment, the differentially expressed CIRS genes, transcripts, and proteins are selected from Tables 3-4 and Appendices A-D. In still another embodiment, the CIRS genes include innate immune response genes such as genes encoding complement factors, neuropeptides, hormones, transcription factors, cytokines, etc.

In one aspect, the differential expression of CIRS genes is diagnosed by measuring the levels of expression of one or more polypeptides, mRNA and/or micro RNA in a biological sample obtained from a subject with CIRS and a biological sample obtained from a healthy individual. The biological sample may be blood, nasal swab, a bodily waste sample or any other body fluid or tissue that can provide a meaningful diagnosis of differentially expressed CIRS genes.

In one aspect, levels of protein markers listed in Table 3, mRNA markers selected from Appendices A, B and/or C, and micro-RNA markers listed in Appendix D in a biological sample may be detected by methods known in the art. In one example, levels of protein markers listed in Table 3 may be determined using antibodies or fragments of antibodies specific for these markers. In another example, levels of protein markers may be detected using methods such as enzyme-linked immunosorbent assays (ELISA), radio-immuno assay (RIA), or western blot analysis. In another example, levels of protein markers may be detected using direct methods such as mass spectrometry. In yet another example, levels of protein markers listed in Table 3 may be determined using commercially available kits such as those available from Laboratory Corporation of America (LabCorp) or Quest Diagnostics, Inc. Although ELISA is one preferred technique for detecting the protein markers used in the invention, alternative techniques such as immunoblotting nuclease protection assays, in situ hybridization, microarrays, immunohistochemistry, are also envisioned, and appropriate apparatus, and reagents for use in carrying out these well-known techniques are envisioned for use in the methods and included as components of the kits.

In an embodiment, levels of mRNA markers selected from Appendices A, B and/or C and levels of micro-RNA markers listed in Appendix D in a biological sample may be determined by extracting total RNA from the biological sample and hybridizing the extracted RNA to labeled nucleic acid probes complementary to mRNA and micro-RNA markers using any state of the art techniques. Techniques for detecting mRNAs and micro-RNAs using labeled nucleic acid probes include microarray analysis, northern blot analysis, and nuclease protection assays. Alternatively, mRNA and micro-RNA markers can be detected using reverse transcription-polymerase chain reaction (RT-PCR) with or without labeled nucleic acid probes. Additionally, newer techniques that do not rely on complementary target-probe hybridization, such as Next Generation Sequencing (NGS), may be used to determine levels of transcripts.

The present invention also provides pharmaceutical compositions useful for treating or preventing CIRS. In one embodiment, the pharmaceutical compositions of the present invention include a pharmaceutically acceptable carrier and at least one polynucleotide encoded by a CIRS gene that is over-expressed or under-expressed in CIRS subjects relative to healthy subjects. The pharmaceutical compositions can also include a variant or an allele of the polynucleotide.

In one example, the pharmaceutical compositions are compositions comprising at least one micro-RNA listed in Appendix D.

In another embodiment, the pharmaceutical compositions of the present invention include a pharmaceutically acceptable carrier and at least one active component selected from (i) agents capable of modulating the expression of one or more CIRS genes which are over-expressed or under-expressed in CIRS subjects relative to healthy subjects, (ii) agents capable of binding to, or modulating the biological activity of, the polypeptide(s) encoded by the CIRS gene, (iii) agents capable of modulating Treg cells, or (iv) Treg cells. Exemplary modulations include, but are not limited to, up-regulation, induction, stimulation, inhibition, down-regulation, and suppression.

In one example, the active component is a polynucleotide comprising or encoding an RNA that is capable of inhibiting or decreasing expression of the CIRS gene by RNA interference or an antisense mechanism. In another example, the active component is an agonist or antagonist of a protein encoded by the CIRS gene. In yet another example, the active component is a monoclonal antibody or a fragment thereof. Proteins encoded by CIRS genes can be, for example, innate immune response proteins such as complement factors, neuropeptides, hormones, transcription factors, cytokines, etc. These proteins and genes are potential targets for drug action and development.

In still yet another aspect, the present invention provides methods for screening anti-CIRS agents based on their effects on the expression or function of CIRS genes.

In a further aspect, the present invention provides kits useful for diagnosing CIRS. Each kit can include at least one of the following: (a) one or more polynucleotide probes capable of hybridizing under reduced stringent, stringent, or highly stringent conditions to one or more CIRS genes (or a complement thereof), or (ii) one or more antibodies capable of specifically binding to one or more polypeptides encoded by CIRS genes (e.g., antibodies to the polypeptides). The kits may include a carrier where the polynucleotide probes or antibodies are immobilized and one or more reagents or detection agents for detecting a reaction between the one or more probes or antibodies and target nucleic acids or polypeptides. The kit may also include one or more software and/or instructions to analyze the data generated by using the kit.

In another embodiment, the invention is directed to an antibody or antibodies that specifically bind to proteins or protein fragments that are differentially expressed in subjects with CIRS.

It is further intended that the inventions not be limited only to the specific structure, material or acts that are described in the preferred embodiments, but in addition, include any and all structures, materials or acts that are capable of performing the claimed function, along with any and all known or later-developed equivalent structures, materials or acts capable of performing the claimed function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
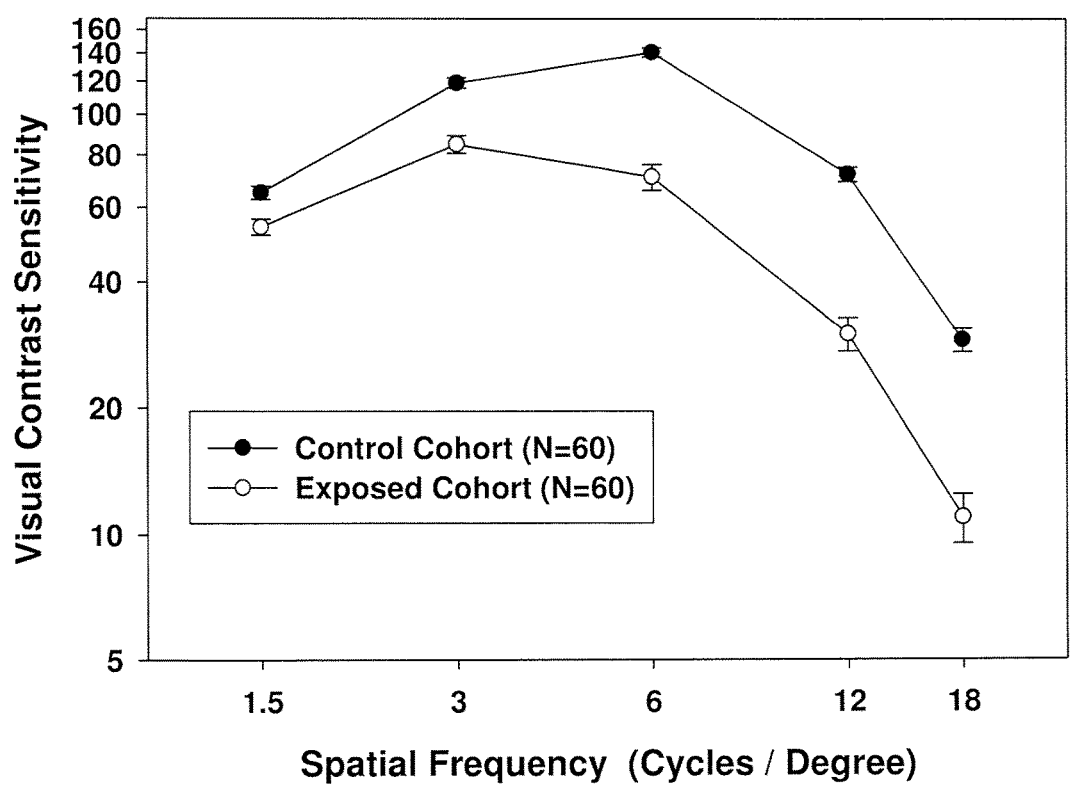
FIG. 1 shows that patients with CIRS exhibit defects in visual contrast sensitivity as compared to control healthy individuals.

The present invention provides methods of diagnosing, treating and monitoring CIRS, as well as test kits for use in the methods. In one aspect, the method of diagnosing CIRS in a subject suspected of having CIRS comprises a) obtaining case definition parameters listed in Table 1 for the subject, comprising: i) obtaining medical history of the subject, ii) performing differential diagnosis; iii) optionally performing visual contrast sensitivity testing on the subject, iv) determining levels of one or more protein markers listed in Table 3 in a biological sample obtained from the subject, v) determining levels of one or more mRNA markers selected from Appendices A, B and/or C in the biological sample, vi) optionally performing brain scanning on the subject, vii) determining levels of one or more micro-RNA markers listed in Appendix D in the biological sample; and b) diagnosing the subject as having CIRS if the subject shows the presence of three or more, preferably four or more, and most preferably five or more of the case definition parameters listed in Table 1.

TABLE 1

| Case Definition Parameters |
|---|
| Parameters |
| Symptoms score > 8 |
| VCS deficit |
| MSH < 25 pg/mL |
| VIP < 23 pg/mL |
| C4a > 2830 ng/mL |
| TGF-β1 > 2380 pg/mL |
| MMP9 > 332 ng/mL |
| ADH/osmolality dysregulation |
| ACTH/cortisol dysregulation |
| Genomic SVM confidence > 0.9 |

The case definition parameters listed in Table 1 are explained in more detail below.

Symptoms Score:

Symptoms score is obtained by obtaining a detailed medical history of a subject. Medical history evaluates both subjective patient complaints and causative environmental parameters for potential exposure to biotoxins in the home, school or workplace. Medical history includes a detailed analysis of past medical conditions and current symptoms experienced by the subject. A symptom roster (Table 2) may be used to determine the symptoms experienced by the subject. The symptom roster comprises a list of symptoms grouped by symptom clusters which are discussed in the following references: Shoemaker et al., "Sick Building Syndrome in water-damaged buildings: Generalization of the chronic biotoxin-associated illness paradigm to indoor toxigenic fungi," *Bioaerosols, Fungi, Bacteria, Mycotoxins and Human Health*, Johanning, E., editor, 2005, pages 66-77; Shoemaker et al., "A time-series of sick building syndrome; chronic, biotoxin-associated illness from exposure to water-damaged buildings," *Neurotoxicology and Teratology*, 2005, 27(1) 29-46; Shoemaker et al., "SBS and exposure to water damaged buildings: time series study, clinical trial and mechanisms," *Neurotoxicology and Teratology*, 2006, 28: 573-588; Shoemaker et al., "Innate immunity, MR spectroscopy, HLA DR, TGF beta-1, VIP and capillary hypoperfusion define acute and chronic human illness acquired following exposure to water-damaged buildings," Healthy Buildings, Syracuse, N.Y., 2009; Shoemaker, "Innate immune responses define pediatric CFS," International Association for CFS/ME Conference, 2009, Reno, Nev.; Shoemaker, "Exposure to water-damaged buildings causes a readily identifiable chronic inflammatory response syndrome that is successfully treated by a sequential intervention protocol," 9th International Mycology Congress, Edinburgh, Scotland, 2010; Shoemaker, "Vasoactive Intestinal Polypeptide (VIP): a final step in correction of the inflammatory illness acquired following exposure to water-damaged buildings," "T regulatory cells in chronic inflammatory response syndrome from water-damaged buildings (CIRS-WDB)," and "HERTSMI-2 Simplifying analysis of safety of WDB," 6th International Scientific Conference on Bioaerosols, Fungi, Bacteria, Mycotoxins in Indoor and Outdoor Environments and Human Health, Saratoga Springs, N.Y., September 2011. Each of these references is hereby incorporated by reference herein in its entirety.

Each symptom cluster may comprise one or more symptoms. A symptoms score is the number of symptom clusters experienced by the subject. For example, a symptoms score of 5 means the symptoms experienced by the subject belong to 5 symptom clusters. A symptoms score of 8 or more indicates that a subject may be suffering from CIRS.

TABLE 2

Symptom Roster

| Symptom/Cluster | Score Patient |
|---|---|
| Fatigue/1 | |
| Weak/2 | |
| Ache/2 | |
| Cramp/5 | |
| Unusual pain/10 | |
| Ice pick pain/10 | |
| Headache/2 | |
| Light sensitivity/2 | |
| Red eyes/10 | |
| Blurred vision/10 | |
| Tearing/12 | |
| Sinus/7 | |
| Cough/8 | |
| Shortness of breath/7 | |
| Abdominal pain/11 | |
| Diarrhea/11 | |
| Joint pain/5 | |
| Morning stiffness/5 | |
| Memory/3 | |
| Focus/concentration/4 | |
| Word recall/3 | |
| Decreased assimilation/2 | |
| Confusion/8 | |
| Disorientation/12 | |
| Skin sensitivity/6 | |
| Mood swings/10 | |
| Appetite/9 | |
| Sweats/10 | |
| Temp regulation/9 | |
| Thirst/8 | |
| Increased urination/9 | |
| Static shocks/13 | |
| Numbness/11 | |
| Tingling/6 | |
| Vertigo/13 | |
| Metallic taste/12 | |

2. Visual Contrast Sensitivity (VCS) Testing:

VCS testing measures the neurologic function called contrast that permits an eye to resolve patterns. This test is regarded as the best current test of functional vision. VCS deficiencies due to an exposure to CIRS causative agents such as biotoxins have been shown to correlate with capillary hypoperfusion in the retina and neural rim of the optic nerve head as measured by a dual laser device, Heidelberg Retinal Flowmeter (Hudnell, EPA 2003). Since excessive optical-refraction errors can cause abnormal VCS readings, a visual acuity as measured by Snellen Distance Equivalent Score of better than 20:50 is required for inclusion of this element in the diagnosis of CIRS. Apart from CIRS, VCS deficiencies may occur in certain neurologic conditions such as neurologic conditions developed due to an exposure to mercury, organic solvents, hydrocarbons, or Parkinson's disease (see, e.g., Residential and Recreational Acquisition of Possible Estuarine Associated Syndrome: A New approach to Successful Diagnosis and Therapy, Environmental Health Perspectives, Special CDC Pfiesteria Supplement, 2001; 109S5; 791-796). However, according to the present invention, a combination of symptoms score and VCS can differentially diagnose CIRS subjects from those experiencing non-CIRS illnesses such as the neurologic conditions described above (Table 5). Differences in VCS between subjects exposed to CIRS causative agents and control subjects are shown in FIG. 1.

3. Protein Markers:

The present invention uses a panel of protein markers (Table 3) that are differentially expressed in CIRS subjects compared to healthy individuals. These protein markers are indicative of the physiologic status of inflammatory responses in CIRS subjects. Methods for detecting levels of protein markers listed in Table 3 are known in the art, and include commercially-available enzyme linked immunosorbent assays (ELISAs), radioimmunoassays, and other immunoassay technologies. Additional detection methods may also be employed in order to identify biomarkers, including PCR and related technologies. Various techniques for the detection of the biomarkers may be used in accordance with the invention, such as those described in Ausubel et al., *Current Protocols In Molecular Biology*, John Wiley & Sons, New York, N.Y., 2002, or Sambrook et al., *Molecular Cloning: A Laboratory Manual*, Cold Spring Harbor Press, Cold Spring Harbor, N.Y., 1989. In one embodiment, levels of protein markers listed in Table 3 in a biological sample may be determined using commercially available test kits such as those available from LabCorp or Quest Diagnostics, Inc.

TABLE 3

Protein markers

| Protein marker |
|---|
| C4a |
| VIP |
| MSH |
| TGF-β1 |
| MMP9 |
| ACTH/Cortisol |
| ADH/Osmolality |
| Von Willebrand's profile |
| HLA-DR |

The protein markers that may be measured in accordance with the invention can be obtained from any sample of a biological material that is suspected of containing the protein markers as an analyte of interest. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, etc. Preferably, the test sample is a blood, serum, or urine sample. The test sample may be used directly as obtained or following a pretreatment to modify the sample. For example, pretreatment may include preparing plasma or serum from blood. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that the analyte of interest remains in the test sample at a concentration proportional to that in an untreated test sample (e.g., a test sample that is not subjected to any such pretreatment method(s)).

3.1. C4a is a split product of complement component 4. The complement system is an important component of both innate and adaptive immune responses. CIRS patients show a statistically significant difference from normal levels of C4a. Interestingly, CIRS patients, mainly those with CIRS-WDB or CIRS-ciguatera, are not likely to show an increase in the levels of C3a, a product immediately downstream of C4 activation. Complement activation through both the classical pathway and mannose binding lectin system generates increased levels of C4a.

3.2. And 3.3. Vasoactive Intestinal Peptide (VIP) and Alpha Melanocyte stimulating hormone (MSH):

VIP and MSH are neuropeptides critical for the regulation of inflammation. CIRS patients consistently exhibit low levels of VIP and MSH, suggesting lack of regulation of inflammation in the development and persistence of CIRS. These two neuropeptides have been shown to have profound anti-inflammatory effects both in vivo and in vitro and could be used for treating inflammatory diseases.

VIP and/or MSH deficiencies can be acquired either acutely or at an advanced stage of CIRS, as well as through diverse mechanisms such as acute brain injuries (S. Magnoni, et al., Alpha-melanocyte-stimulating hormone is decreased in plasma of patients with acute brain injury, *J Neurotrauma* 20 (2003) 251-60) or persistent viral infection (Y.-R. Tan, et al., Pulmonary peptidergic innervation remodeling and development of airway hyperresponsiveness induced by RSV persistent infection, *Peptides* 29 (2008) 47-56). It has been shown that VIP agonists effectively protect against Alzheimer-related learning impairment in rats (I. Gozes, et al., Neuropeptides and neuronal survival: neuroprotective strategy for Alzheimer's disease, *Annals of the New York Academy of Sciences* 814 (1997) 161-6) while deficiency of VIP has been shown to cause cognitive defects in mice (D. Chaudhury, et al., Select cognitive deficits in vasoactive intestinal peptide deficient mice, *BMC Neurosci* 9 (2008) 63), common symptoms observed in CIRS subjects. One important role of these two neuropeptides is the induction of tolerogenic dendritic cells and generation of T regulatory cells (Tregs), which suppress autoreactive T cells and autoimmune progression (M. Delgado and D. Ganea, Anti-inflammatory neuropeptides: A new class of endogenous immunoregulatory agents, *Brain, Behavior, and Immunity* 22 (2008) 1146-1151). Even in healthy individuals autoreactive T cells can escape clonal deletion and must be policed in the periphery by Tregs to prevent pathologic autoimmunity (N. A. Danke, et al., Autoreactive T Cells in Healthy Individuals, *J Immunol* 172 (2004) 5967-5972). Decreased levels of Treg cells due to lower levels of VIP and MSH could be the reason that both pediatric and adult CIRS patients show certain features of autoimmune disease such as markedly elevated levels of anti-gliadin and anti-cardiolipin antibodies compared to healthy individuals.

3.4. And 3.5. Matrix Metalloproteinase 9 (MMP9) and Transforming Growth Factor Beta-1 (TGF-β1):

CIRS patients often show high levels of MMP9 and TGF-β1. These two proteins have been demonstrated to have wide ranging effects on the immune system, including important roles in autoimmune and inflammatory diseases. The timing, duration and target tissues are important aspects for protection or pathological activity of these proteins.

Similar to VIP and MSH, TGF-β1 has been shown to regulate T-cell differentiation pathways and is considered to have an anti-inflammatory action (M. A. Kriegel, et al., Transforming growth factor-beta: recent advances on its role in immune tolerance, *Curr Rheumatol Rep* 8 (2006) 138-44). However, in the presence of low levels of Treg cells in blood and increased levels of inflammatory cytokines in tissues, TGF-β1 may act in a pro-inflammatory manner. TGF-β1 requires a proteolytic cleavage for its transformation from a latent to a mature complex. Interestingly, MMP9 can drive this transformation. MMP9 expression is also up regulated by TGF-β1 and can influence disease progression by both tissue destruction and cytokine processing (P. Van Lint and C. Libert, Chemokine and cytokine processing by matrix metalloproteinases and its effect on leukocyte migration and inflammation, *J Leukoc Biol* 82 (2007) 1375-1381). Elevated levels of both MMP9 and TGF-β1 have been reported in systemic sclerosis, a generalized disorder of the microvascular characterized by excessive fibrosis (M. Ram, et al., Matrix Metalloproteinase-9 and Autoimmune Diseases, *Journal of Clinical Immunology* 26 (2006) 299-307). Further, the role of TGF-β1 as a stimulant to pro-fibrotic effects in lung parenchyma, including epithelial to mesenchymal transformation, may support an explanation of restrictive pulmonary function seen in some CIRS cases.

3.6. and 3.7. ACTH/Cortisol and ADH/Osmolality:

Levels of ACTH and cortisol as well as levels of ADH along with osmolality values are important diagnostic parameters in the differential diagnosis of CIRS. Antidiuretic hormone (ADH), also known as vasopressin, is an important hormone in regulating body osmolality or salt balance. All cells in the body rely on maintenance of voltage potential between the intracellular and extracellular compartments, which is maintained by an appropriate concentration of salts in each compartment. Absence of adequate ADH can result in intravascular and systemic dehydration.

Abnormal osmolality values can result in widespread cellular dysfunction. Abnormalities in ADH/osmolality are recorded as "absolute" if ADH is less than 1.3 pg/ml or more than 13.3 pg/ml or if osmolality is more than 295 mOsm/kg or less than 275 mOsm/kg. Abnormalities in ADH/osmolality are recorded as "relative or dysregulated" if simultaneous readings for ADH and osmolality are ADH less than 2.3 pg/ml and osmolality of 292-295 mOsm/kg or ADH more than 4.0 pg/ml and osmolality of 275-278 mOsm/kg. Symptoms associated with dysregulation of ADH include migraine-like headaches, dehydration, frequent urination, excessive thirst and sensitivity to static electrical shocks. Elevated levels of ADH can cause edema and rapid weight gain due to fluid retention.

ACTH/cortisol: Abnormalities in ACTH/cortisol are recorded as "absolute" if morning cortisol levels are more than 18 μg/ml or less than 5 μg/ml; or if morning ACTH levels are more than 45 pg/ml or less than 6 pg/ml. Abnormalities in ACTH/cortisol are recorded as "relative or dysregulated" if simultaneous readings for cortisol and adrenocorticotropic hormone (ACTH), also known as corticotropin, are greater than 16 µg/ml and ACTH greater 20 pg/ml or cortisol less than 12 µg/ml and ACTH less than 10 pg/ml. At an early stage of CIRS, levels of ACTH may remain high; however, at later stages, ACTH levels begin to fall. Simultaneously high levels of cortisol and ACTH could be interpreted to indicate the presence of ACTH secreting tumors. However, in contrast to ACTH secreting tumors, in CIRS, high levels of cortisol and ACTH are usually corrected with treatment.

3.8 von Willebrand's Profile:

von Willebrand's profile consists of measuring the levels of clotting factor Factor VIII as well as von Willebrand's antigen and ristocetin-associated cofactor. More than 66% of CIRS patients show a lack of normal levels of one or more of these components. Combined low levels of ristocetin-associated co-factor and multimers of von Willebrand's factor are called acquired von Willebrand's disease, a rare entity except in CIRS-WDB.

3.9 HLA-DR Typing:

HLA-DR typing is offered by LabCorp as a standard typing assay of 10 alleles using a PCR technique. HLA-DR typing using PCR provides greater specificity in distinguishing individual allele polymorphisms compared to serologic assays for HLA-DR genotypes. CIRS patients show a strong linkage disequilibrium with multiple associations to inflammatory and autoimmune disease. HLA-DR typing by itself may not conclusively indicate the presence or absence of CIRS, but it helps in assessing the susceptibility of a subject to develop CIRS. The role of HLA allele types in determining subjects at risk of chronic illnesses has been investigated, for example, in U.S. Published Application No. 2003/0219400, the contents of which are incorporated herein by reference.

4. Aerobic Culture:

An aerobic culture may be used to detect the presence of biofilm-forming coagulase-negative staphylococci in CIRS patients. API-STAPH nasal culture test can identify slow-growing, commensal biofilm-forming, multiple-antibiotic resistant coagulase-negative staphylococci. These staphylococci differ significantly from non-pathogenic staphylococci and alter levels of MSH, C4a, and TGF-β1. CIRS patients with an ongoing colonization of multiple-antibiotic resistant coagulase-negative staphylococci may not show a significant improvement in their symptoms until the organism is eradicated. If detected, these infections may be treated using medications and treatment regimens known to those skilled in the art.

5. CD4+ CD25+ Treg Cells:

CD4+ CD25+ Treg cells in CIRS patients can be measured by flow cytometry. CD4+ CD25+ Treg cells mature in response to an inflammatory stimulation, and in particular, in response to increasing levels of TGF-β1. Matured CD4+ CD25+ Treg cells migrate to tissues to suppress inflammation and autoimmunity. However, if there is a pre-existing inflammatory response ongoing in tissues, CD4+ CD25+ Treg cells may turn into autoreactive T cells. Therefore, the determination of CD4+ CD25+ Treg cells in blood as well as in tissues may be helpful in assessing the status of inflammation in CIRS patients.

6. Brain Abnormalities:

It has been found that subjects with CIRS may exhibit brain abnormalities. Specifically, it has been found that subjects with CIRS may exhibit structural brain volumes abnormalities including, but not limited to, an increase in forebrain parenchyma, an increase in cortical gray area, an increase in the volume of the hippocampus, a decrease in the volume of caudate, and/or an increase in the volume of pallidum. These structural brain abnormalities have been identified, for example, in subjects suffering from CIRS-WDB. Accordingly, methods for diagnosing, treating, and monitoring CIRS may further include detecting one or more brain abnormalities using presently known or as-yet undeveloped techniques. Methods known in the art for detecting brain abnormalities may include, but are not limited to, CT scans, MRI scans, PET scans, brain volume measurement (i.e., FreeSurfer, Martinos Center for Biomedical Imaging, Charlestown, Mass.), and NeuroQuant® (CorTechs Labs, La Jolla, Calif.).

7. Genomic SVM Confidence>0.9:

The present invention uses gene expression microarrays and micro-RNA profiling to identify changes in expression profiles of genes, mRNAs, and/or micro-RNAs in subjects suspected of having CIRS compared to healthy subjects. The data obtained in whole genome microarray experiments and micro-RNA profiling experiments may be analyzed, for example, by using a Support Vector Machine (SVM) classification algorithm to predict whether a given sample is from a CIRS patient or a healthy individual. If the algorithm indicates that it has greater than 90% confidence (confidence>0.9) in its prediction, then the subject suspected of having CIRS is considered to be positive for this parameter.

7A. mRNA Markers:

In an embodiment, one or more of mRNA markers, listed in Appendices A, B and/or C, are differentially expressed between CIRS patients and healthy controls.

7B. Micro-RNA Markers:

In an embodiment, one or more of micro-RNA markers, provided in Appendix D, is differentially expressed between CIRS patients and healthy controls. Preferably, one or more of the subset of micro-RNA markers provided in Appendix E is differentially expressed in CIRS patients as compared to healthy controls.

In one embodiment, a physician's order sheet, such as the sample shown in Table 4, may be used to obtain case definition parameters described above.

TABLE 4

| Sample Physician's Order Sheet. | | | | |
|---|---|---|---|---|
| Test | Lab to Use | Spec | Code # | DX Codes |
| HLA DR by PCR | Lab Corp | Yellow, refrig | 012542 | 279.10, 377.34, 279.8 |
| VIP | Quest | Lav - freeze-Trasylol | 10397 | 279.8, 286.5, 710.0 |
| MSH | Lab Corp | Lav - freeze-Trasylol | 010421 | 253.2 |
| Leptin | Quest | SST-freeze | 84657N | 253.2 |
| ADH | Quest | SST refrig LAV freeze | 31260P | 253.5 |
| Osmo | Quest | SST - refrig | 677X | 253.5 |

TABLE 4-continued

Sample Physician's Order Sheet.

| Test | Lab to Use | Spec | Code # | DX Codes |
|---|---|---|---|---|
| ACTH | LabCorp | Lav - freeze | 004440 | 255.41 |
| Cortisol | Quest | SST refrig | 11281X | 255.41 |
| DHEAS | Quest | SST - freeze | 21915R | M 257.2 F 256.39 |
| Testosterone | Quest | SST - freeze | 29868W | M 257.2 F 256.39 |
| Androstenedione | Quest | SST - freeze | 17182X | M 607.84 F 256.39 |
| CRP | Lab Corp | SST - refrig | 006627 | 378.54 |
| ESR | Here | Lav | | — |
| TGF-B1 | Quest | Lav freeze | 99895 | platelet poor plasma |
| TGF-B1 | Lab Corp | Lav freeze | 905036 | platelet poor plasma |
| MMP-9 | Quest | SST- freeze | 41865 | 340 |
| PAI-1 | Lab Corp | Blue freeze | 146787 | 437.6 |
| Lipid with Phenotype | Lab Corp | SST - refrig | 033886 | 272.0 |
| CBC | Quest | Lav - refrig | 6399X | 285.0 |
| CMP | Quest | SST - refrig | 10231X | 780.79 |
| GGT | Quest | SST - refrig | 23242E | 250.00 |
| Nasal Culture | API-STAPH | Rm temp | DLM | 478.21 |
| VEGF | Quest | Lav - freeze | 14512X | 416.9, 253.2, 710.0 |
| Erythropoietin | Quest | Red - freeze | 22376R | 285.9 |
| Anticardiolipins | Quest | SST - refrig | 36333X | 710.0 |
| Antigliadin, IgA, IgG | Quest | SST - refrig | 3517N | 579.0 |
| B-Type Natriuretic Peptide | LabCorp | Plastic Tube Lav-Freeze | 140889 | 428.0 |
| C3a  RIA | Quest | Lav - freeze | 42003 | 279.8, 286.5 |
| C4a  RIA | Quest | Lav - freeze | 42658 | 279.8 |
| IgE | Quest | SST - refrig | 002170 | 493.01 |
| Lyme WB | Lab Corp | SST freeze | 163600 | 088.81 |
| TSH | Quest | SST - refrig | 30163E | 244.8 |
| von Willebrands profile | Quest | Blue freeze | 15540X | 279.8, 286.5 710.0 |
| Fe | Quest | SST-refrig | 24984R | 280.1 |
| IBC | Quest | SST-refrig | 7573X | 720.0 |
| Ferritin | Quest | SST-refrig | 457X | |
| HgB A1C | Quest | Lav-refrig | 496X | 250.00 |
| PAXgene | Research | whole blood | | Two aliquots |

In another embodiment, blood drawn from CIRS patients may be used to determine the levels of one or more protein markers, mRNA markers, and/or micro-RNA markers listed in Tables 3-4, Appendices A, B and/or C, and Appendix D, respectively. The testing of protein markers listed in Table 3 is preferably conducted at CLIA-approved facilities and handled according to the facility's standard operating protocol (SOP). In certain aspects of the invention, one of the tubes used for blood draw is a specialized tube, PAXgene™ Blood DNA tube (Qiagen, Venlo, Netherlands), for stabilizing RNA, and is processed according to a Proteogenomics, LLC SOP. Briefly, PAXgene™ tubes are incubated at room temperature for 5 hours and frozen until they are shipped overnight to a processing facility. The tubes may be processed using a Qiagen PAXgene™ RNA blood processing kit, preferably according to an FDA-approved manufacturer's protocol. Extracted RNA may be quantified, for example, using a UV-Visible spectrophotometer, and the quality of the extracted RNA may be analyzed, for example, using Agilent 2100 Bioanalyzer (Agilent Technologies, Inc., Santa Clara, Calif.).

The extracted RNA may be subjected to an nCounter digital gene expression detection assay (nanoString Technologies, Seattle, Wash.), for example, in order to concurrently measuring mRNAs and micro-RNAs to determine differential expression of genes in CIRS patients.

Once diagnosed, subjects having CIRS may be treated in accordance with the methods of the invention. Treatment may include removing the subject from the source of the agent (toxins, biotoxins, inflammagens, etc.) responsible for causing CIRS, and/or removing or reducing the agent or its metabolites or byproducts from the subject.

In accordance with the methods of the invention, treating CIRS in a subject who has been diagnosed as having CIRS may include administering cholestyramine and/or VIP to the subject. When cholestyramine is administered to the subject, dosage amounts and schedules are within the ability of the skilled practitioner to determine, and may be, for example, in the range of 1 to 40 grams per day, preferably 8 to 36 grams per day, more preferably 16 to 24 grams per day. The doses may be provided from 1 to 6 times per day, preferably 2 to 4 times per day. The doses of cholestyramine are preferably administered orally. When VIP (aviptadil) is administered to the subject, dosage amounts and schedules are within the ability of the skilled practitioner to determine, and may be, for example, in the range of 5 to 200 micrograms, preferably 10 to 100 micrograms, more preferably 25 to 75 micrograms. According to one embodiment, a dose of 50 micrograms is administered. The doses may be provided from 1 to 4 times per day, preferably 1 time per day. The doses of VIP may be administered nasally or injected, although nasal instillation is a preferred method of administration. Cholestyramine and/or VIP may be administered for any period of time necessary to achieve relief from CIRS. However, it should be noted that the present invention is not limited by the dosage amount, administration route, or length of administration.

Figure 2:
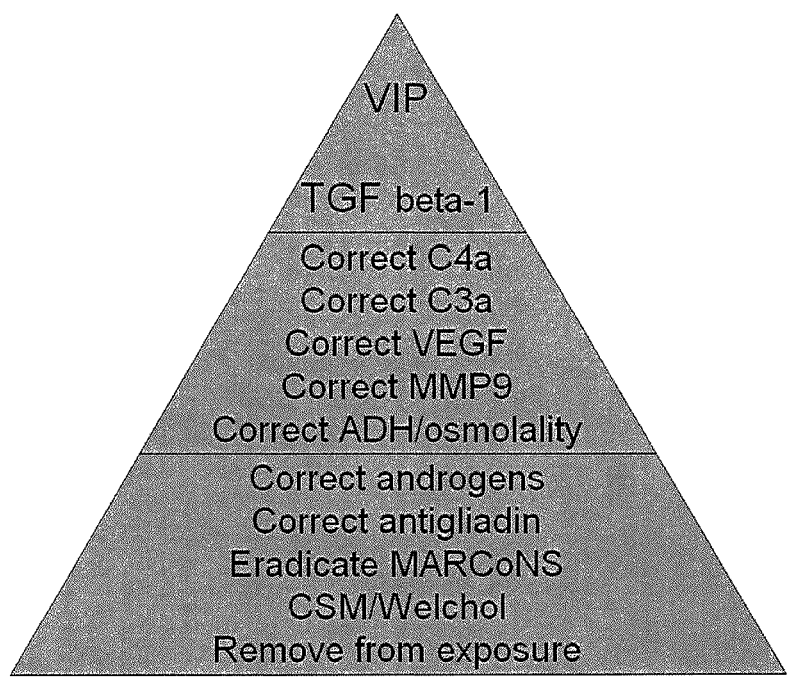
FIG. 2 shows a sequential therapeutic intervention for treating subjects with CIRS according to one embodiment of the invention.

The methods of treating CIRS in a subject may further include sequential therapeutic intervention, such as those shown in FIG. 2. According to this embodiment, a method of treating CIRS in a subject includes: administering a therapeutically effective dose of cholestyramine to the subject; treating the subject to eliminate MARCoNS infection if the subject has MARCoNS infection; correcting or restoring levels of antigliadin, androgens, ADH/osmolality, MMP9, VEGF, C3a, C4a, TGF-β1; and administering a therapeutically effective dose of VIP to the subject.

The treatment may be monitored in accordance with further methods of the invention in which testing of one or more of the parameters used to diagnose a subject with CIRS is repeated during the course of treatment, and compared with the results obtained for that parameter prior to treatment. Improvement in the selected parameter or parameters over time may be used as an indication that the treatment is effective.

The present invention is illustrated by the following examples, which are set forth to illustrate certain embodiments of the present invention and are not to be construed as limiting.

EXAMPLES

Example 1: Subjects, VCS Testing, Blood Analysis and Statistical Analysis

1A. Subjects: For all subjects, medical history was obtained concerning possible biotoxin exposure from dinoflagellates, fungi, actinomycetes, mycobacteria, endotoxin-producing bacteria, cyanobacteria, apicomplexans and spirochetes, as well as undiagnosed neurologic disease, alcoholism, occupational exposure to solvents, petroleum products, known neurotoxicants and metal fumes. Symptoms roster and VCS testing was used to determine whether or not a cause of illness other than WDB-CIRS or ciguatera could be identified. Differential diagnosis was performed. Subjects were included as patients with CIRS (n>1650) if they were considered to have symptoms that persisted beyond three months, had a non-exclusionary differential diagnosis and had abnormalities in laboratory parameters listed in Table 4. Patients coming to the clinic for well-physicals as well as volunteers were included as controls (n>150) if they had (i) no illness of any kind requiring acute intervention during the office visit; (ii) no history of acute multi-system, multi-symptom illness following exposure to environmentally produced biotoxins as described above; (iii) any untreated chronic illness. Patients meeting inclusion criteria received a physical examination and blood analyses. Pregnant or nursing patients were excluded from study participation. All participants signed a HIPAA waiver permitting use of their clinical data. Internal review board's (IRB) approval for retrospective analysis was obtained from the Copernicus Group IRB, Cary, N.C. Participants were not remunerated for study participation.

1B. VCS testing: Visual contrast sensitivity (VCS) testing measures the eye's ability to resolve patterns and was performed by an experienced physician using a previously published protocol (R. C. Shoemaker, Residential and recreational acquisition of possible estuary-associated syndrome: a new approach to successful diagnosis and treatment, Environmental Health Perspectives 109 Suppl 5 (2001) 791-6). Visual acuity and VCS testing were administered monocularly, with patients wearing any necessary corrective lenses, under a "daylight" illuminator (exceeding 70 foot lamberts) in a clinical unit with normal background lighting. A test card holder was used to position the acuity and VCS test cards at a constant, standardized distance (acuity—36 cm, contrast sensitivity—46 cm).

Visual acuity using Snellen score (e.g. 20/20) was determined for each eye using the acuity test card (MIS Pocket Vision Guide, ©1997 MIS, Inc.). To avoid inaccurate VCS results, a visual acuity of 20:50 or better was required for each eye to be included in analysis. All participants had at least one eye included in analysis. Two-tailed Student t-tests were performed, using the mean score±S.E.M. of each participant's two eyes, to determine if acuity scores differed significantly ($p \leq 0.05$) between cohorts.

The contrast sensitivity test card (Functional Acuity Contrast Test, (FACT), Stereo Optical Co., Chicago, Ill.) contained a matrix (5×9) of circles filled with sinusoidal gratings (dark and light bars) with spatial frequencies of 1.5, 3, 6, 12 and 18 cycles/degree of visual arc. The grating bars were oriented either vertically, or tilted 15 degrees to the left or right. Subjects identified the orientation of the grating by saying either: vertical, left, right or blank. The contrast sensitivity score for each row (spatial frequency) was recorded as the contrast of the last circle correctly identified on that row following verification by repeated testing of that circle. The procedure was repeated for each row in descending order. The units of analysis for the VCS test were the mean scores±S.E.M. of the participant's two eyes at each spatial frequency.

It was found that using a combination of symptoms roster, VCS test results, and results of laboratory parameters listed in Table 4, 98.2% patients were accurately diagnosed as having CIRS (Table 5). The statistical significance of the rate of accuracy in case detection is shown in Table 6.

TABLE 5

|  | Predicted Controls | Predicted Cases | Row Total |
|---|---|---|---|
| Observed Controls | 37 | 2 | 39 |
| Observed Cases | 3 | 243 | 246 |
| Column Total | 40 | 245 | 285 |
| Percent Agreement |  |  | 98.2 |

Agreement Odds: 280/285
Standard Deviation: 0.78%
95% confidence interval:
(96.72%, 96.72%) or (1 to 9 disparities)

TABLE 6

| Test of Agreement | | |
|---|---|---|
| Test | Chi-sq | P-value |
| Likelihood | 183.01 | <.0001 |
| Pearson | 244.71 | <.0001 |

1C. Blood tests: Laboratory measurements were performed by CLIA licensed facilities, LabCorp, Quest Diagnostics, National Jewish Center, Cambridge Biomedical, and Diagnostic Laboratory Medicine. Testing included HLA-DR by PCR, alpha melanocyte stimulating hormone (MSH), vasoactive intestinal peptide (VIP), leptin, matrix metalloproteinase 9 (MMP9), split product of complement component 3 (C3a) and component 4 (C4a), transforming growth factor beta-1 (TGF-β1), IgG for gliadin (AGA), and IgM for cardiolipin (ACLA), vascular endothelial growth factor (VEGF), plasminogen activator inhibitor (PAI-1), cortisol, erythrocyte sedimentation rate, C reactive protein (CRP), lipid profile, complete blood count (CBC), comprehensive metabolic panel (CMP), gamma-glutamyl transpeptidase (GGTP), thyroid stimulating hormone (TSH), lipid profile, and von Willebrand's profile.

Patients were classified abnormal for von Willebrand's antigen if the values were less than 50 IU or greater than 150 IU. Dysregulation of simultaneously measured ACTH/cortisol and ADH/osmolality was determined by adding (i) the number of cases with absolute high (ACTH>45 or cortisol>21; ADH>13 or osmolality>300) or low (ACTH<5 or cortisol<4; ADH<1.3 or osmolality<275) values for the two paired tests; to the cases (ii) in which ACTH was below 10 when cortisol was below 7; or ADH was below 2.2 when osmolality was 292-300; to the cases (iii) in which ACTH was >15 when cortisol was >16; and ADH>4.0 when osmolality was 275-278. The results of prior in-house analysis showed that such dysregulation was highly associated with low MSH and was essentially not found in normal-MSH patients.

1D. Statistical analysis of symptoms, results of blood test and VCS testing: To determine the most accurate indicators of illness, we tested 37 symptoms and 22 blood parameters measured in this study for a total of 59 variables not including VCS. Because of the presence of multiple variables, the Bonferroni correction was applied to symptom and blood variables which resulted in a single variable p-value being considered statistically significant if $p<0.001$ (0.05/59 rounded) in order to have an experiment wise $p<0.05$. The units of analysis for the VCS test were the mean scores of the participant's two eyes at each spatial frequency. The VCS data were analyzed using multivariate analyses of variance (MANOVA, with the Wilks' lambda statistic) procedures suitable for repeated measures with an $\alpha=0.05$. The factors in this model were group, spatial frequency, age and their interaction terms. A factor for gender was not included as no gender differences in VCS have been reported. Results further showed that a significant group-by-spatial-frequency interaction were further analyzed in step down, two-tailed Student's t-tests ($\alpha=0.05$), the equivalent of a univariate ANOVA, to determine which spatial frequencies accounted for the overall effect.

Symptoms:

The prevalence of each symptom in the illness and control groups was compared for statistical significance ($p<0.001$) using Fisher's exact test.

Blood Testing Parameters:

For each blood parameter, the difference between the two groups was tested for statistical significance ($p<0.001$) using the two-tailed two-sample Student t-test.

VCS:

The VCS data were analyzed using multivariate analyses of variance procedures suitable for repeated measures. The factors in the model were group, spatial frequency, and their interaction. A significant ($p<0.05$) overall group by spatial frequency interaction was further analyzed by a two-tailed Student t-test at each spatial frequency to determine which frequencies accounted for the effect.

HLA Haplotype Relative Risk:

Differences in relative risk were assessed using incidence in cases to incidence in an established control population. Results were considered significant if the ratio exceeded 2.0. Such relative risk ratios were observed in the following HLA-DR types: 4-3-53, 7-2/3-53, 11-3-52B, 12-3-52B, 13-6-52ABC, 17-2-52A.

Example 2: RNA Collection, Microarray Testing for mRNA and Micro-RNA Markers, and Statistical Analysis of Microarray Data 2A. RNA collection: Blood samples were collected from willing participants after written consent using PAXgene tubes under manufacturers recommended protocol (Qiagen, Valencia, Calif.). The patient samples were all drawn at the Center for Research on Biotoxin Associated Illness (CRBAI, Pocomoke Md.). Illness status was determined using a combination of medical history, physical findings, VCS testing, pulmonary functions, laboratory findings and response to clinical treatment to avoid possible mis-diagnosis. Reference samples from 80 healthy subjects were drawn at 3 separate locations, CRBAI, Washington D.C. metro area, and Charleston, S.C. All samples were first incubated at room temperature, as recommended by manufacturer, and then frozen at −40 or −80° C. for storage. All blood samples were extracted according to manufacturer's protocol. Total RNA was quantified by UV-Visible spectroscopy and the quality was assessed using Agilent 2100 Bioanalyzer. Only samples with a RIN score of 7.5 or better were used for analysis.

Of the 280 blood samples collected, 200 were chosen for analysis due to quality and quantity of RNA or age and gender to balance the study. Of these 200 samples, 60 samples were considered clinically healthy since their participation was not based on seeking medical attention and their presentation was not that of any illness. RNA from blood was extracted using the PAXGene Blood RNA Kit according to manufacturer (Qiagen, Valencia, Calif.). RNA was then quantified using a NanoDrop N. Dak.-1000 (Wilmington, Del.), qualified on an Agilent 2100 Bioanalyzer (Foster City, Calif.) and stored at −80° C. until needed for gene expression profiling.

2B. Microarray labeling and hybridization: All RNA labeling and microarray hybridizations were performed according to the manufacturer's instructions in the Agilent One-Color Microarray-Based Gene Expression Analysis manual (Agilent Technologies, Santa Clara, Calif.) with one exception. The amount of recommended labeled material for hybridization is 1.65 micrograms, this study used 2.45 micrograms. This amount of material was rigorously tested and found to give highly reproducible results before adopting the experimental protocol described here. Total RNA was amplified and labeled with Cy3 labeled CTP with the Agilent Quick Amp labeling kit (Agilent Technologies, Santa Clara, Calif.). The amplification product was measured for quantity and dye incorporation using the NanoDrop 1000. 2.45 micrograms of amplified, fluorescently labeled RNA was hybridized to an Agilent human whole genome microarray at and incubated at 65° C. in a rotating oven. After 17 hours, the hybridization arrays were washed consecutively in solutions of 6×SSPE with 0.005% N-lauroylsarcosine and 0.06×SSPE with 0.005% N-lauroylsarcosine for 1 min each at room temperature. This was followed by a final 15 sec wash in acetonitrile.

2C. Microarray Data Analysis: Microarrays were imaged on an Agilent microarray scanner, extracted with Agilent Feature Extraction software version A8.5.3, and data analyzed with both Rosetta Resolver 7.0 gene expression analysis system (Rosetta Informatics, Seattle, Wash.) as well as GeneSpring 11.5.1 (Agilent Technologies, Santa Clara, Calif.).

One color gene expression arrays were normalized by removing control and flagged data, applying a trimming function to remove the top and bottom 5% of intensity data, then scaling to the mean intensity. Samples, cases, and controls were segregated by sex. The arrays from each treatment/gender group (Patient and Control and Male and Female) were then combined and feature intensities underwent averaging and ratios were built between patient and control groups. These ratio data were initially filtered using a $p<0.05$ cutoff and 1.3 fold change to feed into an SVM classification algorithm. This gene set was then used for unsupervised clustering using K-means with both Euclidean and Pearson metrics, and principal component analysis using z-score values.

2D. Micro RNA Data Analysis: Micro RNA populations from the same total RNA samples used for gene expression microarrays were elucidated using the nCounter® Human v1 miRNA Expression Assay Kit, with two probes, mir191 and mir451 removed because of signal saturation. The assays were run according to manufacturer's recommendations and read on the nCounter array reader. Micro RNA data was imported into GeneSpring v12 as single color generic assays. The data were normalized with a 75 percentile shift and using the median of all samples as baseline.

Samples, cases and controls, were segregated and underwent class prediction using a support vector machine classification algorithm. The results obtained using an SVM to stratify patients and controls are shown in Appendix F. As shown in Appendix F, the total successful prediction rate was approximately 90% using an n-fold validation. Subjects were segregated by gender before classification was attempted.

Example 3: Treatment of CIRS Subjects with VIP

3A. Treatment: Human research approval for this study was provided by Copernicus Group IRB, Cary, N.C. After providing informed consent, 20 patients (11 Caucasian females, mean age 51.1; and 9 Caucasian males, mean age 48.2) with clinically-confirmed CIRS-WDB refractory to all prior treatment modalities (steps 1-10 (removal from exposure to correcting C4a), as described in FIG. 2) were enrolled in this trial. Specifically, prior to the treatment with VIP, patients were treated sequentially in 30-day steps by 1) removal from exposure; 2) treatment with cholestyramine for at least one month and ongoing; 3) eradication biofilm-forming coagulase negative staphylococci; 4) discontinuance of consumption of gluten if they had a positive anti-gliadin antibody titer (three months minimum required); 5) correction of abnormalities in androgens; 6) correction of abnormalities in regulation of salt and water with synthetic desmopressin as shown by simultaneous ADH and osmolality; 7) normalizing MMP9 with pioglitazone 45 mg daily; 8) normalizing VEGF with high dose omega-3 fish oils (4.2 grams daily); 9) correction of C3a with high dose statins; 10) attempting to correct C4a with erythropoietin but only if entry criteria met; 11) attempting to correct TGF beta-1 with losartan 25 mg daily, monitoring blood pressure carefully. Further, certain patients were excluded from the trial for the following reason. Specifically, initial use of low dose VIP by nasal instillation was shown to be safe in human volunteers; its use provided prompt reduction in symptoms and blunted accentuated pulmonary artery responses to exercise. However, benefit of replacement VIP in earlier trials was not observed to be universal. Specifically, the presence of any one of the following three parameters was associated with reduced efficacy: 1) depressed visual contrast sensitivity (VCS); 2) measurement of fungal DNA in settled dust using QPCR that resulted in an Environmental Relative Mold Index (ERMI)>2; and 3) presence of multiply antibiotic resistant biofilm-forming coagulase negative staphylococci (MAR-CoNS) in deep nasal aerobic spaces. Patients with these findings were excluded from the formal replacement trial.

All patients enrolled in the trial were confirmed to be exposed to WDB by observation of illness acquisition solely following water intrusion followed by either (1) visible microbial growth; (2) specification of molds by QPCR DNA testing; or (3) musty smells. All patients met the case criteria established by the GAO (US GAO 2008). Patients were known to the clinic with a 36-month mean duration of prior treatment following exposure to WDB. No patients had been treated with VIP previously.

Entry criteria also included a rise in pulmonary artery systolic pressure (PASP) in exercise as measured by stress echocardiography that exceeded 8 mm Hg as compared to resting PASP. Standard Bruce protocols were employed during stress echocardiography testing. Target heart rate of 85% of maximum was obtained after baseline recording showed no evidence of PASP greater than 30 mm Hg or left ventricular ejection fraction of less than 50%. All patients achieved target heart rate; none developed ischemic changes on EKG or chest pain during stress testing. Each had a repeat measurement of the tricuspid regurgitation jet (TR) immediately after exercise with recordings of TR performed within 30 seconds of cessation of exercise.

For the experimental protocol, subjects self-administered 50 mcg VIP (Aviptadil; Bachem AG, Switzerland) four times a day via nasal aerosol and returned to the clinic to review symptoms and clinical course, and undergo interval physical exam and laboratory exam at scheduled intervals. Clinical data were collected before any treatments, or baseline (BASE); after all other treatments and before VIP (AC2); after 12 months of VIP (12M); and after 18 months of VIP (18M). Data collection included physician recorded symptoms in a medical history (Table 2); levels of VIP, MSH, C4a, TGF beta-1, VEGF, MMP9, estradiol, testosterone, 25-0H vitamin D, lipase, CBC and CMP. Measurement of CD4+CD25+T regulatory (Treg) cells was not available at BASE; Treg testing was performed at AC2 and 18 month time periods. Laboratory testing for all analytes was performed by high complexity CLIA-certified labs including LabCorp and Quest Diagnostics. All data were compared to either established normative values or values from prior testing of healthy control populations (N=850) performed at this clinic. Data were analyzed by two-sample T-tests for each of two study time points and one-sample T-tests that compared the specified data to the corresponding historical control values. A Bonferroni correction to the p-values was done to control the experiment-wise error rate. A p value of <0.001 was chosen as the determinant of significance for the study.

Figure 3:
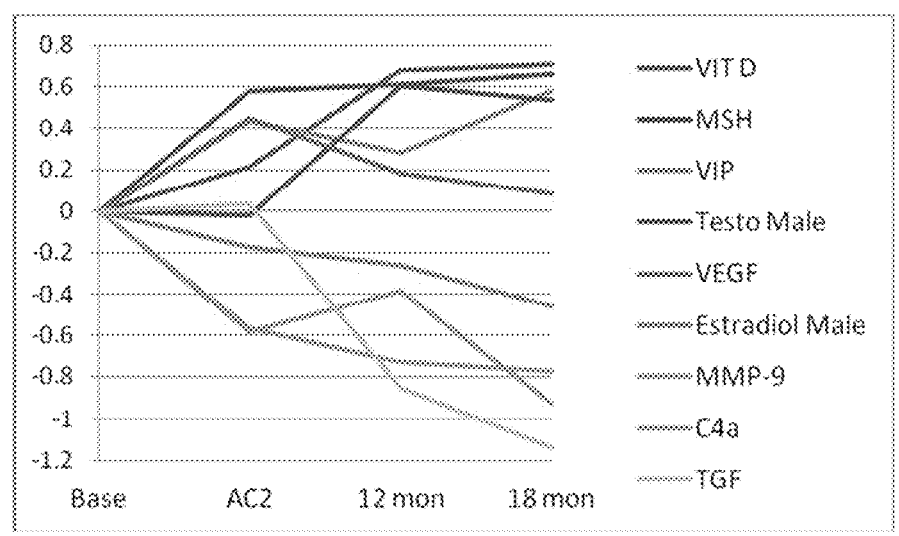
FIG. 3 shows mean values of various laboratory parameters with significant differences between baseline and controls.

3B. Results: Patients tolerated the drug well and there were no dropouts due to adverse effects over the course of the 18 month study. Use of replacement doses of the regulatory neuropeptide VIP in a nasal spray (i) safely reduced refractory symptoms to control levels; (ii) corrected inflammatory parameters to be not significantly different from controls; (iii) raised levels of VIP and MSH; (iv) returned PASP during exercise to normal; and (v) enhanced quality of life in 20 patients in an open-label trial. Follow-up as long as 18 months after initiation of the study showed durable salutary responses without significant adverse effects. Elevated PASP in stress exercise testing was reduced to <8 mm Hg in all subjects within two months. Symptom reduction to equal those of controls occurred in all treated patients. Laboratory results showed a marked improvement over both baseline values and following all previously employed therapies (Table 7 and FIG. 3) although MSH and VIP continued to be significantly depressed compared to controls. In FIG. 3, values from Table 7 were log transformed and normalized to baseline.

TABLE 7

| LAB | Control | Base | AC2 | 12 mon | 18 mon |
|---|---|---|---|---|---|
| SX | 2.9 | 29.8 | 17.8 | 5.5 | 3.4 |
| VIP | 28.9 | 9.3 | 14.4 | 12.3 | 16.6 |
| MSH | 37.2 | 9.4 | 16.8 | 17.3 | 18.2 |
| C4a | 2830 | 8346 | 4662 | 5679 | 3306 |
| TGF | 2380 | 12579 | 13015 | 5359 | 4040 |
| VEGF | 65 | 61 | 95.3 | 73.4 | 66.2 |
| MMP-9 | 332 | 628 | 358 | 302 | 290 |
| Estra-F | 29.8 | 28 | 26.6 | 27.8 | 28.9 |

TABLE 7-continued

| LAB | Control | Base | AC2 | 12 mon | 18 mon |
|---|---|---|---|---|---|
| Estra-M | 23.1 | 36 | 30.3 | 27.7 | 22.8 |
| Test-F | 282 | 20 | 18.9 | 22.6 | 25.2 |
| Test-M | 415 | 298.8 | 293.5 | 546.7 | 511.5 |
| VIT D | 38.4 | 19.4 | 24.1 | 38.3 | 39.3 |
| Lipase | 30.1 | 24.2 | 30.8 | 30.7 | 27.9 |

Symptoms and laboratory parameters mean values for patients and controls. Sx = symptoms, Estra-F = estradiol in females, Estra-M = estradiol in males, Test-F = testosterone in females, Test-M = testosterone in males.

Cases were similar at baseline to known cases of CIRS-WDB in large cohorts previously published (Shoemaker et al. "Innate immunity, MR spectroscopy, HLA DR, TGF beta-1, VIP and capillary hypoperfusion define acute and chronic human illness acquired following exposure to water-damaged buildings," Healthy Buildings, Syracuse, N.Y., 2009; and Shoemaker "Exposure to water-damaged buildings causes a readily identifiable chronic inflammatory response syndrome that is successfully treated by a sequential intervention protocol," 9th International Mycology Congress, Edinburgh, Scotland, August 2010) with excessive numbers of symptoms in cases compared to controls and multiple laboratory abnormalities (Tables 8 and 9) in cases compared to controls. This cohort may be affected by an innate immune inflammatory process with nearly 23 health symptoms at baseline; marked reduction in VIP and MSH; significant elevation of C4a, MMP9 and TGF beta-1; evidence of increased activity of aromatase with reduction of testosterone and elevated estradiol in males but not females; and reduced Vitamin D3 levels. Lipase levels did not rise in this cohort during the trial.

TABLE 8

| | 2007 Control N | Mean | Case N | Mean | P value | 2009 Control N | Mean | Case N | Mean | P value |
|---|---|---|---|---|---|---|---|---|---|---|
| Age | 37 | 51.1 | 202 | 46.1 | 0.027 | 132 | 50.3 | 815 | | |
| Symptoms | 37 | 2.5 | 202 | 22.9 | <0.0001 | 132 | 2.9 | 815 | 22.6 | <.001 |
| VIP | | | | | | 132 | 36.6 | 815 | 12.8 | <.001 |
| MSH | 37 | 34.7 | 201 | 14.1 | <0.0001 | 132 | 41.2 | 815 | 13.1 | <.001 |
| Leptin | 36 | 14.5 | 197 | 27.9 | 0.546 | 132 | 17.9 | 815 | | |
| ADH | 34 | 3.9 | 192 | 3.3 | 0.709 | 132 | 3.7 | 815 | | |
| Osmo | 34 | 238 | 200 | 298 | <0.0001 | 132 | 288 | 815 | | |
| ADH/osmo | | | | | | 132 | 5 | 815 | 69 | <.001 |
| ACTH | 35 | 23.2 | 200 | 15.8 | 0.084 | 132 | 22 | 815 | | |
| Cortisol | 36 | 16.8 | 201 | 15.4 | 0.811 | 132 | 21.7 | 815 | | >.5 |
| ACTH/cortisol | | | | | | 132 | 3 | 815 | 58 | <.001 |
| MMP-9 | 37 | 284 | 201 | 376 | 0.04 | 132 | 269 | 815 | 419 | <.001 |
| PAI-1 | 37 | 6.63 | 182 | 5.72 | 0.561 | 132 | 6.3 | 815 | 21 | <.001 |
| VEGF | 30 | 67.2 | 198 | 64.7 | 0.888 | 132 | 67.9 | 815 | | |
| C3A | 24 | 242 | 185 | 929 | 0.24 | 132 | 253 | 815 | | |
| C4A | 22 | 1852 | 190 | 8818 | <0.001 | 132 | 2303 | 815 | 9924 | <.001 |
| TGF Beta-1 | | | | | | 132 | 2365 | 815 | 4602 | <.001 |
| GGTP | | | | | | 132 | 16 | 815 | | <.5 |
| CRP | 35 | 2.6 | 187 | 5.12 | 2.4 | 132 | 2.4 | 815 | 1.9 | 0.424 |
| ESR | 37 | 0.08 | 187 | 27.9 | <0.0001 | 132 | 9 | 815 | | >.5 |
| IgE | 36 | 49 | 191 | 82.5 | 0.732 | 132 | 34 | 815 | | >.5 |
| CBC | | | | | | 132 | nl | 815 | 5 | 0.999 |
| CMP | | | | | | 132 | nl | 815 | 5 | 0.999 |
| Lipids | | | | | | 132 | nl | 815 | | >.5 |
| VwF | | | | | | 132 | 2 | 815 | 71 | <.001 |
| ACLA | | | | | | 132 | 7 | 815 | 23 | <.001 |
| AGA | | | | | | | 8 | 815 | 17 | <.001 |
| HLA DR RR >2 | 6 | | | | | | 0 | 815 | | |
| 4-3-53 | 1 | | | | | | 0 | | | |
| 7-2-53 | 1 | | | | | | 0 | | | |
| 11-3-52B | 1 | | | | | | 0 | | | |
| 13-6-52A | 1 | | | | | | 0 | | | |
| 14-5-52B | 1 | | | | | | 0 | | | |
| 17-2-52A | 1 | | | | | | 0 | | | |

TABLE 9

| | 2010 Control N | Mean | Case N | Mean | P value |
|---|---|---|---|---|---|
| Age | 132 | 50.3 | 812 | 47.8 | 0.0378 |
| Symptoms | 132 | 2.9 | 812 | 22.7 | <.0001 |
| VIP | 132 | 36.6 | 812 | 12.8 | <.0001 |
| MSH | 132 | 41.2 | 799 | 13.1 | <.0001 |
| Leptin | 132 | 17.9 | 697 | 19.4 | 0.816 |
| ADH | 132 | 3.7 | 692 | 3.1 | 0.544 |
| Osmo | 132 | 288 | 709 | 302 | <.0001 |
| ADH/osmo | 132 | | | | |
| ACTH | 132 | 22 | 687 | 16.8 | 0.0007 |
| Cortisol | 132 | 21.7 | 689 | 13 | 0.0009 |
| ACTH/cortisol | 132 | | | | |
| MMP-9 | 132 | 269 | 812 | 420 | <.0001 |
| PAI-1 | 132 | 6.3 | 636 | 7 | 0.6605 |
| VEGF | 132 | 67.9 | 656 | 62.2 | 0.4084 |
| C3A | 132 | 253 | 808 | 427 | <.0001 |
| C4A | 132 | 2303 | 812 | 9661 | <.0001 |
| TGF Beta-1 | 132 | 2365 | 812 | 6412 | <.0001 |

TABLE 9-continued

|  | 2010 Control N | Mean | Case N | Mean | P value |
|---|---|---|---|---|---|
| GGTP | 132 | 16 | 788 | 21 | Not signif |
| CRP | 132 | 1.2 | 812 | 1.8 | Not signif |
| ESR | 132 | 9 | 792 | 6 | Not signif |
| IgE | 132 | 34 | 802 | 39 | Not signif |
| CBC | 132 | nl | 812 | nl | Not signif |
| CMP | 132 | nl | 812 | nl | Not signif |
| Lipids | 132 | nl | 812 | IV* |  |
| VwF | 132 | 5 | 704 | 67 |  |
| ACLA | 132 | 1 | 812 | 24 |  |
| AGA |  | 2 | 812 | 32 |  |
| HLA DR RR > 2 |  | 0 | 812 | 6 |  |
| 4-3-53 |  | 0 |  | 1 |  |
| 7-2-53 |  | 0 |  | 1 |  |
| 11-3-526 |  | 0 |  | 1 |  |
| 13-6-52A |  | 0 |  | 1 |  |
| 14-5-52B |  | 0 |  | 1 |  |
| 17-2-52A |  | 0 |  | 1 |  |

While significant differences (p<0.01) were identified between controls and baseline lab values in patients for symptoms, MSH, VIP, MMP9, C4a, TGF-β1, 25-OH Vitamin D, and testosterone (in males), by the end of the trial patient values were not statistically different from controls, except for VIP and MSH. Flow cytometry showed a significant increase of CD4+CD25+ Treg cells from a mean of 8.9 to 22.5. No changes in CBC and CMP were noted. One patient had a transient elevated level of lipase without abdominal pain that resolved without cessation of use of VIP. After six months patients titrated use of VIP to these symptoms with verification of benefit obtained by clinical exam and blood testing at three month intervals. Eight patients consistently used VIP at three or four times a day; four patients used VIP once or twice a day. Three patients used VIP before strenuous activity only; five patients stopped using VIP at various points during the trial as they had correction of symptoms and no evidence of relapse without protocol medications. For these patients, only data while using VIP was collected for statistical calculation.

This study confirms the hypotheses that the use of VIP in VIP-deficient patients is both durably safe and effective for up to 18 months. When used by nasal instillation, VIP is well-tolerated, has few side effects and is unlikely to result in an over-dosage. Treatment with VIP restored clinical functioning in a cohort of CIRS-WDB patients with severe illness characterized by profound, refractory abnormalities in innate immune inflammatory responses (see BASE on Table 7). Symptom improvement was remarkable, including correction of chronic fatigue, shortness of breath and asthma-like conditions, executive cognitive deficits, neurologic symptoms and chronic joint pain. The known effects of VIP in the normalization of Treg levels and controlling cytokine responses were also confirmed by this study. Use of VIP corrected abnormal PASP responses during exercise; reduced total number of symptoms to equal controls; and down-regulated inflammatory responses as measured by MMP9, TGF beta-1 and C4a levels, with positive effects occurring over time. The benefit of restoration of androgen levels to equal control levels suggests a down-regulating effect of VIP on the enzyme aromatase. The normalization of Vitamin D3 levels was unexpected, suggesting additional but as yet undefined upstream aspects of VIP as a pluripotent immunoregulatory hormone.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

APPENDIX A

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_33_P3270084 | 0.00612545 | 1.3278185 | down | -0.16680224 | 0.2422558 | | "CDC2L1S13 PITSLRE protein kinase alpha SV9 isoform {Homo sapiens} (exp = -1; wgp = 0; cg = 0), partial (38%) [THC2524986]" | |
| A_33_P3323607 | 0.093110725 | 1.3602716 | up | 0.49521056 | 0.05131583 | CCDC129 | "coiled-coil domain containing 129 [Source: HGNC Symbol; Acc: 27363] [ENST00000409717]" | ENST00000409717 |
| A_33_P3223397 | 0.05119932 | 1.4744513 | up | 0.67229843 | 0.1121203 | | "DHH_HUMAN (O43323) Desert hedgehog protein precursor (DHH) (HHG-3) [Contains: Desert hedgehog protein N-product; Desert hedgehog protein C-product], partial (19%) [THC2641433]" | THC2641433 |
| A_33_P3267118 | 0.001896308 | 1.5818226 | down | -0.18506314 | 0.47652474 | EIF4G3 | "eukaryotic translation initiation factor 4 gamma, 3 [Source: HGNC Symbol; Acc: 3298] [ENST00000374933]" | ENST00000374933 |
| A_33_P3741678 | 0.07977711 | 1.4179299 | up | 0.55385005 | 0.050063804 | LOC284926 | "full-length cDNA clone CS0DB004YM09 of Neuroblastoma Cot 10-normalized of Homo sapiens (human). [CR624447]" | CR624447 |
| A_33_P3353921 | 0.01310896 | 1.355142 | down | -0.3329265 | 0.105517514 | GNLY | "granulysin [Source: HGNC Symbol; Acc: 4414] [ENST00000489214] HCG198685 [Source: UniProtKB/TrEMBL; Acc: Q8TCB4] [ENST00000309874]" | AK310057 |
| A_32_P170397 | 0.002955175 | 1.3198497 | down | -0.21135516 | 0.18901852 | | | AK057625 |
| A_33_P3245489 | 0.07131087 | 1.4297409 | up | 0.5176838 | 0.001930128 | ADAMTSL5 | "Homo sapiens ADAMTS-like 5 (ADAMTSL5), mRNA [NM_213604]" | NM_213604 |
| A_33_P3396010 | 5.68E-04 | 1.3479198 | down | -0.06803578 | 0.36269885 | AGER | "Homo sapiens advanced glycosylation end product-specific receptor (AGER), transcript variant 9, mRNA [NM_001206966]" | NM_001206966 |
| A_24_P419087 | 0.016834442 | 1.3516667 | down | -0.08188986 | 0.3528496 | AVIL | "Homo sapiens advillin (AVIL), mRNA [NM_006576]" | NM_006576 |
| A_23_P157299 | 2.52E-04 | 1.4233145 | down | -0.3408891 | 0.16836533 | AEBP1 | "Homo sapiens AE binding protein 1 (AEBP1), mRNA [NM_001129]" | NM_001129 |
| A_23_P138541 | 0.009355155 | 1.3682036 | down | -0.39919707 | 0.0530859 | AKR1C3 | "Homo sapiens aldo-keto reductase family 1, member C3 (3-alpha hydroxysteroid dehydrogenase, type II) (AKR1C3), mRNA [NM_003739]" | NM_003739 |
| A_33_P3239854 | 0.0542805 | 1.3841722 | up | 0.42232788 | -0.046695653 | ALKBH5 | "Homo sapiens alkB, alkylation repair homolog 5 (E. coli) (ALKBH5), mRNA [NM_017758]" | NM_017758 |
| A_33_P3213288 | 0.079706766 | 1.3334428 | up | 0.41348496 | -0.001670848 | AIF1 | "Homo sapiens allograft inflammatory factor 1 (AIF1), transcript variant 2, mRNA [NM_004847]" | NM_004847 |
| A_33_P3245454 | 0.062027268 | 1.3335233 | up | 0.24097094 | -0.17427202 | LOC389834 | "Homo sapiens ankyrin repeat domain 57 pseudogene (LOC389834), non-coding RNA [NR_027420]" | NR_027420 |
| A_32_P148345 | 0.021261923 | 1.4266403 | up | 0.19728537 | -0.31533623 | ANXA2 | "Homo sapiens annexin A2 (ANXA2), transcript variant 2, mRNA [NM_001002857]" | NM_001002857 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_23_P55373 | 0.035340752 | 1.4090601 | up | 0.25950173 | -0.2352314 | ALOX15 | "Homo sapiens arachidonate 15-lipoxygenase (ALOX15), mRNA [NM_001140]" | NM_001140 |
| A_23_P146325 | 0.001061829 | 1.5097016 | down | -0.23241776 | 0.36184567 | ASAP1-IT1 | "Homo sapiens ASAP1 intronic transcript 1 (non-protein coding) (ASAP1-IT1), non-coding RNA [NR_002765]" | NR_002765 |
| A_33_P3320782 | 0.077936664 | 1.4928937 | up | 0.81035405 | 0.23224276 | ATXN7 | "Homo sapiens ataxin 7 (ATXN7), transcript variant SCA7a, mRNA [NM_000333]" | NM_000333 |
| A_23_P98686 | 8.34E-04 | 1.3329782 | down | -0.19140579 | 0.22324742 | ATHL1 | "Homo sapiens ATH1, acid trehalase-like 1 (yeast) (ATHL1), mRNA [NM_025092]" | NM_025092 |
| A_33_P3372563 | 0.09315603 | 1.323163 | up | 0.6748213 | 0.27083063 | ABCC10 | "Homo sapiens ATP-binding cassette, sub-family C (CFTR/MRP), member 10 (ABCC10), transcript variant MRP7A, mRNA [NM_033450]" | NM_033450 |
| A_23_P254797 | 0.086991735 | 1.5577642 | up | 0.63674116 | -0.002735821 | BPIL1 | "Homo sapiens bactericidal/permeability-increasing protein-like 1 (BPIL1), mRNA [NM_025227]" | NM_025227 |
| A_23_P379034 | 1.32E-06 | 1.3577511 | down | -0.16047189 | 0.28074712 | BAIAP2L2 | "Homo sapiens BAI1-associated protein 2-like 2 (BAIAP2L2), mRNA [NM_025045]" | NM_025045 |
| A_23_P370682 | 0.032763295 | 1.3114529 | down | -0.21279402 | 0.17837192 | BATF2 | "Homo sapiens basic leucine zipper transcription factor, ATF-like 2 (BATF2), mRNA [NM_138456]" | NM_138456 |
| A_23_P71946 | 4.27E-04 | 1.420993 | down | -0.34374356 | 0.16315591 | BSPRY | "Homo sapiens B-box and SPRY domain containing (BSPRY), mRNA [NM_017688]" | NM_017688 |
| A_33_P3373775 | 0.084006816 | 1.3487155 | up | 0.53638214 | 0.10479598 | BCL2L15 | "Homo sapiens BCL2-like 15 (BCL2L15), mRNA [NM_001010922]" | NM_001010922 |
| A_23_P1833 | 0.026519855 | 1.4303471 | down | -0.52439135 | -0.00802621 | B3GAT1 | "Homo sapiens beta-1,3-glucuronyltransferase 1 (glucuronosyltransferase P) (B3GAT1), transcript variant 2, mRNA [NM_054025]" | NM_054025 |
| A_23_P158297 | 2.52E-05 | 1.677964 | down | 7.7513523 | 8.498064 | BTNL3 | "Homo sapiens butyrophilin-like 3 (BTNL3), mRNA [NM_197975]" | NM_197975 |
| A_23_P501933 | 0.019021226 | 1.4456453 | up | 0.4912875 | -0.04042622 | CACNG6 | "Homo sapiens calcium channel, voltage-dependent, gamma subunit 6 (CACNG6), transcript variant 1, mRNA [NM_145814]" | NM_145814 |
| A_33_P3260307 | 0.08299556 | 1.31045521 | up | 0.63487047 | 0.24480557 | CARHSP1 | "Homo sapiens calcium regulated heat stable protein 1, 241 kDa (CARHSP1), transcript variant 2, mRNA [NM_001042476]" | NM_001042476 |
| A_23_P431933 | 8.82E-04 | 1.3190647 | down | -0.26084927 | 0.13866611 | CAMKK1 | "Homo sapiens calcium/calmodulin-dependent protein kinase kinase 1, alpha (CAMKK1), transcript variant 1, mRNA [NM_032294]" | NM_032294 |
| A_23_P18017 | 0.034780383 | 1.446666 | up | 0.41961122 | -0.1131207 | CPA3 | "Homo sapiens carboxypeptidase A3 (mast cell) (CPA3), mRNA [NM_001870]" | NM_001870 |
| A_23_P380240 | 0.023509948 | 1.5988463 | down | -0.70409876 | -0.027067412 | CEACAM8 | "Homo sapiens carcinoembryonic antigen-related cell adhesion molecule 8 (CEACAM8), mRNA [NM_001816]" | NM_001816 |
| A_23_P253791 | 0.029807681 | 1.3400142 | down | -0.43290272 | -0.010654482 | CAMP | "Homo sapiens cathelicidin antimicrobial peptide (CAMP), mRNA [NM_004345]" | NM_004345 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_23_P140384 | 0.002161369 | 1.6987963 | down | -0.67417175 | 0.09034092 | CTSG | "Homo sapiens cathepsin G (CTSG), mRNA [NM_001911]" | NM_001911 |
| A_23_P259863 | 5.98E-05 | 2.142295 | down | -0.712246 | 0.38691115 | CD177 | "Homo sapiens CD177 molecule (CD177), mRNA [NM_020406]" | NM_020406 |
| A_23_P76364 | 0.020633294 | 1.3664228 | up | 0.36852786 | -0.08187599 | CD9 | "Homo sapiens CD9 molecule (CD9), mRNA [NM_001769]" | NM_001769 |
| A_33_P3243652 | 0.0462046 | 1.4135683 | up | 0.5954616 | 0.09612002 | LOC100131831 | "Homo sapiens cDNA FLJ26174 fis, clone ADG03920. [AK129685]" | AK129685 |
| A_33_P3250253 | 0.07040643 | 1.3652743 | up | 0.5216825 | 0.0724917 | LOC100131150 | "Homo sapiens cDNA FLJ38875 fis, clone MESAN2013936. [AK096194]" | AK096194 |
| A_33_P3423700 | 0.001282435 | 1.3389032 | down | -0.22081345 | 0.2002382 | LOC100131829 | "Homo sapiens cDNA FLJ1142008 fis, clone SPLEN2031724. [AK124002]" | AK124002 |
| A_33_P3289476 | 0.006421264 | 1.3492424 | down | -0.16770722 | 0.26444238 | LOC100128697 | "Homo sapiens cDNA FLJ1142049 fis, clone SPLEN2041720. [AK124043]" | AK124043 |
| A_33_P3294177 | 0.012347413 | 1.3150665 | down | -0.1425866 | 0.25254914 | LOC100131043 | "Homo sapiens cDNA FLJ42228 fis, clone THYMU2041252. [AK124222]" | AK124222 |
| A_33_P3570228 | 0.08450483 | 1.3391069 | up | 0.59726006 | 0.17598878 | LOC644962 | "Homo sapiens cDNA FLJ46065 fis, clone TBAES2007862. [AK127954]" | AK127954 |
| A_33_P3367850 | 0.001904829 | 2.156447 | down | -0.006115405 | 1.1025405 | CHRM4 | "Homo sapiens cholinergic receptor, muscarinic 4 (CHRM4), mRNA [NM_000741]" | NM_000741 |
| A_33_P3370521 | 0.00145644 | 2.722483 | up | 1.2393239 | -0.20559905 | | "Homo sapiens chromosome 1 genomic contig, GRCh37.p5 Primary Assembly" | XM_001721393 |
| A_33_P3390673 | 0.010252777 | 1.3512726 | down | -0.22451176 | 0.20980695 | | "Homo sapiens chromosome 10 genomic contig, GRCh37.p5 Primary Assembly" | |
| A_33_P3363305 | 0.002453787 | 2.1227565 | up | 0.7126395 | -0.37329924 | | "Homo sapiens chromosome 11 genomic contig, GRCh37.p5 Primary Assembly" | |
| A_33_P3406255 | 0.023001177 | 1.3501295 | up | 0.07665181 | -0.35644597 | | "Homo sapiens chromosome 12 genomic contig, GRCh37.p5 Primary Assembly" | |
| A_33_P3354728 | 0.042722464 | 1.3140639 | up | 0.26061577 | -0.13341968 | | "Homo sapiens chromosome 14 genomic contig, GRCh37.p5 Primary Assembly" | |
| A_33_P3399755 | 0.003660518 | 1.9749763 | up | 0.5097168 | -0.47211847 | | "Homo sapiens chromosome 15 genomic contig, GRCh37.p5 Primary Assembly" | |
| A_33_P3286929 | 0.081707925 | 1.315834 | down | -0.642461 | -0.2464835 | | "Homo sapiens chromosome 15 genomic contig, GRCh37.p5 Primary Assembly" | |
| A_33_P3396275 | 0.085680954 | 1.4504157 | up | 0.59298533 | 0.056519065 | C15orf62 | "Homo sapiens chromosome 15 open reading frame 62 (C15orf62), mRNA [NM_001130448]" | NM_001130448 |
| A_33_P3280502 | 0.001151151 | 1.4021606 | down | -0.22208095 | 0.26557073 | | "Homo sapiens chromosome 16 genomic contig, GRCh37.p5 Primary Assembly" | |
| A_33_P3382887 | 0.001611512 | 2.5672042 | up | 0.5943423 | -0.7658557 | | "Homo sapiens chromosome 18 genomic contig, GRCh37.p5 Primary Assembly" | |
| A_23_P97120 | 0.037768755 | 1.3278565 | up | -0.19747072 | -0.6065707 | C19orf77 | "Homo sapiens chromosome 19 open reading frame 77 (C19orf77), mRNA [NM_001136503]" | NM_001136503 |
| A_33_P3227010 | 0.06222416 | 1.4045763 | up | 0.62080085 | 0.13066588 | | "Homo sapiens chromosome 2 genomic contig, GRCh37.p5 Primary Assembly" | |
| A_33_P3308553 | 0.08915168 | 1.4213793 | up | 0.6727052 | 0.16541366 | | "Homo sapiens chromosome 2 genomic contig, GRCh37.p5 Primary Assembly" | |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_33_P3251462 | 0.011439879 | 1.3474795 | up | 0.38007137 | -0.05019189 | C20orf141 | "Homo sapiens chromosome 20 open reading frame 141 (C20orf141), mRNA [NM_080739]" | NM_080739 |
| A_33_P3251412 | 0.01645751 | 1.4453737 | down | -0.3556638 | 0.17577872 | | "Homo sapiens chromosome 22 genomic contig, GRCh37.p5 Primary Assembly" | |
| A_33_P3310588 | 0.07022539 | 1.3154078 | up | 0.40690875 | 0.011398749 | | "Homo sapiens chromosome 22 genomic contig, GRCh37.p5 Primary Assembly" | |
| A_33_P3212799 | 5.33E-06 | 1.4400822 | down | -0.13911884 | 0.38703233 | C22orf34 | "Homo sapiens chromosome 22 open reading frame 34 (C22orf34), non-coding RNA [NR_026997]" | NR_026997 |
| A_33_3267865 | 0.006212906 | 1.5480765 | down | -0.37141854 | 0.25905824 | | "Homo sapiens chromosome 6 genomic contig, GRCh37.p5" | |
| A_33_P3274001 | 0.027731817 | 1.3519478 | up | 0.46000475 | 0.024965255 | | "Homo sapiens chromosome 6 genomic contig, GRCh37.p5 Primary Assembly" | |
| A_24_P3804 | 7.77E-04 | 1.3040819 | down | -0.05207756 | 0.33095688 | C6orf26 | "Homo sapiens chromosome 6 open reading frame 26 (C6orf26), mRNA [NM_001039651]" | NM_001039651 |
| A_33_P3407049 | 1.04E-06 | 1.4317865 | down | -0.29225388 | 0.2255625 | | "Homo sapiens chromosome 7 genomic contig, GRCh37.p5 Primary Assembly" | |
| A_23_P25069 | 0.06541135 | 1.3128676 | up | 0.30542582 | -0.08729571 | | "Homo sapiens chromosome 7 genomic contig, GRCh37.p5 Primary Assembly" | XM_003319523 |
| A_33_P3295814 | 0.08207279 | 1.3790425 | up | 0.5061583 | 0.042491328 | | "Homo sapiens chromosome 9 genomic contig, GRCh37.p5 Primary Assembly" | |
| A_33_P3348151 | 0.09765747 | 1.4145614 | up | 0.7725938 | 0.272239 | | "Homo sapiens chromosome X genomic contig, GRCh37.p5 Primary Assembly" | |
| A_33_P3422712 | 0.013273941 | 1.8041428 | up | 0.5600057 | -0.2913078 | | "Homo sapiens chromosome X genomic contig, GRCh37.p5 Primary Assembly" | |
| A_33_P3303355 | 0.06306925 | 1.3997774 | up | 0.43767375 | -0.04752365 | | "Homo sapiens chromosome X genomic contig, GRCh37.p5 Primary Assembly" | |
| A_32_P101352 | 6.90E-06 | 1.3438206 | down | -0.14233096 | 0.28400952 | CXorf65 | "Homo sapiens chromosome X open reading frame 65 (CXorf65), transcript variant 1, mRNA [NM_001025265]" | NM_001025265 |
| A_23_P51711 | 0.032540936 | 1.336754 | up | 0.3910381 | -0.027695797 | CELA2B | "Homo sapiens chymotrypsin-like elastase family, member 2B (CELA2B), mRNA [NM_015849]" | NM_015849 |
| A_33_P3233945 | 0.030156614 | 1.329383 | up | 0.09898835 | -0.31176832 | F2RL1 | "Homo sapiens coagulation factor II (thrombin) receptor-like 1 (F2RL1), mRNA [NM_005242]" | NM_005242 |
| A_33_P3216448 | 0.08353515 | 1.4946696 | up | 0.52763623 | -0.05219024 | COL11A2 | "Homo sapiens collagen, type XI, alpha 2 (COL11A2), transcript variant 4, mRNA [NM_001163771]" | NM_001163771 |
| A_24_P418203 | 0.051317006 | 1.3029847 | up | 0.24762823 | -0.13419197 | CNTNAP3 | "Homo sapiens contactin associated protein-like 3 (CNTNAP3), mRNA [NM_033655]" | NM_033655 |
| A_33_P3242614 | 0.001806715 | 1.3097177 | down | -0.13025276 | 0.25900304 | LOC606724 | "Homo sapiens coronin, actin binding protein, 1A pseudogene (LOC606724), non-coding RNA [NR_002454]" | NR_002454 |
| A_23_P215331 | 0.06954535 | 1.3630785 | up | 0.4849613 | 0.038092636 | CRHR2 | "Homo sapiens corticotropin releasing hormone receptor 2 (CRHR2), transcript variant 1, mRNA [NM_001883]" | NM_001883 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_23_P141505 | 3.90E-04 | 1.3431782 | up | 0.3066318 | -0.11901883 | CLEC10A | "Homo sapiens C-type lectin domain family 10, member A (CLEC10A), transcript variant 1, mRNA [NM_182906]" | NM_182906 |
| A_23_P206501 | 0.00173709 | 1.3321601 | down | -0.15516487 | 0.2586026 | CLEC18B | "Homo sapiens C-type lectin domain family 18, member B (CLEC18B), mRNA [NM_001011880]" | NM_001011880 |
| A_23_P166306 | 0.014803309 | 1.6775806 | down | -0.51784945 | 0.22853269 | CBS | "Homo sapiens cystathionine-beta-synthase (CBS), transcript variant 1, mRNA [NM_000071]" | NM_000071 |
| A_23_P44724 | 0.006138469 | 1.3435929 | down | -0.3317573 | 0.09433877 | CSRP2 | "Homo sapiens cysteine and glycine-rich protein 2 (CSRP2), mRNA [NM_001321]" | NM_001321 |
| A_23_P431330 | 1.23E-04 | 1.3079846 | down | -0.042533595 | 0.34481198 | CRIPAK | "Homo sapiens cysteine-rich PAK1 inhibitor (CRIPAK), mRNA [NM_175918]" | NM_175918 |
| A_33_P3379341 | 0.015433097 | 1.328918 | down | -0.023474546 | 0.38677746 | LOC391322 | "Homo sapiens D-dopachrome tautomerase-like (LOC391322), mRNA [NM_001144931]" | NM_001144931 |
| A_23_P31816 | 0.05428833 | 1.4323628 | down | -0.6479673 | -0.12957029 | DEFA3 | "Homo sapiens defensin, alpha 3, neutrophil-specific (DEFA3), mRNA [NM_005217]" | NM_005217 |
| A_23_P326080 | 0.053808365 | 1.4519137 | down | -0.6926883 | -0.15473257 | DEFA4 | "Homo sapiens defensin, alpha 4, corticostatin (DEFA4), mRNA [NM_001925]" | NM_001925 |
| A_23_P4494 | 0.008288973 | 1.4349773 | down | -0.18896562 | 0.3320622 | DSC2 | "Homo sapiens desmocollin 2 (DSC2), transcript variant Dsc2a, mRNA [NM_024422]" | NM_024422 |
| A_32_P2785 | 0.08880611 | 1.309323 | up | 0.1742377 | -0.2145833 | DAAM2 | "Homo sapiens dishevelled associated activator of morphogenesis 2 (DAAM2), transcript variant 2, mRNA [NM_015345]" | NM_015345 |
| A_23_P131139 | 0.001917165 | 1.6789535 | up | 0.61781263 | -0.1297497 | DIRC1 | "Homo sapiens disrupted in renal carcinoma 1 (DIRC1), mRNA [NM_052952]" | NM_052952 |
| A_23_P316472 | 4.37E-05 | 1.3186158 | down | -0.20222439 | 0.19679987 | DNHD1 | "Homo sapiens dynein heavy chain domain 1 (DNHD1), transcript variant 1, mRNA [NM_144666]" | NM_144666 |
| A_23_P130961 | 0.08317351 | 1.3075476 | down | -0.4996647 | -0.11280126 | ELANE | "Homo sapiens elastase, neutrophil expressed (ELANE), mRNA [NM_001972]" | NM_001972 |
| A_33_P3413701 | 0.0011926 | 1.6410688 | down | -0.7812019 | -0.06656598 | ERAP1 | "Homo sapiens endoplasmic reticulum aminopeptidase 1 (ERAP1), transcript variant 2, mRNA [NM_001040458]" | NM_001040458 |
| A_33_P3417626 | 0.001605189 | 1.3939557 | up | 0.265658 | -0.21352668 | ENHO | "Homo sapiens energy homeostasis associated (ENHO), mRNA [NM_198573]" | NM_198573 |
| A_33_P3216532 | 0.002821366 | 1.8402331 | up | 0.9307808 | 0.050892483 | EPHB4 | "Homo sapiens EPH receptor B4 (EPHB4), mRNA [NM_004444]" | NM_004444 |
| A_23_P76488 | 0.005429512 | 1.4041661 | up | 0.58240914 | 0.09269561 | EMP1 | "Homo sapiens epithelial membrane protein 1 (EMP1), mRNA [NM_001423]" | NM_001423 |
| A_33_P3265504 | 0.09525203 | 1.440512 | up | 0.68339294 | 0.15681118 | EIF5AL1 | "Homo sapiens eukaryotic translation initiation factor 5A-like 1 (EIF5AL1), mRNA [NM_001099692]" | NM_001099692 |
| A_24_P169073 | 0.046566848 | 1.3259208 | up | 0.31766993 | -0.089324735 | FAM131C | "Homo sapiens family with sequence similarity 131, member C (FAM131C), mRNA [NM_182623]" | NM_182623 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_33_P3222501 | 0.029998186 | 1.3356988 | down | −0.27530906 | 0.14228569 | FAM157A | "Homo sapiens family with sequence similarity 157, member A (FAM157A), mRNA [NM_001145248]" | NM_001145248 |
| A_23_P103765 | 0.036611106 | 1.4173152 | up | 0.25399694 | −0.24916382 | FCER1A | "Homo sapiens Fc fragment of IgE, high affinity I, receptor for; alpha polypeptide (FCER1A), mRNA [NM_002001]" | NM_002001 |
| A_23_P63390 | 0.041602947 | 1.3429631 | down | −0.08972688 | 0.33569276 | FCGR1B | "Homo sapiens Fc fragment of IgG, high affinity Ib, receptor (CD64) (FCGR1B), transcript variant 1, mRNA [NM_001017986]" | NM_001017986 |
| A_23_P149368 | 0.016182061 | 1.3384151 | down | −0.3338697 | 0.08665597 | FCRL1 | "Homo sapiens Fc receptor-like 1 (FCRL1), transcript variant 1, mRNA [NM_052938]" | NM_052938 |
| A_24_P319647 | 0.002448884 | 1.4621583 | down | −0.5400526 | 0.008046966 | FCRL2 | "Homo sapiens Fc receptor-like 2 (FCRL2), mRNA [NM_030764]" | NM_030764 |
| A_23_P201211 | 0.072885185 | 1.3331984 | down | −0.34657237 | 0.06831916 | FCRL5 | "Homo sapiens Fc receptor-like 5 (FCRL5), transcript variant 1, mRNA [NM_031281]" | NM_031281 |
| A_24_P226069 | 0.038782354 | 1.3155049 | down | −0.52783656 | −0.13221988 | FGFBP2 | "Homo sapiens fibroblast growth factor binding protein 2 (FGFBP2), mRNA [NM_031950]" | NM_031950 |
| A_33_P3414789 | 0.001758171 | 1.8266654 | up | 0.9952169 | 0.12600459 | FSD1 | "Homo sapiens fibronectin type III and SPRY domain containing 1 (FSD1), mRNA [NM_024333]" | NM_024333 |
| A_24_P414308 | 0.08055564 | 1.3528732 | up | 0.6390451 | 0.20301853 | FLCN | "Homo sapiens folliculin (FLCN), transcript variant 2, mRNA [NM_144606]" | NM_144606 |
| A_33_P3849275 | 0.013713419 | 1.3071018 | up | 0.03065578 | −0.35571575 | FHL1 | "Homo sapiens four and a half LIM domains 1 (FHL 1), transcript variant 4, mRNA [NM_001159704]" | NM_001159704 |
| A_23_P74609 | 0.020694846 | 1.425474 | down | −0.41793794 | 0.09170383 | G0S2 | "Homo sapiens G0/G1switch 2 (G0S2), mRNA [NM_015714]" | NM_015714 |
| A_33_P3550894 | 0.037090957 | 1.499201 | down | −0.8526115 | −0.2684176 | GATA2 | "Homo sapiens GATA binding protein 2 (GATA2), transcript variant 1, mRNA [NM_001145661]" | NM_001145661 |
| A_23_P115407 | 0.010135848 | 1.3188878 | up | 0.31084928 | −0.08847254 | GSTM1 | "Homo sapiens glutathione S-transferase mu 1 (GSTM1), transcript variant 2, mRNA [NM_146421]" | NM_146421 |
| A_23_P12343 | 0.01809803 | 1.4180923 | up | 0.31395653 | −0.18999486 | GSTM3 | "Homo sapiens glutathione S-transferase mu 3 (brain) (GSTM3), transcript variant 1, mRNA [NM_000849]" | NM_000849 |
| A_24_P50972 | 0.047969874 | 1.3672184 | down | −0.56622344 | −0.11497975 | GOLGA6L6 | "Homo sapiens golgin A6 family-like 6 (GOLGA6L6), mRNA [NM_001145004]" | NM_001145004 |
| A_33_P3331687 | 0.07681634 | 1.4575082 | up | 0.5978242 | 0.054320335 | GPSM1 | "Homo sapiens G-protein signaling modulator 1 (GPSM1), transcript variant 1, mRNA [NM_001145638]" | NM_001145638 |
| A_23_P51487 | 0.020316713 | 1.3146726 | down | −0.26225594 | 0.13244759 | GBP3 | "Homo sapiens guanylate binding protein 3 (GBP3), mRNA [NM_018284]" | NM_018284 |
| A_23_P74290 | 8.34E−05 | 1.36265 | down | −0.25034246 | 0.19607258 | GBP5 | "Homo sapiens guanylate binding protein 5 (GBP5), transcript variant 1, mRNA [NM_052942]" | NM_052942 |
| A_33_P3364060 | 0.041923005 | 1.3391094 | up | 0.38413158 | −0.03714231 | HR | "Homo sapiens hairless homolog (mouse) (HR), transcript variant 1, mRNA [NM_005144]" | NM_005144 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_23_P2601 | 0.0556336 | 1.3637878 | up | 0.6045371 | 0.15691787 | HSP90B1 | "*Homo sapiens* heat shock protein 90 kDa beta (Grp94), member 1 (HSP90B1), mRNA [NM_003299]" | NM_003299 |
| A_33_P3235400 | 0.09289805 | 1.4275789 | up | 0.57690924 | 0.06333871 | HDGF | "*Homo sapiens* hepatoma-derived growth factor (HDGF), transcript variant 1, mRNA [NM_004494]" | NM_004494 |
| A_24_P136161 | 0.005481314 | 1.3070174 | up | 0.08381522 | −0.30246323 | HNRNPCL1 | "*Homo sapiens* heterogeneous nuclear ribonucleoprotein C-like 1 (HNRNPCL1), mRNA [NM_001013631]" | NM_001013631 |
| A_23_P117662 | 0.030373184 | 1.733141 | up | 0.53507316 | −0.25831598 | HDC | "*Homo sapiens* histidine decarboxylase (HDC), mRNA [NM_002112]" | NM_002112 |
| A_33_P3257678 | 0.050762586 | 1.3800672 | down | −0.1279434 | 0.33679512 | HIST2H3A | "*Homo sapiens* histone cluster 2, H3a (HIST2H3A), mRNA [NM_001005464]" | NM_001005464 |
| A_23_P134684 | 3.45E-04 | 1.3789066 | down | −0.39460433 | 0.06892046 | HMBOX1 | "*Homo sapiens* homeobox containing 1 (HMBOX1), transcript variant 1, mRNA [NM_024567]" | NM_024567 |
| A_23_P97990 | 0.019677851 | 1.374254 | down | −0.27780554 | 0.18084311 | HTRA1 | "*Homo sapiens* HtrA serine peptidase 1 (HTRA1), mRNA [NM_002775]" | NM_002775 |
| A_24_P63548 | 0.002504433 | 1.4040958 | down | −0.18716349 | 0.30247787 | HIP1 | "*Homo sapiens* huntingtin interacting protein 1 (HIP1), mRNA [NM_005338]" | NM_005338 |
| A_33_P3308481 | 5.75E-05 | 1.4845908 | down | −0.3298521 | 0.24021314 | HYMAI | "*Homo sapiens* hydatidiform mole associated and imprinted (non-protein coding) (HYMAI), non-coding RNA [NR_002768]" | NR_002768 |
| A_32_P211248 | 7.56E-04 | 2.5825121 | up | 1.3989235 | 0.030148894 | LOC100131138 | "*Homo sapiens* hypothetical LOC100131138 (LOC100131138), non-coding RNA [NR_036513]" | NR_036513 |
| A_24_P586390 | 0.014898183 | 1.3297529 | down | −0.17911632 | 0.23204184 | LOC100133331 | "*Homo sapiens* hypothetical LOC100133331 (LOC100133331), non-coding RNA [NR_028327]" | NR_028327 |
| A_33_P3390042 | 0.08727153 | 1.4229659 | up | 0.5128816 | 0.003980539 | LOC143188 | "*Homo sapiens* hypothetical LOC143188 (LOC143188), non-coding RNA [NR_015409]" | NR_015409 |
| A_23_P3327697 | 0.001619901 | 1.352933 | down | −0.30568862 | 0.1304018 | LOC145474 | "*Homo sapiens* hypothetical LOC145474 (LOC145474), non-coding RNA [NR_027046]" | NR_027046 |
| A_23_P406227 | 5.47E-04 | 1.3153083 | up | 0.2099269 | −0.18547417 | MGC23284 | "*Homo sapiens* hypothetical LOC197187 (MGC23284), transcript variant 2, non-coding RNA [NR_024399]" | NR_024399 |
| A_23_P405282 | 0.089760005 | 1.5368778 | up | 0.6276134 | 0.007610971 | MGC45922 | "*Homo sapiens* hypothetical LOC284365 (MGC45922), non-coding RNA [NR_038359]" | NR_038359 |
| A_33_P3234472 | 0.005810714 | 1.4360186 | down | −0.24649546 | 0.27557907 | LOC284751 | "*Homo sapiens* hypothetical LOC284751 (LOC284751), non-coding RNA [NR_034124]" | NR_034124 |
| A_33_P3243502 | 5.36E-04 | 1.3541956 | down | −0.14575173 | 0.29168436 | LOC389634 | "*Homo sapiens* hypothetical LOC389634 (LOC389634), non-coding RNA [NR_024420]" | NR_024420 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_24_P366787 | 0.083696164 | 1.3104081 | up | 0.38772547 | −0.002290747 | FLJ42875 | "Homo sapiens hypothetical LOC440556 (FLJ42875), transcript variant 2, non-coding RNA [NR_024371]" | NR_024371 |
| A_24_P709377 | 0.023045259 | 1.4163723 | down | −0.32548106 | 0.17671943 | LOC654433 | "Homo sapiens hypothetical LOC654433 (LOC654433), non-coding RNA [NR_015377]" | NR_015377 |
| A_33_P3226380 | 0.019924704 | 1.3318514 | down | −0.24102229 | 0.17241085 | LOC731275 | "Homo sapiens hypothetical LOC731275 (LOC731275), non-coding RNA [NR_029401]" | NR_029401 |
| A_33_P3395859 | 0.006850161 | 1.3092291 | up | 0.1764826 | −0.21223497 | LOC147646 | "Homo sapiens hypothetical protein LOC147646 (LOC147646), mRNA [NM_001193623]" | NM_001193623 |
| A_33_P3394868 | 0.048862364 | 1.5409874 | up | 0.24851498 | −0.37534 | LOC388588 | "Homo sapiens hypothetical protein LOC388588 (LOC388588), mRNA [NM_001163724]" | NM_001163724 |
| A_33_P3714341 | 0.02940068 | 1.326508 | down | −0.15401596 | 0.25361747 | | "Homo sapiens IGK mRNA for immunoglobulin kappa light chain, partial cds, clone: F010-014L. [AB363267]" | AB363267 |
| A_33_P2787857 | 0.02768785 | 1.3015393 | up | 0.19036265 | −0.18985619 | IDO1 | "Homo sapiens indoleamine 2,3-dioxygenase 1 (IDO1), mRNA [NM_002164]" | NM_002164 |
| A_23_P112026 | 0.0912217 | 1.345673 | down | −0.18211056 | 0.24621743 | IGF2 | "Homo sapiens insulin-like growth factor 2 (somatomedin A) (IGF2), transcript variant 1, mRNA [NM_000612]" | NM_000612 |
| A_23_P150609 | 0.024961589 | 1.3794471 | up | 0.1452673 | −0.31882286 | IRF5 | "Homo sapiens interferon regulatory factor 5 (IRF5), transcript variant 3, mRNA [NM_001098627]" | NM_001098627 |
| A_23_P500271 | 0.001459079 | 1.3767601 | down | −0.37895703 | 0.08232018 | IL18RAP | "Homo sapiens interleukin 18 receptor accessory protein (IL18RAP), mRNA [NM_003853]" | NM_003853 |
| A_33_P3221960 | 0.032091603 | 1.3400984 | up | 0.08808277 | −0.3342561 | IL5RA | "Homo sapiens interleukin 5 receptor, alpha (IL5RA), transcript variant 3, mRNA [NM_175725]" | NM_175725 |
| A_33_P3328254 | 3.36E-04 | 1.3071045 | up | 0.09673596 | −0.28963846 | IQSEC2 | "Homo sapiens IQ motif and Sec7 domain 2 (IQSEC2), transcript variant 3, non-coding RNA [NR_024449]" | NR_024449 |
| A_33_P3253234 | 0.002548156 | 1.3464185 | down | −0.38539615 | 0.043730713 | JAKMIP1 | "Homo sapiens janus kinase and microtubule interacting protein 1 (JAKMIP1), transcript variant 2, mRNA [NM_144720]" | NM_144720 |
| A_33_P3221114 | 0.004402624 | 1.3701937 | down | −0.51986045 | −0.06548052 | JAKMIP2 | "Homo sapiens janus kinase and microtubule interacting protein 2 (JAKMIP2), mRNA [NM_014790]" | NM_014790 |
| A_33_P3255290 | 0.022671197 | 1.5983387 | up | 0.7085939 | 0.0320207 | KRT1 | "Homo sapiens keratin 1 (KRT1), mRNA [NM_006121]" | NM_006121 |
| A_33_P3379396 | 0.042684495 | 1.3185656 | down | −0.37402976 | 0.024939574 | KRT23 | "Homo sapiens keratin 23 (histone deacetylase inducible) (KRT23), mRNA [NM_015515]" | NM_015515 |
| A_33_P3299761 | 0.06718372 | 1.3514819 | up | 0.5921231 | 0.15758102 | KRTAP10-3 | "Homo sapiens keratin associated protein 10-3 (KRTAP10-3), mRNA [NM_198696]" | NM_198696 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_24_P142495 | 0.016049417 | 1.4313754 | up | 0.5575752 | 0.040173087 | KRTAP1-3 | "Homo sapiens keratin associated protein 1-3 (KRTAP1-3), mRNA [NM_030966]" | NM_030966 |
| A_33_P3311267 | 0.00196464 | 2.0485787 | up | 0.5750864 | -0.45953703 | KRTAP19-2 | "Homo sapiens keratin associated protein 19-2 (KRTAP19-2), mRNA [NM_181608]" | NM_181608 |
| A_33_P3247473 | 0.055842146 | 1.555453 | up | 0.601481 | -0.035857 | KRTAP23-1 | "Homo sapiens keratin associated protein 23-1 (KRTAP23-1), mRNA [NM_181624]" | NM_181624 |
| A_24_P61753 | 0.001950238 | 1.4875685 | up | 0.48825037 | -0.08470581 | KIAA0664 | "Homo sapiens KIAA0664 (KIAA0664), mRNA [NM_015229]" | NM_015229 |
| A_33_P3265222 | 0.037706073 | 1.4690068 | down | -0.38025752 | 0.17458357 | KIAA1324 | "Homo sapiens KIAA1324 (KIAA1324), mRNA [NM_020775]" | NM_020775 |
| A_23_P166848 | 0.012082896 | 1.7126892 | down | -0.8880412 | -0.111777835 | LTF | "Homo sapiens lactotransferrin (LTF), transcript variant 1, mRNA [NM_002343]" | NM_002343 |
| A_33_P3311285 | 0.087441646 | 1.4525914 | up | 0.511191515 | -0.026713826 | LMNA | "Homo sapiens lamin A/C (LMNA), transcript variant 1, mRNA [NM_170707]" | NM_170707 |
| A_33_P3356811 | 0.002943031 | 1.6657962 | up | 0.694400465 | -0.04220723 | LCE1E | "Homo sapiens late cornified envelope 1E (LCE1E), mRNA [NM_178353]" | NM_178353 |
| A_23_P120902 | 0.090559945 | 1.3033013 | down | -0.55106217 | -0.16889149 | LGALS2 | "Homo sapiens lectin, galactoside-binding, soluble, 2 (LGALS2), mRNA [NM_006498]" | NM_006498 |
| A_33_P3269844 | 0.08599462 | 1.4475169 | up | 0.6968315 | 0.1632513 | LRRC26 | "Homo sapiens leucine rich repeat containing 26 (LRRC26), mRNA [NM_001013653]" | NM_001013653 |
| A_33_P3420446 | 0.00271936 | 2.366392 | up | 0.7168905 | -0.52579856 | LRRD1 | "Homo sapiens leucine-rich repeats and death domain containing 1 (LRRD1), mRNA [NM_001161528]" | NM_001161528 |
| A_23_P209129 | 0.01875381 | 1.6142532 | down | -0.2496036 | 0.4412632 | LAIR2 | "Homo sapiens leukocyte-associated immunoglobulin-like receptor 2 (LAIR2), transcript variant 1, mRNA [NM_002288]" | NM_002288 |
| A_23_P215461 | 0.002549152 | 1.300507 | down | -0.18881646 | 0.19025768 | LIMK1 | "Homo sapiens LIM domain kinase 1 (LIMK1), transcript variant 1, mRNA [NM_002314]" | NM_002314 |
| A_33_P3223678 | 0.083056256 | 1.3900585 | up | 0.42437238 | -0.050773323 | LHX3 | "Homo sapiens LIM homeobox 3 (LHX3), transcript variant 2, mRNA [NM_014564]" | NM_014564 |
| A_33_P3883985 | 2.77E-04 | 1.4781803 | down | -0.39256123 | 0.17126101 | LMF1 | "Homo sapiens lipase maturation factor 1 (LMF1), transcript variant 4, non-coding RNA [NR_036442]" | NR_036442 |
| A_23_P169437 | 0.026562108 | 1.3425556 | down | -0.27172977 | 0.15325205 | LCN2 | "Homo sapiens lipocalin 2 (LCN2), mRNA [NM_005564]" | NM_005564 |
| A_33_P3418194 | 0.08478003 | 1.3773015 | up | 0.4566962 | -0.005148216 | LYNX1 | "Homo sapiens Ly6/neurotoxin 1 (LYNX1), transcript variant 1, mRNA [NM_023946]" | NM_023946 |
| A_23_P94186 | 0.011679071 | 1.5363395 | up | 0.18567842 | -0.43381873 | LYPD2 | "Homo sapiens LY6/PLAUR domain containing 2 (LYPD2), mRNA [NM_205545]" | NM_205545 |
| A_24_P148907 | 0.001661408 | 2.865912 | up | 1.2227665 | -0.29622796 | MAB21L2 | "Homo sapiens mab-21-like 2 (C. elegans) (MAB21L2), mRNA [NM_006439]" | NM_006439 |
| A_33_P3424222 | 0.017523954 | 1.3362783 | up | 0.07366995 | -0.34455052 | HLA-DQB1 | "Homo sapiens major histocompatibility complex, class II, DQ beta 1 (HLA-DQB1), mRNA [NM_002123]" | NM_002123 |
| A_23_P116614 | 3.10E-05 | 1.4666952 | down | -0.10582965 | 0.44673944 | ME3 | "Homo sapiens malic enzyme 3, NADP(+)-dependent, mitochondrial (ME3), nuclear gene encoding mitochondrial protein," | NM_001014811 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_33_P3255434 | 0.060425054 | 1.3492434 | up | 0.28156415 | −0.15058652 | MEG3 | "Homo sapiens maternally expressed 3 (non-protein coding) (MEG3), transcript variant 3, non-coding RNA [NR_003531]" | NR_003531 |
| A_33_P3329444 | 0.001861639 | 1.7145877 | up | 0.9819033 | 0.20404148 | MAMSTR | "Homo sapiens MEF2 activating motif and SAP domain containing transcriptional regulator (MAMSTR), transcript variant 2, mRNA [NM_182574]" | NM_182574 |
| A_33_P75769 | 0.001481862 | 1.3274643 | up | 0.29444453 | −0.11422854 | MS4A4A | "Homo sapiens membrane-spanning 4-domains, subfamily A, member 4 (MS4A4A), transcript variant 1, mRNA [NM_024021]" | NM_024021 |
| A_33_P3375576 | 0.002459711 | 1.3197386 | up | 0.08183793 | −0.3184143 | MAP7 | "Homo sapiens microtubule-associated protein 7 (MAP7), transcript variant 4, mRNA [NM_003980]" | NM_003980 |
| A_23_P116235 | 0.09601189 | 1.4094809 | up | 0.6359941 | 0.14083026 | MDK | "Homo sapiens midkine (neurite growth-promoting factor 2) (MDK), transcript variant 1, mRNA [NM_001012334]" | NM_001012334 |
| A_33_P3713035 | 0.06089847 | 1.3921365 | up | 0.49190181 | 0.014601317 | LOC221814 | Homo sapiens mRNA; cDNA DKFZp564C0371 (from clone DKFZp564C0371) [AL122087] | AL122087 |
| A_33_P3576797 | 5.14E-05 | 1.3676219 | down | −0.19595735 | 0.25571203 | LOC158863 | Homo sapiens mRNA; cDNA DKFZp586I1922 (from clone DKFZp586I1922) [AL110203] | AL110203 |
| A_24_P239177 | 0.07026498 | 1.3379579 | up | 0.37570342 | −0.044329308 | MUC4 | "Homo sapiens mucin 4, cell surface associated (MUC4), transcript variant 1, mRNA [NM_018406]" | NM_018406 |
| A_23_P153616 | 0.037463963 | 1.3608772 | up | 0.15519878 | −0.28933802 | MADCAM1 | "Homo sapiens mucosal vascular addressin cell adhesion molecule 1 (MADCAM1), transcript variant 1, mRNA [NM_130760]" | NM_130760 |
| A_24_P926960 | 0.007280337 | 1.3126051 | down | −0.11324262 | 0.27919033 | MEGF6 | "Homo sapiens multiple EGF-like-domains 6 (MEGF6), mRNA [NM_001409]" | NM_001409 |
| A_23_P258912 | 0.004170403 | 2.2495987 | up | 1.0578427 | −0.11182482 | MYOM2 | "Homo sapiens myomesin (M-protein) 2, 165 kDa (MYOM2), mRNA [NM_003970]" | NM_003970 |
| A_23_P148737 | 0.021698399 | 1.3982097 | down | −0.10234106 | 0.38123974 | MYBPH | "Homo sapiens myosin binding protein H (MYBPH), mRNA [NM_004997]" | NM_004997 |
| A_32_P475513 | 2.20E-04 | 1.3007798 | down | −0.16332881 | 0.21604796 | MYO15B | "Homo sapiens myosin XVB pseudogene (MYO15B), non-coding RNA [NR_003587]" | NR_003587 |
| A_23_P59888 | 0.022967694 | 1.4164991 | up | 0.1757084 | −0.3266213 | NACAP1 | "Homo sapiens nascent-polypeptide-associated complex alpha polypeptide pseudogene 1 (NACAP1), non-coding RNA [NR_002182]" | NR_002182 |
| A_33_P3363799 | 0.001432941 | 1.3627709 | down | −0.32955402 | 0.11698904 | NCAM1 | "Homo sapiens neural cell adhesion molecule 1 (NCAM1), transcript variant 5, mRNA [NM_001242607]" | NM_001242607 |
| A_33_P3293524 | 5.14E-04 | 1.7614166 | up | 0.5752742 | −0.24146186 | NEURL | "Homo sapiens neuralized homolog (Drosophila) (NEURL), mRNA [NM_004210]" | NM_004210 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_33_P3417880 | 0.09242977 | 1.4802772 | up | 0.7100061 | 0.1441387 | NKAPL | "Homo sapiens NFKB activating protein-like (NKAPL), mRNA [NM_001007531]" | NM_001007531 |
| A_32_P29954 | 0.09568178 | 1.323937 | up | 0.31786942 | -0.0869652 | NCRNA00168 | "Homo sapiens non-protein coding RNA 168 (NCRNA00168), non-coding RNA [NR_033387]" | NR_033387 |
| A_23_P348257 | 0.005219493 | 1.3868356 | down | -0.49135873 | -0.019561974 | NUAK1 | "Homo sapiens NUAK family, SNF1-like kinase, 1 (NUAK1), mRNA [NM_014840]" | NM_014840 |
| A_24_P181254 | 1.12E-05 | 2.610649 | down | -0.9120534 | 0.47229984 | OLFM4 | "Homo sapiens olfactomedin 4 (OLFM4), mRNA [NM_006418]" | NM_006418 |
| A_23_P123164 | 0.086086884 | 1.4242122 | up | 0.74071884 | 0.23055477 | OR6W1P | "Homo sapiens olfactory receptor, family 6, subfamily W, member 1 pseudogene (OR6W1P), non-coding RNA [NR_002140]" | NR_002140 |
| A_23_P154849 | 9.79E-04 | 1.3476431 | up | 0.24389891 | -0.18653955 | OLIG1 | "Homo sapiens oligodendrocyte transcription factor 1 (OLIG1), mRNA [NM_138983]" | NM_138983 |
| A_33_P3424057 | 0.036320634 | 1.4471698 | down | -0.04955366 | 0.48368058 | PEG3 | "Homo sapiens paternally expressed 3 (PEG3), transcript variant 1, mRNA [NM_006210]" | NM_006210 |
| A_33_P3358213 | 0.07315914 | 1.3551917 | down | -0.50678235 | -0.06828541 | PADI6 | "Homo sapiens peptidyl arginine deiminase, type VI (PADI6), mRNA [NM_207421]" | NM_207421 |
| A_33_P3389649 | 6.15E-04 | 1.4486274 | down | -0.36063802 | 0.17404853 | PDE4D | "Homo sapiens phosphodiesterase 4D, cAMP-specific (PDE4D), transcript variant 4, mRNA [NM_001197218]" | NM_001197218 |
| A_23_P50508 | 0.038823243 | 1.3111038 | down | -0.10175071 | 0.28903127 | PLA2G4C | "Homo sapiens phospholipase A2, group IVC (cytosolic, calcium-independent) (PLA2G4C), transcript variant 1, mRNA [NM_003706]" | NM_003706 |
| A_32_P220750 | 9.14E-04 | 1.3145334 | down | -0.19883072 | 0.19572005 | PLGLB1 | "Homo sapiens plasminogen-like B1 (PLGLB1), mRNA [NM_001032392]" | NM_001032392 |
| A_23_P208293 | 0.003093129 | 1.7755167 | down | -0.106243365 | 0.7219956 | PVRL2 | "Homo sapiens poliovirus receptor-related 2 (herpesvirus entry mediator B) (PVRL2), transcript variant delta, mRNA [NM_001042724]" | NM_001042724 |
| A_23_P3412233 | 0.001612926 | 1.3889495 | down | -0.14588183 | 0.32811236 | POMZP3 | "Homo sapiens POM121 and ZP3 fusion (POMZP3), transcript variant 2, mRNA [NM_152992]" | NM_152992 |
| A_33_P3835524 | 0.08983538 | 1.3188908 | up | 0.3992639 | -6.13E-05 | POU2F2 | "Homo sapiens POU class 2 homeobox 2 (POU2F2), transcript variant 3, mRNA [NM_001207026]" | NM_001207026 |
| A_33_P3253440 | 0.04686745 | 1.3020296 | up | 0.4306891 | 0.049926866 | PQLC3 | "Homo sapiens PQ loop repeat containing 3 (PQLC3), mRNA [NM_152391]" | NM_152391 |
| A_23_P135257 | 0.042998407 | 1.3288782 | up | 0.42078122 | 0.010572314 | PRSS3 | "Homo sapiens protease, serine, 3 (PRSS3), transcript variant 2, mRNA [NM_002771]" | NM_002771 |
| A_24_P412734 | 0.0017587 | 2.3318243 | up | 0.60075295 | -0.6126407 | PRSS36 | "Homo sapiens protease, serine, 36 (PRSS36), mRNA [NM_173502]" | NM_173502 |
| A_33_P3284197 | 0.08594889 | 1.3667958 | up | 0.65785617 | 0.20705844 | POMGNT1 | "Homo sapiens protein O-linked mannose beta1,2-N-acetylglucosaminyltransferase (POMGNT1), transcript variant 1, mRNA [NM_017739]" | NM_017739 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_24_P350649 | 1.59E-04 | 1.3157947 | down | -0.19939834 | 0.1965361 | PDPR | "Homo sapiens pyruvate dehydrogenase phosphatase regulatory subunit (PDPR), mRNA [NM_017990]" | NM_017990 |
| A_23_P395632 | 0.092577755 | 1.3042655 | up | 0.41154584 | 0.02308326 | R3HDML | "Homo sapiens R3H domain containing-like (R3HDML), mRNA [NM_178491]" | NM_178491 |
| A_23_P412214 | 0.012191882 | 1.4418955 | down | 0.008509423 | 0.53647596 | RAP1GAP2 | "Homo sapiens RAP1 GTPase activating protein 2 (RAP1GAP2), transcript variant 1, mRNA [NM_015085]" | NM_015085 |
| A_24_P321525 | 0.09530078 | 1.4714687 | up | 0.7249367 | 0.1676798 | RERG | "Homo sapiens RAS-like, estrogen-regulated, growth inhibitor (RERG), transcript variant 1, mRNA [NM_032918]" | NM_032918 |
| A_33_P3233906 | 0.031552453 | 1.3244379 | up | 0.13838409 | -0.26699603 | RAMP1 | "Homo sapiens receptor (G protein-coupled) activity modifying protein 1 (RAMP1), mRNA [NM_005855]" | NM_005855 |
| A_23_P207842 | 0.07773515 | 1.6012361 | up | 0.8123088 | 0.13312276 | RARA | "Homo sapiens retinoic acid receptor, alpha (RARA), transcript variant 2, mRNA [NM_001024809]" | NM_001024809 |
| A_24_P218814 | 7.21E-06 | 1.3163062 | down | -0.13313852 | 0.2633566 | RDH5 | "Homo sapiens retinol dehydrogenase 5 (11-cis/9-cis) (RDH5), transcript variant 2, mRNA [NM_002905]" | NM_002905 |
| A_33_P3234794 | 0.08135664 | 1.5102085 | up | 0.80040497 | 0.20565729 | ARHGAP40 | "Homo sapiens Rho GTPase activating protein 40 (ARHGAP40), mRNA [NM_001164431]" | NM_001164431 |
| A_33_P3299110 | 6.68E-04 | 2.0504975 | up | 1.26873314 | 0.23275743 | ARHGAP42 | "Homo sapiens Rho GTPase activating protein 42 (ARHGAP42), mRNA [NM_152432]" | NM_152432 |
| A_23_P253221 | 4.89E-05 | 1.3480966 | up | 0.232708 | -0.19821592 | ARHGEF4 | "Homo sapiens Rho guanine nucleotide exchange factor (GEF) 4 (ARHGEF4), transcript variant 2, mRNA [NM_032995]" | NM_032995 |
| A_33_P3389394 | 0.024702093 | 1.319288 | up | -0.025534749 | -0.42529428 | RPPH1 | "Homo sapiens ribonuclease P RNA component H1 (RPPH1), RNase P RNA [NR_002312]" | NR_002312 |
| A_23_P151637 | 0.006104208 | 1.3874338 | up | 0.44583097 | -0.02658796 | RNASE2 | "Homo sapiens ribonuclease, RNase A family, 2 (liver, eosinophil-derived neurotoxin) (RNASE2), mRNA [NM_002934]" | NM_002934 |
| A_23_P163025 | 0.022805661 | 1.34434 | up | 0.38591552 | -0.04098246 | RNASE3 | "Homo sapiens ribonuclease, RNase A family, 3 (RNASE3), mRNA [NM_002935]" | NM_002935 |
| A_23_P143526 | 0.019984735 | 1.6951951 | down | -0.11775185 | 0.64369947 | S100B | "Homo sapiens S100 calcium binding protein B (S100B), mRNA [NM_006272]" | NM_006272 |
| A_23_P150583 | 0.09199147 | 1.4211044 | up | 0.7121389 | 0.20512642 | SCGB1A1 | "Homo sapiens secretoglobin, family 1A, member 1 (uteroglobin) (SCGB1A1), mRNA [NM_003357]" | NM_003357 |
| A_24_P917866 | 0.014710876 | 1.3474284 | up | 0.06467435 | -0.36553437 | SET | "Homo sapiens SET nuclear oncogene (SET), transcript variant 2, mRNA [NM_003011]" | NM_003011 |
| A_33_P3270636 | 0.002022835 | 1.3082175 | up | 0.41448945 | 0.02687037 | SHISA5 | "Homo sapiens shisa homolog 5 (Xenopus laevis) (SHISA5), mRNA [NM_016479]" | NM_016479 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_24_P40001 | 0.011109361 | 1.4188412 | up | 0.22393192 | −0.28078127 | SIGLEC8 | "Homo sapiens sialic acid binding Ig-like lectin 8 (SIGLEC8), mRNA [NM_014442]" | NM_014442 |
| A_33_P3252333 | 0.09818985 | 1.4077512 | up | −0.3091631 | −0.80255544 | SNORD3B-1 | "Homo sapiens small nucleolar RNA, C/D box 3B-1 (SNORD3B-1), small nucleolar RNA [NR_003271]" | NR_003271 |
| A_33_P3227217 | 0.04919367 | 1.354897 | up | 0.25370643 | −0.18447681 | SNORA81 | "Homo sapiens small nucleolar RNA, H/ACA box 81 (SNORA81), small nucleolar RNA [NR_002989]" | NR_002989 |
| A_23_P325562 | 0.00332791 | 1.4054743 | down | −0.43519023 | 0.0558669 | SLC1A7 | "Homo sapiens solute carrier family 1 (glutamate transporter), member 7 (SLC1A7), mRNA [NM_006671]" | NM_006671 |
| A_23_P160159 | 1.37E−04 | 1.3007578 | down | −0.22973682 | 0.14961547 | SLC2A5 | "Homo sapiens solute carrier family 2 (facilitated glucose/fructose transporter), member 5 (SLC2A5), transcript variant 1, mRNA [NM_003039]" | NM_003039 |
| A_33_P3335920 | 0.08877471 | 1.330463 | up | 0.45973876 | 0.047810316 | SYNE1 | "Homo sapiens spectrin repeat containing, nuclear envelope 1 (SYNE1), transcript variant 1, mRNA [NM_182961]" | NM_182961 |
| A_33_P3216438 | 7.26E−04 | 2.372752 | up | 1.3489308 | 0.10236969 | SPATA21 | "Homo sapiens spermatogenesis associated 21 (SPATA21), mRNA [NM_198546]" | NM_198546 |
| A_23_P163567 | 0.01641856 | 1.3127929 | up | 0.21629916 | −0.17634013 | SMPD3 | "Homo sapiens sphingomyelin phosphodiesterase 3, neutral membrane (neutral sphingomyelinase II) (SMPD3), mRNA [NM_018667]" | NM_018667 |
| A_33_P3871347 | 0.053434405 | 1.3910446 | up | 0.6208837 | 0.14471498 | SNED1 | "Homo sapiens sushi, nidogen and EGF-like domains 1 (SNED1), mRNA [NM_001080437]" | NM_001080437 |
| A_23_P62893 | 0.086125314 | 1.3498223 | up | 0.4291114 | −0.003657948 | TEAD1 | "Homo sapiens TEA domain family member 1 (SV40 transcriptional enhancer factor) (TEAD1), mRNA [NM_021961]" | NM_021961 |
| A_33_P3209386 | 6.43E−04 | 1.5380307 | up | 0.5672639 | −0.053820457 | TXNDC17 | "Homo sapiens thioredoxin domain containing 17 (TXNDC17), mRNA [NM_032731]" | NM_032731 |
| A_23_P57118 | 0.026512504 | 1.3210843 | up | 0.28625846 | −0.11546404 | TGM3 | "Homo sapiens transglutaminase 3 (E polypeptide, protein-glutamine-gamma-glutamyltransferase) (TGM3), mRNA [NM_003245]" | NM_003245 |
| A_33_P3387696 | 0.05355964 | 1.3100442 | up | 0.04848023 | −0.3411352 | TMBIM4 | "Homo sapiens transmembrane BAX inhibitor motif containing 4 (TMBIM4), mRNA [NM_016056]" | NM_016056 |
| A_23_P369899 | 0.08287382 | 1.3267201 | up | −0.22741964 | −0.63528365 | TMEM158 | "Homo sapiens transmembrane protein 158 (gene/pseudogene) (TMEM158), mRNA [NM_015444]" | NM_015444 |
| A_33_P3277611 | 0.003524825 | 1.6475877 | up | 0.87635684 | 0.15600152 | TMEM8C | "Homo sapiens transmembrane protein 8C (TMEM8C), mRNA [NM_001080483]" | NM_001080483 |
| A_32_P396186 | 2.71E−04 | 1.3270874 | down | −0.21896301 | 0.18930034 | TRIM66 | "Homo sapiens tripartite motif containing 66 (TRIM66), mRNA [NM_014818]" | NM_014818 |
| A_23_P62386 | 5.48E−04 | 1.373854 | up | 0.257141 | −0.2010878 | TPPP3 | "Homo sapiens tubulin polymerization-promoting protein family member 3 (TPPP3), mRNA [NM_016140]" | NM_016140 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_23_P19291 | 0.007322263 | 2.2345412 | down | −0.85803705 | 0.30194163 | TUBB2A | "Homo sapiens tubulin, beta 2A (TUBB2A), mRNA [NM_001069]" | NM_001069 |
| A_23_P254271 | 0.006233792 | 1.3433877 | up | 0.21792516 | −0.20795049 | TUBB6 | "Homo sapiens tubulin, beta 6 (TUBB6), mRNA [NM_032525]" | NM_032525 |
| A_24_P813147 | 0.044909976 | 1.3454928 | down | −0.10447685 | 0.32365793 | TUBB8 | "Homo sapiens tubulin, beta 8 (TUBB8), transcript variant 1, mRNA [NM_177987]" | NM_177987 |
| A_33_P3409518 | 0.002293216 | 2.2983027 | up | 1.0949807 | −0.10558822 | TUBBP5 | "Homo sapiens tubulin, beta pseudogene 5 (TUBBP5), non-coding RNA [NR_027156]" | NR_027156 |
| A_23_P52986 | 0.014557628 | 1.4165095 | up | 0.41923535 | −0.08310499 | VWCE | "Homo sapiens von Willebrand factor C and EGF domains (VWCE), mRNA [NM_152718]" | NM_152718 |
| A_33_P3222019 | 0.062055603 | 1.4264376 | up | 0.49954265 | −0.012873986 | WSCD2 | "Homo sapiens WSC domain containing 2 (WSCD2), mRNA [NM_014653]" | NM_014653 |
| A_23_P131024 | 0.012060405 | 1.3444775 | down | −0.33537063 | 0.09167503 | ZBTB32 | "Homo sapiens zinc finger and BTB domain containing 32 (ZBTB32), mRNA [NM_014383]" | NM_014383 |
| A_33_P3263538 | 9.06E-05 | 1.586441 | down | −0.104649104 | 0.56114477 | NEAT1 | "Human MEN1 region clone epsilon/beta mRNA, 3' fragment. [AF001893]" | AF001893 |
| A_33_P3299329 | 0.008540989 | 1.3169246 | up | −0.020110765 | −0.41728345 | | "Human mRNA for T-cell receptor V beta gene segment V-beta-7, clone IGRb18. [X58812]" | A25969 |
| A_33_P3351180 | 0.043619018 | 1.4690309 | down | −0.12071315 | 0.4341515 | | immunoglobulin heavy constant alpha 1 [Source: HGNC Symbol; Acc: 5478] [ENST00000390547] | XR_114797 |
| A_33_P3370019 | 0.05750756 | 1.3361309 | down | −0.1561117 | 0.26194954 | | immunoglobulin heavy constant delta [Source: HGNC Symbol; Acc: 5480] [ENST00000390556] | AK093943 |
| A_33_P3424591 | 0.029236636 | 1.4456568 | down | −0.15465923 | 0.3770659 | | immunoglobulin heavy constant gamma 1 (G1m marker) [Source: HGNC Symbol; Acc: 5525] [ENST00000390549] | CR611254 |
| A_33_P3263319 | 0.028584455 | 1.5212795 | down | −0.34599957 | 0.25928557 | | immunoglobulin heavy constant gamma 3 (G3m marker) [Source: HGNC Symbol; Acc: 5527] [ENST00000390551] | AY172958 |
| A_23_P361654 | 0.015799953 | 1.3459028 | down | −0.2903985 | 0.13817567 | | immunoglobulin kappa variable 1D-16 [Source: HGNC Symbol; Acc: 5748] [ENST00000492446] | BC073764 |
| A_24_P173566 | 0.025859203 | 1.3649294 | down | −0.15881252 | 0.29001373 | | immunoglobulin lambda variable 3-1 [Source: HGNC Symbol; Acc: 5896] [ENST00000390319] | X57818 |
| A_33_P3226085 | 0.053354543 | 1.4504704 | down | −0.117482714 | 0.41903824 | | immunoglobulin lambda variable 3-10 [Source: HGNC Symbol; Acc: 5897] [ENST00000390315] | AF063703 |
| A_33_P3287610 | 0.011096977 | 1.3215991 | down | −0.113103464 | 0.2891812 | | immunoglobulin lambda variable 3-12 [Source: HGNC Symbol; Acc: 5898] [ENST00000390313] | DQ098743 |
| A_33_P3424489 | 0.03241414 | 1.3218818 | down | −0.122637704 | 0.2799555 | | immunoglobulin lambda variable 3-25 [Source: HGNC Symbol; Acc: 5908] [ENST00000390305] | S73129 |
| A_33_P3251205 | 0.01186517 | 1.4074701 | down | −0.2519347 | 0.2411696 | | immunoglobulin lambda variable 3-9 (gene/pseudogene) [Source: HGNC Symbol; Acc: 5918] [ENST00000390316] | AF194657 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_33_P3398143 | 0.05249057 | 1.9251307 | up | 0.8772388 | -0.067711604 | ITGB2 | "integrin, beta 2 (complement component 3 receptor 3 and 4 subunit) [Source: HGNC Symbol; Acc: 6155] [ENST00000397846]" | |
| A_33_P3423721 | 0.001939164 | 1.3729306 | up | 0.2945948 | -0.16266395 | JPH3 | junctophilin 3 [Source: HGNC Symbol; Acc: 14203] [ENST00000301008] | AB593088 |
| A_33_P3399208 | 0.050488997 | 1.379161 | up | 0.03240173 | -0.43138912 | HLA-B*1531 | "major histocompatibility complex, class I, B [Source: HGNC Symbol; Acc: 4932] [ENST00000466304]" | AF298582 |
| A_33_P3409765 | 0.043177925 | 1.3497835 | down | -0.26763448 | 0.16509363 | MGAM | maltase-glucoamylase (alpha-glucosidase) [Source: HGNC Symbol; Acc: 7043] [ENST00000312952] | ENST00000312952 |
| A_23_P420942 | 0.07993442 | 1.3811071 | up | 0.5835465 | 0.11772156 | | metallothionein 1E [Source: HGNC Symbol; Acc: 73971 [ENST00000330439] | AF495759 |
| A_33_P3323699 | 0.089966744 | 1.4933032 | up | 0.6035198 | 0.025012754 | NPPA | natriuretic peptide A [Source: HGNC Symbol; Acc: 7939] [ENST00000376476] | ENST00000376476 |
| A_33_P3300495 | 2.46E-05 | 1.6870832 | down | -0.45745656 | 0.2970746 | | plasminogen-like B1 [Source: HGNC Symbol; Acc: 9072] [ENST00000409310] | BC022294 |
| A_33_P3221055 | 0.014507352 | 1.33372 | down | -0.2336753 | 0.18178049 | LOC100128729 | "PREDICTED: Homo sapiens hypothetical LOC100128729, transcript variant 1 (LOC100128729), partial miscRNA [XR_110743]" | XR_110743 |
| A_33_P3369245 | 0.07990449 | 1.3084261 | up | 0.4190942 | 0.031261757 | LOC100129826 | "PREDICTED: Homo sapiens hypothetical LOC100129826 (LOC100129826), miscRNA [XR_114456]" | XR_114456 |
| A_33_P3514859 | 2.30E-04 | 1.3660825 | down | -0.2139588 | 0.23608589 | LOC100506342 | "PREDICTED: Homo sapiens hypothetical LOC100506342 (LOC100506342), partial miscRNA [XR_108862]" | XR_108862 |
| A_33_P3589543 | 7.69E-04 | 1.349322 | down | -0.08960023 | 0.34263444 | | "PREDICTED: Homo sapiens hypothetical locus LOC692247 (LOC692247), miscRNA [XR_109057]" | XR_109057 |
| A_33_P3789693 | 0.017359855 | 1.3408446 | down | -0.33839023 | 0.084751904 | MGC24103 | "PREDICTED: Homo sapiens hypothetical MGC24103 (MGC24103), miscRNA [XR_108934]" | XR_108934 |
| A_33_P3214072 | 0.067344286 | 1.3672006 | up | 0.46909365 | 0.01786866 | LOC729175 | "PREDICTED: Homo sapiens hypothetical protein LOC729175 (LOC729175), mRNA [XM_001129558]" | XM_001129558 |
| A_33_P3402257 | 0.08375601 | 1.3421152 | up | 0.46482745 | 0.040318932 | LOC100508241 | "PREDICTED: Homo sapiens membrane-spanning 4-domains subfamily A member 18-like (LOC100508241), mRNA [XM_003119499]" | XM_003119499 |
| A_32_P49668 | 0.009767092 | 1.4546022 | down | -0.35131896 | 0.1893057 | LOC100510697 | "PREDICTED: Homo sapiens putative POM121-like protein 1-like (LOC100510697), mRNA [XM_003118465]" | XM_003118465 |
| A_24_P312325 | 4.08E-05 | 1.337715 | down | -0.27505833 | 0.14471245 | | "PREDICTED: Homo sapiens uncharacterized protein C8orf15-like (LOC100505981), mRNA [XM_003119008]" | XM_003119008 |
| A_23_P359870 | 1.74E-04 | 1.3308623 | down | -0.2763381 | 0.13602321 | | "PREDICTED: Homo sapiens uncharacterized protein C8orf16-like | XM_003119009 |

APPENDIX A-continued

| ProbeName | p | FC (abs) | Regulation | "[control, male](normalized)" | "[patient, male](normalized)" | GeneSymbol | Description | GenbankAccession |
|---|---|---|---|---|---|---|---|---|
| A_24_P316019 | 0.002571515 | 1.3050936 | down | −0.23434815 | 0.14980525 | | (LOC100506010), mRNA [XM_003119009]" Putative golgin subfamily A member 6-like protein 11 [Source: UniProtKB/Swiss-Prot; Acc: A6NCC3] [ENST00000333156] | XM_003118656 |
| A_33_P3292130 | 0.027860254 | 1.3341794 | up | −0.014861028 | −0.43081373 | | "Q2JG47_FRASC (Q2JG47) Methyltransferase type 11, partial (6%) [THC2566648]" | |
| A_33_P3369716 | 0.0608446 | 1.3832763 | down | −0.5539065 | −0.08581712 | | "Q9VKG5_DROME (Q9VKG5) CG14930-PA (AT28291p), partial (5%) [THC2679405]" | |
| A_33_P3254121 | 0.06008231 | 1.4974492 | up | 0.86985826 | 0.2873513 | RNASET2 | ribonuclease T2 [Source: HGNC Symbol; Acc: 21686] [ENST00000358165] | AK001769 |
| A_24_P24972 | 0.007481211 | 1.5367382 | up | 0.3232862 | −0.29658514 | | ribosomal protein L22 pseudogene 11 [Source: HGNC Symbol; Acc: 35603] [ENST00000538228] | CR590757 |
| A_32_P133090 | 0.0117861 | 1.3314247 | up | 0.28210762 | −0.13086325 | | "RST35951 Athersys RAGE Library Homo sapiens cDNA, mRNA sequence [BG216262]" | BG216262 |
| A_23_P311201 | 0.064578146 | 1.5723459 | up | 0.6262721 | −0.026644652 | | serine/arginine-rich splicing factor 10 [Source: HGNC Symbol; Acc: 16713] [ENST00000344989] | XM_003119082 |
| A_33_P3250750 | 0.00418700S | 1.8083831 | up | −0.119524024 | −0.9742244 | | Synthetic construct Homo sapiens gateway clone IMAGE: 100018551 3' read RAB35 mRNA. [CU677518] | CU677518 |
| A_33_P3233404 | 0.03517226 | 1.4829948 | down | −0.40898976 | 0.15952376 | | T cell receptor beta variable 28 [Source: HGNC Symbol; Acc: 12209] [ENST00000390400] | AB305916 |
| A_33_P3297545 | 0.002523841 | 1.7698867 | up | 1.0880127 | 0.26435575 | | T cell receptor beta variable 6-8 [Source: HGNC Symbol; Acc: 12233] [ENST00000390376] | |
| A_33_P3786807 | 0.005465086 | 1.3740717 | up | 0.13381559 | −0.32464167 | SNAR-E | "UI-H-DF1-auh-i-18-0-UI.s1 NCI_CGAP_DF1 Homo sapiens cDNA clone UI-H-DF1-auh-i-18-0-UI 3', mRNA sequence [CA436475]" | CA436475 |

APPENDIX B

MALES: Technology: Agilent.SingleColor:26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P120048 | BAZ2B | bromodomain adjacent to zinc finger domain, 2B (BAZ2B), mRNA [NM_013450] | NM_013450 | ENST00000392783 | 29994 | NM_013450 | THC2491976 |
| A_23_P250800 | ST3GAL6 | ST3 beta-galactoside alpha-2,3-sialyltransferase 6 (ST3GAL6), mRNA [NM_006100] | NM_006100 | ENST00000477899 | 10402 | NM_006100 | THC2493961 |
| A_23_P150583 | SCGB1A1 | secretoglobin, family 1A, member 1 (uteroglobin) (SCGB1A1), mRNA [NM_003357] | NM_003357 | ENST00000278282 | 7356 | NM_003357 | THC2472230 |
| A_23_P250302 | CCR3 | chemokine (C-C motif) receptor 3 (CCR3), transcript variant 1, mRNA [NM_001837] | NM_001837 | ENST00000357422 | 1232 | NM_001837 | THC2516499 |
| A_33_P3349637 | PCDH1 | protocadherin 1 (PCDH1), transcript variant 1, mRNA [NM_002587] | NM_002587 | ENST00000456271 | 5097 | NM_002587 | NP099071 |
| A_23_P131024 | ZBTB32 | zinc finger and BTB domain containing 32 (ZBTB32), mRNA [NM_014383] | NM_014383 | ENST00000262630 | 27033 | NM_014383 | THC2760977 |
| A_24_P272451 | C17orf87 | cDNA FLJ32580 fis, clone SPLEN2000270. [AK057142] | AK057142 | | 388325 | | THC2484848 |
| A_33_P3337609 | | chromosome 2 genomic contig, GRCh37.p5 | | | | | NP113779 |
| A_32_P396186 | TRIM66 | tripartite motif containing 66 (TRIM66), mRNA [NM_014818] | NM_014818 | ENST00000299550 | 9866 | NM_014818 | THC2602835 |
| A_23_P87879 | CD69 | CD69 molecule (CD69), mRNA [NM_001781] | NM_001781 | ENST00000228434 | 969 | NM_001781 | THC2461298 |
| A_33_P3287610 | | immunoglobulin lambda variable 3-12 [ENST00000390313] | DQ098743 | ENST00000390313 | | | NP1087705 |
| A_23_P109322 | PCP4 | Purkinje cell protein 4 (PCP4), mRNA [NM_006198] | NM_006198 | ENST00000468717 | 5121 | NM_006198 | THC2617631 |
| A_33_P3388016 | CCDC72 | coiled-coil domain containing 72 (CCDC72), mRNA [NM_015933] | NM_015933 | ENST00000477624 | 51372 | NM_015933 | THC2469917 |
| A_23_P23850 | DAB1 | disabled homolog 1 (Drosophila) (DAB1), mRNA [NM_021080] | NM_021080 | ENST00000371231 | 1600 | NM_021080 | THC2533734 |
| A_23_P56736 | TUBA3D | tubulin, alpha 3d (TUBA3D), mRNA [NM_080386] | NM_080386 | ENST00000321253 | 113457 | NM_080386 | THC2628673 |
| A_33_P3246010 | | cDNA FLJ35175 fis, clone PLACE6013400. [AK092494] | AK092494 | | | | THC2636441 |
| A_23_P113572 | CD19 | CD19 molecule (CD19), transcript variant 2, mRNA [NM_001770] | NM_001770 | ENST00000537306 | 930 | NM_001770 | THC2473305 |
| A_23_P50907 | ITGAV | integrin, alpha V (vitronectin receptor, alpha polypeptide, antigen CD51) (ITGAV), transcript variant 1, mRNA [NM_002210] | NM_002210 | ENST00000374907 | 3685 | NM_002210 | THC2544883 |
| A_23_P138881 | ACTN3 | actinin, alpha 3 (ACTN3), mRNA [NM_001104] | NM_001104 | ENST00000502692 | 89 | NM_001104 | THC2472718 |
| A_24_P110242 | | immunoglobulin heavy variable 3/OR16-8 (non-functional) [Source: HGNC Symbol; Acc: 5643] [ENST00000438532] | | ENST00000354689 | | | THC2579601 |
| A_33_P3412125 | | chromosome 19 genomic contig, GRCh37 | | | | | |
| A_33_P3254121 | RNASET2 | ribonuclease T2 [Source: HGNC Symbol; Acc: 21686] [ENST00000358165] | AK001769 | ENST00000358165 | 8635 | | THC2479694 |
| A_33_P3247534 | LOC389834 | ankyrin repeat domain 57 pseudogene (LOC389834), non-coding RNA [NR_027420] | NR_027420 | | 389834 | NR_027420 | THC2542997 |
| A_23_P316472 | DNHD1 | dynein heavy chain domain 1 (DNHD1), transcript variant 1, mRNA [NM_144666] | NM_144666 | ENST00000254579 | 144132 | NM_144666 | THC2629994 |
| A_33_P3415551 | GPAT2 | glycerol-3-phosphate acyltransferase 2, mitochondrial (GPAT2), nuclear gene encoding mitochondrial protein, mRNA [NM_207328] | NM_207328 | ENST00000377137 | 150763 | NM_207328 | THC2483887 |
| A_33_P3253234 | IQSEC2 | IQ motif and Sec7 domain 2 (IQSEC2), transcript variant 3, non-coding RNA [NR_024449] | NR_024449 | | 23096 | NR_024449 | THC2765959 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3277883 | LOC100129931 | hypothetical LOC100129931 (LOC100129931), non-coding RNA [NR_033828] | NR_033828 | | 100129931 | NR_033828 | THC2623255 |
| A_33_P3292844 | NEUROG3 | neurogenin 3 (NEUROG3), mRNA [NM_020999] | NM_020999 | ENST00000242462 | 50674 | NM_020999 | THC2483225 |
| A_33_P3356811 | LCE1E | late cornified envelope 1E (LCE1E), mRNA [NM_178353] | NM_178353 | ENST00000368771 | 353135 | NM_178353 | THC2643480 |
| A_33_P3412233 | POMZP3 | POM121 and ZP3 fusion (POMZP3), transcript variant 2, mRNA [NM_152992] | NM_152992 | ENST00000275569 | 22932 | NM_152992 | THC2487398 |
| A_33_P3223467 | VCPIP1 | valosin containing protein (p97)/p47 complex interacting protein 1 (VCPIP1), mRNA [NM_025054] | NM_025054 | ENST00000310421 | 80124 | NM_025054 | THC2602555 |
| A_33_P3304696 | | clone ASPBLL50 immunoglobulin lambda light chain VJ region mRNA, partial cds. [AF058072] | AF058072 | | | | THC2560573 |
| A_33_P3514487 | VSTM1 | V-set and transmembrane domain containing 1 (VSTM1), mRNA [NM_198481] | NM_198481 | ENST00000377626 | 284415 | NM_198481 | NP1474893 |
| A_32_P153725 | KIAA1033 | KIAA1033 (KIAA1033), mRNA [NM_015275] | NM_015275 | ENST00000550053 | 23325 | NM_015275 | THC2601307 |
| A_23_P94009 | NAA38 | N(alpha)-acetyltransferase 38, NatC auxiliary subunit (NAA38), mRNA [NM_016200] | NM_016200 | ENST00000249299 | 51691 | NM_016200 | THC2492301 |
| A_23_P375419 | TTC16 | tetratricopeptide repeat domain 16 (TTC16), mRNA [NM_144965] | NM_144965 | ENST00000316259 | 158248 | NM_144965 | THC2491012 |
| A_33_P3327470 | | Q6I984_HUMAN (Q6I984) Acidic neurotrophin 6 alpha (Fragment), complete [THC2606816] | | | | | THC2606816 |
| A_23_P156826 | C6orf105 | chromosome 6 open reading frame 105 (C6orf105), transcript variant 2, mRNA [NM_032744] | NM_032744 | ENST00000514824 | 84830 | NM_032744 | THC2473206 |
| A_33_P3378284 | COX6B2 | cytochrome c oxidase subunit VIb polypeptide 2 (testis) (COX6B2), mRNA [NM_144613] | NM_144613 | ENST00000326529 | 125965 | NM_144613 | NP1157598 |
| A_24_P28811 | C2orf14 | chromosome 2 open reading frame 14 (C2orf14), non-coding RNA [NR_023391] | NR_023391 | ENST00000439137 | 100132708 | NR_023391 | THC2535623 |
| A_33_P21425 | GPR119 | G protein-coupled receptor 119 (GPR119), mRNA [NM_178471] | NM_178471 | ENST00000276218 | 139760 | NM_178471 | THC2479570 |
| A_33_P3317431 | | chromosome 7 genomic contig, GRCh37 | | | | | |
| A_33_P3411315 | KRTAP3-3 | keratin associated protein 3-3 (KRTAP3-3), mRNA [NM_033185] | NM_033185 | ENST00000391586 | 85293 | NM_033185 | THC2485385 |
| A_23_P44724 | CSRP2 | cysteine and glycine-rich protein 2 (CSRP2), mRNA [NM_001321] | NM_001321 | ENST00000548783 | 1466 | NM_001321 | NP1153753 |
| A_23_P157007 | TMEM176B | transmembrane protein 176B (TMEM176B), transcript variant 1, mRNA [NM_014020] | NM_014020 | ENST00000528038 | 28959 | NM_014020 | THC2467726 |
| A_23_P84910 | ZNF157 | zinc finger protein 157 (ZNF157), mRNA [NM_003446] | NM_003446 | ENST00000377073 | 7712 | NM_003446 | THC2478782 |
| A_23_P53467 | IKBIP | IKBKB interacting protein (IKBIP), transcript variant 2, mRNA [NM_201612] | NM_201612 | ENST00000393042 | 121457 | NM_201612 | THC2478224 |
| A_23_P3246995 | | chromosome 7 genomic contig, GRCh37 | | | | | |
| A_23_P157117 | CREB5 | cAMP responsive element binding protein 5 (CREB5), transcript variant 1, mRNA [NM_182898] | NM_182898 | ENST00000409603 | 9586 | NM_182898 | NP082957 |
| A_23_P3281435 | | immunoglobulin kappa variable 1D-8 [Source: HGNC Symbol; Acc: 5759] [ENST00000471857] | AF035035 | ENST00000471857 | | | THC2548990 |
| A_33_P3389394 | RPPH1 | ribonuclease P RNA component H1 (RPPH1), RNase P RNA [NR_002312] | NR_002312 | | 85495 | NR_002312 | THC2674967 |
| A_33_P3345036 | POMC | proopiomelanocortin (POMC), transcript variant 1, mRNA [NM_001035256] | NM_001035256 | ENST00000395826 | 5443 | NM_001035256 | THC2481015 |
| A_33_P3227686 | FLJ43860 | FLJ43860 protein (FLJ43860), mRNA [NM_207414] | NM_207414 | ENST00000521053 | 389690 | NM_207414 | THC2480285 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3281437 | | immunoglobulin kappa variable 1D-8 [Source: HGNC Symbol; Acc: 5759] [ENST00000471857] | AF035035 | ENST00000471857 | | | NP1465439 |
| A_33_P3327592 | RNF13 | ring finger protein 13 (RNF13), transcript variant 1, mRNA [NM_007282] | NM_007282 | ENST00000392894 | 11342 | NM_007282 | THC2483942 |
| A_23_P30956 | KIAA0776 | KIAA0776 (KIAA0776), mRNA [NM_015323] | NM_015323 | ENST00000369278 | 23376 | NM_015323 | THC2461444 |
| A_33_P3371785 | DTNA | dystrobrevin, alpha (DTNA), transcript variant 9, mRNA [NM_001128175] | NM_001128175 | ENST00000315456 | 1837 | NM_001128175 | THC2748155 |
| A_33_P3377399 A_32_P211248 | LOC100131138 | hypothetical LOC100131138 (LOC100131138), non-coding RNA [NR_036513] | NR_036513 | ENST00000520078 | 100131138 | NR_036513 | THC2471096 |
| A_33_P3287105 A_33_P3245841 A_23_P213661 | PPIP5K2 | diphosphoinositol pentakisphosphate kinase 2 (PPIP5K2), mRNA [NM_015216] | NM_015216 | ENST00000451606 | 23262 | NM_015216 | THC2462111 |
| A_33_P3354539 | CHURC1 | churchill domain containing 1 (CHURC1), transcript variant 1, mRNA [NM_145165] | NM_145165 | ENST00000359118 | 91612 | NM_145165 | |
| A_24_P15765 | RPS7P5 | ribosomal protein S7 pseudogene 5 (RPS7P5), non-coding RNA [NR_036695] | NR_036695 | | 645884 | NR_036695 | THC2681026 |
| A_23_P384857 | | chromosome 6 genomic contig | | | | | NP274062 |
| A_24_P274615 | ARRDC3 | arrestin domain containing 3 (ARRDC3), mRNA [NM_020801] | NM_020801 | ENST00000265138 | 57561 | NM_020801 | THC2491990 |
| A_33_P3397150 | FLJ22184 | hypothetical protein FLJ22184 (FLJ22184), mRNA [NM_001190467] | NM_001190467 | ENST00000327607 | 80164 | NM_001190467 | THC2477241 |
| A_23_P257478 | CYP21A2 | cytochrome P450, family 21, subfamily A, polypeptide 2 (CYP21A2), transcript variant 1, mRNA [NM_000500] | NM_000500 | ENST00000547683 | 1589 | NM_000500 | THC2469155 |
| A_32_P334325 | RIMBP2 | RIMS binding protein 2 (RIMBP2), mRNA [NM_015347] | NM_015347 | ENST00000392375 | 23504 | NM_015347 | THC2782045 |
| A_24_P235988 | CLEC7A | C-type lectin domain family 7, member A (CLEC7A), transcript variant 1, mRNA [NM_197947] | NM_197947 | ENST00000534609 | 64581 | NM_197947 | THC2485854 |
| A_23_P83073 | HIATL1 | hippocampus abundant transcript-like 1 (HIATL1), mRNA [NM_032558] | NM_032558 | ENST00000375344 | 84641 | NM_032558 | THC2465988 |
| A_23_P110362 | LAMTOR3 | late endosomal/lysosomal adaptor, MAPK and MTOR activator 3 (LAMTOR3), transcript variant 1, mRNA [NM_021970] | NM_021970 | ENST00000515100 | 8649 | NM_021970 | THC2609212 |
| A_23_P2129 | TMEM126B | transmembrane protein 126B (TMEM126B), transcript variant 1, mRNA [NM_018480] | NM_018480 | ENST00000530783 | 55863 | NM_018480 | THC2619491 |
| A_23_P10559 | AATK | apoptosis-associated tyrosine kinase (AATK), transcript variant 1, mRNA [NM_001080395] | NM_001080395 | ENST00000374792 | 9625 | NM_001080395 | THC2471583 |
| A_32_P230868 | FAM65A | family with sequence similarity 65, member A (FAM65A), transcript variant 1, mRNA [NM_024519] | NM_024519 | ENST00000422602 | 79567 | NM_024519 | THC2468574 |
| A_33_P3300495 | | plasminogen-like B1 [Source: HGNC Symbol; Acc: 9072] [ENST00000409310] | BC022294 | ENST00000409310 | | | THC2475376 |
| A_33_P3360814 | NFE4 | transcription factor NF-E4 (NFE4), mRNA [NM_001085386] | NM_001085386 | | 58160 | NM_001085386 | NP1072324 |
| A_24_P172768 | GMFB | glia maturation factor, beta (GMFB), mRNA [NM_004124] | NM_004124 | ENST00000358056 | 2764 | NM_004124 | THC2494751 |
| A_23_P140069 | FBXL3 | F-box and leucine-rich repeat protein 3 (FBXL3), mRNA [NM_012158] | NM_012158 | ENST00000355619 | 26224 | NM_012158 | THC2468176 |
| A_33_P3244347 | PC | pyruvate carboxylase (PC), nuclear gene encoding mitochondrial protein, transcript variant 3, mRNA [NM_001040716] | NM_001040716 | ENST00000393960 | 5091 | NM_001040716 | THC2463909 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_24_P117147 | KIR3DL1 | killer cell immunoglobulin-like receptor, three domains, long cytoplasmic tail, 1 (KIR3DL1), mRNA [NM_013289] | NM_013289 | ENST00000400847 | 3811 | NM_013289 | THC2470697 |
| A_24_P281395 | | C1D nuclear receptor corepressor pseudogene 3 [Source: HGNC Symbol; Acc: 31661] [ENST00000412019] | XM_003119469 | ENST00000412019 | | XM_003119469 | |
| A_23_P983 | PRDX6 | peroxiredoxin 6 (PRDX6), mRNA [NM_004905] | NM_004905 | ENST00000470017 | 9588 | NM_004905 | THC2531006 |
| A_23_P422083 | TMEM55A | transmembrane protein 55A (TMEM55A), mRNA [NM_018710] | NM_018710 | ENST00000283419 | 55529 | NM_018710 | THC2463130 |
| A_23_P429491 | C11orf82 | chromosome 11 open reading frame 82 (C11orf82), mRNA [NM_145018] | NM_145018 | ENST00000329143 | 220042 | NM_145018 | THC2642949 |
| A_23_P116614 | ME3 | malic enzyme 3, NADP(+)-dependent, mitochondrial (ME3), nuclear gene encoding mitochondrial protein, transcript variant 2, mRNA [NM_001014811] | NM_001014811 | ENST00000393324 | 10873 | NM_001014811 | THC2614244 |
| A_23_P31671 | UQCRB | ubiquinol-cytochrome c reductase binding protein (UQCRB), nuclear gene encoding mitochondrial protein, transcript variant 1, mRNA [NM_006294] | NM_006294 | ENST00000521948 | 7381 | NM_006294 | THC2546410 |
| A_33_P3350643 | LMX1B | LIM homeobox transcription factor 1, beta (LMX1B), transcript variant 3, mRNA [NM_001174146] | NM_001174146 | ENST00000355497 | 4010 | NM_001174146 | THC2611342 |
| A_33_P3324878 | GOLGA6L9 | golgin A6 family-like 9 (GOLGA6L9), mRNA [NM_198181] | NM_198181 | ENST00000306827 | 440295 | NM_198181 | THC2475605 |
| A_24_P100517 | C9orf140 | chromosome 9 open reading frame 140 (C9orf140), mRNA [NM_178448] | NM_178448 | ENST00000409687 | 89958 | NM_178448 | THC2461698 |
| A_33_P3250750 | | Synthetic construct gateway clone IMAGE: 100018551 3' read RAB35 mRNA. [CU677518] | CU677518 | | | | |
| A_33_P3370226 | RPL7 | ribosomal protein L7 (RPL7), mRNA [NM_000971] | NM_000971 | ENST00000352983 | 6129 | NM_000971 | THC2551101 |
| A_33_P3700019 | | immunoglobulin heavy constant delta [Source: HGNC Symbol; Acc: 5480] [ENST00000390556] | AK093943 | ENST00000390556 | | | THC2503414 |
| A_33_P3280950 | LOC144571 | hypothetical LOC144571 (LOC144571), non-coding RNA [NR_026971] | NR_026971 | | 144571 | NR_026971 | THC2505447 |
| A_32_P207124 | CT47A11 | cancer/testis antigen family 47, member A11 (CT47A11), mRNA [NM_173571] | NM_173571 | ENST00000371280 | 255313 | NM_173571 | THC2477537 |
| A_24_P50554 | | | | | | | |
| A_33_P3354203 | NELL1 | NEL-like 1 (chicken) [Source: HGNC Symbol; Acc: 7750] [ENST00000534263] | AB085898 | ENST00000534263 | 4745 | | THC2486544 |
| A_33_P3335920 | SYNE1 | spectrin repeat containing, nuclear envelope 1 (SYNE1), transcript variant 1, mRNA [NM_182961] | NM_182961 | ENST00000367255 | 23345 | NM_182961 | NP1154489 |
| A_23_P216023 | ANGPT1 | angiopoietin 1 (ANGPT1), transcript variant 1, mRNA [NM_001146] | NM_001146 | ENST00000395820 | 284 | NM_001146 | THC2463915 |
| A_23_P119593 | EPHX3 | epoxide hydrolase 3 (EPHX3), transcript variant 1, mRNA [NM_024794] | NM_024794 | ENST00000435261 | 79852 | NM_024794 | THC2653397 |
| A_24_P50554 | | | | | | | |
| A_33_P3233981 | NASP | nuclear autoantigenic sperm protein (histone-binding) (NASP), transcript variant 2, mRNA [NM_002482] | NM_002482 | ENST00000481782 | 4678 | NM_002482 | THC2496068 |
| A_33_P3283906 | NIP7 | nuclear import 7 homolog (S. cerevisiae) (NIP7), transcript variant 1, mRNA [NM_016101] | NM_016101 | ENST00000254941 | 51388 | NM_016101 | THC2482970 |
| A_23_P114414 | LONRF3 | LON peptidase N-terminal domain and ring finger 3 (LONRF3), transcript variant 1, mRNA [NM_001031855] | NM_001031855 | ENST00000371628 | 79836 | NM_001031855 | THC2485491 |
| A_33_P3316928 | PELI1 | pellino homolog 1 (Drosophila) (PELI1), mRNA [NM_020651] | NM_020651 | ENST00000358912 | 57162 | NM_020651 | THC2468725 |
| A_23_P143526 | S100B | S100 calcium binding protein B (S100B), mRNA [NM_006272] | NM_006272 | ENST00000291700 | 6285 | NM_006272 | THC2260592 |
| A_23_P501080 | ZNF92 | zinc finger protein 92 (ZNF92), transcript variant 1, mRNA [NM_007139] | NM_007139 | ENST00000450302 | 168374 | NM_007139 | THC2470444 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P101374 | CYP2S1 | cytochrome P450, family 2, subfamily S, polypeptide 1 (CYP2S1), mRNA [NM_030622] | NM_030622 | ENST00000310054 | 29785 | NM_030622 | THC2546669 |
| A_24_P66125 | STAG2 | stromal antigen 2 (STAG2), transcript variant 1, mRNA [NM_001042749] | NM_001042749 | ENST00000371160 | 10735 | NM_001042749 | THC2787590 |
| A_23_P167856 | TMEM63B | transmembrane protein 63B (TMEM63B), mRNA [NM_018426] | NM_018426 | ENST00000323267 | 55362 | NM_018426 | THC2462238 |
| A_23_P143774 | MOV10L1 | Mov10l1, Moloney leukemia virus 10-like 1, homolog (mouse) (MOV10L1), transcript variant 1, mRNA [NM_018995] | NM_018995 | ENST00000545383 | 54456 | NM_018995 | THC2473678 |
| A_23_P3364741 | MRC2 | mannose receptor, C type 2 (MRC2), mRNA [NM_006039] | NM_006039 | ENST00000303375 | 9902 | NM_006039 | THC2608201 |
| A_33_P3613358 | | cDNA FLJ39824 fis, clone SPLEN2011981. [AK097143] | AK097143 | | | | THC2489859 |
| A_33_P3499692 | LOC645261 | PP565 mRNA, complete cds. [AF258587] | AF258587 | | 645261 | | NP1472476 |
| A_33_P3270451 | TXNDC5 | thioredoxin domain containing 5 (endoplasmic reticulum) (TXNDC5), transcript variant 1, mRNA [NM_030810] | NM_030810 | ENST00000439343 | 81567 | NM_030810 | THC2520615 |
| A_33_P3375451 | NYNRIN | NYN domain and retroviral integrase containing (NYNRIN), mRNA [NM_025081] | NM_025081 | ENST00000206466 | 57523 | NM_025081 | THC2483568 |
| A_33_P3358957 | PAPL | iron/zinc purple acid phosphatase-like protein (PAPL), mRNA [NM_001004318] | NM_001004318 | ENST00000331256 | 390928 | NM_001004318 | THC2482977 |
| A_23_P3231888 | C5orf15 | chromosome 5 open reading frame 15 (C5orf15), mRNA [NM_020199] | NM_020199 | ENST00000451255 | 56951 | NM_020199 | THC2469485 |
| A_23_P122724 | VNN2 | vanin 2 (VNN2), transcript variant 1, mRNA [NM_004665] | NM_004665 | ENST00000392389 | 8875 | NM_004665 | NP195731 |
| A_23_P204850 | RB1 | retinoblastoma 1 (RB1), mRNA [NM_000321] | NM_000321 | ENST00000267163 | 5925 | NM_000321 | THC2601211 |
| A_24_P317450 | OSTCL | oligosaccharyltransferase complex subunit-like (OSTCL), non-coding RNA [NR_028496] | NR_028496 | ENST00000522287 | 202459 | NR_028496 | THC2486050 |
| A_33_P3227774 | AGSK1 | golgin subfamily A member 2-like (AGSK1), non-coding RNA [NR_026811] | NR_026811 | ENST00000357253 | 80154 | NR_026811 | THC2476453 |
| A_23_P207058 | SOCS3 | suppressor of cytokine signaling 3 (SOCS3), mRNA [NM_003955] | NM_003955 | ENST00000330871 | 9021 | NM_003955 | THC2461868 |
| A_24_P228130 | CCL3L3 | chemokine (C-C motif) ligand 3-like 3 (CCL3L3), mRNA [NM_001001437] | NM_001001437 | ENST00000425833 | 414062 | NM_001001437 | THC2605779 |
| A_24_P922631 | C5orf58 | chromosome 5 open reading frame 58 (C5orf58), mRNA [NM_001102609] | NM_001102609 | ENST00000521850 | 133874 | NM_001102609 | THC2771591 |
| A_33_P3416762 | LYPLA1 | lysophospholipase I (LYPLA1), mRNA [NM_006330] | NM_006330 | ENST00000316963 | 10434 | NM_006330 | THC2469064 |
| A_33_P3358740 | OSBPL7 | oxysterol binding protein-like 7 (OSBPL7), transcript variant 1, mRNA [NM_145798] | NM_145798 | ENST00000007414 | 114881 | NM_145798 | THC2471195 |
| A_23_P26468 | RHBDL1 | rhomboid, veinlet-like 1 (Drosophila) (RHBDL1), mRNA [NM_003961] | NM_003961 | ENST00000219551 | 9028 | NM_003961 | THC2606656 |
| A_24_P134195 | MYADM | myeloid-associated differentiation marker (MYADM), transcript variant 1, mRNA [NM_001020818] | NM_001020818 | ENST00000415619 | 91663 | NM_001020818 | THC2480965 |
| A_23_P65768 | RSL24D1 | ribosomal L24 domain containing 1 (RSL24D1), mRNA [NM_016304] | NM_016304 | ENST00000260443 | 51187 | NM_016304 | THC2535982 |
| A_32_P8813 | LOC283663 | hypothetical LOC283663 (LOC283663), non-coding RNA [NR_024433] | NR_024433 | | 283663 | NR_024433 | THC2513469 |
| A_33_P3274001 | | | | | | | |
| A_23_P103034 | CRYBA4 | crystallin, beta A4 (CRYBA4), mRNA [NM_001886] | NM_001886 | ENST00000466315 | 1413 | NM_001886 | THC2467739 |
| A_23_P116765 | LALBA | lactalbumin, alpha- (LALBA), mRNA [NM_002289] | NM_002289 | ENST00000301046 | 3906 | NM_002289 | THC2481150 |
| A_33_P3407105 | YTHDF1 | YTH domain family, member 1 (YTHDF1), mRNA [NM_017798] | NM_017798 | ENST00000342761 | 54915 | NM_017798 | THC2465870 |
| A_33_P3768930 | | MYE4344 Myeloma (MYE) cDNA library cDNA, mRNA sequence [BF175071] | BF175071 | | | | THC2543611 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_24_P272917 | USP17 | ubiquitin specific peptidase 17 (USP17), mRNA [NM_001105662] | NM_001105662 | ENST00000421288 | 391627 | NM_001105662 | THC2525229 |
| A_33_P3223869 A_23_P3258324 A_23_P134684 | HMBOX1 | homeobox containing 1 (HMBOX1), transcript variant 1, mRNA [NM_024567] | NM_024567 | ENST00000521516 | 79618 | NM_024567 | THC2498923 |
| A_23_P11843 | LRRN2 | leucine rich repeat neuronal 2 (LRRN2), transcript variant 2, mRNA [NM_201630] | NM_201630 | ENST00000367175 | 10446 | NM_201630 | THC2471115 |
| A_24_P183864 | IMPA1 | inositol(myo)-1(or 4)-monophosphatase 1 (IMPA1), transcript variant 1, mRNA [NM_005536] | NM_005536 | ENST00000256108 | 3612 | NM_005536 | THC2466293 |
| A_23_P8763 | PTPN12 | protein tyrosine phosphatase, non-receptor type 12 (PTPN12), transcript variant 1, mRNA [NM_002835] | NM_002835 | ENST00000248594 | 5782 | NM_002835 | THC2466264 |
| A_23_P217384 | AP1S2 | adaptor-related protein complex 1, sigma 2 subunit (AP1S2), mRNA [NM_003916] | NM_003916 | ENST00000329235 | 8905 | NM_003916 | THC2618612 |
| A_33_P3227320 | MIER3 | mesoderm induction early response 1, family member 3 (MIER3), mRNA [NM_152622] | NM_152622 | ENST00000452157 | 166968 | NM_152622 | THC2634883 |
| A_33_P3232038 | RBAK-LOC389458 | RBAK-LOC389458 readthrough (RBAK-LOC389458), mRNA [NM_001204513] | NM_001204513 | ENST00000498308 | 100533952 | NM_001204513 | THC2464334 |
| A_33_P3259708 A_33_P3263319 | CMA1 | chymase 1, mast cell (CMA1), mRNA [NM_001836] immunoglobulin heavy constant gamma 3 (G3m marker) [Source: HGNC Symbol; Acc: 5527] [ENST00000390551] | NM_001836 AY172958 | ENST00000206446 ENST00000390551 | 1215 | NM_001836 | THC2480549 NP594088 |
| A_23_P324495 | ZFP41 | zinc finger protein 41 homolog (mouse) (ZFP41), mRNA [NM_173832] | NM_173832 | ENST00000330701 | 286128 | NM_173832 | THC2498694 |
| A_33_P3339202 A_23_P500271 | IRF5 | interferon regulatory factor 5 (IRF5), transcript variant 3, mRNA [NM_001098627] | NM_001098627 | ENST00000412326 | 3663 | NM_001098627 | THC2489805 |
| A_33_P3246950 | | BX117927 Soares_NFL_T_GBC_S1 cDNA clone IMAGp998E153901, mRNA sequence [BX117927] | BX117927 | ENST00000434321 | | | THC2685258 |
| A_24_P65722 | LILRB4 | leukocyte immunoglobulin-like receptor, subfamily B (with TM and ITIM domains), member 4 [Source: HGNC Symbol; Acc: 6608] [ENST00000391736] | BC026309 | ENST00000391736 | 11006 | | THC2464369 |
| A_23_P3424222 | HLA-DQB1 | major histocompatibility complex, class II, DQ beta 1 (HLA-DQB1), mRNA [NM_002123] | NM_002123 | ENST00000484729 | 3119 | NM_002123 | THC2557334 |
| A_23_P252082 | TMEM176A | transmembrane protein 176A (TMEM176A), mRNA [NM_018487] | NM_018487 | ENST00000484928 | 55365 | NM_018487 | THC2624423 |
| A_33_P3460043 | C8orf56 | chromosome 8 open reading frame 56 (C8orf56), non-coding RNA [NR_027071] | NR_027071 | ENST00000436771 | 157556 | NR_027071 | THC2481642 |
| A_33_P3292130 | | Q2JG47_FRASC (Q2JG47) Methyltransferase type 11, partial (6%) [THC2566648] | | | | | THC2566648 |
| A_23_P72503 | KLHL2 | kelch-like 2, Mayven (Drosophila) (KLHL2), transcript variant 1, mRNA [NM_007246] | NM_007246 | ENST00000226725 | 11275 | NM_007246 | THC2464595 |
| A_23_P8640 | GPER | G protein-coupled estrogen receptor 1 (GPER), transcript variant 3, mRNA [NM_001039966] | NM_001039966 | ENST00000508834 | 2852 | NM_001039966 | THC2471419 |
| A_23_P18325 | PDCD10 | programmed cell death 10 (PDCD10), transcript variant 1, mRNA [NM_007217] | NM_007217 | ENST00000470131 | 11235 | NM_007217 | THC2764223 |
| A_33_P3372189 | | . Similar to LOC223018, clone IMAGE: 4732541, mRNA. [BC029410] | BC029410 | | | | THC2501412 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3234641 A_23_P259863 | CD177 | CD177 molecule (CD177), mRNA [NM_020406] | NM_020406 | ENST00000378009 | 57126 | NM_020406 | NP924649 |
| A_23_P145006 | SCGB3A2 | secretoglobin, family 3A, member 2 (SCGB3A2), mRNA [NM_054023] | NM_054023 | ENST00000507160 | 117156 | NM_054023 | THC2472125 |
| A_33_P3410849 | C8orf58 | chromosome 8 open reading frame 58 (C8orf58), transcript variant 1, mRNA [NM_001013842] | NM_001013842 | ENST00000381191 | 541565 | NM_001013842 | THC2609844 |
| A_23_P18372 | B3GNT5 | UDP-GlcNAc: betaGal beta-1,3-N-acetylglucosaminyltransferase 5 (B3GNT5), mRNA [NM_032047] | NM_032047 | ENST00000326505 | 84002 | NM_032047 | THC2462855 |
| A_23_P44257 | COMMD8 | COMM domain containing 8 (COMMD8), mRNA [NM_017845] | NM_017845 | ENST00000381571 | 54951 | NM_017845 | THC2602334 |
| A_23_P55356 | VMO1 | vitelline membrane outer layer 1 homolog (chicken) (VMO1), transcript variant 1, mRNA [NM_182566] | NM_182566 | ENST00000441199 | 284013 | NM_182566 | THC2477391 |
| A_33_P3352349 | KRTAP9-1 | keratin associated protein 9-1 (KRTAP9-1), mRNA [NM_001190460] | NM_001190460 | ENST00000377723 | 728318 | NM_001190460 | |
| A_24_P230328 A_32_P159192 | SUB1 | SUB1 homolog (S. cerevisiae) (SUB1), mRNA [NM_006713] immunoglobulin kappa variable 3-7 (non-functional) [Source: HGNC Symbol; Acc: 5821] [ENST00000390247] | NM_006713 X85155 | ENST00000511988 ENST00000390247 | 10923 | NM_006713 | THC2521496 |
| A_23_P113005 | EFNA1 | ephrin-A1 (EFNA1), transcript variant 1, mRNA [NM_004428] | NM_004428 | ENST00000469878 | 1942 | NM_004428 | THC2506968 |
| A_24_P297537 | MAMSTR | MEF2 activating motif and SAP domain containing transcriptional regulator (MAMSTR), transcript variant 2, mRNA [NM_182574] | NM_182574 | ENST00000356751 | 284358 | NM_182574 | THC2487203 |
| A_23_P2431 | C3AR1 | complement component 3a receptor 1 (C3AR1), mRNA [NM_004054] | NM_004054 | ENST00000307637 | 719 | NM_004054 | THC2461342 |
| A_24_P408955 | E2F2 | E2F transcription factor 2 (E2F2), mRNA [NM_004091] | NM_004091 | ENST00000361729 | 1870 | NM_004091 | THC2471250 |
| A_33_P3383606 | KCP | kielin/chordin-like protein (KCP), transcript variant 1, mRNA [NM_001135914] | NM_001135914 | ENST00000476647 | 375616 | NM_001135914 | THC2609353 |
| A_23_P86801 | RAPSN | receptor-associated protein of the synapse (RAPSN), transcript variant 2, mRNA [NM_032645] | NM_032645 | ENST00000352508 | 5913 | NM_032645 | NP091080 |
| A_24_P363745 | LRRC14 | leucine rich repeat containing 14 (LRRC14), mRNA [NM_014665] | NM_014665 | ENST00000292524 | 9684 | NM_014665 | |
| A_33_P3374117 | | anoctamin 7-like 1 [Source: HGNC Symbol; Acc: 32248] [ENST00000475369] | BU656309 | ENST00000475369 | | | THC2713054 |
| A_24_P626951 | | immunoglobulin kappa variable 1-16 [Source: HGNC Symbol; Acc: 5732] [ENST00000479981] | AF078945 | ENST00000479981 | | | NP074934 |
| A_23_P77980 | SLC4A1 | solute carrier family 4, anion exchanger, member 1 (erythrocyte membrane protein band 3, Diego blood group) (SLC4A1), mRNA [NM_000342] | NM_000342 | ENST00000262418 | 6521 | NM_000342 | THC2474664 |
| A_23_P99693 | ZBTB1 | zinc finger and BTB domain containing 1 (ZBTB1), transcript variant 2, mRNA [NM_014950] | NM_014950 | ENST00000358738 | 22890 | NM_014950 | THC2505601 |
| A_32_P178966 | TMEM170B | transmembrane protein 170B (TMEM170B), mRNA [NM_001100829] | NM_001100829 | ENST00000379426 | 100113407 | NM_001100829 | THC2634604 |
| A_33_P3332627 A_33_P3334895 | GRIN2A | glutamate receptor, ionotropic, N-methyl D-aspartate 2A (GRIN2A), transcript variant 3, mRNA [NM_001134408] | NM_001134408 | ENST00000396575 | 2903 | NM_001134408 | THC2475567 |
| A_23_P20275 | PLEKHF2 | pleckstrin homology domain containing, family F (with FYVE domain) member 2 (PLEKHF2), mRNA [NM_024613] | NM_024613 | ENST00000315367 | 79666 | NM_024613 | THC2462394 |
| A_23_P111583 | CD36 | CD36 molecule (thrombospondin receptor) (CD36), transcript variant 2, mRNA [NM_001001547] | NM_001001547 | ENST00000419819 | 948 | NM_001001547 | NP097737 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3251901 | APBB2 | amyloid beta (A4) precursor protein-binding, family B, member 2 (APBB2), transcript variant 1, mRNA [NM_004307] | NM_004307 | ENST00000316212 | 323 | NM_004307 | THC2536043 |
| A_32_P145153 | RPL31 | ribosomal protein L31 (RPL31), transcript variant 1, mRNA [NM_000993] | NM_000993 | ENST00000456292 | 6160 | NM_000993 | THC2465680 |
| A_32_P31182 | RPL7 | ribosomal protein L7 (RPL7), mRNA [NM_000971] | NM_000971 | ENST00000352983 | 6129 | NM_000971 | THC2573169 |
| A_33_P3620488 | CATSPERG | cation channel, sperm-associated, gamma (CATSPERG), mRNA [NM_021185] | NM_021185 | ENST00000492088 | 57828 | NM_021185 | NP1144122 |
| A_33_P3235891 | | cDNA FLJ46681 fis, clone TRACH3010382. [AK128523] | AK128523 | | | | |
| A_23_P211047 | BACH1 | BTB and CNC homology 1, basic leucine zipper transcription factor 1 (BACH1), transcript variant 1, mRNA [NM_206866] | NM_206866 | ENST00000399921 | 571 | NM_206866 | THC2646890 |
| A_32_P192474 | PRRT1 | proline-rich transmembrane protein 1 (PRRT1), mRNA [NM_030651] | NM_030651 | ENST00000375152 | 80863 | NM_030651 | THC2463883 |
| A_23_P59798 | MKRN1 | makorin ring finger protein 1 (MKRN1), transcript variant 1, mRNA [NM_013446] | NM_013446 | ENST00000539898 | 23608 | NM_013446 | THC2508588 |
| A_33_P3229288 | ACE | angiotensin I converting enzyme (peptidyl-dipeptidase A) 1 (ACE), transcript variant 1, mRNA [NM_000789] | NM_000789 | ENST00000290863 | 1636 | NM_000789 | THC2470503 |
| A_23_P7144 | CXCL1 | chemokine (C-X-C motif) ligand 1 (melanoma growth stimulating activity, alpha) (CXCL1), mRNA [NM_001511] | NM_001511 | ENST00000395761 | 2919 | NM_001511 | THC2462921 |
| A_23_P152002 | BCL2A1 | BCL2-related protein A1 (BCL2A1), transcript variant 1, mRNA [NM_004049] | NM_004049 | ENST00000267953 | 597 | NM_004049 | THC2486797 |
| A_24_P196592 | MMP28 | matrix metallopeptidase 28 (MMP28), transcript variant 3, mRNA [NM_001032278] | NM_001032278 | ENST00000250144 | 79148 | NM_001032278 | THC2778644 |
| A_23_P149375 | THEM4 | thioesterase superfamily member 4 (THEM4), mRNA [NM_053055] | NM_053055 | ENST00000483207 | 117145 | NM_053055 | THC2516317 |
| A_33_P3359012 | DUSP8 | dual specificity phosphatase 8 (DUSP8), mRNA [NM_004420] | NM_004420 | ENST00000331588 | 1850 | NM_004420 | THC2474457 |
| A_24_P13041 | RTKN2 | rhotekin 2 (RTKN2), mRNA [NM_145307] | NM_145307 | ENST00000373789 | 219790 | NM_145307 | |
| A_23_P142070 | TSPAN16 | tetraspanin 16 (TSPAN16), mRNA [NM_012466] | NM_012466 | ENST00000316737 | 26526 | NM_012466 | THC2483075 |
| A_23_P303260 | STX7 | syntaxin 7 (STX7), mRNA [NM_003569] | NM_003569 | ENST00000367941 | 8417 | NM_003569 | THC2468285 |
| A_33_P3272823 | MAG | myelin associated glycoprotein (MAG), transcript variant 1, mRNA [NM_002361] | NM_002361 | ENST00000262624 | 4099 | NM_002361 | THC2517997 |
| A_33_P3424612 | | immunoglobulin kappa variable 3-11 [Source: HGNC Symbol; Acc: 5815] [ENST00000483158] | XM_003120829 | ENST00000483158 | | XM_003120829 | NP1455229 |
| A_23_P112187 | FIBCD1 | fibrinogen C domain containing 1 (FIBCD1), transcript variant 1, mRNA [NM_032843] | NM_032843 | ENST00000372338 | 84929 | NM_032843 | THC2474476 |
| A_23_P3602 | NUDT7 | nudix (nucleoside diphosphate linked moiety X)-type motif 7 (NUDT7), transcript variant 1, mRNA [NM_001105663] | NM_001105663 | ENST00000268533 | 283927 | NM_001105663 | THC2521963 |
| A_33_P3278475 A_33_P3399755 | FOXN2 | forkhead box N2 (FOXN2), mRNA [NM_002158] | NM_002158 | ENST00000340553 | 3344 | NM_002158 | THC2601791 |
| A_23_P116942 | LAG3 | lymphocyte-activation gene 3 (LAG3), mRNA [NM_002286] | NM_002286 | ENST00000203629 | 3902 | NM_002286 | THC2475230 |
| A_33_P3408305 | CERS3 | ceramide synthase 3 (CERS3), mRNA [NM_178842] | NM_178842 | ENST00000538112 | 204219 | NM_178842 | THC2475513 |
| A_33_P3314441 | FBXL17 | F-box and leucine-rich repeat protein 17 (FBXL17), mRNA [NM_001163315] | NM_001163315 | ENST00000542267 | 64839 | NM_001163315 | THC2473457 |
| A_33_P3419419 | PIK3C2B | phosphoinositide-3-kinase, class 2, beta polypeptide [Source: HGNC Symbol; Acc: 8972] [ENST00000367184] | | ENST00000367184 | 5287 | | THC2703322 |
| A_23_P202587 | KIAA1598 | KIAA1598 (KIAA1598), transcript variant 2, mRNA [NM_018330] | NM_018330 | ENST00000469231 | 57698 | NM_018330 | THC2491701 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P212354 | CCR2 | chemokine (C-C motif) receptor 2 (CCR2), transcript variant A, mRNA [NM_001123041] | NM_001123041 | ENST00000292301 | 729230 | NM_001123041 | THC2475638 |
| A_33_P3228252 | | DA666023 NCRRM1 cDNA clone NCRRM1000040 5', mRNA sequence [DA666023] | DA666023 | | | | |
| A_24_P312325 | | PREDICTED: uncharacterized protein C8orf15-like (LOC100505981), mRNA [XM_003119008] | XM_003119008 | ENST00000500944 | | XM_003119008 | THC2481137 |
| A_33_P3407049 | | | | | | | |
| A_24_P150874 | GNA13 | guanine nucleotide binding protein (G protein), alpha 13 (GNA13), mRNA [NM_006572] | NM_006572 | ENST00000439174 | 10672 | NM_006572 | THC2603923 |
| A_23_P59099 | OR11A1 | olfactory receptor, family 11, subfamily A, member 1 (OR11A1), mRNA [NM_013937] | NM_013937 | ENST00000377149 | 26531 | NM_013937 | THC2487340 |
| A_32_P158746 | RPL17 | ribosomal protein L17 (RPL17), transcript variant 1, mRNA [NM_000985] | NM_000985 | ENST00000392739 | 6139 | NM_000985 | THC2554858 |
| A_33_P3381943 | DMTF1 | cyclin D binding myb-like transcription factor 1 (DMTF1), transcript variant 4, non-coding RNA [NR_024549] | NR_024549 | ENST00000394702 | 9988 | NR_024549 | THC2504564 |
| A_33_P3358104 | CD300E | CD300e molecule (CD300E), mRNA [NM_181449] | NM_181449 | ENST00000412268 | 342510 | NM_181449 | THC2480696 |
| A_33_P3390177 | FLJ34208 | hypothetical LOC401106 (FLJ34208), non-coding RNA [NR_033929] | NR_033929 | | 401106 | NR_033929 | THC2503254 |
| A_33_P3277611 | TMEM8C | transmembrane protein 8C (TMEM8C), mRNA [NM_001080483] | NM_001080483 | ENST00000333996 | 389827 | NM_001080483 | THC2645713 |
| A_24_P63347 | PF4V1 | platelet factor 4 variant 1 (PF4V1), mRNA [NM_002620] | NM_002620 | ENST00000330244 | 5197 | NM_002620 | THC2488247 |
| A_24_P418418 | RPS17 | ribosomal protein S17 (RPS17), mRNA [NM_001021] | NM_001021 | ENST00000377314 | 6218 | NM_001021 | THC2513112 |
| A_33_P3285077 | COMMD8 | COMM domain containing 8 (COMMD8), mRNA [NM_017845] | NM_017845 | ENST00000381571 | 54951 | NM_017845 | THC263032 |
| A_23_P128470 | CLEC12A | C-type lectin domain family 12, member A (CLEC12A), transcript variant 1, mRNA [NM_138337] | NM_138337 | ENST00000396507 | 160364 | NM_138337 | NP923350 |
| A_23_P216438 | SPATA21 | spermatogenesis associated 21 (SPATA21), mRNA [NM_198546] | NM_198546 | ENST00000335496 | 374955 | NM_198546 | THC2485745 |
| A_24_P218814 | RDH5 | retinol dehydrogenase 5 (11-cis/9-cis) (RDH5), transcript variant 2, mRNA [NM_002905] | NM_002905 | ENST00000548123 | 5959 | NM_002905 | THC2499847 |
| A_33_P3255290 | JAKMIP2 | janus kinase and microtubule interacting protein 2 (JAKMIP2), mRNA [NM_014790] | NM_014790 | ENST00000333010 | 9832 | NM_014790 | THC2471193 |
| A_24_P84808 | EAF2 | ELL associated factor 2 (EAF2), mRNA [NM_018456] | NM_018456 | ENST00000490434 | 55840 | NM_018456 | THC2482477 |
| A_23_P252201 | PGM5 | phosphoglucomutase 5 (PGM5), mRNA [NM_021965] | NM_021965 | ENST00000377314 | 5239 | NM_021965 | THC2767986 |
| A_33_P3260575 | CERCAM | cerebral endothelial cell adhesion molecule (CERCAM), mRNA [NM_016174] | NM_016174 | ENST00000372842 | 51148 | NM_016174 | THC2468263 |
| A_24_P357847 | LOC100510044 | immunoglobulin kappa variable 3-15 [Source: HGNC Symbol; Acc: 5816] [ENST00000390252] | XM_003120829 | ENST00000390252 | 100510044 | XM_003120829 | NP1170004 |
| A_33_P3555937 | STEAP4 | STEAP family member 4 (STEAP4), transcript variant 2, mRNA [NM_001205315] | NM_001205315 | ENST00000301959 | 79689 | NM_001205315 | THC2475717 |
| A_23_P84596 | MZB1 | marginal zone B and B1 cell-specific protein (MZB1), mRNA [NM_016459] | NM_016459 | ENST00000503351 | 51237 | NM_016459 | THC2605618 |
| A_33_P3215412 | C2CD4C | C2 calcium-dependent domain containing 4C (C2CD4C), mRNA [NM_001136263] | NM_001136263 | ENST00000332235 | 126567 | NM_001136263 | THC2615089 |
| A_23_P117380 | FAM181A | family with sequence similarity 181, member A (FAM181A), transcript variant 1, mRNA [NM_138344] | NM_138344 | ENST00000267594 | 90050 | NM_138344 | THC2478030 |
| A_33_P3372004 | IGSF6 | immunoglobulin superfamily, member 6 (IGSF6), mRNA [NM_005849] | NM_005849 | ENST00000268389 | 10261 | NM_005849 | THC2475474 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_24_P368943 | EVX1 | even-skipped homeobox 1 (EVX1), mRNA [NM_001989] | NM_001989 | ENST00000496902 | 2128 | NM_001989 | THC2484995 |
| A_33_P3210399 | SLC14A1 | solute carrier family 14 (urea transporter), member 1 (Kidd blood group) (SLC14A1), transcript variant 4, mRNA [NM_001146037] | NM_001146037 | ENST00000402943 | 6563 | NM_001146037 | THC2514421 |
| A_23_P153390 | CLEC4G | C-type lectin domain family 4, member G (CLEC4G), mRNA [NM_198492] | NM_198492 | ENST00000328853 | 339390 | NM_198492 | THC2479109 |
| A_33_P3349252 | DKFZp547L112 | mRNA; cDNA DKFZp547L112 (from clone DKFZp547L112). [AL512723] | AL512723 | | 81787 | | NP304591 |
| A_24_P419028 | MOP-1 | mRNA for MOP-1, complete cds. [AB014771] | AB014771 | | 643616 | | NP373383 |
| A_23_P134935 | DUSP4 | dual specificity phosphatase 4 (DUSP4), transcript variant 1, mRNA [NM_001394] | NM_001394 | ENST00000240100 | 1846 | NM_001394 | THC2466297 |
| A_32_P100830 | KIF19 | kinesin family member 19 (KIF19), mRNA [NM_153209] | NM_153209 | ENST00000038916 | 124602 | NM_153209 | THC2686967 |
| A_33_P3419970 | NPB | neuropeptide B (NPB), mRNA [NM_148896] | NM_148896 | ENST00000033383 | 256933 | NM_148896 | THC2489574 |
| A_23_P391857 | ESRRB | estrogen-related receptor beta (ESRRB), mRNA [NM_004452] | NM_004452 | ENST00000261532 | 2103 | NM_004452 | THC2636775 |
| A_32_P82623 | AGBL3 | ATP/GTP binding protein-like 3 (AGBL3), mRNA [NM_178563] | NM_178563 | ENST00000359383 | 340351 | NM_178563 | THC2620109 |
| A_24_P191417 | NAB1 | NGFI-A binding protein 1 (EGR1 binding protein 1) (NAB1), mRNA [NM_005966] | NM_005966 | ENST00000337386 | 4664 | NM_005966 | |
| A_23_P71946 | BSPRY | B-box and SPRY domain containing (BSPRY), mRNA [NM_017688] | NM_017688 | ENST00000374183 | 54836 | NM_017688 | THC2464724 |
| A_33_P3283601 | LOC389033 | placenta-specific 9 pseudogene (LOC389033), non-coding RNA [NR_026740] | NR_026740 | ENST00000433290 | 389033 | NR_026740 | THC2691539 |
| A_33_P3424591 | | immunoglobulin heavy constant gamma 1 (G1m marker) [Source: HGNC Symbol; Acc: 5525] [ENST00000390549] | CR611254 | ENST00000390549 | | | NP232832 |
| A_23_P76488 | EMP1 | epithelial membrane protein 1 (EMP1), mRNA [NM_001423] | NM_001423 | ENST00000256951 | 2012 | NM_001423 | THC2465394 |
| A_33_P3576797 | LOC158863 | mRNA; cDNA DKFZp586J1922 (from clone DKFZp586J1922) [AL110203] | AL110203 | | 158863 | | THC2504931 |
| A_23_P167168 | IGJ | immunoglobulin J polypeptide, linker protein for immunoglobulin alpha and mu polypeptides (IGJ), mRNA [NM_144646] | NM_144646 | ENST00000254801 | 3512 | NM_144646 | THC2469801 |
| A_24_P187970 | PADI2 | peptidyl arginine deiminase, type II (PADI2), mRNA [NM_007365] | NM_007365 | ENST00000375481 | 11240 | NM_007365 | THC2486805 |
| A_33_P3251205 | | immunoglobulin lambda variable 3-9 (gene/pseudogene) [Source: HGNC Symbol; Acc: 5918] [ENST00000390316] | AF194657 | ENST00000390316 | | | NP078180 |
| A_33_P3318444 | RNF222 | ring finger protein 222 (RNF222), mRNA [NM_001146684] | NM_001146684 | ENST00000399398 | 643904 | NM_001146684 | |
| A_33_P3257568 | CNTRL | centrosomal protein 110 kDa [Source: HGNC Symbol; Acc: 1858] [ENST00000373851] | AK097636 | ENST00000373851 | 11064 | | THC2721284 |
| A_32_P72940 | RPL35 | ribosomal protein L35 (RPL35), mRNA [NM_007209] | NM_007209 | ENST00000348462 | 11224 | NM_007209 | THC2590230 |
| A_33_P3212799 | C22orf34 | chromosome 22 open reading frame 34 (C22orf34), non-coding RNA [NR_026997] | NR_026997 | ENST00000400023 | 348645 | NR_026997 | THC2483736 |
| A_23_P109881 | ITIH4 | inter-alpha (globulin) inhibitor H4 (plasma Kallikrein-sensitive glycoprotein) (ITIH4), transcript variant 1, mRNA [NM_002218] | NM_002218 | ENST00000538421 | 3700 | NM_002218 | NP1161208 |
| A_24_P213783 | RPL31 | ribosomal protein L31 (RPL31), transcript variant 1, mRNA [NM_000993] | NM_000993 | ENST00000409733 | 6160 | NM_000993 | THC2465680 |
| A_33_P3263938 | LCN15 | lipocalin 15 (LCN15), mRNA [NM_203347] | NM_203347 | ENST00000316144 | 389812 | NM_203347 | THC2485824 |
| A_23_P136683 | HLA-DQB1 | major histocompatibility complex, class II, DQ beta 1 (HLA-DQB1), mRNA [NM_002123] | NM_002123 | ENST00000484729 | 3119 | NM_002123 | THC2506278 |
| A_23_P315122 | EMX1 | empty spiracles homeobox 1 (EMX1), mRNA [NM_004097] | NM_004097 | ENST00000491023 | 2016 | NM_004097 | THC2602195 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P57941 | RBM6 | RNA binding motif protein 6 (RBM6), transcript variant 1, mRNA [NM_005777] | NM_005777 | ENST00000454079 | 10180 | NM_005777 | THC2785726 |
| A_23_P128663 | SACS | spastic ataxia of Charlevoix-Saguenay (sacsin) (SACS), mRNA [NM_014363] | NM_014363 | ENST00000382298 | 26278 | NM_014363 | NP843920 |
| A_23_P7325 | BST1 | bone marrow stromal cell antigen 1 (BST1), mRNA [NM_004334] | NM_004334 | ENST00000265016 | 683 | NM_004334 | THC2677068 |
| A_33_P3283201 | | cDNA FLJ45443 fis, clone BRSSN2012157. [AK128779] | AK128779 | | | | THC2482363 |
| A_33_P3327697 | LOC145474 | hypothetical LOC145474 (LOC145474), non-coding RNA [NR_027046] | NR_027046 | | 145474 | NR_027046 | |
| A_23_P42353 | ETV7 | ets variant 7 (ETV7), transcript variant 1, mRNA [NM_016135] | NM_016135 | ENST00000339796 | 51513 | NM_016135 | NP190936 |
| A_33_P3351529 | | | | | | | |
| A_24_P242036 | RRP7B | ribosomal RNA processing 7 homolog B (S. cerevisiae) (RRP7B), non-coding RNA [NR_002184] | NR_002184 | ENST00000458605 | 91695 | NR_002184 | THC2463180 |
| A_33_P3422712 | | | | | | | |
| A_33_P3806721 | JMJD5 | jumonji domain containing 5 (JMJD5), transcript variant 1, mRNA [NM_001145348] | NM_001145348 | ENST00000540888 | 79831 | NM_001145348 | THC2632015 |
| A_23_P260240 | MYEOV | myeloma overexpressed (in a subset of t(11; 14) positive multiple myelomas) (MYEOV), mRNA [NM_138768] | NM_138768 | ENST00000535653 | 26579 | NM_138768 | THC2470814 |
| A_33_P3279708 | RNU2-2 | RNA, U2 small nuclear 2 (RNU2-2), small nuclear RNA [NR_002761] | NR_002761 | ENST00000538098 | 26855 | NR_002761 | THC2591139 |
| A_33_P3384694 | | | | | | | |
| A_23_P359870 | | PREDICTED: uncharacterized protein C8orf16-like (LOC100506010), mRNA [XM_003119009] | XM_003119009 | ENST00000400102 | | XM_003119009 | THC2478877 |
| A_33_P3683 | 2-Mar | membrane-associated ring finger (C3HC4) 2 (MARCH2), transcript variant 1, mRNA [NM_016496] | NM_016496 | ENST00000393944 | 51257 | NM_016496 | THC2532151 |
| A_33_P3256334 | PRB3 | proline-rich protein BstNI subfamily 3 (PRB3), mRNA [NM_006249] | NM_006249 | ENST00000279573 | 5544 | NM_006249 | THC2479522 |
| A_23_P3321205 | BEGAIN | brain-enriched guanylate kinase-associated homolog (rat) (BEGAIN), transcript variant 1, mRNA [NM_001159531] | NM_001159531 | ENST00000443071 | 57596 | NM_001159531 | THC2475256 |
| A_23_P156842 | EEF1E1 | eukaryotic translation elongation factor 1 epsilon 1 (EEF1E1), transcript variant 1, mRNA [NM_004280] | NM_004280 | ENST00000429723 | 9521 | NM_004280 | THC2708665 |
| A_33_P3713035 | LOC221814 | mRNA; cDNA DKFZp564C0371 (from clone DKFZp564C0371) [AL122087] | AL122087 | | 221814 | | THC2606193 |
| A_23_P213832 | SPINK7 | serine peptidase inhibitor, Kazal type 7 (putative) (SPINK7), mRNA [NM_032566] | NM_032566 | ENST00000514646 | 84651 | NM_032566 | THC2734765 |
| A_32_P2452 | TMTC1 | transmembrane and tetratricopeptide repeat containing 1 (TMTC1), transcript variant 2, mRNA [NM_175861] | NM_175861 | ENST00000256062 | 83857 | NM_175861 | THC2470774 |
| A_33_P3245818 | PQLC1 | PQ loop repeat containing 1 [Source: HGNC Symbol; Acc: 26188] [ENST00000466449] | AK126188 | ENST00000466449 | 80148 | | THC2483810 |
| A_24_P398940 | CASC4 | cancer susceptibility candidate 4 (CASC4), transcript variant 1, mRNA [NM_138423] | NM_138423 | ENST00000345795 | 113201 | NM_138423 | THC2469136 |
| A_32_P110390 | TMEM171 | transmembrane protein 171 (TMEM171), transcript variant 1, mRNA [NM_173490] | NM_173490 | ENST00000287773 | 134285 | NM_173490 | THC2480044 |
| A_33_P3217719 | TLE1 | transducin-like enhancer of split 1 (E(sp1) homolog, Drosophila) (TLE1), mRNA [NM_005077] | NM_005077 | ENST00000376472 | 7088 | NM_005077 | THC2594224 |
| A_33_P3222664 | | PREDICTED: hypothetical protein LOC100133214 (LOC100133214), mRNA [XM_001718031] | XM_001718031 | | | XM_001718031 | |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P305198 | STAT4 | signal transducer and activator of transcription 4 (STAT4), mRNA [NM_003151] | NM_003151 | ENST00000450994 | 6775 | NM_003151 | THC2501921 |
| A_33_P3260053 | AIF1L | allograft inflammatory factor 1-like (AIF1L), transcript variant 3, mRNA [NM_001185095] | NM_001185095 | ENST00000372312 | 83543 | NM_001185095 | THC2520939 |
| A_23_P417921 | DNAJC5G | DnaJ (Hsp40) homolog, subfamily C, member 5 gamma (DNAJC5G), mRNA [NM_173650] | NM_173650 | ENST00000296097 | 285126 | NM_173650 | THC2478898 |
| A_33_P3212350 | CARD11 | cDNA FLJ39820 fis, clone SPLEN2010625. [AK097139] | AK097139 | | 84433 | | THC2480953 |
| A_33_P3347040 | LOC100131094 | hypothetical LOC100131094 (LOC100131094), mRNA [NM_001242901] | NM_001242901 | ENST00000381796 | 100131094 | NM_001242901 | THC2483730 |
| A_32_P152696 | FCRL2 | Fc receptor-like 2 (FCRL2), mRNA [NM_030764] | NM_030764 | ENST00000392274 | 79368 | NM_030764 | NP458656 |
| A_24_P319647 | | PREDICTED: hypothetical protein LOC100507169 (LOC100507169), mRNA [XM_003119710] | XM_003119710 | | | XM_003119710 | THC2486918 |
| A_33_P3881056 | | | | | | | |
| A_33_P3402615 | SLC6A9 | solute carrier family 6 (neurotransmitter transporter, glycine), member 9 (SLC6A9), transcript variant 2, mRNA [NM_201649] | NM_201649 | ENST00000372310 | 6536 | NM_201649 | THC2615837 |
| A_33_P3284476 | LOC100128697 | cDNA FLJ42049 fis, clone SPLEN2041720. [AK124043] | AK124043 | | 100128697 | | THC2485306 |
| A_33_P3309849 | | | | | | | |
| A_23_P90273 | CHST8 | carbohydrate (N-acetylgalactosamine 4-0) sulfotransferase 8 (CHST8), transcript variant 3, mRNA [NM_022467] | NM_022467 | ENST00000262622 | 64377 | NM_022467 | THC2603946 |
| A_24_P64407 | HMX2 | H6 family homeobox 2 (HMX2), mRNA [NM_005519] | NM_005519 | ENST00000339992 | 3167 | NM_005519 | THC2478985 |
| A_23_P100326 | NPRL3 | nitrogen permease regulator-like 3 (S. cerevisiae) (NPRL3), transcript variant 2, mRNA [NM_001039476] | NM_001039476 | ENST00000399953 | 8131 | NM_001039476 | THC2589758 |
| A_33_P3333018 | FGL2 | fibrinogen-like 2 (FGL2), mRNA [NM_006682] | NM_006682 | ENST00000248598 | 10875 | NM_006682 | THC2610602 |
| A_33_P3343485 | HIP1 | huntingtin interacting protein 1 [Source: HGNC Symbol; Acc: 4913] [ENST00000479835] | AY358103 | ENST00000479835 | 3092 | | THC2760507 |
| A_33_P3321432 | FAM198B | family with sequence similarity 198, member B (FAM198B), transcript variant 2, mRNA [NM_016613] | NM_016613 | ENST00000393807 | 51313 | NM_016613 | THC2461168 |
| A_32_P148345 | ANXA2 | annexin A2 (ANXA2), transcript variant 2, mRNA [NM_001002857] | NM_001002857 | ENST00000504475 | 302 | NM_001002857 | NP1174962 |
| A_23_P36658 | MGST1 | microsomal glutathione S-transferase 1 (MGST1), transcript variant 1c, mRNA [NM_145791] | NM_145791 | ENST00000539708 | 4257 | NM_145791 | THC2625515 |
| A_33_P3413701 | ERAP1 | endoplasmic reticulum aminopeptidase 1 (ERAP1), transcript variant 2, mRNA [NM_001040458] | NM_001040458 | ENST00000443439 | 51752 | NM_001040458 | THC2533844 |
| A_33_P3403773 | ZNF569 | zinc finger protein 569 (ZNF569), mRNA [NM_152484] | NM_152484 | ENST00000316950 | 148266 | NM_152484 | THC2472283 |
| A_33_P3419806 | RPS29 | ribosomal protein S29 (RPS29), transcript variant 1, mRNA [NM_001032] | NM_001032 | ENST00000245458 | 6235 | NM_001032 | THC2465277 |
| A_24_P132787 | RAB18 | RAB18, member RAS oncogene family (RAB18), mRNA [NM_021252] | NM_021252 | ENST00000540268 | 22931 | NM_021252 | THC2778145 |
| A_33_P3299110 | ARHGAP42 | Rho GTPase activating protein 42 (ARHGAP42), mRNA [NM_152432] | NM_152432 | ENST00000298815 | 143872 | NM_152432 | THC2655447 |
| A_23_P169494 | ORM1 | orosomucoid 1 (ORM1), mRNA [NM_000607] | NM_000607 | ENST00000477456 | 5004 | NM_000607 | THC2558758 |
| A_23_P150407 | CREB3L1 | cAMP responsive element binding protein 3-like 1 (CREB3L1), mRNA [NM_052854] | NM_052854 | ENST00000530244 | 90993 | NM_052854 | THC2501749 |
| A_32_P208178 | RPS3A | ribosomal protein S3A (RPS3A), mRNA [NM_001006] | NM_001006 | ENST00000512797 | 6189 | NM_001006 | THC2568491 |
| A_33_P3234540 | | | | | | | |
| A_32_P209624 | MKRN7P | makorin ring finger protein 7, pseudogene (MKRN7P), non-coding RNA [NR_026640] | NR_026640 | | 7686 | NR_026640 | THC2522223 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P74609 | G0S2 | G0/G1switch 2 (G0S2), mRNA [NM_015714] | NM_015714 | ENST00000367029 | 50486 | NM_015714 | THC2463882 |
| A_33_P2270084 | | CDC2L1S13 PITSLRE protein kinase alpha SV9 isoform { } (exp = -1; wgp = 0; cg = 0), partial (38%) [THC2524986] | | | | | THC2524986 |
| A_33_P3223874 | ZMYND17 | mRNA; cDNA DKFZp686D03167 (from clone DKFZp686D03167). [CR936824] | CR936824 | | 118490 | | THC2502061 |
| A_23_P160751 | FCRL2 | Fc receptor-like 2 (FCRL2), mRNA [NM_030764] | NM_030764 | ENST00000368181 | 79368 | NM_030764 | NP1165213 |
| A_23_P19673 | SGK1 | serum/glucocorticoid regulated kinase 1 (SGK1), transcript variant 1, mRNA [NM_005627] | NM_005627 | ENST00000367857 | 6446 | NM_005627 | THC2495241 |
| A_33_P3251322 | MTMR14 | cDNA FLJ46453 fis, clone THYMU3019916. [AK128312] | AK128312 | | 64419 | | THC2484657 |
| A_33_P3267118 | EIF4G3 | eukaryotic translation initiation factor 4 gamma, 3 [Source: HGNC Symbol; Acc: 3298] [ENST00000374933] | | ENST00000374933 | 8672 | | THC2511801 |
| A_33_P3883912 | ZCCHC10 | zinc finger, CCHC domain containing 10 (ZCCHC10), mRNA [NM_017665] | NM_017665 | ENST00000324170 | 54819 | NM_017665 | THC2522779 |
| A_23_P347198 | SP3 | Sp3 transcription factor (SP3), transcript variant 1, mRNA [NM_003111] | NM_003111 | ENST00000465379 | 6670 | NM_003111 | THC2466406 |
| A_23_P7066 | RPL9 | ribosomal protein L9 (RPL9), transcript variant 2, mRNA [NM_001024921] | NM_001024921 | ENST00000437992 | 6133 | NM_001024921 | THC2541724 |
| A_23_P3398862 | RHOB | ras homolog gene family, member B (RHOB), mRNA [NM_004040] | NM_004040 | ENST00000272233 | 388 | NM_004040 | THC2711134 |
| A_33_P3366073 | EBPL | emopamil binding protein-like [Source: HGNC Symbol; Acc: 18061] [ENST00000378274] | BC073152 | ENST00000378274 | 84650 | | THC2760012 |
| A_32_P190488 | | HUMRPL26X ribosomal protein L26 { } (exp = -1; wgp = 0; cg = 0), partial (91%) [THC2550570] | | | | | THC2550570 |
| A_23_P111092 | OR2H1 | olfactory receptor, family 2, subfamily H, member 1 (OR2H1), mRNA [NM_030883] | NM_030883 | ENST00000461453 | 26716 | NM_030883 | THC2734737 |
| A_24_P410516 | GOLGA6L9 | golgin A6 family-like 9 (GOLGA6L9), mRNA [NM_198181] | NM_198181 | ENST00000306827 | 440295 | NM_198181 | THC2574212 |
| A_33_P3214310 | FOXP1 | forkhead box P1 (FOXP1), transcript variant 2, mRNA [NM_001012505] | NM_001012505 | ENST00000318779 | 27086 | NM_001012505 | THC2480877 |
| A_32_P200237 | LOC157740 | mRNA for chromosome 8 open reading frame 9 (c8ORF9). [AJ291676] | AJ291676 | | 157740 | | THC2480673 |
| A_33_P3414789 | FSD1 | fibronectin type III and SPRY domain containing 1 (FSD1), mRNA [NM_024333] | NM_024333 | ENST00000221856 | 79187 | NM_024333 | THC2693421 |
| A_32_P77102 | LOC100128420 | hypothetical LOC100128420 (LOC100128420), transcript variant 1, non-coding RNA [NR_038461] | NR_038461 | ENST00000454385 | 100128420 | NR_038461 | THC2660884 |
| A_32_P226786 | FAM126B | family with sequence similarity 126, member B (FAM126B), mRNA [NM_173822] | NM_173822 | | 285172 | NM_173822 | THC2492001 |
| A_33_P3221458 | ZNF204P | zinc finger protein 204, pseudogene (ZNF204P), non-coding RNA [NR_002722] | NR_002722 | | 7754 | NR_002722 | THC2495874 |
| A_23_P92994 | MFF | mitochondrial fission factor (MFF), nuclear gene encoding mitochondrial protein, mRNA [NM_020194] | NM_020194 | ENST00000409565 | 56947 | NM_020194 | NP1211685 |
| A_33_P3295415 | ZBTB3 | zinc finger and BTB domain containing 3 (ZBTB3), mRNA [NM_024784] | NM_024784 | ENST00000394807 | 79842 | NM_024784 | THC2477256 |
| A_33_P3389837 | GPN3 | GPN-loop GTPase 3 (GPN3), transcript variant 2, mRNA [NM_001164372] | NM_001164372 | ENST00000537466 | 51184 | NM_001164372 | THC2461939 |
| A_33_P3221761 | MLL4 | myeloid/lymphoid or mixed-lineage leukemia 4 (MLL4), mRNA [NM_014727] | NM_014727 | ENST00000341701 | 9757 | NM_014727 | THC2491229 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P89380 | SLC4A1 | solute carrier family 4, anion exchanger, member 1 (erythrocyte membrane protein band 3, Diego blood group) (SLC4A1), mRNA [NM_000342] | NM_000342 | ENST00000399246 | 6521 | NM_000342 | THC2474785 |
| A_33_P3422822 | GJC2 | gap junction protein, gamma 2, 47 kDa (GJC2), mRNA [NM_020435] | NM_020435 | ENST00000366714 | 57165 | NM_020435 | |
| A_23_P107051 | TCAP | titin-cap (telethonin) (TCAP), mRNA [NM_003673] | NM_003673 | ENST00000309889 | 8557 | NM_003673 | THC2512009 |
| A_23_P34597 | CDA | cytidine deaminase (CDA), mRNA [NM_001785] | NM_001785 | ENST00000461985 | 978 | NM_001785 | NP1079190 |
| A_33_P3288135 | CPLX2 | complexin 2 [Source: HGNC Symbol; Acc: 2310] | | ENST00000506642 | 10814 | | |
| A_23_P1712 | RNASE2 | ribonuclease, RNase A family, 2 (liver, eosinophil-derived neurotoxin) (RNASE2), mRNA [NM_002934] | NM_002934 | ENST00000258817 | 6036 | NM_002934 | NP103298 |
| A_32_P157927 | | immunoglobulin kappa variable 4-1 [Source: HGNC Symbol; Acc: 5834] [ENST00000390243] | S62210 | ENST00000390243 | | | NP836564 |
| A_33_P3293524 | NEURL | neuralized homolog (Drosophila) (NEURL), mRNA [NM_004210] | NM_004210 | ENST00000369780 | 9148 | NM_004210 | THC2463576 |
| A_24_P372625 | RNF141 | ring finger protein 141 (RNF141), mRNA [NM_016422] | NM_016422 | ENST00000534281 | 50862 | NM_016422 | THC2492115 |
| A_33_P3629678 | COL5A1 | collagen, type V, alpha 1 (COL5A1), mRNA [NM_000093] | NM_000093 | ENST00000371817 | 1289 | NM_000093 | THC2469461 |
| A_23_P149368 | FCRL1 | Fc receptor-like 1 (FCRL1), transcript variant 1, mRNA [NM_052938] | NM_052938 | ENST00000495126 | 115350 | NM_052938 | THC2478058 |
| A_33_P3420446 | LRRD1 | leucine-rich repeats and death domain containing 1 (LRRD1), mRNA [NM_001161528] | NM_001161528 | ENST00000430130 | 401387 | NM_001161528 | |
| A_23_P3248900 | FLJ45445 | hypothetical LOC399844 (FLJ45445), non-coding RNA [NR_028324] | NR_028324 | ENST00000425496 | 399844 | NR_028324 | THC2466370 |
| A_23_P58390 | C4orf32 | chromosome 4 open reading frame 32 (C4orf32), mRNA [NM_152400] | NM_152400 | ENST00000309733 | 132720 | NM_152400 | THC2471790 |
| A_33_P3345614 A_23_P208482 | CLEC4M | C-type lectin domain family 4, member M (CLEC4M), transcript variant 2, mRNA [NM_001144904] | NM_001144904 | ENST00000327325 | 10332 | NM_001144904 | NP076516 |
| A_33_P3294277 | CYP4F3 | cytochrome P450, family 4, subfamily F, polypeptide 3 (CYP4F3), transcript variant 1, mRNA [NM_000896] | NM_000896 | ENST00000221307 | 4051 | NM_000896 | THC2633164 |
| A_23_P131139 | DIRC1 | disrupted in renal carcinoma 1 (DIRC1), mRNA [NM_052952] | NM_052952 | ENST00000308100 | 116093 | NM_052952 | THC2479514 |
| A_23_P92035 | SETD5 | SET domain containing 5 (SETD5), mRNA [NM_001080517] | NM_001080517 | ENST00000466826 | 55209 | NM_001080517 | THC2521629 |
| A_32_P122240 | ASCL5 | PREDICTED: achaete-scute complex homolog 5 (Drosophila) (ASCL5), mRNA [XM_940966] | XM_940966 | | 647219 | XM_940966 | THC2659820 |
| A_23_P208293 | PVRL2 | poliovirus receptor-related 2 (herpesvirus entry mediator B) (PVRL2), transcript variant delta, mRNA [NM_001042724] | NM_001042724 | ENST00000252483 | 5819 | NM_001042724 | THC2582406 |
| A_23_P310460 | MDGA1 | MAM domain containing glycosylphosphatidylinositol anchor 1 (MDGA1), mRNA [NM_153487] | NM_153487 | ENST00000297153 | 266727 | NM_153487 | THC2479103 |
| A_33_P3238433 | ALDH3A1 | aldehyde dehydrogenase 3 family, member A1 (ALDH3A1), transcript variant 1, mRNA [NM_001135168] | NM_001135168 | ENST00000457844 | 218 | NM_001135168 | THC2506362 |
| A_24_P136161 | HNRNPCL1 | heterogeneous nuclear ribonucleoprotein C-like 1 (HNRNPCL1), mRNA [NM_001013631] | NM_001013631 | ENST00000317869 | 343069 | NM_001013631 | THC2493506 |
| A_33_P3325349 | TSPAN5 | tetraspanin 5 (TSPAN5), mRNA [NM_005723] | NM_005723 | ENST00000305798 | 10098 | NM_005723 | THC2462540 |
| A_32_P224666 | CAPZA2 | capping protein (actin filament) muscle Z-line, alpha 2 (CAPZA2), mRNA [NM_006136] | NM_006136 | ENST00000361183 | 830 | NM_006136 | THC2470172 |
| A_23_P116890 | PRB3 | proline-rich protein BstNI subfamily 3 (PRB3), mRNA [NM_006249] | NM_006249 | ENST00000538488 | 5544 | NM_006249 | THC2479522 |
| A_23_P89755 | RNF138 | ring finger protein 138 (RNF138), transcript variant 1, mRNA [NM_016271] | NM_016271 | ENST00000257190 | 51444 | NM_016271 | THC2601652 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_24_P321511 | GOLT1B | golgi transport 1B (GOLT1B), mRNA [NM_016072] | NM_016072 | ENST00000229314 | 51026 | NM_016072 | THC2466175 |
| A_33_P3325011 | | | | | | | |
| A_23_P336554 | IL1RAP | interleukin 1 receptor accessory protein (IL1RAP), transcript variant 2, mRNA [NM_134470] | NM_134470 | ENST00000422485 | 3556 | NM_134470 | THC2473060 |
| A_24_P142495 | KRTAP1-3 | keratin associated protein 1-3 (KRTAP1-3), mRNA [NM_030966] | NM_030966 | ENST00000344363 | 81850 | NM_030966 | NP367289 |
| A_23_P209652 | INO80D | INO80 complex subunit D (INO80D), mRNA [NM_017759] | NM_017759 | ENST00000233270 | 54891 | NM_017759 | THC2699199 |
| A_33_P3321369 | LOC145757 | PREDICTED: hypothetical LOC145757 (LOC145757), miscRNA [XR_109231] | XR_109231 | | 145757 | XR_109231 | THC2646184 |
| A_23_P120435 | WFDC3 | WAP four-disulfide core domain 3 (WFDC3), mRNA [NM_080614] | NM_080614 | ENST00000467679 | 140686 | NM_080614 | NP819189 |
| A_23_P129629 | MT3 | metallothionein 3 (MT3), mRNA [NM_005954] | NM_005954 | ENST00000200691 | 4504 | NM_005954 | THC2602129 |
| A_33_P3283669 | ATP1A3 | ATPase, Na+/K+ transporting, alpha 3 polypeptide (ATP1A3), mRNA [NM_152296] | NM_152296 | ENST00000545399 | 478 | NM_152296 | THC2493019 |
| A_23_P201747 | PADI2 | peptidyl arginine deiminase, type II (PADI2), mRNA [NM_007365] | NM_007365 | ENST00000375486 | 11240 | NM_007365 | THC2503010 |
| A_23_P248072 | SIRPB1 | signal-regulatory protein beta 1 (SIRPB1), transcript variant 3, mRNA [NM_001135844] | NM_001135844 | ENST00000279477 | 10326 | NM_001135844 | THC2475815 |
| A_23_P157299 | AEBP1 | AE binding protein 1 (AEBP1), mRNA [NM_001129] | NM_001129 | ENST00000413907 | 165 | NM_001129 | THC2469029 |
| A_32_P170397 | | HCG1998685 [Source: UniProtKB/TrEMBL; Acc: Q8TCB4] [ENST00000309874] | AK057625 | ENST00000309874 | | | THC2627263 |
| A_23_P222069 | SPHK1 | sphingosine kinase 1 (SPHK1), transcript variant 2, mRNA [NM_182965] | NM_182965 | ENST00000545180 | 8877 | NM_182965 | THC2474958 |
| A_33_P3305763 | | PREDICTED: uncharacterized protein C8orf6-like (LOC100506042), mRNA [XM_003119010] | XM_003119010 | ENST00000531549 | | XM_003119010 | THC2483388 |
| A_33_P3368560 | AHSA2 | AHA1, activator of heat shock 90 kDa protein ATPase homolog 2 (yeast), mRNA (cDNA clone IMAGE: 5735095), partial cds. [BC050395] | BC050395 | | 130872 | | THC2533385 |
| A_33_P3294826 | CRABP2 | cellular retinoic acid binding protein 2 (CRABP2), transcript variant 2, mRNA [NM_001199723] | NM_001199723 | ENST00000368220 | 1382 | NM_001199723 | |
| A_23_P82047 | STXBP5 | syntaxin binding protein 5 (tomosyn) (STXBP5), transcript variant 2, mRNA [NM_001127715] | NM_001127715 | ENST00000367479 | 134957 | NM_001127715 | THC2505040 |
| A_33_P3246833 | IL1RN | interleukin 1 receptor antagonist (IL1RN), transcript variant 4, mRNA [NM_173843] | NM_173843 | ENST00000259206 | 3557 | NM_173843 | THC2498493 |
| A_33_P3338152 | HIF3A | hypoxia inducible factor 3, alpha subunit [Source: HGNC Symbol; Acc: 15825] [ENST00000457865] | AB118749 | ENST00000457865 | 64344 | | THC2485400 |
| A_33_P3818959 | SAMD11 | sterile alpha motif domain containing 11 (SAMD11), mRNA [NM_152486] | NM_152486 | ENST00000342066 | 148398 | NM_152486 | THC2480231 |
| A_33_P3224710 | TFEC | transcription factor EC (TFEC), transcript variant 1, mRNA [NM_012252] | NM_012252 | ENST00000393485 | 22797 | NM_012252 | THC2474951 |
| A_23_P413796 | HAUS1 | HAUS augmin-like complex, subunit 1 (HAUS1), mRNA [NM_138443] | NM_138443 | ENST00000282058 | 115106 | NM_138443 | THC2467428 |
| A_33_P3308481 | HYMAI | hydatidiform mole associated and imprinted (non-protein coding) (HYMAI), non-coding RNA [NR_002768] | NR_002768 | | 57061 | NR_002768 | THC2645509 |
| A_33_P3279861 | | clone 1120 immunoglobulin lambda light chain variable region mRNA, partial cds. [AF194718] | AF194718 | | | | NP079543 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_32_P193322 | RICTOR | RPTOR independent companion of MTOR, complex 2 (RICTOR), mRNA [NM_152756] | NM_152756 | ENST00000357387 | 253260 | NM_152756 | THC2491721 |
| A_23_P216108 | ANK1 | ankyrin 1, erythrocytic (ANK1), transcript variant 3, mRNA [NM_000037] | NM_000037 | ENST00000265709 | 286 | NM_000037 | NP1475647 |
| A_23_P75769 | MS4A4A | membrane-spanning 4-domains, subfamily A, member 4 (MS4A4A), transcript variant 1, mRNA [NM_024021] | NM_024021 | ENST00000529991 | 51338 | NM_024021 | THC2628883 |
| A_24_P90097 | ADD3 | adducin 3 (gamma) (ADD3), transcript variant 1, mRNA [NM_016824] | NM_016824 | ENST00000277900 | 120 | NM_016824 | THC2759750 |
| A_23_P141549 | RPS7 | ribosomal protein S7 (RPS7), mRNA [NM_001011] | NM_001011 | ENST00000406376 | 6201 | NM_001011 | THC2557544 |
| A_23_P103532 | GPR161 | G protein-coupled receptor 161 (GPR161), transcript variant 2, mRNA [NM_153832] | NM_153832 | ENST00000493800 | 23432 | NM_153832 | THC2628589 |
| A_23_P328069 | HPS1 | Hermansky-Pudlak syndrome 1 (HPS1), transcript variant 1, mRNA [NM_000195] | NM_000195 | ENST00000325103 | 3257 | NM_000195 | THC2603389 |
| A_24_P40001 | SIGLEC8 | sialic acid binding Ig-like lectin 8 (SIGLEC8), mRNA [NM_014442] | NM_014442 | ENST00000321424 | 27181 | NM_014442 | THC2478774 |
| A_23_P217609 | RPL36A | ribosomal protein L36a (RPL36A), transcript variant 1, mRNA [NM_021029] | NM_021029 | ENST00000372849 | 6173 | NM_021029 | THC2465210 |
| A_33_P3417626 | ENHO | energy homeostasis associated (ENHO), mRNA [NM_198573] | NM_198573 | ENST00000303992 | 375704 | NM_198573 | THC2482843 |
| A_33_P3372910 | DDX58 | DEAD (Asp-Glu-Ala-Asp) box polypeptide 58 (DDX58), mRNA [NM_014314] | NM_014314 | ENST00000379882 | 23586 | NM_014314 | NP1162083 |
| A_33_P3210443 | LOC145216 | hypothetical LOC145216 (LOC145216), non-coding RNA [NR_038436] | NR_038436 | | 145216 | NR_038436 | NP1154465 |
| A_24_P172993 | UBE2O | ubiquitin-conjugating enzyme E2O (UBE2O), mRNA [NM_022066] | NM_022066 | ENST00000319380 | 63893 | NM_022066 | THC2624034 |
| A_23_P14734 | RPS27L | ribosomal protein S27-like (RPS27L), mRNA [NM_015920] | NM_015920 | ENST00000462430 | 51065 | NM_015920 | THC2473897 |
| A_24_P390833 | MPPE1 | metallophosphoesterase 1 (MPPE1), transcript variant 1, mRNA [NM_023075] | NM_023075 | ENST00000399978 | 65258 | NM_023075 | NP1162383 |
| A_33_P3279124 | FAM21C | family with sequence similarity 21, member C (FAM21C), transcript variant 3, mRNA [NM_001169107] | NM_001169107 | ENST00000434114 | 253725 | NM_001169107 | THC2572798 |
| A_33_P3233404 | | T cell receptor beta variable 28 [Source: HGNC Symbol; Acc: 12209] [ENST00000390400] | AB305916 | ENST00000390400 | | | NP285374 |
| A_23_P67127 | TMEM145 | transmembrane protein 145 (TMEM145), mRNA [NM_173633] | NM_173633 | ENST00000301204 | 284339 | NM_173633 | THC2483750 |
| A_33_P3415859 | NLRC3 | NLR family, CARD domain containing 3 [Source: HGNC Symbol; Acc: 29889] [ENST00000324659] | AK090476 | ENST00000324659 | 197358 | | THC2563500 |
| A_33_P3280502 | | | | | | | |
| A_33_P3406567 | MS4A1 | membrane-spanning 4-domains, subfamily A, member 1 (MS4A1), transcript variant 1, mRNA [NM_152866] | NM_152866 | ENST00000389939 | 931 | NM_152866 | THC2461914 |
| A_33_P3408244 | SPRNP1 | shadow of prion protein homolog (zebrafish) pseudogene 1 (SPRNP1), non-coding RNA [NR_033789] | NR_033789 | ENST00000450958 | 399833 | NR_033789 | THC2482646 |
| A_33_P3224803 | NCF1 | neutrophil cytosolic factor 1 (NCF1), mRNA [NM_000265] | NM_000265 | ENST00000438106 | 653361 | NM_000265 | THC2505727 |
| A_33_P3408962 | FLJ33996 | PREDICTED: hypothetical protein FLJ33996 (FLJ33996), miscRNA [XR_110352] | XR_110352 | | 283401 | XR_110352 | THC2475169 |
| A_33_P3327818 | | | AL157466 | ENST00000366116 | | | THC2612300 |
| A_33_P3338793 | KCNC3 | potassium voltage-gated channel, Shaw-related subfamily, member 3 (KCNC3), mRNA [NM_004977] | NM_004977 | ENST00000477616 | 3748 | NM_004977 | THC2481537 |
| A_33_P3395675 | | immunoglobulin lambda constant 2 (Kern-Oz- marker) [Source: HGNC Symbol; Acc: 5856] [ENST00000390323] | EU937523 | ENST00000390323 | | | NP093469 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3878772 | JAK2 | Janus kinase 2 (JAK2), mRNA [NM_004972] | NM_004972 | ENST00000381652 | 3717 | NM_004972 | THC2472565 |
| A_33_P3629131 | CDRT3 | DKFZp686P15240_r1 686 (synonym: hlcc3) cDNA clone DKFZp686P15240 5', mRNA sequence [BX484257] | BX484257 | | 94145 | | |
| A_33_P3250730 | ACCN4 | amiloride-sensitive cation channel 4, pituitary (ACCN4), transcript variant 1, mRNA [NM_018674] | NM_018674 | ENST00000358078 | 55515 | NM_018674 | NP835056 |
| A_33_P3390773 | TRIM66 | tripartite motif containing 66 (TRIM66), mRNA [NM_014818] | NM_014818 | ENST00000299550 | 9866 | NM_014818 | THC2604054 |
| A_33_P3293391 | LOC642826 | hypothetical LOC642826 (LOC642826), non-coding RNA [NR_024495] | NR_024495 | | 642826 | NR_024495 | THC2517511 |
| A_33_P3315268 | KRT78 | keratin 78 (KRT78), mRNA [NM_173352] | NM_173352 | ENST00000539860 | 196374 | NM_173352 | THC2473566 |
| A_33_P3269723 | ZSWIM7 | zinc finger, SWIM-type containing 7 (ZSWIM7), transcript variant 1, mRNA [NM_001042697] | NM_001042697 | ENST00000399277 | 125150 | NM_001042697 | THC2492535 |
| A_23_P349083 | FCHO2 | FCH domain only 2 (FCHO2), transcript variant 1, mRNA [NM_138782] | NM_138782 | ENST00000341845 | 115548 | NM_138782 | THC2508618 |
| A_33_P3256793 | KIAA1324 | KIAA1324 (KIAA1324), mRNA [NM_020775] | NM_020775 | ENST00000369938 | 57535 | NM_020775 | THC2629991 |
| A_33_P3275835 | TOR2A | torsin family 2, member A (TOR2A), transcript variant 3, mRNA [NM_001134430] | NM_001134430 | ENST00000336067 | 27433 | NM_001134430 | THC2485391 |
| A_33_P3415744 | ANKRD36B | ankyrin repeat domain 36B (ANKRD36B), mRNA [NM_025190] | NM_025190 | ENST00000357042 | 57730 | NM_025190 | THC2477306 |
| A_33_P3278649 | ENTPD2 | ectonucleoside triphosphate diphosphohydrolase 2 (ENTPD2), transcript variant 1, mRNA [NM_203468] | NM_203468 | ENST00000355097 | 954 | NM_203468 | THC2487916 |
| A_33_P3326653 | TMEM82 | transmembrane protein 82 (TMEM82), mRNA [NM_001013641] | NM_001013641 | ENST00000375782 | 388595 | NM_001013641 | THC2477712 |
| A_23_P3232945 | F2RL1 | coagulation factor II (thrombin) receptor-like 1 (F2RL1), mRNA [NM_005242] | NM_005242 | ENST00000296677 | 2150 | NM_005242 | THC2464357 |
| A_33_P3789693 | MGC24103 | PREDICTED: hypothetical MGC24103 (MGC24103), miscRNA [XR_108934] | XR_108934 | | 158295 | XR_108934 | NP1159657 |
| A_24_P148151 | TSNAX | translin-associated factor X (TSNAX), mRNA [NM_005999] | NM_005999 | ENST00000475168 | 7257 | NM_005999 | THC2467018 |
| A_23_P52986 | VWCE | von Willebrand factor C and EGF domains (VWCE), mRNA [NM_152718] | NM_152718 | ENST00000335613 | 220001 | NM_152718 | THC2474163 |
| A_23_P301995 | LIN9 | lin-9 homolog (C. elegans) (LIN9), mRNA [NM_173083] | NM_173083 | ENST00000366807 | 286826 | NM_173083 | THC2484578 |
| A_33_P3883985 | LMF1 | lipase maturation factor 1 (LMF1), transcript variant 4, non-coding RNA [NR_036442] | NR_036442 | | 64788 | NR_036442 | THC2605210 |
| A_23_P25445 | FAM186B | family with sequence similarity 186, member B (FAM186B), transcript variant 1, mRNA [NM_032130] | NM_032130 | ENST00000257894 | 84070 | NM_032130 | THC2706486 |
| A_33_P3302070 A_33_P3324675 | | GB | | | | | NP1243929 |
| A_33_P3326235 | HBM | hemoglobin, mu (HBM), mRNA [NM_001003938] | NM_001003938 | ENST00000472539 | 3042 | NM_001003938 | THC2477716 |
| A_23_P134835 | CSGALNACT1 | chondroitin sulfate N-acetylgalactosaminyltransferase 1 (CSGALNACT1), transcript variant 2, mRNA [NM_018371] | NM_018371 | ENST00000311540 | 55790 | NM_018371 | THC2486893 |
| A_23_P338168 | FBXL19 | F-box and leucine-rich repeat protein 19 (FBXL19), mRNA [NM_001099784] | NM_001099784 | ENST00000338343 | 54620 | NM_001099784 | THC2686436 |
| A_33_P3358403 | DNLZ | DNL-type zinc finger (DNLZ), mRNA [NM_001080849] | NM_001080849 | ENST00000481053 | 728489 | NM_001080849 | THC2612845 |
| A_33_P3362068 | LOC100129149 | full-length cDNA clone CS0DI084YD11 of Placenta Cot 25-normalized of (human). [CR595361] | CR595361 | | 100129149 | | THC2688744 |
| A_32_P20367 | RPS7 | ribosomal protein S7 (RPS7), mRNA [NM_001011] | NM_001011 | ENST00000406376 | 6201 | NM_001011 | THC2578871 |
| A_24_P510357 | | immunoglobulin lambda variable 2-14 [Source: HGNC Symbol; Acc: 5888] [ENST00000390312] | S76132 | ENST00000390312 | | | NP1087720 |
| A_33_P3589543 | | PREDICTED: hypothetical locus LOC692247 (LOC692247), miscRNA [XR_109057] | XR_109057 | ENST00000527620 | | XR_109057 | THC2480441 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3290672 | SELT | selenoprotein T (SELT), mRNA [NM_016275] | NM_016275 | | 51714 | NM_016275 | THC2731852 |
| A_33_P3313411 | ARHGAP33 | Rho GTPase activating protein 33 (ARHGAP33), transcript variant 2, mRNA [NM_001172630] | NM_001172630 | ENST00000007510 | 115703 | NM_001172630 | NP107616 |
| A_33_P3248749 | RSPH9 | radial spoke head 9 homolog (Chlamydomonas) [Source: HGNC Symbol; Acc: 21057] [ENST00000372154] | AK055407 | ENST00000372154 | 221421 | | THC2478697 |
| A_33_P3252146 | HMX3 | H6 family homeobox 3 (HMX3), mRNA [NM_001105574] | NM_001105574 | ENST00000357878 | 340784 | NM_001105574 | |
| A_23_P500410 | ATP6V1G2 | ATPase, H+ transporting, lysosomal 13 kDa, V1 subunit G2 (ATP6V1G2), transcript variant 1, mRNA [NM_130463] | NM_130463 | ENST00000303892 | 534 | NM_130463 | THC2504847 |
| A_33_P3363305 A_33_P3335506 | FCRL5 | Fc receptor-like 5 [Source: HGNC Symbol; Acc: 18508] [ENST00000368190] | AF343662 | ENST00000368190 | 83416 | | THC2478268 |
| A_33_P255663 | MANEA | man nosidase, endo-alpha (MANEA), mRNA [NM_024641] | NM_024641 | ENST00000358812 | 79694 | NM_024641 | THC2492910 |
| A_33_P3339109 | POLR1C | polymerase (RNA) I polypeptide C, 30 kDa [Source: HGNC Symbol; Acc: 20194] [ENST00000512472] | CA416988 | ENST00000512472 | 9533 | | THC2626465 |
| A_33_P3358213 | PADI6 | peptidyl arginine deiminase, type VI (PADI6), mRNA [NM_207421] | NM_207421 | ENST00000434762 | 353238 | NM_207421 | THC2488002 |
| A_33_P3369761 | PDP1 | pyruvate dehyrogenase phosphatase catalytic subunit 1 (PDP1), nuclear gene encoding mitochondrial protein, transcript variant 2, mRNA [NM_001161779] | NM_001161779 | ENST00000396200 | 54704 | NM_001161779 | THC2466932 |
| A_33_P3272352 | | HCG1988162Uncharacterized protein [Source: UniProtKB/TrEMBL; Acc: A8MIT3] [ENST00000397064] | | ENST00000397064 | | | |
| A_33_P3364240 | PAEP | progestagen-associated endometrial protein (PAEP), transcript variant 2, mRNA [NM_002571] | NM_002571 | ENST00000344007 | 5047 | NM_002571 | NP192436 |
| A_23_P39453 | MEX3D | mex-3 homolog D (C. elegans) (MEX3D), transcript variant 1, mRNA [NM_203304] | NM_203304 | ENST00000402693 | 399664 | NM_203304 | THC2473313 |
| A_33_P3424861 | FAM118A | family with sequence similarity 118, member A (FAM118A), transcript variant 1, mRNA [NM_001104595] | NM_001104595 | ENST00000216214 | 55007 | NM_001104595 | THC2595955 |
| A_33_P3408665 A_24_P188800 | 1-Mar | membrane-associated ring finger (C3HC4) 1 (MARCH1), transcript variant 2, mRNA [NM_017923] | NM_017923 | ENST00000339875 | 55016 | NM_017923 | THC2483811 |
| A_23_P103891 | LCE1C | late cornified envelope 1C (LCE1C), mRNA [NM_178351] | NM_178351 | ENST00000368768 | 353133 | NM_178351 | NP1250118 |
| A_23_P44974 | MRPL13 | mitochondrial ribosomal protein L13 (MRPL13), nuclear gene encoding mitochondrial protein, mRNA [NM_014078] | NM_014078 | ENST00000523316 | 28998 | NM_014078 | THC2498425 |
| A_33_P3284463 | ASAH1 | N-acylsphingosine amidohydrolase (acid ceramidase) 1 (ASAH1), transcript variant 1, mRNA [NM_177924] | NM_177924 | ENST00000417108 | 427 | NM_177924 | THC2495793 |
| A_33_P3806676 | | T cell receptor beta variable 28 [Source: HGNC Symbol; Acc: 12209] [ENST00000390400] | AY751906 | ENST00000390400 | | | NP161158 |
| A_24_P169073 | FAM131C | family with sequence similarity 131, member C (FAM131C), mRNA [NM_182623] | NM_182623 | ENST00000375662 | 348487 | NM_182623 | THC2475284 |
| A_24_P366165 A_24_P229871 | | chromosome 17 open reading frame 54 [Source: HGNC Symbol; Acc: 26863] [ENST00000321800] | BC101214 | ENST00000321800 | | | NP1465661 |
| A_33_P3385656 | FNDC9 | fibronectin type III domain containing 9 (FNDC9), mRNA [NM_001001343] | NM_001001343 | ENST00000312349 | 408263 | NM_001001343 | THC2644705 |
| A_33_P3352664 | SP7 | Sp7 transcription factor (SP7), transcript variant 1, mRNA [NM_001173467] | NM_001173467 | ENST00000303846 | 121340 | NM_001173467 | THC2479201 |
| A_33_P3253832 | | | FV367791 | | | | |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P430670 | CHST5 | carbohydrate (N-acetylglucosamine 6-O) sulfotransferase 5 (CHST5), mRNA [NM_024533] | NM_024533 | ENST00000336257 | 23563 | NM_024533 | NP175264 |
| A_23_P379034 | BAIAP2L2 | BAI1-associated protein 2-like 2 (BAIAP2L2), mRNA [NM_025045] | NM_025045 | ENST00000402500 | 80115 | NM_025045 | THC2618191 |
| A_23_P116235 | MDK | midkine (neurite growth-promoting factor 2) (MDK), transcript variant 1, mRNA [NM_001012334] | NM_001012334 | ENST00000407067 | 4192 | NM_001012334 | NP1464770 |
| A_33_P3247095 | | | | ENST00000447610 | | | |
| A_23_P170857 | IL1RAP | interleukin 1 receptor accessory protein (IL1RAP), transcript variant 1, mRNA [NM_002182] | NM_002182 | ENST00000447382 | 3556 | NM_002182 | THC2628876 |
| A_33_P3264444 | PFDN6 | prefoldin subunit 6 [Source: HGNC Symbol; Acc: 4926] [ENST00000482292] | CR609151 | ENST00000482292 | 10471 | | THC2557117 |
| A_23_P26386 | TPPP3 | tubulin polymerization-promoting protein family member 3 (TPPP3), mRNA [NM_016140] | NM_016140 | ENST00000290942 | 51673 | NM_016140 | NP211869 |
| A_23_P372848 | P2RX1 | purinergic receptor P2X, ligand-gated ion channel, 1 (P2RX1), mRNA [NM_002558] | NM_002558 | ENST00000225538 | 5023 | NM_002558 | THC2488665 |
| A_33_P3356641 | MSL1 | male-specific lethal 1 homolog (Drosophila) (MSL1), mRNA [NM_001012241] | NM_001012241 | ENST00000398532 | 339287 | NM_001012241 | THC2629023 |
| A_23_P59888 | NACAP1 | nascent-polypeptide-associated complex alpha polypeptide pseudogene 1 (NACAP1), non-coding RNA [NR_002182] | NR_002182 | ENST00000419462 | 83955 | NR_002182 | THC2490918 |
| A_23_P92520 | ANP32C | acidic (leucine-rich) nuclear phosphoprotein 32 family, member C (ANP32C), mRNA [NM_012403] | NM_012403 | ENST00000330377 | 23520 | NM_012403 | NP175117 |
| A_24_P239076 | IGLL1 | immunoglobulin lambda-like polypeptide 1 (IGLL1), transcript variant 1, mRNA [NM_020070] | NM_020070 | | 3543 | NM_020070 | THC2471192 |
| A_33_P3386297 | | MSTP159 (MST159) mRNA, complete cds. [AF190162] | AF190162 | | | | THC2488126 |
| A_24_P82630 | SMCHD1 | structural maintenance of chromosomes flexible hinge domain containing 1 (SMCHD1), mRNA [NM_015295] | NM_015295 | ENST00000320876 | 23347 | NM_015295 | THC2657862 |
| A_33_P3395314 | | DB335107 SYNOV4 cDNA clone SYNOV4009599 3', mRNA sequence [DB335107] | DB335107 | | | | |
| A_33_P3261024 | | | | | | | |
| A_33_P3389649 | PDE4D | phosphodiesterase 4D, cAMP-specific (PDE4D), transcript variant 4, mRNA [NM_001197218] | NM_001197218 | ENST00000502575 | 5144 | NM_001197218 | NP285196 |
| A_23_P361654 | | immunoglobulin kappa variable 1D-16 [Source: HGNC Symbol; Acc: 5748] [ENST00000492446] | BC073764 | ENST00000492446 | | | THC2251789 |
| A_33_P3344574 | SFTPA2 | surfactant protein A2 (SFTPA2), mRNA [NM_001098668] | NM_001098668 | ENST00000372325 | 729238 | NM_001098668 | NP073518 |
| A_23_P48495 | TCL1B | T-cell leukemia/lymphoma 1B (TCL1B), transcript variant 1, mRNA [NM_004918] | NM_004918 | ENST00000461160 | 9623 | NM_004918 | NP1459415 |
| A_33_P3417502 | WNT3A | wingless-type MMTV integration site family, member 3A (WNT3A), mRNA [NM_033131] | NM_033131 | ENST00000366753 | 89780 | NM_033131 | THC2487359 |
| A_33_P3229863 | LOC100128714 | hypothetical LOC100128714 (LOC100128714), non-coding RNA [NR_040082] | NR_040082 | ENST00000383019 | 100128714 | NR_040082 | THC2480904 |
| A_33_P3322388 | SPRR2D | small proline-rich protein 2D (SPRR2D), mRNA [NM_006945] | NM_006945 | ENST00000439437 | 6703 | NM_006945 | THC2501809 |
| A_33_P3338071 | | | | | | | |
| A_23_P4282 | C4B | complement component 4B (Chido blood group) (C4B), mRNA [NM_001002029] | NM_001002029 | ENST00000463249 | 721 | NM_001002029 | THC2585044 |
| A_33_P3369128 | LOC100132966 | cDNA FLJ42565 fis, clone BRACE3007472. [AK124556] | AK124556 | | 100132966 | | NP165804 |
| A_33_P3304707 | | immunoglobulin lambda variable 2-8 [Source: HGNC Symbol; Acc: 5895] [ENST00000390317] | Z46314 | ENST00000390317 | | | |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P29079 | PFKL | phosphofructokinase, liver (PFKL), transcript variant 2, mRNA [NM_002626] | NM_002626 | ENST00000495274 | 5211 | NM_002626 | NP1150810 |
| A_23_P151637 | RNASE2 | ribonuclease, RNase A family, 2 (liver, eosinophil-derived neurotoxin) (RNASE2), mRNA [NM_002934] | NM_002934 | ENST00000304625 | 6036 | NM_002934 | THC2473665 |
| A_23_P412214 | RAP1GAP2 | RAP1 GTPase activating protein 2 (RAP1GAP2), transcript variant 1, mRNA [NM_015085] | NM_015085 | ENST00000254695 | 23108 | NM_015085 | THC2680829 |
| A_33_P3279620 | | cDNA FLJ37513 fis, clone BRCAN2000620. [AK094832] | AK094832 | | | | THC2579088 |
| A_24_P68311 | SYNE2 | spectrin repeat containing, nuclear envelope 2 (SYNE2), transcript variant 1, mRNA [NM_015180] | NM_015180 | ENST00000356081 | 23224 | NM_015180 | NP590721 |
| A_33_P3550894 | GATA2 | GATA binding protein 2 (GATA2), transcript variant 1, mRNA [NM_001145661] | NM_001145661 | ENST00000430265 | 2624 | NM_001145661 | NP099465 |
| A_23_P3370364 | PRLHR | prolactin releasing hormone receptor (PRLHR), mRNA [NM_004248] | NM_004248 | ENST00000369169 | 2834 | NM_004248 | THC2605922 |
| A_24_P412734 | PRSS36 | protease, serine, 36 (PRSS36), mRNA [NM_173502] | NM_173502 | ENST00000268281 | 146547 | NM_173502 | THC2477817 |
| A_24_P387869 | PKN2 | protein kinase N2 (PKN2), mRNA [NM_006256] | NM_006256 | ENST00000370521 | 5586 | NM_006256 | THC2648997 |
| A_33_P3215788 | ANKRD36 | ankyrin repeat domain 36 (ANKRD36), mRNA [NM_001164315] | NM_001164315 | ENST00000447597 | 375248 | NM_001164315 | THC2498566 |
| A_33_P3269844 | LRRC26 | leucine rich repeat containing 26 (LRRC26), mRNA [NM_001013653] | NM_001013653 | ENST00000371542 | 389816 | NM_001013653 | THC2675561 |
| A_33_P3271395 | LOC100129534 | small nuclear ribonucleoprotein polypeptide N pseudogene (LOC100129534), non-coding RNA [NR_024489] | NR_024489 | | 100129534 | NR_024489 | THC2481166 |
| A_23_P22433 | RP2 | retinitis pigmentosa 2 (X-linked recessive) (RP2), mRNA [NM_006915] | NM_006915 | ENST00000218340 | 6102 | NM_006915 | THC2526448 |
| A_23_P140190 | KIAA0125 | KIAA0125 (KIAA0125), non-coding RNA [NR_026800] | NR_026800 | ENST00000484511 | 9834 | NR_026800 | THC2483256 |
| A_33_P3320782 | ATXN7 | ataxin 7 (ATXN7), transcript variant SCA7a, mRNA [NM_000333] | NM_000333 | ENST00000398590 | 6314 | NM_000333 | THC2471545 |
| A_33_P3226154 | | immunoglobulin kappa constant [Source: HGNC Symbol; Acc: 5716] [ENST00000390237] | AY538254 | ENST00000390237 | | | NP1073961 |
| A_33_P3257486 | LOC651536 | PREDICTED: immunoglobulin lambda variable 5-45 [Source: HGNC Symbol; Acc: 5924] [ENST00000390296] | XM_001719621 | ENST00000390296 | 651536 | XM_001719621 | NP084478 |
| A_32_P186981 | RPL17 | ribosomal protein L17 (RPL17), transcript variant 1, mRNA [NM_000985] | NM_000985 | ENST00000418495 | 6139 | NM_000985 | THC2596675 |
| A_23_P411723 | PLAG1 | pleiomorphic adenoma gene 1 (PLAG1), transcript variant 1, mRNA [NM_002655] | NM_002655 | ENST00000316981 | 5324 | NM_002655 | THC2649104 |
| A_33_P3324805 | LOC100130345 | PREDICTED: cadherin-related family member 3-like (LOC100130345), mRNA [XM_001716484] | XM_001716484 | | 100130345 | XM_001716484 | |
| A_33_P3370521 | | | XM_001721393 | ENST00000427872 | | XM_001721393 | THC2698492 |
| A_23_P350059 | C1orf152 | chromosome 1 open reading frame 152 (C1orf152), non-coding RNA [NR_003242] | NR_003242 | | 767846 | NR_003242 | THC2476417 |
| A_33_P3375934 | NAMPT | nicotinamide phosphoribosyltransferase (NAMPT), mRNA [NM_005746] | NM_005746 | ENST00000222553 | 10135 | NM_005746 | THC2554375 |
| A_23_P02808 | PRIMA1 | proline rich membrane anchor 1 (PRIMA1), mRNA [NM_178013] | NM_178013 | ENST00000477603 | 145270 | NM_178013 | THC2489283 |
| A_33_P3364493 A_33_P3281468 | STARD9 | StAR-related lipid transfer (START) domain containing 9 (STARD9), mRNA [NM_020759] | NM_020759 | ENST00000290607 | 57519 | NM_020759 | THC2602580 |
| A_33_P3403082 | NCRNA00176 | non-protein coding RNA 176 (NCRNA00176), transcript variant 1, non-coding RNA [NR_027686] | NR_027686 | | 284739 | NR_027686 | |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_24_P290751 | DTX1 | deltex homolog 1 (Drosophila) (DTX1), mRNA [NM_004416] | NM_004416 | ENST00000547974 | 1840 | NM_004416 | THC2471651 |
| A_32_P125549 | | | | | | | |
| A_33_P3408203 | TGFA | transforming growth factor, alpha (TGFA), transcript variant 1, mRNA [NM_003236] | NM_003236 | ENST00000418333 | 7039 | NM_003236 | THC2490361 |
| A_33_P3246829 | IL1RN | interleukin 1 receptor antagonist (IL1RN), transcript variant 4, mRNA [NM_173843] | NM_173843 | ENST00000409930 | 3557 | NM_173843 | THC2498493 |
| A_33_P3229390 | | | | | | | |
| A_32_P21384 | RPL17 | ribosomal protein L17 (RPL17), transcript variant 1, mRNA [NM_000985] | NM_000985 | ENST00000418495 | 6139 | NM_000985 | THC2355265 |
| A_33_P3786807 | SNAR-E | UI-H-DF1-auh-i-18-0-UI.s1 NCI_CGAP_DF1 cDNA clone UI-H-DF1-auh-i-18-0-UI 3', mRNA sequence [CA436475] | CA436475 | | 100170220 | | |
| A_33_P3325843 | FLJ40039 | cDNA FLJ40039 fis, clone SYNOV2000397. [AK097358] | AK097358 | | 647662 | | THC2490969 |
| A_23_P146325 | ASAP1-IT1 | ASAP1 intronic transcript 1 (non-protein coding) (ASAP1-IT1), non-coding RNA [NR_002765] | NR_002765 | | 29065 | NR_002765 | THC2490392 |
| A_24_P131580 | ALPPL2 | alkaline phosphatase, placental-like 2 (ALPPL2), mRNA [NM_031313] | NM_031313 | ENST00000295453 | 251 | NM_031313 | THC2603490 |
| A_33_P3335461 | | putative CHST11/IgH oncoprotein (CHST11/IgH fusion) mRNA, complete cds. [AY533203] | AY533203 | | | | THC2490416 |
| A_32_P49616 | EEF1B2 | eukaryotic translation elongation factor 1 beta 2 (EEF1B2), transcript variant 1, mRNA [NM_001959] | NM_001959 | ENST00000392221 | 1933 | NM_001959 | THC2570764 |
| A_23_P30283 | FAM174A | family with sequence similarity 174, member A (FAM174A), mRNA [NM_198507] | NM_198507 | ENST00000312637 | 345757 | NM_198507 | THC2464536 |
| A_23_P42144 | PEX6 | peroxisomal biogenesis factor 6 (PEX6), mRNA [NM_000287] | NM_000287 | ENST00000304611 | 5190 | NM_000287 | THC2461072 |
| A_24_P148796 | MST1 | macrophage stimulating 1 (hepatocyte growth factor-like) (MST1), mRNA [NM_020998] | NM_020998 | ENST00000493836 | 4485 | NM_020998 | NP299055 |
| A_24_P63136 | P2RY13 | purinergic receptor P2Y, G-protein coupled, 13 (P2RY13), mRNA [NM_176894] | NM_176894 | ENST00000325602 | 53829 | NM_176894 | THC2474658 |
| A_32_P148122 | | immunoglobulin kappa variable 1D-33 [Source: HGNC Symbol; Acc: 5753] [ENST00000390265] | BC095489 | ENST00000390265 | | | NP093301 |
| A_23_P30900 | | Uncharacterized protein [Source: UniProtKB/TrEMBL; Acc: E7ET45] [ENST00000552745] | XM_003119089 | ENST00000552745 | | XM_003119089 | THC2538530 |
| A_23_P302550 | RGS18 | regulator of G-protein signaling 18 (RGS18), mRNA [NM_130782] | NM_130782 | ENST00000367460 | 64407 | NM_130782 | THC2474032 |
| A_24_P75680 | SLC4A8 | solute carrier family 4, sodium bicarbonate cotransporter, member 8 (SLC4A8), transcript variant 2, mRNA [NM_004858] | NM_004858 | ENST00000546663 | 9498 | NM_004858 | THC2617779 |
| A_33_P3381851 | KRTAP10-10 | keratin associated protein 10-10 (KRTAP10-10), mRNA [NM_181688] | NM_181688 | ENST00000380095 | 353333 | NM_181688 | NP883181 |
| A_23_P2582 | HDAC7 | histone deacetylase 7 (HDAC7), transcript variant 1, mRNA [NM_015401] | NM_015401 | ENST00000459625 | 51564 | NM_015401 | THC2506329 |
| A_23_P414978 | NUDT14 | nudix (nucleoside diphosphate linked moiety X)-type motif 14 (NUDT14), mRNA [NM_177533] | NM_177533 | ENST00000339418 | 256281 | NM_177533 | THC2529116 |
| A_23_P251937 | CPEB4 | cytoplasmic polyadenylation element binding protein 4 (CPEB4), mRNA [NM_030627] | NM_030627 | ENST00000334035 | 80315 | NM_030627 | THC2503739 |
| A_32_P38467 | SNHG8 | small nucleolar RNA host gene 8 (non-protein coding) (SNHG8), transcript variant 1, non-coding RNA [NR_003584] | NR_003584 | | 100093630 | NR_003584 | THC2722842 |
| A_23_P114839 | FHL3 | four and a half LIM domains 3 (FHL3), mRNA [NM_004468] | NM_004468 | ENST00000477194 | 2275 | NM_004468 | THC2657002 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3261433 | LOC100131473 | PREDICTED: hypothetical protein LOC100131473 (LOC100131473), mRNA [XM_001720331] | XM_001720331 | | 100131473 | XM_001720331 | THC2660992 |
| A_33_P3299487 | AIM1L | absent in melanoma 1-like (AIM1L), mRNA [NM_001039775] | NM_001039775 | ENST00000374207 | 55057 | NM_001039775 | THC2773713 |
| A_23_P74668 | C1orf158 | chromosome 1 open reading frame 158 (C1orf158), mRNA [NM_152290] | NM_152290 | ENST00000376210 | 93190 | NM_152290 | NP1155029 |
| A_24_P97342 | PROK2 | prokineticin 2 (PROK2), transcript variant 2, mRNA [NM_021935] | NM_021935 | ENST00000353065 | 60675 | NM_021935 | THC2479819 |
| A_23_P396299 | LOC100129827 | hypothetical LOC100129827 (LOC100129827), non-coding RNA [NR_034094] | NR_034094 | ENST00000529979 | 100129827 | NR_034094 | THC2480303 |
| A_33_P3724155 | DERL3 | Derl-like domain family, member 3 (DERL3), transcript variant 3, mRNA [NM_198440] | NM_198440 | ENST00000290730 | 91319 | NM_198440 | THC2488725 |
| A_33_P3251412 A_33_P3359856 | MZT2A | mitotic spindle organizing protein 2A [Source: HGNC Symbol; Acc: 33187] [ENST00000445782] | | ENST00000445782 | 653784 | | THC2544251 |
| A_33_P3419691 | GATS | GATS, stromal antigen 3 opposite strand (GATS), transcript variant 2, non-coding RNA [NR_028038] | NR_028038 | | 352954 | NR_028038 | THC2463982 |
| A_33_P3291821 | ANKRD26P1 | ankyrin repeat domain 26 pseudogene 1 (ANKRD26P1), non-coding RNA [NR_026556] | NR_026556 | ENST00000329373 | 124149 | NR_026556 | THC2621756 |
| A_33_P3226788 A_33_P3494109 | LOC146795 | cDNA F1132815 fis, clone TESTI20028340. [AK057377] | AK057377 | | 146795 | | |
| A_33_P3376644 | SENP6 | SUMO1/sentrin specific peptidase 6 (SENP6), transcript variant 1, mRNA [NM_015571] | NM_015571 | ENST00000447266 | 26054 | NM_015571 | THC2650795 |
| A_23_P3424057 | PEG3 | paternally expressed 3 (PEG3), transcript variant 1, mRNA [NM_006210] | NM_006210 | ENST00000326441 | 5178 | NM_006210 | THC2462814 |
| A_33_P3714341 | | IGK mRNA for immunoglobulin kappa light chain, partial cds, clone: F010–014L. [AB363267] | AB363267 | | | | |
| A_33_P3285092 | LOC100129763 | cDNA FLJ44135 fis, clone THYMU2009134. [AK126123] | AK126123 | | 100129763 | | THC2486333 |
| A_33_P3691916 | FAM13A | family with sequence similarity 13, member A (FAM13A), transcript variant 1, mRNA [NM_014883] | NM_014883 | ENST00000264344 | 10144 | NM_014883 | THC2510194 |
| A_24_P461497 A_24_P400832 | LOC100130950 | hypothetical LOC100130950 (LOC100130950), non-coding RNA [NR_034082] | NR_034082 | | 100130950 | NR_034082 | THC2632507 |
| A_33_P3336696 | ND4L | mitochondrially encoded NADH dehydrogenase 4L [Source: HGNC Symbol; Acc: 7460] [ENST00000361335] | AK311996 | ENST00000361335 | 4539 | | THC2595339 |
| A_33_P3320538 | NUPL1 | nucleoporin like 1 [Source: HGNC Symbol; Acc: 20261] [ENST00000381745] | CR605945 | ENST00000381745 | 9818 | | THC2526330 |
| A_24_P29001 | LSM3 | LSM3 homolog, U6 small nuclear RNA associated (S. cerevisiae) (LSM3), mRNA [NM_014463] | NM_014463 | ENST00000306024 | 27258 | NM_014463 | THC2466049 |
| A_23_P151506 | PLEK2 | pleckstrin 2 (PLEK2), mRNA [NM_016445] | NM_016445 | ENST00000216446 | 26499 | NM_016445 | THC2462892 |
| A_23_P258381 | SPSB4 | spIA/ryanodine receptor domain and SOCS box containing 4 (SPSB4), mRNA [NM_080862] | NM_080862 | ENST00000508126 | 92369 | NM_080862 | THC2632742 |
| A_33_P3370930 | LAMB1 | laminin, beta 1 [Source: HGNC Symbol; Acc: 6486] [ENST00000393559] | | ENST00000393559 | 3912 | | THC2637518 |
| A_33_P3209321 | LOC729558 | cDNA FLJ39676 fis, clone SMINT2009832. [AK096995] | AK096995 | | 729558 | | THC2616799 |
| A_23_P200298 | AGL | amylo-alpha-1, 6-glucosidase, 4-alpha-glucanotransferase (AGL), transcript variant 4, mRNA [NM_000028] | NM_000028 | ENST00000294724 | 178 | NM_000028 | THC2461565 |
| A_33_P3424489 | | immunoglobulin lambda variable 3-25 [Source: HGNC Symbol; Acc: 5908] [ENST00000390305] | S73129 | ENST00000390305 | | | NP084490 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3317258 | | T cell receptor gamma variable 5 [Source: HGNC Symbol; Acc: 12290] [ENST00000390344] | X15019 | ENST00000390344 | | | THC2556814 |
| A_33_P3405213 | PECAM1 | platelet/endothelial cell adhesion molecule (PECAM1), mRNA [NM_000442] | NM_000442 | ENST00000545548 | 5175 | NM_000442 | THC2557337 |
| A_33_P3220612 | FAM89B | family with sequence similarity 89, member B (FAM89B), transcript variant 3, mRNA [NM_001098784] | NM_001098784 | ENST00000377088 | 23625 | NM_001098784 | THC2494467 |
| A_33_P3230259 | NCAPH | non-SMC condensin I complex, subunit H (NCAPH), mRNA [NM_015341] | NM_015341 | | 23397 | NM_015341 | THC2461132 |
| A_33_P3308434 | MORN1 | MORN repeat containing 1 (MORN1), mRNA [NM_024848] | NM_024848 | ENST00000378525 | 79906 | NM_024848 | THC2519762 |
| A_33_P3424217 | | major histocompatibility complex, class II, DQ beta 1 [Source: HGNC Symbol; Acc: 4944] [ENST00000399670] | XM_003119092 | ENST00000399670 | | XM_003119092 | THC2560922 |
| A_33_P3218120 | LOC402036 | PREDICTED: hCG1646661-like (LOC402036), mRNA [XM_001719325] | XM_001719325 | | 402036 | XM_001719325 | |
| A_23_P50508 | PLA2G4C | phospholipase A2, group IVC (cytosolic, calcium-independent) (PLA2G4C), transcript variant 1, mRNA [NM_003706] | NM_003706 | ENST00000354276 | 8605 | NM_003706 | NP1152204 |
| A_23_P76951 | TMX1 | thioredoxin-related transmembrane protein 1 (TMX1), mRNA [NM_030755] | NM_030755 | ENST00000457354 | 81542 | NM_030755 | THC2466402 |
| A_23_P1206 | RPS24 | ribosomal protein S24 (RPS24), transcript variant c, mRNA [NM_001026] | NM_001026 | ENST00000467106 | 6229 | NM_001026 | THC2572247 |
| A_33_P3250148 | SP8 | Sp8 transcription factor (SP8), transcript variant 2, mRNA [NM_198956] | NM_198956 | ENST00000297210 | 221833 | NM_198956 | THC2481338 |
| A_23_P16415 | LRP3 | low density lipoprotein receptor-related protein 3 (LRP3), mRNA [NM_002333] | NM_002333 | ENST00000431491 | 4037 | NM_002333 | THC2461289 |
| A_23_P98580 | FADS2 | fatty acid desaturase 2 (FADS2), mRNA [NM_004265] | NM_004265 | ENST00000523235 | 9415 | NM_004265 | THC2512429 |
| A_23_P21800 | | immunoglobulin kappa variable 3-20 [Source: HGNC Symbol; Acc: 5817] [ENST00000492167] | DQ187531 | ENST00000492167 | | | NP511624 |
| A_33_P3373185 | LOC399744 | hypothetical LOC399744 (LOC399744), non-coding RNA [NR_024497] | NR_024497 | ENST00000438516 | 399744 | NR_024497 | THC2594684 |
| A_24_P813550 | | immunoglobulin heavy variable 4-59 [Source: HGNC Symbol; Acc: 5654] [ENST00000390629] | XM_003119589 | ENST00000390629 | | XM_003119589 | NP1077996 |
| A_33_P3374253 | | PREDICTED: similar to hCG1645807 (LOC100127987), mRNA [XM_001717762] | XM_001717762 | | | XM_001717762 | |
| A_23_P75800 | RAB3IL1 | RAB3A interacting protein (rabin3)-like 1 (RAB3IL1), mRNA [NM_013401] | NM_013401 | ENST00000394836 | 5866 | NM_013401 | THC2472895 |
| A_24_P38572 | NOL6 | nucleolar protein family 6 (RNA-associated) (NOL6), transcript variant alpha, mRNA [NM_022917] | NM_022917 | ENST00000325914 | 65083 | NM_022917 | NP287178 |
| A_23_P134744 A_24_P152325 | RNF122 | ring finger protein 122 (RNF122), mRNA [NM_024787] | NM_024787 | ENST00000256257 | 79845 | NM_024787 | THC2476886 |
| A_33_P3331882 | CRTC1 | CREB regulated transcription coactivator 1 (CRTC1), transcript variant 3, mRNA [NM_001098482] | NM_001098482 | ENST00000262813 | 23373 | NM_001098482 | THC2472431 |
| A_33_P3361991 | OR9A2 | olfactory receptor, family 9, subfamily A, member 2 (OR9A2), mRNA [NM_001001658] | NM_001001658 | ENST00000350513 | 135924 | NM_001001658 | THC2603293 |
| A_24_P917866 | SET | SET nuclear oncogene (SET), transcript variant 2, mRNA [NM_003011] | NM_003011 | ENST00000322030 | 6418 | NM_003011 | THC2465434 |
| A_32_P224234 | LOC645195 | cDNA FLJ41456 fis, clone BRSTN2012320. [AK123450] | AK123450 | | 645195 | | THC2479813 |
| A_23_P161968 | SLC22A10 | solute carrier family 22, member 10 (SLC22A10), mRNA [NM_001039752] | NM_001039752 | ENST00000332793 | 387775 | NM_001039752 | THC2480380 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3332135 | PHOSPHO1 | phosphatase, orphan 1 (PHOSPHO1), transcript variant 1, mRNA [NM_001143804] | NM_001143804 | ENST00000413580 | 162466 | NM_001143804 | THC2478263 |
| A_23_P60227 | CCIN | calicin (CCIN), mRNA [NM_005893] | NM_005893 | ENST00000335119 | 881 | NM_005893 | THC2461601 |
| A_23_P159650 | COX7B | cytochrome c oxidase subunit VIIb (COX7B), nuclear gene encoding mitochondrial protein, mRNA [NM_001866] | NM_001866 | ENST00000373335 | 1349 | NM_001866 | THC2693234 |
| A_33_P3306352 | C20orf108 | chromosome 20 open reading frame 108 [Source: HGNC Symbol; Acc: 16102] [ENST00000437418] | | ENST00000437418 | 116151 | | THC2691510 |
| A_33_P3395859 | LOC147646 | hypothetical protein LOC147646 (LOC147646), mRNA [NM_001193623] | NM_001193623 | | 147646 | NM_001193623 | THC2602398 |
| A_33_P3232798 | RAB11FIP1 | RAB11 family interacting protein 1 (class I) (RAB11FIP1), transcript variant 1, mRNA [NM_025151] | NM_025151 | ENST00000343853 | 80223 | NM_025151 | THC2751555 |
| A_33_P3386487 A_33_P3245620 | | | | | | | |
| A_24_P161144 | ZNF843 | zinc finger protein 843 (ZNF843), mRNA [NM_001136509] | NM_001136509 | | 283933 | NM_001136509 | THC2483860 |
| A_33_P3314176 | FAM46C | family with sequence similarity 46, member C (FAM46C), mRNA [NM_017709] | NM_017709 | ENST00000369448 | 54855 | NM_017709 | THC2496506 |
| A_33_P3258593 | PRB1 | proline-rich protein BstNI subfamily 1 (PRB1), transcript variant 1, mRNA [NM_005039] | NM_005039 | ENST00000240636 | 5542 | NM_005039 | THC2476439 |
| A_33_P375849 | | Q8BT90_MOUSE (Q8BT90) 10, 11 days embryo whole body cDNA, RIKEN full-length enriched library, clone: 2810021H19 product: ribosomal protein S17, full insert sequence. (Fragment), partial (98%) [THC2555910] | | | | | THC2555910 |
| A_33_P3290235 | LOC149950 | hypothetical LOC149950 (LOC149950), non-coding RNA [NR_034152] | NR_034152 | ENST00000375671 | 149950 | NR_034152 | THC2488463 |
| A_23_P3216448 | COL11A2 | collagen, type XI, alpha 2 (COL11A2), transcript variant 4, mRNA [NM_001163771] | NM_001163771 | ENST00000383088 | 1302 | NM_001163771 | THC2481257 |
| A_23_P103690 | FAM189B | family with sequence similarity 189, member B (FAM189B), transcript variant 1, mRNA [NM_006589] | NM_006589 | ENST00000487649 | 10712 | NM_006589 | NP1167666 |
| A_24_P303647 | C7orf60 | chromosome 7 open reading frame 60 (C7orf60), mRNA [NM_152556] | NM_152556 | ENST00000297145 | 154743 | NM_152556 | THC2610927 |
| A_23_P209269 | PPM1B | protein phosphatase, Mg2+/Mn2+ dependent, 1B (PPM1B), transcript variant 5, mRNA [NM_001033557] | NM_001033557 | ENST00000409432 | 5495 | NM_001033557 | THC2491147 |
| A_33_P3362933 | GYPA | glycophorin A (MNS blood group) (GYPA), mRNA [NM_002099] | NM_002099 | ENST00000508337 | 2993 | NM_002099 | NP082322 |
| A_33_P3327663 | SUSD4 | sushi domain containing 4 [Source: HGNC Symbol; Acc: 25470] [ENST00000366877] | | ENST00000366877 | 55061 | | THC2679732 |
| A_24_P166094 | ARFIP1 | ADP-ribosylation factor interacting protein 1 (ARFIP1), transcript variant 1, mRNA [NM_001025595] | NM_001025595 | ENST00000353617 | 27236 | NM_001025595 | THC2462556 |
| A_33_P3351052 | POU3F1 | POU class 3 homeobox 1 (POU3F1), mRNA [NM_002699] | NM_002699 | ENST00000373012 | 5453 | NM_002699 | THC2498352 |
| A_32_P8074 | RPS3A | ribosomal protein S3A (RPS3A), mRNA [NM_001006] | NM_001006 | ENST00000515818 | 6189 | NM_001006 | THC2559600 |
| A_24_P48539 | SIGLEC5 | sialic acid binding Ig-like lectin 5 (SIGLEC5), mRNA [NM_003830] | NM_003830 | ENST00000429354 | 8778 | NM_003830 | THC2472472 |
| A_33_P3222744 | ZNF117 | zinc finger protein 117 (ZNF117), mRNA [NM_015852] | NM_015852 | | 51351 | NM_015852 | THC2518471 |
| A_33_P3210363 | LOC100128191 | hypothetical LOC100128191 (LOC100128191), non-coding RNA [NR_027157] | NR_027157 | | 100128191 | NR_027157 | THC2492437 |
| A_23_P170901 | PACRG | PARK2 co-regulated (PACRG), transcript variant 1, mRNA [NM_152410] | NM_152410 | ENST00000545186 | 135138 | NM_152410 | THC2691532 |
| A_24_P15502 | | | | | | | |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3570228 | LOC644962 | cDNA FLJ46065 fis, clone TBAES2007862. [AK127954] | AK127954 | | 644962 | | THC2485964 |
| A_33_P3406873 | NFASC | neurofascin (NFASC), transcript variant 5, mRNA [NM_001005389] | NM_001005389 | ENST00000403080 | 23114 | NM_001005389 | NP1247431 |
| A_33_P3291484 | ST8SIA4 | ST8 alpha-N-acetyl-neuraminide alpha-2,8-sialyltransferase 4 (ST8SIA4), transcript variant 1, mRNA [NM_005668] | NM_005668 | | 7903 | NM_005668 | THC2531659 |
| A_33_P3403851 | | O52K2_HUMAN (Q8NGK3) Olfactory receptor 52K2, partial (29%) [THC2647746] | | | | | THC2647746 |
| A_23_P61042 | | immunoglobulin heavy constant alpha 2 (A2m marker) [Source: HGNC Symbol; Acc: 5479] [ENST00000390539] | XR_111480 | ENST00000390539 | | XR_111480 | NP1154471 |
| A_33_P3214635 | FECH | ferrochelatase (FECH), nuclear gene encoding mitochondrial protein, transcript variant 1, mRNA [NM_001012515] | NM_001012515 | ENST00000262093 | 2235 | NM_001012515 | THC2650625 |
| A_33_P132139 | C21orf58 | chromosome 21 open reading frame 58 (C21orf58), mRNA [NM_058180] | NM_058180 | ENST00000417060 | 54058 | NM_058180 | THC2482412 |
| A_33_P3305790 | NOS3 | nitric oxide synthase 3 (endothelial cell) (NOS3), transcript variant 1, mRNA [NM_000603] | NM_000603 | ENST00000461406 | 4846 | NM_000603 | THC2520376 |
| A_24_P335620 | SLC7A5 | solute carrier family 7 (amino acid transporter light chain, L system), member 5 (SLC7A5), mRNA [NM_003486] | NM_003486 | ENST00000261622 | 8140 | NM_003486 | THC2545199 |
| A_24_P383999 | RPS3A | ribosomal protein S3A (RPS3A), mRNA [NM_001006] | NM_001006 | ENST00000515818 | 6189 | NM_001006 | THC2559600 |
| A_24_P31275 | ATP1B2 | ATPase, Na+/K+ transporting, beta 2 polypeptide (ATP1B2), mRNA [NM_001678] | NM_001678 | ENST00000250111 | 482 | NM_001678 | THC2559283 |
| A_33_P3389342 | ARID5A | AT rich interactive domain 5A (MRF1-like) (ARID5A), mRNA [NM_212481] | NM_212481 | ENST00000359765 | 10865 | NM_212481 | THC2627646 |
| A_24_P349636 A_33_P3386132 | C2orf49 | chromosome 2 open reading frame 49 [Source: HGNC Symbol; Acc: 28772] [ENST00000437250] | AK304268 | ENST00000437250 | 79074 | | THC2507880 |
| A_33_P3261074 A_24_P371053 | ORMDL1 | ORM1-like 1 (S. cerevisiae) (ORMDL1), transcript variant 1, mRNA [NM_016467] | NM_016467 | ENST00000325795 | 94101 | NM_016467 | THC2466861 |
| A_23_P62115 | TIMP1 | TIMP metallopeptidase inhibitor 1 (TIMP1), mRNA [NM_003254] | NM_003254 | ENST00000218388 | 7076 | NM_003254 | NP1132335 |
| A_23_P350719 | PRSS30P | protease, serine, 30 homolog (mouse), pseudogene (PRSS30P), non-coding RNA [NR_026864] | NR_026864 | ENST00000390681 | 124221 | NR_026864 | THC2484024 |
| A_24_P104512 | EVPL | envoplakin (EVPL), mRNA [NM_001988] | NM_001988 | ENST00000301607 | 2125 | NM_001988 | THC2471184 |
| A_23_P20234 | GUCY2GP | guanylate cyclase 2G homolog (mouse), pseudogene (GUCY2GP), non-coding RNA [NR_028134] | NR_028134 | ENST00000490269 | 390003 | NR_028134 | THC2662526 |
| A_33_P3589819 A_33_P3495962 | LOC100507637 SNORA71A | cDNA: FLJ22849 fis, clone KAIA987. [AK026502] AGENCOURT_6611325 NIH_MGC_106 cDNA clone IMAGE: 5485440 5', mRNA sequence [BM918074] | AK026502 BM918074 | | 100507637 26777 | | THC2515177 |
| A_33_P3416622 | NCRNA00322 | PREDICTED: chromosome 21 open reading frame 136 (C21orf136), miscRNA [XR_109689] | XR_109689 | | 100126693 | XR_109689 | THC2482602 |
| A_24_P358245 | ATP8B5P | ATPase, class I, type 8B, member 5, pseudogene (ATP8B5P), transcript variant 2, non-coding RNA [NR_003582] | NR_003582 | ENST00000430846 | 158381 | NR_003582 | THC2536226 |
| A_23_P8900 | COX6C | cytochrome c oxidase subunit VIc (COX6C), nuclear gene encoding mitochondrial protein, mRNA [NM_004374] | NM_004374 | ENST00000522940 | 1345 | NM_004374 | THC2509868 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3391536 A_23_P55616 | SLC14A1 | solute carrier family 14 (urea transporter), member 1 (Kidd blood group) (SLC14A1), transcript variant 4, mRNA [NM_001146037] | NM_001146037 | ENST00000321925 | 6563 | NM_001146037 | THC2629557 |
| A_33_P3292241 A_33_P3224020 | ARAF2P | v-raf murine sarcoma 3611 viral oncogene homolog pseudogene, mRNA (cDNA clone IMAGE: 5295529). [BC033982] | BC033982 | | 644000 | | THC2605425 |
| A_33_P3387696 | TMBIM4 | transmembrane BAX inhibitor motif containing 4 (TMBIM4), mRNA [NM_016056] | NM_016056 | ENST00000358230 | 51643 | NM_016056 | THC2544517 |
| A_33_P3238215 | COBLL1 | COBL-like 1 (COBLL1), mRNA [NM_014900] | NM_014900 | ENST00000493868 | 22837 | NM_014900 | THC2566941 |
| A_23_P163025 | RNASE3 | ribonuclease, RNase A family, 3 (RNASE3), mRNA [NM_002935] | NM_002935 | ENST00000304639 | 6037 | NM_002935 | THC2477182 |
| A_24_P173566 | | immunoglobulin lambda variable 3-1 [Source: HGNC Symbol; Acc: 5896] [ENST00000390319] | X57818 | ENST00000390319 | | | NP1458222 |
| A_24_P11436 | TTC22 | tetratricopeptide repeat domain 22 (TTC22), transcript variant 2, mRNA [NM_017904] | NM_017904 | ENST00000488771 | 55001 | NM_017904 | THC2655240 |
| A_33_P3253672 | KCNH3 | potassium voltage-gated channel, subfamily H (eag-related), member 3 (KCNH3), mRNA [NM_012284] | NM_012284 | ENST00000257981 | 23416 | NM_012284 | |
| A_32_P128701 | USP53 | ubiquitin specific peptidase 53 (USP53), mRNA [NM_019050] | NM_019050 | ENST00000450251 | 54532 | NM_019050 | THC2516580 |
| A_33_P3267640 | HGFAC | HGF activator (HGFAC), mRNA [NM_001528] | NM_001528 | ENST00000382774 | 3083 | NM_001528 | THC2478808 |
| A_23_P63751 | PRDX3 | peroxiredoxin 3 (PRDX3), nuclear gene encoding mitochondrial protein, transcript variant 1, mRNA [NM_006793] | NM_006793 | ENST00000298510 | 10935 | NM_006793 | THC2782087 |
| A_23_P79094 | LILRA3 | leukocyte immunoglobulin-like receptor, subfamily A (without TM domain), member 3 (LILRA3), transcript variant 1, mRNA [NM_006865] | NM_006865 | ENST00000251390 | 11026 | NM_006865 | NP081039 |
| A_33_P3262156 | SLC8A1 | solute carrier family 8 (sodium/calcium exchanger), member 1 (SLC8A1), transcript variant A, mRNA [NM_021097] | NM_021097 | ENST00000403092 | 6546 | NM_021097 | THC2483436 |
| A_33_P3216532 | EPHB4 | EPH receptor B4 (EPHB4), mRNA [NM_004444] | NM_004444 | ENST00000487222 | 2050 | NM_004444 | NP1473086 |
| A_24_P287043 | IFITM2 | interferon induced transmembrane protein 2 (1-8D) (IFITM2), mRNA [NM_006435] | NM_006435 | ENST00000527146 | 10581 | NM_006435 | THC2548091 |
| A_23_P421032 | SEC14L4 | SEC14-like 4 (S. cerevisiae) (SEC14L4), transcript variant 1, mRNA [NM_174977] | NM_174977 | ENST00000320982 | 284904 | NM_174977 | THC2478128 |
| A_33_P3208970 | ZNF683 | zinc finger protein 683 (ZNF683), transcript variant 1, mRNA [NM_001114759] | NM_001114759 | ENST00000349618 | 257101 | NM_001114759 | THC2475548 |
| A_23_P394605 | SEC24A | SEC24 family, member A (S. cerevisiae) (SEC24A), mRNA [NM_021982] | NM_021982 | ENST00000398844 | 10802 | NM_021982 | THC2493017 |
| A_32_P112910 | UBL4B | ubiquitin-like 4B (UBL4B), mRNA [NM_203412] | NM_203412 | ENST00000334179 | 164153 | NM_203412 | THC2477239 |
| A_33_P3228642 | ZNF584 | zinc finger protein 584 [Source: HGNC Symbol; Acc: 27318] [ENST00000322834] | AK298929 | ENST00000322834 | 201514 | | THC2518340 |
| A_32_P40547 | MEG3 | maternally expressed 3 (non-protein coding) (MEG3), transcript variant 1, non-coding RNA [NR_002766] | NR_002766 | ENST00000452514 | 55384 | NR_002766 | THC2722032 |
| A_24_P295543 | BLOC1S2 | biogenesis of lysosomal organelles complex-1, subunit 2 (BLOC1S2), transcript variant 2, mRNA [NM_001001342] | NM_001001342 | ENST00000370372 | 282991 | NM_001001342 | THC2467480 |
| A_33_P3324949 | C3orf65 | chromosome 3 open reading frame 65 (C3orf65), non-coding RNA [NR_027317] | NR_027317 | ENST00000296270 | 646600 | NR_027317 | THC2484692 |
| A_23_P9485 | ORM2 | orosomucoid 2 (ORM2), mRNA [NM_000608] | NM_000608 | ENST00000412657 | 5005 | NM_000608 | THC2562815 |
| A_33_P3110784 | TM6SF1 | transmembrane 6 superfamily member 1 (TM6SF1), transcript variant 1, mRNA [NM_023003] | NM_023003 | ENST00000379386 | 53346 | NM_023003 | THC2478123 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P78595 | CEACAM21 | carcinoembryonic antigen-related cell adhesion molecule 21 (CEACAM21), transcript variant 2, mRNA [NM_033543] | NM_033543 | ENST00000401445 | 90273 | NM_033543 | THC2603785 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3274691 | LOC619207 | scavenger receptor protein family member (LOC619207), non-coding RNA [NR_002934] | NR_002934 | ENST00000356567 | 619207 | NR_002934 | NP1076594 |
| A_33_P3406281 | SAMHD1 | SAM domain and HD domain 1 (SAMHD1), mRNA [NM_015474] | NM_015474 | ENST00000262878 | 25939 | NM_015474 | |
| A_24_P52921 | BCAT1 | branched chain amino-acid transaminase 1, cytosolic (BCAT1), transcript variant 1, mRNA [NM_005504] | NM_005504 | ENST00000544418 | 586 | NM_005504 | THC2739017 |
| A_33_P3265941 A_33_P3347772 A_33_P3326892 | 2-Sep | septin 2 [Source: HGNC Symbol; Acc: 7729] [ENST00000473479] cDNA FLJ26718 fis, clone PNC03325 [Source: UniProtKB/TrEMBL; Acc: Q6ZP17] [ENST00000398957] | AK025163 AK130228 | ENST00000473479 ENST00000398957 | 4735 | | THC2514366 NP852683 |
| A_33_P3289396 | LOC729737 | hypothetical LOC729737 (LOC729737), non-coding RNA [NR_039983] | NR_039983 | ENST00000438516 | 729737 | NR_039983 | THC2577343 |
| A_24_P50437 | | cDNA clone IMAGE: 30404477, partial cds. [BC065737] | BC065737 | | | | |
| A_33_P3396010 | AGER | advanced glycosylation end product-specific receptor (AGER), transcript variant 9, mRNA [NM_001206966] | NM_001206966 | ENST00000438221 | 177 | NM_001206966 | NP868672 |
| A_33_P4110279 | DOCK9 | dedicator of cytokinesis 9 [Source: HGNC Symbol; Acc: 14132] [ENST00000340449] | AK090793 | ENST00000340449 | 23348 | | THC2485517 |
| A_33_P3294252 | ATF1 | activating transcription factor 1 (ATF1), mRNA [NM_005171] | NM_005171 | ENST00000262053 | 466 | NM_005171 | THC2552669 |
| A_32_P86150 | CTRB2 | chymotrypsinogen B2 (CTRB2), mRNA [NM_001025200] | NM_001025200 | ENST00000303037 | 440387 | NM_001025200 | THC2562346 |
| A_23_P159937 | SLC6A8 | solute carrier family 6 (neurotransmitter transporter, creatine), member 8 (SLC6A8), transcript variant 1, mRNA [NM_005629] | NM_005629 | ENST00000253122 | 6535 | NM_005629 | THC2469137 |
| A_33_P3270346 | KIR2DL5A | killer cell immunoglobulin-like receptor, two domains, long cytoplasmic tail, 5A (KIR2DL5A), mRNA [NM_020535] | NM_020535 | ENST00000391731 | 57292 | NM_020535 | THC2489091 |
| A_24_P38702 | NKX2-3 | NK2 homeobox 3 (NKX2-3), mRNA [NM_145285] | NM_145285 | ENST00000344586 | 159296 | NM_145285 | NP1246719 |
| A_23_P7172 | PGM2 | phosphoglucomutase 2 (PGM2), mRNA [NM_018290] | NM_018290 | ENST00000512556 | 55276 | NM_018290 | THC2466583 |
| A_33_P3351062 A_33_P3395743 | VWA1 | von Willebrand factor A domain containing 1 (VWA1), transcript variant 1, mRNA [NM_022834] | NM_022834 | ENST00000476993 | 64856 | NM_022834 | THC2469429 |
| A_24_P148907 | MAB21L2 | mab-21-like 2 (C. elegans) (MAB21L2), mRNA [NM_006439] | NM_006439 | ENST00000317605 | 10586 | NM_006439 | THC2472779 |
| A_33_P3401711 | USH1G | Usher syndrome 1G (autosomal recessive) (USH1G), mRNA [NM_173477] | NM_173477 | ENST00000319642 | 124590 | NM_173477 | |
| A_33_P3401169 | | T cell receptor beta variable 21/OR9-2 (non-functional) [Source: HGNC Symbol; Acc: 12199] [ENST00000331828] | | ENST00000331828 | | | THC2565247 |
| A_32_P202859 | H1FNT | H1 histone family, member N, testis-specific (H1FNT), mRNA [NM_181788] | NM_181788 | ENST00000335017 | 341567 | NM_181788 | THC2475276 |
| A_23_P168229 | TXNDC5 | thioredoxin domain containing 5 (endoplasmic reticulum) (TXNDC5), transcript variant 1, mRNA [NM_030810] | NM_030810 | ENST00000439343 | 81567 | NM_030810 | THC2483613 |
| A_33_P3382887 A_23_P377882 | KCNH2 | potassium voltage-gated channel, subfamily H (eag-related), member 2 (KCNH2), transcript variant 2, mRNA [NM_172056] | NM_172056 | ENST00000430723 | 3757 | NM_172056 | THC2730451 |
| A_24_P854492 | MIAT | myocardial infarction associated transcript (non-protein coding) (MIAT), transcript variant 1, non-coding RNA [NR_003491] | NR_003491 | | 440823 | NR_003491 | THC2574058 |
| A_33_P3399468 | | cDNA, FLJ18157. [AK311115] | AK311115 | | | | |
| A_23_P335039 | ZNF721 | zinc finger protein 721 (ZNF721), mRNA [NM_133474] | NM_133474 | ENST00000338977 | 170960 | NM_133474 | THC2491441 |
| A_33_P3393170 | CAPN5 | calpain 5 (CAPN5), mRNA [NM_004055] | NM_004055 | ENST00000360841 | 726 | NM_004055 | THC2669168 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P19510 | HLA-DQB2 | major histocompatibility complex, class II, DQ beta 2 (HLA-DQB2), mRNA [NM_001198858] | NM_001198858 | ENST00000416131 | 3120 | NM_001198858 | THC2477776 |
| A_23_P218126 | | immunoglobulin heavy constant gamma 1 (G1m marker) [Source: HGNC Symbol; Acc: 5525] [ENST00000390549] | BC024289 | ENST00000390549 | | | NP852618 |
| A_33_P3367701 | TMEM164 | transmembrane protein 164 (TMEM164), transcript variant 2, mRNA [NM_032227] | NM_032227 | ENST00000288381 | 84187 | NM_032227 | THC2483947 |
| A_23_P43946 | SARNP | SAP domain containing ribonucleoprotein (SARNP), transcript variant 1, mRNA [NM_033082] | NM_033082 | ENST00000336133 | 84324 | NM_033082 | THC2468200 |
| A_23_P143958 | RPL22L1 | ribosomal protein L22-like 1 (RPL22L1), mRNA [NM_001099645] | NM_001099645 | ENST00000494771 | 200916 | NM_001099645 | THC2463114 |
| A_24_P95723 | KIAA0125 | KIAA0125 (KIAA0125), non-coding RNA [NR_026800] | NR_026800 | | 9834 | NR_026800 | THC2657912 |
| A_33_P3360886 | | GRP33_ARTSA (P13230) Glycine-rich protein GRP33, partial (8%) [THC2642603] | | | | | THC2642603 |
| A_32_P114215 | COMMD6 | COMM domain containing 6 (COMMD6), transcript variant 1, mRNA [NM_203497] | NM_203497 | ENST00000483290 | 170622 | NM_203497 | NP1189257 |
| A_33_P3291891 | LOC100130825 | PREDICTED: hypothetical protein LOC100130825 (LOC100130825), mRNA [XM_001720026] | XM_001720026 | | 100130825 | XM_001720026 | |
| A_24_P382579 | OXT | oxytocin, prepropeptide (OXT), mRNA [NM_000915] | NM_000915 | ENST00000217386 | 5020 | NM_000915 | THC2480057 |
| A_23_P127446 | DPF2 | D4, zinc and double PHD fingers family 2 (DPF2), mRNA [NM_006268] | NM_006268 | ENST00000532052 | 5977 | NM_006268 | THC2604046 |
| A_33_P3409518 | TUBBP5 | tubulin, beta pseudogene 5 (TUBBP5), non-coding RNA [NR_027156] | NR_027156 | | 643224 | NR_027156 | THC2493332 |
| A_33_P3352103 | LYPLAL1 | lysophospholipase-like 1 (LYPLAL1), mRNA [NM_138794] | NM_138794 | ENST00000366927 | 127018 | NM_138794 | THC2613276 |
| A_23_P434518 | LFNG | LFNG O-fucosylpeptide 3-beta-N-acetylglucosaminyltransferase (LFNG), transcript variant 2, mRNA [NM_001040168] | NM_001040168 | ENST00000359574 | 3955 | NM_001040168 | THC2486300 |
| A_23_P379630 | SLC38A10 | solute carrier family 38, member 10 (SLC38A10), transcript variant 2, mRNA [NM_138570] | NM_138570 | ENST00000288439 | 124565 | NM_138570 | THC2464913 |
| A_24_P148235 | RPS27 | ribosomal protein S27 (RPS27), mRNA [NM_001030] | NM_001030 | ENST00000392558 | 6232 | NM_001030 | THC2596064 |
| A_23_P253012 | GRAMD1C | GRAM domain containing 1C (GRAMD1C), transcript variant 1, mRNA [NM_017577] | NM_017577 | ENST00000440446 | 54762 | NM_017577 | THC2614903 |
| A_24_P295999 | CD4 | CD4 molecule (CD4), transcript variant 1, mRNA [NM_000616] | NM_000616 | ENST00000011653 | 920 | NM_000616 | THC2470142 |
| A_33_P3369245 | LOC100129826 | PREDICTED: hypothetical LOC100129826 (LOC100129826), miscRNA [XR_114456] | XR_114456 | | 100129826 | XR_114456 | THC2479538 |
| A_33_P3235132 | LOC400968 | cDNA FLJ45884 fis, clone OCBBF3021166. [AK127783] | AK127783 | ENST00000412149 | 400968 | | THC2481983 |
| A_24_P375599 | | | | | | | |
| A_33_P3220160 | RAC2 | cDNA FLJ39605 fis, clone SKNSH2005981, weakly similar to RAS-RELATED C3 BOTULINUM TOXIN SUBSTRATE 2. [AK096924] | AK096924 | ENST00000401529 | 5880 | | THC2510406 |
| A_32_P20750 | PLGLB1 | plasminogen-like B1 (PLGLB1), mRNA [NM_001032392] | NM_001032392 | ENST00000324709 | 5343 | NM_001032392 | THC2555295 |
| A_33_P3376958 | LOC96610 | BMS1 homolog, ribosome assembly protein (yeast) pseudogene (LOC96610), non-coding RNA [NR_027293] | NR_027293 | ENST00000390290 | 96610 | NR_027293 | NP162580 |
| A_23_P410965 | KIAA1522 | KIAA1522 (KIAA1522), transcript variant 1, mRNA [NM_020888] | NM_020888 | ENST00000401073 | 57648 | NM_020888 | THC2578126 |
| A_33_P3272479 | NPM2 | nucleophosmin/nucleoplasmin 2 (NPM2), mRNA [NM_182795] | NM_182795 | ENST00000520180 | 10361 | NM_182795 | NP1074998 |
| A_33_P3379535 | | cDNA FLJ45698 fis, clone FEBRA2017811. [AK127601] | AK127601 | | | | NP851257 |
| A_23_P325726 | ACOT11 | acyl-CoA thioesterase 11 (ACOT11), transcript variant 1, mRNA [NM_015547] | NM_015547 | ENST00000481208 | 26027 | NM_015547 | THC2707621 |
| A_33_P3298159 | PTGDS | prostaglandin D2 synthase 21 kDa (brain) (PTGDS), mRNA [NM_000954] | NM_000954 | ENST00000224167 | 5730 | NM_000954 | THC2470120 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P33045 | RPL26 | ribosomal protein L26 (RPL26), mRNA [NM_000987] | NM_000987 | ENST00000293842 | 6154 | NM_000987 | THC2561695 |
| A_33_P3399634 | RASSF10 | Ras association (RalGDS/AF-6) domain family (N-terminal) member 10 (RASSF10), mRNA [NM_001080521] | NM_001080521 | | 644943 | NM_001080521 | |
| A_33_P3239347 | NKX3-1 | NK3 homeobox 1 (NKX3-1), mRNA [NM_006167] | NM_006167 | ENST00000380871 | 4824 | NM_006167 | THC2607070 |
| A_33_P3411985 | RABGAP1 | RAB GTPase activating protein 1 [Source: HGNC Symbol; Acc: 17155] [ENST00000402311] | | ENST00000402311 | 23637 | | THC2679929 |
| A_33_P3351180 | | immunoglobulin heavy constant alpha 1 [Source: HGNC Symbol; Acc: 5478] [ENST00000390547] | XR_114797 | ENST00000390547 | | XR_114797 | NP852642 |
| A_33_P3430391 | LOC389273 | cDNA FLJ27351 fis, clone TST05050. [AK130861] | AK130861 | ENST00000506021 | 389273 | | NP1157119 |
| A_23_P126613 | AQP10 | aquaporin 10 (AQP10), mRNA [NM_080429] | NM_080429 | ENST00000484864 | 89872 | NM_080429 | THC2480695 |
| A_24_P215804 | CKLF | chemokine-like factor (CKLF), transcript variant 1, mRNA [NM_016951] | NM_016951 | ENST00000264001 | 51192 | NM_016951 | THC2503188 |
| A_33_P3257943 | RPL26 | ribosomal protein L26 (RPL26), mRNA [NM_000987] | NM_000987 | ENST00000293842 | 6154 | NM_000987 | THC2570124 |
| A_33_P3267263 | RNU1-5 | RNA, U1 small nuclear 5 (RNU1-5), small nuclear RNA [NR_004400] | NR_004400 | | 26863 | NR_004400 | THC2542861 |
| A_33_P3240512 | KCTD12 | potassium channel tetramerisation domain containing 12 (KCTD12), mRNA [NM_138444] | NM_138444 | ENST00000377474 | 115207 | NM_138444 | THC2567965 |
| A_24_P92016 | HUWE1 | HECT, UBA and WWE domain containing 1 (HUWE1), mRNA [NM_031407] | NM_031407 | ENST00000218328 | 10075 | NM_031407 | THC2470054 |
| A_23_P426305 | AOC3 | amine oxidase, copper containing 3 (vascular adhesion protein 1) (AOC3), mRNA [NM_003734] | NM_003734 | ENST00000308423 | 8639 | NM_003734 | THC2468389 |
| A_33_P3376925 A_24_P307306 A_23_P254756 | CD164 | CD164 molecule, sialomucin (CD164), transcript variant 1, mRNA [NM_006016] | NM_006016 | ENST00000310786 | 8763 | NM_006016 | NP088058 |
| A_32_P194821 | RPL21 | ribosomal protein L21 (RPL21), mRNA [NM_000982] | NM_000982 | ENST00000473558 | 6144 | NM_000982 | THC2553670 |
| A_33_P3257607 | PPP1R12B | protein phosphatase 1, regulatory (inhibitor) subunit 12B (PPP1R12B), transcript variant 7, mRNA [NM_001197131] | NM_001197131 | | 4660 | NM_001197131 | |
| A_33_P3265222 | KIAA1324 | KIAA1324 (KIAA1324), mRNA [NM_020775] | NM_020775 | ENST00000529753 | 57535 | NM_020775 | THC2629991 |
| A_33_P3376154 | LOC100130825 | PREDICTED: hypothetical protein LOC100130825 (LOC100130825), mRNA [XM_001720026] | XM_001720026 | | 100130825 | XM_001720026 | |
| A_23_P164927 A_33_P3340065 | SYNGR4 | synaptogyrin 4 (SYNGR4), mRNA [NM_012451] | NM_012451 | ENST00000344846 | 23546 | NM_012451 | THC2478295 |
| A_23_P25069 | DOCK3 | dedicator of cytokinesis 3 (DOCK3), mRNA [NM_004947] | XM_003119523 | ENST00000542925 | 1795 | XM_003119523 | THC2503104 |
| A_24_P272845 | | | NM_004947 | ENST00000266037 | | NM_004947 | THC2472118 |
| A_23_P140675 | EPB42 | erythrocyte membrane protein band 4.2 (EPB42), transcript variant 1, mRNA [NM_000119] | NM_000119 | ENST00000397027 | 2038 | NM_000119 | NP1465858 |
| A_33_P3245623 | TSPY17P | PREDICTED: testis specific protein, Y-linked 17 (pseudogene) (TSPY17P), mRNA [XM_003118834] | XM_003118834 | | 100132124 | XM_003118834 | |
| A_33_P3263538 | NEAT1 | Human MEN1 region clone epsilon/beta mRNA, 3′ fragment. [AF001893] | AF001893 | | 283131 | | THC2583960 |
| A_24_P263548 | HIP1 | huntingtin interacting protein 1 (HIP1), mRNA [NM_005338] | NM_005338 | ENST00000336926 | 3092 | NM_005338 | THC2501285 |
| A_33_P3302210 | LOC100129129 | PREDICTED: hypothetical LOC100129129 (LOC100129129), partial miscRNA [XR_113108] | XR_113108 | ENST00000525867 | 100129129 | XR_113108 | THC2610893 |
| A_23_P132910 | RBM47 | RNA binding motif protein 47 (RBM47), transcript variant 2, mRNA [NM_019027] | NM_019027 | ENST00000510871 | 54502 | NM_019027 | THC2467007 |
| A_24_P316074 | | | | | | | |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_33_P3355418 A_24_P212024 | AGBL1 | ATP/GTP binding protein-like 1 (AGBL1), mRNA [NM_152336] immunoglobulin kappa variable 1-27 [Source: HGNC Symbol; Acc: 5735] [ENST00000498435] | NM_152336 AY867113 | ENST00000389298 ENST00000498435 | 123624 | NM_152336 | NP1400333 |
| A_33_P3305320 | LOC100289383 | PREDICTED: protein capicua homolog (LOC100289383), mRNA [XM_002344123] | XM_002344123 | | 100289383 | XM_002344123 | THC2481163 |
| A_24_P605563 | | immunoglobulin lambda constant 2 (Kern-Oz-marker) [Source: HGNC Symbol; Acc: 5856] [ENST00000390323] | AY172962 | ENST00000390323 | | | NP493030 |
| A_23_P145657 A_33_P3294217 | STAG3 UTF1 | stromal antigen 3 (STAG3), mRNA [NM_012447] undifferentiated embryonic cell transcription factor 1 (UTF1), mRNA [NM_003577] | NM_012447 NM_003577 | ENST00000426455 ENST00000304477 | 10734 8433 | NM_012447 NM_003577 | THC2471871 THC2486743 |
| A_33_P3290403 | IMPA2 | inositol(myo)-1(or 4)-monophosphatase 2 (IMPA2), mRNA [NM_014214] | NM_014214 | ENST00000383376 | 3613 | NM_014214 | THC2664101 |
| A_33_P3379039 | IGLL5 | immunoglobulin lambda-like polypeptide 5 (IGLL5), transcript variant 1, mRNA [NM_001178126] | NM_001178126 | ENST00000390321 | 100423062 | NM_001178126 | NP492959 |
| A_32_P205110 A_33_P3383034 | FOXC1 UBA2 | forkhead box C1 (FOXC1), mRNA [NM_001453] ubiquitin-like modifier activating enzyme 2 (UBA2), mRNA [NM_005499] | NM_001453 NM_005499 | ENST00000380874 ENST00000439527 | 2296 10054 | NM_001453 NM_005499 | THC2495614 THC2746225 |
| A_23_P170453 A_33_P3320953 A_24_P886040 | CST5 CTXN1 DCP2 | cystatin D (CST5), mRNA [NM_001900] cortexin 1 (CTXN1), mRNA [NM_206833] DCP2 decapping enzyme homolog (S. cerevisiae) (DCP2), transcript variant 1, mRNA [NM_152624] | NM_001900 NM_206833 NM_152624 | ENST00000304710 ENST00000318978 ENST00000389063 | 1473 404217 167227 | NM_001900 NM_206833 NM_152624 | THC2477887 THC2471562 THC2497286 |
| A_33_P3312682 | REXO1 | REX1, RNA exonuclease 1 homolog (S. cerevisiae) (REXO1), mRNA [NM_020695] | NM_020695 | ENST00000170168 | 57455 | NM_020695 | THC2612197 |
| A_33_P3864411 | | ARP3 actin-related protein 3 homolog B (yeast) pseudogene 5 [Source: HGNC Symbol; Acc: 38682] [ENST00000541147] | AY026352 | ENST00000541147 | | | THC2487688 |
| A_33_P3350748 A_23_P117363 | KRT7 SERPINA6 | keratin 7 (KRT7), mRNA [NM_005556] serpin peptidase inhibitor, clade A (alpha-1 antiproteinase, antitrypsin), member 6 (SERPINA6), mRNA [NM_001756] | NM_005556 NM_001756 | ENST00000422319 ENST00000341584 | 3855 866 | NM_005556 NM_001756 | THC2465320 NP705151 |
| A_33_P3364959 | | isolate N1408L immunoglobulin lambda light chain variable region (IGLV2) mRNA, IGLV2-23*02 allele, partial cds. [DQ098707] | DQ098707 | | | | THC2524123 |
| A_33_P3326285 | GAS5 | growth arrest-specific 5 (non-protein coding) (GAS5), non-coding RNA [NR_002578] | NR_002578 | ENST00000381007 | 60674 | NR_002578 | THC2570454 |
| A_33_P3371089 | SGTB | small glutamine-rich tetratricopeptide repeat (TPR)-containing, beta (SGTB), mRNA [NM_019072] | NM_019072 | | 54557 | NM_019072 | THC2497751 |
| A_33_P3233906 | RAMP1 | receptor (G protein-coupled) activity modifying protein 1 (RAMP1), mRNA [NM_005855] | NM_005855 | ENST00000254661 | 10267 | NM_005855 | THC2464432 |
| A_33_P3230037 A_23_P254442 | | FKSG58 (FKSG58) mRNA, complete cds. [AF336885] AI894139 pseudogene (LOC155060), non-coding RNA [NR_036573] | AF336885 NR_036573 | ENST00000378052 | 155060 | NR_036573 | NP316843 THC2518474 |
| A_33_P3325429 | LOC155060 | mRNA for T cell receptor beta variable 5, partial cds, clone: un 66. [AB306153] | AB306153 | | | | NP404580 |
| A_24_P4972 | | ribosomal protein L22 pseudogene 11 [Source: HGNC Symbol; Acc: 35603] [ENST00000538228] | CR590757 | ENST00000538228 | | | THC2549395 |
| A_33_P3710442 A_33_P3256257 | FLJ11710 KRTAP4-7 | cDNA FLJ11710 fis, clone HEMBA1005149. [AK021772] keratin associated protein 4-7 (KRTAP4-7), mRNA [NM_033061] | AK021772 NM_033061 | ENST00000391417 | 79904 100132476 | NM_033061 | THC2653222 THC2488799 |

APPENDIX B-continued

MALES: Technology: Agilent.SingleColor.26652
Created On: Tue Jan 31 13:34:51 EST 2012

| ProbeName | Gene | Description | Gb Accession | EnsemblID | Entrez GeneID | RefSeq Accession | TIGRID |
|---|---|---|---|---|---|---|---|
| A_23_P149775 | ARHGAP12 | Rho GTPase activating protein 12 (ARHGAP12), mRNA [NM_018287] | NM_018287 | ENST00000396144 | 94134 | NM_018287 | NP1403916 |
| A_33_P3485976 | | cDNA FLJ37762 fis, clone BRHIP2024347, weakly similar to GALECTIN-3. [AK095081] | AK095081 | ENST00000528482 | | | THC2629979 |
| A_33_P3397180 | LOC100129324 | cDNA FLJ46397 fis, clone THYMU3003958. [AK128261] | AK128261 | | 100129324 | | THC2484056 |
| A_23_P21495 | FCGBP | Fc fragment of IgG binding protein (FCGBP), mRNA [NM_003890] | NM_003890 | ENST00000221347 | 8857 | NM_003890 | THC2466782 |
| A_33_P3311267 | KRTAP19-2 | keratin associated protein 19-2 (KRTAP19-2), mRNA [NM_181608] | NM_181608 | ENST00000334055 | 337969 | NM_181608 | THC2488580 |
| A_23_P74799 | SLC25A24 | solute carrier family 25 (mitochondrial carrier; phosphate carrier), member 24 (SLC25A24), nuclear gene encoding mitochondrial protein, transcript variant 2, mRNA [NM_213651] | NM_213651 | ENST00000370041 | 29957 | NM_213651 | THC2477421 |
| A_33_P3368950 | LOC389333 | hypothetical protein LOC389333 (LOC389333), mRNA [NM_001161546] | NM_001161546 | ENST00000434752 | 389333 | NM_001161546 | THC2603790 |
| A_33_P3281444 | | immunoglobulin kappa variable 1D-43 [ENST00000468879] [Source: HGNC Symbol; Acc: 5758] | DQ100647 | ENST00000468879 | | | THC2561290 |
| A_33_P3424507 | OR51F1 | olfactory receptor, family 51, subfamily F, member 1 (OR51F1), mRNA [NM_001004752] | NM_001004752 | ENST00000380383 | 256892 | NM_001004752 | NP1461808 |
| A_33_P3310976 A_33_P3258316 | LOC100507269 | PREDICTED: hypothetical protein LOC100507269 (LOC100507269), mRNA [XM_003118986] | XM_003118986 | | 100507269 | XM_003118986 | THC2558116 |
| A_23_P7827 | FAM26F | family with sequence similarity 26, member F (FAM26F), mRNA [NM_001010919] | NM_001010919 | ENST00000368605 | 441168 | NM_001010919 | THC2606591 |
| A_33_P3336223 | | ALU6_HUMAN (P39193) Alu subfamily SP sequence contamination warning entry, partial (18%) [THC2521288] | | ENST00000398067 | | | THC2521288 |
| A_33_P3420852 | KIRREL2 | kin of IRRE like 2 (Drosophila) (KIRREL2), transcript variant 3, mRNA [NM_199180] | NM_199180 | ENST00000360202 | 84063 | NM_199180 | THC2603242 |
| A_33_P3227010 A_23_P162596 | ACTR6 | ARP6 actin-related protein 6 homolog (yeast) (ACTR6), mRNA [NM_022496] | NM_022496 | ENST00000188312 | 64431 | NM_022496 | THC2519245 |
| A_33_P3303086 | HNRPLL | heterogeneous nuclear ribonucleoprotein L-like (HNRPLL), transcript variant 1, mRNA [NM_138394] | NM_138394 | ENST00000272249 | 92906 | NM_138394 | NP1156896 |
| A_23_P201211 | FCRL5 | Fc receptor-like 5 (FCRL5), transcript variant 1, mRNA [NM_031281] | NM_031281 | ENST00000461387 | 83416 | NM_031281 | THC2617135 |
| A_32_P162250 | ARHGAP18 | Rho GTPase activating protein 18 (ARHGAP18), mRNA [NM_033515] | NM_033515 | ENST00000275189 | 93663 | NM_033515 | THC2461353 |
| A_24_P174341 | CCNT2 | cyclin T2 (CCNT2), transcript variant b, mRNA [NM_058241] | NM_058241 | ENST00000419781 | 905 | NM_058241 | THC2631629 |
| A_23_P12784 | FRAT2 | frequently rearranged in advanced T-cell lymphomas 2 (FRAT2), mRNA [NM_012083] | NM_012083 | ENST00000371019 | 23401 | NM_012083 | THC2618275 |

APPENDIX C

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P2683 | RPAP3 | *Homo sapiens* RNA polymerase II associated protein 3 (RPAP3), transcript variant 1, mRNA [NM_024604] | NM_024604 | ENST00000380650 | 79657 | RN polymerase II associated protein 3 | chr12:48060809-48057361 | GO:0005488 | NM_024604 | THC2462582 | Hs.437855 |
| A_32_P14850 | | nuclear pore complex interacting protein-like 2 [Source:HGNC Symbol;Acc:34409] [ENST00000429990] | XM_003118720 | ENST00000429990 | | | chr16:7442543 6-74425495 | | XM_003118720 | THC2549472 | Hs.448833 |
| A_24_P497186 | IRF2BP2 | *Homo sapiens* interferon regulatory factor 2 binding protein 2 (IRF2BP2), transcript variant 1, mRNA [NM_182972] | NM_182972 | ENST00000366609 | 359948 | interferon regulatory factor 2 binding protein 2 | chr1:23474003 1-234740001 | GO:0005634|GO:004549 | NM_182972 | THC2501773 | Hs.350268 |
| A_33_P3344292 | LOC644925 | full-length cDNA clone CS0DI020Y21 of Placenta Cot 25-normalized of *Homo sapiens* (human). [CR618938] | CR618938 | | 64492b | hypothetical LOC644925 | chr14:5503385 4-55033913 | | | THC2779729 | Hs.632349 |
| A_33_P3223631 | LOC100132217 | *Homo sapiens* cDNA FLJ46348 fis, clone TESTI4047569. [AK128836] | AK128836 | | 100132217 | hypothetical LOC 100132217 | chr7:63219509 63219568 | | | THC2481823 | Hs.520384 |
| A_32_P815507 | LOC100130920 | *Homo sapiens* cDNA FLJ36320 fis, clone THYMU2005480, [AK093639] | AK093639 | | 100130920 | hypothetical protein LOC 100130920 | chr10:6568397 6568338 | | | THC2487672 | Hs.683904 |
| A_23_P163113 | PRPF39 | *Homo sapiens* PRP39 pre-mRNA processing factor 39 homolog (S. cerevisiae) (PRPF39), mRNA [NM_017922] | NM_017922 | ENST00000355846 | 55015 | PRP39 pre-mRNA processing factor 39 homolog (S. cerevisiae) | chr14:4558425 2-45584311 | GO:0008380|GO:0006397|NM_017922| GO:0005622|GO:0005488| GO:0005730|GO:0005634 | | THC2483434 | Hs.274337 |
| A_32_P34876 | WDR93 | *Homo sapiens* WD repeat domain 93 (WDR93), mRNA [NM_020212] | NM_020212 | ENST00000268130 | 56964 | WD repeat domain 93 | chr15:9028134 5-90281404 | | NM_020212 | NP498805 | Hs.177557 |
| A_33_P3388745 | LOC100132207 | *Homo sapiens* cDNA FLJ41345 fis, | AK123339 | | 100132207 | hypothetical LOC | chr3:12932767 2-129327731 | | | THC2482232 | Hs.633570 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P331598 | | clone BRAWH2002761. [AK123339] | | | 100132207 | | | | | | |
| A_23_P120048 | IPO7 | Homo sapiens importin 7 (IPO7), mRNA [NM_006391] | NM_006391 | ENST00000379719 | 10527 | importin 7 | chr11:9467009-9467068 | GO:0005215\|GO:0005625\|NM_006391<br>GO:0008536\|GO:0008565\|<br>GO:0005737\|GO:0005643\|<br>GO:0044419\|GO:0007165\|<br>GO:0042393\|GO:0005083\|<br>GO:0005634\|GO:0006606\|<br>GO:0006886 | | THC2467487 | Hs.523470 |
| A_23_P250800 | BAZ2B | Homo sapiens bromodomain adjacent to zinc finger domain, 2B (BAZ2B), mRNA [NM_013450] | NM_013450 | ENST00000392783 | 29994 | bromo-domain adjacent to zinc finger domain, 2B | chr2:160175985-160175926 | GO:0005515\|GO:0008270\|NM_013450<br>GO:0046872\|GO:0045449\|<br>GO:0005634\|GO:0003677 | | THC2491976 | Hs.470369 |
| A_23_P134454 | ST3GAL6 | Homo sapiens ST3 beta-galactoside alpha-2,3-sialyltransferase 6 (ST3GAL6), mRNA [NM_006100] | NM_006100 | ENST00000177899 | 10402 | ST3 beta-galactoside alpha 2,3-sialyl transferase 6 | chr3:98510738-98510797 | GO:0006664\|GO:0030173\|NM_006100<br>GO:0008373\|GO:0005794\|<br>GO:0016020\|GO:0009249\|<br>GO:0006040\|GO:0006486\|<br>GO:0016021 | | THC2493961 | Hs.148716 |
| | CAV1 | Homo sapiens caveolin 1, caveolae protein, 22 kDa (CAV1), transcript variant 1, mRNA [NM_001753] | NM_001753 | ENST00000341049 | 857 | caveolin 1, caveolae protein, 22 kDa | chr7:116200742-116200801 | GO:0043627\|GO:0019915\|NM_001753<br>GO:0010524\|GO:0006940\|<br>GO:0052547\|GO:0070836\|<br>GO:0042802\|GO:0005622\|<br>GO:0016050\|GO:0009925\|<br>GO:0044419\|GO:0051260\|<br>GO:0032207\|GO:0005938\|<br>GO:0010332\|GO:0042632\|<br>GO:0005811\|GO:0019905\|<br>GO:0033344\|GO:0005794\|<br>GO:0009986\|GO:0051384\|<br>GO:0019217\|GO:0016504\|<br>GO:0051592\|GO:0043234\|<br>GO:0048554\|GO:0007519\|<br>GO:0005887\|GO:0032570\|<br>GO:0006641\|GO:0005925\|<br>GO:0050998\|GO:0048471\|<br>GO:0051899\|GO:0005886\|<br>GO:0005783\|GO:0042524\|<br>GO:0005829\|GO:0045807\|<br>GO:0043409\|GO:0000188\|<br>GO:0005739\|GO:0005737\|<br>GO:0033138\|GO:0008104\|<br>GO:0045907\|GO:0001960\|<br>GO:0045019\|GO:0033484\|<br>GO:0015485\|GO:0030857\|<br>GO:0033137\|GO:0045908\|<br>GO:0006816\|GO:0019900 | | NP1154468 | Hs.74034 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | | | | | | | GO:0001666\|GO:0031116\|GO:0007584\|GO:0060056\|GO:0051480\|GO:0042493\|GO:0005625\|GO:0009967\|GO:0031410\|GO:0045768\|GO:0046426\|GO:0009612\|GO:0032947\|GO:0000139\|GO:0007595\|GO:0030193\|GO:0001937\|GO:0005901\|GO:0000299\|GO:0001570 | | | |
| A_23_P8431 | HMBS | *Homo sapiens* hydroxymethylbilane synthase (HMBS), transcript variant 1, mRNA [NM_000190] | NM_000190 | ENST00000537841 | 3145 | hydroxy-methylbil-ane synthase | chr11:118964129-118964188 | GO:0031406\|GO:0005739\|GO:0050662\|GO:0000793\|GO:0005737\|GO:0043176\|GO:0005634\|GO:0004418\|GO:0016740\|GO:0006783 | NM_000190 | THC2603650 | Hs.82609 |
| A_33_P3269864 | LOC284009 | *Homo sapiens* hypothetical LOC284009 (LOC284009), non-coding RNA [NR_028335] | NR_028335 | ENST00000381977 | 284009 | hypothetical LOC284009 | chr17:2310351-2310292 | | NR_028335 | THC2487357 | Hs.632244 |
| A_33_P3323607 | CCDC129 | coiled-coil domain containing 129 [Source: HGNC Symbol; Acc:27363] [ENST00000409717] | | ENST00000409717 | 223075 | coiled-coil domain containing 129 | chr7:31553759-31553818 | | | | |
| A_23_P48088 | CD27 | *Homo sapiens* CD27 molecule (CD27), mRNA [NM_001242] | NM_001242 | ENST00000266557 | 939 | CD27 molecule | chr12:6560640-6560699 | GO:0005515\|GO:0016064\|GO:0045471\|GO:0045579\|GO:0046330\|GO:0005624\|GO:0006915\|GO:0005576\|GO:0006916\|GO:0006917\|GO:0006955\|GO:0008588\|GO:0016020\|GO:0005887\|GO:0043027\|GO:0007166\|GO:0004888 | NM_001242 | THC2472153 | Hs.355307 |
| A_33_P3234222 | TSPO2 | *Homo sapiens* translocator protein 2 (TSPO2), transcript variant 1, mRNA [NM_001010873] | NM_001010873 | ENST00000373161 | 222642 | translocator protein 2 | chr6:41011969-41012028 | GO:0016020\|GO:0004872\|GO:0016021 | NM_001010873 | THC2482465 | Hs.357392 |
| A_33_P3235454 | | Q3SZ59_BOVIN (Q3SZ59) Ribosomal protein L36a, partial (96%) [THC2542270] | | | | | chr15:0606827-40-060682799 | | | THC2542270 | |
| A_23_P5983 | PLTP | *Homo sapiens* phospholipid transfer protein (PLTP), | NM_006227 | ENST00000477313 | 5360 | phospholipid transfer protein | chr20:4452770-1-44527642 | GO:0006629\|GO:0006869\|GO:0005576\|GO:0008289 | NM_006227 | NP199660 | Hs.439312 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq Accession | TIGRID | UniGene ID |
|---|---|---|---|---|---|---|---|---|---|---|---|
| A_33_P3388618 | TNK1 | transcript variant 1, mRNA [NM_006227] Homo sapiens tyrosine kinase, non-receptor, 1 (TNK1), mRNA [NM_003985] | NM_003985 | ENST00000311668 | 8711 | tyrosine kinase, non-receptor, 1 | chr17:7292997-7293056 | GO:0005515\|GO:0007165\|GO:0030308\|GO:0005737\|GO:0046777\|GO:0016020\|GO:0000166\|GO:0004871\|GO:0005524\|GO:0004715\|GO:0016740\|GO:0019898 | NM_003985 | THC2629027 | Hs.203420 |
| A_23_P104025 | TSEN15 | Homo sapiens tRNA splicing endo-nuclease 15 homolog (S. cerevisiae) (TSEN15), transcript variant 1, mRNA [NM_052965] | NM_052965 | ENST00000462677 | 116461 | tRNA splicing endonuclease 15 homolog (S. cerevisiae) | chr1:184042890-184042949 | GO:0006397\|GO:0005515\|GO:0005730\|GO:0005634\|GO:0008033 | NM_052965 | THC2462261 | Hs.548197 |
| A_23_P110846 | CNOT8 | Homo sapiens CCR4-NOT transcription complex, subunit 8 (CNOT8), mRNA [NM_004779] | NM_004779 | ENST00000517876 | 9337 | CCR4-NOT transcription complex, subunit 8 | chr5:154255813-154255872 | GO:0005622\|GO:0005515\|GO:0006355\|GO:0005737\|GO:0008285\|GO:0003700\|GO:0005634\|GO:0003676 | NM_004779 | THC2468160 | Hs.26703 |
| A_33_P3364060 | HR | Homo sapiens hairless homolog (mouse) (HR), transcript variant 1, mRNA [NM_005144] | NM_005144 | ENST00000522016 | 55806 | hairless homolog (mouse) | chr8:21972885-21972826 | GO:0005515\|GO:0006355\|GO:0003700\|GO:0042826\|GO:0003714\|GO:0005634\|GO:0051291\|GO:0043433\|GO:0046872\|GO:0046966\|GO:0016604\|GO:0000118\|GO:0042809\|GO:0016481\|GO:0008270 | NM_005144 | THC2464466 | Hs.272367 |
| A_23_P112026 | IDO1 | Homo sapiens indoleamine 2,3-dioxygenase 1 (IDO1), mRNA [NM_002164] | NM_002164 | ENST00000523779 | 3620 | indoleamine 2,3-dioxygenase 1 | chr8:39785529-39785588 | GO:0070233\|GO:0032693\|GO:0046007\|GO:0019674\|GO:0046872\|GO:0032735\|GO:0005737\|GO:0005829\|GO:0032496\|GO:0002678\|GO:0007565\|GO:0007610\|GO:0009055\|GO:0004833\|GO:0033555\|GO:0005625\|GO:0019441\|GO:0002666\|GO:0033754\|GO:0019825\|GO:0002830\|GO:0016491\|GO:0016597\|GO:0034276\|GO:0020037\|GO:0055114 | NM_002164 | THC2489025 | Hs.840 |
| A_33_P3222019 | WSCD2 | Homo sapiens WSC domain containing 2 (WSCD2), mRNA [NM_014653] | NM_014653 | ENST00000547525 | 9671 | WSC domain containing 2 | chr12:108589508-108589567 | GO:0016020\|GO:0016021 | NM_014653 | THC2465113 | Hs.143591 |
| A_23_P369815 | FASLG | Homo sapiens Fas ligand | NM_000639 | ENST00000367721 | 356 | Fas ligand (TNF | chr1:172635681-172635744 | GO:0008625\|GO:0005164\|GO:0008633\|GO:0070265 | NM_000639 | THC2477997 | Hs.2007 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (TNF superfamily, member 6) (FASLG), mRNA [NM_000639] | | | | superfamily, member 6) | | GO:0048471\|GO:0060554\| GO:0005886\|GO:0060555\| GO:0007267\|GO:0005576\| GO:0006925\|GO:0005125\| GO:0005615\|GO:0007165\| GO:0006955\|GO:0005887\| GO:0005901\|GO:0046666\| GO:0032496\|GO:0016023\| GO:0043123\|GO:0009897 | | | |
| A_33_P3219682 | | yx87g09.r1 Soares melanocyte 2NbHM Homo sapiens cDNA clone IMAGE:268768 5', mRNA sequence [N35358] | N35358 | | | | chr6:147486881-147486940 | | | THC2778743 | Hs.575390 |
| A_33_P3335682 | PPP1R14A | Homo sapiens protein phosphatase 1, regulatory (inhibitor) subunit 14A (PPP1R14A), mRNA [NM_033256] | NM_033256 | ENST00000347262 | 94274 | protein phosphatase 1, regulatory (inhibitor) subunit 14A | chr19:38741996-38741937 | GO:0005515\|GO:0042325\|NM_033256\| GO:0005737\|GO:0004864 | | NP383096 | Hs.6315679 |
| A_23_P53137 | HBG1 | Homo sapiens hemoglobin, gamma A (HBG1), mRNA [NM_000559] | NM_000559 | ENST00000330597 | 3047 | hemoglobin, gamma A | chr11:5269593-5269534 | GO:0005515\|GO:0019825\|NM_000559\| GO:0005833\|GO:0006810\| GO:0005344\|GO:0046872\| GO:0020037\|GO:0015671 | | NP094052 | Hs.7123539 |
| A_24_P91094 | RUNDC3A | Homo sapiens RUN domain containing 3A (RUNDC3A), transcript variant 2, mRNA [NM_006695] | NM_006695 | ENST00000225441 | 10900 | RUN domain containing 3A | chr17:42393791-42393850 | GO:0005515\|GO:0005083\|NM_006695\| GO:0030250\|GO:0007264\| GO:0009898\|GO:0005829 | | THC2504630 | Hs.500197 |
| A_23_P316531 | GPR25 | Homo sapiens G protein-coupled receptor 25 (GPR25), mRNA [NM_005298] | NM_005298 | ENST00000304244 | 2848 | G protein-coupled receptor 25 | chr1:200843145-200843204 | GO:0007165\|GO:0007186\|NM_005298\| GO:0005886\|GO:0005887\| GO:0004930\|GO:0004872 | | THC2646268 | Hs.534316 |
| A_23_P150583 | SCGB1A1 | Homo sapiens secretoglobin, family 1A, member 1 (uteroglobin) (SCGB1A1), mRNA [NM_003357] | NM_003357 | ENST00000278282 | 7356 | secretoglobin, family 1A, member 1 (uteroglobin) | chr11:62189823-62190532 | GO:0043488\|GO:0007566\|NM_003357\| GO:0032714\|GO:0032713\| GO:0050727\|GO:0005576\| GO:0000122\|GO:0019834\| GO:0042130\|GO:0007165\| GO:0005737\|GO:0005488\| GO:0032696\|GO:0032689 | | THC2472230 | Hs.523732 |
| A_23_P121533 | SPON2 | Homo sapiens spondin 2, extracellular matrix | NM_012445 | ENST00000431380 | 10417 | spondin 2, extracellular matrix | chr4:1160797-1160738 | GO:0006955\|GO:0007411\|NM_012445\| GO:0005509\|GO:0005578\| GO:0005102\|GO:0005576 | | THC2601265 | Hs.635350 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P110196 | HERC5 | Homo sapiens hect domain and RLD5(HERC5), mRNA [NM_016323] | NM_016323 | ENST00000502913 | 51191 | hect domain and RLD 5 | chr4:89426889-89426948 | GO:0005622\|GO:0048471\|GO:0005737\|GO:0016881\|GO:0019941\|GO:0016874\|GO:0000079\|GO:0006464 | NM_016323 | THC2472533 | Hs.26663 |
| A_23_P109026 | KCNK15 | Homo sapiens potassium channel, subfamily K, member 15 (KCNK15), mRNA [NM_022358] | NM_022358 | ENST00000372861 | 60598 | potassium channel, subfamily K, member 15 | chr20:4337959 3-43379652 | GO:0005244\|GO:0016020\|GO:0005267\|GO:0030955\|GO:0016021\|GO:0006813\|GO:0006811 | NM_022358 | THC2478658 | Hs.528664 |
| A_33_P3264346 | | | | | | protein | chr16:0030501 84-003050243 | GO:0007155 | | THC2780215 | |
| A_33_P3260307 | CARHSP1 | Homo sapiens calcium regulated heat stable protein 1, 24 kDa (CARHSP1), transcript variant 2, mRNA [NM_001042476] | NM_001042476 | ENST00000311052 | 23589 | calcium regulated heat stable protein 1, 24 kDa | chr16:8946862-8946803 | GO:0005515\|GO:0007242\|GO:0006355\|GO:0005737\|GO:0019902\|GO:0003677 | NM_001042476 | THC2468995 | Hs.632184 |
| A_23_P422044 | PCDHGA2 | Homo sapiens protocadherin gamma subfamily A, 2 (PCDHGA2), transcript variant 2, mRNA [NM_032009] | NM_032009 | ENST00000528330 | 56113 | protocadherin gamma subfamily A, 2 | chr5:14072084 0-140720899 | GO:0005515\|GO:0005886\|GO:0005509\|GO:0005624\|GO:0016021\|GO:0007155\|GO:0007156 | NM_032009 | NP362372 | Hs.368160 |
| A_23_P131024 | ZBTB32 | Homo sapiens zinc finger and BTB domain containing 32(ZBTB32), mRNA [NM_014383] | NM_014383 | ENST00000262630 | 27033 | zinc finger and BTB domain containing 32 | chr19:3620786 6-36207925 | GO:0005515\|GO:0030097\|GO:0003714\|GO:0003704\|GO:0005634\|GO:0000122\|GO:0000228\|GO:0001817\|GO:0003677\|GO:0046872\|GO:0005622\|GO:0042098\|GO:0005654\|GO:0008270\|GO:0045449 | NM_014383 | THC2760977 | Hs.99430 |
| A_33_P3346826 | IL32 | Homo sapiens interleukin 32(IL32), transcript variant 4, mRNA [NM_001012633] | NM_001012633 | ENST00000528652 | 9235 | interleukin 32 | chr16:3119014-3119073 | GO:0006955\|GO:0006952\|GO:0005576\|GO:0007155\|GO:0005615\|GO:0005125 | NM_001012633 | THC2531803 | Hs.943 |
| A_23_P105562 | VWF | Homo sapiens von Willebrand | NM_000552 | ENST00000261405 | 7450 | von Willebrand | chr12:6058242-6058183 | GO:0033093\|GO:0005783\|GO:0031889\|GO:0005518 | NM_000552 | THC2468950 | Hs.440848 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | factor (VWF), mRNA [NM_000552] | | | | factor | | GO:0051087\|GO:0005578\| GO:0009611\|GO:0030168\| GO:0005576\|GO:0001890\| GO:0002020\|GO:0042803\| GO:0001889\|GO:0047485\| GO:0001948\|GO:0005178\| GO:0019865\|GO:0031091\| GO:0051260\|GO:0009897 | | | |
| A_33_P3354851 | | Human mRNA for T cell receptor V alpha gene segment V-alpha-w29, clone [GRa07. [X58768] | X58768 | | | | chr14:22636811-22636870 | | NP089254 | | Hs.495158 |
| A_24_P272451 | C17orf87 | Homo sapiens cDNA FLJ32580 fis, clone SPLEN2000270. [AK057142] | AK057142 | | 388325 | chromosome 17 open reading frame 87 | chr17:5116499-5116440 | GO:0016020\|GO:0016021 | | THC2484848 | Hs.462080 |
| A_33_P3251252 | | | | | | | chr3:04571892 7-045718868 | | | | |
| A_23_P74290 | GBP5 | Homo sapiens guanylate binding protein 5 (GBP5), transcript variant 1, mRNA [NM_052942] | NM_052942 | ENST00000490568 | 115362 | guanylate binding protein 5 | chr1:89726446-89726387 | GO:0005886\|GO:0000166\|NM_052942 GO:0003924\|GO:0005525 | | THC2666692 | Hs.515726 |
| A_23_P108501 | EPHA4 | Homo sapiens EPH receptor A4 (EPHA4), mRNA [NM_004438] | NM_004438 | ENST00000392071 | 2043 | EPH receptor A4 | chr2:22229077 6-222290717 | GO:0005515\|GO:0005524\|NM_004438 GO:0007165\|GO:0005003\| GO:0000166\|GO:0016020\| GO:0005887\|GO:0007411\| GO:0007628\|GO:0004872\| GO:0006468\|GO:0007169\| GO:0016740 | | THC2466360 | Hs.371218 |
| A_33_P3337609 | | GB | | | | | chr2:09772605 5-097726114 | | | NP113779 | |
| A_23_P106661 | CMTM1 | Homo sapiens CKLF-like MARVEL transmembrane domain containing 1 (CMTM1), transcript variant 17, mRNA [NM_052999] | NM_052999 | ENST00000379490 | 113540 | CKLF-like MARVEL transmembrane domain containing 1 | chr16:6661297 2-66613031 | GO:0016020\|GO:0006935\|NM_052999 GO:0016021\|GO:0005615\| GO:0005125 | | NP813866 | Hs.698621 |
| A_23_P120316 | MTHFD2 | Homo sapiens methylenetetra- | NM_006636 | ENST00000394053 | 10797 | methylene tetrahydro- | chr2:74441985-74442044 | GO:0000287\|GO:0004477\|NM_006636 GO:0005739\|GO:0004488\| | | THC2543784 | Hs.469030 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | hydrofolate dehydrogenase (NADP+dependent) 2, methenyl-tetrahydrofolate cyclohydrolase (MTHFD2), nuclear gene encoding mitochondrial protein, transcript variant 1, mRNA [NM_006636] | | | | folate-dehydrogenase (NADP+ dependent) 2, methenyl-tetrahydrofolate cyclohydrolase | | GO:0004487|GO:0016787| GO:0005488|GO:0042301| GO:0016491|GO:0046653| GO:0009396|GO:0006730| GO:0055114 | | | |
| A_23_P163992 | GRB7 | Homo sapien growth factors receptor-bound protein 7 (GRB7), transcript variant 1, mRNA [NM_005310] | NM_005310 | ENST00000394204 | 2886 | growth factor receptor-bound protein 7 | chr17:37902381-37902440 | GO:0005515|GO:0007165|GO:0007173|GO:0005070 | NM_005310 | THC2490644 | Hs.86859 |
| A_23_P230561 | C19orf59 | Homo sapiens chromosome 19 open reading frame 59 (C19orf59), mRNA [NM_174918] | NM_174918 | ENST00000333598 | 199675 | chromosome 19 open reading frame 59 | chr19:7744452-7744511 | GO:0016020|GO:0016021 | NM_174918 | THC2475479 | Hs.709539 |
| A_23_P113634 | CBFB | Homo sapiens core-binding factor, beta subunit (CBFB), transcript variant 2, mRNA [NM_001755] | NM_001755 | ENST00000412916 | 865 | core-binding factor, beta subunit | chr16:67134630-67134689 | GO:0005515|GO:0003700|GO:0006366|GO:0003702|GO:0003713|GO:0005634 | NM_001755 | THC2466980 | Hs.460988 |
| A_33_P3250394 | LOC100510596 | PREDICTED: Homo sapiens hypothetical protein LOC100510596 (LOC100510596), mRNA [XM_003120681] | XM_003120681 | | 100510596 | hypothetical protein LOC 100510596 | chr11:3635894-3635953 | | XM_003120681 | THC2720990 | |
| A_33_P3383174 | LOC644366 | PREDICTED: Homo sapiens hypothetical protein LOC644366 (LOC644366), mRNA [XM_003120886] | XM_003120886 | | 644366 | hypothetical protein LOC644366 | chr17:44908061-44908002 | | XM_003120886 | THC2652786 | Hs.210896 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P366122 | ACBD4 | Homo sapiens acyl-CoA binding domain containing 4 (ACBD4), transcript variant 2, mRNA [NM_024722] | NM_024722 | ENST00000376955 | 79777 | acyl-CoA binding domain containing 4 | chr17:43213187-43213931 | GO:0005488\|GO:0000062 | NM_024722 | THC2605010 | Hs.110298 |
| A_33_P3420695 | | | | | | | chrY:00849285 3-008492794 | | | | |
| A_23_P122144 | UGT3A1 | Homo sapiens UDP glyco-syltransferase 3 family, polypeptide A1 (UGT3A1), transcript variant 1, mRNA [NM_152404] | NM_152404 | ENST00000515801 | 133688 | UDP glycosyl transferase 3 family, polypeptide A1 | chr5:35954141-35954082 | GO:0016020\|GO:0008152\|GO:0015020\|GO:0016021 | NM_152404 | NP1157777 | Hs.254699 |
| A_33_P3334205 | TMEM184A | Homo sapiens transmembrane protein 184A (TMEM184A), mRNA [NM_001097620] | NM_001097620 | ENST00000297477 | 202915 | trans-membrane protein 184A | chr7:1585889-1585830 | GO:0016020\|GO:0016021 | NM_001097620 | THC2573151 | Hs.592174 |
| A_23_P87879 | CD69 | Homo sapiens CD69 molecule (CD69), transcript variant 1, mRNA [NM_001781] | NM_001781 | ENST00000228434 | | CD69 molecule | chr12:9905320-9905261 | GO:0016020\|GO:0005887\|GO:0005529\|GO:0009897\|GO:0005488\|GO:0005509\|GO:0004888 | NM_001781 | THC2461298 | Hs.208854 |
| A_33_P3354646 | PNLIPRP1 | Homo sapiens pancreatic lipase-related protein 1 (PNLIPRP1), mRNA [NM_006229] | NM_006229 | ENST00000470678 | 5407 | pancreatic lipase-related protein 1 | chr10:11835137 7-118351436 | GO:0016042\|GO:0005515\|GO:0004806\|GO:0016787\|GO:0043434\|GO:0051384\|GO:0005576\|GO:0009791\|GO:0005615 | NM_006229 | THC2517682 | Hs.73923 |
| A_33_P3564409 | | melanoma antigen family D, 4B [Source: HGNC Symbol; Acc:22880] [ENST00000481096] | AK094541 | ENST00000481096 | | | chrX:5193360 3-51933662 | | | THC2626934 | Hs.729070 |
| A_33_P3287610 | | immunoglobulin lambda variable 3-12 [Source: HGNC Symbol; Acc:5898] [ENST00000390313] | DQ098743 | ENST00000390313 | | | chr22:2311482 3-23114882 | | | NP1087705 | |
| A_23_P115366 | CMPK1 | Homo sapiens cytidine monophosphate (UMP-CMP) | NM_016308 | ENST00000371873 | 51727 | cytidine mono-phosphate (UMP-CMP) | chr1:47843918-47843977 | GO:0006139\|GO:0005737\|GO:0000166\|GO:0004849\|GO:0004127\|GO:0009220\|GO:0005634\|GO:0016776 | NM_016308 | THC2540218 | Hs.11463 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq Accession | TIGRID | UniGene ID |
|---|---|---|---|---|---|---|---|---|---|---|---|
| A_33_P3416376 | | kinase 1, cytosolic (CMPK1), transcript variant 1, mRNA [NM_016308] | | | | kinase 1, cytosolic | | GO:0005524|GO:0016740 | | | Hs.61823 |
| | | NCI_CGAP_FL1 Homo sapiens cDNA clone UI-H-FL1-bgt-o-17-0-UI 3', mRNA sequence [BU633092] | BU633092 | | | | chr19:5116265 6-51162715 | | | | |
| A_33_P3312030 | | | | ENST00000507296 | | | chr4:15855898 9-158559048 | | | | |
| A_33_P3275826 | | | | | | | chr11:0006274 79-000627420 | | | | |
| A_23_P109322 | PCP4 | Homo sapiens Purkinje cell protein 4 (PCP4), mRNA [NM_006198] | NM_006198 | ENST00000468717 | 5121 | Purkinje cell protein 4 | chr21:4130104 7-41301106 | GO:0005634|GO:0007417|NM_006198 GO:0005829 | | THC2617631 | Hs.80296 |
| A_33_P3239884 | NCAM2 | Homo sapiens neural cell adhesion molecule 2 (NCAM2), mRNA [NM_004540] | NM_004540 | ENST00000400546 | 4685 | neural cell adhesion molecule 2 | chr21:2291041 7-22910476 | GO:0005515|GO:0030424|NM_004540 GO:0007608|GO:0007413| GO:0005886|GO:0016021| GO:0007155|GO:0007158 | | THC2471832 | Hs.473450 |
| A_23_P12343 | GSTM3 | Homo sapiens glutathione S-transferase mu 3 (brain) (GSTM3), transcript variant 1, mRNA [NM_000849] | NM_000849 | ENST00000488824 | 2947 | glutathione S-transferase mu 3 (brain) | chr1:11027967 3-110279614 | GO:0043627|GO:0005737|NM_000849 GO:0008065|GO:0008152| GO:0005625|GO:0004364| GO:0016740|GO:0042802 | | THC2487629 | Hs.2006 |
| A_33_P3228751 | LOC388152 | Homo sapiens hypothetical LOC388152, (LOC388152) non-coding RNA [NR_027001] | NR_027001 | ENST00000357253 | 388152 | hypothetical LOC388152 | chr15:8486915 2-84869093 | | NR_027001 | THC2590266 | Hs.681665 |
| A_33_P3353330 | | Homo sapiens cDNA FLJ40828 fis, clone TRACH2011574. [AK098147] | AK098147 | ENST00000442126 | | | chr22:3088873 2-30888791 | | | THC2490419 | |
| A_23_P85240 | TLR7 | Homo sapiens toll-like receptor 7 (TLR7), mRNA [NM_016562] | NM_016562 | ENST00000380659 | 51284 | toll-like receptor 7 | chrX:12908260-12908319 | GO:0032755|GO:0003725|NM_016562 GO:0005515|GO:0003727| GO:0045416|GO:0007249| GO:0002224|GO:0042221| GO:0007165|GO:0051607| GO:0045359|GO:0006954 | | THC2475229 | Hs.659215 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3246733 | MNT | *Homo sapiens* MAX binding protein (MNT), mRNA [NM_020310] | NM_020310 | ENST00000404961 | 4335 | MAX binding protein | chr17:2289691-2289632 | GO:0035197\|GO:0016020\|GO:0052033\|GO:0045087\|GO:0045078\|GO:0008144\|GO:0045356\|GO:0002282\|GO:0016021\|GO:0010008\|GO:0004888 | NM_020310 | THC2534076 | Hs.632239 |
| A_23_P23850 | DAB1 | *Homo sapiens* disabled homolog 1 (*Drosophila*) (DAB1), mRNA [NM_021080] | NM_021080 | ENST00000371231 | 1600 | disabled homolog 1 (*Drosophila*) | chr1:57480698-57480639 | GO:0006355\|GO:0008285\|GO:0007264\|GO:0007275\|GO:0003700\|GO:0006366\|GO:0007569\|GO:0003714\|GO:0003713\|GO:0051726\|GO:0042981\|GO:0007275\|GO:0005634 | NM_020310 | THC2533734 | Hs.477370 |
| A_23_P103775 | LRRC8C | *Homo sapiens* leucine rich repeat containing 8 family, member C (LRRC8C), mRNA [NM_032270] | NM_032270 | ENST00000370454 | 84230 | leucine rich repeat containing 8 family, member C | chr1:90180832-90180383 | GO:0005515\|GO:0048471\|GO:0007275\|GO:0007264\|GO:0021942\|GO:0021813\|GO:0007399\|GO:0030154\|GO:0007162\|GO:0021589\|GO:0045860\|GO:0021799\|GO:0001764 | NM_021080 | THC2474475 | Hs.412836 |
| A_23_P104054 | C1orf9 | *Homo sapiens* chromosome 1 open reading frame 9 (C1orf9), transcript variant 2, mRNA [NM_016227] | NM_016227 | ENST00000367723 | 51430 | chromosome 1 open reading frame 9 | chr1:172582075-172580815 | GO:0005515\|GO:0016020\|GO:0016021 | NM_032270 | THC2481620 | Hs.62306 |
| A_33_P3400823 | C1orf190 | *Homo sapiens* chromosome 1 open reading frame 190 (C1orf190), mRNA [NM_001013615] | NM_001013615 | ENST00000371980 | 541468 | chromosome 1 open reading frame 190 | chr1:46868680-46868623 | GO:0016020\|GO:0016021 | NM_016227 | THC2476177 | Hs.568642 |
| A_23_P150064 | MMRN2 | *Homo sapiens* multimerin 2 (MMRN2), mRNA [NM_024756] | NM_024756 | ENST00000443699 | 79812 | multimerin 2 | chr10:88696220-88696161 | GO:0005576\|GO:0005615\|GO:0005604 | NM_024756 | THC2465974 | Hs.524479 |
| A_23_P201918 | ABCB10 | *Homo sapiens* ATP-binding cassette, sub-family B (MDR/TAP), family B (MDR | NM_012089 | ENST00000344517 | 23456 | ATP-binding cassette, subfamily B (MDR/TAP), | chr1:229652770-229652711 | GO:0005739\|GO:0016020\|GO:0005743\|GO:0000166\|GO:0016021\|GO:0042626\|GO:0055085\|GO:0043190 | NM_012089 | THC2463247 | Hs.17614 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID Gene Name | Genomic Coordinates | Go | RefSeq-Accession | TIGRID | UniGene ID |
|---|---|---|---|---|---|---|---|---|---|---|
| | | TAP), member 10 (ABCB10), nuclear gene encoding mitochondrial protein, mRNA [NM_012089] | | | member 10 | | GO:0016887|GO:0005524 | | | |
| A_33_P3293760 | KRTAP10-8 | Homo sapiens keratin associated protein 10-8 (KRTAP10-8), mRNA [NM_198695] | NM_198695 | ENST00000334662 | 386681 keratin associated protein 10-8 | chr21:46032417-46032476 | GO:0045095 | NM_198695 | THC2782326 | Hs.528021 |
| A_32_P3036 | | Synthetic construct Homo sapiens gateway clone IMAGE:100023427 3' read APOE mRNA. [CU678501] | CU678501 | | | chr19:04541196-045411897 | | | | |
| A_33_P3466016 | LOC200830 | Homo sapiens cDNA FLJ30391 fis, clone BRACE2008336. [AK054953] | AK054953 | | 200830 hypothetical protein LOC200830 | chr3:160983747-160983806 | | | THC2511954 | Hs.691402 |
| A_23_P103765 | FCER1A | Homo sapiens Fc fragment of IgE, high affinity I, receptor for; alpha polypeptide (FCER1A), mRNA [NM_002001] | NM_002001 | ENST00000368115 | 2205 Fc fragment of IgE, high affinity I, receptor for; alpha polypeptide | chr1:159276034-159277595 | GO:0001812|GO:0019370|NM_002001<br>GO:0045401|GO:0001820|<br>GO:0045425|GO:0005886|<br>GO:0050731|GO:0007257|<br>GO:0050850|GO:0043306|<br>GO:0004872|GO:0019767|<br>GO:0005887|GO:0007166|<br>GO:0009897 | | THC2611062 | Hs.897 |
| A_33_P3411612 | TMEM221 | Homo sapiens transmembrane protein 221 (TMEM221), mRNA [NM_001190844] | NM_001190844 | ENST00000341130 | 100130519 transmembrane protein 221 | chr19:17556068-17556009 | GO:0016020|GO:0016021 | NM_001190844 | THC2532568 | Hs.436603 |
| A_33_P3378659 | TARP | Homo sapiens TCR gamma alternate reading frame protein (TARP), nuclear gene encoding mitochondrial protein, transcript variant 1, mRNA [NM_001003799] | NM_001003799 | ENST00000443402 | 445347 TCR gamma alternate reading frame protein | chr7:38299809-38299750 | | NM_001003799 | NP092351 | Hs.534032 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3212630 | FAM90A10 | Homo sapiens family with sequence similarity 90, member A10 (FAM90A10), mRNA [NM_001164447] | NM_001164447 | ENST00000400118 | 441328 | family with sequence similarity 90, member A10 | chr8:7629451-7629510 | GO:0008270\|GO:0003676 | NM_001164447 | THC2482537 | Hs.694406 |
| A_23_P56736 | TUBA3D | Homo sapiens tubulin, alpha 3d (TUBA3D), mRNA [NM_080386] | NM_080386 | ENST00000321253 | 113457 | tubulin, alpha 3d | chr2:132240430-132240489 | GO:0005515\|GO:0051258\|GO:0000166\|GO:0005198\|GO:0005874\|GO:0003924\|GO:0005525\|GO:0007018 | NM_080386 | THC2628673 | Hs.503749 |
| A_33_P3218435 | | Homo sapiens cDNA clone TESTI4016447 5', mRNA sequence [DB073168] | DB073168 | ENST00000523591 | | | chr5:170107629-170107570 | | | | Hs.631237 |
| A_33_P3246010 | | Homo sapiens cDNA FLJ35175 fis, clone PLACE6013400. [AK092494] | AK092494 | | | | chr16:88775474-88775415 | | | THC2636441 | Hs.592074 |
| A_23_P113572 | CD19 | Homo sapiens CD19 molecule (CD19), transcripts variant 2, mRNA [NM_001770] | NM_001770 | ENST00000537306 | 930 | CD19 molecule | chr16:28950600-28950659 | GO:0050853\|GO:0005515\|GO:0006968\|GO:0005886\|GO:0005887\|GO:0005057\|GO:0009897\|GO:0007166 | NM_001770 | THC2473305 | Hs.652262 |
| A_23_P117662 | HDC | Homo sapiens histidine de-carboxylase (HDC), mRNA [NM_002112] | NM_002112 | ENST00000267845 | 3067 | histidine decarboxylase | chr15:50534229-50534170 | GO:0006547\|GO:0005625\|GO:0005626\|GO:0004398\|GO:0016829\|GO:0030425\|GO:0005829\|GO:0001692\|GO:0030170\|GO:0043025\|GO:0016597\|GO:0019752\|GO:0006519\|GO:0042423 | NM_002112 | THC2627567 | Hs.1481 |
| A_33_P3374589 | ATXN10 | ataxin 10 [Source: HGNC Symbol; Acc:10549] [ENST00000402380] | | ENST00000402380 | 25814 | ataxin 10 | chr22:46189551-46189618 | | | THC2652118 | |
| A_33_P3239790 | ZNF646 | Homo sapiens zinc finger protein 646 (ZNF646), mRNA [NM_014699] | NM_014699 | ENST00000439353 | 9726 | zinc finger protein 646 | chr16:31091549-31091608 | GO:0005622\|GO:0008270\|GO:0005634\|GO:0003677\|GO:0046872\|GO:0045449 | NM_014699 | THC2471197 | Hs.119273 |
| A_23_P209694 | PAPOLG | Homo sapiens poly(A) polymerase gamma (PAPOLG), mRNA [NM_022894] | NM_022894 | ENST00000414060 | 64895 | poly(A) polymerase gamma | chr2:61025238-61025297 | GO:0006397\|GO:0004652\|GO:0000166\|GO:0003723\|GO:0016779\|GO:0043631\|GO:0005634\|GO:0005524\|GO:0016740\|GO:0006350 | NM_022894 | THC2614617 | Hs.387471 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P145024 | ADRB2 | Homo sapiens adrenergic, beta-2-, receptor, surface (ADRB2), mRNA [NM_000024] | NM_000024 | ENST00000305988 | 154 | adrenergic, beta-2-, receptor, surface | chr5:148208080-148208139 | GO:0051927\|GO:0045453\|GO:0009409\|GO:0004941\|GO:0002024\|GO:0002025\|GO:0015459\|GO:0043268\|GO:0005764\|GO:0032403\|GO:0042803\|GO:0007171\|GO:0010765\|GO:0045823\|GO:0004935\|GO:0005792\|GO:0030501\|GO:0008179\|GO:0004930\|GO:0008333\|GO:0035240\|GO:0006898\|GO:0002032\|GO:0043235\|GO:0048633\|GO:0007186\|GO:0050873\|GO:0005887\|GO:0044424\|GO:0007189\|GO:0051930\|GO:0030424\|GO:0008284\|GO:0005634\|GO:0030425\|GO:0051380\|GO:0031649\|GO:0016324\|GO:0030279\|GO:0040015\|GO:0045986\|GO:0008144\|GO:0045909\|GO:0045944\|GO:0004872\|GO:0043065\|GO:0005730\|GO:0005624\|GO:0042383\|GO:0005901\|GO:0050728\|GO:0043410\|GO:0005768 | | | |
| A_23_P322845 | PPAPDC1B | Homo sapiens phosphatide acid phosphatase type 2 domain containing IB (PPAPDC1B), transcript variant 1, mRNA [NM_001102559] | NM_001102559 | ENST00000424479 | 84513 | phosphatide acid phosphatase type 2 domain containing IB | chr8:38120995-38120936 | GO:0016787\|GO:0016020\|GO:0016021 | NM_001102559 | THC2464061 | Hs.567619 |
| A_23_P23966 | ZNF488 | Homo sapiens zinc finger protein 488 (ZNF488), mRNA [NM_153034] | NM_153034 | ENST00000395702 | 118738 | zinc finger protein 488 | chr10:48373505-48373564 | GO:0016564\|GO:0005622\|GO:0005515\|GO:0048714\|GO:0014003\|GO:0008270\|GO:0046872\|GO:0003677 | NM_153034 | THC2462545 | Hs.27788 |
| A_23_P122775 | RTN4IP1 | Homo sapiens reticulon 4 interacting protein 1 (RTN4IP1), | NM_032730 | ENST00000498091 | 84816 | reticulon 4 interacting protein 1 | chr6:107031286-107031227 | GO:0005634\|GO:0045449\|GO:0005739\|GO:0005488\|GO:0016491\|GO:0008270\|GO:0055114 | NM_032730 | NP411809 | Hs.155839 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3393801 | PDZK1IP1 | nuclear gene encoding mitochondrial protein, mRNA [NM_032730] Homo sapiens PDZK1 interacting protein 1 (PDZK1IP1), mRNA [NM_005764] | NM_005764 | ENST00000371885 | 10158 | PDZK1 interacting protein 1 | chr1:47650734-47650675 | GO:0016020|GO:0016021 | NM_005764 | THC2612502 | Hs.431099 |
| A_23_P124003 | P2RX2 | Homo sapiens purinergic receptor P2X, ligand-gated ion channel, 2 (P2RX2), transcript variant 4, mRNA [NM_170683] | NM_170683 | ENST00000343948 | 22953 | purinergic receptor P2X, ligand-gated ion channel, 2 | chr12:133198203-133198262 | GO:0004698|GO:0016020|GO:0001614|GO:0010524|GO:0004931|GO:0004872|GO:0016021|GO:0005524|GO:0042803|GO:0050850|GO:0015276|GO:0006811 | NM_170683 | NP1457348 | Hs.258580 |
| A_23_P420417 | TLCD1 | Homo sapiens TLC domain containing 1 (TLCD1), transcript variant 1, mRNA [NM_138463] | NM_138463 | ENST00000394933 | 116238 | TLC domain containing 1 | chr17:2705171 5-27051656 | GO:0016020|GO:0016021 | NM_138463 | THC2473493 | Hs.499952 |
| A_23_P44207 | ACOT12 | Homo sapiens acyl-CoA thioesterase 12 (ACOT12), mRNA [NM_130767] | NM_130767 | ENST00000506440 | 134526 | acyl-CoA thioesterase 12 | chr5:80626341-80626282 | GO:0006629|GO:0004091|GO:0006637|GO:0005737|GO:0016787|GO:0003986|GO:0006084|GO:0005524|GO:0005829 | NM_130767 | THC2477338 | Hs.591756 |
| A_33_P3419180 | LOC283547 | Homo sapiens hypothetical LOC283547 (LOC283547), non-coding RNA [NR_039982] | NR_039982 | | 283547 | hypothetical LOC283547 | chr14:3930719 0-39307131 | | NR_039982 | THC2503396 | Hs.675941 |
| A_23_P17330 | UCKL1 | Homo sapiens uridine-cytidine kinase 1-like 1 (UCKL1), transcript variant 1 mRNA [NM_017859] | NM_017859 | ENST00000369908 | 54963 | uridine-cytidine kinase 1-like 1 | chr20:6257600 2-62575943 | GO:0005737|GO:0000166|GO:0016301|GO:0005783|GO:0004849|GO:0044419|GO:0008152|GO:0016773|GO:0005634|GO:0005524|GO:0016740 | NM_017859 | NP283210 | Hs.504998 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P110242 | | immunoglobulin heavy variable 3/OR16-8 (non-functional) [Source:HGNC Symbol:Acc:5643] | | ENST00000354689 | | | chr16:32077490-32077549 | | | THC2579601 | |
| A_23_P15414 | SCARF1 | Homo sapiens scavenger receptor class F, member 1 (SCARF1), transcript variant 5, mRNA [NM_145352] | NM_145352 | ENST00000434376 | 8578 | scavenger receptor class F, member 1 | chr17:1537812-1537753 | GO:0005515|GO:0006707|NM_145352|GO:0016020|GO:0030169|GO:0016021|GO:0007155|GO:0016358|GO:0006898|GO:0005044 | NP494816 | | Hs.647430 |
| A_33_P3254121 | RNASET2 | ribonuclease T2 [Source: HGNC Symbol: Acc:21686] [ENST00000358165] | AK001769 | ENST00000358165 | 8635 | ribonuclease T2 | chr6:16734748-167347428 | | | THC2479694 | |
| A_24_P920188 | ZNF24 | Homo sapiens zinc finger protein (ZNF24), mRNA [NM_006965] | NM_006965 | ENST00000261332 | 7572 | zinc finger protein 24 | chr18:3291274-32912689 | GO:0016564|GO:0005622|NM_006965|GO:0005515|GO:0006355|GO:0003700|GO:0016481|GO:0008270|GO:0005634|GO:0046872 | | THC2717584 | Hs.S14802 |
| A_33_P3416814 | MGAT1 | mannosyl (alpha-1,3-)-glycoprotein beta-1,2-N-acetylglucosaminyl-transferase [Source: HGNC Symbol: Acc:7044] [ENST00000510962] | | ENST00000510962 | 4245 | mannosyl (alpha-1,3-)-glycoprotein beta 1,2-N-acetyl-glucosamin yltransferase | chr5:18023780-8-180237749 | | | | |
| A_23_P30634 | BACH | Homo sapiens BTB and CNC homology 1, basic leucine zipper transcription factor 2 (BACH2), transcript variant 1, mRNA [NM_021813] | NM_021813 | ENST00000257749 | 60468 | BTB and CNC homo-logy 1, basic leucine zipper transcription factor 2 | chr6:90636664-90636605 | GO:0043565|GO:0006355|NM_021813|GO:0003700|GO:0046983|GO:0005634 | | THC2649840 | Hs.269764 |
| A_33_P3236340 | LOC100133131 | Homo sapiens clone pp7683 | AF289593 | | 100133131 | hypothetical protein | chr4:6823580-6823521 | | NP426365 | | Hs.543740 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P80382 | | unknown mRNA. [AF289593] | | | | LOC100133131 | | | | | |
| | PRR5 | Homo sapiens proline rich 5 (renal) (PRR5), transcript variant 2, mRNA [NM_015366] | NM_015366 | ENST00000432916 | 55615 | proline rich 5 (renal) | chr22:45133267-45133326 | GO:0007049 | NM_015366 | NP1183640 | Hs.102336 |
| A_33_P3247534 | LOC389834 | Homo sapiens ankyrin repeat domain 57 pseudogene (LOC389834), non-coding RNA [NR_027420] | NR_027420 | | 389834 | ankyrin repeat domain 57 pseudogene | chr21:9917195-9917136 | | NR_027420 | THC2524997 | |
| A_23_P41424 | SLC39A8 | Homo sapiens solute carrier family 39 (zinc transporter), member 8 (SLC39A8), transcript variant 1, mRNA [NM_022154] | NM_022154 | ENST00000394833 | 64116 | solute carrier family 39 (zinc transporter), member 8 | chr4:103183010-103182951 | GO:0016020\|GO:0046873\|GO:0008270\|GO:0006829\|GO:0016021\|GO:0055085\|GO:0030001\|GO:0006811 | NM_022154 | THC2465848 | Hs.288034 |
| A_24_P40776 | BDP1 | Homo sapiens B double prime 1, subunit of RNA polymerase III transcription initiation factor IIIB (BDP1), mRNA [NM_018429] | NM_018429 | ENST00000541414 | 55814 | B double prime 1, subunit of RNA polymerase III transcription initiation factor IIIB | chr5:70862873-70862932 | GO:0005634\|GO:0003677\|GO:0045449 | NM_018429 | THC2613479 | Hs.258272 |
| A_33_P3382309 | PRDM16 | Homo sapiens PR domain containing 16 (PRDM16), transcript variant 2, mRNA [NM_199454] | NM_199454 | ENST00000378398 | 63976 | PR domain containing 16 | chr1:3350316-3350375 | GO:0016564\|GO:0003713\|GO:0005634\|GO:0046332\|GO:0000122\|GO:0043457\|GO:0046872\|GO:0005622\|GO:0043565\|GO:0050873\|GO:0017053\|GO:0008270\|GO:0030512\|GO:0045449\|GO:0022008 | NM_199454 | THC2487287 | Hs.99500 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P111804 | PARP12 | *Homo sapiens* poly (ADP-ribose) polymerase family, member 12 (PARP12), mRNA [NM_022750] | NM_022750 | ENST00000488726 | 64761 | poly (ADP-ribose) polymerase family, member 12 | chr7:139724005-139723946 | GO:0008270\|GO:0005634\|NM_022750 GO:0003676\|GO:0046872\| GO:0016740\|GO:0003950 | THC2462153 | Hs.12646 |
| A_24_P941148 | HAUS6 | *Homo sapiens* HAUS augmin-like complex, subunit 6 (HAUS6), mRNA [NM_017645] | NM_017645 | ENST00000380502 | 54801 | HAUS augmin-like complex, subunit 6 | chr9:19053295-19053236 | GO:0051297\|GO:0003674\|NM_017645 GO:0007067\|GO:0007049\| GO:0005813\|GO:0005737\| GO:0005874\|GO:0005819\| GO:0070652\|GO:0005856\| GO:0051225\|GO:0051301 | THC2525167 | Hs.533468 |
| A_33_P3273369 | SH3BP4 | *Homo sapiens* SH3-domain binding protein 4 (SH3BP4), mRNA [NM_014521] | NM_014521 | ENST00000420127 | 23677 | SH3-domain binding protein 4 | chr2:235962235-235962415 | GO:0005515\|GO:0008150\|NM_014521 GO:0003674\|GO:0007049\| GO:0005905\|GO:0016020\| GO:0030136\|GO:0005634\| GO:0031410\|GO:0005575\| GO:0004871\|GO:0006897 | THC2777683 | Hs.516777 |
| A_33_P3318624 | CTBP2 | C-terminal binding protein 2 [Source: HGNC Symbol; Acc: 2495] [ENST00000530930] | BC052276 | ENST00000530930 | 1488 | C-terminal binding protein 2 | chr10:1268221 73-126822114 | | THC2484146 | Hs.501345 |
| A_23_P132121 | SIK1 | *Homo sapiens* salt-inducible kinase 1 (SIK1), mRNA [NM_173354] | NM_173354 | ENST00000270162 | 150094 | salt-inducible kinase 1 | chr21:4483481 9-44834760 | GO:0016564\|GO:0005515\|NM_173354 GO:0000287\|GO:0005634\| GO:0007275\|GO:0000122\| GO:0005524\|GO:0007243\| GO:0005829\|GO:0007346\| GO:0005737\|GO:0007049\| GO:0000166\|GO:0004674\| GO:0045595\|GO:0006468\| GO:0016740 | THC2468197 | Hs.282113 |
| A_23_P424734 | EXOC3L1 | *Homo sapiens* exocyst complex component 3-like 1 (EXOC3L1), mRNA [NM_178516] | NM_178516 | ENST00000314553 | 283849 | exocyst complex component 3-like 1 | chr16:6721859 9-67218459 | GO:0003674\|GO:0000145\|NM_178516 GO:0030141\|GO:0030072\| GO:0006887 | THC2475659 | Hs.647356 |
| A_23_P110234 | CSN1S1 | *Homo sapiens* casein alpha s1 (CSN1S1), transcript | NM_001890 | ENST00000505782 | 1446 | casein alpha s1 | chr4:70810602-70810661 | GO:0005515\|GO:0052215\|NM_001890 GO:0006810\|GO:0005576 | THC2759870 | Hs.3155 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P68486 | C20orf108 | Homo sapiens chromosome 20 open reading frame 108 (C20orf108), mRNA [NM_080821] | NM_080821 | ENST00000371384 | 116151 | chromosome 20 open reading frame 108 | chr20:54943040-54943099 | GO:0016020\|GO:0016021 | NM_080821 | THC2468290 | Hs.143736 |
| A_33_P3358686 | | Homo sapiens Q8IWC7_HUMAN (Q8IWC7) LRRC37A protein, partial (5%) [THC2657523] | | | | | chr17:041999971-041999912 | | | THC2657523 | |
| A_23_P121596 | PPBP | Homo sapiens pro-platelet basic protein (chemokine (C-X-C motif) ligand 7) (PPBP), mRNA [NM_002704] | NM_002704 | ENST00000296028 | 5473 | pro-platelet basic protein (chemokine (C-X-C motif) ligand 7) | chr4:74853358-74853299 | GO:0008009\|GO:0006955\|GO:0015758\|GO:0007186\|GO:0006935\|GO:0031093\|GO:0005576\|GO:0005781\|GO:0008083\|GO:0005615\|GO:0042742\|GO:0005355 | NM_002704 | THC2473736 | Hs.2164 |
| A_33_P3277259 | PCYT2 | Homo sapiens phosphate cytidylyltransferase 2, ethanolamine (PCYT2), transcript variant 1, mRNA [NM_001184917] | NM_001184917 | ENST00000538721 | 5833 | phosphate cytidylyl-transferase 2, ethanolamine | chr17:79860851-79860792 | | NM_001184917 | THC2492265 | Hs.569843 |
| A_33_P3330877 | | | | | | | chr2:062422413-062422472 | | | | |
| A_33_P3277883 | LOC100129931 | Homo sapiens hypothetical LOC100129931 (LOC100129931), non-coding RNA [NR_033828] | NR_033828 | | 100129931 | hypothetical LOC100129931 | chr4:7035198-7035139 | | NR_033828 | THC2623255 | Hs.707753 |
| A_33_P3271460 | GOLGA1 | golgin A1 [Source: HGNC Symbol; Acc: 4424] | | ENST00000373551 | 2800 | golgin A1 | chr9:12766255-127652199 | | | THC2748759 | |
| A_33_P3267745 | | Q3W7R2_9ACTO (Q3W7R2) ABC transporter, | | | | | chr9:13900997-139099919 | | | THC2534319 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P399980 | HEPH | partial (4%) [THC2534319] *Homo sapiens* hephaestin (HEPH), transcript variant 2, mRNA [NM_014799] | NM_014799 | ENST00000343002 | 9843 | hephaestin | chrX:65486328-65486387 | GO:0016020\|GO:0005506\|NM_014799<br>GO:0005507\|GO:0030218\|<br>GO:0016491\|GO:0006826\|<br>GO:0016021\|GO:0046872\|<br>GO:0006825\|GO:0055114\|<br>GO:0006811 | NM_014799 | THC2461505 | Hs.31720 |
| A_33_P3356752 | GPER | *Homo sapiens* G protein-coupled estrogen receptor 1 (GPER), transcript variant 3, mRNA [NM_001039966] | NM_001039966 | ENST00000401670 | 2852 | G protein-coupled estrogen receptor 1 | chr7:1132386-1132445 | GO:0007165\|GO:0005794\|NM_001039966<br>GO:0007186\|GO:0005886\|<br>GO:0005887\|GO:0005783\|<br>GO:0004930\|GO:0004872 | | THC2471419 | Hs.20961 |
| A_33_P3210069 | | | | | | | chr16:0335737 50-033573809 | | | | |
| A_33_P3376026 | | PREDICTED: *Homo sapiens* hypothetical LOC100128770 (LOC100128770), miscRNA [XR_109245] | XR_109245 | ENST00000382225 | | | chr16:3086692-3086751 | | XR_109245 | THC2483708 | Hs.666223 |
| A_23_P156683 | LTA | *Homo sapiens* lymphotoxin alpha (TNF superfamily, member 1) (LTA), transcript variant 2, mRNA [NM_000595] | NM_000595 | ENST00000383303 | 4049 | lymphotoxin alpha (TNF superfamily, member 1) | chr6:315411541 31541213 | GO:0005164\|GO:0007584\|NM_000595<br>GO:0007267\|GO:0048147\|<br>GO:0005576\|GO:0006917\|<br>GO:0005125\|GO:0005615\|<br>GO:0048535\|GO:0007165\|<br>GO:0016020\|GO:0006959\|<br>GO:0032496 | | THC2609500 | Hs.36 |
| A_33_P3350575 | OC90 | *Homo sapiens* otoconin 90 (OC90), mRNA [NM_001080399] | NM_001080399 | ENST00000443356 | 729330 | otoconin 90 | chr8:13303678 7-133036728 | GO:0016042\|GO:0008150\|NM_001080399<br>GO:0003674\|GO:0005509\|<br>GO:0004623\|GO:0005578\|<br>GO:0005576\|GO:0006644 | | | Hs.653174 |
| A_33_P3261937 | RNASE13 | *Homo sapiens* ribonuclease, RNase A family, 13 (non-active) (RNASE13), mRNA [NM_001012264] | NM_001012264 | ENST00000382951 | 440163 | ribonuclease, RNase A family, 13 (non-active) | chr14:2150104 9-21500990 | GO:0005576\|GO:0004522\|NM_001012264<br>GO:0003676 | | | Hs.666729 |
| A_23_P162734 | RNF6 | *Homo sapiens* ring finger protein | NM_005977 | ENST00000381570 | 6049 | ring finger protein | chr13:2678736 4-26787305 | GO:0005515\|GO:0006511\|NM_005977<br>GO:0030424\|GO:0004842 | | THC2466322 | Hs.136885 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | protein (C3H2C3 type) 6 (RNF6), transcript variant 1, mRNA [NM_005977] | | | | (C3H2C3 type) 6 | | GO:0016563\|GO:0005575\| GO:0003677\|GO:0046872\| GO:0008150\|GO:0005737\| GO:0030517\|GO:0016605\| GO:0008270\|GO:0045893 | | | |
| A_23_P121806 | ENOPH1 | Homo sapiens enolase-phosphatase 1 (ENOPH1), mRNA [NM_021204] | NM_021204 | ENST00000505846 | 58478 | enolase-phospha-tase 1 | chr4:83381838-83381897 | GO:0008967\|GO:0000287\|NM_021204\| GO:0016787\|GO:0019509\| GO:0008152\|GO:0009086\| GO:0008652\|GO:0005575\| GO:0043874 | THC2501913 | Hs.18442 |
| A_33_P3297611 | | wn53g02.x1 NCI_CGAP_Lu19 Homo sapiens cDNA clone IMAGE: 2449202 3', mRNA sequence [AI924184] | AI924184 | | | | chr2:119254784-119254843 | | | | Hs.580542 |
| A_23_P109171 | BFSP1 | Homo sapiens beaded filament structural protein 1, filensin (BFSP1), transcript variant 1, mRNA [NM_001195] | NM_001195 | ENST00000536626 | 631 | beaded filament structural protein 1, filensin | chr20:17474629-17474570 | GO:0005882\|GO:0005515\|NM_001195\| GO:0008150\|GO:0005737\| GO:0005212\|GO:0016020\| GO:0005200\|GO:0005856 | THC2464659 | Hs.129702 |
| A_23_P404685 | LCE1A | Homo sapiens late cornified envelope 1A (LCE1A), mRNA [NM_178348] | NM_178348 | ENST00000335123 | 353131 | late cornified envelope 1A | chr1:152800026-152800085 | GO:0031424 | NM_178348 | NP1246950 | Hs.534645 |
| A_23_P51565 | TNNI1 | Homo sapiens troponin 1 type 1 (skeletal, slow) (TNNI1), mRNA [NM_003281] | NM_003281 | ENST00000336092 | 7135 | troponin 1 type 1 (skeletal, slow) | chr1:201386936-201384353 | GO:0005861\|GO:0006942\|NM_003281\| GO:0003779\|GO:0005523 | | THC2568212 | Hs.320890 |
| A_24_P341535 | LOC388152 | Homo sapiens hypothetical LOC388152 (LOC388152), non-coding RNA [NR_027001] | NR_027001 | ENST00000442755 | 388152 | hypothetical LOC388152 | chr15:84873671-84873612 | | NR_027001 | THC2526769 | Hs.405809 |
| A_23_P23728 | SV2A | Homo sapiens synaptic vesicle glycoprotein 2A | NM_014849 | ENST00000369146 | 9900 | synaptic vesicle glyco- | chr1:149876051-149875992 | GO:0005515\|GO:0005215\|NM_014849\| GO:0030054\|GO:0031594\| GO:0005783\|GO:0006874 | | THC2629537 | Hs.516153 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3341568 | | (SV2A), mRNA [NM_014849] | | | | protein 2A | chr13:01924175 3-01924 1812 | GO:0031410|GO:0055085| GO:0005737|GO:0016020| GO:0006836|GO:0030672| GO:0016021 | | | |
| A_33_P3260747 | NHSL2 | NHS-like 2 (Source: HGNC Symbol; Acc: 33737) [ENST00000373677] | BC033261 | ENST00000373677 | 340527 | NHS-like 2 | chrX:71361153-71361212 | | | THC2604813 | Hs.397836 |
| A_23_P362759 | PRDM5 | Homo sapiens PR domain containing 5 (PRDM5), mRNA [NM_018699] | NM_018699 | ENST00000428209 | 11107 | PR domain containing 5 | chr4:12161630 8-121616249 | GO:0005622|GO:0016575|NM_018699 GO:0016566|GO:0070491| GO:0010843|GO:0008270| GO:0000278|GO:0046872| GO:0005634|GO:0045449| GO:0051567|GO:0016568 | | THC2476650 | Hs.666782 |
| A_33_P3292844 | NEUROG3 | Homo sapiens neurogenin 3 (NEUROG3), mRNA [NM_020999] | NM_020999 | ENST00000242462 | 50674 | neurogenin 3 | chr10:7133190 1-71331842 | GO:0005737|GO:0003700|NM_020999 GO:0003690|GO:0045666| GO:0045944|GO:0030855| GO:0016563|GO:0007422| GO:0007275|GO:0005634| GO:0007417|GO:0045449 | | THC2483225 | Hs.532682 |
| A_33_P3356811 | LCE1E | Homo sapiens late cornified envelope 1E (LCE1E), mRNA [NM_178353] | NM_178353 | ENST00000368771 | 353135 | late cornified envelope 1E | chr1:15276011 9-152760178 | GO:0031424 | NM_178353 | THC2643480 | Hs.250236 |
| A_33_P3355608 | PCDHA7 | Homo sapiens protocadherin alpha 7 (PCDHA7), transcript variant 2, mRNA [NM_031852] | NM_031852 | ENST00000378125 | 56141 | protocadherin alpha 7 | chr5:14021627 9-140216338 | GO:0005515|GO:0005886|NM_031852 GO:0005887|GO:0005509| GO:0007155|GO:0007156| GO:0007399 | | THC2709681 | Hs.199343 |
| A_33_P3245489 | ADAMTSL5 | Homo sapiens ADAMTS-like 5 (ADAMTSL5), mRNA [NM_213604] | NM_213604 | ENST00000395467 | 339366 | ADAMTS-like 5 | chr19:1506798-1506739 | GO:0005515|GO:0005578|NM_213604 GO:0008270|GO:0005576| GO:0004222 | | THC2734163 | Hs.371b74 |
| A_33_P3371727 | SAT1 | Homo sapiens spermidine/ spermine N1-acetyltransferase 1 [Source: HGNC Symbol; Acc: 10540] [ENST00000379253] | AK310078 | ENST00000379253 | 6303 | spermidine/ spermine N1-acetyl-transferase 1 | chrX:23802269 23802328 | | | THC2523522 | Hs.28491 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P100711 | PMP22 | Homo sapiens peripheral myelin protein 22 (PMP22), transcript variant 1, mRNA [NM_000304] | NM_000304 | ENST00000312280 | 5376 | peripheral myelin protein 22 | chr17:15133267-15133208 | GO:0008285\|GO:0016020\|GO:0043218\|GO:0007422\|GO:0007268\|GO:0016021\|GO:0005923\|GO:0030154\|GO:0032288 | NM_000304 | THC2500334 | Hs.372031 |
| A_33_P3209591 | AQP3 | Homo sapiens aquaporin 3 (Gill blood group) (AQP3), mRNA [NM_004925] | NM_004925 | ENST00000343952 | 360 | aquaporin 3 (Gill blood group) | chr9:33442956-33442897 | GO:0005215\|GO:0007588\|GO:0005886\|GO:0033280\|GO:0002684\|GO:0055085\|GO:0016323\|GO:0045616\|GO:0051592\|GO:0015250\|GO:0006833\|GO:0015254\|GO:0016021\|GO:0032526 | NM_004925 | THC2670748 | Hs.234642 |
| A_33_P3423551 | IER3 | Homo sapiens immediate early response 3 (IER3), mRNA [NM_003897] | NM_003897 | ENST00000376382 | 8870 | immediate early response 3 | chr6:30711635-30711576 | GO:0005515\|GO:0016020\|NM_003897\|GO:0006915\|GO:0006916\|GO:0016021\|GO:0009653 | | THC2617196 | Hs.76095 |
| A_33_P3598363 | LOC400662 | Homo sapiens cDNA FLJ30849 fis, clone FEBRA2002882. [AK055411] | AK055411 | | 400662 | hypothetical LOC400662 | chr18:7590075-75900812 | | | THC2630304 | Hs.531297 |
| A_23_P125772 | SRPK3 | Homo sapiens SRSF protein kinase 3 (SRPK3), transcript variant 1, mRNA [NM_014370] | NM_014370 | ENST00000370101 | 26576 | SRSF protein kinase 3 | chrX:153050866-153050925 | GO:0007517\|GO:0000166\|NM_014370\|GO:0004674\|GO:0007275\|GO:0006468\|GO:0005575\|GO:0005524\|GO:0030154\|GO:0016740 | | THC2687284 | Hs.104865 |
| A_33_P3229869 | LOC100128714 | Homo sapiens hypothetical LOC100128714 (LOC100128714), non-coding RNA [NR_040082] | NR_040082 | ENST00000383019 | 100128714 | hypothetical LOC100128714 | chr15:2626073-26260795 | | NR_040082 | THC2487359 | Hs.587854 |
| A_33_P3300152 | LOC100506972 | PREDICTED: Homo sapiens uncharacterized protein C14orf113-like (LOC100506972), mRNA [XM_003118914] | XM_003118914 | | 100506972 | uncharacterized protein C14orf113-like | chr14:9593016-95930107 | | XM_003118914 | THC2696735 | Hs.675410 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3230798 | MUSK | muscle, skeletal, receptor tyrosine kinase [Source: HGNC Symbol; Acc: 7525] [ENST00000374441] | | ENST00000374441 | 4593 | muscle, skeletal, receptor tyrosine kinase | chr9:113550154-113550213 | | | THC2660930 | |
| A_33_P3256848 | ADAM12 | Homo sapiens ADAM metallopeptidase domain 12 (ADAM12), transcript variant 2, mRNA [NM_021641] | NM_021641 | ENST00000368676 | 8038 | ADAM metallopeptidase domain 12 | chr10:127731711-127731652 | GO:0005515\|GO:0017124\|NM_021641\|GO:0005886\|GO:0006508\|GO:0008270\|GO:0008233\|GO:0007520\|GO:0005576\|GO:0016021\|GO:0007155\|GO:0004222\|GO:0046872 | | THC2487430 | Hs.594537 |
| A_33_P3378545 | | Homo sapiens TESTI4 cDNA clone TEST14041634 5', mRNA sequence [DB092099] | DB092099 | | | | chr14:80077804-2-80077983 | | | | Hs.589247 |
| A_33_P3294986 | LIPE | Homo sapiens lipase, hormone-sensitive (LIPE), mRNA [NM_05357] | NM_005357 | ENST00000244289 | 3991 | lipase, hormone-sensitive | chr19:42905725-42905666 | GO:0046340\|GO:0005515\|NM_005357\|GO:0007565\|GO:0004806\|GO:0005886\|GO:0042493\|GO:0005615\|GO:0005829\|GO:0016042\|GO:0005737\|GO:0016787\|GO:0005901\|GO:0008152\|GO:0047372\|GO:0006468\|GO:0019433\|GO:0033878\|GO:0008202\|GO:0008203 | | THC2470363 | Hs.656980 |
| A_33_P3364582 | TNXB | Homo sapiens tenascin XB (TNXB), transcript variant XB, mRNA [NM_019105] | NM_019105 | ENST00000404514 | 7148 | tenascin XB | chr6:32010593-32010534 | GO:0005622\|GO:0007165\|NM_019105\|GO:0030036\|GO:0005178\|GO:0032963\|GO:0005578\|GO:0005576\|GO:0007155\|GO:0005583\|GO:0008201\|GO:0005615\|GO:0048251 | | THC2737940 | Hs.485104 |
| A_33_P3254996 | DSCR9 | Homo sapiens Down syndrome critical region gene 9 (non-protein coding) (DSCR9), non-coding RNA [NR_026719] | NR_026719 | | 257203 | Down syndrome critical region gene 9 (nonprotein coding) | chr21:38592834-38592893 | GO:0008150\|GO:0003674\|NR_026719\|GO:0005575 | | THC2475035 | Hs.720778 |
| A_23_P119943 | IGFBP2 | Homo sapiens insulin-like | NM_000597 | ENST00000490362 | 3485 | insulin-like growth factor | chr2:217529086-217529145 | GO:0007565\|GO:0007584\|NM_000597\|GO:0042493\|GO:0007568 | | THC2466327 | Hs.438102 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
|  |  | growth factor binding protein 2, 36 kDa (IGFBP2), mRNA [NM_000597] |  |  |  | binding protein 2, 36 kDa |  | GO:0006950\|GO:0031994\| GO:0031995\|GO:0051384\| GO:0005576\|GO:0031410\| GO:0001558\|GO:0005615\| GO:0032870\|GO:0009612\| GO:0007165\|GO:0016324\| GO:0010226\|GO:0043567\| GO:0032526\|GO:0032355 |  |  |  |
| A_33_P3397865 | TNNT1 | *Homo sapiens* troponin T type 1 (skeletal, slow) (TNNT1), transcript variant 1, mRNA [NM_003283] | NM_003283 | ENST00000291901 | 7138 | troponin T type 1 (skeletal, slow) | chr19:55644255-55644196 | GO:0005515\|GO:0031014\| GO:0045932\|GO:0005861\| GO:0003009\|GO:0031444\| GO:0005523 | NM_003283 | THC2560689 | Hs.631558 |
| A_33_P3214943 | SPOCK2 | *Homo sapiens* sparc/osteonectin, cwcv and kazal-like domains proteoglycan (testican) 2 (SPOCK2), transcript variant 1, mRNA [NM_001134434] | NM_001134434 | ENST00000412663 | 9806 | sparc/ osteonectin, cwcv and kazal-like domains proteoglycan (testican) 2 | chr10:73846187-73846128 | GO:0007165\|GO:0030198\| GO:0005509\|GO:0005578\| GO:0045595\|GO:0005576\| GO:0007416 | NM_001134434 | THC2529803 | Hs.523009 |
| A_24_P415601 | RNH1 | *Homo sapiens* ribonuclease/ angiogenin inhibitor 1 (RNH1), transcript variant 1, mRNA [NM_002939] | NM_002939 | ENST00000524464 | 6050 | ribonuclease/ angiogenin inhibitor 1 | chr11:498093-498034 | GO:0005515\|GO:0005737\|GO:0032311\|GO:0008428\| GO:0045765\|GO:0006402 | NM_002939 | NP194622 | Hs.530687 |
| A_33_P3386508 | LOC100132273 | *Homo sapiens* hypothetical LOC100132273 (LOC100132273), non-coding RNA [NR_034118] | NR_034118 | ENST00000417327 | 100132273 | hypothetical LOC100132273 | chr22:42252049-42520556 |  | NR_034118 | THC2492791 | Hs.709677 |
| A_23_P209962 | SMC6 | *Homo sapiens* structural maintenance of chromosomes 6 (SMC6), transcript | NM_024624 | ENST00000402989 | 79677 | structural maintenance of chromosomes 6 | chr2:17851726-17847762 | GO:0005622\|GO:0005694\| GO:0006281\|GO:0000166\| GO:0006310\|GO:0005634\| GO:0005524\|GO:0006974 | NM_024624 | THC2610758 | Hs.526728 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P123672 | TDRD7 | variant 2, mRNA [NM_024624] Homo sapiens tudor domain containing 7 (TDRD7), mRNA [NM_014290] | NM_014290 | ENST00000422139 | 23424 | tudor domain containing 7 | chr9:10025823 6-100258295 | GO:0005737\|GO:0047485\|GO:0030529\|GO:0005759\| GO:0043186\|GO:0003676\| GO:0007281 | NM_014290 | NP340636 | Hs.193842 |
| A_33_P3354176 | MYOF | myoferlin [Source: HGNC Symbol; Acc: 3656] [ENST00000371488] | | ENST00000371488 | 26509 | myoferlin | chr10:9518555 7-95185498 | | | | |
| A_24_P175187 | SAMD9 | Homo sapiens sterile alpha motif domain containing 9 (SAMD9), transcript variant 1, mRNA [NM_017654] | NM_017654 | ENST00000379958 | 54809 | sterile alpha motif domain containing 9 | chr7:9272984 1-92729782 | GO:0005737 | NM_017654 | THC2464095 | Hs.65641 |
| A_33_P3223467 | VCPIP1 | Homo sapiens valosin containing protein (p97)/ p47 complex interacting protein 1 (VCPIP1), mRNA [NM_025054] | NM_025054 | ENST00000310421 | 80124 | valosin containing protein (p97)/ p47 complex interacting protein 1 | chr8:67542631- 67542572 | GO:0007067\|GO:0005737\|GO:0016567\|GO:0005794\| GO:0004843\|GO:0005795\| GO:0005783\|GO:0019941\| GO:0016320\|GO:0007030\| GO:0008233\|GO:0008234 | NM_025054 | THC2602555 | Hs.632066 |
| A_33_P3355717 | | Homo sapiens cDNA FLJ39779 fis, clone SPLEN2001945. [AK097098] | AK097098 | ENST00000408913 | | | chr14:6926257 0-69262511 | | | THC2475408 | Hs.655774 |
| A_23_P40174 | MMP9 | Homo sapiens matrix metallopeptidase 9 (gelatinase B, 92 kDa gelatinase, 92 kDa type IV collagenase) (MMP9), mRNA [NM_004994] | NM_004994 | ENST00000545925 | 4318 | matrix metallopeptidase 9 (gelatinase B, 92 kDa gelatinase, 92 kDa type IV collagenase) | chr20:4464512 1-44645180 | GO:0043065\|GO:0051549\|GO:0005509\|GO:0005518\| GO:0005615\|GO:0005576\| GO:0030198\|GO:0030574\| GO:0008152\|GO:0006508\| GO:0030225\|GO: 0008233\| GO:0008270\|GO:0004222 | NM_004994 | THC2596473 | Hs.297413 |
| A_23_P311201 | | Homo sapiens serine/arginine-rich splicing factor 10 [Source: HGNC Symbol; | XM_003119082 | ENST00000344989 | | | chr1:24291533- 24291474 | GO:0000244\|GO:0008380\|GO:0048025\|GO:0003723\| GO:0006376\|GO:0005634\| GO:0050733\|GO:0005737 | XM_003119082 | THC2558154 | Hs.652334 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | Acc: 16713] [ENST00000344989] | | | | | | GO:0006406\|GO:0000166\| GO:0016607\|GO:0016482\| GO:0035654\|GO:0051082\| GO:0045449 | | | |
| A_23_P112482 | AQP3 | Homo sapiens aquaporin 3 (Gill blood group) (AQP3), mRNA [NM_004925] | NM_004925 | ENST00000494313 | 360 | aquaporin 3 (Gill blood group) | chr9:33441824-33441765 | GO:0005215\|GO:0007588\| GO:0005886\|GO:0033280\| GO:0002684\|GO:0055085\| GO:0016323\|GO:0045616\| GO:0051592\|GO:0015250\| GO:0006833\|GO:0015254\| GO:0016021\|GO:0032526 | NM_004925 | THC2604824 | Hs.234642 |
| A_33_P3272539 | PLEKHG5 | Homo sapiens pleckstrin homology domain containing, family G (with RhoGef domain) member 5 (PLEKHG5), transcript variant 2, mRNA [NM_198681] | NM_198681 | ENST00000377725 | 57449 | pleckstrin homology domain containing, family G (with RhoGef domain) member 5 | chr1:6528219-6528160 | GO:0005622\|GO:0005085\| GO:0008624\|GO:0005737\| GO:0048471\|GO:0005737\| GO:0035023\|GO:0069915\| GO:0004871\|GO:0043123\| GO:0005089\|GO:0005829 | NM_198681 | NP1205923 | Hs.284232 |
| A_24_P6388 | HIF1A | Homo sapiens hypoxia inducible factor 1, alpha subunit (basic helix-loop-helix transcription factor) (HIF1A), transcript variant 2, mRNA [NM_181054] | NM_181054 | ENST00000394997 | 3091 | hypoxia inducible factor 1, alpha subunit (basic helix-loop-helix transcription factor) | chr14:6221484 5-62214904 | GO:0030949\|GO:0003705\| GO:0051879\|GO:0005634\| GO:0001837\|GO:0051541\| GO:0043193\|GO:0005737\| GO:0045941\|GO:0046886\| GO:0045944\|GO:0042789\| GO:0004871\|GO:0045821\| GO:0035035\|GO:0005667\| GO:0001666\|GO:0006355\| GO:0046982\|GO:0005730\| GO:0002248\|GO:0043619\| GO:0032722\|GO:0010575\| GO:0045766\|GO:0043565\| GO:0007165\|GO:0032909\| GO:0001938\|GO:0051000\| GO:0045648\|GO:0032963\| GO:0010634\|GO:0032364\| GO:0008134 | NM_181054 | THC2465290 | Hs.597216 |
| A_33_P3423425 | ZNF770 | Homo sapiens zinc finger protein 770 (ZNF770), mRNA [NM_014106] | NM_014106 | ENST00000356321 | 54989 | zinc finger protein 770 | chr15:3527062 7-35270568 | GO:0005622\|GO:0008270\| GO:0005634\|GO:0003677\| GO:0046872\|GO:0045449 | NM_014106 | THC2775225 | Hs.730754 |
| A_33_P3367850 | CHRM4 | Homo sapiens cholinergic receptor, muscarinic 4 (CHRM4), mRNA [NM_000741] | NM_000741 | ENST00000443765 | 1132 | cholinergic receptor, muscarinic 4 | chr11:4640672 8-46406669 | GO:0005515\|GO:0030054\| GO:0004930\|GO:0008283\| GO:0005624\|GO:0007197\| GO:0014069\|GO:0032279\| GO:0005085\|GO:0042383 | NM_000741 | THC2602240 | Hs.248100 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | mRNA [NM_000741] | | | | | | GO:0004981\|GO:0005887\|GO:0045211\|GO:0043025\|GO:0044424\|GO:0043679\|GO:0004872 | | | |
| A_23_P355471 | TBXA2R | Homo sapiens thromboxane A2 receptor (TBXA2R), transcript variant b, mRNA [NM_201636] | NM_201636 | ENST00000411851 | 6915 | thromboxane A2 receptor | chr19:3599878-3595904 | GO:0007165\|GO:0007186\|NM_201636\|GO:0005886\|GO:0005887\|GO:0004930\|GO:0004961\|GO:0004872 | | THC2485563 | Hs.442530 |
| A_23_P114670 | ARHGEF16 | Homo sapiens Rho guanine nucleotide exchange factor (GEF) 16 (ARHGEF16), mRNA [NM_014448] | NM_014448 | ENST00000378378 | 27237 | Rho guanine nucleotide exchange factor (GEF) 16 | chr1:3397479-3397538 | GO:0005622\|GO:0005085\|NM_014448\|GO:0008624\|GO:0035023\|GO:0006915\|GO:0005089\|GO:0005829 | | THC2470604 | Hs.87435 |
| A_33_P3369956 | ATXN2L | Homo sapiens ataxin 2-like (ATXN2L), transcript variant E, mRNA [NM_148416] | NM_148416 | ENST00000382686 | 11273 | ataxin 2-like | chr16:28847384-28847443 | GO:0008150\|GO:0003674\|NM_148416\|GO:0016020\|GO:0005575\|GO:0019898 | | NP589496 | Hs.460499 |
| A_23_P115407 | GSTM1 | Homo sapiens glutathione S-transferase mu 1 (GSTM1), transcript variant 2, mRNA [NM_146421] | NM_146421 | ENST00000489913 | 2944 | glutathione S-transferase mu 1 | chr1:110231672-110231731 | GO:0005737\|GO:0008152\|NM_146421\|GO:0004364\|GO:0016740 | | THC2563659 | Hs.301961 |
| A_24_P411899 | RNF19A | Homo sapiens ring finger protein 19A (RNF19A), transcript variant 1, mRNA [NM_183419] | NM_183419 | ENST00000341084 | 25897 | ring finger protein 19A | chr8:101269850-101269791 | GO:0005813\|GO:0016020\|NM_183419\|GO:0019941\|GO:0016874\|GO:0000226\|GO:0008270\|GO:0016021\|GO:0046872\|GO:0006464\|GO:0008134 | | THC2744210 | Hs.292882 |
| A_33_P3245454 | LOC389834 | Homo sapiens ankyrin repeat domain 57 pseudogene (LOC389834), non-coding RNA [NR_027420] | NR_027420 | | 389834 | ankyrin repeat domain 57 pseudogene | chr21:9921497-9921438 | | NR_027420 | THC2474667 | Hs.720653 |
| A_33_P3411848 | CNFN | Homo sapiens cornifelin (CNFN), mRNA [NM_032488] | NM_032488 | ENST00000222032 | 84518 | cornifelin | chr19:42891318-42891259 | GO:0005737\|GO:0031424\|NM_032488\|GO:0001533 | | THC2478456 | Hs.148590 |

APPENDIX C-continued

FEMALES: Technology: Agilent.SingleColor.26652
Created On: Tue Jan 31 14:14:22 EST 2012

| ProbeName | Gene | Description | Gb_Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3312754 | | | | | | | | | | | |
| A_24_P96474 | LDOC1L | *Homo sapiens* leucine zipper, down-regulated in cancer 1-like (LDOC1L), mRNA [NM_032287] | NM_032287 | ENST00000341255 | 84247 | leucine zipper, down-regulated in cancer 1-like | chr16:0797552 83-079755224 chr22:4488879 1-44888732 | | NM_032287 | THC2462399 | Hs.332795 |
| A_23_P123393 | KCNQ3 | *Homo sapiens* potassium voltage-gated channel, KQT-like subfamily, member 3 (KCNQ3), transcript variant 1, mRNA [NM_004519] | NM_004519 | ENST00000519589 | 3786 | potassium voltage-gated channel, KQT-like subfamily, member 3 | chr8:13314152 8-133141469 | GO:0005244\|GO:0016020\|GO:0008076\|GO:0005249\|GO:0007268\|GO:0030955\|GO:0016021\|GO:0055085\|GO:0006813\|GO:0006811 | NM_004519 | NP1473798 | Hs.374023 |
| A_24_P709377 | LOC654433 | *Homo sapiens* hypothetical LOC654433 (LOC654433), non-coding RNA [NR_015377] | NR_015377 | | 654433 | hypothetical LOC654433 | chr2:11402424 8-114024307 | | NR_015377 | THC2472587 | Hs.656660 |
| A_23_P250571 | DMXL1 | *Homo sapiens* Dmx-like 1 (DMXL1), mRNA [NM_005509] | NM_005509 | ENST00000514595 | 1657 | Dmx-like 1 | chr5:11858447 3-118584532 | GO:0005515 | NM_005509 | NP1159462 | Hs.181042 |
| A_33_P3327470 | | Q61984_HUMAN (Q61984) Acidic neurotropism 6 alpha (Fragment), complete [THC2606816] | JF432775 | | | | chr19:0495423 03-049542244 | | | THC2606816 | |
| A_33_P3334404 | CA6 | carbonic anhydrase VI [Source: HGNC Symbol; Acc: 1380] [ENST00000319474] | | ENST00000319474 | 765 | carbonic anhydrase VI | chr1:9011597-9011656 | | | THC2490642 | Hs.100322 |
| A_33_P3308432 | MORN1 | MORN repeat containing 1 [Source: HGNC Symbol; Acc: 25852] [ENST00000449373] | | ENST00000449373 | 79906 | MORN repeat containing 1 | chr1:2310557-2310498 | | | THC2519762 | |
| A_33_P3383524 | LOC91948 | *Homo sapiens* hypothetical | NR_024172 | | 91948 | hypothetical LOC91948 | chr15:9828595 7-98285898 | | NR_024172 | THC2567547 | Hs.130423 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3230290 | | LOC91948 (LOC91948), transcript variant 1, non-coding RNA [NR_024172] | | | | | | | | | |
| | ACAP3 | Homo sapiens ArfGAP with coiled-coil, ankyrin repeat and PH domains 3 (ACAP3), mRNA [NM_030649] | NM_030649 | ENST00000492936 | 116983 | ArfGAP with coiled-coil, ankyrin repeat and PH domains 3 | chr1:1227895-1227836 | GO:0008060|GO:0032312|NM_030649| GO:0008270|GO:0046872 | | THC2462386 | Hs.535257 |
| A_33_P3222783 | SURF4 | Homo sapiens surfeit 4 (SURF4), mRNA [NM_033161] | NM_033161 | ENST00000537106 | 6836 | surfeit 4 | chr9:136231776-136231717 | GO:0005515|GO:0008150|NM_033161| GO:0003674|GO:0005793| GO:0016020|GO:0005783| GO:0016021 | | THC2539228 | Hs.512465 |
| A_23_P215956 | MYC | Homo sapiens v-myc myelocytomatosis viral oncogene homolog (avian) (MYC), mRNA [NM_002467] | NM_002467 | ENST00000454617 | 4609 | v-myc myelocyto-matosis viral oncogene homolog (avian) | chr8:128755326-128753327 | GO:0006879|GO:0005515|NM_002467| GO:0008284|GO:0003700| GO:0006357|GO:0005819| GO:0032204|GO:0007050| GO:0005634 | | THC2468611 | Hs.202453 |
| A_33_P3401084 | | | | | | | chr17:0373082 91-037308350 chr3:45989385-45989443 | | | | |
| A_23_P109913 | CXCR6 | Homo sapiens chemokine (C-X-C motif) receptor 6 (CXCR6), mRNA [NM_006564] | NM_006564 | ENST00000438735 | 10663 | chemokine (C-X-C motif) receptor 6 | | GO:0007165|GO:0007186|NM_006564| GO:0005886|GO:0016494| GO:0005887|GO:0004930| GO:0016493|GO:0015026| GO:0019079 | | THC2485202 | Hs.34526 |
| A_24_P363896 | COL27A1 | Homo sapiens collagen, type XXVII, alpha 1 (COL27A1), mRNA [NM_032888] | NM_032888 | ENST00000357257 | 85301 | collagen, type XXVII, alpha 1 | chr9:11707289 5-117072954 | GO:0005581|GO:0005576|NM_032888| GO:0007155|GO:0005201 | | THC2493513 | Hs.494892 |
| A_33_P3378284 | COX6B2 | Homo sapiens cytochrome c oxidase subunit VIb polypeptide 2 (testis) (COX6B2), mRNA [NM_144613] | NM_144613 | ENST00000326529 | 125965 | cytochrome c oxidase subunit VIb polypep-tide 2 (testis) | chr19:5586141 6-55861357 | GO:0005739|GO:0005758|NM_144613| GO:0004129|GO:0030061 | | NP1157598 | Hs.550544 |
| A_23_P210425 | MYL9 | Homo sapiens myosin, light chain 9, regulatory | NM_181526 | ENST00000279022 | 10398 | myosin, light chain 9, regulatory | chr20:3517754 1-35177600 | GO:0006937|GO:0003774|NM_181526| GO:0005509|GO:0016459| GO:0005859|GO:0008307 | | THC2598537 | Hs.504687 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3326025 | KANK3 | (MYL9), transcript variant 2, mRNA [NM_181526] KN motif and ankyrin repeat domains 3 [Source: HGNC Symbol; Acc: 24796] [ENST00000381056] | AY203940 | ENST00000381056 | 256949 | KN motif and ankyrin repeat domains 3 | chr19:8398739-8398680 | | | THC2556942 | |
| A_23_P104563 | CPT1A | Homo sapiens carnitine palmitoyl-transferase 1A (liver) (CPT1A), nuclear gene encoding mitochondrial protein, transcript variant 2, mRNA [NM_001031847] | NM_001031847 | ENST00000539743 | 1374 | carnitine palmitoyl-transferase 1A (liver) | chr11:68527126-68527063 | GO:0006629 GO:0006635 GO:0005739 GO:0006810 GO:0042755 GO:0016740 | GO:0005792 GO:0004095 GO:0005741 GO:0050796 GO:0016020 GO:0006631 GO:0006006 GO:0016021 GO:0008415 | NM_001031847 | THC2464485 | Hs.503043 |
| A_33_P3314810 | | AF059569 actin binding protein MAYVEN {Homo sapiens} (exp = −1; wgp = 0; cg = 0), partial (29%) [THC2733494] | | | | | chr6:000143659-000143718 | | | THC2733494 | |
| A_24_P28811 | C2orf14 | Homo sapiens chromosome 2 open reading frame 14 (C2orf14), non-coding RNA [NR_023391] | NR_023391 | ENST00000439137 | 100132708 | chromosome open reading 2 frame 14 | chr2:131438196-131438255 | | NR_023391 | THC2535623 | Hs.710729 |
| A_33_P3260426 | SPRR2A | Homo sapiens small proline-rich protein 2A (SPRR2A), mRNA [NM_005988] | NM_005988 | ENST00000392653 | 6700 | small-proline rich protein 2A | chr1:153028985-153028926 | GO:0005737 GO:0005488 GO:0001533 | GO:0008544 GO:0031424 | NM_005988 | THC2517261 | Hs.355542 |
| A_23_P210886 | BCL2L1 | Homo sapiens BCL2-like 1 (BCL2L1), nuclear gene encoding mitochondrial | NM_138578 | ENST00000420653 | 598 | BCL2-like 1 | chr20:30253383-30253324 | GO:0042542 GO:0008284 GO:0005741 GO:0005739 GO:0007281 | GO:0014070 GO:0043434 GO:0005634 GO:0007283 GO:0042802 GO:0005622 | NM_138578 | THC2507989 | Hs.516966 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | protein, transcript variant 1, mRNA [NM_138578] | | | | | | GO:0005829\|GO:0051789\| GO:0043524\|GO:0001541\| GO:0010035\|GO:0034097\| GO:0006979\|GO:0043027\| GO:0008634\|GO:0009314\| GO:0046902\|GO:0001666\| GO:0010288\|GO:0043065\| GO:0046982\|GO:0051811\| GO:0010243\|GO:0046898\| GO:0045768\|GO:0001701\| GO:0009566\|GO:0016020\| GO:0016021\|GO:0040007\| GO:0008584 | | | |
| A_33_P3209581 | IQSEC3 | *Homo sapiens* IQ motif and Sec7 domain 3 (IQSEC3), transcript variant 1, mRNA [NM_001170738] | NM_001170738 | ENST00000552304 | 440073 | IQ motif and Sec7 domain 3 | chr12:176547-208312 | | NM_001170738 | NP437544 | Hs.536319 |
| A_33_P3211965 | | *Homo sapiens* UI-E-EJO-ahi-b-22-O-UI.s1 UI-E-EJO *Homo sapiens* cDNA clone UI-E-EJO-ahi-b-22-O-UI 3', mRNA sequence [BM674043] | BM674043 | | | | chr16:30832743-30832684 | | | | Hs.681104 |
| A_24_P185036 | FTSJD1 | *Homo sapiens* FtsJ methyltransferase domain containing 1 (FTSJD1), transcript variant 1, mRNA [NM_018348] | NM_018348 | ENST00000434935 | 55783 | FtsJ methyl-transferase domain containing 1 | chr16:71316895-71316836 | GO:0016020\|GO:0008168\|NM_018348 GO:0016021\|GO:0003676\| GO:0032259\|GO:0016740 | | THC2464150 | Hs.72782 |
| A_23_P21425 | GPR119 | *Homo sapiens* G protein-coupled receptor 119 (GPR119), mRNA [NM_178471] | NM_178471 | ENST00000276218 | 139760 | G protein-coupled receptor 119 | chrX:129518731-129518672 | GO:0007165\|GO:0007186\|NM_178471 GO:0005886\|GO:0001619\| GO:0004930\|GO:0004872\| GO:0016021\|GO:0030073\| GO:0008289 | | THC2479570 | Hs.496762 |
| A_23_P63896 | FAS | *Homo sapiens* Fas (TNF receptor superfamily, member 6) (FAS), transcript variant 1, mRNA [NM_000043] | NM_000043 | ENST00000355740 | 355 | Fas (TNF receptor superfamily, member 6) | chr10:90774545-90774604 | GO:0008624\|GO:0008633\|NM_000043 GO:0005886\|GO:0031264\| GO:0042981\|GO:0005576\| GO:0005625\|GO:0006916\| GO:0042802\|GO:0005829\| GO:0007165\|GO:0006955\| GO:0006461\|GO:0016021 | | THC2522452 | Hs.244139 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3367924 | PABPN1L | Homo sapiens poly(A) binding protein, nuclear 1-like (cytoplasmic) (PABPN1L), mRNA [NM_001080487] | NM_001080487 | ENST00000411789 | 390743 | poly(A) binding protein, nuclear 1-like (cytoplasmic) | chr16:88932843-88932785 | GO:0019900|GO:0004888| GO:0010940 GO:0005737|GO:0003723 | NM_001080487 | | Hs.730522 |
| A_23_P11697 | HMGB4 | Homo sapiens high mobility group box 4 (HMGB4), transcript variant 1, mRNA [NM_145205] | NM_145205 | ENST00000522796 | 127540 | high mobility group box 4 | chr1:34329965-34330024 | GO:0005694|GO:0005634| GO:0003677 | NM_145205 | THC2471340 | Hs.568628 |
| A_23_P162322 | WNT10B | Homo sapiens wingless-type MMTV integration site family, member 10B (WNT10B), mRNA [NM_003394] | NM_003394 | ENST00000301061 | 7480 | wingless-type MMTV integration site family, member 10B | chr12:49359496-49359437 | GO:0007165|GO:0005578| GO:0007275|GO:0005576| GO:0004871|GO:0007223 | NM_003394 | NP1456377 | Hs.91985 |
| A_33_P3316691 | | | | | | | chr18:01444495 14-01444957 3 | | | | |
| A_23_P410613 | C12orf23 | Homo sapiens chromosome 12 open reading frame 23 (C12orf23), mRNA [NM_152261] | NM_152261 | ENST00000280756 | 90488 | chromosome 12 open reading frame 23 | chr12:107367533-107367592 | GO:0016020|GO:0016021 | NM_152261 | THC2499724 | Hs.257664 |
| A_24_P751074 | ETS1 | Homo sapiens v-ets erythroblastosis virus E26 oncogene homolog 1 (avian) (ETS1), transcript variant 2, mRNA [NM_005238] | NM_005238 | ENST00000392668 | 2113 | v-ets erythroblastosis virus E26 oncogene homolog 1 (avian) | chr11:128328679-128328656 | GO:0043565|GO:0006955| GO:0030578|GO:0008285| GO:0003700|GO:0045648| GO:0048870|GO:0010552| GO:0005634|GO:0045893| GO:0051272|GO:0008134 | NM_005238 | THC2609159 | Hs.369438 |
| A_23_P11543 | FUCA1 | Homo sapiens fucosidase, alpha-L-1, tissue (FUCA1), mRNA [NM_000147] | NM_000147 | ENST00000371479 | 2517 | fucosidase, alpha L-1, tissue | chr1:24171909-24171850 | GO:0005737|GO:0005975| GO:0004560|GO:0016798| GO:0008152|GO:0005529| GO:0006027|GO:0005625| GO:0006004|GO:0005764 | NM_000147 | THC2518697 | Hs.370858 |
| A_33_P3422030 | FXYD5 | FXYD domain containing ion transport regulators [Source: HGNC Symbol; Acc: 4029] [ENST00000392218] | | ENST00000392218 | 53827 | FXYD domain containing ion transport regulator 5 | chr19:3565077 3-35650832 | | | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3275199 | JRK | *Homo sapiens* jerky homolog (mouse) (JRK), transcript variant 1, mRNA [NM_003724] | NM_003724 | ENST00000422119 | 8629 | jerky homolog (mouse) | chr8:143739085-143739026 | GO:0008150|GO:0003674|NM_003724|GO:0005737|GO:0030529|GO:0005634|GO:0005575|GO:0003729|GO:0003677|GO:0045449 | NM_003724 | THC2526551 | Hs.535903 |
| A_23_P123071 | CAV2 | *Homo sapiens* caveolin 2 (CAV2), transcript variant 1, mRNA [NM_001233] | NM_001233 | ENST00000498493 | 858 | caveolin 2 | chr7:116140389-116140448 | GO:0051219|GO:0030133|NM_001233|GO:0048471|GO:0005886|GO:0007268|GO:0005634|GO:0051259|GO:0006906|GO:0042803|GO:0070836|GO:0005829|GO:0005622|GO:0005737|GO:0060161|GO:0048278|GO:0005811|GO:0019905|GO:0007088|GO:0005794|GO:0009986|GO:0005624|GO:0048741|GO:0031234|GO:0043234|GO:0005887|GO:0001937|GO:0005901|GO:0007005|GO:0007029 | | THC2788990 | Hs.212332 |
| A_33_P3411315 | KRTAP3-3 | *Homo sapiens* keratin associated protein 3-3 (KRTAP3-3), mRNA [NM_033185] | NM_033185 | ENST00000391586 | 85293 | keratin associated protein 3-3 | chr17:39150112-39150053 | GO:0005198|GO:0045095 | NM_033185 | THC2485385 | Hs662759 |
| A_33_P3255176 | | | | | | | chr1:026551643-026551702 | | | | |
| A_33_P3283485 | LOC440337 | PREDICTED: *Homo sapiens* hypothetical LOC440337 (LOC440337), misc-RNA [XR_111632] | XR_111632 | | 440337 | hypothetical LOC440337 | chr16:64279926428051 | | XR_111632 | THC2688565 | Hs.683875 |
| A_23_P106773 | SULT1A2 | *Homo sapiens* sulfotransferase family, cytosolic, 1A, phenol-preferring, member 2 (SULT1A2), transcript variant 2, mRNA [NM_177528] | NM_177528 | ENST00000395630 | 6799 | sulfotransferase family, cytosolic, 1A, phenol-preferring, member 2 | chr16:28603326-28603267 | GO:0006629|GO:0005737|NM_177528|GO:0006584|GO:0004062|GO:0009309|GO:0016740|GO:0008202 | NM_177528 | THC2495029 | Hs.546304 |
| A_33_P3305023 | WWOX | *Homo sapiens* WW domain containing oxidoreductase (WWOX), transcript variant 3, mRNA [NM_130844] | NM_130844 | | 51741 | WW domain containing oxidoreductase | chr16:78134036-78134095 | GO:0050662|GO:0005794|NM_130844|GO:0030178|GO:0048705|GO:0005634|GO:0006917|GO:0001649|GO:0005739|GO:0005737|GO:0016491 | | THC2619560 | Hs.461453 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3357651 | KRTAP10-12 | *Homo sapiens* keratin associated protein 10-12 (KRTAP10-12), mRNA [NM_198699] | NM_198699 | ENST00000452870 | 386685 | keratin associated protein 10-12 | chr21:46117543-46117602 | GO:0046983\|GO:0008202\|GO:0055114\|GO:0045095 | NM_198699 | THC2483182 | Hs.297526 |
| A_23_P151598 | CPNE6 | *Homo sapiens* copine VI (neuronal) (CPNE6), mRNA [NM_006032] | NM_006032 | ENST00000537691 | 9362 | copine VI (neuronal) | chr14:24544734-24544793 | GO:0006629\|GO:0030424\|GO:0005215\|GO:0005509\|GO:0001786\|GO:0007268\|GO:0005624\|GO:0016192\|GO:0030425\|GO:0007399 | NM_006032 | THC2488672 | Hs.6132 |
| A_33_P3288871 | SLC38A1 | solute carrier family 38, member 1 [Source: HGNC Symbol; Acc: 13447] [ENST00000550173] | DC378344 | ENST00000550173 | 81539 | solute carrier family 38, member 1 | chr12:46663597-46663538 | | | | Hs.719858 |
| A_23_P155514 | AHSG | *Homo sapiens* alpha-2-HS-glycoprotein (AHSG), mRNA [NM_001622] | NM_001622 | ENST00000541510 | 197 | alpha-2-HS-glycoprotein | chr3:186338832-186338891 | GO:0005515\|GO:0050766\|GO:0006907\|GO:0001501\|GO:0004869\|GO:0019210\|GO:0046627\|GO:0050727\|GO:0005576\|GO:0006953\|GO:0030502\|GO:0005615 | NM_001622 | THC2469134 | Hs.324746 |
| A_23_P253221 | ARHGEF4 | *Homo sapiens* Rho guanine nucleotide exchange factor (GEF) 4 (ARHGEF4), transcript variant 2, mRNA [NM_032995] | NM_032995 | ENST00000522839 | 50649 | Rho guanine nucleotide exchange factor (GEF) 4 | chr2:131180476-131804821 | GO:0007242\|GO:0008624\|GO:0005886\|GO:0035023\|GO:0019904\|GO:0006915\|GO:0005575\|GO:0042995\|GO:0005829\|GO:0005085\|GO:0005622\|GO:0005737\|GO:0005089 | NM_032995 | THC2487810 | Hs.469935 |
| A_33_P3237784 | PORCN | *Homo sapiens* porcupine homolog (*Drosophila*) (PORCN), transcript variant B, mRNA [NM_203473] | NM_203473 | ENST00000326194 | 64840 | porcupine homolog (*Drosophila*) | chrX:48379104-48379163 | GO:0005515\|GO:0009100\|GO:0016020\|GO:0005783\|GO:0030176\|GO:0016021\|GO:0016055\|GO:0016740\|GO:0008415 | NM_203473 | THC2483690 | Hs.386453 |
| A_23_P115824 | HNRNPH3 | *Homo sapiens* heterogeneous nuclear ribonucleoprotein H3 (2H9) (HNRNPH3), transcript | NM_012207 | ENST00000265866 | 3189 | heterogeneous nuclear ribonucleo-protein H3(2H9) | chr10:70102702-70102761 | GO:0008380\|GO:0005515\|GO:0000166\|GO:0000398\|GO:0003723\|GO:0005634\|GO:0030530 | NM_012207 | THC2509619 | Hs.643472 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P209799 | MYO7B | variant 2H9, mRNA [NM_012207] Homo sapiens myosin VIIB (MYO7B), mRNA [NM_001080527] | NM_001080527 | ENST00000494959 | 4648 | myosin VIIB | chr2:128394487-128394948 | GO:0016324\|GO:0003774\|GO:0005886\|GO:0000166\|GO:0003779\|GO:0016459\|GO:0005856\|GO:0005524 | NM_001080527 | THC2604874 | Hs.154578 |
| A_33_P3281435 | | Homo sapiens immunoglobulin kappa variable 1D-8 [Source: HGNC Symbol; Acc: 57591 [ENST00000471857] | AF035035 | ENST00000471857 | | | chr2:90260191-90260248 | | | THC2548990 | Hs.574701 |
| A_33_P3235029 | | MGC3.5.1.2.1.H09.F.1 NIH_MGC_331 Homo sapiens cDNA clone MGC3.5.1.2.1.H09, mRNA sequence [DR731407] | DR731407 | | | | chr14:20908874-20908933 | | | | Hs.556125 |
| A_24_P48069 | DOK4 | Homo sapiens docking protein 4 (DOK4), mRNA [NM_018110] | NM_018110 | ENST00000340099 | 55715 | docking protein 4 | chr16:57506193-57506134 | GO:0005619\|GO:0005158\|GO:0005066\|GO:0007169\|GO:0007399 | NM_018110 | THC2467241 | Hs.279832 |
| A_33_P3236591 | RLTPR | Homo sapiens RGD motif, leucine rich repeats, tropo-modulin domain and proline-rich containing (RLTPR), mRNA [NM_001013838] | NM_001013838 | ENST00000398282 | 146206 | RGD motif, leucine rich repeats, tropomodulin domain and proline-rich containing | chr16:67691397-67691456 | | NM_001013838 | THC2720275 | Hs.611432 |
| A_23_P24234 | OPN4 | Homo sapiens opsin 4 (OPN4), transcript variant 2, mRNA [NM_001030015] | NM_001030015 | ENST00000372071 | 94233 | opsin 4 | chr10:88426117-88426176 | GO:0005502\|GO:0018298\|GO:0007165\|GO:0016020\|GO:0007186\|GO:0042752\|GO:0048511\|GO:0016021\|GO:0007602\|GO:0007601\|GO:0050896\|GO:0008020 | NM_001030015 | THC2482526 | Hs.283922 |
| A_23_P6633 | CXorf48 | Homo sapiens chromosome X open reading frame 48 (CXorf48), transcript variant 1, mRNA [NM_001031705] | NM_001031705 | ENST00000344129 | 54967 | chromosome X open reading frame 48 | chrX:134290762-134290704 | | NM_001031705 | THC2487724 | Hs.272804 |
| A_33_P3281437 | | Homo sapiens immunoglobulin kappa variable | AF035035 | LNbT00000471857 | | | chr2:90260030-90260089 | | NP1465439 | | Hs.574701 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3221489 | KIRREL | 1D-8 [Source: HGNC Symbol; Acc: 5759] [ENST00000471857] Homo sapiens kin of IRRE like (Drosophila) (KIRREL), mRNA [NM_018240] | NM_018240 | ENST00000359209 | 55243 | kin of IRRE like (Drosophila) | chr1:158065293-158065352 | GO:0005886|GO:0016021 | NM_018240 | NP436211 | Hs.657006 |
| A_23_P148047 | PTGER4 | Homo sapiens prostaglandin E receptor 4 (subtype EP4) (PTGER4), mRNA [NM_000958] | NM_000958 | ENST00000302472 | 5734 | prostaglandin E receptor 4 (subtype EP4) | chr5:40693563-40693622 | GO:0007165|GO:0006955|GO:0030278|GO:0007186|GO:0005886|GO:0004930|GO:0007188|GO:0004872|GO:0016021|GO:0004957 | NM_000958 | THC2463869 | Hs.199248 |
| A_24_P203056 | BCL7A | Homo sapiens B-cell CLL/lymphoma 7A (BCL7A), transcript variant 1, mRNA [NM_020993] | NM_020993 | ENST00000538010 | 605 | B-cell CLL/lymphoma 7A | chr12:122499758-122499817 | GO:0003674|GO:0016481|GO:0005575 | NM_020993 | THC2777702 | Hs.530970 |
| A_23_P116624 | SLC6A5 | Homo sapiens solute carrier family 6 (neurotransmitter transporter, glycine), member 5 (SLC6A5), mRNA [NM_004211] | NM_004211 | ENST00000298923 | 9152 | solute carrier family 6 (neurotransmitter transporter, glycine), member 5 | chr11:20673953-20676268 | GO:0015375|GO:0015816|GO:0016020|GO:0005887|GO:0005328|GO:0006836|GO:0007268|GO:0015293 | NM_004211 | THC2480373 | Hs.136557 |
| A_23_P214977 | SEC63 | Homo sapiens SEC63 homolog (S. cerevisiae) (SEC63), mRNA [NM_007214] | NM_007214 | ENST00000459782 | 11231 | SEC63 homolog (S. cerevisiae) | chr6:108192374-108192315 | GO:0016020|GO:0006457|GO:0005783|GO:0031072|GO:0006612|GO:0004872|GO:0051082|GO:0016021|GO:0015031 | NM_007214 | THC2688372 | Hs.26904 |
| A_33_P3327592 | RNF13 | Homo sapiens ring finger protein 13 (RNF13), transcript variant 1, mRNA [NM_007282] | NM_007282 | ENST00000392894 | 11342 | ring finger protein 13 | chr3:149679866-149679925 | GO:0005515|GO:0005737|GO:0008270|GO:0005634|GO:0046872 | NM_007282 | THC2483942 | Hs.12333 |
| A_33_P3388958 | SNX32 | Homo sapiens sorting nexin 32 (SNX32), mRNA [NM_152760] | NM_152760 | ENST00000308342 | 254122 | sorting nexin 32 | chr11:65621110-65621169 | GO:0005515|GO:0007154|GO:0035091|GO:0015031 | NM_152760 | THC2478732 | Hs.591950 |
| A_23_P78750 | SLC17A7 | Homo sapiens solute carrier family 17 | NM_020309 | ENST00000543531 | 57030 | solute carrier family 17 | chr19:49933575-49933516 | GO:0030054|GO:0031410|GO:0015319|GO:0031402 | NM_020309 | THC2757650 | Hs.375616 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | family 17 (sodium-dependent inorganic phosphate cotransporter), member 7 (SLC17A7), mRNA [NM_020309] | | | | (sodium-dependent inorganic phosphate cotransporter), member 7 | | GO:0060076\|GO:0055085\|GO:0015321\|GO:0016020\|GO:0008836\|GO:0006817\|GO:0042137\|GO:0030672\|GO:0016021\|GO:0006814\|GO:0019717\|GO:0006811\|GO:0015293 | | | |
| A_33_P3422265 | LOC729305 | PREDICTED: Homo sapiens hypothetical LOC729305 (LOC729305), partial miscRNA [XR_114546] | XR_114546 | ENST00000513405 | 729305 | hypothetical LOC729305 | chr11:134606350-134606409 | | XR_114546 | THC2678881 | Hs.148365 |
| A_33_P3369944 | ADAM21 | Homo sapiens ADAM metallopeptidase domain 21 (ADAM21), mRNA [NM_003813] | NM_003813 | ENST00000530196 | 8747 | ADAM metallopeptidase domain 21 | chr14:70926003-70926062 | GO:0007338\|GO:0016020\|NM_003813\|GO:0006508\|GO:0008270\|GO:0008233\|GO:0016021\|GO:0004222\|GO:0046872 | | THC2637652 | Hs.178748 |
| A_33_P3216483 | LOC644277 | PREDICTED: Homo sapiens hypothetical LOC644277 (LOC644277), miscRNA [XR_110541] | XR_110541 | ENST00000528953 | 644277 | hypothetical LOC644277 | chr11:111327269-111327328 | | XR_110541 | | Hs.577348 |
| A_24_P218074 | ZNF467 | Homo sapiens zinc finger protein 467 (ZNF467), mRNA [NM_207336] | NM_207336 | ENST00000302017 | 168544 | zinc finger protein 467 | chr7:149462406-149462347 | GO:0005622\|GO:0008270\|NM_207336\|GO:0005634\|GO:0003677\|GO:0046872\|GO:0045449 | | THC2463585 | Hs.726477 |
| A_33_P3357879 | | | | | | | chr10:133274691-133274632 | | | | |
| A_33_P3400643 | LOC643529 | Homo sapiens hCG2024094 (LOC643529), non-coding RNA [NR_038382] | NR_038382 | | 643529 | hCG2024094 | chr9:91597402-91597461 | | NR_038382 | THC2641103 | HS.618956 |
| A_33_P3371785 | DTNA | Homo sapiens dystrobrevin, alpha (DTNA), transcript variant 9, mRNA [NM_001128175] | NM_001128175 | ENST00000315456 | 1837 | dystrobrevin, alpha | chr18:32407580-32407639 | GO:0005515\|GO:0007165\|NM_001128175\|GO:0005737\|GO:0030054\|GO:0005509\|GO:0006941\|GO:0045202\|GO:0008270\|GO:0007274 | | THC2748155 | Hs.643454 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P327022 | MDFIC | Homo sapiens MyoD family inhibition domain containing (MDFIC), transcript variant 1, mRNA [NM_199072] | NM_199072 | ENST00000257724 | 29969 | MyoD family inhibition domain containing | chr7:114658631-114658690 | GO:0005737\|GO:0030111\|GO:0044419\|GO:0030332\|GO:0005730\|GO:0005634\|GO:0007257\|GO:0030957\|GO:0045449\|GO:0050434 | NM_199072 | THC2564826 | Hs.427236 |
| A_23_P100660 | SERPINF1 | Homo sapiens serpin peptidase inhibitor, clade F (alpha-2 antiplasmin, pigment epithelium derived factor), member 1 (SERPINF1), mRNA [NM_002615] | NM_002615 | ENST00000254722 | 5176 | serpin peptidase inhibitor, clade F (alpha-2 antiplasmin, pigment epithelium derived factor), member 1 | chr17:1680668-1680727 | GO:0042470\|GO:0050769\|GO:0008283\|GO:0004867\|GO:0050728\|GO:0016525\|GO:0007275\|GO:0005576\|GO:0005615 | NM_002615 | NP1187984 | Hs.532768 |
| A_23_P318300 | ZAK | Homo sapiens sterile alpha motif and leucine zipper containing kinase AZK (ZAK), transcript variant 2, mRNA [NM_133646] | NM_133646 | ENST00000338983 | 51776 | sterile alpha motif and leucine zipper containing kinase AZK | chr2:174091756-174091815 | GO:0009314\|GO:0008219\|GO:0043065\|GO:0000287\|GO:0008283\|GO:0006950\|GO:0005634\|GO:0007257\|GO:0005524\|GO:0030154\|GO:0007243\|GO:0042802\|GO:0000186\|GO:0005737\|GO:0007049\|GO:0000166\|GO:0004674\|GO:0000075\|GO:0007050\|GO:0000077\|GO:0004713\|GO:0004709\|GO:0016740 | NM_133646 | THC2572394 | Hs.444451 |
| A_23_P5165 | SEMA4B | Homo sapiens sema domain, immunoglobulin domain (Ig), transmembrane domain (TM) and short cytoplasmic domain, (semaphorin) 4B (SEMA4B), transcript variant 1, mRNA [NM_020210] | NM_020210 | ENST00000332496 | 10509 | sema domain, immunoglobulin domain (Ig), transmembrane domain (TM) and short cytoplasmic domain, (semaphorin) 4B | chr15:90771532-90771591 | GO:0016020\|GO:0007275\|GO:0004872\|GO:0016021\|GO:0030154\|GO:0007399 | NM_020210 | THC2469032 | Hs.474935 |
| A_21_P300847 | DIO3OS | Homo sapiens clone 6 DIO3AS mRNA, partial sequence; | AF469204 | | 64150 | DIO3 opposite strand (nonprotein coding) | chr14:102025111-102025052 | | NP1139581 | | Hs.525597 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3386775 | ADAM11 | Homo sapiens ADAM metallopeptidase domain 11 (ADAM11), mRNA [NM_002390] alternatively spliced. [AF469204] | NM_002390 | ENST00000355638 | 4185 | ADAM metallopeptidase domain 11 | chr17:42857869-42857928 | GO:0005178\|GO:0005886\|NM_002390 GO:0007229\|GO:0006508\| GO:0008270\|GO:0016021\| GO:0004222 | | THC2477011 | Hs.6088 |
| A_33_P3410296 | DPYSL4 | Homo sapiens dihydropyrimidinase-like 4 (DPYSL4), mRNA [NM_006426] | NM_006426 | ENST00000368629 | 10570 | dihydropyrimidinase-like 4 | chr10:134018522-134018581 | GO:0005737\|GO:0016810\|NM_006426 GO:0007399 | | THC2730511 | Hs.100058 |
| A_23_P59677 | RINT1 | Homo sapiens RAD50 interactor 1 (RINT1), mRNA [NM_021930] | NM_021930 | ENST00000497979 | 60561 | RAD 50 interactor 1 | chr7:105207999-105208058 | GO:0005515\|GO:0007049\|NM_021930 GO:0005737\|GO:0016020\| GO:0005783\|GO:0031572\| GO:0016192\|GO:0015031\| GO:0019898 | | THC2467373 | Hs.531388 |
| A_24_P274270 | STAT1 | Homo sapiens signal transducer and activator of transcription 1, 91 kDa (STAT1), transcript variant beta, mRNA [NM_139266] | NM_139266 | ENST00000540176 | 6772 | signal of transducer and activator transcription 1, 91 kDa | chr2:191841733-191841674 | GO:0005515\|GO:0042542\|NM_139266 GO:0007260\|GO:0014070\| GO:0030424\|GO:0003700\| GO:0006366\|GO:0008015\| GO:0019221\|GO:0007249\| GO:0043434\|GO:0005634\| GO:0051591\|GO:0030425\| GO:0005737\|GO:0044419\| GO:0005062\|GO:0032496\| GO:0004871\|GO:0034097\| GO:0031663\|GO:0032869\| GO:0006355\|GO:0006919\| GO:0007584\|GO:0042493\| GO:0005509\|GO:0005730\| GO:0006917\|GO:0009615\| GO:0048661\|GO:0009612\| GO:0043565\|GO:0007165\| GO:0043330 | | THC2545270 | Hs.642990 |
| A_33_P3242416 | | | | | | | chr1:22373879-22373735 | | | | |
| A_33_P3377399 | | | | ENST00000520078 | | | chr8:106810426-106810367 | | | | |
| A_23_P84230 | OTP | Homo sapiens orthopedia homeobox (OTP), mRNA [NM_032109] | NM_032109 | ENST00000306422 | 23440 | orthopedia homeobox | chr5:76924844-76924785 | GO:0043565\|GO:0021985\|NM_032109 GO:0006355\|GO:0003700\| GO:0021879\|GO:0021979\| GO:0002052\|GO:0007275\| GO:0005634\|GO:0007399 | | THC2477504 | Hs.202247 |
| A_23_P395632 | R3HDML | Homo sapiens R3H domain containing-like | NM_178491 | ENST00000217043 | 140902 | R3H domain containing-like | chr20:42969934-42972055 | GO:0005576\|GO:0030414 NM_178491 | | THC2485270 | Hs.580807 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P211248 | LOC100131138 | containing-like (R3HDML), mRNA [NM_178491] Homo sapiens hypothetical LOC100131138 (LOC100131138), non-coding RNA [NR_036513] | NR_036513 | | 100131138 | hypothetical LOC100131138 | chr12:111375193-111375252 | | NR_036513 | THC2471096 | Hs.152129 |
| A_24_P194420 | CCDC134 | Homo sapiens coiled-coil domain containing 134 (CCDC134), mRNA [NM_024821] | NM_024821 | ENST00000255784 | 79879 | coiled-coil domain containing 134 | chr22:42209346-42209405 | GO:0005576 | NM_024821 | THC2474399 | Hs.474991 |
| A_33_P3287105 | | | | | | | chr1:161209136-161209077 | | | | |
| A_33_P3245841 | | | | | | | chr1:161416792-161416733 | | | | |
| A_33_P3300308 | MAP1LC3A | Homo sapiens microtubule-associated protein 1 light chain 3 alpha (MAP1LC3A), transcript variant 1, mRNA [NM_032514] | NM_032514 | ENST00000397709 | 84557 | microtubule-associated protein 1 light chain 3 alpha | chr20:33147644-33147703 | GO:0005515|GO:0005737|NM_032514 GO:0005776|GO:0008429| GO:0019941|GO:0031090| GO:0005874|GO:0006914| GO:0031410|GO:0031225| GO:0000045|GO:0005829 | | THC2673701 | Hs.632273 |
| A_24_P213643 | TSPAN10 | Homo sapiens tetraspanin 10 (TSPAN10), mRNA [NM_031945] | NM_031945 | ENST00000328585 | 83882 | tetraspanin 10 | chr17:79612546-79612605 | GO:0016020|GO:0016021 | NM_031945 | NP074767 | Hs.208219 |
| A_33_P3354539 | CHURC1 | Homo sapiens churchill domain containing 1 (CHURC1), transcript variant 1, mRNA [NM_145165] | NM_145165 | ENST00000359118 | 91612 | churchill domain containing 1 | chr14:65401707-65401766 | GO:0045941|GO:0016563|NM_145165 GO:0008270|GO:0007275| GO:0046872 | | | Hs.325531 |
| A_23_P164258 | PIPOX | Homo sapiens pipecolic acid oxidase (PIPOX), mRNA [NM_016518] | NM_016518 | ENST00000323372 | 51268 | pipecolic acid oxidase | chr17:27383435-27383494 | GO:0008115|GO:0050031|NM_016518 GO:0046653|GO:0016491| GO:0055114|GO:0005777 | | NP212032 | Hs.462585 |
| A_23_P308603 | SRC | Homo sapiens v-src sarcoma (Schmidt-Ruppin A-2) viral oncogene | NM_005417 | ENST00000445403 | 6714 | v-src sarcoma (Schmidt-Ruppin A-2) viral oncogene | chr20:36033496-36033555 | GO:0005515|GO:0005886|NM_005417 GO:0007265|GO:0005524| GO:0007243|GO:0005829| GO:0007172|GO:0000166| GO:0044419|GO:0005070 | | THC2628771 | Hs.195659 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P129288 | | homolog (avian) (SRC), transcript variant 1, mRNA [NM_005417] | | | | homolog (avian) | | GO:0005901\|GO:0006468\|GO:0042169\|GO:0004715\|GO:0070555\|GO:0016740 | | | |
| | RAB1B | Homo sapiens RAB1B, member RAS oncogene family (RAB1B), mRNA [NM_030981] | NM_030981 | ENST00000314965 | 81876 | RAB1B, member RAS oncogene family | chr11:66044466-66044724 | GO:0005515\|GO:0005737\|NM_030981\|GO:0005794\|GO:0016020\|GO:0000166\|GO:0007264\|GO:0015031\|GO:0005525 | THC2469371 | Hs.300816 |
| A_33_P3264731 | | Uncharacterized protein [Source: UniProtKB/TrEMBL; Acc: A8MVZ5] [ENST00000400948] | | ENST00000400948 | | | chr1:228699703-228699644 | | | THC2613385 | |
| A_33_P3229452 | FLJ44477 | Homo sapiens cDNA FLJ44477 fis, clone UTERU2031703. [AK126441] | AK126441 | | 401157 | FLJ44477 protein | chr4:143768284-143768343 | | | THC2484299 | Hs.531403 |
| A_24_P194931 | SMEK2 | Homo sapiens SMEK homolog 2, suppressor of mek1 (Dictyostelium) (SMEK2), transcript variant 2, mRNA [NM_020463] | NM_020403 | ENST00000272313 | 57223 | SMEK homolog 2, suppressor of mek1 (Dictyostelium) | chr2:55776250-55776191 | GO:0005515\|GO:0005813\|NM_020403\|GO:0005737\|GO:0005634 | THC2468527 | Hs.516182 |
| A_33_P3238521 | LOC100131884 | Homo sapiens cDNA FLJ40382 fis, clone TESTI2035775. [AK097701] | AK097701 | ENST00000307499 | 100131884 | capicua homolog (Drosophila) pseudogene | chr4:12032661-120326677 | | | THC24811M | Hs 730223 |
| A_33_P3386019 | | | | ENST00000552575 | | | chr7:57084356-57084297 | | | | |
| A_23_P53276 | TIMELESS | Homo sapiens timeless homolog (Drosophila) (TIMELESS), mRNA [NM_003920] | NM_003920 | ENST00000229201 | 8914 | timeless homolog (Drosophila) | chr12:5681100-4-56810945 | GO:0005515\|GO:0000790\|NM_003920\|GO:0046982\|GO:0033261\|GO:0030324\|GO:0005634\|GO:0007275\|GO:0042803\|GO:0006974\|GO:0007049 | THC2788675 | Hs.118631 |
| A_33_P3390042 | LOC143188 | Homo sapiens hypothetical LOC143188 (LOC143188), non-coding RNA [NR_015409] | NR_015409 | | 143188 | hypothetical LOC143188 | chr10:1146148-04-114614863 | GO:0007067\|GO:0009582\|NR_015409\|GO:0042127\|GO:0007623\|GO:0016481\|GO:0048754\|GO:0002009\|GO:0051301 | THC2602015 | Hs.287723 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3357573 | MAML3 | Homo sapiens mastermind-like 3 (Drosophila) (MAML3), mRNA [NM_018717] | NM_018717 | ENST00000327122 | 55534 | mastermind-like 3 (Drosophila) | chr4:140810806-140810747 | GO:0016607\|GO:0003713\|GO:0007219\|GO:0045944\|GO:0005634\|GO:0045449 | NM_018717 | THC2481167 | Hs.586165 |
| A_24_P173823 | PBX1 | Homo sapiens pre-B-cell leukemia homeobox 1 (PBX1), transcript variant 1, mRNA [NM_002585] | NM_002585 | ENST00000420696 | 5087 | pre-B-cell leukemia homeobox 1 | chr1:164820976-164821035 | GO:0005515\|GO:0008284\|GO:0006694\|GO:0001658\|GO:0003700\|GO:0030325\|GO:0001655\|GO:0048706\|GO:0048538\|GO:0005634\|GO:0009954\|GO:0030326\|GO:0009952\|GO:0048536\|GO:0030154\|GO:0005737\|GO:0030278\|GO:0045944\|GO:0009887\|GO:0007548\|GO:0035162\|GO:0005667\|GO:0006355\|GO:0046982\|GO:0005730\|GO:0043565\|GO:0045665 | NM_002585 | THC2491993 | Hs.57097 |
| A_33_P3211078 | HMGA2 | Homo sapiens high mobility group AT-hook 2 (HMGA2), transcript variant 2, mRNA [NM_003484] | NM_003484 | ENST00000537275 | 8091 | high mobility group AT-hook 2 | chr12:66219101-66219160 | GO:0005515\|GO:0006355\|GO:0005694\|GO:0006325\|GO:0005634\|GO:0007275\|GO:0003677\|GO:0007049\|GO:0007067\|GO:0003680\|GO:0007785\|GO:0040008\|GO:0051301 | NM_003484 | NP1474910 | Hs.505924 |
| A_32_P27317 | DDX11L2 | Homo sapiens DEAD/H (Asp-Glu-Ala-Asp/His) box polypeptide 11 like 2 (DDX11L2), transcript variant 2, non-coding RNA [NR_024005] | NR_024005 | | 84771 | DEAD/H (Asp-Glu-Ala-Asp/His) box polypeptide 11 like 2 | chr2:114357599-114357540 | | NR_024005 | | Hs.712940 |
| A_33_P3362371 | RTN3 | Homo sapiens reticulon 3 (RTN3), transcript variant 4, mRNA [NM_201430] | NM_201430 | ENST00000543123 | 10313 | reticulon 3 | chr11:63449006-63449065 | GO:0005515\|GO:0005794\|GO:0016020\|GO:0005783\|GO:0044419\|GO:0006950\|GO:0005730\|GO:0006915\|GO:0005634\|GO:0016021\|GO:0016192\|GO:0005615 | NM_201430 | THC2541012 | Hs.473761 |
| A_25_P112135 | TRAM1 | Homo sapiens translocation associated membrane protein 1 (TRAM1), mRNA [NM_014294] | NM_014294 | ENST00000262213 | 23471 | translocation associated membrane protein 1 | chr8:71485966-71485907 | GO:0005515\|GO:0016020\|GO:0005783\|GO:0006613\|GO:0005789\|GO:0004872\|GO:0016021\|GO:0015031\|GO:0055085 | NM_014244 | THC2719697 | Hs.491988 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P116512 | PRR5L | *Homo sapiens* proline rich 5 like (PRR5L), transcript variant 2, mRNA [NM_024841] | NM_024841 | ENST00000389693 | 79899 | proline rich 5 like | chr11:36486438-36486497 | | NM_024841 | THC2490143 | Hs.19987 |
| A_23_P406385 | FBXL16 | *Homo sapiens* F-box and leucine-rich repeat protein 16 (FBXL16), mRNA [NM_153350] | NM_153350 | ENST00000324361 | 146330 | F-box and leucine rich repeat protein 16 | chr16:742597-742538 | GO:0019941 | NM_153350 | THC2462888 | Hs.513244 |
| A_33_P3381613 | | | | | | | chr7:064328915-06432857 | | | | |
| A_23_P75288 | ATAD1 | *Homo sapiens* ATPase family, AAA domain containing 1 (ATAD1), mRNA [NM_032810] | NM_032810 | ENST00000328142 | 84896 | ATPase family, AAA domain containing 1 | chr10:89513058-89512999 | GO:0017111\|GO:0000166\|GO:0005524 | NM_032810 | THC2466494 | Hs.435948 |
| A_23_P384857 | | GB | | | | | chr6:027932965-027933024 | | | NP274062 | |
| A_23_P401106 | PDE2A | *Homo sapiens* phosphodiesterase 2A, cGMP-stimulated (PDE2A), transcript variant 1, mRNA [NM_002599] | NM_002599 | ENST00000429363 | 5138 | phosphodiesterase 2A, cGMP-stimulated | chr11:72287309-72287250 | GO:0005515\|GO:0007165\|GO:0016787\|GO:0016020\|GO:0004118\|GO:0019898 | NM_002599 | THC2466953 | Hs.503163 |
| A_23_P3312 | ISLR | *Homo sapiens* immunoglobulin superfamily containing leucine-rich repeat (ISLR), transcript variant 1, mRNA [NM_005545] | NM_005545 | ENST00000249842 | 3071 | immuno globulin superfamily containing leucine-rich repeat | chr15:74469121-74469180 | GO:0005515\|GO:0005576\|GO:0007155 | NM_005545 | THC2469953 | Hs.699822 |
| A_23_P29257 | H1F0 | *Homo sapiens* H1 histone family, member 0 (H1F0), mRNA [NM_005318] | NM_005318 | ENST00000340857 | 3005 | H1 histone family, member 0 | chr22:38203147-3803206 | GO:0005794\|GO:0005694\|GO:0006334\|GO:0005634\|GO:0005856\|GO:0000786\|GO:0003677 | NM_005318 | THC2513918 | Hs.226117 |
| A_23_P103601 | MAN1C1 | *Homo sapiens* mannosidase, alpha, class 1C, member 1 (MAN1C1), mRNA [NM_020379] | NM_020379 | ENST00000263979 | 57134 | mannosidase, alpha, class 1C, member 1 | chr1:26110835-26110894 | GO:0030173\|GO:0005794\|GO:0016020\|GO:0016798\|GO:0008152\|GO:0005509\|GO:0004571\|GO:0016021\|GO:0006487 | NM_020379 | NP1210903 | Hs.197043 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P6943 | GPR15 | Homo sapiens G protein-coupled receptor 15 (GPR15), mRNA [NM_005290] | NM_005290 | ENST00000284311 | 2838 | G protein-coupled receptor 15 | chr3:98251643-98251702 | GO:0007165\|GO:0007186\|NM_005290\|GO:0005886\|GO:0045028\|GO:0005887\|GO:0004930\|GO:0004872 | NM_005290 | THC2479762 | Hs.563128 |
| A_33_P3404336 | | Homo sapiens PREDICTED: hypothetical protein LOC100289105 (LOC100289105), mRNA [XM_002343592] | XM_002343592 | | | | chr17:80214991-80215050 | | XM_002343592 | THC2483688 | Hs.676976 |
| A_33_P3353906 | | | | | | | chr5:178157612-178157671 | | | | |
| A_23_P257478 | CYP21A2 | Homo sapiens cytochrome P450, family 21, subfamily A, polypeptide 2 (CYP21A2), transcript variant 1, mRNA [NM_000500] | NM_000500 | ENST00000547683 | 1589 | cytochrome P450, family 21, subfamily A, polypeptide 2 | chr6:32009191-32009250 | GO:0005792\|GO:0006694\|NM_000500\|GO:0016020\|GO:0005783\|GO:0004509\|GO:0009055\|GO:0005496\|GO:0046872\|GO:0055114\|GO:0020037\|GO:0019898 | NM_000500 | THC2469155 | Hs.654479 |
| A_32_P334325 | RIMBP2 | Homo sapiens RIMS binding protein 2 (RIMBP2), mRNA [NM_015347] | NM_015347 | ENST00000392375 | 23504 | RIMS binding protein 2 | chr12:130921667-130921608 | GO:0030054\|GO:0005886\|NM_015347\|GO:0045202 | NM_015347 | THC2782045 | Hs.657441 |
| A_23_P2705 | LPAR6 | Homo sapiens lysophosphatidic acid receptor 6 (LPAR6), transcript variant 1, mRNA [NM_005767] | NM_005767 | ENST00000345941 | 10161 | lysophosphatidic acid receptor 6 | chr13:48985730-48985671 | GO:0007165\|GO:0007186\|NM_005767\|GO:0005886\|GO:0045028\|GO:0004930\|GO:0004872\|GO:0016021 | NM_005767 | THC2461047 | Hs.123464 |
| A_23_P118633 | SPATA20 | Homo sapiens spermatogenesis associated 20 (SPATA20), mRNA [NM_022827] | NM_022827 | ENST00000512071 | 64847 | spermatogenesis associated 20 | chr17:48632985-48633044 | GO:0005515\|GO:0007275\|NM_022827\|GO:0007283\|GO:0003824\|GO:0030154 | NM_022827 | THC2610588 | Hs.103147 |
| A_24_P19544 | STK39 | Homo sapiens serine threonine kinase 39 (STK39), mRNA [NM_013233] | NM_013233 | ENST00000355999 | 27347 | serine threonine kinase 39 | chr2:168810921-168810862 | GO:0005515\|GO:0006950\|NM_013233\|GO:0005624\|GO:0005634\|GO:0005524\|GO:0016323\|GO:0005737\|GO:0016324\|GO:0000166\|GO:0004702\|GO:0006468\|GO:0005856\|GO:0016740 | NM_013233 | THC2630318 | Hs.276271 |
| A_23_P398854 | DOK7 | Homo sapiens docking protein | NM_173660 | ENST00000515886 | 285489 | docking protein 7 | chr4:3496146-3496205 | GO:0030054\|GO:0005886\|NM_173660\|GO:0005158\|GO:0045202 | NM_173660 | THC2474438 | Hs.122110 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3399181 | | 7 (DOK7), transcript variant 1, mRNA [NM_73660] | | | | | | GO:0019898 | | | |
| A_23_P202496 | NOC3L | *Homo sapiens* nucleolar complex associated 3 homolog (*S. cerevisiae*) (NOC3L), mRNA [NM_022451] | NM_022451 | ENST00000371350 | 64318 | nucleolar complex associated 3 homolog (*S. cerevisiae*) | chr10:9609309-96093038 | GO:0016607|GO:0005730|GO:0045444|GO:0005634 | NM_022451 | THC2463979 | Hs.74899 |
| A_23_P75149 | SFXN4 | *Homo sapiens* sideroflexin 4 (SFXN4), mRNA [NM_213649] | NM_213649 | ENST00000330036 | 119559 | sideroflexin 4 | chr10:120900750-120900691 | GO:0005739|GO:0016020|GO:0005506|GO:0008324|GO:0006826|GO:0016021|GO:0055085|GO:0006812 | NM_213649 | NP1135821 | Hs.655168 |
| A_33_P3382849 | ACR | *Homo sapiens* acrosin (ACR), mRNA [NM_001097] | NM_001097 | ENST00000527761 | 49 | acrosin | chr22:5118322-51183281 | GO:0005515|GO:0043159|GO:0004252|GO:0005507|GO:0005798|GO:0042806|GO:0048545|GO:0007339|GO:0003677|GO:0005537|GO:0009607|GO:0043234|GO:0004040|GO:0007190|GO:0002077|GO:0008144|GO:0006508|GO:0008270|GO:0008233|GO:0007341 | NM_001097 | THC2478327 | Hs.370870 |
| A_33_P3283897 | LOC100130761 | *Homo sapiens* cDNA FLJ38192 fis, clone FCBBF1000270. [AK095511] | AK095511 | | 100130761 | hypothetical LOC100130761 | chr2:16229078-162290846 | | | THC2687374 | Hs.638437 |
| A_33_P3370787 | EPHB2 | *Homo sapiens* EPH receptor B2 (EPHB2), transcript variant 2, mRNA [NM_004442] | NM_004442 | ENST00000374625 | 2048 | EPH receptor B2 | chr1:23240041-23240100 | GO:0031290|GO:0048013|GO:0005102|GO:0021952|GO:0018108|GO:0048593|GO:0005524|GO:0007399|GO:0009902|GO:0005005|GO:0048168|GO:0000166|GO:0016020|GO:0005887|GO:0043025|GO:0009887|GO:0050771|GO:0004872|GO:0007612|GO:0021631|GO:0008046|GO:0016740|GO:0048170 | NM_004442 | THC2642207 | Hs.523329 |
| A_33_P3279353 | AZU1 | *Homo sapiens* azurocidin 1 (AZU1), mRNA [NM_001700] | NM_001700 | ENST00000334630 | 566 | azurocidin 1 | chr19:831799-831858 | GO:0008347|GO:0004252|GO:0042582|GO:0003824|GO:0007205|GO:0045348|GO:0050766|GO:0006954 | NM_001700 | THC2476639 | Hs.72885 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq- Accession | TIGRID | UniGene ID |
|---|---|---|---|---|---|---|---|---|---|---|---|
| A_23_P320739 | MEF2C | Homo sapiens myocyte enhancer factor 2C (MEF2C), transcript variant 1, mRNA [NM_002397] | NM_002397 | ENST00000510942 | 4208 | myocyte enhancer factor 2C | chr5:88016876-88016817 | GO:0006935\|GO:0006508\| GO:0008201\|GO:0001774\| GO:0042535\|GO:0006916\| GO:0005576\|GO:0050725\| GO:0045785\|GO:0050930\| GO:0050829\|GO:0050754\| GO:0042117\|GO:0015643\| GO:0043114\|GO:0045123\| GO:0048246 GO:0045885\|GO:0005515\|NM_002397 GO:0006355\|GO:0003700\| GO:0003702\|GO:0006915\| GO:0010553\|GO:0005634\| GO:0007275\|GO:0010552\| GO:0030154\|GO:0007399\| GO:0043565\|GO:0007517\| GO:0016607 | THC2465936 | Hs.649965 |
| A_24_P391604 | KRTAP6-3 | Homo sapiens keratin associated protein 6-3 (KRTAP6-3), mRNA [NM_181605] | NM_181605 | ENST00000391624 | 337968 | keratin associated protein 6-3 | chr21:31964993-31965052 | GO:0005882 | NM_181605 | NP1462383 | Hs.553691 |
| A_23_P250982 | ISOC1 | Homo sapiens isochorismatase domain containing 1 (ISOC1), mRNA [NM_016048] | NM_016048 | ENST00000173527 | 51015 | isochorismatase domain containing 1 | chr5:128449367-128449426 | GO:0008152\|GO:0003824\|NM_016048 GO:0005777 | | THC2466517 | Hs.483296 |
| A_33_P3260455 | | | | | | | chr1:247497826-247497885 | | | | |
| A_23_P169437 | LCN2 | Homo sapiens lipocalin 2 (LCN2), mRNA [NM_005564] | NM_005564 | ENST00000373017 | 3934 | lipocalin 2 | chr9:130914244-130914303 | GO:0005215\|GO:0005488\|NM_005564 GO:0006810\|GO:0005576 | | NP1247777 | Hs.204238 |
| A_23_P122906 | AUTS2 | Homo sapiens autism susceptibility candidate 2 (AUTS2), transcript variant 1, mRNA [NM_015570] | NM_015570 | ENST00000406775 | 26053 | autism susceptibility candidate 2 | chr7:70257414-70257473 | GO:0008150\|GO:0003674\|NM_015570 GO:0005575 | | NP651821 | Hs.21631 |
| A_33_P3240333 | PITX1 | Homo sapiens paired-like homeodomain 1 (PITX1), mRNA [NM_002653] | NM_002653 | ENST00000265340 | 5307 | paired-like homeo-domain 1 | chr5:134364825-134364766 | GO:0043565\|GO:0035137\|NM_002653 GO:0006355\|GO:0003700\| GO:0051216\|GO:0021983\| GO:0005730\|GO:0007275\| GO:0005634\|GO:0014707\| GO:0009653\|GO:0048625 | | THC2620379 | Hs.84136 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_21_P8021 | SELENBP1 | *Homo sapiens* selenium binding protein 1 (SELENBP1), mRNA [NM_003944] | NM_003944 | ENST00000463664 | 8991 | selenium binding protein 1 | chr1:151336906-151336847 | GO:0008430\|GO:0005737\|NM_003944 GO:0016020\|GO:0005634\| GO:0015031\|GO:0019898\| GO:0005829 | NP1180129 | Hs.632460 |
| A_24_P130792 | NSUN4 | *Homo sapiens* NOP2/Sun domain family, member 4 (NSUN4), mRNA [NM_199044] | NM_199044 | ENST00000475281 | 387338 | NOP2/Sun domain family, member 4 | chr1:46810756-46810815 | GO:0008168\|GO:0016740 NM_199044 | THC2552243 | Hs.163424 |
| A_32_P104746 | ZFYVE28 | *Homo sapiens* zinc finger, FYVE domain containing 28 (ZFYVE28), transcript variant 2, mRNA [NM_020972] | NM_020972 | ENST00000290974 | 57732 | zinc finger, FYVE domain containing 28 | chr4:2271519-2271460 | GO:0005515\|GO:0005737\|NM_020972 GO:0016020\|GO:0031901\| GO:0007175\|GO:0008270\| GO:0032266\|GO:0046872\| GO:0005829\|GO:0005768 | THC2623946 | Hs.292056 |
| A_24_P135628 |  | Uncharacterized protein [Source: UniProtKB/TrEMBL; Acc: A6NF06] [ENST00000335083] | CR599847 | ENST00000335083 |  |  | chr10:4776943-47769492 |  |  | NP1185779 | Hs.463110 |
| A_23_P2129 | TMEM126B | *Homo sapiens* transmembrane protein 126B (TMEM126B), mRNA [NM_018480] | NM_018480 | ENST00000530783 | 55863 | transmembrane protein 126B | chr11:85345243-85345302 | GO:0008150\|GO:0003674\|NM_018480 GO:0016020\|GO:0016021\| GO:0005575 | THC2619491 | Hs.525063 |
| A_33_P3396139 | CTLA4 | *Homo sapiens* cytotoxic T-lymphocyte-associated protein 4 (CTLA4), transcript variant 1, mRNA [NM_005214] | NM_005214 | ENST00000302823 | 1493 | cytotoxic T-lymphocyte-associated protein 4 | chr2:204738564-204738623 | GO:0005515\|GO:0048471\|NM_005214 GO:0045334\|GO:0005794\| GO:0050777\|GO:0016020\| GO:0005887\|GO:0045590\| GO:0009897\|GO:0042130 | THC2476969 | Hs.247824 |
| A_32_P230868 | FAM65A | *Homo sapiens* family with sequence similarity 65, member A (FAM65A), transcript variant 1, mRNA [NM_024519] | NM_024519 | ENST00000422602 | 79567 | family with sequence similarity 65, member A | chr16:67580460-67580519 | GO:0005488 | NM_024519 | THC2468574 | Hs.152717 |
| A_23_P89981 | CYP2F1 | *Homo sapiens* cytochrome P450, family | NM_000774 | ENST00000439903 | 1572 | cytochrome P450, family | chr19:41634185-41634244 | GO:0005792\|GO:0070330\|NM_000774 GO:0005783\|GO:0009055 | NP098390 | Hs.558318 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | family 2, subfamily F, polypeptide 1 (CYP2F1), mRNA [NM_000774] | | | | 2, subfamily F, polypeptide 1 | | GO:0009636\|GO:0018931\|GO:0046872\|GO:0016020\|GO:0019825\|GO:0005789\|GO:0019898\|GO:0020037\|GO:0055114 | | | |
| A_33_P3307363 | LPHN2 | Homo sapiens latrophilin 2 (LPHN2), mRNA [NM_012302] | NM_012302 | ENST00000370728 | 23266 | latrophilin 2 | chr1:82458036-82458095 | GO:0005886\|GO:0007218\|NM_012302\|GO:0004930\|GO:0016524\|GO:0005529\|GO:0016021 | | THC2601192 | Hs.24212 |
| A_24_P286527 | RABL5 | Homo sapiens RAB, member RAS oncogene family-like 5 (RABL5), transcript variant 1, mRNA [NM_022777] | NM_022777 | ENST00000422177 | 64792 | RAB, member RAS oncogene family-like 5 | chr7:100957126-100957067 | GO:0000166\|GO:0005525 NM_022777 | | THC2463773 | Hs.389104 |
| A_23_P254797 | BPIL1 | Homo sapiens bactericidal/permeability-increasing protein-like 1 (BPIL1), mRNA [NM_025227] | NM_025227 | ENST00000170150 | 80341 | bactericidal/per meability-increasing protein-like 1 | chr20:31608368-31609120 | GO:0005576\|GO:0008289 NM_025227 | | THC2474857 | Hs.257045 |
| A_33_P3289466 | | | | | | | chr14:0503609 85-050360926 | | | | |
| A_33_P3297245 | RRAS2 | Homo sapiens related RAS viral (r-ras) oncogene homolog 2 (RRAS2), transcript variant 1, mRNA [NM_012250] | NM_012250 | | 22800 | related RAS viral (r-ras) oncogene homolog 2 | chr11:14299525-14299466 | GO:0005622\|GO:0005515\|NM_012250\|GO:0007165\|GO:0030335\|GO:0005886\|GO:0000166\|GO:0009987\|GO:0005783\|GO:0003924\|GO:0007265\|GO:0005525 | | THC2744937 | Hs.502004 |
| A_33_P3277826 | ZSCAN1 | zinc finger and SCAN domain containing 1 [Source: HGNC Symbol; Acc: 23712] [ENST00000391700] | AY280370 | ENST00000391700 | 284312 | zinc finger and SCAN domain containing 1 | chr19:58549738-58549797 | | | THC2483242 | Hs.643437 |
| A_33_P3265872 | | Q9AHE7_9RHIZ (Q9AHE7) Amide/urea-binding FmdD-like protein, partial (5%) [THC2660495] | | ENST00000419668 | | | chr7:92546426-92546485 | | | THC2660495 | |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq- Accession | TIGRID | UniGene ID |
|---|---|---|---|---|---|---|---|---|---|---|---|
| A_24_P20630 | LEF1 | Homo sapiens lymphoid enhancer-binding factor 1 (LEF1), transcript variant 1, mRNA [NM_016269] | NM_016269 | ENST00000503879 | 51176 | lymphoid enhancer-binding factor 1 | chr4:108968805-108968746 | GO:0005515\|GO:0014070\|GO:0030111\|GO:0003705\|GO:0001756\|GO:0016563\|GO:0005634\|GO:0030879\|GO:0001837\|GO:0030326\|GO:0005737\|GO:0045944\|GO:0060021\|GO:0042475\|GO:0048468\|GO:0007155\|GO:0045449\|GO:0005667\|GO:0021542\|GO:0001822\|GO:0008301\|GO:0005730\|GO:0001890\|GO:0000122\|GO:0045843\|GO:0043565\|GO:0010226\|GO:0003682\|GO:0048341\|GO:0043588 | NM_016269 | THC2603330 | Hs.555947 |
| A_33_P3388865 | LRRC10 | Homo sapiens leucine rich repeat containing 10 (LRRC10), mRNA [NM_201550] | NM_201550 | ENST00000361484 | 376132 | leucine rich repeat containing 10 | chr12:70003844-70003785 | GO:0005739\|GO:0005515\|GO:0005634\|GO:0005856 | NM_201550 | THC2480475 | Hs.448708 |
| A_33_P3346048 | POM121L1P | Homo sapiens POM121 membrane glycoprotein-like 1, pseudogene (POM121L1P), non-coding RNA [NR_024591] | NR_024591 | ENST00000427789 | 25812 | POM121 membrane glycoprotein-like 1, pseudogene | chr22:22986248-22986189 | | NR_024591 | THC2463379 | Hs.546584 |
| A_24_P30194 | IFIT5 | Homo sapiens interferon-induced protein with tetratricopeptide repeats 5 (IFIT5), mRNA [NM_012420] | NM_012420 | ENST00000371795 | 24138 | interferon-induced protein with tetratricopeptide repeats 5 | chr10:91179559-91179618 | GO:0008150\|GO:0005488\|GO:0005575 | NM_012420 | THC2634773 | Hs.252839 |
| A_24_P100190 | NCRNA00315 | PREDICTED: Homo sapiens chromosome 21 open reading frame 93 (C21orf93), misc-RNA [XR_109683] | XR_109683 | ENST00000441947 | 246704 | non-protein coding RNA 315 | chr21:46723274-46723215 | | XR_109683 | THC2485435 | Hs.171428 |
| A_33_P3357964 | | | | | | | chr16:00265238-002652330 | | | | |
| A_21_P140069 | FBXL3 | Homo sapiens F-box and leucine | NM_012158 | ENST00000355619 | 26224 | F-box and leucine | chr13:77579939-77579880 | GO:0005515\|GO:0005737\|GO:0004842\|GO:0016567 | NM_012158 | THC2468176 | Hs.508284 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | leucine-rich repeat protein 3 (FBXL3), mRNA [NM_012158] | | | | rich repeat protein 3 | | GO:0019941\|GOD000151\|GO:0005634 | | | |
| A_23_P21086 | LGI3 | *Homo sapiens* leucine-rich repeat LGI family, member 3 (LGI3), mRNA [NM_139278] | NM_139278 | ENST00000520124 | 203190 | leucine-rich repeat LGI family, member 3 | chr8:22004762-22004703 | GO:0005515\|GO:0005576\|GO:0019717\|GO:0008021 | NM_139278 | NP1467703 | Hs.33470 |
| A_33_P3244347 | PC | *Homo sapiens*, pyruvate carboxylase (PC), nuclear gene encoding mitochondrial protein, transcript variant 3 mRNA [NM_001040716] | NM_001040716 | ENST00000393960 | 5091 | pyruvate carboxylase | chr11:66616157-66616098 | GO:0031406\|GO:0008610\|GO:0030145\|GO:0016874\|GO:0005743\|GO:0006094\|GO:0006107\|GO:0005625\|GO:0005524\|GO:0046872\|GO:0005739\|GO:0005737\|GO:0000166\|GO:0005759\|GO:0008152\|GO:0004736\|GO:0009374 | NM_001040716 | THC2463909 | Hs.89890 |
| A_23_P7862 | HSD17B14 | *Homo sapiens* hydroxysteroid (17-beta) dehydrogenase 14 (HSD17B14), mRNA [NM_016246] | NM_016246 | ENST00000263278 | 51171 | hydroxysteroid (17-beta) dehydrogenase 14 | chr19:4933754-1-49335939 | GO:0006629\|GO:0005515\|GO:0006706\|GO:0005737\|GO:0004303\|GO:0016491\|GO:0047045\|GO:0055114\|GO:0005829 | NM_016246 | THC2620516 | Hs.18788 |
| A_23_P116797 | C12orf10 | *Homo sapiens* chromosome 12 open reading frame 10 (C12orf10), mRNA [NM_021640] | NM_021640 | ENST00000550199 | 60314 | chromosome 12 open reading frame 10 | chr12:5370051-2-53700571 | GO:0005739\|GO:0003674\|NM_021640\|GO:0043473\|GO:0005634\|GO:0005575 | NM_021640 | THC2620574 | Hs.655988 |
| A_24_P117147 | KIR3DL1 | *Homo sapiens* killer cell immunoglobulin-like receptor, three domains, long cytoplasmic tail, 1 (KIR3DL1), mRNA [NM_013289] | NM_013289 | ENST00000400847 | 3811 | killer cell immunoglobulin-like receptor, three domains, long cytoplasmic tail, 1 | chr19:5533331-1-55340821 | GO:0006955\|GO:0005886\|GO:0005887\|GO:0004872\|GO:0030109 | NM_013289 | THC2470697 | Hs.645228 |
| A_33_P3391275 | LOC284749 | *Homo sapiens* hypothetical LOC284749 (LOC284749), non-coding RNA [NR_026958] | NR_026958 | | 284749 | hypothetical LOC284749 | chr20:4699925-5-46999314 | | NR_026958 | THC2619139 | Hs.299080 |
| A_33_P3255716 | LOC285095 | PREDICTED: *Homo sapiens* hypothetical | XM_001722643 | ENST00000401641 | 285095 | hypothetical protein LOC285095 | chr2:24283627-6-242836217 | | XM_001722643 | THC2726347 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P256784 | | protein LOC285095, transcript variant 1 (LOC285095), mRNA [XM_001722643] | | | | | | | | | |
| A_23_P256784 | MUC2 | Homo sapiens mucin 2, oligomeric mucus/gel-forming (MUC2), mRNA [NM_002457] | NM_002457 | ENST00000441003 | 4583 | mucin 2, oligomeric mucus/gel-forming | chr11:1103558-1103831 | GO:0005515 GO:0070703 GO:0070702 GO:0005576 | NM_002457 | THC2461569 | Hs.315 |
| A_33_P3316522 | DEFB124 | Homo sapiens defensin, beta 124 (DEFB124), mRNA [NM_001037500] | NM_001037500 | ENST00000317676 | 245937 | defensin, beta 124 | chr20:30053368-30053309 | GO:0005576 GO:0042742 | NM_001037500 | THC2769744 | Hs.381373 |
| A_23_P416894 | PION | Homo sapiens pigeon homolog (Drosophila) (PION), mRNA [NM_017439] | NM_017439 | ENST00000482866 | 54103 | pigeon homolog (Drosophila) | chr7:76940446-76940387 | | NM_017439 | THC2493049 | Hs.186649 |
| A_33_P3665553 | LOC100233156 | Homo sapiens cDNA FLJ44253 fis, clone TKIDN2009092. [AK126241] | AK126241 | | 100233156 | tektin 4 pseudogene | chrUn_gl000218:60884-60825 | | | THC2508069 | Hs.595418 |
| A_33_P3386770 | | PREDICTED: Homo sapiens putative IQ motif and ankyrin repeat domain-containing protein LOC642574-like (LOC100508128), mRNA [XM_003120088] | XM_003120088 | ENST00000532625 | | | chr8:144872316-144872375 | | XM_003120088 | | Hs.449407 |
| A_24_P417352 | | immunoglobulin heavy constant mu [Source: HGNC Symbol; Acc: 5541] [ENST00000390559] | BX161420 | ENST00000390559 | | | chr14:10632124-106321184 | | | NP1181174 | Hs.510635 |
| A_33_P3308626 | MON1B | Homo sapiens MON1 homolog B (yeast) (MON1B), mRNA [NM_014940] | NM_014940 | ENST00000320859 | 22879 | MON1 homolog B (yeast) | chr16:77229498-77229557 | | NM_014940 | THC2466642 | Hs.513743 |
| A_33_P3225278 | | Homo sapiens, clone IMAGE: 4940607, mRNA. [BC039705] | BC039705 | | | | chr4:730227-730168 | | | | Hs.623860 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P281636 | | *Homo sapiens* unknown mRNA sequence. [AY010113] | AY010113 | ENST00000553821 | | | chr11:89515450-89515509 | | | | Hs.445846 |
| A_33_P3227703 | | | | | | | chr22:0248201 18-024820059 | | | | |
| A_23_P48481 | RAD51B | *Homo sapiens* RAD51 homolog B (*S. cerevisiae*) (RAD51B), transcript variant 2, mRNA [NM_133510] | NM_133510 | ENST00000468382 | 5890 | RAD51 homolog B (S. cerevisiae) | chr14:68878192-68934895 | GO:0017111\|GO:0006281\|NM_133510\|GO:0000166\|GO:0005634\|GO:0005524\|GO:0003677\|GO:0006974\|GO:0008094\|GO:0007131 | THC2753750 | Hs.172587 |
| A_24_P350622 | KIR2DL4 | *Homo sapiens* killer cell immunoglobulin-like receptor, two domains, long cytoplasmic tail, 4 (KIR2DL4), transcript variant 1, mRNA [NM_002255] | NM_002255 | ENST00000400852 | 3805 | killer cell immunoglobulin-like receptor, two domains, long cytoplasmic tail, 4 | chr19:55317688-55320335 | GO:0007165\|GO:0006968\|NM_002255\|GO:0005886\|GO:0005887\|GO:0004888 | NP365687 | Hs.661219 |
| A_33_P3226085 | | *Homo sapiens* immunoglobulin lambda variable 3-10[Source: HGNC Symbol; Acc: 5897] [ENST00000390315] | AF063703 | ENST00000390315 | | | chr22:23154719-23154778 | | | THC2464004 | Hs.449585 |
| A_33_P3312209 | | | | | | | chr5:017498695-017498754 | | | | |
| A_23_P115022 | TMEM125 | *Homo sapiens* transmembrane protein 125 (TMEM125), mRNA [NM_144626] | NM_144626 | ENST00000432792 | 128218 | transmembrane protein 125 | chr1:43739605-43739664 | GO:0008150\|GO:0003674\|NM_144626\|GO:0016020\|GO:0016021\|GO:0005575 | THC2464236 | Hs.104476 |
| A_33_P3323699 | NPPA | natriuretic peptide A [Source: HGNC Symbol; Acc: 79391 [ENST00000376476] | | ENST00000376476 | 4878 | natriuretic peptide A | chr1:11908277-11908218 | | THC2538172 | | |
| A_24_P319923 | MYLK | *Homo sapiens* myosin light chain kinase (MYLK), transcript variant 1, mRNA [NM_053025] | NM_053025 | ENST00000418370 | 4638 | myosin light chain kinase | chr3:123331220-123331161 | GO:0005516\|GO:0000287\|NM_053025\|GO:0000166\|GO:0005509\|GO:0004687\|GO:0006468\|GO:0003779\|GO:0005524\|GO:0016740 | NP500946 | Hs.477375 |
| A_33_P3415820 | THBS1 | *Homo sapiens* thrombospondin 1 mRNA [NM_003246] | NM_003246 | ENST00000397591 | 7057 | thrombospondin 1 | chr15:39874546-39874605 | GO:0010670\|GO:0043499\|NM_003246\|GO:0043032\|GO:0032914 | THC2470159 | Hs.164226 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (THBS1), mRNA [NM_003246] | | | | | | | | | |
| A_33_P3263027 | | Novel protein [Source: UniProtKB/TrEMBL; Acc: Q5JPQ1] [ENST00000370707] | BE266556 | ENST00000370707 | | | | GO:0042802\|GO:0034605\|GO:0010763\|GO:0032026\|GO:0048603\|GO:0005509\|GO:0030169\|GO:0010748\|GO:0043394\|GO:0010751\|GO:0051592\|GO:0043536\|GO:0005178\|GO:0010754\|GO:0043236\|GO:0010759\|GO:0032570\|GO:0010757\|GO:0070051\|GO:0070052\|GO:0043537\|GO:0009897\|GO:0010811\|GO:0002040\|GO:0051895\|GO:0000187\|GO:0006955\|GO:0050921\|GO:0007050\|GO:0031093\|GO:0007155\|GO:0001968\|GO:0008201\|GO:0030511\|GO:0001666\|GO:0050431\|GO:0002605\|GO:0051918\|GO:0006915\|GO:0005577\|GO:0045727\|GO:0006916\|GO:0005576\|GO:0002544\|GO:0043652\|GO:0002581\|GO:0045766\|GO:0009749\|GO:0031012\|GO:0018149\|GO:0001937\|GO:0005198\|GO:0030194\|GO:0032695\|GO:0016525\|GO:0040037\|GO:0042327 | | | Hs.611445 |
| A_33_P3332112 | FAS | Homo sapiens Fas (TNF receptor superfamily, member 6) (FAS), transcript variant 1, mRNA [NM_000043] | NM_000043 | ENST00000540197 | 355 | Fas (TNF receptor superfamily, member 6) | chr10:90774148-90774207 | GO:0008624\|GO:0008633\|GO:0005886\|GO:0031264\|GO:0042981\|GO:0005576\|GO:9005625\|GO:0069916\|GO:0042802\|GO:0005829\|GO:0007165\|GO:0006955\|GO:0006461\|GO:0160211\|GO:0019900\|GO:0004888\|GO:0010940 | NM_000043 | NP1173846 | Hs.244139 |
| A_33_P3554053 | NCRNA00106 | UI-H-EDI-axv-n-20-0-UI.s1 NCI_CGAP_ED1 Homo sapiens cDNA clone | BQ009527 | | 751580 | non-protein coding RNA 106 | chrX:1517725-1517666 | | | | Hs.495569 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3374504 | | IMAGE: 5834323 3', mRNA sequence [BQ009527] | BQ009527 | | | | | | | | |
| A_33_P3313635 | | thioredoxin reductase 2 [Source: HGNC Symbol; Acc: 18155] [ENST00000334363] | BC099923 | ENST00000334363 | | | chr22:19882715-19882656 | | | THC2482873 | Hs.443430 |
| | | 6013445F6F1 NIH_MGC_8 Homo sapiens cDNA clone IMAGE:3677250 5', mRNA sequence [BE561442] | BE561442 | | | | chr16:30194909-30194896 | | | THC2528843 | Hs.569588 |
| A_33_P3275235 | AKT1 | Homo sapiens v-akt murine thymoma viral oncogene homolog 1 (AKT1), transcript variant 1, mRNA [NM_005163] | NM_005163 | ENST00000402615 | | v-akt murine thymoma viral oncogene homolog 1 | chr14:105236034-105235975 | GO:0007242 GO:0009408 GO:0042640 GO:0030307 GO:0034405 GO:0008643 GO:0007281 GO:0042802 GO:0010907 GO:0046889 GO:0030163 GO:0046777 GO:0046329 GO:0008637 GO:0000166 GO:0015758 GO:0018105 GO:0010765 GO:0046326 GO:0005856 GO:0000060 GO:0030334 GO:0045884 GO:0005975 GO:0005547 GO:0005819 GO:0010748 GO:0001890 GO:0030027 GO:0070141 GO:0032270 GO:0045792 GO:0007186 GO:0051000 GO:0030030 GO:0045600 GO:0043491 GO:0005654 GO:0019899 GO:0008286 GO:0016567 GO:0005886 GO:0031999 GO:0032436 GO:0005634 GO:0006924 GO:0032094 GO:0045429 GO:0005829 GO:0032880 GO:0005737 GO:0006954 GO:0040018 GO:0009725 GO:0030235 GO:0008633 GO:0001568 GO:0045725 GO:0043325 GO:0005625 GO:0005524 GO:0006417 GO:0031659 GO:0004674 | NM_005163 | NP1242654 | Hs.525622 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3228271 | CST3 | cystatin C [Source: HGNC Symbol; Acc: 2475] [ENST00000398411] | BX647523 | ENST00000398411 | 1471 | cystatin C | chr20:23608763-23608704 | GO:0048009\|GO:0006469\| GO:0006464\|GO:0016740\| GO:0004869\|GO:0010703\| GO:0010711\|GO:0010466\| GO:0005576\|GO:0006952\| GO:0002020\|GO:0030414\| GO:0005615\|GO:0010716\| GO:0001540\|GO:0034103\| GO:0060313\|GO:0060311\| GO:004 3206 | | THC2521202 | Hs.304682 |
| A_23_P104741 | KIRREL3 | Homo sapiens kin of IRRE like 3 (Drosophila) (KIRREL3), transcript variant 1, mRNA [NM_032531] | NM_032531 | ENST00000525144 | 84623 | kin or IRRE like 3 (Drosophila) | chr11:126293470-126293411 | GO:0030097\|GO:0005515\| GO:0005886\|GO:0005576\| GO:0016021 | NM_032531 | NP1136546 | Hs.376015 |
| A_23_P400515 | KIF17 | Homo sapiens kinesin family member 17 (KIF17), transcript variant 1, mRNA [NM_020816] | NM_020816 | ENST00000247986 | 57576 | kinesin family member 17 | chr1:20990700-20990641 | GO:0005515\|GO:0005871\| GO:0000166\|GO:0031503\| GO:0005874\|GO:0016192\| GO:0015031\|GO:0003777\| GO:0005524\|GO:0007018 | NM_020816 | THC2781237 | Hs.130411 |
| A_33_P3259861 | REREP3 | Homo sapiens arginine-glutamic acid dipeptide (RE) repeats pseudogene 3 (REREP3), non-coding RNA [NR_033735] | NR_033735 | | 646396 | arginine-glutamic acid dipeptide (RE) repeats pseudogene 3 | chr15:22546691-22546750 | | NR_033735 | THC2607431 | Hs.451294 |
| A_33_P3253804 | CEBPD | Homo sapiens CCAAT/enhancer binding protein (C/EBP), delta (CEBPD), mRNA [NM_005195] | NM_005195 | ENST00000542385 | 1052 | CCAAT/ enhancer binding protein (C/EBP), delta | chr8:48649932-48649873 | GO:0043565\|GO:0006355\| GO:0003700\|GO:0006366\| GO:0046983\|GO:0005634 | NM_005195 | THC2568931 | Hs.440829 |
| A_23_P349416 | ERBB3 | Homo sapiens v-erb-b2 erythroblastic leukemia viral oncogene homolog 3 (avian) (ERBB3), transcript variant 1, mRNA [NM_001982] | NM_001982 | ENST00000551242 | 2065 | v-erb-b2 erythroblastic leukemia viral oncogene homolog 3 (avian) | chr12:56496160-56496219 | GO:0005886\|GO:0051048\| GO:0005634\|GO:0007409\| GO:0005615\|GO:0042803\| GO:0007507\|GO:0014037\| GO:0016323\|GO:0043524\| GO:0016324\|GO:0030296\| GO:0000166\|GO:0019838\| GO:0046326\|GO:0045211\| GO:0042127\|GO:0042476\| GO:0009968\|GO:0032869\| GO:0046982\|GO:0060056\| GO:0042493\|GO:0021545 | NM_001982 | NP136988 | Hs.118681 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | | | | | | | GO:0005576\|GO:0014068\| GO:0018108\|GO:0005524\| GO:0016328\|GO:0043235\| GO:0007162\|GO:0005887\| GO:0007519\|GO:0042060\| GO:0007623\|GO:0043586\| GO:0004714\|GO:0007169\| GO:0004716\|GO:0016740\| GO:0004888 | | | |
| A_33_P3313519 | CHRFAM7A | Homo sapiens CHRFAM7A (cholinergic receptor, nicotinic, alpha 7, exons 5-10) and FAM7A (family with sequence similarity 7A, exons A-E) fusion (CHRFAM7A), transcript variant 1, mRNA[NM_139320] | NM_139320 | ENST00000299847 | 89832 | CHRNA7 (cholinergic receptor, nicotinic, alpha 7, exons 5-10) and FAM7A (family with sequence similarity 7A, exons A-E) fusion | chr15:30653354-30653485 | GO:0005230\|GO:0045211\|NM_139320 GO:0016021\|GO:0006811 | | THC2500519 | Hs.510853 |
| A_23_P78152 | MIS12 | Homo sapiens MIS12, MIND kinetochore complex component, homolog (S. pombe) (MIS12), mRNA [NM_024039] | NM_024039 | ENST00000381165 | 79003 | MIS12, MIND kinetochore complex component, homolog (S. pombe) | chr17:5393710-5393769 | GO:0005515\|GO:0007067\|NM_024039 GO:0007049\|GO:0051382\| GO:0007059\|GO:0005634\| GO:0000444\|GO:0000775\| GO:0051301 | | THC2462610 | Hs.267194 |
| A_24_P288915 | | Homo sapiens coiled-coil domain containing 144B (CCDC144B), non-coding RNA [Source: RefSeq DNA; Acc: NR_036647] [ENST00000445752] | AK093811 | ENST00000445752 | | | chr17:1850695-18506895 | | | THC2483620 | Hs.721149 |
| A_23_P337033 | GMEB2 | Homo sapiens glucocorticoid modulatory element binding protein 2 (GMEB2), mRNA [NM_012384] | NM_012384 | ENST00000266068 | 26205 | glucocorticoid modulatory element binding protein 2 | chr20:6221954-62219487 | GO:0005737\|GO:0006366\|NM_012384 GO:0005488\|GO:0003702\| GO:0008270\|GO:0005634\| GO:0003677\|GO:0046872\| GO:0045449 | | THC2463374 | Hs.473286 |
| A_33_P3250750 | | Synthetic construct Homo sapiens gateway clone IMAGE: 100018551 3' read RAB35 mRNA. [CU677518] | CU677518 | | | | chr12:1205350-66-120535125 | | | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3296067 | CDC14C | Homo sapiens CDC14 cell division cycle 14 homolog C (S. cerevisiae) (CDC14C), non-coding RNA [NR_003595] | NR_003595 | | 168448 | CDC14 cell division cycle 14 homolog C (S. cerevisiae) | chr7:48886139-48886081 | GO:0006470\|GO:0016787\|GO:0016020\|GO:0005730\|GO:0005634\|GO:0016021\|GO:0008138\|GO:0004725 | NR_003595 | | Hs.567757 |
| A_33_P3218564 | | | | | | | chr14:0196254 95-019625436 | | | | |
| A_23_P171336 | NXF3 | Homo sapiens nuclear RNA export factor 3 (NXF3), mRNA [NM_022052] | NM_022052 | ENST00000497850 | 56000 | nuclear RNA export factor 3 | chrX:10233085 3-102330794 | GO:0005622\|GO:0005515\|GO:0005737\|GO:0000166\|GO:0016973\|GO:0006810\|GO:0042272\|GO:0005634\|GO:0003729 | NM_022052 | THC2635545 | Hs.60386 |
| A_23_P1833 | B3GAT1 | Homo sapiens beta-1,3-glucuronyl-transferase 1 (glucuronosyltransferase P) (B3GAT1), transcript variant 2, mRNA [NM_054025] | NM_054025 | ENST00000312527 | 27087 | beta-1,3-glucuronyl-transferase 1 (glucuronosyl-transferase P) | chr11:1342487 53-134248694 | GO:0015018\|GO:0030145\|GO:0005794\|GO:0016020\|GO:0008499\|GO:0005975\|GO:0016021\|GO:0046872\|GO:0016740 | NM_054025 | THC2470938 | Hs.381050 |
| A_23_P41365 | SMR3A | Homo sapiens submaxillary gland androgen regulated protein 3A (SMR3A), mRNA [NM_012390] | NM_012390 | ENST00000226460 | 26952 | submaxillary gland androgen regulated protein 3A | chr4:71232551-71232610 | GO:0005576 | NM_012390 | THC2508570 | Hs.701334 |
| A_33_P3280950 | LOC144571 | Homo sapiens hypothetical LOC144571 (LOC144571), non-coding RNA [NR_026971] | NR_026971 | ENST00000369603 | 144571 | hypothetical LOC144571 | chr12:9220592-9220651 | | NR_026971 | THC2505447 | Hs.592432 |
| A_33_P3274618 | LOC731275 | Homo sapiens hypothetical LOC731275 (LOC731275), non-coding RNA [NR_029401] | NR_029401 | ENST00000427210 | 731275 | hypothetical LOC731275 | chr1:24324540 8-243245349 | | NR_029401 | THC2508557 | Hs.722350 |
| A_23_P127233 | SMNDC1 | Homo sapiens survival motor neuron domain containing 1 (SMNDC1), mRNA [NM_005871] | NM_005871 | ENST00000369603 | 10285 | survival motor neuron domain containing 1 | chr10:1120529 32-112052873 | GO:0008380\|GO:0006397\|GO:0005515\|GO:0000245\|GO:0005737\|GO:0015030\|GO:0016607\|GO:0003723\|GO:0006915\|GO:0005681\|GO:0005634\|GO:0006917 | NM_005871 | THC2461341 | Hs.62093 |
| A_24_P76300 | | zinc finger protein 154 [Source: | AB095924 | ENST00000317656 | | | chr19:5820918 7-58209128 | | | THC2476043 | Hs.649031 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P104617 | GYLTL1B | HGNC Symbol; Acc: 12939] [ENST00000512439] Homo sapiens glycosyltransferase-like 1B (GYLTL1B), mRNA [NM_152312] | NM_152312 | ENST00000530437 | 120071 | glycosyl-transferase-like 1B | chr11:45950427-45950486 | GO:0005794|GO:0016020|NM_152312 GO:0016757|GO:0016021| GO:0046716 | NM_152312 | THC2479774 | Hs.86543 |
| A_33_P3303772 | SLC6A3 | Homo sapiens solute carrier family 6 (neuro-transmitter transporter, dopamine), member 3 (SLC6A3), mRNA [NM_001044] | NM_001044 | ENST00000270349 | 6531 | solute carrier family 6 (neurotrans-mitter trans-porter, do-pamine), member 3 | chr5:1393704-1393645 | GO:0021984|GO:0007608|NM_001044 GO:0005886|GO:0045471| GO:0042220|GO:0051591| GO:0042403|GO:0042053| GO:0042416|GO:0005737| GO:0008144|GO:0010039| GO:0006836|GO:0007626| GO:0040018|GO:0019717| GO:0015293|GO:0005330| GO:0060134|GO:0015872| GO:0042493|GO:0007568| GO:0035240|GO:0007595| GO:0003887|GO:0042420| GO:0015844|GO:0035094 | NM_001044 | NP107244 | Hs.406 |
| A_23_P501933 | CACNG6 | Homo sapiens, calcium channel, voltage-dependent, gamma subunit 6 (CACNG6) transcript variant 1, mRNA [NM_145814] | NM_145814 | ENST00000352529 | 59285 | calcium chan-nel, voltage-dependent, gamma subunit 6 | chr19:5451579-5-54515854 | GO:0005244|GO:0016020|NM_145814 GO:0005245|GO:0005509| GO:0006816|GO:0016021| GO:0005891|GO:0006811 | NM_145814 | NP520196 | Hs.631560 |
| A_33_P3244361 | | | | | | | chrX:073436828-073436887 | | | | |
| A_33_P3369844 | CD24 | Homo sapiens CD24 molecule (CD24), mRNA [NM_013230] | NM_013230 | | 100133941 | CD24 molecule | chrY:211152726-211152667 | GO:0005515|GO:0043627|NM_013230 GO:0043499|GO:0030262| GO:0006800|GO:0050731| GO:0031528|GO:0031225| GO:0031362|GO:0032597| GO:0007406|GO:0031175| GO:0032913|GO:0008637| GO:0030296|GO:0002904| GO:0032600|GO:0046641| GO:0002329|GO:0002842| GO:0016055|GO:0034119| GO:0042632|GO:0019901| GO:0002523|GO:0030889| GO:0048488|GO:0007274| GO:0001959|GO:0002768| GO:0045121|GO:0009897| GO:0045730|GO:0045577 | NM_013230 | THC2546089 | Hs.644105 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3281478 | | | | | | | | GO:0008624\|GO:0060170\|GO:0005886\|GO:0002863\|GO:0031295\|GO:0002237\|GO:0033625\|GO:0007204\|GO:0050850\|GO:0042103\|GO:0042104\|GO:0006955\|GO:0030856\|GO:0043406\|GO:0043408\|GO:0007159\|GO:0046014\|GO:0004871\|GO:0007157\|GO:0001775\|GO:0001666\|GO:0005624\|GO:0042325\|GO:0034107\|GO:0033634\|GO:0034109\|GO:0045665\|GO:0016477\|GO:0030246\|GO:0008629 | | | |
| A_23_P153616 | MADCAM1 | *Homo sapiens* mucosal vascular addressin cell adhesion molecule 1 (MADCAM1), transcript variant 1, mRNA [NM_130760] | NM_130760 | ENST00000215637 | 8174 | mucosal vascular addressin cell adhesion molecule 1 | chr15:0308734 72-030873413 chr19:505192-505251 | GO:0005515\|GO:0007165\|GO:0005886\|GO:0006955\|GO:0005624\|GO:0030216\|GO:0016021\|GO:0007155 | NM_130760 | THC2621878 | Hs.102598 |
| A_33_P3354203 | NELL1 | NEL-like 1 (chicken) [Source: HGNC Symbol; Acc: 7750] [ENST00000534263] | AB085898 | ENST00000534263 | 4745 | NEL-like 1 (chicken) | chr11:2130560 0-21305659 | | | THC2486544 | Hs.657172 |
| A_33_P3240078 A_23_P502047 | CHRD | *Homo sapiens* chordin (CHRD), mRNA[NM_003741] | NM_003741 | ENST00000545352 | 8646 | chordin | chr3:18410749 3-184107552 | GO:0007389\|GO:0030336\|GO:0001707\|GO:0033504\|GO:0021919\|GO:0005576\|GO:0009953\|GO:0007417\|GO:0005615\|GO:0001702\|GO:0045785\|GO:0030514\|GO:0001501\|GO:0045668\|GO:0019955\|GO:0030900\|GO:0045545\|GO:0008201 | NM_003741 | NP1473743 | Hs.166186 |
| A_23_P51761 | OR6K2 | *Homo sapiens* olfactory receptor, family 6, subfamily K, member 2 (OR6K2), mRNA [NM_001005279] | NM_001005279 | ENST00000359610 | 81448 | olfactory receptor, family 6, subfamily K, member 2 | chr1:15866994 5-158669886 | GO:0007608\|GO:0007165\|NM_001005279\|GO:0004984\|GO:0007186\|GO:0005886\|GO:0004872\|GO:0016021\|GO:0050896 | | NP1461786 | Hs.554489 |
| A_33_P3363560 | TMEM51 | *Homo sapiens* transmembrane protein 51 | NM_001136216 | ENST00000376014 | 55092 | transmembrane protein 51 | chr1:15546776-15546835 | GO:0016020\|GO:0016021 | NM_001136216 | THC2478353 | Hs.465305 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3335920 | | protein 51 (TMEM51), transcript variant 1, mRNA [NM_001136216] | | | | | | | | | |
| | SYNE1 | Homo sapiens spectrin repeat containing, nuclear envelope 1 (SYNE1), transcript variant 1, mRNA [NM_182961] | NM_182961 | ENST00000367255 | 23345 | spectrin repeat containing, nuclear envelope 1 | chr6:152443528 7-152443528 | GO:0008219|GO:0006997|GO:0003779| GO:0005794|GO:0003779| GO:0005634|GO:0005635| GO:0030017|GO:0042692| GO:0005737|GO:0045211| GO:0007030|GO:0016021| GO:0005856|GO:0005521 | NP1154489 | Hs.12967 |
| A_23_P120902 | LGALS2 | Homo sapiens lectin, galactoside-binding, soluble, 2 (LGALS2), mRNA [NM_006498] | NM_006498 | ENST00000215886 | 3957 | lectin, galactoside-binding, soluble, 2 | chr22:37966322 9-37966270 | GO:0005529|GO:0016936|NM_006498 | THC2474966 | Hs.531776 |
| A_23_P107454 | KRTAP3-1 | Homo sapiens keratin associated protein 3-1 (KRTAP3-1), mRNA [NM_031958] | NM_031958 | ENST00000391588 | 83896 | keratin associated protein 3-1 | chr17:3916490 2-39164843 | GO:0005198|GO:0045095 NM_031958 | THC2488283 | Hs.307027 |
| A_33_P3310706 | | DB043695 TESTI2 Homo sapiens cDNA clone TESTI2031475 5', mRNA sequence [DB043695] | DB043695 | | | | chr10:1232863 85-123286444 | | | | Hs.576915 |
| A_23_P130435 | LIM2 | Homo sapiens lens intrinsic membrane protein 2, 19 kDa (LIM2), transcript variant 1, mRNA [NM_030657] | NM_030657 | ENST00000221973 | 3982 | lens intrinsic membrane protein 2, 19 kDa | chr19:5188338 7-51883328 | GO:0005212|GO:0030054|NM_030657| GO:0016020|GO:0007043| GO:0016021 | THC2481842 | Hs.162754 |
| A_23_P119593 | EPHX3 | Homo sapiens epoxide hydrolase 3 (EPHX3), transcript variant 1, mRNA [NM_024794] | NM_024794 | ENST00000435261 | 79852 | epoxide hydrolase 3 | chr19:1533787 0-15337811 | GO:0008150|GO:0016787|NM_024794| GO:0005575 | THC2653397 | Hs.156457 |
| A_32_P42574 | C1orf198 | Homo sapiens chromosome 1 open reading frame 198 (C1orf198), transcript variant 1, mRNA [NM_032800] | NM_032800 | ENST00000366663 | 84886 | chromosome 1 open reading frame 198 | chr1:23097300 4-230972945 | | NM_032800 | THC2468585 | Hs.520494 |
| A_23_P23947 | MAP3K8 | Homo sapiens mitogen-activated protein kinase kinase 8 (MAP3K8), mRNA [NM_005204] | NM_005204 | ENST00000263056 | 1326 | mitogen-activated protein kinase kinase 8 | chr10:3074998 0-30750039 | GO:0005515|GO:0007165|NM_005204| GO:0007049|GO:0005737| GO:0000287|GO:0000166| GO:0004674|GO:0006468 | THC2465022 | Hs.432453 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P339954 | | (MAP3K8), mRNA [NM_005204] Nuclear pore complex-interacting protein-like 2 [Source: UniProtKB/Swiss-Prot; Acc: A6NHN6] [ENST00000355290] | XM_003118719 | ENST00000355290 | | | chr16:28669494-28669553 | GO:0005524\|GO:0004709\|GO:0016740\|GO:0005829 | XM_003118719 | THC2516834 | Hs.710214 |
| A_23_P211355 | DGCR8 | Homo sapiens DiGeorge syndrome critical region gene 8 (DGCR8), transcript variant 1, mRNA [NM_022720] | NM_022720 | ENST00000351989 | 54487 | DiGeorge syndrome critical region gene 8 | chr22:20098916-20098975 | GO:0005622\|GO:0005515\|GO:0003725\|GO:0005737\|GO:0031053\|GO:0005730\|GO:0005634 | NM_022720 | THC2741608 | Hs.643452 |
| A_24_P60845 | ACHE | Homo sapiens acetylcholinesterase (ACHE), transcript variant E4-E6, mRNA [NM_000665] | NM_000665 | ENST00000422451 | 43 | acetyl-cholinesterase | chr7:100490066-100490007 | GO:0048471\|GO:0003990\|GO:0030054\|GO:0005886\|GO:0008283\|GO:0004104\|GO:0005518\|GO:0050714\|GO:0045202\|GO:0005634\|GO:0031225\|GO:0042803\|GO:0001540\|GO:0042166\|GO:0017171\|GO:0007155\|GO:0005794\|GO:0005605\|GO:0009611\|GO:0005576\|GO:0042982\|GO:0007416\|GO:0006260\|GO:0007517\|GO:0032223\|GO:0002076\|GO:0043237\|GO:0001507\|GO:0019898 | NM_000665 | THC2604591 | Hs.154495 |
| A_33_P3388527 | | | | | | | chr17:07936753 8-079367597 | | | | |
| A_33_P3322428 | MARK4 | Homo sapiens MAP/microtubule affinity-regulating kinase 4 (MARK4), transcript variant 1, mRNA [NM_001199867] | NM_001199867 | ENST00000262893 | 57787 | MAP/microtubule affinity-regulating kinase 4 | chr19:45783668-45783727 | GO:0005515\|GO:0008017\|GO:0043130\|GO:0043005\|GO:0005813\|GO:0043015\|GO:0001578\|GO:0050321\|GO:0005524\|GO:0007399\|GO:0043068\|GO:0000166\|GO:0004674\|GO:0006468\|GO:0016740 | NM_001199867 | NP105710 | Hs.34314 |
| A_33_P3284152 | LOC285191 | Homo sapiens cDNA FLJ39618 fis, clone SMINT2000824. [AK096937] | AK096937 | ENST00000407635 | 285191 | hypothetical protein LOC285191 | chr2:241628480-241628539 | | | THC2622724 | Hs.729906 |
| A_33_P3233981 | NASP | Homo sapiens nuclear autoantigenic sperm protein | NM_002482 | ENST00000481782 | 4678 | nuclear autoantigenic sperm protein | chr1:46083827-46083886 | GO:0006260\|GO:0005515\|GO:0007049\|GO:0005737\|GO:0043486\|GO:0008283 | NM_002482 | THC2496068 | Hs.319334 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3283906 | NIP7 | (histone-binding) (NASP), transcript variant 2, mRNA [NM_002482] Homo sapiens nuclear import 7 homolog (S. cerevisiae) (NIP7), transcript variant 1, mRNA [NM_016101] | NM_016101 | ENST00000254941 | 51388 | (histone-binding) nuclear import 7 homolog (S. cerevisiae) | chr16:69376816-69376875 | GO:0001824|GO:0051879| GO:0005634|GO:0015031 GO:0005515|GO:0042255|NM_016101| GO:0003723|GO:0005730| GO:0005634 | THC2482970 | Hs.730815 |
| A_24_P258235 | OR5L2 | Homo sapiens olfactory receptor, family 5, subfamily L, member 2 (OR5L2), mRNA [NM_001004739] | NM_001004739 | ENST00000378397 | 26338 | olfactory receptor, family 5, subfamily L, member 2 | chr11:55595193-55595252 | GO:0007608|GO:0007165|NM_001004739| GO:0004984|GO:0007186| GO:0005886|GO:0004872| GO:0016021|GO:0050896 | THC2604332 | Hs.528356 |
| A_33_P3218491 | LONRF3 | Homo sapiens LON peptidase N-terminal domain and ring finger 3 (LONRF3), transcript variant 1, mRNA [NM_001031855] | NM_001031855 | ENST00000371628 | 79836 | LON peptidase N-terminal domain and ring finger 3 | chr19:045997517-045997576 chrX:118151680-118151739 | GO:0005515|GO:0004176|NM_001031855| GO:0006508|GO:0008270| GO:0046872 | THC2485491 | Hs.144266 |
| A_24_P945096 | CACNA1I | Homo sapiens calcium channel, voltage-dependent, T type, alpha 1I subunit (CACNA1I), transcript variant 1, mRNA [NM_021096] | NM_021096 | ENST00000336649 | 8911 | calcium channel, voltage-dependent, T type, alpha 1I subunit | chr22:40085423-40085482 | GO:0005515|GO:0007165|NM_021096| GO:0005244|GO:0016020| GO:0008332|GO:0005509| GO:0006816|GO:0016021| GO:0055085|GO:0005891| GO:0006811 | THC2600930 | Hs.125116 |
| A_33_P3296687 | KRT33A | Homo sapiens keratin 33A (KRT33A), mRNA [NM_004138] | NM_004138 | ENST00000007735 | 3883 | keratin 33A | chr17:39502430-39502371 | GO:0005882|GO:0005515|NM_004138| GO:0005198 | THC2620435 | Hs.512579 |
| A_23_P24135 | TACR2 | Homo sapiens tachykinin receptor 2 (TACR2), mRNA [NM_001057] | NM_001057 | ENST00000373306 | 6865 | tachykinin receptor 2 | chr10:71164785-71164726 | GO:0004995|GO:0007588|NM_001057| GO:0007165|GO:0006936| GO:0005886|GO:0005887| GO:0004930|GO:0007217 | | Hs.88372 |
| A_23_P143526 | S100B | Homo sapiens S100 calcium binding protein B (S100B), mRNA [NM_006272] | NM_006272 | ENST00000291700 | 6285 | S100 calcium binding protein B | chr21:48019158-48019099 | GO:0008283|GO:0005509|NM_006272| GO:0048156|GO:0005634| GO:0007409|GO:0007417| GO:0001726|GO:0042803| GO:0048154|GO:0005737 | THC2605292 | Hs.422181 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3366667 | EYA1 | Homo sapiens eyes absent homolog 1 (Drosophila) (EYA1), transcript variant 3, mRNA [NM_000503] | NM_000503 | ENST00000388740 | 2138 | eyes absent homolog 1 (Drosophila) | chr8:72110532-72110473 | GO:0007611\|GO:0008270\|GO:0048306 GO:0005515\|GO:0021984\|GO:0007389\|GO:0001657\|GO:0001658\|GO:0007605\|GO:0048704\|GO:0005634\|GO:0045739\|GO:0006302\|GO:0005737\|GO:0010212\|GO:0009887\|GO:0042474\|GO:0042473\|GO:0004725\|GO:0045449\|GO:0043066\|GO:0000287\|GO:0016576\|GO:0042472\|GO:0006974\|GO:0045165\|GO:0016787\|GO:0008152\|GO:0045664\|GO:0016568 | NM_000503 | THC2472858 | Hs.491997 |
| A_23_P27215 | UBB | Homo sapiens ubiquitin B (UBB), mRNA [NM_018955] | NM_018955 | ENST00000302182 | 7314 | ubiquitin B | chr17:16285505-16285564 | GO:0005515\|GO:0008624\|GO:0016567\|GO:0051437\|GO:0006915\|GO:0005634\|GO:0006916\|GO:0051436\|GO:0030433\|GO:0031145\|GO:0005829\|GO:0042062\|GO:0005737\|GO:0007049\|GO:0045941\|GO:0048167\|GO:0007411\|GO:0022627\|GO:0030528\|GO:0005654 | NM_018955 | THC2583951 | Hs.730603 |
| A_23_P215331 | CRHR2 | Homo sapiens corticotropin releasing hormone receptor 2 (CRHR2), transcript variant 1, mRNA[NM_001883] | NM_001883 | ENST00000506074 | 1395 | corticotropin releasing hormone receptor 2 | chr7:30695225-30694667 | GO:0005515\|GO:0015056\|GO:0007186\|GO:0005886\|GO:0005887\|GO:0007188 | NM_001883 | THC2485141 | Hs.546246 |
| A_24_P28550 | TUBB1 | Homo sapiens tubulin, beta 1 (TUBB1), mRNA [NM_030773] | NM_030773 | ENST00000217133 | 81027 | tubulin, beta 1 | chr20:57601244-57601303 | GO:0051258\|GO:0000166\|GO:0005874\|GO:0005200\|GO:0003924\|GO:0005525\|GO:0051225\|GO:0007018 | NM_030773 | THC2472803 | Hs.303023 |
| A_33_P3250253 | LOC100131150 | Homo sapiens cDNA FLJ38875 fis, clone MESAN2013936. [AK096194] | AK096194 | | 100131150 | hypothetical protein LOC100131150 | chr11:67008076-67008135 | | | THC2480126 | Hs.124147 |
| A_33_P3417880 | NKAPL | Homo sapiens NFKB activating protein-like (NKAPL), mRNA [NM_001007531] | NM_001007531 | ENST00000343684 | 222698 | NFKB activating protein-like | chr6:28228606-28228665 | | NM_001007531 | THC2472731 | Hs.239181 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P404033 | C15orf38 | Homo sapiens chromosome 15 open reading frame 38 (C15orf38), mRNA [NM_182616] | NM_182616 | ENST00000460685 | 348110 | chromosome 15 open reading frame 38 | chr15:90444899-90444840 | | NM_182616 | THC2490900 | Hs.728822 |
| A_24_P24053 | | Homo sapiens immunoglobulin heavy variable 3-66 [Source: HGNC Symbol; Acc: 5619] [ENST00000390632] | JF810271 | ENST00000390632 | | | chr14:107131181-107131122 | | | NP1166771 | Hs.705292 |
| A_33_P3230264 | GPC3 | Homo sapiens glypican 3 (GPC3), transcript variant 1, mRNA [NM_001164617] | NM_001164617 | ENST00000394299 | 2719 | glypican 3 | chrX:132669886-132669827 | GO:0030513|GO:0001658|GO:0008285|GO:0005886|GO:0005887|GO:0005578|GO:0009887|GO:0043395|GO:0005576|GO:0031225|GO:0005615|GO:0045926 | NM_001164617 | THC2583194 | Hs.644108 |
| A_33_P3221019 | ZAN | Homo sapiens zonadhesin (ZAN), transcript variant 6, mRNA [NM_173059] | NM_173059 | ENST0000546213 | 7455 | zonadhesin | chr7:100352964-100353023 | GO:0005515|GO:0016337|GO:0005886|GO:0016021|GO:0007339 | NM_173059 | NP104330 | Hs.307004 |
| A_23_P83094 | TLE4 | Homo sapiens transducin-like enhancer of split 4 (E(sp1) homolog, Drosophila) (TLE4), mRNA [NM_007005] | NM_007005 | ENST00000376520 | 7091 | transducin-like enhancer of split 4 (E(sp1) homolog, Drosophila) | chr9:82341057-82341116 | GO:0008150|GO:0003674|GO:0007005|GO:0005634|GO:0016055|GO:0045449 | NM_007005 | THC2471161 | Hs.444213 |
| A_33_P3394769 | TMEM8C | Homo sapiens transmembrane protein 8C (TMEM8C), mRNA [NM_001080483] | NM_001080483 | ENST00000339996 | 389827 | transmembrane protein 8C | chr9:136379767-136379708 | GO:0016020|GO:0016021 | NM_001080483 | THC2645713 | Hs.512467 |
| A_23_P122007 | C5orf30 | Homo sapiens chromosome 5 open reading frame 30 (C5orf30), mRNA [NM_033211] | NM_033211 | ENST00000510890 | 90355 | chromosome 5 open reading frame 30 | chr5:102613812-102613871 | | NM_033211 | THC2461293 | Hs.482976 |
| A_33_P3231428 | | Homo sapiens cDNA FLJ44760 fis, clone BRACE3031579. [AK126714] | AK126714 | | | | chr20:20445946-20445887 | | | THC2480753 | Hs.677538 |
| A_24_P175176 | PHTF2 | Homo sapiens putative homeo-domain transcription factor 2 (PHTF2), transcript variant 2, mRNA [NM_020432] | NM_020432 | ENST00000248550 | 57157 | putative homeodomain transcription factor 2 | chr7:77586179-77586238 | GO:0005783|GO:0005634|NM_020432|GO:0003677|GO:0045449 | | THC2483055 | Hs.203965 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P109069 | SYT15 | Homo sapiens synaptotagmin XV (SYT15), transcript variant b, mRNA [NM_181519] | NM_181519 | ENST00000503753 | 83849 | synaptotagmin XV | chr10:46963983-46963924 | GO:0005886\|GO:0016021 | NM_181519 | THC2602435 | Hs.696346 |
| A_23_P167856 | TMEM63B | Homo sapiens transmembrane protein 63B (TMEM63B), mRNA [NM_018426] | NM_018426 | ENST00000323267 | 55362 | transmembrane protein 63B | chr6:44122880044122939 | GO:0016020\|GO:0016021 | NM_018426 | THC2462238 | Hs.414473 |
| A_33_P3221528 | IREB2 | Homo sapiens iron-responsive element binding protein 2 (IREB2), mRNA [NM_004136] | NM_004136 | ENST00000258886 | 3658 | iron-responsive element binding protein 2 | chr15:78793507-78793566 | GO:0010468\|GO:0051539\|NM_004136 GO:0005506\|GO:0003723\| GO:0034101\|GO:0006782\| GO:0009791\|GO:0006417\| GO:0046872\|GO:0005829\| GO:0006879\|GO:0050892\| GO:0005737\|GO:0008152\| GO:0030350 | | THC2534298 | Hs.436031 |
| A_33_P3306452 | | COBW domain containing 5 [Source: HGNC Symbol; Acc: 24584] [ENST00000465474] | XR_114261 | ENST00000465474 | | | chr9:70434183-70434124 | | XR_114261 | THC2536071 | Hs.635227 |
| A_33_P3339915 | REXO1L1 | Homo sapiens REX1, RNA exonuclease 1 homolog (S. cerevisiae)-like 1 (REXO1L1), mRNA [NM_172239] | NM_172239 | ENST00000425429 | 254958 | REX1, RNA exonuclease 1 homolog (S. cerevisiae)-like 1 | chr8:86788048-86787989 | GO:0005622\|GO:0005737\|NM_172239 GO:0004527\|GO:0016787\| GO:0005634\|GO:0003676 | | THC2603070 | Hs.373854 |
| A_33_P3326817 | | | | | | | chr2:038830256-038830315 | | | | |
| A_23_P143774 | MOV10L1 | Homo sapiens Mov10l1, Moloney leukemia virus 10-like 1, homolog (mouse) (MOV10L1), transcript variant 1, mRNA [NM_018995] | NM_018995 | ENST00000545383 | 54456 | Mov10l1, Moloney leukemia virus 10-like 1, homolog (mouse) | chr22:50599418-50599477 | GO:0000287\|GO:0008283\|NM_018995 GO:0003723\|GO:0004386\| GO:0007275\|GO:0007283\| GO:0045786\|GO:0005524\| GO:0007281\|GO:0004004\| GO:0005622\|GO:0016787\| GO:0000166\|GO:0016787 | | THC2473678 | Hs.62880 |
| A_33_P3263284 | LOC100130238 | Homo sapiens hypothetical LOC100130238 (LOC100130238), non-coding RNA [NR_024563] | NR_024563 | | 100130238 | hypothetical LOC100130238 | chr12:132857426-132857485 | | NR_024563 | THC2629253 | |
| A_23_P140170 | SEC23A | Homo sapiens Sec23 homolog A | NM_006364 | ENST00000307712 | 10484 | Sec23 homolog A (S. | chr14:39501728-39501669 | GO:0005515\|GO:0048471\|NM_006364 GO:0005794\|GO:0030127 | | THC2508310 | Hs.272927 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (S. cerevisiae) (SEC23A), mRNA [NM_006364] | | | | cerevisiae) | | GO:0005783\|GO:0006886\| GO:0005829\|GO:0006888\| GO:0000139\|GO:0016020\| GO:0008270\|GO:0016192\| GO:0016044\|GO:0019898 | | | |
| A_33_P3364741 | MRC2 | Homo sapiens mannose receptor, C type 2 (MRC2), mRNA [NM_006039] | NM_006039 | ENST00000303375 | 9902 | mannose receptor, C type 2 | chr17:60770 82 7-60770886 | GO:0016020\|GO:0005488\|NM_006039 GO:0005509\|GO:0005529\| GO:0004872\|GO:0016021\| GO:0006897 | | THC2608201 | Hs.7835 |
| A_33_P3499692 | LOC645261 | Homo sapiens PP565 mRNA, complete cds. [AF258587] | AF258587 | | 645261 | PP565 | chr5:86344779-86344720 | | | NP1472476 | |
| A_33_P3359748 | SARS | Homo sapiens seryl-tRNA synthetase (SARS), transcript variant 3, non-coding RNA [NR_034073] | NR_034073 | ENST00000369923 | 6301 | seryl-tRNA synthetase | chr1:10977943 2-109779491 | | NR_034073 | THC2493814 | Hs.531176 |
| A_23_P110473 | NAIP | Homo sapiens NLR family, apoptosis inhibitory protein (NAIP), transcript variant 1, mRNA [NM_004536] | NM_004536 | ENST00000517649 | 4671 | NLR family, apoptosis inhibitory protein | chr5:70264650-70264591 | GO:0005622\|GO:0017111\|NM_004536 GO:0001166\|GO:0006915\| GO:0008270\|GO:0006916\| GO:0046872\|GO:0007399 | | THC2464586 | Hs.654500 |
| A_24_P56689 | ZNF205 | Homo sapiens zinc finger protein 205 (ZNF205), transcript variant 1, mRNA [NM_003456] | NM_003456 | ENST00000219091 | 7755 | zinc finger protein 205 | chr16:3169835-3169894 | GO:0005622\|GO:0005515\|NM_003456 GO:0006355\|GO:0008270\| GO:0005634\|GO:0003677\| GO:0046872 | | THC2470721 | Hs.592088 |
| A_33_P3216869 | CRABP1 | Homo sapiens cellular retinoic acid binding protein 1 (CRABP1), mRNA [NM_004378] | NM_004378 | ENST00000299529 | 1381 | cellular retinoic acid binding protein 1 | chr15:7864036 1-78640420 | GO:0007165\|GO:0005215\|NM_004378 GO:0005737\|GO:0016918\| GO:0006810\|GO:0007275\| GO:0019841\|GO:0008289 | | THC2464817 | Hs.346950 |
| A_23_P130653 | RTBDN | Homo sapiens retbindin (RTBDN), transcript variant 2, mRNA [NM_031429] | NM_031429 | ENST00000322912 | 83546 | retbindin | chr19:1293635 7-12936298 | GO:0005576 | NM_031429 | THC2482585 | Hs.21162 |
| A_32_P393316 | RAPGEF3 | Homo sapiens Rap guanine nucleotide exchange factor (GEF) 3 (RAPGEF3), transcript variant 1, mRNA [NM_001098531] | NM_001098531 | ENST00000405493 | 10411 | Rap guanine nucleotide exchange factor (GEF) 3 | chr12:4812851 4-48128455 | GO:0005622\|GO:0005085\|NM_001098531 GO:0051056\|GO:0005952\| GO:0030552\|GO:0016020\| GO:0008603\|GO:0000166\| GO:0008283\|GO:0005624\| GO:0001932\|GO:0012505 | | THC2696603 | Hs.8578 |
| A_23_P163492 | BAIAP3 | Homo sapiens BAI1-associated | NM_003933 | ENST00000397489 | 8938 | BAI1-associated | chr16:1398879-1398938 | GO:0008022\|GO:0007269 NM_003933 | | THC2622475 | Hs.458427 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | protein 3 (BAIAP3), transcript variant 1, mRNA [NM_003933] | | | | protein 3 | | | | | |
| A_33_P3270451 | TXNDC5 | Homo sapiens thioredoxin domain containing 5 (endoplasmic reticulum) (TXNDC5), transcript variant 1, mRNA [NM_030810] | NM_030810 | ENST00000439343 | 81567 | thioredoxin domain containing 5 (endoplasmic reticulum) | chr6:7883436-7883377 | GO:0005783\|GO:0006892\|NM_030810 GO:0005788\|GO:0045454\| GO:0006916\|GO:0016853\| GO:0016044 | THC2520615 | Hs.150837 |
| A_23_P4241 | OR5V1 | Homo sapiens olfactory receptor, family 5, subfamily V, member 1 (OR5V1), mRNA [NM_030876] | NM_030876 | ENST00000377154 | 81696 | olfactory receptor, family 5, subfamily V, member 1 | chr6:29323467-29323408 | GO:0007608\|GO:0007165\|NM_030876 GO:0004984\|GO:0007186\| GO:0005886\|GO:0004872\| GO:0016021\|GO:0050896 | THC2602991 | Hs.666316 |
| A_32_P722809 | | Homo sapiens immunoglobulin kappa variable 2D-28 [Source: HGNC Symbol; Acc: 5799] [ENST00000453166] | BC034142 | ENST00000453166 | | | chr2:89999481-89999540 | | NP073702 | | Hs.449621 |
| A_33_P3411805 | | | | ENST00000412714 | | | chr13:1918462 2-19184563 | | | | |
| A_23_P207967 | CTIF | Homo sapiens CBP80/20-dependent translation initiation factor (CTIF), transcript variant 1, mRNA [NM_014772] | NM_014772 | ENST00000382998 | 9811 | CBP80/20-dependent translation initiation factor | chr18:4638918 3-46389242 | GO:0005515\|GO:0048471\|NM_014772 GO:0016070\|GO:0000184\| GO:0006446 | THC2507982 | Hs.145230 |
| A_33_P3358957 | PAPL | Homo sapiens iron/zinc purple acid phosphatase-like protein (PAPL), mRNA [NM_001004318] | NM_001004318 | ENST00000331256 | 390928 | iron/zinc purple acid phosphatase like protein | chr19:3960141 9-39601478 | GO:0016787\|GO:0005506\|NM_001004318 GO:0003993\|GO:0008270\| GO:0005576\|GO:0046872 | THC2482977 | Hs.448934 |
| A_33_P3215288 | LOC284757 | Homo sapiens cDNA FLJ46426 fis, clone THYMU3013897. [AK128288] | AK128288 | | 284757 | hypothetical protein LOC284757 | chr20:5889449 4-58894553 | | THC2481282 | Hs.534781 |
| A_23_P115842 | CCAR1 | Homo sapiens cell division cycle and apoptosis regulator 1 (CCAR1), mRNA [NM_018237] | NM_018237 | ENST00000540210 | 55749 | cell division cycle and apoptosis regulator 1 | chr10:7055099 8-70551057 | GO:0048471\|GO:0007049\|NM_018237 GO:0005737\|GO:0005794\| GO:0000398\|GO:0006915\| GO:0005634\|GO:0003676\| GO:0045449 | THC2468937 | Hs.49853 |
| A_33_P3284197 | POMGNT1 | Homo sapiens protein O-linked mannose beta 1, 2-N-acetylglucosaminyl- | NM_017739 | ENST00000371992 | 55624 | protein O-linked mannose beta 1,2 N-acetyl- | chr1:46654450-46654391 | GO:0005792\|GO:0003827\|NM_017739 GO:0030145\|GO:0005794\| GO:0016020\|GO:0006493\| GO:0000139\|GO:0016757 | THC2537515 | Hs.525134 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | transferase (POMGNT1), transcript variant 1, mRNA [NM_017739] | | | | glucosamin-yltransferase | | GO:0047223\|GO:0016021\|GO:0006487 | | | |
| A_33_P3231888 | C5orf15 | Homo sapiens chromosome 5 open reading frame 15 (C5orf15), mRNA [NM_020199] | NM_020199 | ENST00000451255 | 56951 | chromosome 5 open reading frame 15 | chr5:133291966-133291907 | GO:0016020\|GO:0016021 | NM_020199 | THC2469485 | Hs.730670 |
| A_23_P204850 | RB1 | Homo sapiens retinoblastoma 1 (RB1), mRNA [NM_000321] | NM_000321 | ENST00000267163 | 5925 | retinoblastoma 1 | chr13:49055845-49055904 | GO:0051219\|GO:0016564\|GO:0030308\|GO:0003700\|GO:0050681\|GO:0005634\|GO:0000083\|GO:0043353\|GO:0045944\|GO:0016514\|GO:0051318\|GO:0044419\|GO:0045445\|GO:0035189\|GO:0006338\|GO:0007050\|GO:0000785\|GO:0019900\|GO:0043550\|GO:0031625\|GO:0045786\|GO:0005819\|GO:0045749\|GO:0000122\|GO:0000075\|GO:0016605\|GO:0006469\|GO:0005654\|GO:0030521\|GO:0051146\|GO:0000279\|GO:0051301\|GO:0008134 | NM_000321 | THC2601211 | Hs.408528 |
| A_33_P3393091 | | DA197111 BRASW1 Homo sapiens cDNA clone BRASW1000106 5', mRNA sequence [DA197111] | DA197111 | | | | chr2:132121555-132121618 | | | | Hs.712140 |
| A_33_P3399291 | GUK1 | Homo sapiens guanylate kinase 1 (GUK1), transcript variant 5, mRNA [NM_001242840] | NM_001242840 | ENST00000493209 | 2987 | guanylate kinase 1 | chr1:228334579-228334638 | GO:0000166\|GO:0016301\|GO:0004385\|GO:0019206\|GO:0005524\|GO:0016740\|GO:0006163\|GO:0005829 | NM_001242840 | NP1277184 | Hs.376933 |
| A_33_P3378056 | TFAP2A | Homo sapiens transcription factor AP-2 alpha (activating enhancer binding protein 2 alpha) [Source: HGNC Symbol; Acc: 11742] [ENST00000478375] | M61156 | ENST00000478375 | 7020 | transcription factor AP-2 alpha (activating enhancer binding protein 2 alpha) | chr6:10402318-10402259 | GO:0003700\|GO:0006357\|GO:0003713\|GO:0046983\|GO:0048705\|GO:0005634\|GO:0007398\|GO:0048701\|GO:0021506 | | THC2493408 | Hs.519880 |
| A_33_P3355266 | TINAGL1 | Homo sapiens tubulointerstitial nephritis antigen- | NM_022164 | ENST00000481165 | 64129 | tubulointerstitial nephritis anti- | chr1:32052808-32052867 | GO:0004197\|GO:0006955\|GO:0016197\|GO:0006508\|GO:0030247\|GO:0005576 | NM_022164 | THC2584652 | Hs.199368 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3271594 | TRIM54 | like 1 (TINAGL1), transcript variant 1, mRNA [NM_022164] Homo sapiens tripartite motif containing 54 (TRIM54), transcript variant 1, mRNA [NM_032546] | NM_032546 | ENST00000380075 | 57159 | tripartite motif containing 54 | chr2:27530243-27530302 | GO:0005201|GO:0005044 GO:0005515|GO:0030018|NM_032546 GO:0005874|GO:0007275| GO:0046872|GO:0030154| GO:0005622|GO:0007165| GO:0005737|GO:0007026| GO:0008270|GO:0044871| GO:0005856|GO:0007017 | THC2602749 | Hs.516036 |
| A_33_P3300877 |  |  |  |  |  | gen like 1 | chr17:081012862 21-081012862 |  |  |  |  |
| A_33_P3394599 | HMG20B | Homo sapiens high mobility group 20B (HMG20B), mRNA [NM_006339] | NM_006339 | ENST00000487894 | 10362 | high mobility group 20B | chr19:3578051-3578110 | GO:0005515|GO:0007049|NM_006339 GO:0006355|GO:0003700| GO:0005634|GO:0016568 |  | THC2580877 | Hs.406534 |
| A_33_P3394605 | HMG20B | Homo sapiens high mobility group 20B (HMG20B), mRNA [NM_006339] | NM_006339 | ENST00000402569 | 10362 | high mobility group 20B | chr19:3578660-3578719 | GO:0005515|GO:0007049|NM_006339 GO:0006355|GO:0003700| GO:0005634|GO:0016568 |  | THC2515693 | Hs.406534 |
| A_23_P2601 | HSP90B1 | Homo sapiens heat shock protein 90 kDa beta (Grp94), member 1 (HSP90B1), mRNA [NM_003299] | NM_003299 | ENST00000421266 | 7184 | heat shock protein 90 kDa beta (Grp94), member 1 | chr12:1043415 36-104341595 | GO:0042470|GO:0001666|NM_003299 GO:0005792|GO:0051208| GO:0048471|GO:0005783| GO:0003723|GO:0005509| GO:0046790|GO:0006916| GO:0030433|GO:0015031| GO:0005524|GO:0005829| GO:0000166|GO:0006457| GO:0005789|GO:0005788| GO:0051082|GO:0050750 |  | THC2465650 | Hs.192374 |
| A_33_P3248024 |  | Homo sapiens cDNA, FLJ18474, [AK311432] | AK311432 | ENST00000446816 |  |  | chr2:96874597-96874656 |  |  | THC2556209 | Hs.58648 |
| A_33_P3326275 |  | Homo sapiens cDNA: FLJ23120 fis, clone LNG07989. [AK026773] | AK026773 |  |  |  | chr2:47799886-47799945 |  |  | THC2554846 | Hs.287726 |
| A_24_P631848 | LOC100132147 | Homo sapiens cDNA clone IMAGE: 4816083, partial cds. [BC036435] | BC036435 | ENST00000451828 | 100132147 | hypothetical LOC100132147 | chr1:16860558-16860499 |  |  |  | Hs.645945 |
| A_24_P228130 | CCL3L3 | Homo sapiens chemokine (C-C motif) ligand 3-like 3 (CCL3L3), mRNA [NM_001001437] | NM_001001437 | ENST00000425833 | 414062 | chemokine (C-C motif) ligand 3-like 3 | chr17:3452326 0-34523201 | GO:0008009|GO:0006955|NM_001001437 GO:0008285|GO:0006954| GO:0006935|GO:0005576| GO:0005615 | THC2605779 | Hs.512304 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3229335 | HIST3H2BB | *Homo sapiens* histone cluster 3, H2bb (HIST3H2BB), mRNA [NM_175055] | NM_175055 | ENST00000369160 | 128312 | histone cluster 3, H2bb | chr1:228646192-228646251 | GO:0005694\|GO:0006334\|GO:0000786\|GO:0005634\|GO:0000786\|GO:0003677 | NM_175055 | THC2785974 | Hs.376691 |
| A_23_P26557 | C16orf59 | *Homo sapiens* chromosome 16 open reading frame 59 (C16orf59), mRNA [NM_025108] | NM_025108 | ENST00000483320 | 80178 | chromosome 16 open reading frame 59 | chr16:2514795-2514854 | | NM_025108 | THC2601798 | Hs.534491 |
| A_24_P288298 | KIR2DL4 | *Homo sapiens* killer cell immunoglobulin-like receptor, two domains, long cytoplasmic tail, 4 (KIR2DL4), transcript variant 1, mRNA [NM_002255] | NM_002255 | ENST00000396293 | 3805 | killer cell immuno-globulin-like receptor, two domains, long cyto-plasmic tail, 4 | chr19:55325337-55325396 | GO:0007165\|GO:0006968\|GO:0005886\|GO:0005887\|GO:0004888 | NM_002255 | NP365687 | Hs.661219 |
| A_33_P3369266 | | CR997556 RZPD no. 9016 *Homo sapiens* cDNA clone RZPDp9016l2412 5', mRNA sequence [CR997556] | CR997556 | | | | chr2:114345109-114345168 | | | | Hs.682246 |
| A_23_P50343 | ADAM33 | *Homo sapiens* ADAM metallopeptidase domain 33 (ADAM33), transcript variant 1, mRNA [NM_025220] | NM_025220 | ENST00000444535 | 80332 | ADAM metallo-peptidase domain 33 | chr20:3649151-3649092 | GO:0016020\|GO:0006508\|GO:0008270\|GO:0008233\|GO:0016021\|GO:0004222\|GO:0046872 | NM_025220 | NP1168293 | Hs.173716 |
| A_23_P26468 | RHBDL1 | *Homo sapiens* rhomboid, veinlet-like 1 (*Drosophila*) (RHBDL1), mRNA [NM_003961] | NM_003961 | ENST00000219551 | 9028 | rhomboid, veinlet-like 1 (*Drosophila*) | chr16:726855-726988 | GO:0007165\|GO:0016020\|GO:0004252\|GO:0005887\|GO:0005624\|GO:0008233 | NM_003961 | THC2606656 | Hs.137572 |
| A_23_P71649 | MUSK | *Homo sapiens* muscle, skeletal, receptor tyrosine kinase (MUSK), transcript variant 1, mRNA [NM_005592] | NM_005592 | ENST00000189978 | 4593 | muscle, skeletal, receptor tyrosine kinase | chr9:113563075-113563134 | GO:0005515\|GO:0007275\|GO:0005524\|GO:0007517\|GO:0000166\|GO:0016020\|GO:0005887\|GO:0007528\|GO:0004872\|GO:0006468\|GO:0004714\|GO:0007169\|GO:0016740 | NM_005592 | NP1245860 | Hs.521653 |
| A_23_P65768 | RSL24D1 | *Homo sapiens* ribosomal L24 domain containing 1 (RSL24D1), mRNA [NM_016304] | NM_016304 | ENST00000260443 | 51187 | ribosomal L24 domain containing 1 | chr15:55474228-55474169 | GO:0005622\|GO:0003735\|GO:0042254\|GO:0005730\|GO:0005840\|GO:0005634\|GO:0006412 | NM_016304 | THC2535982 | Hs.274772 |
| A_33_P3229328 | NBPF6 | *Homo sapiens* neuroblastoma breakpoint family, member | NM_001143988 | ENST00000294652 | 653149 | neuroblastoma breakpoint family, | chr1:108993403-108993401 | GO:0005737 | NM_001143988 | THC2493504 | Hs.712226 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | 6 (NBPF6), transcript variant 2, mRNA [NM_001143988] | | | | member 6 | | | | | |
| A_32_P8813 | LOC283663 | Homo sapiens hypothetical LOC283663 (LOC283663), non-coding RNA [NR_024433] | NR_024433 | | 283663 | hypothetical LOC283663 | chr15:57599800-57599859 | | NR_024433 | THC2513469 | Hs.181297 |
| A_23_P138262 | PADI4 | Homo sapiens peptidyl arginine deiminase, type IV (PADI4), mRNA [NM_012387] | NM_012387 | ENST00000375448 | 23569 | peptidyl arginine deiminase, type IV | chr1:17685353-17685783 | GO:0018101|GO:0005737|NM_012387| GO:0016787|GO:0005509| GO:0005634|GO:0004668| GO:0045449|GO:0006464| GO:0016568 | | THC2472236 | Hs.522969 |
| A_33_P3296169 | CDCA7 | Homo sapiens cell division cycle associated 7 (CDCA7), transcript variant 1, mRNA [NM_031942] | NM_031942 | ENST00000496441 | 83879 | cell division cycle associated 7 | chr2:174232387-174232446 | GO:0042127|GO:0005634|NM_031942 GO:0045449 | | NP1165009 | Hs.470654 |
| A_33_P3398877 | | ZDH11_HUMAN (Q9H8X9) Probable palmitoyltransferase ZDHHC11 (Zinc finger DHHC domain-containing protein 11) (DHHC-11) (Zinc finger protein 399), complete [THC2515810] | | | | | chr5:000851156-000851097 | | | THC2515810 | |
| A_23_P31816 | DEFA3 | Homo sapiens defensin, alpha 3, neutrophil-specific (DEFA3), mRNA [NM_005217] | NM_005217 | ENST00000535841 | 1668 | defensin, alpha 3, neutrophil-specific | chr8:6873570-6873511 | GO:0050832|GO:0031640|NM_005217 GO:0005576|GO:0009615| GO:0005615|GO:0042742 | | THC2468638 | Hs.654448 |
| A_23_P81717 | FRMD1 | Homo sapiens FERM domain containing 1 (FRMD1), transcript variant 1, mRNA [NM_024919] | NM_024919 | ENST00000468647 | 79981 | FERM domain containing 1 | chr6:168457299-168457240 | GO:0005488|GO:0005856|NM_024919 | | THC2478439 | Hs.266746 |
| A_24_P161581 | SHISA7 | Homo sapiens shisa homolog 7 (Xenopus laevis) (SHISA7), mRNA [NM_001145176] | NM_001145176 | ENST00000376325 | 729956 | shisa homolog 7 (Xenopus laevis) | chr19:55949046-55948987 | GO:0016020|GO:0016021 NM_001145176 | | THC2658872 | Hs.6664 |
| A_33_P3274001 | | | | | | | chr6:108939648-108939589 | | | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P200780 | TGFBR3 | Homo sapiens transforming growth factor, beta receptor III (TGFBR3), transcript variant 1, mRNA [NM_003243] | NM_003243 | ENST00000532540 | 7049 | transforming growth factor, beta receptor III | chr1:92148947-92148888 | GO:0055010\|GO:0005886\|NM_003243 GO:0050680\|GO:0046332\| GO:0034673\|GO:0005615\| GO:0007243\|GO:0005114\| GO:0043231\|GO:0060317\| GO:0060318\|GO:0069955\| GO:0034695\|GO:0060021\| GO:0007179\|GO:0008201\| GO:0032354\|GO:0050431\| GO:0005576\|GO:0030509\| GO:0015026\|GO:0030165\| GO:0060038\|GO:0070123\| GO:0034699\|GO:0060347\| GO:0001889\|GO:0016477\| GO:0005887\|GO:0016049\| GO:0060389\|GO:0051271\| GO:0009897 | THC2463693 | Hs.482390 |
| A_33_P3333708 | | | | | | | chrX:00614442 7-00614368 | | | | |
| A_33_P3319581 | FIGNL2 | Homo sapiens fidgetin-like 2 (FIGNL2), mRNA [NM_001013690] | NM_001013690 | | 401720 | fidgetin-like 2 | chr12:5221384 7-52213788 | GO:0017111\|GO:0000166\|NM_001013690 GO:0005524 | THC2614540 | Hs.648218 |
| A_33_P3258013 | UBE3B | ubiquitin protein ligase E3B [Source: HGNC Symbol; Acc: 13478] | CR614569 | ENST00000340074 | 89910 | ubiquitin protein ligase E3B | chr12:1099283 40-109928399 | | THC2484472 | Hs.374067 |
| A_23_P351148 | SH2D1B | Homo sapiens SH2 domain containing 1B (SH2D1B), mRNA [NM_053282] | NM_053282 | ENST00000359567 | 117157 | SH2 domain containing 1B | chr1:16236590 4-162365845 | GO:0005515\|GO:0008150\|NM_053282 GO:0003674\|GO:0005575 | THC2487991 | Hs.350581 |
| A_23_P103034 | CRYBA4 | Homo sapiens crystallin, beta A4 (CRYBA4), mRNA [NM_001886] | NM_001886 | ENST00000466315 | 1413 | crystallin, beta A4 | chr22:2702432 2-27024381 | GO:0003674\|GO:0005212\|NM_001886 GO:0043010\|GO:0005625\| GO:0007601 | THC2467739 | Hs.57690 |
| A_33_P3401826 | CMPK2 | Homo sapiens cytidine monophosphate (UMP-CMP) kinase 2, mitochondrial (CMPK2), nuclear gene encoding mitochondrial protein, mRNA [NM_207315] | NM_207315 | ENST00000478738 | 129607 | cytidine monophosphate (UMP-CMP) kinase 2, mitochondrial | chr2:6988526-6988467 | GO:0005739\|GO:0000166\|NM_207315 GO:0016301\|GO:0004127\| GO:0006221\|GO:0005524\| GO:0016740 | THC2601942 | Hs.7155 |
| A_33_P3422298 | | [pseudogene] IgV lambda II psi C lambda 6 = Ig lambda chain | S77011 | | | | chr22:2326176 5-23261824 | | | Hs.547600 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P85200 | | surface Ig receptor VJC region {truncated light chain constant region} [human, B lymphoma cell line OCI LY8, mRNA Partial, 623 nt]. [S77011] | | | | | | | | | |
| A_23_P116765 | C14orf43 | Homo sapiens chromosome 14 open reading frame 43 (C14orf43), transcript variant 1, mRNA [NM_194278] | NM_194278 | ENST00000286523 | 9748 | chromosome 14 open reading frame 43 | chr14:74182252-74182193 | GO:0005634\|GO:0003677\|GO:0045449 | NM_194278 | THC2656133 | Hs.594157 |
| A_23_P116765 | LALBA | Homo sapiens lactalbumin, alpha- (LALBA), mRNA [NM_002289] | NM_002289 | ENST00000301046 | 3906 | lactalbumin, alpha- | chr12:48962883-48962335 | GO:0005989\|GO:0007165\|GO:0005509\|GO:0007267\|GO:0004461\|GO:0005576\|GO:0006917\|GO:0005615\|GO:0042742 | NM_002289 | THC2481150 | Hs.72938 |
| A_33_P3407105 | YTHDF1 | Homo sapiens YTH domain family, member 1(YTHDF1), mRNA [NM_017798] | NM_017798 | ENST00000342761 | 54915 | YTH domain family, member 1 | chr20:61834205-61834146 | | NM_017798 | THC2465870 | Hs.11747 |
| A_33_P3235098 | FAM22D | Homo sapiens family with sequence similarity 22, member D (FAM22D), mRNA [NM_001009610] | NM_001009610 | ENST00000372321 | 728130 | family with sequence similarity 22, member D | chr10:89127618-89127677 | | NM_001009610 | THC2543079 | Hs.701044 |
| A_33_P3342081 | PRDM1 | Homo sapiens PR domain containing 1, with ZNF domain (PRDM1), transcript variant 1, mRNA [NM_001198] | NM_001198 | ENST00000369096 | 639 | PR domain containing 1, with ZNF domain | chr6:106557662-106557721 | GO:0010628\|GO:0005622\|GO:0045165\|GO:0003700\|GO:0001893\|GO:0001892\|GO:0008270\|GO:0005634\|GO:0000122\|GO:0046872\|GO:0045449 | NM_001198 | THC2470627 | Hs.436023 |
| A_33_P3303355 | | | | | | | chrX:103358074-103358133 | | | THC2554141 | |
| A_33_P3768930 | | MYE4344 Myeloma (MYE) cDNA library Homo sapiens cDNA, mRNA sequence [BF175071] | BF175071 | | | | | | | THC2543611 | Hs.636467 |
| A_24_P225468 | ANP32E | Homo sapiens acidic (leucine-rich) nuclear phosphoprotein 32 | NM_030920 | ENST00000369116 | 81611 | acidic (leucine-rich) nuclear phosphoprotein | chr1:150191136-150191077 | GO:0005515\|GO:0005737\|GO:0016023\|GO:0005634\|GO:0019212 | NM_030920 | THC2467881 | Hs.656466 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID Gene Name | Genomic Coordinates | Go | RefSeq-Accession | TIGRID | UniGene ID |
|---|---|---|---|---|---|---|---|---|---|---|
| | | family, member E (ANP32E), transcript variant 1, mRNA [NM_030920] | | | 32 family, member E | | | | | |
| A_23_P108157 | TJP3 | Homo sapiens tight junction protein 3 (zona occludens 3) (TJP3), mRNA [NM_014428] | NM_014428 | ENST00000262968 | 27134 tight junction protein 3 (zona occludens 3) | chr19:3746516-3746575 | GO:0005515\|GO:0030054\|NM_014428 GO:0005886\|GO:0005923 | | THC2608759 | Hs.25527 |
| A_32_P85591 | H2BFXP | Homo sapiens H2B histone family, member X, pseudogene (H2BFXP), non-coding RNA [NR_003238] | NR_003238 | | 767811 H2B histone family, member X, pseudogene | chrX:103231321-103231580 | | NR_003238 | THC2587717 | Hs.496530 |
| A_33_P3409625 | SORBS3 | Homo sapiens sorbin and SH3 domain containing 3 (SORBS3), transcript variant 1, mRNA [NM_005775] | NM_005775 | ENST00000428103 | 10174 sorbin and SH3 domain containing 3 | chr8:22432948-22433007 | GO:0030054\|GO:0031589\|NM_005775 GO:0005634\|GO:0000122\| GO:0005737\|GO:0051495\| GO:0017166\|GO:0051496\| GO:0005200\|GO:0005856\| GO:0043410\|GO:0005925\| GO:0008134 | | THC2745544 | Hs.528572 |
| A_33_P3317168 | EPS8L3 | Homo sapiens EPS8-like 3 (EPS8L3), transcript variant 1, mRNA [NM_139053] | NM_139053 | ENST00000369805 | 79574 EPS8-like 3 | chr1:110292762-110292703 | GO:0005737 | NM_139053 | THC2462418 | Hs.485352 |
| A_23_P11507 | ZZZ3 | Homo sapiens zinc finger, ZZ-type containing 3 (ZZZ3), mRNA [NM_015534] | NM_015534 | ENST00000476275 | 26009 zinc finger, ZZ-type containing 3 | chr1:78030621-78030562 | GO:0008270\|GO:0005634\|NM_015534 GO:0003677\|GO:0046872\| GO:0045449 | | THC2461379 | Hs.480506 |
| A_33_P3381127 | FAS | Homo sapiens Fas (TNF receptor super-family, member 6) (FAS), transcript variant 1, mRNA [NM_000043] | NM_000043 | ENST00000355740 | 355 Fas (TNF receptor superfamily, member 6) | chr10:90774517-90774576 | GO:0008624\|GO:0008633\|NM_000043 GO:0005886\|GO:0031264\| GO:0042981\|GO:0005576\| GO:0005625\|GO:0006916\| GO:0042802\|GO:0005829\| GO:0007165\|GO:0006955\| GO:0006461\|GO:0016021\| GO:0019900\|GO:0004888\| GO:0010940 | | THC2522452 | Hs.244139 |
| A_23_P416212 | HSPB9 | Homo sapiens heat shock protein, alpha-crystallin-related, B9 (HSPB9), mRNA [NM_033194] | NM_033194 | ENST00000355067 | 94086 heat shock protein, alpha-crystallin-related, B9 | chr17:40275148-40275207 | GO:0005515\|GO:0006950 | NM_033194 | THC2634040 | Hs.620611 |
| A_33_P3414242 | MOG | Homo sapiens myelin oligodendrocyte | NM_001008229 | ENST00000396704 | 4340 myelin oligodendrocyte | chr6:29633982-29634041 | GO:0005886\|GO:0016021\|NM_001008229 GO:0007417 | | NP1465457 | Hs.141308 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P143734 | | glycoprotein (MOG), transcript variant beta2, mRNA [NM_001008229] | | | | glycoprotein | | | | | |
| | CYP2D6 | Homo sapiens cytochrome P450, family 2, subfamily D, polypeptide 6 (CYP2D6), transcript variant 1, mRNA [NM_000106] | NM_000106 | ENST00000542856 | 1565 | cytochrome P450, family 2, subfamily D, polypeptide 6 | chr22:42523968-42523909 | GO:0005792|GO:0070330|GO:0016020|GO:0017144|GO:0005783|GO:0009055|GO:0046872|GO:0055114|GO:0020037|GO:0019898 | NM_000106 | NP1462558 | Hs.64256 |
| A_24_P272917 | USP17 | Homo sapiens ubiquitin specific peptidase 17 (USP17), mRNA [NM_001105662] | NM_001105662 | ENST00000421288 | 391627 | ubiquitin specific peptidase 17 | chr4:9361479-9361538 | GO:0006511|GO:0005730|GO:0006915|GO:0008233|GO:0005634|GO:0008234|GO:0004221 | NM_001105662 | THC2525229 | Hs.631527 |
| A_23_P94819 | RPH3AL | Homo sapiens rabphilin 3A-like (without C2 domains) (RPH3AL), transcript variant 1, mRNA [NM_006987] | NM_006987 | ENST00000540633 | 9501 | rabphilin 3A-like (without C2 domains) | chr17:62615-62556 | GO:0008092|GO:0017137|GO:0045744|GO:0031410|GO:0042593|GO:0006887|GO:0006886|GO:0046872|GO:0017158|GO:0005737|GO:0016020|GO:0030274|GO:0008270|GO:0030667 | NM_006987 | THC2486836 | Hs.651925 |
| A_33_P3351474 | SMARCAD1 | Homo sapiens SWI/SNF-related, matrix-associated actin-dependent regulator of chromatin, subfamily a, containing DEAD/H box 1 (SMARCAD1), transcript variant 1, mRNA [NM_001128429] | NM_001128429 | ENST00000394961 | 56916 | SWI/SNF-related, matrix-associated actin-dependent regulator of chromatin, subfamily a, containing DEAD/H box 1 | chr4:95210929-95210988 | GO:0005515|GO:0004386|GO:0005730|GO:0005634|GO:0003677|GO:0005524|GO:0016363|GO:0045941|GO:0000166|GO:0016787|GO:0051260|GO:0000018|GO:0009117|GO:0016568 | NM_001128429 | THC2461621 | Hs.410406 |
| A_33_P3317317 | KRTAP5-4 | Homo sapiens keratin associated protein 5-4 (KRTAP5-4), mRNA [NM_001012709] | NM_001012709 | ENST00000328953 | 387267 | keratin associated protein 5-4 | chr11:1642696-1642637 | GO:0045095 | NM_001012709 | NP1461693 | Hs.539087 |
| A_33_P3234794 | ARHGAP40 | Homo sapiens Rho GTPase activating protein 40 (ARHGAP40), mRNA [NM_001164431] | NM_001164431 | ENST00000373345 | 343578 | Rho GTPase activating protein 40 | chr20:37272739-37272457 | GO:0005622|GO:0007165|GO:0005096 | NM_001164431 | THC2749375 | Hs.451997 |
| A_33_P3290588 | ASPSCR1 | Homo sapiens cDNA FLJ45222 fis, clone BRCAN2019953. | AK127159 | | 79058 | alveolar soft part sarcoma chromosome | chr17:7996571-7990577 | GO:0005515|GO:0008150|GO:0003674|GO:0016020|GO:0005575|GO:0019898 | | THC2485264 | Hs.298351 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq- Accession | TIGRID | UniGene ID |
|---|---|---|---|---|---|---|---|---|---|---|---|
| A_33_P3296991 | FLJ42393 | Homo sapiens hypothetical LOC401105 (FLJ42393), non-coding RNA [NR_024413] | NR_024413 | ENST00000392468 | 401105 | hypothetical LOC401105 | chr3:187897865-187897924 | | NR_024413 | THC2481460 | Hs.679026 |
| A_33_P3211423 | PANK3 | BX648891 pantothenate kinase 3 [Source: HGNC Symbol; Acc: 19365] [ENST00000239231] | BX648891 | ENST00000239231 | 79646 | pantothenate kinase 3 | chr5:167975662-167975603 | GO:0004594\|GO:0005737\|GO:0000166\|GO:0015937\|GO:0005524\|GO:0016740 | | THC2570326 | Hs.388400 |
| A_33_P3231086 | | Q6P1G7_MOUSE (Q6P1G7) Myoneurin (In vitro fertilized eggs cDNA, RIKEN full-length enriched library, clone: 7420457K05 product: myoneurin, full insert sequence), partial (4%) [THC2631347] | | | | | chr20:062689140-062689199 | | | THC2631347 | |
| A_23_P132159 | USP18 | Homo sapiens ubiquitin specific peptidase 18 (USP18), mRNA [NM_017414] | NM_017414 | ENST00000215794 | 11274 | ubiquitin specific peptidase 18 | chr22:18659618-18659677 | GO:0006511\|GO:0004843\|NM_017414\|GO:0008233\|GO:0005634\|GO:0008234\|GO:0004221 | | THC2471774 | Hs.38260 |
| A_23_P50052 | C18orf12 | PREDICTED: Homo sapiens chromosome 18 open reading frame 12 (C18orf12), misc RNA [XR_109479] | XR_109479 | | 84322 | chromosome 18 open reading frame 12 | chr18:45778947-45779006 | | XR_109479 | NP340945 | Hs.334493 |
| A_23_P168993 | ADRB3 | Homo sapiens adrenergic, beta-3-, receptor (ADRB3), mRNA [NM_000025] | NM_000025 | ENST00000345060 | 155 | adrenergic, beta-3-, receptor | chr8:37821117-37821058 | GO:0005515\|GO:0005886\|NM_000025\|GO:0004930\|GO:0005975\|GO:0051379\|GO:0006091\|GO:0042803\|GO:0006898\|GO:0015052\|GO:0002032\|GO:0043235\|GO:0051380\|GO:0007165\|GO:0006112\|GO:0005887\|GO:0004872\|GO:0007189\|GO:0043410 | | THC2474800 | Hs.2549 |
| A_33_P3360077 | LOC100130745 | Homo sapiens cDNA FLJ46338 fis, clone TESTI4046328. [AK128206] | AK128206 | | 100130745 | hypothetical LOC100130745 | chr7:1506804-1506745 | | | THC2483234 | Hs.634078 |
| A_33_P3376828 | CMTM7 | Homo sapiens CKLF-like MARVEL | NM_138410 | ENST00000454304 | 112616 | CKLF-like MARVEL | chr3:32490977-32491036 | GO:0016020\|GO:0006935\|NM_138410\|GO:0016021\|GO:0005615 | | THC2464715 | Hs.440494 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3258324 | | transmembrane domain containing 7 (CMTM7), transcript variant 1, mRNA [NM_138410] | | | | transmembrane domain containing 7 | chr19:015962862-015962803 | GO:0005125 | | | |
| A_23_P3038 | GPX2 | Homo sapiens glutathione peroxidase 2 (gastrointestinal) (GPX2), mRNA [NM_002083] | NM_002083 | ENST00000389614 | 2877 | glutathione peroxidase 2 (gastrointestinal) | chr14:65406396-65406396 | GO:0004602 GO:0008430 GO:0002862 GO:0051702 GO:0009609 GO:0016491 GO:0009055 GO:0006979 GO:0055114 | NM_002083 | THC2578470 | Hs.2704 |
| A_33_P3364211 | | Homo sapiens cDNA FLJ44459 fis, clone UTERU2024656. [AK126423] | AK126423 | | | | chr3:73674377-73674436 | | | | Hs.434900 |
| A_33_P3377994 | WNK4 | Homo sapiens WNK lysine deficient protein kinase 4 (WNK4), mRNA [NM_032387] | NM_032387 | ENST00000316085 | 65266 | WNK lysine deficient protein kinase 4 | chr17:40946814-40946873 | GO:0005515 GO:0006821 GO:0030054 GO:0005524 GO:0007243 GO:0005737 GO:0008104 GO:0000166 GO:0004674 GO:0050794 GO:0006468 GO:0005923 GO:0016740 GO:0006811 | NM_032387 | THC2488534 | Hs.105448 |
| A_23_P145218 | | butyrophilin, subfamily 2, member A3 [Source: HGNC Symbol; Acc: 13229] [ENST00000297020] | BC166633 | ENST00000297020 | | | chr6:26431721-26431780 | | | NP319744 | Hs.729655 |
| A_24_P392925 | GLTPD2 | Homo sapiens glycolipid transfer protein domain containing 2 (GLTPD2), mRNA [NM_001014985] | NM_001014985 | ENST00000331264 | 388323 | glycolipid transfer protein domain containing 2 | chr17:4693360-4693419 | GO:0005737 GO:0051861 GO:0017089 GO:0046836 | NM_001014985 | THC2495934 | Hs.721461 |
| A_23_P12128 | TSHB | Homo sapiens thyroid stimulating hormone, beta (TSHB), mRNA [NM_000549] | NM_000549 | ENST00000369517 | 7252 | thyroid stimulating hormone, beta | chr1:115576682-115576741 | GO:0051592 GO:0043627 GO:0007186 GO:0005179 GO:0033189 GO:0007267 GO:0005576 GO:0009653 | NM_000549 | THC2666358 | Hs.406687 |
| A_32_P360193 | DNHD1 | Homo sapiens dynein heavy chain domain 1 (DNHD1), transcript variant 1, mRNA [NM_144666] | NM_144666 | ENST00000532027 | 144132 | dynein heavy chain domain 1 | chr11:6569440-6569499 | GO:0030286 GO:0016020 GO:0016021 GO:0003777 GO:0007018 | NM_144666 | THC2574634 | Hs.720080 |
| A_23_P11843 | LRRN2 | Homo sapiens leucine rich repeat neuronal 2 (LRRN2), mRNA [NM_201630] | NM_201630 | ENST00000367175 | 10446 | leucine rich repeat neuronal 2 | chr1:204586412-204586353 | GO:0005515 GO:0007165 GO:0016020 GO:0004872 GO:0016021 GO:0007155 | NM_201630 | THC2471115 | Hs.26312 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P38328 | DBF4B | transcript variant 2, mRNA [NM_201630] DBF4 homolog B (S. cerevisiae) [Source: HGNC Symbol; Acc: 17883] [ENST00000439818] | AK023149 | ENST00000439818 | 80174 | DBF4 homolog B (S. cerevisiae) | chr17:42809611-42809670 | GO:0007049|GO:0008270| GO:0005634|GO:0003676| GO:0046872 | THC2479406 | Hs.461819 |
| A_33_P3297030 | LOC100129974 | Homo sapiens cDNA FLJ46583 fis, clone THYMU3043482. [AK128440] | AK128440 | | 100129974 | hypothetical protein LOC100129974 | chr17:441183-441124 | | | THC2485946 | Hs.350588 |
| A_33_P3222942 | GPR78 | Homo sapiens G protein-coupled receptor 78 (GPR78), mRNA [NM_080819] | NM_080819 | | 27201 | G protein-coupled receptor 78 | chr4:8589448-8589507 | GO:0007165|GO:0007186|NM_080819 GO:0005886|GO:0004930| GO:0004872|GO:0016021 | THC2481606 | |
| A_33_P3392677 | | | | | | | chr7:06631363 0-066313689 | | | THC2539584 | Hs.407654 |
| A_32_P481377 | KRTAP11-1 | Homo sapiens keratin associated protein 11-1 (KRTAP11-1), mRNA [NM_175858] | NM_175858 | ENST00000332378 | 337880 | keratin associated protein 11-1 | chr21:3225328 3-32253224 | GO:0005198|GO:0045095 | NM_175858 | THC2490936 | Hs.656694 |
| A_24_P183864 | IMPA1 | Homo sapiens inositol(myo)-1(or 4)-monophosphatase 1 (IMPA1), transcript variant 1, mRNA [NM_005536] | NM_005536 | ENST00000256108 | 3612 | inositol(myo)-1(or4)-monophosphatase 1 | chr8:82570477-82570418 | GO:0007165|GO:0005737|NM_005536 GO:0010226|GO:0000287| GO:0016787|GO:0006661| GO:0006796|GO:0031403| GO:0008934|GO:0042802 | THC2466293 | Hs.649234 |
| A_23_P380614 | ATP9A | Homo sapiens ATPase, class II, type 9A (ATP9A), mRNA [NM_006045] | NM_006045 | ENST00000338821 | 10079 | ATPase, class II, type 9A | chr20:5021341 8-50213359 | GO:0006754|GO:0000287|NM_006045 GO:0016787|GO:0016020| GO:0015914|GO:0000166| GO:0008152|GO:0004012| GO:0016820|GO:0016021| GO:0005524|GO:0015662 | THC2510679 | Hs.149363 |
| A_24_P130363 | C18orf1 | Homo sapiens chromosome 18 open reading frame 1 (C18orf1), transcript variant a2, mRNA [NM_181482] | NM_181482 | ENST00000359446 | 753 | chromosome 18 open reading frame 1 | chr18:1365255 0-13652609 | GO:0008150|GO:0003674|NM_181482 GO:0005886|GO:0016021 | THC2552483 | |
| A_33_P3264746 | | | | | | | chr22:0170113 55-017011414 | | | | |
| A_32_P4228 | | chromosome 20 open reading frame 61 [Source: HGNC Symbol; Acc: 16194] [ENST00000427835] | XR_109647 | ENST00000427835 | | | chr20:1179103 6-11790977 | | XR_109647 | THC2559950 | Hs 560990 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3417990 | VRK2 | Homo sapiens vaccinia related kinase 2 (VRK2), transcript variant 1, mRNA [NM_006296] | NM_006296 | ENST00000394539 | 7444 | vaccinia related kinase 2 | chr2:58373548-58373607 | GO:0005515\|GO:0046777\|GO:0016020\|GO:0000166\|GO:0005783\|GO:0004674\|GO:0005624\|GO:0016021\|GO:0005524\|GO:0016740 | NM_006296 | THC2485121 | Hs.728198 |
| A_33_P3255131 | KCTD19 | Homo sapiens potassium channel tetramerisation domain containing 19 (KCTD19), mRNA [NM_001100915] | NM_001100915 | ENST00000304372 | 146212 | potassium channel tetramerisation domain containing 19 | chr16:67323452-67323393 | GO:0005515\|GO:0016020\|GO:0008076\|GO:0005249\|GO:0006813 | NM_001100915 | THC2528087 | Hs.299127 |
| A_23_P217384 | AP1S2 | Homo sapiens adaptor-related protein complex 1, sigma 2 subunit (AP1S2), mRNA [NM_003916] | NM_003916 | ENST00000329235 | 8905 | adaptor-related protein complex 1, sigma 2 subunit | chrX:15844638-15844579 | GO:0005515\|GO:0030131\|GO:0005794\|GO:0006892\|GO:0031410\|GO:0006886\|GO:0005829\|GO:0006897\|GO:0005905\|GO:0016020\|GO:0008565\|GO:0030130\|GO:0016044 | NM_003916 | THC2618612 | Hs.653504 |
| A_24_P117942 | TOMM20L | Homo sapiens translocase of outer mitochondrial membrane 20 homolog (yeast)-like (TOMM20L), nuclear gene encoding mitochondrial protein, mRNA [NM_207377] | NM_207377 | ENST00000360945 | 387990 | translocase of outer mitochondrial membrane 20 homolog (yeast)-like | chr14:58874116-58874175 | GO:0005739\|GO:0016020\|GO:0005742\|GO:0016021\|GO:0006605 | NM_207377 | NP1214232 | Hs.592307 |
| A_23_P75867 | OR10A4 | Homo sapiens olfactory receptor, family 10, subfamily A, member 4 (OR10A4), mRNA [NM_207186] | NM_207186 | ENST00000379829 | 283297 | olfactory receptor, family 10, subfamily A, member 4 | chr11:6898050-6898109 | GO:0007608\|GO:0007165\|GO:0004984\|GO:0007186\|GO:0005886\|GO:0004872\|GO:0016021\|GO:0050896 | NM_207186 | THC2611959 | Hs.448685 |
| A_33_P3416366 | CHAF1A | Homo sapiens chromatin assembly factor 1, subunit A (p150) (CHAF1A), mRNA [NM_005483] | NM_005483 | ENST00000344143 | 10036 | chromatin assembly factor 1, subunit A (p150) | chr19:4431965-4432024 | GO:0006260\|GO:0007049\|GO:0006461\|GO:0006281\|GO:0005678\|GO:0003682\|GO:0006335\|GO:0005634\|GO:0051082\|GO:0045449\|GO:0006974 | NM_005483 | THC2515229 | Hs.79018 |
| A_33_P3385662 | | PREDICTED: Homo sapiens Golgin subfamily A member 8A-like (LOC644800), mRNA [XM_003118682] | XM_003118682 | | | | chr15:100332814-100332873 | | XM_003118682 | | Hs.730017 |
| A_33_P3409210 | | PREDICTED: Homo sapiens hypothetical protein LOC100509198 (LOC100509198), mRNA [XM_003119962] | XM_003119962 | ENST00000502514 | | | chr5:177378897-177378956 | | XM_003119962 | THC2696085 | Hs.710582 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3387562 | BCAP29 | Homo sapiens B-cell receptor-associated protein 29 (BCAP29), transcript variant 2, mRNA [NM_018844] | NM_018844 | ENST00000005259 | 55973 | B-cell receptor-associated protein 29 | chr7:107260832-107260891 | GO:0016020\|GO:0005783\|NM_018844 GO:0006915\|GO:0016021\| GO:0016192\|GO:0006886 | THC2519372 | Hs.303787 |
| A_23_P427217 | JMJD1C | Homo sapiens jumonji domain containing 1C (JMJD1C), transcript variant 1, mRNA [NM_032776] | NM_032776 | ENST00000542921 | 221037 | jumonji domain containing 1C | chr10:64928279-64928220 | GO:0046966\|GO:0005622\|NM_032776 GO:0005515\|GO:0006355\| GO:0005506\|GO:0016491\| GO:0008270\|GO:0005634\| GO:0016702\|GO:0046872\| GO:0055114\|GO:0016568 | THC2501681 | Hs.413416 |
| A_33_P3233038 | RBAK-LOC389458 | Homo sapiens RBAK-LOC389458 readthrough (RBAK-LOC389458), mRNA [NM_001204513] | NM_001204513 | ENST00000498308 | 100533952 | RBAK-LOC389458 readthrough | chr7:5112794-5112853 | | NM_001204513 | THC2464334 | Hs.396178 |
| A_33_P3259708 | CMA1 | Homo sapiens chymase 1, mast cell (CMA1), mRNA [NM_001836] | NM_001836 | ENST00000206446 | 1215 | chymase 1, mast roll | chr14:24974771-24974712 | GO:0005622\|GO:0004252\|NM_001836 GO:0050727\|GO:0006508\| GO:0008233\|GO:0005576\| GO:0050720 | THC2480549 | Hs.135626 |
| A_23_P17844 | PVALB | Homo sapiens parvalbumin (PVALB), mRNA [NM_002854] | NM_002854 | ENST00000404171 | 5816 | parvalbumin | chr22:37209739-37196953 | GO:0030424\|GO:0005737\|NM_002854 GO:0005509 | THC2464797 | Hs.295449 |
| A_33_P3387561 | OSCAR | Homo sapiens osteoclast associated, immunoglobulin-like receptor (OSCAR), transcript variant 1, mRNA [NM_206818] | NM_206818 | ENST00000391760 | 126014 | osteoclast associated, immunoglobulin-like receptor | chr19:54599098-54599039 | GO:0005886\|GO:0004872\|NM_206818 GO:0016021 | NP957263 | Hs.347655 |
| A_33_P3399268 | IL15RA | interleukin 15 receptor, alpha [Source: HGNC Symbol; Acc: 5978] [ENST00000379971] | | ENST00000379971 | 3601 | interleukin 15 receptor, alpha | chr10:5995250-5995191 | | | | |
| A_33_P3379763 | | | | | | | chr18:0121022 30-012102171 | | | | |
| A_33_P3312544 | GABRB1 | gamma-aminobutyric acid (GABA) A receptor, beta 1 [Source: HGNC Symbol; Acc: 4081] [ENST00000381582] | AK296023 | ENST00000381582 | 2560 | gamma-aminobutyric acid (GABA) A receptor, beta 1 | chr4:47034971-47035030 | | | | Hs.27283 |
| A_23_P135257 | PRSS3 | Homo sapiens protease, serine, 3 (PRSS3), transcript variant 2, mRNA [NM_002771] | NM_002771 | ENST00000477653 | 5646 | protease, serine, 3 | chr9:33797923-33797982 | GO:0005515\|GO:0004252\|NM_002771 GO:0043542\|GO:0007586\| GO:0005509\|GO:0006508\| GO:0008233\|GO:0005576\| GO:0005615\|GO:0031638 | THC2480679 | Hs.654513 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P935345 | | NNP6167 [Source: UniProtKB/TrEMBL; Acc: Q6UXV6] [ENST00000378432] | XM_003118774 | ENST00000378432 | | | chr19:40780795-40780736 | | XM_003118774 | THC2482404 | Hs.676497 |
| A_33_P3233055 | | UI-H-BW1-anr-f-12-0-UI.s1 NCI_CGAP_Sub7 Homo sapiens cDNA clone IMAGE: 3083302 3', mRNA sequence [BF515046] | BF515046 | | | | chr4:38664825-38664766 | | | | Hs.720773 |
| A_33_P3263319 | | immunoglobulin heavy constant gamma 3 (G3m marker) [Source: HGNC Symbol; Acc: 5527] [ENST00000390551] | AY172958 | ENST00000390551 | | | chr14:106235653-106235594 | | | NP594088 | Hs.510635 |
| A_33_P3378702 | | Homo sapiens cDNA FLJ45887 fis, clone OCBBF3021502. [AK127786] | AK127786 | | | | chr3:98622279-9862220 | | | | |
| A_33_P3324495 | ZFP41 | Homo sapiens zinc finger protein 41 homolog (mouse) (ZFP41), mRNA [NM_173832] | NM_173832 | ENST00000330701 | 286128 | zinc finger protein 41 homolog (mouse) | chr8:144344481-144344875 | GO:0005622\|GO:0008270\|GO:0007275\|GO:0005634\|GO:0007283\|GO:0003677\|GO:0046872\|GO:0045449\|GO:0030154 | NM_173832 | THC2498694 | Hs.668016 |
| A_33_P3327158 | LOC100131432 | Homo sapiens cDNA FLJ45862 fis, clone OCBBF3000830. [AK127761] | AK127761 | | 100131432 | hypothetical LOC100131432 | chr11:45073130-45073071 | | | THC2657439 | Hs.640116 |
| A_23_P128215 | SOCS2 | Homo sapiens suppressor of cytokine signaling 2 (SOCS2), mRNA [NM_003877] | NM_003877 | ENST00000549206 | 8835 | suppressor of cytokine signaling 2 | chr12:93969979-93969858 | GO:0005515\|GO:0007242\|GO:0005148\|GO:0005159\|GO:0005131\|GO:0007568\|GO:0043434\|GO:0060396\|GO:0006916\|GO:0001558\|GO:0007259\|GO:0005737\|GO:0008269\|GO:0019941\|GO:0005070\|GO:0009968\|GO:0032355 | NM_003877 | THC2495423 | Hs.485572 |
| A_24_P280497 | FBRSL1 | Homo sapiens fibrosin-like 1 (FBRSL1), mRNA [NM_001142641] | NM_001142641 | ENST00000261673 | 57666 | fibrosin-like 1 | chr12:133159754-133159813 | | NM_001142641 | THC2541094 | Hs.411138 |
| A_23_P212383 | SACM1L | Homo sapiens SAC1 suppressor of actin mutations 1-like (yeast) (SACM1L), mRNA [NM_014016] | NM_014016 | ENST00000455997 | 22908 | SAC1 suppressor of actin mutations 1-like (yeast) | chr3:45786011-45786070 | GO:0008150\|GO:0005794\|GO:0016787\|GO:0016020\|GO:0005783\|GO:0046856\|GO:0004437\|GO:0005789\|GO:0030176\|GO:0016021 | NM_014016 | THC2610192 | Hs.156509 |
| A_33_P3342569 | | Putative UPF0607 protein FLJ37424 | XM_001723085 | ENST00000359888 | | | chr10:31652256-31652197 | | XM_001723085 | THC2485807 | Hs.730227 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P48455 | AMN | [Source: UniProtKB/Swiss-Prot; Acc: Q8N9G6] [ENST00000359888] Homo sapiens amnionless homolog (mouse) (AMN), mRNA [NM_030943] | NM_030943 | ENST00000541086 | 81693 | amnionless homolog (mouse) | chr14:103397053-103397112 | GO:0007588\|GO:0008104\|NM_030943 GO:0016020\|GO:0045177\| GO:0007275\|GO:0016021 | THC2462398 | Hs.534494 |
| A_33_P3339202 | | | | | | | chr1:03197477 6-031974835 | | | | |
| A_23_P500271 | IRF5 | Homo sapiens interferon regulatory factor 5 (IRF5), transcript variant 3, mRNA [NM_001098627] | NM_001098627 | ENST00000412326 | 3663 | interferon regulatory factor 5 | chr7:128589323-128589382 | GO:0006355\|GO:0003700\|NM_001098627 GO:0005634 | THC2489805 | Hs.521181 |
| A_33_P3245133 | | | | | | | chr7:05643708 6-056437027 | | | | |
| A_23_P136870 | MAGEA6 | Homo sapiens melanoma antigen family A, 6 (MAGEA6), transcript variant 2, mRNA [NM_175868] | NM_175868 | ENST00000329342 | 4105 | melanoma antigen family A, 6 | chrX:151870169-151870228 | GO:0005515\|GO:0008150\|NM_175868 GO:0003674\|GO:0005575 | THC2461617 | Hs.441113 |
| A_33_P3246950 | | BX117927 Soares_NFL_T_GBC_Sl Homo sapiens cDNA clone IMAGE998E153901, mRNA sequence [BX117927] | BX117927 | ENST00000434321 | | | chr7:138940464-13894005 | | THC2685258 | Hs.127078 |
| A_33_P3265593 | LOC100132790 | Homo sapiens cDNA FLJ44869 fis, clone BRAMY2015516. [AK128756] | AK128756 | | 100132790 | hypothetical LOC100132790 | chr9:70348758-70348817 | | THC2481891 | |
| A_23_P87310 | LMO1 | Homo sapiens LIM domain only 1 (rhombotin 1) (LMO1), mRNA [NM_002315] | NM_002315 | ENST00000335790 | 4004 | LIM domain only 1 (rhombotin 1) | chr11:8245980-8245921 | GO:0003700\|GO:0008283\|NM_002315 GO:0008270\|GO:0007275\| GO:0005634\|GO:0046872 | THC2613726 | Hs.654426 |
| A_23_P325562 | SLC1A7 | Homo sapiens solute carrier family 1 (glutamate transporter), member 7 (SLC1A7), mRNA [NM_006671] | NM_006671 | ENST00000448036 | 6512 | solute carrier family 1 (glutamate transporter), member 7 | chr1:53552968-53552909 | GO:0016020\|GO:0005313\|NM_006671 GO:0006810\|GO:0006835\| GO:0017153\|GO:0016021\| GO:0015293 | THC2475068 | Hs.104637 |
| A_33_P3311621 | LOC338739 | Homo sapiens hypothetical LOC338739 (LOC338739), non-coding RNA [NR_034027] | NR_034027 | | 338739 | hypothetical LOC338739 | chr11:3321178 1-32211840 | | NR_034027 | THC2502233 | Hs.423476 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P324011 | KCTD2 | *Homo sapiens* potassium channel tetramerisation domain containing 2 (KCTD2), mRNA [NM_015353] | NM_015353 | ENST00000322444 | 23510 | potassium channel tetramerisation domain containing 2 | chr17:73061300-73061359 | GO:0005515\|GO:0016020\|GO:0008076\|GO:0005249\|GO:0006813 | NM_015353 | THC2538745 | Hs.514468 |
| A_24_P69439 | SLC25A32 | *Homo sapiens* solute carrier family 25, member 32 (SLC25A32), nuclear gene encoding mitochondrial protein, mRNA [NM_030780] | NM_030780 | ENST00000297578 | 81034 | solute carrier family 25, member 32 | chr8:104410937-104410878 | GO:0005739\|GO:0005215\|GO:0016020\|GO:0005488\|GO:0015884\|GO:0005743\|GO:0016021\|GO:0008517\|GO:0055085 | NM_030780 | THC2467509 | Hs.607819 |
| A_23_P62890 | GBP1 | *Homo sapiens* guanylate binding protein 1, interferon-inducible (GBP1), mRNA [NM_002053] | NM_002053 | ENST00000370473 | 2633 | guanylate binding protein 1, interferon-inducible | chr1:89518848-89518789 | GO:0005886\|GO:0000166\|GO:0003924\|GO:0005525 | NM_002053 | THC2468230 | Hs.62661 |
| A_33_P3252286 | CRLF1 | *Homo sapiens* cytokine receptorlike factor 1 (CRLF1), mRNA [NM_004750] | NM_004750 | ENST00000392386 | 9244 | cytokine receptor like factor 1 | chr19:18704107-1870404 | GO:0019955\|GO:0005576\|GO:0004872\|GO:0005615 | NM_004750 | THC2465094 | Hs.114948 |
| A_33_P3351351 | ARHGEF10 | Rho guanine nucleotide exchange factor (GEF) 10 [Source: HGNC Symbol; Acc: 14103] | BC040474 | ENST00000382795 | 9639 | Rho guanine nucleotide exchange factor (GEF) 10 | chr8:1806922-1806981 | | | THC2482286 | Hs.98594 |
| A_23_P215566 | AHR | *Homo sapiens* aryl hydrocarbon receptor (AHR), mRNA [NM_001621] | NM_001621 | ENST000242057 | 196 | aryl hydrocarbon receptor | chr7:17384999-17385058 | GO:0003700\|GO:0006366\|GO:0045899\|GO:0051879\|GO:0006950\|GO:0006915\|GO:0005634\|GO:0007165\|GO:0005737\|GO:0007049\|GO:0004879\|GO:0009410\|GO:0045893\|GO:0008134 | NM_001621 | THC2472989 | Hs.171189 |
| A_24_P190472 | SLPI | *Homo sapiens* secretory leukocyte peptidase inhibitor (SLPI), mRNA [NM_003064] | NM_003064 | ENST00000338380 | 6590 | secretory leukocyte peptidase inhibitor | chr20:4388227-43882220 | GO:0004867\|GO:0005576 | NM_003064 | THC2736360 | Hs.517070 |
| A_33_P3310296 | PKIG | protein kinase (cAMP-dependent, catalytic) inhibitor gamma [Source: HGNC Symbol; Acc: 9019] [ENST00000372887] | | ENST00000372887 | 11142 | protein kinase (cAMP-dependent, catalytic) inhibitor gamma | chr20:4325277-43252830 | | | | |
| A_24_P852756 | HLA-DQA2 | *Homo sapiens* major histocompatibility complex, class II, DQ | NM_020056 | ENST00000447735 | 3118 | major histocompatibility complex, class | chr6:32714597-32714656 | GO:0006955\|GO:0005886\|GO:0005887\|GO:0002504\|GO:0042613\|GO:0032395 | NM_020056 | THC2481749 | Hs.591798 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | alpha 2 (HLA-DQA2), mRNA [NM_020056] | | | | II DQ alpha 2 | | | | | |
| A_33_P3460043 | C8orf56 | Homo sapiens chromosome 8 open reading frame 56 (C8orf56), non-coding RNA [NR_027071] | NR_027071 | ENST00000436771 | 157556 | chromosome 8 open reading frame 56 | chr8:104145252-104145193 | | NR_027071 | THC2481642 | Hs.459124 |
| A_33_P3368109 | | Q6V5H5_9BRAS (Q6V5H5) Pollen coat oleosin-glycine rich protein, partial (13%) [THC2686826] | | | | | chr9:098982070-098982129 | | | THC2686826 | |
| A_33_P3363799 | NCAM1 | Homo sapiens neural cell adhesion molecule 1 (NCAM1), transcript variant 5, mRNA [NM_001242607] | NM_001242607 | ENST00000316851 | 4684 | neural cell adhesion molecule 1 | chr11:1131490 74-113149133 | GO:0005515\|GO:0030424\|NM_001242607 GO:0034109\|GO:0005886\| GO:0005576\|GO:0031225\| GO:0016021\|GO:0007155\| GO:0009897\|GO:0007166\| GO:0050850 | | THC2514411 | Hs.503878 |
| A_33_P3213767 | CCDC157 | Homo sapiens cDNA clone IMAGE: 4798973. [BC018040] | BC018040 | ENST00000399824 | 550631 | coiled-coil domain containing 157 | chr22:3076271 5-30762774 | | | THC2498791 | Hs.505597 |
| A_33_P3243439 | GPR162 | Homo sapiens G protein-coupled receptor 162 (GPR162), transcript variant 1, mRNA [NM_019858] | NM_019858 | ENST00000311268 | 27239 | G protein-coupled receptor 162 | chr12:6936523-6936582 | GO:0007165\|GO:0007186\|NM_019858 GO:0005886\|GO:0004930\| GO:0004872\|GO:0016021 | | THC2463040 | Hs.631654 |
| A_33_P3215640 | PI16 | Homo sapiens peptidase inhibitor 16 (PI16), transcript variant 1, mRNA [NM_153370] | NM_153370 | ENST00000373674 | 221476 | peptidase inhibitor 16 | chr6:36932552-36932611 | GO:0016020\|GO:0005576\|NM_153370 GO:0016021\|GO:0030414 | | THC2644566 | Hs.25391 |
| A_24_P178300 | PRR21 | Homo sapiens proline rich 21 (PRR21), mRNA [NM_001080835] | NM_001080835 | ENST00000486799 | 643905 | proline rich 21 | chr2:240981376-240981317 | | NM_001080835 | NP418173 | Hs.693479 |
| A_24_P301837 | HRH3 | Homo sapiens histamine receptor H3 (HRH3), mRNA [NM_007232] | NM_007232 | ENST00000370797 | 11255 | histamine receptor H3 | chr20:6079178 6-60791727 | GO:0014070\|GO:0005886\|NM_007232 GO:0014050\|GO:0014053\| GO:0045776\|GO:0007194\| GO:0004969\|GO:0007204\| GO:0007269\|GO:0008144\| GO:0043209\|GO:0007613\| GO:0004872\|GO:0007612\| GO:0019717\|GO:0050679\| GO:0014061\|GO:0004930 | | THC2603572 | Hs.251399 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P98022 | SIRT1 | Homo sapiens sirtuin 1 (SIRT1), transcript variant 1, mRNA [NM_012238] | NM_012238 | ENST00000432464 | 23411 | sirtuin 1 | chr10:69677560-69677619 | GO:0014063\|GO:0007165\|GO:0050890\|GO:0007420\|GO:0007187\|GO:0005887\|GO:0042756\|GO:0042755\|GO:0006344\|GO:0034339\|GO:0006343\|GO:0045599\|GO:0016811\|GO:0070403\|GO:0005634\|GO:0005635\|GO:0007283\|GO:0046872\|GO:0043433\|GO:0030154\|GO:0042802\|GO:0003950\|GO:0006471\|GO:0042393\|GO:0002039\|GO:0005737\|GO:0044419\|GO:0042127\|GO:0033158\|GO:0016481\|GO:0031937\|GO:0009267\|GO:0016575\|GO:0017136\|GO:0034983\|GO:0003714\|GO:0007569\|GO:0010904\|GO:0019213\|GO:0005730\|GO:0042981\|GO:0001542\|GO:0007275\|GO:0051097\|GO:0045768\|GO:0008022\|GO:0006974\|GO:0006260\|GO:0006281\|GO:0007517\|GO:0050872\|GO:0016605\|GO:0043518\|GO:0005654\|GO:0008270\|GO:0006642 | NM_012238 | THC2463434 | Hs.369779 |
| A_24_P62800 | KLHDC8A | Homo sapiens kelch domain containing 8A (KLHDC8A), mRNA [NM_018203] | NM_018203 | ENST00000539253 | 55220 | kelch domain containing 8A | chr1:205305747-205305688 | | NM_018203 | THC2644485 | Hs.10414 |
| A_24_P373768 | GIPR | Homo sapiens gastric inhibitory polypeptide receptor (GIPR), mRNA [NM_000164] | NM_000164 | ENST00000304207 | 2696 | gastric inhibitory polypeptide receptor | chr19:4618146 0-46184896 | GO:0016519\|GO:0007186\|GO:0005886\|GO:0007584\|GO:0016021\|GO:0007189\|GO:0006091\|GO:0007204 | NM_000164 | THC2485294 | Hs.658534 |
| A_23_P63313 | SLC16A11 | Homo sapiens solute carrier family 16, member 11 (monocarboxylic acid transporter 11) (SLC16A11), mRNA [NM_153357] | NM_153357 | ENST00000308009 | 162515 | solute carrier family 16, member 11 (monocarboxylic acid transporter 11) | chr17:6945224-6945165 | GO:0005886\|GO:0016021\|GO:0055085\|GO:0015 293 | NM_153357 | THC2479120 | Hs.336564 |
| A_23_P317347 | ESCO1 | Homo sapiens establishment of cohesion 1 homolog | NM_057911 | ENST00000383276 | 114799 | establishment of cohesion 1 homolog 1 | chr18:1910980 6-19109747 | GO:0003684\|GO:0007049\|GO:0006281\|GO:0003887\|GO:0008270\|GO:0005634 | NM_057911 | THC7490390 | Hs.464733 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | 1 (S. cerevisiae) (ESCO1), mRNA [NM_057311] | | | | (S. cerevisiae) | | GO:0046872|GO:0016740|GO:0008415 | | | |
| A_24_P309415 | TMEM123 | Homo sapiens transmembrane protein 123 (TMEM123), mRNA [NM_052932] | NM_052932 | ENST00000398136 | 114908 | transmembrane protein 123 | chr11:102267545-102267486 | GO:0016020|GO:0004872|NM_052932|GO:0016021|GO:0070267|GO:0009897 | | THC2536867 | Hs.503709 |
| A_33_P3380462 | GPR88 | Homo sapiens G protein-coupled receptor 88 (GPR88), mRNA [NM_022049] | NM_022049 | ENST00000315033 | 54112 | G protein-coupled receptor 88 | chr1:101005696-101005755 | GO:0007165|GO:0007186|NM_022049|GO:0005886|GO:0004930|GO:0004872|GO:0016021|GO:0005575 | | THC2478325 | Hs.170053 |
| A_24_P243396 | TCOF1 | Homo sapiens Treacher Collins-Franceschetti syndrome 1 (TCOF1), transcript variant 3, mRNA [NM_001008657] | NM_001008657 | ENST00000394269 | 6949 | Treacher Collins-Franceschetti syndrome 1 | chr5:149763654-149763713 | GO:0005515|GO:0005215|NM_001008657|GO:0001501|GO:0006810|GO:0005730|GO:0005634 | | THC2482504 | Hs.519672 |
| A_33_P3235360 | | | | | | | chr16:0053122 | | | | |
| A_33_P3760937 | LOC497256 | Homo sapiens cDNA FLJ37669 fis, clone BRHIP2011891. [AK094988] | AK094988 | | 497256 | hypothetical LOC497256 | 47-005312188 chr9:90459517-90459458 | | | THC2509358 | Hs.584108 |
| A_33_P3240679 | BRD3 | Homo sapiens bromodomain containing 3 [Source: HGNC Symbol; Acc: 1104] [ENST00000371842] | | ENST00000371842 | 8019 | bromodomain containing 3 | chr1:136021094-136921035 | | | THC2757877 | |
| A_33_P3365002 | TUBB2A | Homo sapiens tubulin, beta 2A (TUBB2A), mRNA [NM_001069] | NM_001069 | ENST00000489942 | 7280 | tubulin, beta 2A | chr6:3154964-3154905 | GO:0005515|GO:0051258|NM_001069|GO:0007067|GO:0000166|GO:0005198|GO:0030182|GO:0005874|GO:0003924|GO:0005525|GO:0007018 | | THC2558431 | Hs.654543 |
| A_24_P296070 | COG3 | Homo sapiens component of oligomeric golgi complex 3 (COG3), mRNA [NM_031431] | NM_031431 | ENST00000349995 | 83548 | component of oligomeric golgi complex 3 | chr13:46110179-46110238 | GO:0005515|GO:0005801|NM_031431|GO:0005794|GO:0033365|GO:0006891|GO:0050821|GO:0006888|GO:0016020|GO:0006865|GO:0017119|GO:0008486|GO:0019898 | | NP1155335 | Hs.507948 |
| A_24_P339514 | CYP2B6 | Homo sapiens cytochrome P450, family 2, subfamily B, polypeptide 6 (CYP2B6), mRNA [NM_000767] | NM_000767 | ENST00000324071 | 1555 | cytochrome P450, family 2, subfamily B, polypeptide 6 | chr19:41524193-41524252 | GO:0005792|GO:0070330|NM_000767|GO:0019825|GO:0016020|GO:0005783|GO:0005789|GO:0009055|GO:0046872|GO:0055114|GO:0020037|GO:0019898 | | THC2479074 | Hs.1360 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P145006 | SCGB3A2 | *Homo sapiens* secretoglobin, family 3A, member 2 (SCGB3A2), mRNA [NM_054023] | NM_054023 | ENST00000507160 | 117156 | secretoglobin, family 3A, member 2 | chr5:14726166 2-147261721 | GO:0005515\|GO:0005576 | NM_054023 | THC2472125 | Hs.483765 |
| A_33_P3410849 | C8orf58 | *Homo sapiens* chromosome 8 open reading frame 58 (C8orf58), transcript variant 1, mRNA [NM_001013842] | NM_001013842 | ENST00000381191 | 541565 | chromosome 8 open reading frame 58 | chr8:22460863-22460922 | | NM_001013842 | THC2609844 | Hs.730863 |
| A_33_P3227217 | SNORA81 | *Homo sapiens* small nucleolar RNA, H/ACA box 81 (SNORA81), small nucleolar RNA [NR_002989] | NR_002989 | ENST00000475409 | 677847 | small nucleolar RNA, H/ACA box 81 | chr3:18650458 2-186504641 | | NR_002989 | THC2509600 | Hs.688848 |
| A_23_P18372 | B3GNT5 | *Homo sapiens* UDP-GlcNAc:betaGal beta-1,3-N-acetylglucos-aminyl-transferase 5 (B3GNT5), mRNA [NM_032047] | NM_032047 | ENST00000326505 | 84002 | UDP-GlcNAc: betaGal beta-1,3-N-acetylgluco-saminyl-transferase 5 | chr3:18299093 3-182990992 | GO:0005622\|GO:0009247\|GO:0005794\|GO:0016020\|GO:0016757\|GO:0008457\|GO:0007275\|GO:0006486\|GO:0016021\|GO:0008917\|GO:0007417\|GO:0008378 | NM_032047 | THC2462855 | Hs.718506 |
| A_23_P207336 | PPY | *Homo sapiens* pancreatic polypeptide (PPY), mRNA [NM_002722] | NM_002722 | ENST00000225992 | 5539 | pancreatic polypeptide | chr17:4201851 2-42018263 | GO:0009306\|GO:0001664\|GO:0005179\|GO:0007586\|GO:0005576 | NM_002722 | THC2463069 | Hs.730974 |
| A_33_P3376762 | LOC388152 | *Homo sapiens* hypothetical LOC388152 (LOC388152), non-coding RNA [NR_027001] | NR_027001 | ENST00000442755 | 388152 | hypothetical LOC388152 | chr15:8487365 9-84873600 | | NR_027001 | THC2489238 | Hs.546614 |
| A_23_P420942 | | metallothionein 1E [Source: HGNC Symbol; Acc: 7397] [ENST00000330439] | AF495759 | ENST00000330439 | | | chr16:5666061 4-56660673 | | | THC2476324 | |
| A_23_P113237 | CRLF2 | *Homo sapiens* cytokine receptor-like factor 2 (CRLF2), transcript variant 2, mRNA [NM_001012288] | NM_001012288 | ENST00000400841 | 64109 | cytokine receptor-like factor 2 | chrX:1321318-1317569 | GO:0005886\|GO:0005576\|GO:0004872\|GO:0016021 | NM_001012288 | THC2484352 | Hs.287729 |
| A_33_P3326423 | POLL | *Homo sapiens* polymerase (DNA directed), lambda (POLL), transcript variant 1, mRNA [NM_001174084] | NM_001174084 | ENST00000370162 | 27343 | polymerase (DNA directed), lambda | chr10:1033387 81-103338722 | GO:0030145\|GO:0003887\|GO:0016779\|GO:0005634\|GO:0016446\|GO:0003677\|GO:0006974\|GO:0016829\|GO:0046872\|GO:0005622 | NM_001174084 | THC2585456 | Hs.523230 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3324894 | | huntingtin interacting protein 1 related [Source: HGNC Symbol; Acc: 18415] [ENST00000376938] [NM_001174084] | AK130532 | ENST00000376938 | | | chr12:1233345 93-123334652 | GO:0006260\|GO:0006289\| GO:0016740 | | THC2487969 | |
| A_33_P3352349 | KRTAP9-1 | Homo sapiens keratin associated protein 9-1 (KRTAP9-1), mRNA [NM_001190460] | NM_001190460 | ENST00000377723 | 728318 | keratin associated protein 9-1 | chr17:3934676 7-39346826 | | NM_001190460 | | Hs.727478 |
| A_23_P309224 | AGK | Homo sapiens acylglycerol kinase (AGK), nuclear gene encoding mitochondrial protein, mRNA [NM_018238] | NM_018238 | ENST00000355413 | 55750 | acylglycerol kinase | chr7:14135318 4-141135243 | GO:0005739\|GO:0031966\|NM_018238 GO:0016020\|GO:0000166\| GO:0004143\|GO:0047620\| GO:0046834\|GO:0005524\| GO:0016740\|GO:0007205\| GO:0001729 | | THC2466706 | Hs.730694 |
| A_33_P3242355 | | Homo sapiens cDNA clone IMAGE:5200632, partial cds. [BC027847] | BC027847 | | | | chr10:1351379 70-135137911 | | | THC2610223 | Hs.551860 |
| A_23_P11652 | USP1 | Homo sapiens ubiquitin specific peptidase 1 (USP1), transcript variant 1, mRNA [NM_003368] | NM_003368 | ENST00000371146 | 7398 | ubiquitin specific peptidase 1 | chr1:62917270-62917329 | GO:0005515\|GO:0004197\|NM_003368 GO:0006511\|GO:0016579\| GO:0004843\|GO:0006282\| GO:0008233\|GO:0005654\| GO:0005634\|GO:0004221\| GO:0009411\|GO:0006974 | | NP1179127 | Hs.35086 |
| A_32_P159192 | | immunoglobulin kappa variable 3-7 (non-functional) [Source: HGNC Symbol; Acc: 5821] [ENST00000390247] | X85155 | ENST00000390247 | | | chr2:89278046-89277987 | | | | Hs.449621 |
| A_23_P318581 | KIAA1430 | Homo sapiens KIAA1430 (KIAA1430), mRNA [NM_020827] | NM_020827 | ENST00000458385 | 57587 | KIAA1430 | chr4:18608146 2-186081403 | | NM_020827 | THC2502160 | Hs.535734 |
| A_33_P3229067 | HIST1H2BN | Homo sapiens histone cluster 1, H2bn (HIST1H2BN), mRNA [NM_003520] | NM_003520 | ENST00000396980 | 8341 | histone cluster 1, H2bn | chr6:27806454-27806513 | GO:0005694\|GO:0006334\|NM_003520 GO:0005634\|GO:0000786\| GO:0003677 | | THC2481405 | Hs.673851 |
| A_23_P113005 | EFNA1 | Homo sapiens ephrin-A1 (EFNA1), transcript variant 1, mRNA [NM_004428] | NM_004428 | ENST00000469878 | 1942 | ephrin-A1 | chr1:15510676 7-155106826 | GO:0000187\|GO:0048013\|NM_004428 GO:0046875\|GO:0005886\| GO:0005887\|GO:0030182\| GO:0007267\|GO:0031225\| GO:0050770 | | THC2506968 | Hs.516664 |
| A_33_P3337009 | PPCS | phosphopanto-thenoylcysteine synthetase [Source: HGNC | | ENST00000372560 | 79717 | phosphopanto-thenoylcysteine synthetase | chr1:42923068-42923127 | | | THC2535535 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P81262 | PCDHB4 | *Homo sapiens* protocadherin beta 4 (PCDHB4), mRNA [NM_018938] Symbol; Acc: 25686 [ENST00000372560] | NM_018938 | ENST00000194152 | 56131 | protocadherin beta 4 | chr5:140504410-140504469 | GO:0016339 GO:0005515 GO:0005737 GO:0005886 GO:0005887 GO:0005509 GO:0007268 GO:0007155 GO:0007416 GO:0007156 | NM_018938 | THC2491639 | Hs.591250 |
| A_23_P58729 | SLC34A1 | *Homo sapiens* solute carrier family 34 (sodium phosphate), member 1 (SLC34A1), transcript variant 1, mRNA [NM_003052] | NM_003052 | ENST00000513614 | 6569 | solute carrier family 34 (sodium phosphate), member 1 | chr5:176825668-176825727 | GO:0010288 GO:0055062 GO:0031526 GO:0031402 GO:0015321 GO:0016020 GO:0046849 GO:0005887 GO:0006817 GO:0006814 GO:0046689 GO:0046686 GO:0006811 GO:0015293 | NM_003052 | THC2605001 | Hs.936 |
| A_23_P135730 | ZNF627 | *Homo sapiens* zinc finger protein 627 (ZNF627), mRNA [NM_145295] | NM_145295 | ENST00000361113 | 199692 | zinc finger protein 627 | chr19:11729303-11729362 | GO:0005622 GO:0006355 GO:0008270 GO:0005634 GO:0003677 GO:0046872 | NM_145295 | THC2618823 | Hs.526665 |
| A_33_P3322634 | C19orf69 | *Homo sapiens* chromosome 19 open reading frame 69 (C19orf69), mRNA [NM_001130514] | NM_001130514 | ENST00000378187 | 100170765 | chromosome 19 open reading frame 69 | chr19:4195007-0-41950129 | | NM_001130514 | | Hs.649452 |
| A_33_P3263423 | TLR5 | *Homo sapiens* toll-like receptor 5 (TLR5), mRNA [NM_003268] | NM_003268 | ENST00000407096 | 7100 | toll-like receptor 5 | chr1:223305886-223305827 | GO:0005515 GO:0007165 GO:0005149 GO:0006954 GO:0005886 GO:0045087 GO:0007249 GO:0016021 GO:0004888 | NM_003268 | THC2626166 | Hs.604542 |
| A_23_P73780 | IRAK1 | *Homo sapiens* interleukin-1 receptor-associated kinase 1 (IRAK1), transcript variant 1, mRNA [NM_001569] | NM_001569 | ENST00000393682 | 3654 | interleukin-1 receptor-associated kinase 1 | chrX:153276900-153276841 | GO:0016563 GO:0051259 GO:0042803 GO:0005829 GO:0045323 GO:0004704 GO:0045941 GO:0046777 GO:0051092 GO:0000166 GO:0002755 GO:0032496 GO:0007178 GO:0031663 GO:0070555 GO:0070498 GO:0005149 GO:0000287 GO:0007250 GO:0046982 GO:0034134 GO:0006916 GO:0032088 GO:0005524 GO:0007165 GO:0001959 GO:0004674 GO:0016740 | NM_001569 | THC2539008 | Hs.522819 |
| A_23_P408955 | E2F2 | *Homo sapiens* E2F transcription factor 2 (E2F2), mRNA [NM_004091] | NM_004091 | ENST00000361729 | 1870 | E2F transcription factor 2 | chr1:23832992-23832933 | GO:0005667 GO:0006355 GO:0006367 GO:0003700 GO:0003702 GO:0051726 GO:0006915 GO:0005654 GO:0005634 GO:0008134 | NM_004091 | THC2471250 | Hs.194333 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3351259 | LOC100130560 | Homo sapiens cDNA FLJ45554 fis, clone BRTHA2038353. [AK127462] | AK127462 | | 100130560 | hypothetical protein LOC100130560 | chr15:90910744-90910803 | | | THC2485942 | Hs.711988 |
| A_24_P143076 | FAM109A | Homo sapiens family with sequence similarity 109, member A (FAM109A), transcript variant 2, mRNA [NM_144671] | NM_144671 | ENST00000450786 | 144717 | family with sequence similarity 109, member A | chr12:111799200-111799141 | | NM_144671 | THC2491205 | Hs.173088 |
| A_33_P3271316 | RPP25 | Homo sapiens ribonuclease P/MRP 25 kDa subunit (RPP25), mRNA [NM_017793] | NM_017793 | ENST00000322177 | 54913 | ribonuclease P/MRP 25 kDa subunit | chr15:75247515-75247456 | GO:0005515\|GO:0016787\|GO:0004526\|GO:0003723\|GO:0005634\|GO:0008033 | NM_017793 | THC2616120 | Hs.8562 |
| A_24_P402836 | ZNF141 | Homo sapiens zinc finger protein 141 (ZNF141), mRNA [NM_003441] | NM_003441 | ENST00000240499 | 7700 | zinc finger protein 141 | chr4:367324-367383 | GO:0005622\|GO:0006355\|GO:0003704\|GO:0008270\|GO:0005634\|GO:0009653\|GO:0003677\|GO:0046872 | NM_003441 | THC2597064 | Hs.654355 |
| A_24_P1054 | TONSL | Homo sapiens tonsoku-like, DNA repair protein (TONSL), mRNA [NM_013432] | NM_013432 | ENST00000422691 | 4796 | tonsoku-like, DNA repair protein | chr8:145663855-145662425 | GO:0005515\|GO:0005737\|GO:0003714\|GO:0042994 | NM_013432 | THC2478718 | Hs.675285 |
| A_23_P140760 | GPR97 | Homo sapiens G protein-coupled receptor 97 (GPR97), mRNA [NM_170776] | NM_170776 | ENST00000450388 | 222487 | G protein-coupled receptor 97 | chr16:57719826-57722310 | GO:0005886\|GO:0007218\|GO:0004930\|GO:0016021 | NM_170776 | THC2474792 | Hs.383403 |
| A_33_P3233700 | LOC100128675 | Homo sapiens hypothetical LOC100128675 (LOC100128675), transcript variant 1, non-coding RNA [NR_024561] | NR_024561 | | 100128675 | hypothetical LOC100128675 | chr19:35566138-35566079 | | NR_024561 | THC2488071 | Hs.633989 |
| A_33_P3383606 | KCP | Homo sapiens kielin/chordin-like protein (KCP), transcript variant 1, mRNA [NM_001135914] | NM_001135914 | ENST00000476647 | 375616 | kielin/chordin-like protein | chr7:128516990-128516931 | GO:0005515\|GO:0030513\|GO:0005576\|GO:0005615 | NM_001135914 | THC2609353 | Hs.371746 |
| A_33_P3339531 | CHADL | Homo sapiens chondroadherin-like (CHADL), mRNA [NM_138481] | NM_138481 | ENST00000216241 | 150356 | chondroadherin-like | chr22:41625598-41625539 | GO:0005515\|GO:0005578\|GO:0005576 | NM_138481 | THC2630437 | Hs.344488 |
| A_23_P133338 | CDHR2 | Homo sapiens cadherin-related family member 2 (CDHR2), transcript | NM_017675 | ENST00000416365 | 54825 | cadherin-related family member 2 | chr5:176017621-176017680 | GO:0005515\|GO:0030308\|GO:0030054\|GO:0005886\|GO:0005509\|GO:0016021\|GO:0007155\|GO:0007156 | NM_017675 | THC2476495 | Hs.4205 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3227934 | LOC100130430 | Homo sapiens cDNA FLJ45052 fis, clone BRAWH3022542. [AK126997] | AK126997 | | 100130430 | hypothetical LOC100130430 | chr16:1358740-1358681 | | | THC2488009 | |
| A_24_P390495 | CX3CL1 | Homo sapiens chemokine (C-X3-C motif) ligand 1 (CX3CL1), mRNA [NM_002196] | NM_002996 | ENST00000006053 | 6376 | chemokine (C-X3-C motif) ligand 1 | chr16:57418025-57418084 | GO:0008009\|GO:0005886\|NM_002996 GO:0009986\|GO:0030595\| GO:0019221\|GO:0005576\| GO:0006952\|GO:0005615\| GO:0050902\|GO:0051041\| GO:0006955\|GO:0006935\| GO:0050729\|GO:0016021\| GO:0007155 | | THC2692786 | Hs.531668 |
| A_23_P84995 | MTMR8 | Homo sapiens myotubularin related protein 8 (MTMR8), mRNA [NM_017677] | NM_017677 | ENST00000247400 | 55613 | myotubularin related protein 8 | chrX:63548765-63548706 | GO:0016791\|GO:0016787\|NM_017677 GO:0016311\|GO:0005634\| GO:0005635\|GO:0004725 | | THC2479596 | Hs.442892 |
| A_24_P79070 | GNG8 | Homo sapiens guanine nucleotide binding protein (G protein), gamma 8 (GNG8), mRNA [NM_033258] | NM_033258 | ENST00000300873 | 94235 | guanine nucleotide binding protein (G protein), gamma 8 | chr19:47137404-47137345 | GO:0007165\|GO:0009755\|NM_033258 GO:0007186\|GO:0005886\| GO:0005834\|GO:0003924\| GO:0005576\|GO:0004871\| GO:0007399 | | THC2743270 | Hs.283961 |
| A_33_P3249818 | CEACAM18 | Homo sapiens carcinoembryonic antigen-related cell adhesion molecule 18 (CEACAM18), mRNA [NM_001080405] | NM_001080405 | ENST00000451626 | 729767 | carcinoembryonic antigen-related cell adhesion molecule 18 | chr19:51986352-51986411 | GO:0016020\|GO:0016021 | NM_001080405 | | Hs.653111 | |
| A_33_P3289848 | CDX1 | Homo sapiens caudal type homeobox 1 (CDX1), mRNA [NM_001804] | NM_001804 | ENST00000394298 | 1044 | caudal type homeobox 1 | chr5:149563184-149563243 | GO:0043565\|GO:0007389\|NM_001804 GO:0006355\|GO:0003700\| GO:0045944\|GO:0009887\| GO:0005634\|GO:0009952 | | THC2474742 | Hs.1545 |
| A_32_P134290 | ZCCHC2 | Homo sapiens zinc finger, CCHC domain containing 2 (ZCCHC2), mRNA [NM_017742] | NM_017742 | ENST00000269499 | 54877 | zinc finger, CCHC domain containing 2 | chr18:60245525-60245584 | GO:0005515\|GO:0005737\|NM_017742 GO:0007154\|GO:0008270\| GO:0035091\|GO:0003676\| GO:0046872 | | THC2470691 | Hs.114191 |
| A_23_P86801 | RAPSN | Homo sapiens receptor-associated protein of the synapse (RAPSN), transcript variant 2, mRNA [NM_032645] | NM_032645 | ENST00000352508 | 5913 | receptor-associated protein of the synapse | chr11:47464364-47464305 | GO:0005515\|GO:0005737\|NM_032645 GO:0031594\|GO:0030054\| GO:0005794\|GO:0005886\| GO:0045211\|GO:0033130\| GO:0007268\|GO:0008270\| GO:0005856\|GO:0046872 | | NP091080 | Hs.81218 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P50799 | OR10H2 | Homo sapiens olfactory receptor, family 10, subfamily H, member 2 (OR10H2), mRNA [NM_013939] | NM_013939 | ENST00000305899 | 26538 | olfactory receptor, family 10, subfamily H, member 2 | chr19:15839700-15839759 | GO:0007608\|GO:0007165\|NM_013939 GO:0004984\|GO:0007186\| GO:0005886\|GO:0004872\| GO:0016021\|GO:0050896 | THC2481403 | Hs.247694 |
| A_33_P3304819 | | | | | | | chr7:105258244-105258303 | | | | Hs.208358 |
| A_33_P3258747 | C21orf63 | Homo sapiens chromosome 21 open reading frame 63 (C21orf63), mRNA [NM_058187] | NM_058187 | ENST00000469079 | 59271 | chromosome 21 open reading frame 63 | chr21:33785261-33785320 | GO:0016020\|GO:0005529\|NM_058187 GO:0016021 | NP650911 | |
| A_23_P21230 | TRIM37 | Homo sapiens tripartite motif containing 37 (TRIM37), transcript variant 1, mRNA [NM_015294] | NM_015294 | ENST00000262294 | 4591 | tripartite motif containing 37 | chr17:57076170-57076117 | GO:0005622\|GO:0005515\|NM_010204 GO:0048471\|GO:0005737\| GO:0005270\|GO:0040872\| GO:0005777 | THC2466521 | Hs 579079 |
| A_33_P3411325 | | Q8IVL_HUMAN (Q8IVL5) Leprecan-like 1 protein, partial (3%) [THC2668129] | | | | | chr16:03225276303-032252704 | | THC2668129 | | |
| A_33_P3276142 | DNM1P46 | Homo sapiens DNM1 pseudogene 46 (DNM1P46), non-coding RNA [NR_003260] | NR_003260 | ENST00000448059 | 196968 | DNM1 pseudogene 46 | chr15:10034000038-100339979 | | NR_003260 | THC2593283 | Hs.567763 |
| A_33_P3374117 | | anoctamin 7-like 1 [Source: HGNC Symbol; Acc: 32248] [ENST00000475369] | BU656309 | ENST00000475369 | | | chr1:16543682-16543623 | | | THC2713054 | Hs.162595 |
| A_24_P62695 | | immunoglobulin kappa variable 1-16 [Source: HGNC Symbol; Acc: 57321] [ENST00000479981] | AF078945 | ENST00000479981 | | | chr2:89399588-89399529 | | | NP074934 | Hs.649954 |
| A_23_P77980 | SLC4A1 | Homo sapiens solute carrier family 4, anion exchanger, member 1 (erythrocyte membrane protein band 3, Diego blood group) (SLC4A1), mRNA [NM_000342] | NM_000342 | ENST00000262418 | 6521 | solute carrier family 4, anion exchanger, member 1 (erythrocyte membrane protein band 3, Diego blood group) | chr17:42328567-42327888 | GO:0006820\|GO:0005215\|NM_000342 GO:0008509\|GO:0030018\| GO:0003779\|GO:0006873\| GO:0042803\|GO:0008022\| GO:0005452\|GO:0016323\| GO:0005887\|GO:0016020\| GO:0043495\|GO:0030863 | THC2474664 | Hs.443948 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3391387 | LOC100268168 | *Homo sapiens* hypothetical LOC100268168 (LOC100268168), transcript variant 1, non-coding RNA [NR_026682] | NR_026682 | | 100268168 | hypothetical LOC100268168 | chr5:172382521-172382462 | | NR_026682 | THC2484612 | |
| A_33_P3454968 | LOC645553 | *Homo sapiens* cDNA clone IMAGE: 5478640, partial cds. [BC062328] | BC062328 | | 645553 | hypothetical LOC645553 | chr19:46692429-46692370 | | | THC2502232 | Hs.613068 |
| A_23_P82959 | FOXH1 | *Homo sapiens* forkhead box H1 (FOXH1), mRNA [NM_003923] | NM_003923 | ENST00000292541 | 8928 | forkhead box H1 | chr8:145699649-145699590 | GO:0048318\|GO:0007368\|NM_003923 GO:0003700\|GO:0016563\| GO:0019904\|GO:0035054\| GO:0070412\|GO:0005634\| GO:0000122\|GO:0032444\| GO:0043565\|GO:0045941\| GO:0045944\|GO:0007179 | | THC2479690 | Hs.708365 |
| A_23_P125204 | OR10G8 | *Homo sapiens* olfactory receptor, family 10, subfamily G, member 8 (OR10G8), mRNA [NM_001004464] | NM_001004464 | ENST00000431524 | 219869 | olfactory receptor, family 10, subfamily G, member K | chr11:123901115-123901174 | GO:0007608\|GO:0007165\|NM_001004464 GO:0004984\|GO:0007186\| GO:0005886\|GO:0004872\| GO:0016021\|GO:0050896 | | | Hs.553635 |
| A_33_P3315899 | | | | | | | chr20:01931930-019193071 | | | | |
| A_33_P3295838 | C17orf53 | *Homo sapiens* chromosome 17 open reading frame 53 (C17orf53), transcript variant 2, mRNA [NM_001171251] | NM_001171251 | ENST00000253405 | 78995 | chromosome 17 open reading frame 53 | chr17:42225966-42226025 | | NM_001171251 | THC2488121 | Hs.437059 |
| A_33_P3332627 | | | | | | | chr7:057245525-057245466 | | | | |
| A_33_P3253440 | PQLC3 | *Homo sapiens* PQ loop repeat containing 3 (PQLC3), mRNA [NM_152391] | NM_152391 | ENST00000487471 | 130814 | PQ loop repeat containing 3 | chr2:11318091-11318150 | GO:0016020\|GO:0016021 | NM_152391 | THC2553661 | Hs.274415 |
| A_23_P202988 | AASDHPPT | *Homo sapiens* aminoadipate-semialdehyde dehydrogenase-phosphopantetheinyl transferase (AASDHPPT), mRNA [NM_015423] | NM_015423 | ENST00000534152 | 60496 | aminoadipate-semialdehyde dehydrogenase-phosphopantetheinyl transferase | chr11:105968976-105969035 | GO:0005515\|GO:0005737\|NM_015423 GO:0000287\|GO:0009059\| GO:0008897\|GO:0016740\| GO:0005829 | | THC2469513 | Hs.524009 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3334895 | GRIN2A | Homo sapiens glutamate receptor, ionotropic, N-methyl D-aspartate 2A (GRIN2A), transcript variant 3, mRNA [NM_001134408] | NM_001134408 | ENST00000396575 | 2903 | glutamate receptor, ionotropic, N-methyl D-aspartate 2A | chr16:9857277-9857218 | GO:0043005\|GO:0030054\|GO:0005886\|GO:0045471\|GO:0005234\|GO:0017146\|GO:0045202\|GO:0022843\|GO:0001964\|GO:0042417\|GO:0008104\|GO:0048167\|GO:0004972\|GO:0045211\|GO:0048169\|GO:0042165\|GO:0006816\|GO:0004872\|GO:0007613\|GO:0019717\|GO:0050839\|GO:0006811\|GO:0022008\|GO:0005262\|GO:0043065\|GO:0000287\|GO:0042177\|GO:0033058\|GO:0042493\|GO:0005509\|GO:0060079\|GO:0009611\|GO:0014069\|GO:0030431\|GO:0042734\|GO:0004428\|GO:0035235\|GO:0001975\|GO:0005887\|GO:0008542\|GO:0048511\|GO:0001508\|GO:0016395\|GO:0051930 | NM_001134408 | THC2475567 | Hs.411472 |
| A_33_P3291567 | TSNARE1 | Homo sapiens t-SNARE domain containing 1 (TSNARE1), mRNA [NM_145003] | NM_145003 | ENST00000307180 | 203062 | t-SNARE domain containing 1 | chr8:143310898-143310839 | GO:0005515\|GO:0016020\|GO:0016021\|GO:0016192 | NM_145003 | THC2478827 | Hs.370931 |
| A_33_P3314974 | LOC100130522 | Homo sapiens hypothetical LOC100130522 (LOC100130522), transcript variant 1, non coding RNA [NR_028339] | NR_028339 | | 100130522 | hypothetical LOC100130522 | chr18:7792042-77920485 | | NR_028339 | THC2628455 | Hs.352602 |
| A_33_P3315824 | | | | | | | chr10:0022643-49-002264408 | | | | |
| A_33_P3269678 | LOC541471 | Homo sapiens hypothetical LOC541471 (LOC541471), transcript variant 1, non-coding RNA [NR_015395] | NR_015395 | | 541471 | hypothetical LOC541471 | chr2:11212464-6-11212587 | | NR_015395 | THC2609308 | |
| A_33_P3298750 | | Homo sapiens cDNA clone IMAGE:3463076. [BC012881] | BC012881 | | | | chr20:4731953-7-47319596 | | | THC2488638 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3384958 | LPPR4 | *Homo sapiens* lipid phosphate phosphatase-related protein type 4 (LPPR4), transcript variant 1, mRNA [NM_014839] | NM_014839 | ENST00000263178 | 9890 | lipid phosphate phosphatase-related protein type 4 | chr1:99771632-99771691 | GO:0042577\|GO:0016787\|GO:0016020\|GO:0046839\|GO:0005887\|GO:0008195\|GO:0007409\|GO:0009897 | NM_014839 | NP1249191 | Hs.13245 |
| A_24_P80338 | NEK4 | *Homo sapiens* NIMA (never in mitosis gene a)-related kinase 4 (NEK4), transcript variant 1, mRNA [NM_003157] | NM_003157 | ENST00000233027 | 6787 | NIMA (never in mitosis gene a)-related kinase 4 | chr3:52744873-52744814 | GO:0007067\|GO:0007049\|GO:0000287\|GO:0000166\|GO:0004674\|GO:0005730\|GO:0006468\|GO:0005634\|GO:0005524\|GO:0016740\|GO:0051301 | NM_003157 | THC2467290 | Hs.631921 |
| A_23_P100220 | ESRP2 | *Homo sapiens* epithelial splicing regulatory protein 2 (ESRP2), mRNA [NM_024939] | NM_024939 | ENST00000251366 | 80004 | epthelial splicing regulatory protein 2 | chr16:6826311 3-68263054 | GO:0006397\|GO:0000166\|GO:0043484\|GO:0005634\|GO:0003729 | NM_024939 | THC2464692 | Hs.592053 |
| A_33_P3392740 | AToH8 | *Homo sapiens* mRNA; cDNA DKFZp761E2117 (from clone DKFZp761E2117). [AL831857] | AL831857 | ENST00000463422 | 84913 | atonal homolog 8 (*Drosophila*) | chr2:85999972-86000031 | | | THC2601465 | Hs.135569 |
| A_33_P3251901 | APBB2 | *Homo sapiens* amyloid beta (A4) precursor protein-binding, family B, member 2 (APBB2), transcript variant 1, mRNA [NM_004307] | NM_004307 | ENST00000316212 | 323 | amyloid beta (A4) precursor protein-binding, family B, member 2 | chr4:40812316-40812257 | GO:0007242\|GO:0043066\|GO:0030308\|GO:0043065\|GO:0045202\|GO:0005634\|GO:0045749\|GO:0030027\|GO:0030426\|GO:0005737\|GO:0001540\|GO:0016020\|GO:0007411\|GO:0030198\|GO:0007050\|GO:0001764\|GO:0045449\|GO:0008134 | NM_004307 | THC2536043 | Hs.479602 |
| A_24_P181422 | CATSPER2 | *Homo sapiens* cation channel, sperm associated 2 (CATSPER2), transcript variant 4, mRNA [NM_172097] | NM_172097 | ENST00000415968 | 117155 | cation channel, sperm associated 2 | chr15:4393190 8-43931849 | GO:0005515\|GO:0005262\|GO:0007283\|GO:0055085\|GO:0030154\|GO:0019861\|GO:0005929\|GO:0006816\|GO:0016021\|GO:0006811 | NM_172097 | THC2475220 | Hs.662284 |
| A_33_P3403494 | LOC646743 | *Homo sapiens* hypothetical LOC646743 (LOC646743), non-coding RNA [NR_033930] | NR_033930 | ENST00000414595 | 646743 | hypothetical LOC646743 | chr2:13129599 9-131295940 | | NR_033930 | THC2606454 | Hs.125706 |
| A_23_P57118 | TGM3 | *Homo sapiens* transglutaminase 3 (E polypeptide, | NM_003245 | ENST00000381458 | 7053 | transgluta-minase 3 (E polypeptide, | chr20:2320506-2320565 | GO:0051262\|GO:0000287\|GO:0016746\|GO:0005509\|GO:0031424\|GO:0003924 | NM_003245 | THC2474581 | Hs.2022 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P163567 | | protein-glutamine-gamma-glutamyltrans-ferase (TGM3), mRNA [NM_003245] | | | | protein-glutamine-gamma-glutamyl-transferase) | | GO:0005525\|GO:0031069\|GO:0031234\|GO:0005737\|GO:0018149\|GO:0003810\|GO:0043163\|GO:0019003\|GO:0006464\|GO:0008415 | | | |
| A_33_P3395310 | SMPD3 | Homo sapiens sphingomyelin phosphodiesterase 3, neutral membrane (neutral sphingomyelinase II) (SMPD3), mRNA [NM_018667] | NM_018667 | ENST00000219334 | 55512 | sphingomyelin phosphodiesterase 3, neutral membrane (neutral sphingomyelinase II) | chr16:68392309-68392250 | GO:0007049\|GO:0006685\|GO:0000137\|GO:0005794\|GO:0000287\|GO:0016787\|GO:0005886\|GO:0004767\|GO:0007275\|GO:0016021\|GO:0030072 | NM_018667 | THC2475296 | Hs-368421 |
| | | BX096650 Soares_testis_NHT Homo sapiens cDNA clone IMAGp998C184111, mRNA sequence [BX096650] | BX096650 | | | | chr4:54244117-54244058 | | | | Hs.717171 |
| A_33_P3256677 | CCDC101 | Homo sapiens coiled-coil domain containing 101 (CCDC101), mRNA [NM_138414] | NM_138414 | ENST00000317058 | 112869 | coiled-coil domain containing 101 | chr16:28602171-28602230 | GO:0005634\|GO:0045449 | NM_138414 | THC2464282 | Hs.655476 |
| A_33_P3399208 | | major histocompatibility complex, class I, B (Source: HGNC Symbol; Acc: 4932) [ENST00000466304] | AF298582 | ENST00000466304 | | | | | | THC2587029 | Hs.77961 |
| A_24_P112160 | UPK3B | Homo sapiens uroplakin 3B (UPK3B), transcript variant 1, mRNA [NM_030570] | NM_030570 | ENST00000334348 | 80761 | uroplakin 3B | chr7:76143315-76143374 | GO:0005886\|GO:0010629\|GO:0016021 | NM_030570 | THC2644791 | Hs.488861 |
| A_33_P3221384 | | | | | | | chr2:13303318-6-133033245 | | | | |
| A_33_P3399064 | RN5-8S1 | Homo sapiens RNA, 5.8S ribosomal 1 (RN5-8S1), ribosomal RNA [NR_003285] | NR_003285 | | 100008587 | RNA, 5.8S ribosomal 1 | chrUn_gl000220:156050-156109 | | NR_003285 | THC2581399 | Hs.631413 |
| A_33_P3418055 | ZNF235 | Homo sapiens zinc finger protein 235 (ZNF235), mRNA [NM_004234] | NM_004234 | ENST00000359844 | 9310 | zinc finger protein 235 | chr19:4479162-4-44791565 | GO:0005622\|GO:0006355\|GO:0008270\|GO:0005634\|GO:0003677\|GO:0046872 | NM_004234 | THC2477654 | Hs.724032 |
| A_23_P64173 | CARD16 | Homo sapiens caspase recruitment domain family, member 16 | NM_001017534 | ENST00000525374 | 114769 | caspase recruitment domain | chr11:1049152-86-104915227 | GO:0005622\|GO:0005515\|GO:0004197\|GO:0004869\|GO:0006508\|GO:0042981 | NM_001017534 | THC2625119 | Hs.348365 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (CARD16), transcript variant 1, mRNA [NM_001017534] | | | | family, member 16 | | GO:0030414 | | | |
| A_33_P3620488 | CATSPERG | Homo sapiens cation channel, sperm-associated, gamma (CATSPERG), mRNA [NM_021185] | NM_021185 | ENST00000492088 | 57828 | cation channel, sperm-associated, gamma | chr19:38861499-38861558 | GO:0016020|GO:0016021 | NM_021185 | NP1144122 | Hs.324335 |
| A_33_P3374833 | PLDN | Homo sapiens pallidin homolog (mouse) (PLDN), mRNA [NM_012388] | NM_012388 | ENST00000220531 | 26258 | pallidin homolog (mouse) | chr15:45901829-45901888 | GO:0016081|GO:0006892|NM_012388 GO:0030318|GO:0005575| GO:0030349|GO:0042802| GO:0032816|GO:0005737| GO:0006944|GO:0016020| GO:0007596|GO:0033299| GO:0043473|GO:0005768| GO:0019898 | NM_012388 | THC2552297 | Hs.730623 |
| A_33_P3365506 | | | | ENST00000513564 | | | chr4:34670959-34671018 | | | | |
| A_32_P192474 | PRRT1 | Homo sapiens proline-rich transmembrane protein 1 (PRRT1), mRNA [NM_030651] | NM_030651 | ENST00000375152 | 80863 | proline-rich transmembrane protein 1 | chr6:32116446-32116387 | GO:0009607|GO:0016020| GO:0016021 | NM_030651 | THC2463883 | Hs.699821 |
| A_23_P71752 | ZFAND5 | Homo sapiens zinc finger, AN1-type domain 5 (ZFAND5), transcript variant c, mRNA [NM_006007] | NM_006007 | ENST00000488164 | 7763 | zinc finger, AN1-type domain 5 | chr9:74969825-74969766 | GO:0048705|GO:0005575|NM_006007 GO:0001701|GO:0003677| GO:0046872|GO:0003674| GO:0008150|GO:0010761| GO:0003016|GO:0048745| GO:0060324|GO:0008270| GO:0048008|GO:0001944 | NM_006007 | THC2469722 | Hs.406096 |
| A_23_P354341 | CD160 | Homo sapiens CD160 molecule (CD160), mRNA [NM_007053] | NM_007053 | ENST00000369290 | 11126 | CD160 molecule | chr1:145696465-145696406 | GO:0006968|GO:0005886|NM_007053 GO:0008283|GO:0005102| GO:0004872|GO:0046658| GO:0007166|GO:0032393 | NM_007053 | NP159654 | Hs.488237 |
| A_33_P3512350 | LOC339807 | Homo sapiens hypothetical LOC339807 (LOC339807), non-coding RNA [NR_034023] | NR_034023 | | 339807 | hypothetical LOC339807 | chr2:64843555-64843614 | | NR_034023 | THC2627404 | Hs.434736 |
| A_33_P3258699 | DUX4 | Homo sapiens double homeobox 4 (DUX4), mRNA [NM_033178] | NM_033178 | ENST00000507734 | 22947 | double homeobox 4 | chrUn_gl000228:77296-77355 | GO:0043565|GO:0006355|NM_033178 GO:0003700|GO:0005634 | NM_033178 | THC2493180 | Hs.553518 |
| A_33_P3229288 | ACE | Homo sapiens angiotensin 1 converting enzyme (peptidyl-dipeptidase A) | NM_000789 | ENST00000290863 | 1636 | angiotensin 1 converting enzyme (peptidyl | chr17:61574915-61574974 | GO:0031404|GO:0005886|NM_000789 GO:0014910|GO:0005615| GO:0046872|GO:0019229| GO:0042312|GO:0003081| | NM_000789 | THC2470503 | Hs.298469 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | 1 (ACE), transcript variant 1, mRNA [NM_000789] | | | | dipeptidase A) | | GO:0002019\|GO:0008144\|GO:0006508\|GO:0004180\|GO:0008241\|GO:0043171\|GO:0050482\|GO:0042277\|GO:0001666\|GO:0031711\|GO:0001822\|GO:0005624\|GO:0005576\|GO:0060218\|GO:0001974\|GO:0042447\|GO:0008217\|GO:0002005\|GO:0008233\|GO:0008270\|GO:0016021\|GO:0032943\|GO:0008237\|GO:0009897\|GO:0005768 | | | |
| A_23_P210581 | KCNG1 | Homo sapiens potassium voltage-gated channel, subfamily G, member 1 (KCNG1), mRNA [NM_002237] | NM_002237 | ENST00000506387 | 3755 | potassium voltage-gated channel, subfamily G, member 1 | chr20:49620322-49620263 | GO:0005515\|GO:0005244\|NM_002237\|GO:0016020\|GO:0008076\|GO:0005249\|GO:0030955\|GO:0016021\|GO:0055085\|GO:0006813\|GO:0006811 | THC2507184 | Hs.118695 |
| A_23_P25475 | SOAT2 | Homo sapiens sterol O-acyltransferase 2 (SOAT2), mRNA [NM_003578] | NM_003578 | ENST00000301466 | 8435 | sterol O-acyltransferase 2 | chr12:53518152-53518211 | GO:0042632\|GO:0006629\|NM_003578\|GO:0033344\|GO:0005792\|GO:0005783\|GO:0007584\|GO:0010742\|GO:0005624\|GO:0034379\|GO:0030299\|GO:0005903\|GO:0034736\|GO:0016020\|GO:0015485\|GO:0005789\|GO:0034435\|GO:0016021\|GO:0000062\|GO:0034737\|GO:0016740\|GO:0008202\|GO:0034738\|GO:0008203\|GO:0008415 | THC2480345 | Hs.656544 |
| A_33_P3230990 | SCUBE1 | Homo sapiens signal peptide, CUB domain, EGF-like 1 (SCUBE1), mRNA [NM_173050] | NM_173050 | ENST00000381243 | 80274 | signal peptide, CUB domain, EGF like 1 | chr22:43599347-43599288 | GO:0005886\|GO:0046982\|NM_173050\|GO:0005509\|GO:0005576\|GO:0009791\|GO:0005615\|GO:0007512\|GO:0042802\|GO:0006954\|GO:0007596\|GO:0051260\|GO:0045446\|GO:0009897\|GO:0019897 | THC2475362 | Hs.133995 |
| A_23_P333129 | DUX4L4 | Homo sapiens double homeobox 4 like 4 (DUX4L4), mRNA [NM_001177376] | NM_001177376 | ENST00000538692 | 441056 | double homeobox 4 like 4 | chr4:190993379-190993446 | | NM_001177376 | | Hs.725918 |
| A_23_P45345 | HTATSF1 | Homo sapiens HIV-1 Tat specific factor 1 (HTATSF1), transcript variant 2, mRNA [NM_014500] | NM_014500 | ENST00000415377 | 27336 | HIV-1 Tat specific factor 1 | chrX:135594216-135594275 | GO:0005515\|GO:0003711\|NM_014500\|GO:0006357\|GO:0000166\|GO:0003702\|GO:0003723\|GO:0005730\|GO:0005634\|GO:0019079\|GO:0045449 | THC2756195 | Hs.204475 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3258339 | C17orf76 | *Homo sapiens* chromosome 17 open reading frame 76 (C17orf76), transcript variant 1, mRNA [NM_001113567] | NM_001113567 | ENST00000409887 | 388341 | chromosome 17 open reading frame 76 | chr17:16346634-16346575 | | NM_001113567 | THC2473528 | Hs.25425 |
| A_24_P196592 | MMP28 | *Homo sapiens* matrix metallopeptidase 28 (MMP28), transcript variant 3, mRNA [NM_001032278] | NM_001032278 | ENST00000250144 | 79148 | matrix metallopeptidase 28 | chr17:34106300-34106073 | GO:0008152\|GO:0005509\|GO:0006508\|GO:0005578\|GO:0008190\|GO:0008233\|GO:0005576\|GO:0004222 | NM_001032278 | THC2778644 | Hs.380710 |
| A_33_P3287379 | COG8 | *Homo sapiens* component of oligomeric golgi complex 8 (COG8), mRNA [NM_032382] | NM_032382 | ENST00000306875 | 84342 | component of oligomeric golgi complex 8 | chr16:69364938-69364878 | GO:0005794\|GO:0016020\|GO:0017119\|GO:0015031\|GO:0019898 | NM_032382 | THC2467033 | Hs.130849 |
| A_33_P3225512 | OAS2 | *Homo sapiens* 2'-5'-oligoadenylate synthetase 2, 69/71 kDa (OAS2), transcript variant 2, mRNA [NM_002535] | NM_002535 | ENST00000392583 | 4939 | 2'-5'-oligo-adenylate synthetase 2, 69/71 kDa | chr12:113444829-113448488 | GO:0005792\|GO:0005783\|GO:0001730\|GO:0003723\|GO:0016779\|GO:0005634\|GO:0005524\|GO:0006401\|GO:0005739\|GO:0006139\|GO:0006955\|GO:0000166\|GO:0016020\|GO:0016740 | NM_002535 | THC2474929 | Hs.414332 |
| A_33_P3227252 | | | | | | | chr6:000145863-000145922 | | | THC2481163 | |
| A_23_P317207 | ATXN7L2 | *Homo sapiens* ataxin 7-like 2 (ATXN7L2), mRNA [NM_153340] | NM_153340 | ENST00000463678 | 127002 | ataxin 7-like 2 | chr1:110033888-110033947 | | NM_153340 | THC2475985 | Hs.118248 |
| A_23_P160226 | HEATR8 | *Homo sapiens* HEAT repeat containing 8 (HEATR8), transcript variant 1, mRNA [NM_001039464] | NM_001039464 | ENST00000421030 | 374977 | HEAT repeat containing 8 | chr1:55175863-55175922 | GO:0016020\|GO:0005488\|GO:0016021 | NM_001039464 | NP509977 | Hs.412482 |
| A_33_P3225572 | | | | | | | chr7:027278509-027278450 | | | | |
| A_33_P3378818 | | | | | | | chr10:043050905-043050964 | | | | |
| A_33_P3372666 | PDGFA | *Homo sapiens* platelet-derived growth factor alpha polypeptide (PDGFA), transcript variant 2, mRNA [NM_033023] | NM_033023 | ENST00000405692 | 5154 | platelet-derived growth factor alpha polypeptide | chr7:557091-557032 | GO:0010544\|GO:0031089\|GO:0043498\|GO:0050730\|GO:0005518\|GO:0007267\|GO:0014910\|GO:0048146\|GO:0009790\|GO:0005615\|GO:0042803\|GO:0010035\|GO:0032956\|GO:0009887\|GO:0051781\|GO:0007179\|GO:0032526\|GO:0032355 | NM_033023 | THC2477221 | Hs.535898 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | | | | | | | GO:0001942|GO:0001775| | | | |
| | | | | | | | | GO:0001666|GO:0048839| | | | |
| | | | | | | | | GO:0010033|GO:0030335| | | | |
| | | | | | | | | GO:0048286|GO:0046982| | | | |
| | | | | | | | | GO:0009986|GO:0048407| | | | |
| | | | | | | | | GO:0042493|GO:0045740| | | | |
| | | | | | | | | GO:0010512|GO:0050919| | | | |
| | | | | | | | | GO:0005576|GO:0002053| | | | |
| | | | | | | | | GO:0001525|GO:0005161| | | | |
| | | | | | | | | GO:0005902|GO:0016020| | | | |
| | | | | | | | | GO:0030031|GO:0042060| | | | |
| | | | | | | | | GO:0043588|GO:0048008| | | | |
| | | | | | | | | GO:0008083 | | | |
| A_32_P134968 | SPTB | *Homo sapiens* spectrin, beta, erythrocytic (SPTB), transcript variant 1, mRNA [NM_001024858] | NM_001024858 | ENST00000335612 | 6710 | spectrin, beta, erythrocytic | chr14:6521307 4-65213015 | GO:0005515|GO:0043234| GO:0008091|GO:0005737| GO:0051015|GO:0031235| GO:0005200|GO:0014731| GO:0015629|GO:0005938| GO:0051693|GO:0005829 | NM_001024858 | THC2475546 | Hs.417303 |
| A_33_P3377786 | LOC649887 | PREDICTED: *Homo sapiens* ETS domain-containing protein Elk-1-like (LOC649887), mRNA [XM_003121052] | XM_003121052 | | 649887 | ETS domain containing protein Elk-1-like | chr14:1060129 62-106012903 | | XM_003121052 | THC2484830 | |
| A_23_P9357 | TBXA2R | *Homo sapiens* thromboxane A2 receptor (TBXA2R), transcript variant a, mRNA [NM_001060] | NM_001060 | ENST00000375190 | 6915 | thromboxane A2 receptor | chr19:3594819-3594760 | GO:0007165|GO:0007186| GO:0005886|GO:0005887| GO:0004930|GO:0004961| GO:0004872 | NM_001060 | THC2641607 | Hs.442530 |
| A_33_P3262580 | ENTPD1 | ectonucleoside triphosphate diphosphohydrolase 1 [Source: HGNC Symbol; Acc: 3363] [ENST00000371206] | AJ133134 | ENST00000371206 | 953 | ectonucleoside triphosphate diphosphohydrolase 1 | chr10:9760533 7-97605396 | | | THC2486629 | |
| A_33_P3359012 | DUSP8 | *Homo sapiens* dual specificity phosphatase 8 (DUSP8), mRNA [NM_004420] | NM_004420 | ENST00000331588 | 1850 | dual specificity phosphatase 8 | chr11:1575341-1575282 | GO:0000188|GO:0005737| GO:0006470|GO:0016787| GO:0005634|GO:0017017| GO:0004725 | NM_004420 | THC2474457 | Hs.41688 |
| A_33_P3367447 | ALDH3B1 | *Homo sapiens* aldehyde dehydrogenase 3 family, member B1 (ALDH3B1), transcript variant 3, mRNA [NM_001161473] | NM_001161473 | ENST00000007633 | 221 | aldehyde dehydrogenase 3 family, member B1 | chr11:6779351 6-67793575 | GO:0006629|GO:0006066| GO:0016491|GO:0006081| GO:0004028|GO:0055114| GO:0004030 | NM_001161473 | NP1157844 | Hs.523841 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3391167 | | | | ENST00000537481 | | | | | | | |
| A_33_P3358019 | | | | | | | | | | | |
| A_33_P3416097 | F13A1 | *Homo sapiens* coagulation factor XIII, A1 polypeptide (F13A1), mRNA [NM_000129] | NM_000129 | ENST00000441301 | 2162 | coagulation factor XIII, A1 polypeptide | chr7:56872218-56872277 chr9:13443152-134431580 | GO:0005737|GO:0018149|NM_000129 GO:0007596|GO:0003810| GO:0005509|GO:0031093| GO:0005576|GO:0016740| GO:0008415 | THC2668771 | Hs.335513 |
| A_33_P3239864 | ANKDD1A | ankyrin repeat and death domain containing 1A [Source: HGNC Symbol; Acc: 28002] [ENST00000319597] | AK307698 | ENST00000319597 | 348094 | ankyrin repeat and death domain containing 1A | chr15:6522377 5-65223834 | | THC2477872 | Hs.207157 |
| A_24_P357100 | RASD2 | *Homo sapiens* RASD family, member 2 (RASD2), mRNA [NM_014310] | NM_014310 | ENST00000216127 | 23551 | RASD family, member 2 | chr22:359496 0-35949669 | GO:0005622|GO:0007165|NM_014310 GO:0005737|GO:0005886| GO:0000166|GO:0007264| GO:0003924|GO:0007626| GO:0031225|GO:0005575| GO:0005525 | THC2471776 | Hs.474711 |
| A_23_P142070 | TSPAN16 | *Homo sapiens* tetraspanin 16 (TSPAN16), mRNA [NM_012466] | NM_012466 | ENST00000316737 | 26526 | tetraspanin 16 | chr19:1141191 2-11411971 | GO:0016020|GO:0016021 NM_012466 | THC2483075 | Hs.579784 |
| A_33_P3349552 | CASKIN1 | *Homo sapiens* CASK interacting protein 1 (CASKIN1), mRNA [NM_020764] | NM_020764 | ENST00000382453 | 57524 | CASK interacting protein 1 | chr16:2228170-2228111 | GO:0007165|GO:0005737|NM_020764 GO:0019904 | THC2648696 | Hs.643537 |
| A_33_P3272823 | MAG | *Homo sapiens* myelin associated glycoprotein (MAG), transcript variant 1, mRNA [NM_002361] | NM_002361 | ENST00000262624 | 4099 | myelin associated glycoprotein | chr19:3580285 8-35802917 | GO:0005515|GO:0005886|NM_002361 GO:0043209|GO:0005529| GO:0050771|GO:0016021| GO:0007155 | THC2517997 | Hs.643440 |
| A_23_P30464 | PRR7 | *Homo sapiens* proline rich 7 (synaptic) (PRR7), transcript variant 1, mRNA [NM_030567] | NM_030567 | ENST00000502922 | 80758 | proline rich 7 (synaptic) | chr5:17688314 4-176883203 | GO:0030054|GO:0005886|NM_030567 GO:0045211|GO:00045202| GO:0016021 | THC2480457 | Hs.534492 |
| A_33_P3390950 | LOC100128338 | *Homo sapiens* cDNA FLJ43864 fis, clone TEST14007799. [AK125852] | AK125852 | | 100128338 | hypothetical LOC100128338 | chr8:14482410 6-144824165 | | THC2513064 | Hs.493171 |
| A_33_P3424612 | | *Homo sapiens* immunoglobulin kappa variable 3-11 [Source: HGNC Symbol; Acc: 5815] [ENST00000483158] | XM_003120829 | ENST00000483158 | | | chr2:89326850-89326791 | | XM_003120829 | NP1455229 | Hs.449621 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3263287 | LOC100129111 | Homo sapiens FLJ44947 fis, clone BRAMY4001913. cDNA [AK126895] | AK126895 | | 100129111 | hypothetical LOC100129111 | chr11:8059834-8059775 | | | THC2638098 | Hs.627496 |
| A_23_P112187 | FIBCD1 | Homo sapiens fibrinogen C domain containing 1 (FIBCD1), transcript variant 1, mRNA [NM_032843] | NM_032843 | ENST00000372338 | 84929 | fibrinogen C domain containing 1 | chr9:133778556-133778497 | GO:0007165|GO:0016020|NM_032843| GO:0005102|GO:0016021| GO:0005615 | | THC2474476 | Hs.133205 |
| A_23_P49674 | ARHGEF15 | Homo sapiens Rho guanine nucleotide exchange factor (GEF) 15 (ARHGEF15), transcript variant 1, mRNA [NM_173728] | NM_173728 | ENST00000421050 | 22899 | Rho guanine nucleotide exchange factor (GEF) 15 | chr17:8224944-8225003 | GO:0005622|GO:0005085|NM_173728| GO:0035023|GO:0005089| GO:0005096 | | THC2464188 | Hs.443109 |
| A_33_P3290955 | KIAA1875 | Homo sapiens KIAA1875 (KIAA1875), non-coding RNA [NR_024207] | NR_024207 | ENST00000488801 | 340390 | KIAA1875 | chr8:14517263-145172680 | | NR_024207 | THC2582104 | Hs.272822 |
| A_23_P103465 | PLA2G5 | Homo sapiens phospholipase A2, group V (PLA2G5), mRNA [NM_000929] | NM_000929 | ENST00000465698 | 5322 | phospholipase A2, group V | chr1:20417423-20417482 | GO:0019370|GO:0048471|NM_000929| GO:0005794|GO:0005886| GO:0009986|GO:0006663| GO:0005509|GO:0005576| GO:0051591|GO:0016042| GO:0016787|GO:0047498| GO:0006644|GO:0034097| GO:0008201|GO:0050482 | | NP1143075 | Hs.319438 |
| A_23_P3602 | NUDT7 | Homo sapiens nudix (nucleoside diphosphate linked moiety X)-type motif 7 (NUDT7), transcript variant 1, mRNA [NM_001105663] | NM_001105663 | ENST00000268533 | 283927 | nudix (nucleoside diphosphate linked moiety X)-type motif 7 | chr16:7777592 1-777775980 | GO:0030145|GO:0000287|NM_001105663 GO:0016787|GO:0009132| GO:0016818|GO:0005777 | | THC2521963 | Hs.282665 |
| A_33_P3421571 | RAPH1 | Homo sapiens Ras association (RalGDS/AF-6) and pleckstrin homology domains 1 (RAPH1), transcript variant 1, mRNA [NM_213589] | NM_213589 | ENST00000374493 | 65059 | Ras association (RalGDS/AF-6) and pleckstrin homology domains 1 | chr2:20430425 0-204304191 | GO:0007165|GO:0005737|NM_213589 GO:0007160|GO:0005886| GO:0005634|GO:0030175| GO:0005856|GO:0030027 | | THC2472794 | Hs.471162 |
| A_23_P137046 | NYX | Homo sapiens nyctalopin (NYX), mRNA[NM_022567] | NM_022567 | ENST00000378220 | 60506 | nyctalopin | chrX:413345704-41334629 | GO:0005622|GO:0005515|NM_022567 GO:0003674|GO:0005578| GO:0005576|GO:0007601| GO:0050896 | | THC2484608 | Hs.302019 |
| A_23_P217088 | AK1 | Homo sapiens adenylate kinase 1 | NM_000476 | ENST00000476274 | 203 | adenylate kinase 1 | chr9:13063071 2-130630653 | GO:0005515|GO:0006139|NM_000476 GO:0005737|GO:0046034| | | THC2510014 | Hs.175473 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (AK1), mRNA [NM_000476] | | | | | | GO:0000166|GO:0005634| GO:0004017|GO:0019206| GO:0005524|GO:0016740| GO:0005829 | | | |
| A_33_P3306624 | HCRT | *Homo sapiens* hypocretin (orexin) neuropeptide precursor (HCRT), mRNA [NM_001524] | NM_001524 | ENST00000293330 | 3060 | hypocretin (orexin) neuropeptide precursor | chr17:40337465-40337406 | GO:0005791|GO:0048471|GO:0030054|GO:0051928| GO:0060079|GO:0043267| GO:0046928|GO:0045202| GO:0007200|GO:0007268 | NM_001524 | THC2659783 | Hs.158348 |
| A_33_P3374903 | | | | | | | chr14:0357045 38-0357045 97 | GO:0051970|GO:0051971| GO:0007204|GO:0007205 | | | |
| A_33_P3399755 | | | | | | | chr15:0434232 26-043423167 | GO:0008021|GO:0031771| GO:0031772|GO:0005737| GO:0007218|GO:0042755| GO:0008156|GO:0005184| GO:0030141 | | | |
| A_23_P207811 | PAIP1 | *Homo sapiens* poly(A) binding protein interacting protein 1 (PAIP1), transcript variant 1, mRNA [NM_006451] | NM_006451 | ENST00000306846 | 10605 | poly(A) binding protein interacting protein 1 | chr5:43526482-43526423 | GO:0005515|GO:0005737| GO:0016070|GO:0003723| GO:0008494|GO:0048255| GO:0006417|GO:0006413 | NM_006451 | THC2476788 | Hs.482038 |
| A_23_P217712 | ARSD | *Homo sapiens* arylsulfatase D (ARSD), mRNA [NM_001669] | NM_001669 | ENST00000217890 | 414 | arylsulfatase D | chrX:2835852-2833682 | GO:0016787|GO:0008152| GO:0005509|GO:0004065| GO:0005764 | NM_001669 | NP164738 | Hs.528631 |
| A_33_P3415923 | FMNL3 | *Homo sapiens* formin-like 3 (FMNL3), transcript variant 1, mRNA [NM_175736] | NM_175736 | ENST00000352151 | 91010 | formin-like 3 | chr12:5003881 4-50038755 | GO:0005515|GO:0030036| GO:0017048|GO:0003779| GO:0016043 | NM_175736 | THC2475096 | Hs.179838 |
| A_24_P2771155 | HLTF | *Homo sapiens* helicase-like transcription factor (HLTF), transcript variant 1, mRNA [NM_003071] | NM_003071 | ENST00000310053 | 6596 | helicase-like transcription factor | chr3:14874845 0-148748391 | GO:0005515|GO:0006357| GO:0003702|GO:0016874| GO:0016563|GO:0004386| GO:0005634|GO:0016818| GO:0003677|GO:0005524| GO:0046872|GO:0006350| GO:0000166|GO:0016787| GO:0019941|GO:0008270| GO:0016887|GO:0016568 | NM_003071 | THC2465857 | Hs.3068 |
| A_33_P3314978 | LOC100130522 | *Homo sapiens* hypothetical LOC100130522 (LOC100130522), transcript variant 3, non-coding RNA | NR_028340 | | 100130522 | hypothetical LOC100130522 | chr18:7793616 3-77936222 | | NR_028340 | THC2622038 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P2492 | C1S | Homo sapiens complement component 1, s subcomponent (C1S), transcript variant 2, mRNA [NM_001734] | NM_001734 | ENST00000360817 | 716 | complements component 1, s subcomponent | chr12:7178093-7178152 | GO:0004252\|GO:0045087\|NM_001734\|GO:0006958\|GO:0005509\|GO:0006308\|GO:0010001\|GO:0008233\|GO:0005576\|GO:0051591 | THC2553139 | Hs.458355 |
| A_33_P3387781 | OR2L1P | Homo sapiens olfactory receptor, family 2, subfamily L, member 1 pseudogene (OR2L1P), non-coding RNA [NR_002145] | NR_002145 | | 26247 | olfactory receptor, family 2, subfamily L, member 1 pseudogene | chr1:24815419 7-248154256 | | NR_002145 | NP1174289 | Hs.684887 |
| A_23_P14072 | KRT8 | Homo sapiens keratin 8 (KRT8), mRNA [NM_002273] | NM_002273 | ENST00000550170 | 3856 | keratin 8 | chr12:5329108 5-53291026 | GO:0005515\|GO:0005737\|NM_002273\|GO:0005198\|GO:0044419\|GO:0007010\|GO:0045095 | THC2514651 | Hs.533782 |
| A_24_P945147 | RABEP1 | Homo sapiens rabaptin, RAB GTPase binding effector protein 1 (RABEP1), transcript variant 1, mRNA[NM_004703] | NM_004703 | ENST00000262477 | 9135 | rabaptin, RAB GTPase binding effector protein 1 | chr17:5288797-5288856 | GO:0005515\|GO:0005737\|NM_004703\|GO:0006944\|GO:0006915\|GO:0055037\|GO:0015031\|GO:0008083\|GO:0005769\|GO:0006897\|GO:0005096 | THC2493766 | Hs.592121 |
| A_33_P3408305 | CERS3 | Homo sapiens ceramide synthase 3 (CERS3), mRNA [NM_178842] | NM_178842 | ENST00000538112 | 204219 | ceramide synthase 3 | chr15:1009428 05-100942746 | GO:0043565\|GO:0008610\|NM_178842\|GO:0006355\|GO:0005737\|GO:0003700\|GO:0016020\|GO:0030148\|GO:0005634\|GO:0050291\|GO:0016021 | THC2475513 | Hs.662371 |
| A_33_P3299329 | | Human mRNA for T-cell receptor V beta gene segment V-beta-7, clone IGRb18. [X58812] | A25969 | | | | | | | NP321619 | Hs.511728 |
| A_33_P3248982 | FAIM2 | Homo sapiens Fas apoptotic inhibitory molecule 2 (FAIM2), mRNA [NM_012306] | NM_012306 | ENST00000320634 | 23017 | Fas apoptotic inhibitory molecule 2 | chr12:5026073 9-50260680 | GO:0005515\|GO:0030054\|NM_012306\|GO:0005886\|GO:0045211\|GO:0045202\|GO:0006915\|GO:0006916\|GO:0016021\|GO:0007417 | THC2511959 | Hs.567424 |
| A_23_P145569 | SLC22A1 | Homo sapiens solute carrier family 22 (organic cation transporter), member 1 (SLC22A1), | NM_153187 | ENST00000539263 | 6580 | solute carrier family 22 (organic cation transporter), member 1 | chr6:16056088 5-160564617 | GO:0005515\|GO:0005215\|NM_153187\|GO:0015695\|GO:0005886\|GO:0015075\|GO:0005887\|GO:0005624\|GO:0055085\|GO:0015101 | THC2636461 | Hs.117367 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3314441 | FBXL17 | transcript variant 2, mRNA [NM_153187] Homo sapiens F-box and leucine-rich repeat protein 17 (FBXL17), mRNA [NM_001163315] | NM_001163315 | ENST00000542267 | 64839 | F-box and leucine rich repeat protein 17 | chr5:107195628-107195569 | GO:0019941 | NM_001163315 | THC2473457 | Hs.657225 |
| A_33_P3322879 | | | | | | | chr7:029238730-029238671 | | | | Hs.516700 |
| A_33_P3361422 | CYP27A1 | Homo sapiens cytochrome P450, family 27, subfamily A, polypeptide 1 (CYP27A1), nuclear gene encoding mitochondrial protein, mRNA [NM_000784] | NM_000784 | ENST00000494263 | 1593 | cytochrome P450, family 27, subfamily A, polypeptide 1 | chr2:219679951-219680010 | GO:0005739\|GO:0031073\|GO:0030343\|GO:0016020\|GO:0047749\|GO:0005759\|GO:0005743\|GO:0009055\|GO:0046872\|GO:0055114\|GO:0020037\|GO:0008203 | NM_000784 | | |
| A_33_P3419419 | PIK3C2B | phosphoinositide-3-kinase, class 2, beta polypeptide [Source: HGNC Symbol; Acc: 8972] [ENST00000367184] | | ENST00000367184 | 5287 | phosphoinositide 3-kinase, class 2, beta polypeptide | chr1:204435959-204435900 | | | THC2703322 | Hs.683861 |
| A_33_P3231572 | LOC100130456 | Homo sapiens cDNA FLJ37693 fis, clone BRHIP2014954. [AK095012] | AK095012 | | 100130456 | hypothetical LOC100130456 | chr7:108979796-1089855 | | | THC2486189 | Hs.683861 |
| A_33_P3303865 | FAM120C | Homo sapiens family with sequence similarity 120C (FAM120C), transcript variant 2, mRNA [NM_198456] | NM_198456 | ENST00000477084 | 54954 | family with sequence similarity 120C | chrX:54208993-54208934 | | NM_198456 | THC2635554 | Hs.86045 |
| A_32_P109683 | PAGE2B | Homo sapiens P antigen family, member 2B (PAGE2B), mRNA [NM_001015038] | NM_001015038 | ENST00000374971 | 389860 | P antigen family, member 2B | chrX:55102473-55102532 | | NM_001015038 | THC2476714 | Hs.293317 |
| A_33_P3311543 | | Q3MF38_ANAVT (Q3MF38) Extracellular solute-binding protein, family 3 precursor, partial (7%) [THC2489055] | | | | | chr15:067899741-067899800 | | | THC2489055 | |
| A_23_P59099 | OR11A1 | Homo sapiens olfactory receptor, family 11, subfamily A, member | NM_013937 | ENST00000377149 | 26531 | olfactory receptor, family 11, subfamily A, | chr6:29394698-29394639 | GO:0007608\|GO:0007165\|GO:0004984\|GO:0007186\|GO:0005886\|GO:0004872\|GO:0016021\|GO:0050896 | NM_013937 | THC2487340 | Hs.676010 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq Accession | TIGRID | UniGene ID |
|---|---|---|---|---|---|---|---|---|---|---|---|
| A_33_P3373560 | SPTAN1 | Homo sapiens spectrin, alpha, non erythrocytic 1 (alpha-fodrin) (SPTAN1), transcript variant 1, mRNA [NM_001130438] | NM_001130438 | ENST00000372721 | 6709 | spectrin, alpha, non-erythrocytic 1 (alpha-fodrin) member 1 | chr9:131388906-131388965 | GO:0008091\|GO:0005516\|GO:0005737\|GO:0005509\|GO:0005200\|GO:0005624\|GO:0003779\|GO:0005856\|GO:0005938\|GO:0051693\|GO:0005829 | NM_001130438 | THC2567178 | Hs.372331 |
| A_24_P56837 | ASB16 | Homo sapiens ankyrin repeat and SOCS box containing 16 (ASB16), mRNA [NM_080863] | NM_080863 | ENST00000293414 | 92591 | ankyrin repeat and SOCS box containing 16 | chr17:42256390-42256449 | GO:0005515\|GO:0007242\|GO:0019941 | NM_080863 | THC2761159 | Hs.534517 |
| A_33_P3358104 | CD300E | Homo sapiens CD300e molecule (CD300E), mRNA [NM_181449] | NM_181449 | ENST00000412268 | 342510 | CD300e molecule | chr17:72613358-72613299 | GO:0006955\|GO:0005886\|GO:0004872\|GO:0016021 | NM_181449 | THC2480696 | Hs.158954 |
| A_33_P3390177 | FLJ34208 | Homo sapiens hypothetical LOC401106 (FLJ34208), non-coding RNA [NR_033929] | NR_033929 |  | 401106 | hypothetical LOC401106 | chr3:194209094-194209153 |  | NR_033929 | THC2503254 | Hs.407087 |
| A_33_P3253501 | HIST2H2BF | Homo sapiens histone cluster 2, H2bf (HIST2H2BF), transcript variant 2, mRNA [NM_001161334] | NM_001161334 | ENST00000369167 | 440689 | histone cluster 2, H2bf | chr1:149783587-149783558 | GO:0005694\|GO:0006334\|GO:0005634\|GO:0000786\|GO:0003677 | NM_001161334 | THC2541318 | Hs.632451 |
| A_33_P3277611 | TMEM8C | Homo sapiens transmembrane protein 8C (TMEM8C), mRNA [NM_001080483] | NM_001080483 | ENST00000339996 | 389827 | transmembrane protein 8C | chr9:136379871-136379812 | GO:0016020\|GO:0016021 | NM_001080483 | THC2645713 | Hs.512467 |
| A_33_P3393537 | PTAFR | Homo sapiens platelet-activating factor receptor (PTAFR), transcript variant 2, mRNA [NM_001164722] | NM_001164722 | ENST00000539896 | 5724 | platelet-activating factor receptor | chr1:28520418-28520359 | GO:0005886\|GO:0048015\|GO:0001875\|GO:0001816\|GO:0007165\|GO:0006955\|GO:0032959\|GO:0004992\|GO:0005543\|GO:0006954\|GO:0006935\|GO:0007186\|GO:0005887\|GO:0032496\|GO:0004872 | NM_001164722 | THC2513589 | Hs.77542 |
| A_33_P3370881 | LOC100508761 | PREDICTED: Homo sapiens hypothetical protein LOC100508761 (LOC100508761), mRNA [XM_003119737] | XM_003119737 |  | 100508761 | hypothetical protein LOC100508761 | chr19:4241327-42413213 |  | XM_003119737 | THC2650123 | Hs.590950 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P2392 | GOLGA8A | Homo sapiens golgin A8 family, member A (GOLGA8A), transcript variant 1, mRNA [NM_181077] | NM_181077 | ENST00000509311 | 23015 | golgin A8 family, member A | chr15:34673339 3-34673334 | GO:0005794|GO:0016020|GO:0019898 | NM_181077 | THC2537280 | Hs.720151 |
| A_24_P212234 | SLC6A18 | Homo sapiens solute carrier family 6, member 18 (SLC6A18), mRNA [NM_182632] | NM_182632 | ENST00000296821 | 348932 | solute carrier family 6, member 18 | chr5:1244392-1244451 | GO:0005886|GO:0005887|NM_182632 GO:0005328|GO:0006865| GO:0006836|GO:0015293 | | NP398860 | Hs.213284 |
| A_33_P3316239 | LOC100130419 | Homo sapiens cDNA FLJ44830 fis, clone BRACE3047018. [AK126781] | AK126781 | | 100130419 | hypothetical protein LOC100130419 | chr19:4564036 1-45640420 | | | THC2629820 | Hs.651773 |
| A_33_P3308456 | HOXB13-AS1 | Homo sapiens HOXB13 antisense RNA 1 (non-protein coding) (HOXB13-AS1), non-coding RNA [NR_024103] | NR_024103 | ENST00000422730 | 360205 | HOXB13 antisense RNA 1 (non-protein coding) | chr17:4680059 3-46800652 | GO:0005634 | NR_024103 | THC2623344 | Hs.236557 |
| A_33_P3289456 | | | | ENST00000438148 | | | chr2:10576182 3-105761882 | | | | |
| A_33_P3378212 | MED25 | Homo sapiens mediator complex subunit 25 (MED25), mRNA [NM_030973] | NM_030973 | ENST00000312881 | 81857 | mediator complex subunit 25 | chr19:5034017 3-50340232 | GO:0005634|GO:0045449 NM_030973 | | THC2481955 | Hs.656639 |
| A_23_P128930 | PSMC6 | Homo sapiens proteasome (prosome, macropain) 26S subunit, ATPase, 6 (PSMC6), mRNA[NM_002806] | NM_002806 | ENST00000445930 | 5706 | proteasome (prosome, macropain) 26S subunit, ATPase, 6 | chr14:5318784 5-53187904 | GO:0006511|GO:0000502|NM_002806 GO:0051437|GO:0005634| GO:0051436|GO:0005524| GO:0031145|GO:0030163| GO:0005737|GO:0000166| GO:0016787|GO:0030674| GO:0016887 | | THC2469599 | Hs.156171 |
| A_24_P327499 | TTI1 | Homo sapiens Tel2 interacting protein 1 homolog (S. pombe) (TTI1), mRNA [NM_014657] | NM_014657 | ENST00000449821 | 9675 | Tel2 interacting protein 1 homolog (S. pombe) | chr20:3663103 5-36627677 | GO:0005488 | NM_014657 | THC246716H | Hs.655481 |
| A_23_P433111 | C5orf35 | Homo sapiens chromosome 5 open reading frame 35 (C5orf35), transcript variant 1, mRNA [NM_153706] | NM_153706 | ENST00000463805 | 133383 | chromosome 5 open reading frame 35 | chr5:56209808-56210738 | | NM_153706 | THC2475697 | Hs.85950 |
| A_23_P119102 | VASP | Homo sapiens vasodilator-stimulated | NM_003370 | ENST00000245932 | 7408 | vasodilator-stimulated | chr19:4602973 8-46029797 | GO:0005515|GO:0017124|NM_003370 GO:0030036|GO:0030054| | | NP1201349 | Hs.515469 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | phosphoprotein (VASP), mRNA [NM_003370] | | | | phosphoprotein | | GO:0005886\|GO:0031258\|GO:0031527\|GO:0001843\|GO:0003779\|GO:0015629\|GO:0005829\|GO:0005737\|GO:0007411\|GO:0005925 | | | |
| A_33_P3405022 | LETM1 | *Homo sapiens* leucine zipper-EF-hand containing transmembrane protein 1 (LETM1), nuclear gene encoding mitochondrial protein, mRNA [NM_012318] | NM_012318 | ENST00000302787 | 3954 | leucine zipper-EF-hand containing transmembrane protein 1 | chr1:04560082 8-04560076 9 | GO:0005739\|GO:0005515\|NM_012318\|GO:0016020\|GO:0005509\|GO:0005743\|GO:0016021\|GO:0042407 | | THC2538032 | Hs.120165 |
| A_23_P3204 | MAPK6 | *Homo sapiens* mitogen-activated protein kinase 6 (MAPK6), mRNA [NM_002748] | NM_002748 | ENST00000261845 | 5597 | mitogen-activated protein kinase 6 | chr15:5235805 5-52358114 | GO:0007165\|GO:0007049\|NM_002748\|GO:0000166\|GO:0004674\|GO:0006468\|GO:0005524\|GO:0016740\|GO:0004707 | | THC2469096 | Hs.411847 |
| A_23_P128993 | GZMH | *Homo sapiens* granzyme H (cathepsin G-like 2, protein h-CCPX) (GZMH), mRNA [NM_033423] | NM_033423 | ENST00000382548 | 2999 | granzyme H (cathepsin G-like 2, protein h-CCPX) | chr14:2507576 8-25075709 | GO:0005737\|GO:0004252\|NM_033423\|GO:0019835\|GO:0006508\|GO:0006915\|GO:0008233 | | NP1073090 | Hs.348264 |
| A_24_P181254 | OLFM4 | *Homo sapiens* olfactomedin 4 (OLFM4), mRNA [NM_006418] | NM_006418 | ENST00000219022 | 10562 | olfactomedin 4 | chr13:5362609 5-53626154 | GO:0005515\|GO:0005576\|NM_006418\|GO:0007155\|GO:0005615 | | NP080242 | Hs.508113 |
| A_23_P165952 | ACTR5 | *Homo sapiens* ARP5 actin-related protein 5 homolog (yeast) (ACTR5), mRNA [NM_024855] | NM_024855 | ENST00000243903 | 79913 | ARP5 actin-related protein 5 homolog (yeast) | chr20:3739618 9-37400210 | GO:0005515\|GO:0005524\|NM_024855\|GO:0045449 | | THC2470844 | Hs.371585 |
| A_33_P3408047 | LOC100289308 | PREDICTED: *Homo sapiens* hypothetical protein LOC100289308 (LOC100289308), mRNA [XM_003119817] | XM_003119817 | | 100289308 | hypothetical protein LOC100289308 | chr20:2346523 8-23465297 | | XM_003119817 | | Hs.589889 |
| A_33_P3318377 | | | | ENST00000398049 | | | chr10:1274454 29-127445488 | | | | |
| A_23_P159237 | GPR20 | *Homo sapiens* G protein-coupled receptor 20 (GPR20), mRNA [NM_005293] | NM_005293 | ENST00000377741 | 2843 | G protein-coupled receptor 20 | chr8:14236670 4-142366645 | GO:0007165\|GO:0007186\|NM_005293\|GO:0005886\|GO:0005887\|GO:0004930\|GO:0004872 | | THC2604553 | Hs.188859 |
| A_33_P3285077 | COMMD8 | *Homo sapiens* COMM domain | NM_017845 | ENST00000381571 | 54951 | COMM domain | chr4:47455136-47455077 | GO:0005515 | NM_017845 | THC2632032 | Hs.23956 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | containing 8 (COMMD8), mRNA [NM_017845] | | | | containing 8 | | | | | |
| A_23_P14493 | DNAAF2 | Homo sapiens dynein, axonemal, assembly factor 2 (DNAAF2), transcript variant 1, mRNA [NM_018139] | NM_018139 | ENST00000298292 | 55172 | dynein, axonemal, assembly factor 2 | chr14:5009235 1-50092292 | GO:0005515\|GO:0060286\|NM_018139\|GO:0005737\|GO:0060285\|GO:0032526\|GO:0070286\|GO:0042221 | | THC2753351 | Hs.231761 |
| A_33_P3335257 | TMEM146 | Homo sapiens transmembrane protein 146 (TMEM146), mRNA [NM_152784] | NM_152784 | ENST00000381614 | 257062 | transmembrane protein 146 | chr19:5771101 1-5771070 | GO:0016020\|GO:0016021 | NM_152784 | THC2478921 | Hs.631842 |
| A_33_P3216438 | SPATA21 | Homo sapiens spermatogenesis associated 21 (SPATA21), mRNA [NM_198546] | NM_198546 | ENST00000335496 | 374955 | spermatogenesis associated 21 | chr1:16725197-16725138 | GO:0005509 | NM_198546 | THC2485745 | Hs.705501 |
| A_24_P6528 | SRP9 | Homo sapiens signal recognition particle 9 kDa (SRP9), transcript variant 2, mRNA [NM_003133] | NM_003133 | ENST00000366838 | 6726 | signal recognition particle 9 kDa | chr1:22597100 9-225971068 | GO:0005515\|GO:0005515\|NM_003133\|GO:0005737\|GO:0005785\|GO:0006614\|GO:0008312\|GO:0005047\|GO:0045900 | | THC2546497 | Hs.511425 |
| A_23_P94095 | ANKRD46 | Homo sapiens ankyrin repeat domain 46 (ANKRD46), mRNA [NM_198401] | NM_198401 | ENST00000520311 | 157567 | ankyrin repeat domain 46 | chr8:10153343 1-101533372 | GO:0016020\|GO:0016021 | NM_198401 | THC2465801 | Hs.700353 |
| A_23_P358542 | KIFC2 | Homo sapiens kinesin family member C2 (KIFC2), mRNA [NM_145754] | NM_145751 | ENST00000301331 | 90990 | kinesin family member C2 | chr8:14569914 9-145699208 | GO:0005515\|GO:0000166\|NM_145754\|GO:0005874\|GO:0003777\|GO:0005524\|GO:0007018 | | THC2464318 | Hs.52713 |
| A_33_P3255290 | JAKMIP2 | Homo sapiens janus kinase and microtubule interacting Protein 2 (JAKMIP2), mRNA [NM_014790] | NM_014790 | ENST00000333010 | 9832 | janus kinase and microtubule interacting protein 2 | chr5:14699754 2-146997483 | GO:0005794 | NM_014790 | THC2471193 | Hs.184323 |
| A_23_P140384 | CTSG | Homo sapiens cathepsin G (CTSG), mRNA [NM_001911] | NM_001911 | ENST00000216336 | 1511 | cathepsin G | chr14:2504284 7-25042788 | GO:0005515\|GO:0006955\|NM_001911\|GO:0009986\|GO:0005886\|GO:0004252\|GO:0006508\|GO:0008233\|GO:0042742 | | THC2786321 | Hs.421724 |
| A_32_P165340 | SRP9 | Homo sapiens signal recognition particle 9 kDA | NM_003133 | ENST00000366839 | 6726 | signal recognition particle 9 | chr1:22597804 3-225978102 | GO:0005786\|GO:0005515\|NM_003133\|GO:0005737\|GO:0005785\|GO:0006614\|GO:0008312 | | THC2549862 | Hs.511425 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (SRP9), transcript variant 2, mRNA [NM_003133] | | | | kDa | | GO:0005047|GO:0045900 | | | |
| A_24_P76854 | KRTAP2-1 | Homo sapiens keratin associated Protein 2-1 (KRTAP2-1), mRNA [NM_001123387] | NM_001123387 | ENST00000391419 | 81872 | keratin associated protein 2-1 | chr17:39203004-39202945 | GO:0045095 | NM_001123387 | NP307251 | Hs.52921 |
| A_23_P166633 | ITGB5 | Homo sapiens integrin, beta 5 (ITGB5), mRNA [NM_002213] | NM_002213 | ENST00000460797 | 3693 | integrin, beta 5 | chr3:124482550-124482491 | GO:0005515|GO:0008305|NM_002213 GO:0007160|GO:0005886 GO:0007229|GO:0004872 GO:0016021|GO:0007155 | | THC2469552 | Hs.536663 |
| A_33_P3252414 | TH | Homo sapiens tyrosine hydroxylase (TH), transcript variant 1, mRNA [NM_199292] | NM_199292 | ENST00000381178 | 7054 | tyrosine hydroxylase | chr11:2185218-2185159 | GO:0005515|GO:0033162|NM_199292 GO:0030424|GO:0045471 GO:0008016|GO:0005634 GO:0048596|GO:0046872 GO:0005829|GO:0005739 GO:0042418|GO:0005737 GO:0043195|GO:0001963 GO:0043204|GO:0007613 GO:0007626|GO:0007612 GO:0001666|GO:0007617 GO:0009072|GO:0035240 GO:0031410|GO:0048545 GO:0008198|GO:0005790 GO:0008021|GO:0008199 GO:0003007|GO:0004511 GO:0006585|GO:0043473 GO:0042421|GO:0009898 GO:0042755|GO:0042136 GO:0042462|GO:0007601 GO:0016597|GO:0055114 | | THC2475255 | Hs.435609 |
| A_33_P3238410 | SBF1 | Homo sapiens SET binding factor 1 (SBF1), mRNA [NM_002972] | NM_002972 | ENST00000356279 | 6305 | SET binding factor 1 | chr22:50899648-50899589 | GO:0016791|GO:0006470|NM_002972 GO:0005634|GO:0016021 GO:0008138 | | THC2491636 | Hs.589924 |
| A_33_P3369716 | | Q9VKG5_DROME (Q9VKG5) CG14930-PA (AT28291p), Partial (5%) [THC2679405] | | ENST00000360485 | | | chr12:6882570-68825641 | | | THC2679405 | |
| A_23_P160849 | FCER1G | Homo sapiens fragment of IgE, high affinity 1, receptor for; gamma Fcpolypeptide (FCER1G), mRNA[NM_004106] | NM_004106 | ENST00000289902 | 2207 | Fc fragment of IgE, high affinity 1, receptor for; gamma polypeptide | chr1:161188875-161188934 | GO:0005515|GO:0019863|NM_004106 GO:0005886|GO:0005887 GO:0007166|GO:0004888 | | THC2463219 | Hs.433300 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3384229 | | | | | | | | | | | |
| A_23_P376172 | C1orf64 | Homo sapiens chromosome 1 open reading frame 64 (C1orf64), mRNA [NM_178840] | NM_178840 | ENST00000329454 | 149563 | chromosome 1 open reading frame 64 | chr14:0398399 05-039839846 chr1:16332535-16332594 | | NM_178840 | NP1140283 | Hs.29190 |
| A_33_P3332052 | SLC26A11 | Homo sapiens solute carrier family 26, member 11 (SLC26A11), transcript variant 1, mRNA[NM_001166347] | NM_001166347 | ENST00000361193 | 284129 | solute carrier family 26, member 11 | chr17:7819965 2-78199711 | GO:0008509|GO:0005215|GO:0005886| GO:0005794|GO:0005783|GO:0008272| GO:0008271|GO:0016021| GO:0013580|GO:0055085| GO:0006811 | NM_001166347 | THC2569879 | Hs.4866 |
| A_24_P18621 | AEBP2 | Homo sapiens AE binding Protein 2 (AEBP2), transcript variant 1, mRNA [NM_153207] | NM_153207 | ENST00000433841 | 121536 | AE binding protein 2 | chr12:1967291 6-19672975 | GO:0005622|GO:0006355|GO:0008270| GO:0003714|GO:0005634|GO:0003677| GO:0046872|GO:0016568 | NM_153207 | THC2463191 | Hs.126497 |
| A_33_P3348670 | LOC100510141 | PREDICTED: Homo sapiens secreted frizzled-related protein 5-like (LOC100510141), mRNA [XM_003120401] | XM_003120401 | | 100510141 | secreted frizzled-related protein 5-like | chr3:49034710-49034651 | | XM_003120401 | | |
| A_33_P3423954 | CBX2 | Homo sapiens chromobox homolog 2 (CBX2), transcript variant 2, mRNA [NM_032647] | NM_032647 | ENST00000269399 | 84733 | chromobox homolog 2 | chr17:7775588 9-77755948 | GO:0031519|GO:0016564|GO:0003682| GO:0005515|GO:0003682| GO:0016481|GO:0005634| GO:0000122|GO:0003677| GO:0000785|GO:0016568| GO:0006333 | NM_032647 | THC2486616 | Hs.368410 |
| A_33_P3346508 | | | | | | | | | | | |
| A_33_P3413958 | OR7E47P | Homo sapiens olfactory receptor, family 7, subfamily E, member 47 Pseudogene, mRNA (cDNA clone IMAGE: 5590288). [BC042060] | BC042060 | ENST00000546390 | 26628 | olfactory receptor, family 7, subfamily E, member 47 Pseudogene | chr14:1045782 89-104578348 chr8:01177767 5-011777616 | | | THC2501952 | Hs.524431 |
| A_33_P3388588 | | CDNA_FLJ27068 fis, clone SPL01475 [Source: UniProtKB/TrEMBL; Acc: Q 6ZNV2] [ENST00000378340] | AK130578 | ENST00000378340 | | | chr16:8923535 2-89235411 | | | NP852605 | Hs.513818 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P357847 | LOC100510044 | immunoglobulin kappA variable 3-15 [Source: HGNC Symbol; Acc: 5816] [ENST00000390252] | XM_003120829 | ENST00000390252 | 100510044 | immunoglobulin kappa locus-like | chr2:89384737-89384678 | | XM_003120829 | NP1170004 | Hs.449621 |
| A_33_P3215422 | LYL1 | Homo sapiens lymphoblastic leukemia derived sequence 1 (LYL1), mRNA [NM_005583] | NM_005583 | ENST00000264824 | 4066 | lymphoblastic leukemia derived sequence 1 | chr19:13211153-13211479 | GO:0030528|GO:0005634|GO:0003677|GO:0045449 | NM_005583 | THC2700985 | Hs.46446 |
| A_23_P24004 | IFIT2 | Homo sapiens interferon-induced protein with tetratricopeptide repeats 2 (IFIT2), mRNA [NM_001547] | NM_001547 | ENST00000371826 | 3433 | interferon-induced protein with tetratricopeptide repeats 2 | chr10:91068397-91068456 | GO:0008150|GO:0005488|GO:0005575 | NM_001547 | THC2463173 | Hs.437609 |
| A_33_P3276758 | | | | | | | chr16:03307079-033070798 | | | | |
| A_23_P24365 | ANKRD49 | Homo sapiens ankyrin repeat domain 49 (ANKRD49), mRNA [NM_017704] | NM_017704 | ENST00000302755 | 54851 | ankyrin repeat domain 49 | chr11:94232501-94232560 | | NM_017704 | THC2464810 | Hs.29052 |
| A_33_P3410895 | POR | P450 (cytochrome) oxidoreductase [Source: HGNC Symbol; Acc: 9208] [ENST00000421059] | | ENST00000421059 | 5447 | P450 (cytochrome) oxidoreductase | chr7:75544784-75544843 | | | THC2629558 | Hs.501890 |
| A_24_P361643 | C19orf55 | Homo sapiens chromosome 19 open reading frame 55 (C19orf55), mRNA [NM_001039887] | NM_001039887 | ENST00000544158 | 148137 | chromosome 19 open reading frame 55 | chr19:36259696-36259755 | | NM_001039887 | THC2475926 | Hs.527982 |
| A_33_P3216938 | AMPD3 | adenosine monophosphate deaminase 3 [Source: HGNC Symbol; Acc: 470] [ENST00000527261] | EF537581 | ENST00000527261 | 272 | adenosine monophosphate deaminase 3 | chr11:10330136-10330195 | | | | Hs.501890 |
| A_33_P3352687 | LOC100133161 | Homo sapiens hypothetical LOC100133161 (LOC100133161), non-coding RNA [NR_028326] | NR_028326 | ENST00000450789 | 100133161 | hypothetical LOC100133161 | chr1:128915-128856 | | NR_028326 | THC2531619 | Hs.512417 |
| A_33_P3399985 | | immunoglobulin kappa variable 2D-24 (non-functional) [Source: HGNC | AJ272081 | ENST00000462693 | | | chr2:90044286-90044345 | | | NP1474898 | Hs.535593 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P84596 | MZB1 | *Homo sapiens* marginal zone B and B1 cell-specific protein (MZB1), mRNA [NM_016459] Symbol; Acc: 5797 [ENST00000462693] | NM_016459 | ENST00000503351 | 51237 | marginal zone B and B1 cell-specific protein | chr5:138723602-138723543 | GO:0005737\|GO:0006915\|GO:0005576 | NM_016459 | THC2605618 | Hs.409563 |
| A_33_P3379454 | UHRF1 | *Homo sapiens* ubiquitin-like with PHD and ring finger domains 1 (UHRF1), transcript variant 2, mRNA [NM_013282] | NM_013282 | ENST00000543616 | 29128 | ubiquitin-like with PHD and ring finger domains 1 | chr19:4960895-4960954 | GO:0005515\|GO:0003700\|GO:0006357\|GO:0003702\|GO:0008283\|GO:0016874\|GO:0005634\|GO:0046872\|GO:0006974\|GO:0007049\|GO:0006281\|GO:0019941\|GO:0008270\|GO:0045449 | NM_013282 | THC2462675 | Hs.108106 |
| A_33_P3215112 | C2CD4C | *Homo sapiens* C2 calcium-dependent domain containing 4C (C2CD4C), mRNA [NM_001136263] | NM_001136263 | ENST00000332235 | 126567 | C2 calcium-dependent domain containing 4C | chr19:405567-405508 | | NM_001136263 | THC2615089 | Hs.223770 |
| A_23_P117380 | FAM181A | *Homo sapiens* family with sequence similarity 181, member A (FAM181A), transcript variant 1, mRNA [NM_138344] | NM_138344 | ENST00000267594 | 90050 | family with sequence similarity 181, member A | chr14:9439578-94395843 | | NM_138344 | THC2478030 | Hs.525550 |
| A_23_P56288 | LENG8 | *Homo sapiens* leukocyte receptor cluster (LRC) member 8 (LENG8), mRNA [NM_052925] | NM_052925 | ENST00000542665 | 114823 | leukocyte receptor cluster (LRC) member 8 | chr19:5497292-54972981 | GO:0005515 | NM_052925 | NP1402212 | Hs.502378 |
| A_33_P3235491 | | | | | | | chr22:0298777 03-029877644 | | | | |
| A_33_P3211327 | LOC100130348 | Uncharacterized protein [Source: UniProtKB/TrEMBL; Acc: E9PME8] [ENST00000334821] | AK124141 | ENST00000334821 | 100130348 | hypothetical LOC100130348 | chr11:6485616 3-64856104 | | | THC2626263 | Hs.98170 |
| A_33_P3233869 | | *Homo sapiens*, clone IMAGE: 6155889, mRNA. [BC043411] | BC043411 | ENST00000437267 | | | chr1:14318413 7-143184078 | | | THC2493596 | Hs.446446 |
| A_33_P3321793 | | UI-CF-EC1-abx-d-10-0-UI.s1 UI-CF-EC1 *Homo sapiens* cDNA clone UI-CF-EC1-abx-d-10-O-UI 3', mRNA | BM973477 | | | | chr17:5024626-5024685 | | | | Hs.681925 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | sequence [BM973477] | | | | | | | | | |
| A_33_P3273364 | YIPF2 | Homo sapiens Yip1 domain family, member 2 (YIPF2), mRNA [NM_024029] | NM_024029 | ENST00000253031 | 78992 | Yip1 domain family, member 2 | chr19:1103378-41103725 | GO:0030133|GO:0016020|GO:0016021 | NM_024029 | THC2462992 | Hs.720136 |
| A_24_P330385 | SLC22A17 | Homo sapiens solute carrier family 22, member 17 (SLC22A17), transcript variant 2, mRNA [NM_016609] | NM_016609 | ENST00000474774 | 51310 | solute carrier family 22, member 17 | chr14:23816808-23816749 | GO:0005215|GO:0016020|GO:0016609|GO:0016021|GO:0055085|GO:0006811 | NM_016609 | THC2735825 | Hs.373498 |
| A_33_P3248602 | DUX4 | Homo sapiens double homeobox 4 (DUX4), mRNA [NM_033178] | NM_033178 | ENST00000507734 | 22947 | double homeobox A | chrUn_gl000228:77296-77355 | GO:0043565|GO:0006355|GO:0003700|GO:0005634 | NM_033178 | THC2493180 | Hs.553518 |
| A_24_P368943 | EVX1 | Homo sapiens even-skipped homeobox 1 (EVX1), mRNA [NM_001989] | NM_001989 | ENST00000496902 | 2128 | even-skipped homeobox 1 | chr7:27285959-27286018 | GO:0043565|GO:0006355|GO:0003700|GO:0045944|GO:0007275|GO:0005634 | NM_001989 | THC2484995 | Hs.369879 |
| A_24_P319640 | LOC151534 | Homo sapiens hypothetical LOC151534 (LOC151534), non-coding RNA [NR_024606] | NR_024606 | | 151534 | hypothetical LOC151534 | chr2:74731712-74731771 | GO:0009792|GO:0021913 | NR_024606 | THC2475501 | Hs.516124 |
| A_23_P41987 | GFRA3 | Homo sapiens GDNF family receptor alpha 3 (GFRA3), mRNA [NM_001496] | NM_001496 | ENST00000378362 | 2676 | GDNF family receptor alpha 3 | chr5:13758839-13758836 | GO:0005886|GO:0005102|GO:0031225|GO:0048485|GO:0007165|GO:0007411|GO:0048666|GO:0007422|GO:0004872|GO:0001764|GO:0008046|GO:0009897|GO:0019898 | NM_001496 | THC2473100 | Hs.58042 |
| A_33_P5577120 | | Homo sapiens hypothetical protein LOC283868, mRNA (cDNA clone IMAGE:5089285), partial cds. [BC033227] | BC033227 | | | | chr16:2032527-2032586 | | | THC2642808 | Hs.620382 |
| A_33_P3329104 | | | | | | | chr19:0078066 44-007806703 | | | | |
| A_23_P36198 | GLCCI1 | Homo sapiens glucocorticoid induced transcript 1 (GLCCI1), mRNA [NM_138426] | NM_138426 | ENST00000482540 | 113263 | glucocorticoid induced transcript 1 | chr7:8128578-8128637 | GO:0005515|GO:0005737 | NM_138426 | THC2601241 | Hs.131673 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P418203 | CNTNAP3 | Homo sapiens contactin associated protein-like 3 (CNTNAP3), mRNA [NM_033655] | NM_033655 | ENST00000323947 | 79937 | contactin associated protein-like 3 | chr9:39171403-39166052 | GO:0007165\|GO:0008037\|GO:0005886\|GO:0005102\|GO:0005576\|GO:0016021\|GO:0007155 | NM_033655 | THC2569253 | Hs.658328 |
| A_33_P398719 | | Homo sapiens immunoglobulin lambda variable 5-48 (non-functional) [Source: HGNC Symbol; Acc: 5925] [ENST00000390293] | | ENST00000390293 | | | chr22:2270758 1-22707640 | | | NP186136 | |
| A_23_P51711 | CELA2B | Homo sapiens chymotrypsin-like elastase family, member 2B (CELA2B), mRNA [NM_015849] | NM_015849 | ENST00000488764 | 51032 | chymotrypsin-like elastase family, member 2 | chr1:15813857 15813916 | GO:0004252\|GO:0006508\|GO:0008233\|GO:0005576 | NM_015849 | THC2462641 | Hs.631871 |
| A_33_P3248137 | OLFML2A | Homo sapiens olfactomedin-like 2A (OLFML2A), mRNA [NM_182487] | NM_182487 | ENST00000342100 | 169611 | olfactomedin-like 2A | chr9:12757263 2-127572691 | GO:0031012\|GO:0016020\|GO:0030198\|GO:0050840\|GO:0005576\|GO:0042803 | NM_182487 | THC2738863 | Hs.357004 |
| A_24_P72750 | SPIN1 | Homo sapiens spindlin 1 (SPIN1), mRNA [NM_006717] | NM_006717 | ENST00000375859 | 10927 | spindlin 1 | chr9:91093209-91093268 | GO:0007049\|GO:0007276\|GO:0005819\|GO:0007275\|GO:0005634 | NM_006717 | THC2517348 | Hs.146804 |
| A_23_P372368 | NCRNA00257 | Homo sapiens non-protein coding RNA 257 (NCRNA00257), non-coding RNA [NR_033800] | NR_033800 | | 257357 | non-protein coding RNA 257 | chr21:4068649 8-40686439 | | NR_033800 | THC2478660 | Hs.729612 |
| A_33_P3369146 | ATP2B3 | Homo sapiens ATPase, Ca++ transporting, plasma membrane 3 (ATP2B3), transcript variant 2, mRNA [NM_001001344] | NM_001001344 | ENST00000393842 | 492 | ATPase, Ca++ transporting, plasma membrane 3 | chrX:15282762 3-152827682 | GO:0005516\|GO:0000287\|GO:0005794\|GO:0005886\|GO:0005509\|GO:0005524\|GO:0005388\|GO:0005754\|GO:0016787\|GO:0000166\|GO:0008152\|GO:0016820\|GO:0006816\|GO:0016021\|GO:0006812 | NM_001001344 | THC2478163 | Hs.533956 |
| A_33_P3712341 | CXCL12 | Homo sapiens chemokine (C-X-C motif) ligand 12 (CXCL12), transcript variant 3, mRNA [NM_001033886] | NM_001033886 | ENST00000374426 | 6387 | chemokine (C-X-C motif) ligand 12 | chr10:4488045 3-44880394 | GO:0008009\|GO:0008015\|GO:0006874\|GO:0005576\|GO:0009615\|GO:0005615\|GO:0007165\|GO:0006955\|GO:0006935\|GO:0007186\|GO:0008064\|GO:0009026\|GO:0004871\|GO:0007155\|GO:0008083 | NM_001033886 | NP1463957 | Hs.522891 |
| A_23_P41166 | B3GALNT1 | Homo sapiens beta-1,3-N-acetyl- | NM_001038628 | ENST00000392781 | 8706 | beta-1,3-N-acetyl- | chr3:16080234 8-160802289 | GO:0009312\|GO:0005794\|GO:0000287\|GO:0016020 | NM_001038628 | THC2490103 | Hs.418062 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | galactosaminyltransferase 1 (globoside blood group) (B3GALNT1), transcript variant 5, mRNA [NM_001038628] | | | | galactosaminyltransferase 1 (globoside blood-group) | | GO:0016757\|GO:0008499\|GO:0006486\|GO:0016021\|GO:0047273\|GO:0008378 | | THC2595453 | Hs.514016 |
| A_33_P3377763 | FLJ36000 | Homo sapiens hypothetical FLJ36000 (FLJ36000), non-coding RNA [NR_027084] | NR_027084 | ENST00000468381 | 284124 | hypothetical FLJ36000 | chr17:21909487-21909546 | | NR_027084 | | Hs.710305 |
| A_33_P3346461 | | NLR family, apoptosis inhibitory protein [Source: HGNC Symbol; Acc: 7634] [ENST00000508794] | XM_003118467 | ENST00000504546 | | | chr5:68919510-68919569 | | XM_003118467 | THC2668955 | Hs.446240 |
| A_33_P3619221 | ZMYND8 | Homo sapiens zinc finger, MYND-type containing 8 (ZMYND8), transcript variant 1, mRNA [NM_183047] | NM_183047 | ENST00000461685 | 23613 | zinc finger, MYND-type containing 8 | chr20:45839491-45839432 | GO:0005515\|GO:0008270\|GO:0046872 | NM_183047 | NP1154284 | Hs.564533 |
| A_33_P3384710 | C17orf63 | Homo sapiens chromosome 17 open reading frame 63 [C17orf63], transcript variant 2, mRNA [NM_018182] | NM_018182 | ENST00000341217 | 55731 | chromosome 17 open reading frame 63 | chr17:2708534-27085288 | | NM_018182 | THC2461997 | Hs.482873 |
| A_24_P54178 | TMED5 | Homo sapiens transmembrane emp24 protein transport domain containing 5 (TMED5), transcript variant 1, mRNA [NM_016040] | NM_016040 | ENST00000370290 | 50999 | transmembrane emp24 protein transport domain containing 5 | chr1:93617749-93617690 | GO:0005793\|GO:0016020\|NM_016040\|GO:0005783\|GO:0006810\|GO:0016021 | | THC2578839 | |
| A_33_P3354935 | CSF1 | Homo sapiens colony stimulating factor 1 (macrophage) (CSF1), transcript variant 4, mRNA [NM_172212] | NM_172212 | ENST00000369802 | 1435 | colony stimulating factor 1 (macrophage) | chr1:110469302-110469361 | GO:0005515\|GO:0048471\|GO:0008284\|GO:0005886\|GO:0005157\|GO:0046579\|GO:0005615\|GO:0030154\|GO:0042803\|GO:0048873\|GO:0030278\|GO:0045657\|GO:0045860\|GO:0042476\|GO:0040018\|GO:0030097\|GO:0030335\|GO:0010744\|GO:0045672\|GO:0005576\|GO:0045651\|GO:0005125 | NM_172212 | | Hs.591402 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3322945 | SPDYC | Homo sapiens speedy homolog C (Xenopus laevis) (SPDYC), mRNA [NM_001008778] | NM_001008778 | ENST00000377185 | 387778 | speedy homolog C (Xenopus laevis) | chr11:64940040-64940464 | GO:0010628\|GO:0043235\|GO:0003006\|GO:0032270\|GO:0032946\|GO:0042117\|GO:0016021\|GO:0008083\|GO:0042488\|GO:0001954\|GO:0007049\|GO:0019901 | NM_001008778 | THC2607520 | Hs.450642 |
| A_24_P419028 | MOP-1 | Homo sapiens mRNA for MOP-1, complete cds. [AB014771] | AB014771 | | 643616 | MOP-1 | chr4:82390257-82390198 | GO:0005634 | | NP373383 | Hs.679418 |
| A_33_P3371144 | | | | | | | chr17:0794548-68-079454809 | | | | |
| A_24_P273865 | MED20 | Homo sapiens mediator complex subunit 20 (MED20), mRNA [NM_004275] | NM_004275 | ENST00000467535 | 9477 | mediator complex subunit 20 | chr6:41873366-41873307 | GO:0005515\|GO:0006357\|GO:0003899\|GO:0016592\|GO:0005634\|GO:0016455\|GO:0045449 | NM_004275 | THC2624422 | Hs.278434 |
| A_23_P134935 | DUSP4 | Homo sapiens dual specificity phosphatase 4 (DUSP4), transcript variant 1, mRNA [NM_001394] | NM_001394 | ENST00000240100 | 1846 | dual specificity phosphatase 4 | chr8:29194441-29194382 | GO:0010033\|GO:0006470\|GO:0016787\|GO:0000165\|GO:0008330\|GO:0005654\|GO:0005634\|GO:0017017\|GO:0004725 | NM_001394 | THC2466297 | Hs.417962 |
| A_33_P3247473 | KRTAP23-1 | Homo sapiens keratin associated protein 23-1 (KRTAP23-1), mRNA [NM_181624] | NM_181624 | ENST00000334160 | 337963 | keratin associated protein 23-1 | chr21:3172090-6-31720847 | GO:0005882\|GO:0003824 | NM_181624 | NP815333 | Hs.553688 |
| A_33_P3345132 | ZNF578 | Homo sapiens zinc finger protein 578 (ZNF578), mRNA [NM_001099694] | NM_001099694 | | 147660 | zinc finger protein 578 | chr19:5301931-9-53019378 | GO:0005622\|GO:0008270\|GO:0005634\|GO:0003677\|GO:0046872\|GO:0045449 | NM_001099694 | THC2742978 | Hs.157287 |
| A_32_P100830 | KIF19 | Homo sapiens kinesin family member 19 (KIF19), mRNA [NM_153209] | NM_153209 | ENST00000389916 | 124602 | kinesin family member 19 | chr17:7235187-8-72351937 | GO:0000166\|GO:0005874\|GO:0003777\|GO:0005524\|GO:0007018 | NM_153209 | THC2686967 | Hs.372773 |
| A_33_P3350259 | FAM129C | Homo sapiens family with sequence similarity 129, member C (FAM129C), transcript variant 2, mRNA [NM_001098524] | NM_001098524 | ENST00000352727 | 199786 | family with sequence similarity 129, member C | chr19:1765294-6-17653005 | | NM_001098524 | NP814710 | Hs.434133 |
| A_33_P3318646 | CALY | Homo sapiens calcyon neuron- | NM_015722 | ENST00000467611 | 50632 | calcyon neuron-specific | chr10:1351389-91-135138932 | GO:0045807\|GO:0005886\|GO:0032051\|GO:0005887 | NM_015722 | THC2647449 | Hs.148680 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3419970 | NPB | specific vesicular protein (CALY), mRNA[NM_015722] *Homo sapiens* neuropeptide B (NPB), mRNA [NM_148896] | NM_148896 | ENST00000333383 | 256933 | vesicular protein neuropeptide B | chr17:79860717-79860776 | GO:0031410|GO:0097212|GO:0050780|GO:0048268 GO:0005515|GO:0001664|NM_148896|GO:0007218|GO:0005576 | | | Hs.708916 Hs.443243 |
| A_23_P14564 | GPR65 | *Homo sapiens* G protein-coupled receptor 65 (GPR65), mRNA [NM_003608] | NM_003608 | ENST00000267549 | 8477 | G protein-coupled receptor 65 | chr14:88478025-88478084 | GO:0007165|GO:0006955|NM_003608|GO:0007186|GO:0005886|GO:0005887|GO:0004930|GO:0006915|GO:0007275|GO:0004872 | | THC2476461 | Hs.435845 |
| A_23_P391857 | ESRRB | *Homo sapiens* estrogen-related receptor beta (ESRRB), mRNA [NM_004452] | NM_004452 | ENST00000261532 | 2103 | estrogen-related receptor beta | chr14:76966256-76966315 | GO:0043565|GO:0006355|NM_004452|GO:0003700|GO:0003707|GO:0008270|GO:0005634|GO:0005496|GO:0046872 | | THC2489574 | |
| A_33_P3220105 | LOC644246 | *Homo sapiens* hypothetical LOC644246 (LOC644246), non-coding, RNA [NR_034172] | NR_034172 | ENST00000398275 | 644246 | hypothetical LOC644246 | chr17:44271044-44271103 | | NR_034172 | THC2648285 | Hs.644600 |
| A_32_P8623 | AGBL3 | *Homo sapiens* ATP/GTP binding protein-like 3 (AGBL3), mRNA [NM_178563] | NM_178563 | ENST00000359383 | 340351 | ATP/GTP binding protein-like 3 | chr7:134674061-134678302 | GO:0005737|GO:0006508|NM_178563|GO:0008270|GO:0008233|GO:0046872|GO:0008237|GO:0004181 | | THC2636775 | Hs.648616 |
| A_24_P191417 | NAB1 | *Homo sapiens* NGFI-A binding protein 1 (EGR1 binding protein 1) (NAB1), mRNA [NM_005966] | NM_005966 | ENST00000337386 | 4664 | NGFI-A binding protein 1 (EGR1 binding protein 1) | chr2:191557095-191557154 | GO:0016564|GO:0014037|NM_005966|GO:0006355|GO:0001958|GO:0005794|GO:0005886|GO:0042552|GO:0045682|GO:0016481|GO:0005634 | | THC2620109 | Hs.730686 |
| A_33_P3237552 | FIBCD1 | *Homo sapiens* fibrinogen C domain containing 1 (FIBCD1), transcript variant 1, mRNA [NM_032843] | NM_032843 | ENST00000253018 | 84929 | fibrinogen C domain containing 1 | chr9:133779394-133779335 | GO:0007165|GO:0016020|NM_032843|GO:0005102|GO:0016021|GO:0005615 | | THC2474476 | Hs.133205 |
| A_33_P3325547 | C10orf53 | *Homo sapiens* chromosome 10 open reading frame 53 (C10orf53), transcript variant 1, mRNA [NM_182554] | NM_182554 | ENST00000533836 | 282966 | chromosome 10 open reading frame 53 | chr10:50916883-50916942 | | NM_182554 | THC2486180 | Hs.131287 |
| A_33_P3268167 | | | | | | | chr10:082419955-082420014 | | | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3351836 | C2orf73 | chromosome 2 open reading frame 73 [Source: HGNC 2 Symbol; Acc: 26861] [ENST00000414747] | | ENST00000414747 | 129852 | chromosome 2 open reading frame 73 | chr2:54610272-54610331 | | | THC2774850 | |
| A_33_P3285754 | | | | | | | chr9:09044080 4-090440863 | | | | Hs.501286 |
| A_33_P3360823 | C10orf88 | Homo sapiens chromosome 10 open reading frame 88 (C10orf88), mRNA [NM_024942] | NM_024942 | ENST00000481909 | 80007 | chromosome 10 open reading frame 88 | chr10:1246911 39-124691080 | | NM_024942 | THC2471563 | Hs.248159 |
| A_33_P3359250 | MAD2L2 | MAD2 mitotic arrest deficient-like 2 (yeast) [Source: HGNC Symbol; Acc: 6764] [ENST00000376664] | | ENST00000376664 | 10459 | MAD2 mitotic arrest deficient-like 2 (yeast) | chr1:11735986-11735927 | | | NP1247987 | Hs.721149 |
| A_23_P410507 | PSPN | Homo sapiens persephin (PSPN), mRNA [NM_004158] | NM_004158 | ENST00000245810 | 5623 | persephin | chr19:6375594-6375535 | GO:0001658|GO:0005576|NM_004158 GO:0007417|GO:0008083| GO:0005615 | | THC2530481 | Hs.526920 |
| A_33_P3311750 | CCDC144A | Homo sapiens coiled-coil domain containing 144A (CCDC144A), mRNA [NM_014695] | NM_014695 | ENST00000456009 | 9720 | coiled-coil domain containing 144A | chr17:1663884 4-16638903 | | NM_014695 | THC2478811 | Hs.510635 |
| A_23_P29153 | RTDR1 | Homo sapiens rhabdoid tumor deletion region gene 1 (RTDR1), mRNA [NM_014433] | NM_014433 | ENST00000216036 | 27156 | rhabdoid tumor deletion region gene 1 | chr22:2340166 8-23401609 | GO:0008150|GO:0005488|NM_014433 GO:0005575 | | THC2476489 | Hs.719042 |
| A_33_P3424591 | | immunoglobulin heavy constant gamma 1 (G1m marker) [Source: HGNC Symbol; Acc: 5525] [ENST00000390549] | CR611254 | ENST00000390549 | | | chr14:1062078 69-106207810 | | | NP232832 | Hs.26268 |
| A_23_P76488 | EMP1 | Homo sapiens epithelial membrane protein 1 (EMP1), mRNA [NM_001423] | NM_001423 | ENST00000256951 | 2012 | epithelial membrane protein 1 | chr12:1336956 2-13369621 | GO:0008544|GO:0005886|NM_001423 GO:0008283|GO:0030855| GO:0016049|GO:0005624| GO:0007275|GO:0016021 | | THC2465394 | Hs.643431 |
| A_33_P3278033 | TUSC1 | Homo sapiens tumor suppressor candidate 1 (TUSC1), mRNA [NM_001004125] | NM_001004125 | ENST00000358022 | 286319 | tumor suppressor candidate 1 | Chr9:25677740-25677681 | | NM_001004125 | THC2472152 | |
| A_23_P167168 | IGJ | Homo sapiens immunoglobulin | NM_144646 | ENST00000254801 | 3512 | immunoglobulin J | chr4:71521933-71521874 | GO:0006955|GO:0005576|NM_144646 GO:0003823 | | THC2469801 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3360728 | BLVRB | J polypeptide, linker protein for immuno-globulin alpha and mu polypeptides (IGJ), mRNA [NM_144646] | | | | J polypeptide, linker protein for immuno-globulin alpha and mu polypeptides | | | | | |
| A_33_P3360728 | BLVRB | Homo sapiens biliverdin reductase B (flavin reductase (NADPH)) (BLVRB), mRNA [NM_000713] | NM_000713 | ENST00000263368 | 645 | biliverdin reductase B (flavin reductase (NADPH)) | chr19:40953760-40953701 | GO:0050662|GO:0005737|NM_000713 GO:0042602|GO:0005488| GO:0004074|GO:0016491| GO:0044237|GO:0055114 | | THC2468607 | Hs.515785 |
| A_33_P3329419 | DNM1 | Homo sapiens dynamin 1 (DNM1), transcript variant 1, mRNA [NM_004408] | NM_004408 | ENST00000475805 | 1759 | dynamin 1 | chr9:131013158-131013217 | GO:0005515|GO:0005737|NM_004408 GO:0003774|GO:0016787| GO:0000166|GO:0005874| GO:0003924|GO:0005856| GO:0005525|GO:0006898 | | THC2563095 | Hs.522413 |
| A_33_P3395209 | | | | | | | chr15:03220131-632201257 | | | | |
| A_33_P3239854 | ALKBH5 | Homo sapiens alkB, alkylation repair homolog 5 (E. coli) (ALKBH5), mRNA [NM_017758] | NM_017758 | ENST00000261650 | 54890 | alkB, alkylation repair homolog 5 (E. coli) | chr17:1811175-18111813 | GO:0016020|GO:0016021 NM_017758 | | THC2510263 | Hs.730752 |
| A_33_P3345474 | | Homo sapiens, clone IMAGE: 3890870, mRNA. [BC036832] | BC036832 | ENST00000381051 | | | chr22:46501501-46501560 | | | THC2609961 | |
| A_33_P3217218 | AGPAT5 | Homo sapiens 1-acyl-glycerol-3-phosphate O-acyltransferase 5 (lysophosphatidic acid acyltransferase, epsilon) (AGPAT5), mRNA [NM_018361] | NM_018361 | | 55326 | 1-acylglycerol-3-phosphate O-acyl-trans-ferase 5(lyso-phosphatidic acid acyltrans-ferase, epsilon) | chr8:6618891-6618950 | GO:0005739|GO:0016020|NM_018361 GO:0008152|GO:0016021| GO:0008654|GO:0005575| GO:0003841|GO:0046027| GO:0016740|GO:0008415| GO:0005829 | | THC2603763 | Hs.64002 |
| A_23_P7074 | C4orf14 | Homo sapiens chromosome 4 open reading frame 14 (C4orf14), mRNA [NM_032313] | NM_032313 | ENST00000264230 | 84273 | chromosome 4 open reading frame 14 | chr4:57829743-57829684 | GO:0005622|GO:0005743|NM_032313 GO:0005525 | | THC2509962 | Hs.8715 |
| A_33_P3394203 | YIPF3 | Yip1 domain family, member 3 [Source: HGNC Symbol; Acc: 21023] [ENST00000372417] | | ENST00000372417 | 25844 | Yip1 domain family, member 3 | chr6:43481455-43481396 | | | THC2559426 | |
| A_33_P3271171 | CNOT3 | CCR4-NOT transcription complex, | AL133647 | ENST00000358389 | 4849 | CCR4-NOT transcription | chr19:5465707-054657129 | | THC2755730 | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | subunit 3 [Source: HGNC Symbol; Acc: 7879] | | ENST00000358389 | | complex, subunit 3 | | | | | |
| A_33_P3314231 | CRYBA2 | Homo sapiens crystallin, beta A2 (CRYBA2), transcript variant 1, mRNA [NM_005209] | NM_005209 | ENST00000295728 | 1412 | crystallin, beta A2 | chr2:219854976-219854917 | GO:0008150\|GO:0003674\|NM_005209 GO:0005212\|GO:0005575\| GO:0042803 | | THC2464517 | Hs.415790 |
| A_33_P3422248 | | nae18g06.x1 NCI_CGAP_Ov18 Homo sapiens cDNA clone IMAGE: 3435827 3'similar to contains Alu repetitive element;; mRNA sequence [BF733045] | BF733045 | | | | | | | THC2703203 | Hs.650086 |
| A_33_P3251205 | | immunoglobulin lambda variable 3-9 (gene/pseudogene) [Source: HGNC Symbol; Acc: 5918] [ENST00000390316] | AF194657 | ENST00000390316 | | | chr22:23162022-23162081 | | | NP078180 | Hs.449585 |
| A_33_P3222139 | SREBF1 | Homo sapiens sterol regulatory element binding transcription factor 1 (SREBF1), transcript variant 1, mRNA [NM_001005291] | NM_001005291 | ENST00000338854 | 6720 | sterol regulatory element binding transcription factor 1 | chr17:17715363-17715304 | GO:0005515\|GO:0006629\|NM_001005291 GO:0003700\|GO:0005794\| GO:0006357\|GO:0032810\| GO:0003702\|GO:0005783\| GO:0005634\|GO:0031410\| GO:0005635\|GO:0016020\| GO:0005789\|GO:0016021\| GO:0045449\|GO:0008202\| GO:0008203\|GO:0009267 | | THC2507720 | Hs.592123 |
| A_32_P221305 | LOC389634 | Homo sapiens hypothetical non-coding LOC389634 (LOC389634), RNA [NR_024420] | NR_024420 | ENST00000420040 | 389634 | hypothetical LOC389634 | chr12:8509646-8509587 | | NR_024420 | THC2545092 | Hs.434403 |
| A_33_P3318444 | RNF222 | Homo sapiens ring finger protein 222 (RNF222), mRNA [NM_001146684] | NM_001146684 | ENST00000399398 | 643904 | ring finger protein 222 | chr17:8296576-8296517 | GO:0005515\|GO:0016020\|NM_001146684 GO:0008270\|GO:0016021\| GO:0046872 | | | Hs.526550 |
| A_23_P501822 | JUP | Homo sapiens junction plakoglobin (JUP), transcript variant 1, mRNA [NM_002230] | NM_002230 | ENST00000547817 | 3728 | junction plakoglobin | chr17:39911209-39911150 | GO:0030057\|GO:0008092\|NM_002230 GO:0030018\|GO:0042153\| GO:0019901\|GO:0005886\| GO:0019903\|GO:0005624\| GO:0005625\|GO:0015629\| GO:0051291\|GO:0016328 | | THC2754348 | Hs.514174 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3266848 | | Q8NH44_HUMAN (Q8NH44) Seven transmembrane helix receptor, complete [THC2605882] | | | | | chr12:048954372-048954431 | GO:0016327\|GO:0005829\|GO:0005916\|GO:0005737\|GO:0016337\|GO:0005198\|GO:0009898\|GO:0019898 | THC2605882 | |
| A_33_P3321225 | | | | ENST00000433238 | | | | | | | |
| A_33_P3270360 | OR1S1 | *Homo sapiens* olfactory receptor, family 1, subfamily S, member 1 (OR1S1), mRNA [NM_001004458] GB | NM_001004458 | ENST00000309433 | 219959 | olfactory receptor, family 1, subfamily S, member 1 | chr20:35141071-35141012 chr11:57982993-57983052 | GO:0007608\|GO:0007165\|GO:0004984\|GO:0007186\|GO:0005886\|GO:0004872\|GO:0016021\|GO:0050896 | NM_001004458 | | Hs.553645 |
| A_33_P3245160 | | | | | | | chr17:003057372-003057313 | | NP511209 | | |
| A_33_P3274164 | DOT1L | DOT1-like, histone H3 methyltransferase (*S. cerevisiae*) [Source: HGNC Symbol; Acc: 24948] [ENST00000221482] | AB058717 | ENST00000221482 | 84444 | DOT1-like, histone H3 methyltransferase (*S. cerevisiae*) | chr19:2228287-2228346 | | | THC2541364 | Hs.713641 |
| A_23_P78734 | MYH14 | *Homo sapiens* myosin, heavy chain 14, non-muscle (MYH14), transcript variant 1, mRNA [NM_001077186] | NM_001077186 | ENST00000440075 | 79784 | myosin, heavy chain 14, non-muscle | chr19:5081331 7-50813376 | GO:0005516\|GO:0003774\|GO:0000166\|GO:0008360\|GO:0003779\|GO:0016459\|GO:0005524 | NM_001077186 | NP861691 | Hs.467142 |
| A_23_P111517 | WBSCR17 | *Homo sapiens* Williams-Beuren syndrome chromosome region 17 (WBSCR17), mRNA [NM_022479] | NM_022479 | ENST00000467723 | 64409 | Williams-Beuren syndrome chromosome region 17 | chr7:71177978-71178037 | GO:0004653\|GO:0030145\|GO:0005794\|GO:0016020\|GO:0016757\|GO:0005509\|GO:0005529\|GO:0016021 | NM_022479 | THC2491805 | Hs.488591 |
| A_33_P3399474 | | ARP3_BOVIN (P61157) Actin-like protein 3 (Actin-related protein 3) (Actin-2), partial (58%) [THC2499666] | | | | | chr2:11464727 8-114647337 | | | THC2499666 | |
| A_32_P52785 | DAAM2 | *Homo sapiens* dishevelled associated activator of morphogenesis 2 (DAAM2), | NM_015345 | ENST00000398904 | 23500 | dishevelled associated activator of morpho- | chr6:39872302-39872361 | GO:0030036\|GO:0017048\|GO:0003779\|GO:0016043 | NM_015345 | THC2495474 | Hs.357128 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P374319 | RAP2C | Homo sapiens RAP2C, member of RAS oncogene family (RAP2C), transcript variant 2, mRNA [NM_015345] Homo sapiens RAP2C, member of RAS oncogene family (RAP2C), mRNA [NM_021183] | NM_021183 | ENST00000342983 | 57826 | RAP2C, member of RAS oncogene family | chrX:131338037-131337978 | GO:0005622\|GO:0007165\|GO:0000166\|GO:0005886\|GO:0000166\|GO:0007264\|GO:0003924\|GO:0005525 | NM_021183 | THC2493165 | Hs.119889 |
| A_33_P3283470 | BAI1 | Homo sapiens brain-specific angiogenesis inhibitor 1 (BAI1), mRNA [NM_001702] | NM_001702 | ENST00000323289 | 575 | brain specific angiogenesis inhibitor 1 | chr8:143626287-143626346 | GO:0005515\|GO:0008285\|GO:0001702\|GO:0005886\|GO:0016527\|GO:0007218\|GO:0005911\|GO:0005887\|GO:0007422\|GO:0007409\|GO:0007155 | NM_001702 | THC2700493 | Hs.194654 |
| A_23_P319133 | DNAJC10 | Homo sapiens DnaJ (Hsp40) homolog, subfamily C, member 10 (DNAJC10), mRNA [NM_018981] | NM_018981 | ENST00000264065 | 54431 | DnaJ (Hsp40) homolog, subfamily C, member 10 | chr2:183643075-183643134 | GO:0006457\|GO:0005783\|GO:0031072\|GO:0005788\|GO:0045454\|GO:0005576\|GO:0051082 | NM_018981 | THC2485027 | Hs.516632 |
| A_23_P353574 | NEK7 | Homo sapiens NIMA (never in mitosis gene a)-related kinase 7 (NEK7), mRNA [NM_133494] | NM_133494 | ENST00000493790 | 140609 | NIMA (never in mitosis gene a)-related kinase 7 | chr1:198288674-198288733 | GO:0005515\|GO:0005737\|GO:0000287\|GO:0000166\|GO:0004674\|GO:0006468\|GO:0005524\|GO:0016740 | NM_133494 | THC2475637 | Hs.728964 |
| A_32_P218228 | FAM109B | Homo sapiens family with sequence similarity 109, member B (FAM109B), mRNA [NM_001002034] | NM_001002034 | ENST00000321753 | 150368 | family with sequence similarity 109, member B | chr22:42474754-42474813 | | NM_001002034 | THC2602221 | Hs.368312 |
| A_33_P3348046 | | PREDICTED: Homo sapiens similar to hCG1985805 (LOC728528), mRNA [XM_001127670] | XM_001127670 | | | | chr1:220109948-220109889 | | XM_001127670 | | |
| A_33_P3428642 | DMWD | Homo sapiens dystrophia myotonica, WD repeat containing (DMWD), mRNA [NM_004943] | NM_004943 | ENST00000270223 | 1762 | dystrophia myotonica, WD repeat containing | chr19:46287419-46287360 | GO:0003674\|GO:0007126\|GO:0005575 | NM_004943 | THC2474876 | Hs.515474 |
| A_33_P3328123 | LOC100127919 | PREDICTED: Homo sapiens developmental pluripotency-associated protein 3 like (LOC100127919), mRNA [XM_001719900] | XM_001719900 | | 100127919 | developmental pluripotency-associated protein 3 pseudogene | chr12:93429166-93429225 | | XM_001719900 | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3404123 | KRTAP9-7 | keratin associated protein 9-7 [Source: HGNC Symbol; Acc: 18915] [ENST00000391154] | XM_003120879 | ENST00000391154 | 1005057211 | keratin associated protein 9-7 | chr17:39432274-39432333 | GO:0045095 | XM_003120879 | | |
| A_33_P3369667 | LOC100288549 | PREDICTED: Homo sapiens hypothetical LOC100288549 (LOC100288549), partial miscRNA [XR_110595] | XR_110595 | | 100288549 | hypothetical LOC100288549 | chr15:82767694-82767753 | | XR_110595 | THC2491431 | |
| A_33_P3367396 | FAM177B | Homo sapiens family with sequence similarity 177, member B (FAM177B), mRNA [NM_207468] | NM_207408 | ENST00000360827 | 400823 | family with sequence similarity 177, member B | chr1:222923479-222923538 | | NM_207468 | THC2482628 | Hs.697608 |
| A_33_P3221114 | JAKMIP1 | Homo sapiens janus kinase and microtubule interacting protein 1 (JAKMIP1), transcript variant 2, mRNA [NM_144720] | NM_144720 | ENST00000409831 | 152789 | janus kinase and microtubule interacting protein 1 | chr4:6055837-6055778 | GO:0005737|GO:0016020|NM_144720 GO:0030529|GO:0003723| GO:0005874|GO:0050811| GO:0015031|GO:0005856| GO:0019898|GO:0000300 | | NP498568 | Hs.479066 |
| A_33_P3245066 | SLC35E2B | Homo sapiens solute carrier family 35, member E2B (SLC35E2B), mRNA [NM_001110781] | NM_001110781 | ENST00000480991 | 728661 | solute carrier family 35, member E2B | chr1:1595787-1595728 | GO:0016020|GO:0016021 | NM_001110781 | THC2514091 | Hs.655255 |
| A_33_P3329444 | MAMSTR | Homo sapiens MEF2 activating motif and SAP domain containing transcriptional regulator (MAMSTR), transcript variant 1, mRNA [NM_182574] | NM_182574 | ENST00000356751 | 284358 | MEF2 activating motif and SAP domain containing transcriptional regulator | chr19:4921631-49216256 | GO:0005634|GO:0003676|NM_182574 GO:0045449 | | THC2487203 | Hs.191815 |
| A_23_P201979 | CREM | Homo sapiens cAMP responsive element modulator (CREM), transcript variant 19, mRNA [NM_183013] | NM_183013 | ENST00000460270 | 1390 | cAMP responsive element modulator | chr10:35501242-35501301 | GO:0005667|GO:0006355|NM_183013 GO:0003700|GO:0006687| GO:0005634|GO:0007275| GO:0007283|GO:0030154| GO:0048384|GO:0043565| GO:0007165|GO:0008140| GO:0046983|GO:0006631| GO:0006006|GO:0042752 | | THC2478984 | Hs.200250 |
| A_23_P71513 | EFR3A | Homo sapiens EFR3 homolog A (S. cerevisiae) (EFR3A), mRNA [NM_015137] | NM_015137 | ENST00000407309 | 23167 | EFR3 homolog A (S. cerevisiae) | chr8:133025157-133025216 | GO:0005886|GO:0005488 | NM_015137 | THC2603295 | Hs.204564 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P315122 | EMX1 | Homo sapiens empty spiracles homeobox 1 (EMX1), mRNA [NM_004097] | NM_004097 | ENST00000491023 | 2016 | empty spiracles homeobox 1 | chr2:73161417-73161476 | GO:0043565\|GO:0021796\|NM_004097 GO:0006355\|GO:0003700\| GO:0007420\|GO:0042493\| GO:0030182\|GO:0005634\| GO:0009791 | | THC2602195 | Hs.516090 |
| A_33_P3605969 | | Homo sapiens cDNA clone IMAGE: 3936577, **** WARNING: chimeric clone ****. [BC071847] | BC071847 | | | | chr1:41848710-41848651 | | | THC2705939 | Hs.559677 |
| A_33_P3272628 | FCER1G | Fc fragment of IgE, high affinity I, receptor for; gamma polypeptide [Source:HGNC Symbol; Acc: 3611] [ENST00000367992] | | ENST00000367992 | 2207 | Fc fragment of IgE, high affinity I, receptor for; gamma polypeptide | chr1:161190430-161190489 | GO:0043565\|GO:0006355\| GO:0005737\|GO:0003700\| GO:0005634 | | | |
| A_33_P3342096 | ZHX3 | Homo sapiens zinc fingers and homeoboxes 3 (ZHX3), mRNA [NM_015035] | NM_015035 | ENST00000373262 | 23051 | zinc fingers and homeoboxes 3 | chr20:39832111-39832052 | GO:0043565\|GO:0005622\|NM_015035 GO:0005515\|GO:0005737\| GO:0003700\|GO:0008270\| GO:0005634\|GO:0045892\| GO:0046872 | | THC2682470 | Hs.380133 |
| A_23_P148641 | TTTY12 | Homo sapiens testis-specific transcript, Y-linked 12 (TTTY12), non-coding RNA [NR_001551] | NR_001551 | ENST00000413466 | 83867 | testis-specific transcript, Y-linked 12 (nonprotein coding) | chrY:7678307-7678366 | | NR_001551 | THC2482065 | Hs.667616 |
| A_23_P128663 | SACS | Homo sapiens spastic ataxia of Charlevoix-Saguenay (sacsin) (SACS), mRNA [NM_014363] | NM_014363 | ENST00000382298 | 26278 | spastic ataxia of Charlevoix-Saguenay (sacsin) | chr13:2390309-23903039 | GO:0003674\|GO:0006457\|NM_014363 GO:0031072\|GO:0005575\| GO:0005524 | | NP843920 | Hs.159492 |
| A_33_P3376090 | OR1J4 | Homo sapiens olfactory receptor, family 1, subfamily J, member 4 (OR1J4), mRNA [NM_001004452] | NM_001004452 | ENST00000340750 | 26219 | olfactory receptor, family 1, subfamily J, member 4 | chr9:125282181-125282240 | GO:0007608\|GO:0007165\|NM_001004452 GO:0004984\|GO:0007186\| GO:0005886\|GO:0004872\| GO:0016021\|GO:0050896 | | THC2503950 | Hs.632679 |
| A_33_P3278159 | | | | | | | chr6:004024918-004024977 | | | | |
| A_33_P3403942 | C20orf123 | Homo sapiens chromosome 20 open reading frame 123 (C20orf123), mRNA [NM_080721] | NM_080721 | ENST00000279028 | 128506 | chromosome 20 open reading frame 123 | chr20:451699365-45169936 | GO:0016020\|GO:0016021 | NM_080721 | THC2608629 | Hs.526636 |
| A_32_P59302 | HIVEP3 | Homo sapiens human immuno-deficiency virus type 1 enhancer | BC080552 | ENST00000372583 | 59269 | human immuno-deficiency | chr1:41972662-41972603 | GO:0005622\|GO:0005737\| GO:0045941\|GO:0016563\| GO:0008270\|GO:0005634 | | THC2628065 | Hs.403972 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | binding protein 3 [Source: HGNC Symbol; Acc: 13561] [ENST00000372583] | | | | virus type 1 enhancer binding protein 3 | | GO:0003677\|GO:0046872 | | | |
| A_24_P36847 | DHX9 | *Homo sapiens* DEAH (Asp-Glu-Ala-His) box polypeptide 9 (DHX9), transcript variant 1, mRNA [NM_001357] | NM_001357 | ENST00000485081 | 1660 | DEAH (Asp-Glu-Ala-His) box polypeptide 9 | chr1:18285625 6-182856315 | GO:0003725\|GO:0005515\|GO:0005813\|GO:0070934\|GO:0005730\|GO:0005634\|GO:0003677\|GO:0005524\|GO:0034605\|GO:0004004\|GO:0005622\|GO:0005737\|GO:0004003\|GO:0016787\|GO:0000166\|GO:0000398\|GO:0030529\|GO:0070937 | NM_001357 | THC2508412 | Hs.191518 |
| A_24_P166661 | TMEM60 | *Homo sapiens* transmembrane protein 60 (TMEM60), mRNA [NM_032936] | NM_032936 | ENST00000257663 | 85025 | transmembrane protein 60 | chr7:77423590-77423531 | GO:0016020\|GO:0016021 | NM_032936 | THC2632847 | Hs.19025 |
| A_24_P58403 | ROCK1 | *Homo sapiens* Rho-associated, coiled-coil containing protein kinase 1 (ROCK1), mRNA [NM_005406] | NM_005406 | ENST00000399799 | 6093 | Rho-associated, coiled-coil containing protein kinase 1 | chr18:1853029 1-18530232 | GO:0007242\|GO:0030036\|GO:0007266\|GO:0050900\|GO:0050901\|GO:0046872\|GO:0005829\|GO:0042802\|GO:0005622\|GO:0000910\|GO:0005737\|GO:0043524\|GO:0000166\|GO:0022614\|GO:0005794\|GO:0005814\|GO:0032060\|GO:0006915\|GO:0005524\|GO:0016020\|GO:0004674\|GO:0006468\|GO:0008270\|GO:0017049\|GO:0016740\|GO:0019898 | NM_005406 | THC2555942 | Hs.306307 |
| A_24_P242036 | RRP7B | *Homo sapiens* ribosomal RNA processing 7 homolog B (*S. cerevisiae*) (RRP7B), non-coding RNA [NR_002184] | NR_002184 | ENST00000458605 | 91695 | ribosomal RNA processing 7 homolog B (*S. cerevisiae*) | chr22:4297032 3-42970264 chr6:10963656 2-109636621 | | NR_002184 | THC2463180 | Hs.728878 |
| A_33_P3345294 | | | | | | | | | | | |
| A_23_P82929 | NOV | *Homo sapiens* nephroblastoma overexpressed gene (NOV), mRNA [NM_002514] | NM_002514 | ENST00000259526 | 4856 | nephroblastoma overexpressed gene | chr8:12043643 5-120436494 | GO:0031012\|GO:0030424\|GO:0043025\|GO:0005576\|GO:0008083\|GO:0001558\|GO:0030425\|GO:0005520 | NM_002514 | THC2467525 | Hs.235935 |
| A_33_P3339436 | LOC145845 | *Homo sapiens* hypothetical LOC145845 (LOC145845), non- | NR_024264 | | 145845 | hypothetical LOC145845 | chr15:3715683 6-37156777 | | NR_024264 | THC2606039 | Hs.302693 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P79816 | EMILIN3 | coding RNA [NR_024264] Homo sapiens elastin microfibril interfacer 3 (EMILIN3), mRNA [NM_052846] | NM_052846 | ENST00000332312 | 90187 | elastin microfibril interfacer 3 | chr20:39989112-39989053 | GO:0005737\|GO:0005578\|NM_052846 GO:0005576 | | THC2472361 | Hs.726525 |
| A_33_P3422712 | | | | | | | chrX:13779376 0-137793819 | | | | |
| A_33_P3806721 | JMJD5 | Homo sapiens jumonji domain containing 5 (JMJD5), transcript variant 1, mRNA [NM_001145348] | NM_001145348 | ENST00000540888 | 79831 | jumonji domain containing 5 | chr16:27231932-27231991 | GO:0008150\|GO:0003674\|NM_001145348 GO:0005575 | | THC2632015 | Hs.145717 |
| A_24_P66716 | CMKLR1 | Homo sapiens chemokine-like receptor 1 (CMKLR1), transcript variant 1, mRNA [NM_001142343] | NM_001142343 | ENST00000312143 | 1240 | chemokine-like receptor 1 | chr12:108681943-108681884 | GO:0007165\|GO:0006955\|NM_001142343 GO:0001501\|GO:0007186 GO:0006935\|GO:0005886 GO:0005887\|GO:0004930 GO:0004950\|GO:0004872 | | THC2699717 | Hs.197143 |
| A_23_P78571 | COX6B2 | Homo sapiens cytochrome c oxidase subunit VIb polypeptide 2 (testis) (COX6B2), mRNA [NM_144613] | NM_144613 | ENST00000326529 | 125965 | cytochrome c oxidase subunit VIb polypeptide 2 (testis) | chr19:55862167-55862108 | GO:0005739\|GO:0005758\|NM_144613 GO:0004129\|GO:0030061 | | THC2491158 | Hs.550544 |
| A_24_P942030 | VAMP4 | Homo sapiens vesicle-associated membrane protein 4 (VAMP4), transcript variant 1, mRNA [NM_003762] | NM_003762 | ENST00000415773 | 8674 | vesicle-associated membrane protein 4 | chr1:171670045-171669986 | GO:0005794\|GO:0016020\|NM_003762 GO:0000139\|GO:0016021 GO:0016192\|GO:0005764 GO:0005768 | | THC2463491 | Hs.6651 |
| A_33_P3423220 | LOC100507050 | Homo sapiens hypothetical LOC441617 (LOC441617), mRNA [NM_001195528] | NM_001195528 | | 100507050 | hypothetical LOC100507050 | chr11:7495302 2-74953081 | | NM_001195528 | THC2471485 | Hs.577323 |
| A_23_P82979 | LAMC3 | Homo sapiens laminin, gamma 3 (LAMC3), mRNA [NM_006059] | NM_006059 | ENST00000462567 | 10319 | laminin, gamma 3 | chr9:133967284-133967341 | GO:0005515\|GO:0016020\|NM_006059 GO:0005198\|GO:0005576 GO:0007155\|GO:0005604 | | THC2471485 | Hs.201805 |
| A_32_P129669 | FRMPD3 | PREDICTED: Homo sapiens FERM and PDZ domain-containing protein 3-like (LOC100510062), mRNA [XM_003121034] | XM_003121034 | ENST00000439554 | 84443 | FERM and PDZ domain containing 3 | chrX:106848038-106848097 | | XM_003121034 | THC2648260 | Hs.496546 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq Accession | TIGRID | UniGene ID |
|---|---|---|---|---|---|---|---|---|---|---|---|
| A_23_P360240 | MYEOV | *Homo sapiens* myeloma overexpressed (in a subset of t(11;14) positive multiple myelomas) (MYEOV), mRNA [NM_138768] | NM_138768 | ENST00000553653 | 26579 | myeloma overexpressed (in a subset of t(11;14) positive multiple myelomas) | chr11:69064410-69064469 | | NM_138768 | THC2470814 | Hs.523848 |
| A_23_P208788 | C19orf33 | *Homo sapiens* chromosome 19 open reading frame 33 (C19orf33), mRNA [NM_033520] | NM_033520 | ENST00000301246 | 64073 | chromosome 19 open reading frame 33 | chr19:38795581-38795640 | GO:0008150|GO:0005730 GO:0005634 | NM_033520 | THC2480610 | Hs.631544 |
| A_33_P70927 | PAGE2 | *Homo sapiens* P antigen family, member 2 (prostate associated) (PAGE2), mRNA [NM_207339] | NM_207339 | ENST00000374968 | 203569 | P antigen family, member 2 (prostate associated) | chrX:55117033-55117813 | | NM_207339 | | Hs.662489 |
| A_23_P131676 | CXCR7 | *Homo sapiens* chemokine (C-X-C motif) receptor 7 (CXCR7), mRNA [NM_020311] | NM_020311 | ENST00000272928 | 57007 | chemokine (C-X-C motif) receptor 7 | chr2:237490783-237490842 | GO:0005515|GO:0008150|GO:0007165|GO:0007186|GO:0005886|GO:0004930|GO:0044419|GO:0004872|GO:0016021 | NM_020311 | THC2461058 | Hs.471751 |
| A_33_P3384694 | | | | | | | chr4:135865487-135865546 | | | | |
| A_33_P3397314 | LOC644587 | PREDICTED: *Homo sapiens* hypothetical protein LOC644587 (LOC644587), mRNA [XM_001713909] | XM_001713909 | | 644587 | hypothetical protein LOC644587 | chr9:44018222-44018163 | | XM_001713909 | THC2496050 | Hs.529800 |
| A_33_P3219578 | ZIC1 | Human clone 23814 mRNA sequence. [U79264] | U79264 | | 7545 | Zic family member 1 | chr3:147127396-147127337 | | | NP1167104 | Hs.598590 |
| A_33_P3411925 | WDR18 | *Homo sapiens* WD repeat domain 18 (WDR18), mRNA [NM_024100] | NM_024100 | ENST00000251289 | 57418 | WD repeat domain 18 | chr19:994510-994569 | | NM_024100 | THC2468321 | Hs.325321 |
| A_33_P3413993 | SERPING1 | serpin peptidase inhibitor, clade G (C1 inhibitor), member 1 [Source: HGNC Symbol; Acc: 1228] [ENST00000405496] | | ENST00000405496 | 710 | serpin peptidase inhibitor, clade G (C1 inhibitor), member 1 | chr11:57365494 2-57365001 | | | THC2538564 | |
| A_23_P107465 | KRT31 | *Homo sapiens* keratin 31 (KRT31), mRNA[NM_002277] | NM_002277 | ENST00000393998 | 3881 | keratin 31 | chr17:39550065-39550006 | GO:0005882|GO:0005515|NM_002277 GO:0008544|GO:0005200 | | THC2475978 | Hs.41696 |
| A_33_P3322859 | HES6 | *Homo sapiens* hairy and enhancer of | NM_018645 | ENST00000409160 | 55502 | hairy and enhancer of | chr2:239147315-239147256 | GO:0003712|GO:0005667|NM_018645 GO:0003700|GO:0006357| | | THC2685338 | Hs.42949 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3407601 | | split 6 (*Drosophila*) (HES6), transcript variant 1, mRNA [NM_018645] Q39AC8_BURS3 (Q39AC8) Cytochrome B561, partial (9%) [THC2753069] | | | | split 6 (*Drosophila*) | chr17:0208411 37-020841078 | GO:0007275\|GO:0005634\|GO:0030154\|GO:0007399 | | THC2753069 | |
| A_33_P3256334 | PRB3 | *Homo sapiens* proline-rich protein BstNl subfamily 3 (PRB3), mRNA [NM_006249] | NM_006249 | ENST00000279573 | 5544 | proline-rich protein BstNl subfamily 3 | chr12:1142018 5-11420126 | GO:0008150\|GO:0007186\|NM_006249 GO:0005576\|GO:0016021\| GO:0008368 | | THC2479522 | Hs.73031 |
| A_33_P3359223 | C9orf173 | *Homo sapiens* chromosome 9 open reading frame 173 (C9orf173), mRNA [NM_001004353] | NM_001004353 | ENST00000388931 | 441476 | chromosome 9 open reading frame 173 | chr9:14014787 5-140147934 | | NM_001004353 | THC2482952 | Hs.372640 |
| A_33_P3327192 | | DA142060 BRALZ2 *Homo sapiens* cDNA clone BRALZ2017105 5', mRNA sequence [DA142060] | DA142060 | ENST00000453179 | | | chr6:24751871-24751930 | | | | Hs.582960 |
| A_33_P3301970 | STRADB | *Homo sapiens* STE20-related kinase adaptor beta (STRADB), transcript variant 1, mRNA [NM_018571] | NM_018571 | ENST00000392249 | 55437 | STE20-related kinase adaptor beta | chr2:20234326 4-202343323 | GO:0005515\|GO:0007254\|NM_018571 GO:0005634\|GO:0006916\| GO:0046320\|GO:0005524\| GO:0032147\|GO:0000902\| GO:0005737\|GO:0007049\| GO:0004672\|GO:0000166\| GO:0006611\|GO:0006468 | | NP1466986 | Hs.652338 |
| A_33_P3277096 | | Lymphocyte antigen 6 complex, locus G6E|Lymphocyte antigen 6 complex, locus G6E, isoform CRA_a [Source: UniProtKB/TrEMBL; Acc: A2ABS3] [ENST00000383417] | AJ315539 | ENST00000383417 | | | chr6:31680458 31680399 | | | NP1164470 | Hs.247883 |
| A_33_P3351279 | GPR37L1 | *Homo sapiens* G protein-coupled receptor 37 like 1 (GPR37L1), mRNA [NM_004767] | NM_004767 | ENST00000367282 | 9283 | G protein-coupled receptor 37 like 1 | chr1:20209857 5-20209834 | GO:0008150\|GO:0007165\|NM_004767 GO:0007186\|GO:0005886\| GO:0004930\|GO:0004872\| GO:0016021 | | THC2464423 | Hs.132049 |
| A_33_P3316410 | FAM 66A | *Homo sapiens* family with sequence similarity 66, member A (FAM66A), non- | NR_026789 | ENST00000526690 | 100133172 | family with sequence similarity 66, member A | chr8:12219964-12220023 | | NR_026789 | THC2571715 | Hs.721640 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3350232 | | Homo sapiens cDNA FLJ45928 fis, clone PLACE6019674, [AK127825] coding RNA [NR_026789] | AK127825 | | | | chr14:76961394-76961335 | | | THC2487473 | Hs.686950 |
| A_23_P15798 | KRTAP4-12 | Homo sapiens keratin associated protein 4-12 (KRTAP4-12), mRNA [NM_031854] | NM_031854 | ENST00000455597 | 83755 | keratin associated protein 4-12 | chr17:39279576-39279517 | GO:0045095 | NM_031854 | NP1465556 | Hs.572443 |
| A_33_P3287418 | RTDR1 | Homo sapiens rhabdoid tumor deletion region gene 1 [Source: HGNC Symbol; Acc: 13437] [ENST00000406876] | | ENST00000406876 | 27156 | rhabdoid tumor deletion region gene 1 | chr22:23478444-23478385 | | | THC2656235 | |
| A_23_P420831 | TRIM10 | Homo sapiens tripartite motif containing 10 (TRIM10), transcript variant 2, mRNA[NM_052828] | NM_052828 | ENST00000448645 | 10107 | tripartite motif containing 10 | chr6:30119937-30119878 | GO:0005622\|GO:0005515\|NM_052828 GO:0008150\|GO:0003674\| GO:0005737\|GO:0030218\| GO:0008270\|GO:0046872 | | THC2474017 | Hs.709483 |
| A_33_P3272347 | LOC100128107 | Homo sapiens cDNA FLJ41726 fis, clone HLUNG2014449. [AK123720] | AK123720 | | 100128107 | hypothetical protein LOC100128107 | chr19:4689378-0046893721 | | | THC2512220 | Hs.707277 |
| A_33_P3713035 | LOC221814 | Homo sapiens mRNA; cDNA DKFZp564C0371 (from clone DKFZp564C0371) [AL122087] | AL122087 | | 221814 | hypothetical protein LOC221814 | chr7:15874795-15874736 | | | THC2606193 | Hs.592173 |
| A_33_P3293049 | HLA-DQA1 | Homo sapiens major histocompatibility complex, class II, DQ alpha 1 (HLA-DQA1), mRNA [NM_002122] | NM_002122 | ENST00000374949 | 3117 | major histo-compatibility complex, class II, DQ alpha 1 | chr6:32610501-32610560 | GO:0006955\|GO:0016020\|NM_002122 GO:0005886\|GO:0005887\| GO:0002504\|GO:0042613\| GO:0016021\|GO:0032395 | | THC2462487 | Hs.387679 |
| A_23_P154771 | DUSP15 | Homo sapiens dual specificity phosphatase 15 (DUSP15), transcript variant 1, mRNA [NM_080611] | NM_080611 | ENST00000486996 | 128853 | dual specificity phosphatase 15 | chr20:3044939-7-30449338 | GO:0005515\|GO:0005737\|NM_080611 GO:0006470\|GO:0016787\| GO:0005886\|GO:0008138\| GO:0004725 | | NP349912 | Hs.585017 |
| A_23_P213832 | SPINK7 | Homo sapiens serine peptidase inhibitor, Kazal type 7 (putative) (SPINK7), mRNA [NM_032566] | NM_032566 | ENST00000514646 | 84651 | serine peptidase inhibitor, Kazal type 7 (putative) | chr5:14769368-0-147693739 | GO:0005515\|GO:0004867\|NM_032566 GO:0005576\|GO:0030414 | | THC2734765 | Hs.244569 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P2452 | TMTC1 | Homo sapiens transmembrane and tetratricopeptide repeat containing 1 (TMTC1), transcript variant 2, mRNA [NM_175861] | NM_175861 | ENST00000256062 | 83857 | transmembrane and tetratricopeptide repeat containing 1 | chr12:29653922-29653863 | GO:0016020\|GO:0005488\|NM_175861 GO:0016021 | | THC2470774 | Hs.401954 |
| A_33_P3226605 | PSIP1 | Homo sapiens PC4 and SFRS1 interacting protein 1 (PSIP1), transcript variant 2, mRNA [NM_033222] | NM_033222 | ENST00000380733 | 11168 | PC4 and SFRS1 interacting protein 1 | chr9:15464389-15464330 | GO:0019047\|GO:0044419\|NM_033222 GO:0005634\|GO:0019059\| GO:0003677\|GO:0045449\| GO:0005829 | | THC2466817 | Hs.708514 |
| A_24_P384397 | RAVER1 | Homo sapiens ribonucleoprotein, PTB-binding 1 (RAVER1), mRNA [NM_133452] | NM_133452 | ENST00000331131 | 125950 | ribonucleoprotein, PTB-binding 1 | chr19:10431850-10431791 | GO:0005515\|GO:0005737\|NM_133452 GO:0000166\|GO:0003723\| GO:0005634 | | THC2467692 | Hs.707428 |
| A_33_P3245818 | PQLC1 | PQ loop repeat containing 1 [Source: HGNC Symbol; Acc: 26188] | AK126188 | ENST00000466449 | 80148 | PQ loop repeat containing 1 | chr18:77703742-77703683 | GO:0016020\|GO:0016021 | | THC2483810 | Hs.288284 |
| A_23_P19423 | KCNK5 | Homo sapiens potassium channel, subfamily K, member 5 (KCNK5), mRNA [NM_003740] | NM_003740 | ENST00000359534 | 8645 | potassium channel, subfamily K, member 5 | chr6:39156880-39156821 | GO:0007588\|GO:0005244\|NM_003740 GO:0016020\|GO:0005887\| GO:0005267\|GO:0030955\| GO:0006813\|GO:0006811 | | THC2529678 | Hs.444448 |
| A_33_P3793307 | LOC339803 | Homo sapiens hypothetical LOC339803 (LOC339803), non-coding RNA [NR_036496] | NR_(Rf.49f. | | 339803 | hypothetical LOC339803 | chr2:61368978-61368919 | | NR_036496 | THC2480323 | Hs.252433 |
| A_23_P94186 | LYPD2 | Homo sapiens LY6/PLAUR domain containing 2 (LYPD2), mRNA [NM_205545] | NM_205545 | ENST00000359228 | 137797 | LY6/PLAUR domain containing 2 | chr8:143832477-143831850 | GO:0005886\|GO:0031225 | NM_205545 | THC2481314 | Hs.441280 |
| A_33_P3354771 | MEF2BNB | Homo sapiens cDNA FLJ32599 fis, clone STOMA1000047. [AK057161] | AK057161 | | 729991 | MEF2B neighbor | chr19:19288990-19288931 | | | THC2479428 | |
| A_23_P141005 | AMFR | Homo sapiens autocrine motility factor receptor (AMFR), mRNA [NM_001144] | NM_001144 | ENST00000492830 | 267 | autocrine motility factor receptor | chr16:56395757-56395698 | GO:0000209\|GO:0005515\|NM_001144 GO:0006511\|GO:0004842\| GO:0005783\|GO:0016874\| GO:0006928\|GO:0030176\| GO:0030433\|GO:0051259\| GO:0046872\|GO:0030968\| GO:0007165\|GO:0016020 | | THC2477387 | Hs.295137 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P22682 | ARMCX1 | Homo sapiens armadillo repeat containing, X-linked 1 (ARMCX1), mRNA [NM_016608] | NM_016608 | ENST00000538894 | 51309 | armadillo repeat containing, X-linked 1 | chrX:100809416-100809475 | GO:0000299\|GO:0004872\|GO:0008270\|GO:0016021\|GO:0016020\|GO:0005488\|NM_016608\|GO:0016021 | THC2490823 | Hs.9728 |
| A_33_P3295523 | RAC3 | Homo sapiens ras-related C3 botulinum toxin substrate 3 (rho family, small GTP binding protein Rac3) (RAC3), mRNA [NM_005052] | NM_005052 | ENST00000306897 | 5881 | ras-related C3 botulinum toxin substrate 3 (rho family, small GTP binding protein Rac3) | chr17:79992018-79992077 | GO:0005515\|GO:0030036\|NM_005052\|GO:0007264\|GO:0003924\|GO:0005525\|GO:0031175\|GO:0030027\|GO:0012505\|GO:0030426\|GO:0005622\|GO:0005737\|GO:0031941\|GO:0000166\|GO:0016020\|GO:0030031\|GO:0050885 | THC2474710 | Hs.45002 |
| A_32_P110390 | TMEM171 | Homo sapiens transmembrane protein 171 (TMEM171), transcript variant 1, mRNA [NM_173490] | NM_173490 | ENST00000287773 | 134285 | transmembrane protein 171 | chr5:72424286-72424345 | GO:0016020\|GO:0016021\|NM_173490\|GO:0043025 | THC2480044 | Hs.162246 |
| A_33_P3217719 | TLE1 | Homo sapiens transducin-like enhancer of split 1 (E(sp1) homology, Drosophila) (TLE1), mRNA [NM_005077] | NM_005077 | ENST00000376472 | 7088 | transducin-like enhancer of split 1 (E(sp1) homolog, Drosophila) | chr9:84225208-84225149 | GO:0007165\|GO:0005667\|NM_005077\|GO:0003714\|GO:0003682\|GO:0030178\|GO:0016481\|GO:0009887\|GO:0007275\|GO:0005634\|GO:0000122\|GO:0008134 | THC2594224 | Hs.197320 |
| A_33_P3222664 |  | PREDICTED: Homo sapiens hypothetical protein LOC100133214 (LOC100133214), mRNA [XM_001718031] | XM_001718031 |  |  |  | chr6:29800627-29800568 |  | XM_001718031 |  |  |
| A_33_P3379396 | KRT1 | Homo sapiens keratin 1 (KRT1), mRNA [NM_006121] | NM_006121 | ENST00000252244 | 3848 | keratin 1 | chr12:5306857-53068520 | GO:0005515\|GO:0008544\|NM_006121\|GO:0005886\|GO:0005529\|GO:0005200\|GO:0045765\|GO:0004872\|GO:0045095\|GO:0005856\|GO:0042730\|GO:0006979\|GO:0001867 | THC2464701 | Hs.80828 |
| A_33_P3336273 | NAV3 | Homo sapiens neuron navigator 3 (NAV3), mRNA [NM_014903] | NM_014903 | ENST00000541270 | 89795 | neuron navigator 3 | chr12:7860462-78604688 | GO:0005640\|GO:0017111\|NM_014903\|GO:0016020\|GO:0000166\|GO:0005634\|GO:0005635 | NP843482 | Hs.655301 |
| A_23_P50389 | NAT14 | Homo sapiens N-acetyltransferase 14 (GCN5-related, putative) (NAT14), mRNA | NM_020378 | ENST00000205194 | 57106 | N-acetyltransferase 14(GCN5-related, | chr19:5599851-55998570 | GO:0006352\|GO:0008080\|NM_020378\|GO:0016020\|GO:0016563\|GO:0008152\|GO:0005634\|GO:0016021\|GO:0003677 | THC2462041 | Hs.31854 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3255434 | MEG3 | Homo sapiens maternally expressed 3 (non-protein coding) (MEG3), transcript variant 3, non-coding RNA [NR_003531] | NR_003531 | ENST00000398461 | 55384 | maternally expressed 3 (nonprotein coding putative) | chr14:101327286-101327345 | GO:0045449\|GO:0016740\|GO:0008415 | NR_003531 | THC2467619 | Hs.728839 |
| A_33_P3289976 | | [NM_020378] | | | | | | | | | |
| A_33_P3415648 | | PREDICTED: Homo sapiens hypothetical LOC649305 (LOC649305), miscRNA [XR_113106] | XR_113106 | ENST00000536864 | | | chr9:067343662-067343603 chr12:8543467-8543408 | | XR_113106 | THC2478567 | Hs.434403 |
| A_33_P3353996 | PPP1R3G | Homo sapiens protein phosphatase 1, regulatory (inhibitor) subunit 3G (PPP1R3G), mRNA [NM_001145115] | NM_001145115 | | 648791 | protein phosphatase 1, regulatory (inhibitor) subunit 3G | chr6:5087402-5087461 | | NM_001145115 | THC2779444 | Hs.653089 |
| A_33_P3667484 | LOC648740 | Homo sapiens actin, beta pseudogene (LOC648740), non-coding RNA [NR_024438] | NR_024438 | ENST00000491397 | 648740 | actin, beta pseudogene | chr1:104113812-104113871 | | NR_024438 | THC2482509 | Hs.721681 |
| A_24_P61753 | KIAA0664 | Homo sapiens KIAA0664 (KIAA0664), mRNA [NM_015229] | NM_015229 | ENST00000435359 | 23277 | KIAA0664 | chr17:2593491 2593432 | GO:0005488 | NM_015229 | THC2466243 | Hs.22616 |
| A_33_P3225522 | OAS2 | Homo sapiens 2'-5'-oligoadenylate synthetase 2, 69/71 kDa (OAS2), transcript variant 3, mRNA [NM_001032731] | NM_001032731 | ENST00000449768 | 4939 | 2'-5'-oligoadenylate synthetase 2, 69/71 kDa | chr12:113426550-113426609 | GO:0005792\|GO:0005783\|GO:0001730\|GO:0003723\|GO:0016779\|GO:0005634\|GO:0005524\|GO:0006401\|GO:0005739\|GO:0006139\|GO:0006955\|GO:0000166\|GO:0016020\|GO:0016740 | NM_001032731 | THC2473802 | Hs.414332 |
| A_33_P3270826 | THEM5 | Homo sapiens thioesterase superfamily member 5 (THEM5), mRNA [NM_182578] | NM_182578 | ENST00000453881 | 284486 | thioesterase superfamily member 5 | chr1:151819642-151819583 | GO:0016787 | NM_182578 | THC2651404 | Hs.132648 |
| A_33_P3260053 | AIF1L | Homo sapiens allograft inflammatory factor 1-like (AIF1L), | NM_001185095 | ENST00000372312 | 83543 | allograft inflammatory factor 1-like | chr9:133995766-133995825 | GO:0051015\|GO:0005884\|GO:0005509\|GO:0005925 | NM_001185095 | THC2520939 | Hs.4944 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P417921 | DNAJC5G | transcript variant 3, mRNA [NM_001185095] Homo sapiens DnaJ (Hsp40) homology subfamily C, member 5 gamma (DNAJC5G), mRNA [NM_173650] | NM_173650 | ENST00000296097 | 285126 | DnaJ (Hsp40) homolog, sub-family C, member 5 gamma | chr2:27504211-27504270 | GO:0016020\|GO:0006457\|NM_173650 GO:0031072\|GO:0051082\| GO:0031225 | | THC2478898 | Hs.116303 |
| A_23_P80827 | FYTTD1 | Homo sapiens forty-two-three domain containing 1 (FYTTD1), transcript variant 2, mRNA [NM_001011537] | NM_001011537 | ENST00000241502 | 84248 | forty-two-three domain containing 1 | chr3:197510301-197510360 | | NM_001011537 | THC2469496 | Hs.277533 |
| A_33_P3315021 | | ribosomal protein L23a pseudogene 7 [Source: HGNC Symbol; Acc: 17336] [ENST00000416673] | AK055264 | ENST00000416673 | | | chr2:114368431-114368372 | | | THC2520247 | Hs.720253 |
| A_33_P3212350 | | Homo sapiens cDNA FLJ39820 fis, clone SPLEN2010625. [AK097139] | AK097139 | | 84433 | caspase recruitment domain family, member 11 | chr7:3082928-3082869 | GO:0050700\|GO:0005515 GO:0045577\|GO:0005886 GO:0030890\|GO:0004385 GO:0042981\|GO:0001819 GO:0005829\|GO:0005622 GO:0045086\|GO:0007165 GO:0045061\|GO:0051092 GO:0045061\|GO:0042101 GO:0050776\|GO:0042102 GO:0045580\|GO:0045121 GO:0043123 | | THC2480953 | Hs.665701 |
| A_33_P3227077 | LOC100132024 | PREDICTED: Homo sapiens hypothetical protein LOC100132024 (LOC100132024), mRNA [XM_001718709] | XM_001718709 | | 100132024 | hypothetical protein LOC100132024 | chr15:30814556-30814497 | | XM_001718709 | | Hs.631706 |
| A_23_P76622 | DCT | Homo sapiens dopachrome tautomerase (dopachrome delta-isomerase, tyrosine-related protein 2) (DCT), transcript variant 1, mRNA [NM_001922] | NM_001922 | ENST00000377021 | 1638 | dopachrome tautomerase (dopachrome delta-, isomerase tyrosine-related protein 2) | chr13:95095805-95095746 | GO:0005792\|GO:0042470\|NM_001922 GO:0005507\|GO:0046872 GO:0006583\|GO:0004167 GO:0005829\|GO:0008544 GO:0016020\|GO:0008152 GO:0016491\|GO:0008270 GO:0016021\|GO:0016853 | | NP220864 | Hs.301865 |
| A_33_P3400292 | | | | | | | chr12:00688206-006861947 | | | | |
| A_33_P3347040 | LOC100131094 | Homo sapiens hypothetical LOC100131094 | NM_001242901 | ENST00000381796 | 100131094 | hypothetical LOC100131094 | chr19:4685870-4685929 | | NM_001242901 | THC2483730 | Hs.678135 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P319647 | FCRL2 | (LOC100131094), mRNA [NM_001242901] Homo sapiens Fc receptor-like 2 (FCRL2), mRNA [NM_030764] | NM_030764 | ENST00000392274 | 79368 | Fc receptor-like 2 | chr1:157773673 6-157736677 | GO:0005886|GO:0005070|NM_030764 GO:0007267|GO:0005625| GO:0004872|GO:0016021 | | NP458656 | Hs.437393 |
| A_33_P3330175 | | | | | | | chr9:06670801 3-066707954 | | | | |
| A_23_P157513 | MOS | Homo sapiens v-mos Moloney murine sarcoma viral oncogene homolog (MOS), mRNA [NM_005372] | NM_005372 | ENST00000311923 | 4342 | v-mos Moloney murine sarcoma viral oncogene homolog | chr8:57025995-57025936 | GO:0005515|GO:0000166|NM_005372 GO:0004674|GO:0006468| GO:0005524|GO:0016740 | | THC2602727 | Hs.533432 |
| A_33_P3315303 | KRT73 | Homo sapiens keratin 73 (KRT73), mRNA [NM_175068] | NM_175068 | ENST00000305748 | 319101 | keratin 73 | chr12:5300141 7-53001358 4-32063533 | GO:0005198|GO:0045095 NM_175068 | | THC2481292 | Hs.55410 |
| A_24_P144346 | | PREDICTED: Homo sapiens ig heavy chain V-III region VH26-like (LOC100132941), mRNA [XM_002346274] | XM_002346274 | ENST00000426099 | | | chr16:3206347 | | XM_002346274 | NP492523 | Hs.460661 |
| A_33_P3406828 | TEKT4P2 | Uncharacterized protein [Source: UniProtKB/TrEMBL; Acc:B 7WNX9] [ENST00000400839] | AK096952 | ENST00000400839 | 100132288 | tektin 4 pseudogene 2 | chr21:0099096 86-009909627 | | | THC2509411 | Hs.632605 |
| A_33_P3406265 | | | | | | | chr7:02556042 0-025560361 | | | | |
| A_24_P165864 | P2RY14 | Homo sapiens purinergic receptor P2Y, G-protein coupled, 14 (P2RY14), transcript variant 2, mRNA [NM_014879] | NM_014879 | ENST00000309170 | 9934 | purinergic receptor P2Y, G-protein coupled, 14 | chr3:15093011 8-150930059 | GO:0007165|GO:0045029|NM_014879 GO:0006955|GO:0007186| GO:0005886|GO:0045028| GO:0004930|GO:0004872| GO:0016021 | | THC2476449 | Hs.2465 |
| A_33_P3287396 | LOC100127940 | Homo sapiens cDNA FLJ33307 fis, clone BNGH42004076. [AK090626] | AK090626 | ENST00000514988 | 100127940 | hypothetical LOC100127940 | chr7:228654-228595 | | | THC2485700 | Hs.638549 |
| A_23_P142255 | SHD | Homo sapiens Src homology 2 domain containing transforming protein D (SHD), mRNA [NM_020209] | NM_020209 | ENST00000543264 | 56961 | Src homology 2 domain containing transforming protein D | chr19:4290646-4290705 | GO:0005515 | NM_020209 | NP228054 | Hs.7423 |
| A_24_P215240 | ENKUR | Homo sapiens enkurin, TRPC channel interacting | NM_145010 | ENST00000376363 | 219670 | enkurin, TRPC channel interacting | chr10:2528462 5-25279530 | GO:0019861|GO:0005929|NM_145010 GO:0005516|GO:0017124 | | NP841402 | Hs.534486 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3246838 | | protein (ENKUR), mRNA [NM_145010] | | | | protein | | | | NP1073023 | Hs.74647 |
| A_33_P3359869 | | Homo sapiens T-cell receptor delta chain HA/801 mRNA, complete cds. [AY312959] | AY312959 | ENST00000390477 | | | chr14:22933255-22933314 | | | | |
| A_33_P3309849 | | | | | | | chr20:06251226-06251324 chr18:07523938-075239439 | | | | |
| A_23_P0273 | CHST8 | Homo sapiens carbohydrate (N-acetylgalactosamine 4-0) sulfotransferase 8 (CHST8), transcript variant 3, mRNA [NM_022467] | NM_022467 | ENST00000262622 | 64377 | carbohydrate (N-acetylgal-actosamine 4-0) sulfotransferase 8 | chr19:3426429 2-34264351 | GO:0016051|GO:0006790|GO:0005794|GO:0016020|GO:0042446|GO:0001537|GO:0016021|GO:0007417|GO:0016740|GO:0030166 | NM_022467 | THC2603946 | Hs.165724 |
| A_33_P3312504 | PSD4 | Homo sapiens pleckstrin and Sec7 domain containing 4 (PSD4), mRNA [NM_012455] | NM_012455 | ENST00000409656 | 23550 | pleckstrin and Sec7 domain containing 4 | chr2:11395884 8-113958907 | GO:0005622|GO:0005086|GO:0005886|GO:0032012 | NM_012455 | NP649911 | Hs.516306 |
| A_24_P64407 | HMX2 | Homo sapiens H6 family homeobox 2 (HMX2), mRNA [NM_005519] | NM_005519 | ENST00000339992 | 3167 | H6 family homeobox 2 | chr10:1249091 35-124909194 | GO:0043565|GO:0008284|GO:0006355|GO:0042472|GO:0003700|GO:0007420|GO:0007275|GO:0005634|GO:0030154|GO:0007399 | NM_005519 | THC2478985 | Hs.444756 |
| A_24_P348083 | C18orf23 | PREDICTED: Homo sapiens chromosome 18 open reading frame 23 (C18orf23), miscRNA [XR_111773] | XR_111773 | | 147341 | chromosome 18 open reading frame 23 | chr18:4391494 3-43915002 | | XR_111773 | NP1164839 | Hs.730381 |
| A_33_P3245248 | TERC | Homo sapiens telomerase RNA component (TERC), telomerase RNA [NR_001566] | NR_001566 | | 7012 | telomerase RNA component | chr3:16948269 5-169482636 | | NR_001566 | THC2687501 | Hs.436182 |
| A_33_P3347869 | C3 | Homo sapiens complement component 3 (C3), mRNA [NM_000064] | NM_000064 | ENST00000463520 | 718 | complement component 3 | chr19:6686195-6686136 | GO:0006957|GO:0007165|GO:0050766|GO:0006954|GO:0007186|GO:0004866|GO:0006958|GO:0005102|GO:0005576|GO:0001798|GO:0005615 | NM_000064 | THC2569813 | Hs.529053 |
| A_24_P472455 | ARF6 | Homo sapiens ADP-ribosylation factor 6 | NM_001663 | | 382 | ADP-ribo-sylation | chr14:5036317 1-50363230 | GO:0005515|GO:0035020|GO:0005886|GO:0007264 | NM_001663 | THC2492454 | Hs.525330 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (ARF6), mRNA [NM_001663] | | | | factor 6 | | GO:0003924\|GO:0006928\| GO:0015031\|GO:0031529\| GO:0005622\|GO:0005737\| GO:0000166\|GO:0030838\| GO:0007155\|GO:0016192\| GO:0005938\|GO:0005794\| GO:0005624\|GO:0006915\| GO:0005525\|GO:0001726\| GO:0001889\|GO:0030866\| GO:0048261\|GO:0055037\| GO:0005769\|GO:0019898 | | | |
| A_33_P3218797 | PPDPF | pancreatic progenitor cell differentiation and proliferation factor homolog (zebrafish) [Source: HGNC Symbol; Acc: 16142] [ENST00000370177] | | ENST00000370177 | 79144 | pancreatic progenitor cell differentiation and proliferation factor homolog (zebrafish) | chr20:62152934-62152993 | | | THC2522513 | |
| A_24_P8079 | MUC6 | Homo sapiens mucin 6, oligomeric mucus/gel-forming (MUC6), mRNA [NM_005961] | NM_005961 | ENST00000421673 | 4588 | mucin 6, oligomeric mucus/ gel-forming | chr11:1015874-1015815 | GO:0030277\|GO:0005576\|NM_005961\| GO:0005201 | NP081518 | | Hs.528432 |
| A_23_P31376 | LRRN3 | Homo sapiens leucine rich repeat neuronal 3 (LRRN3), transcript variant 3, mRNA [NM_018334] | NM_018334 | ENST00000308478 | 54674 | leucine rich repeat neuronal 3 | chr7:110764771-110764830 | GO:0005515\|GO:0000187\|NM_018334\| GO:0016020\|GO:0016021\| GO:0006897 | | THC2462585 | Hs.3781 |
| A_23_P375524 | LCE1D | Homo sapiens late cornified envelope 1D (LCE1D), mRNA [NM_178352] | NM_178352 | ENST00000326233 | 353134 | late cornified envelope ID | chr1:152770331-152770390 | GO:0031424 | NM_178352 | THC2694544 | Hs.490235 |
| A_33_P3297468 | SLC34A3 | Homo sapiens solute carrier family 34 (sodium phosphate), member 3 (SLC34A3), transcript variant 2, mRNA [NM_001177317] | NM_001177317 | ENST00000538474 | 142680 | solute carrier family 34 (sodium phosphate), member 3 | chr9:140129070-140129129 | GO:0005903\|GO:0016324\|NM_001177317\| GO:0005436\|GO:0015321\| GO:0016020\|GO:0030643\| GO:0006817\|GO:0016021\| GO:0031402\|GO:0006814\| GO:0015293\|GO:0006811 | | THC2774767 | Hs.432442 |
| A_33_P3409099 | ATXN1 | Homo sapiens ataxin 1 (ATXN1), transcript variant 1, mRNA [NM_000332] | NM_000332 | ENST00000450222 | 6310 | ataxin 1 | chr6:16302089-16302030 | GO:0016564\|GO:0006396\|NM_000332\| GO:0008219\|GO:0003723\| GO:0005730\|GO:0005634\| GO:0043621\|GO:0008022\| GO:0016363\|GO:0042802\| GO:0008266\|GO:0005737\| GO:0034046\|GO:0042272\| GO:0016481\|GO:0005654\| GO:0051168\|GO:0042405 | | THC2613205 | Hs.434961 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3256685 | TTF2 | Homo sapiens transcription termination factor, RNA polymerase II (TTF2), mRNA [NM_003594] | NM_003594 | ENST00000369466 | 8.158 | transcription termination factor, RNA polymerase II | chr1:117645081-117645022 | GO:0008380\|GO:0005515\|GO:0006353\|GO:0006397\|GO:0008026\|GO:0004386\|GO:0005634\|GO:0003717\|GO:0003677\|GO:0005524\|GO:0008023\|GO:0005737\|GO:0016787\|GO:0000166\|GO:0008270\|GO:0005811\|GO:0045449\|GO:0008094 | NM_003594 | THC2684205 | Hs.486818 |
| A_23_P933 | RWDD3 | Homo sapiens RWD domain containing 3 (RWDD3), transcript variant 1, mRNA [NM_015485] | NM_015485 | ENST00000495272 | 25950 | RWD domain containing 3 | chr1:95712438-95712497 | GO:0005515\|GO:0005737\|GO:0005634 | NM_015485 | THC2622910 | Hs.709591 |
| A_33_P3351559 | ETNK1 | Homo sapiens ethanolamine kinase 1 (ETNK1), transcript variant 1, mRNA [NM_018638] | NM_018638 | ENST00000426005 | 55500 | ethanolamine kinase 1 | chr12:22843337-22843396 | GO:0004305\|GO:0006646\|GO:0005737\|GO:0000166\|GO:0005524\|GO:0016740 | NM_018638 | THC2711794 | Hs.29464 |
| A_33_P3381777 | TREML1 | Homo sapiens triggering receptor expressed on myeloid cells-like 1 (TREML1), mRNA [NM_178174] | NM_178174 | ENST00000338352 | 340205 | triggering receptor expressed on myeloid cells-like 1 | chr6:41117457-41117398 | GO:0005515\|GO:0005737\|GO:0009986\|GO:0005886\|GO:0045087\|GO:0031091\|GO:0030168\|GO:0004872\|GO:0016021 | NM_178174 | NP1465593 | Hs.117331 |
| A_24_P42389 | OTUD6A | Homo sapiens OTU domain containing 6A (OTUD6A), mRNA [NM_207320] | NM_207320 | ENST00000367816 | 139562 | OTU domain containing 6A | chrX:69283505-69283564 | | NM_207320 | THC2491103 | Hs.447381 |
| A_23_P62932 | ATP1B1 | Homo sapiens ATPase, Na+/K+ transporting, beta 1 polypeptide (ATP1B1), mRNA [NM_001677] | NM_001677 | ENST00000537858 | 481 | ATPase, Na+/K+ transporting, beta 1 polypeptide | chr1:169101187-169101936 | GO:0005515\|GO:0001666\|GO:0005886\|GO:0030955\|GO:0031402\|GO:0005890\|GO:0016323\|GO:0006754\|GO:0016324\|GO:0005901\|GO:0016021\|GO:0006814\|GO:0006813\|GO:0005391\|GO:0006811 | NM_001677 | THC2470205 | Hs.291196 |
| A_33_P3380383 | TIFAB | Homo sapiens TRAF-interacting protein with forkhead-associated domain, family member B (TIFAB), mRNA [NM_001099221] | NM_001099221 | ENST00000374115 | 497189 | TRAF-interacting protein with forkhead-associated domain, family member B | chr5:134784664-134784605 | | NM_001099221 | THC2658671 | Hs.552091 |
| A_33_P3270317 | SLC18A3 | Homo sapiens solute carrier family 18 (vesicular acetyl- | NM_003055 | | 6572 | solute carrier family 18 (vesicular | chr10:50820656-50820715 | GO:0060201\|GO:0015870\|GO:0016020\|GO:0005887\|GO:0005277\|GO:0005624 | NM_003055 | THC2477087 | Hs.654374 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3321432 | | choline), member 3 (SLC18A3), mRNA [NM_003055] | | | | acetylcholine), member 3 | | GO:0055085 | | | |
| | FAM198B | Homo sapiens family with sequence similarity 198, member B (FAM198B), transcript variant 2, mRNA [NM_016613] | NM_016613 | ENST00000393807 | 51313 | family with sequence similarity 198, member B | chr4:159046215-159046156 | GO:0005794|GO:0016020|GO:0016613 GO:0016021 | NM_016613 | THC2461168 | Hs.567498 |
| A_33_P3259865 | C1orf220 | Homo sapiens chromosome 1 open reading frame 220 (C1orf220), non-coding RNA [NR_033186] | NR_033186 | ENST00000319387 | 400798 | chromosome 1 open reading frame 220 | chr1:178517965-178518024 | | NR_033186 | THC2483231 | Hs.668085 |
| A_33_P3213419 | LOC100129447 | Homo sapiens cDNA FLJ30384 fis, clone BRACE2008114. [AK054946] | AK054946 | | 100129447 | hypothetical protein LOC100129447 | chr12:113528430-113528489 | | | THC2483097 | Hs.661564 |
| A_23_P328808 | GPR132 | Homo sapiens G protein-coupled receptor 132 (GPR132), mRNA [NM_013345] | NM_013345 | ENST00000551869 | 29933 | G protein-coupled receptor 132 | chr14:105515158-105515899 | GO:0007165|GO:0000082|GO:0007186|GO:0005886 GO:0004930|GO:0006950 GO:0004872|GO:0016021 | NM_013345 | THC2688586 | Hs.532504 |
| A_33_P3407606 | | Q275K3_MYCFV (Q275K3) Phage integrate, partial (4%) [THC2725860] | | | | | chrX:064813223-064813282 | | | THC2725860 | |
| A_33_P3324409 | | | | | | | chr11:049000751010-049007451 | | | | |
| A_33_P3249364 | TMTC1 | transmembrane and tetratricopeptide repeat containing 1 [Source: HGNC Symbol; Acc: 24099] [ENST00000381224] | AK055962 | ENST00000381224 | 83857 | transmembrane and tetratricopeptide repeat containing 1 | chr12:298128733-29812814 | | | THC2511165 | Hs.401954 |
| A_23_P146885 | UTS2R | Homo sapiens urotensin 2 receptor (UTS2R), mRNA [NM_018949] | NM_018949 | ENST00000313135 | 2837 | urotensin 2 receptor | chr17:80333237-80333296 | GO:0005886|GO:0046005|NM_018949 GO:0030307|GO:0004930 GO:0048146|GO:0008015 GO:0010841|GO:0045777 GO:0003105|GO:0007204 GO:0045766|GO:0007165 GO:0045907|GO:0007186 GO:0030080|GO:0001604 GO:0004872|GO:0016021 GO:0055037|GO:0003077 GO:0005769 | NM_018949 | THC2646256 | Hs.192720 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P204144 | KRT85 | *Homo sapiens* keratin 85 (KRT85), mRNA [NM_002283] | NM_002283 | ENST00000544265 | 3891 | keratin 85 | chr12:52754483-52754424 | GO:0005515\|GO:0008544\|NM_002283 GO:0005198\|GO:0045095 | THC2479571 | Hs.182507 |
| A_33_P3280666 | PHF21B | *Homo sapiens* PHD finger protein 21B (PHF21B), transcript variant 1, mRNA [NM_138415] | NM_138415 | ENST00000396103 | 112885 | PHD finger protein 21B | chr22:45279025-45278966 | GO:0005515\|GO:0008270\|NM_138415 GO:0046872 | NP1147183 | Hs.254097 |
| A_32_P219368 | WTAP | *Homo sapiens* Wilms tumor 1 associated protein (WTAP), transcript variant 3, mRNA [NM_152858] | NM_152858 | ENST00000337387 | 9589 | Wilms tumor 1 associated protein | chr6:160169678-160169737 | GO:0008380\|GO:0006397\|NM_152858 GO:0031965\|GO:0007049\| GO:0005730\|GO:0005654\| GO:0005634 | THC2515074 | Hs.446091 |
| A_33_P3877739 | SMCR2 | ag52h12.x5 Gessler Wilms tumor *Homo sapiens* cDNA clone IMAGE: 1126631 3', mRNA sequence [AI821758] | AI821758 | | 140768 | Smith-Magenis syndrome chromosome region, (candidate 2 non-protein coding) | chr17:17579625-17579684 | | | Hs.369680 |
| A_24_P155502 | INHBC | *Homo sapiens* inhibin, beta C (INHBC), mRNA [NM_005538] | NM_005538 | ENST00000309668 | 3626 | inhibin, beta C | chr12:57844125-57844184 | GO:0005179\|GO:0005576\|NM_005538 GO:0008083\|GO:0005160 | THC2482175 | Hs.632722 |
| A_33_P3413701 | ERAP1 | *Homo sapiens* endoplasmic reticulum aminopeptidase 1 (ERAP1), transcript variant 2, mRNA [NM_001040458] | NM_001040458 | ENST00000443439 | 51752 | endoplasmic reticulum aminopeptidase 1 | chr5:96110275-96110216 | GO:0005138\|GO:0005515\|NM_001040458 GO:0005783\|GO:0005576\| GO:0001525\|GO:0005151\| GO:0046872\|GO:0005829\| GO:0009617\|GO:0006955\| GO:0016020\|GO:0019885\| GO:0004177\|GO:0045088\| GO:0008235\|GO:0006508\| GO:0008217\|GO:0045444\| G 0:0005788\|GO: 0008270\| GO:0008233\|GO:0016021\| GO:0006509 | THC2533844 | Hs.684061 |
| A_33_P3403773 | ZNF569 | *Homo sapiens* zinc finger protein 569 (ZNF569), mRNA [NM_152484] | NM_152484 | ENST00000316950 | 148266 | zinc finger protein 569 | chr19:37902138-37902079 | GO:0005622\|GO:0006355\|NM_152484 GO:0008270\|GO:0005634\| GO:0003677\|GO:0046872 | THC2472283 | Hs.511848 |
| A_33_P3871347 | SNED1 | *Homo sapiens* sushi, nidogen and EGF-like domains 1 (SNED1), mRNA [NM_001080437] | NM_001080437 | ENST00000342631 | 25992 | sushi, nidogen and EGF-like domains 1 | chr2:242032388-242032447 | GO:0007160\|GO:0005509 NM_001080437 | THC2471466 | Hs.471834 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P168306 | WASF1 | Homo sapiens WAS protein family, member 1 (WASF1), transcript variant 1, mRNA [NM_003931] | NM_003931 | ENST00000392589 | 8936 | WAS protein family, member 1 | Chr6:110421185-110421126 | GO:0005739\|GO:0005515\|NM_003931\|GO:0005737\|GO:0006461\|GO:0030041\|GO:0006928\|GO:0005741\|GO:0003779\|GO:0015629\|GO:0030027 | THC2482774 | Hs.75850 |
| A_33_P3299110 | ARHGAP42 | Homo sapiens Rho GTPase activating protein 42 (ARHGAP42), mRNA [NM_152432] | NM_152432 | ENST00000298815 | 143872 | Rho GTPase activating protein 42 | chr11:100861597-100861656 | GO:0005622\|GO:0007165\|NM_152432\|GO:0005096 | THC2655447 | Hs.269837 |
| A_23_P169494 | ORM1 | Homo sapiens orosomucoid 1 (ORM1), mRNA [NM_000607] | NM_000607 | ENST00000477456 | 5004 | orosomucoid 1 | chr9:117087130-117087340 | GO:0005515\|GO:0006954\|NM_000607\|GO:0002682\|GO:0005576\|GO:0006953\|GO:0005615 | THC2558758 | Hs.522356 |
| A_33_P3387756 | C20orf201 | Homo sapiens chromosome 20 open reading frame 201 (C20orf201), mRNA [NM_001007125] | NM_001007125 | ENST00000308906 | 198437 | chromosome 20 open reading frame 201 | chr20:62714996-62714937 | | NM_001007125 | THC2617670 | Hs.570316 |
| A_23_P150407 | CREB3L1 | Homo sapiens cAMP responsive element binding protein 3-like 1 (CREB3L1), mRNA [NM_052854] | NM_052854 | ENST00000530244 | 90993 | cAMP responsive element binding protein 3-like 1 | chr11:46342759-46342818 | GO:0043565\|GO:0006986\|NM_052854\|GO:0006355\|GO:0003700\|GO:0016020\|GO:0005783\|GO:0046983\|GO:0005634\|GO:0016021 | THC2501749 | Hs.405961 |
| A_33_P3557274 | LOC644686 | Homo sapiens cDNA FLJ26926 fis, clone RCT05265. [AK130436] | AK130436 | | 644686 | hypothetical protein LOC644686 | chr2:637454122-63745353 | | | NP852640 | Hs.689344 |
| A_33_P3343845 | CBX7 | Homo sapiens chromobox homolog 7 (CBX7), mRNA [NM_175709] | NM_175709 | ENST00000490741 | 23492 | chromobox homolog 7 | chr22:395297198-39529719 | GO:0005515\|GO:0003682\|NM_175709\|GO:0005634\|GO:0000785\|GO:0045449\|GO:0016568\|GO:0006333 | THC2534858 | Hs.356416 |
| A_33_P3331687 | GPSM1 | Homo sapiens G-protein signaling modulator 1 (GPSM1), transcript variant 1, mRNA [NM_001145638] | NM_001145638 | ENST00000392944 | 26086 | G-protein signaling modulator 1 | chr9:139252936-139252995 | GO:0005515\|GO:0007165\|NM_001145638\|GO:0005737\|GO:0008277\|GO:0005794\|GO:0005886\|GO:0005783\|GO:0007275\|GO:0030154\|GO:0007399\|GO:0005829\|GO:0005096 | THC2464217 | Hs.239370 |
| A_23_P217528 | KLF8 | Homo sapiens Kruppel-like factor 8 (KLF8), transcript variant 1, mRNA [NM_007250] | NM_007250 | ENST00000358094 | 11279 | Kruppel-like factor 8 | chrX:56311439-56311498 | GO:0005622\|GO:0008270\|NM_007250\|GO:0005634\|GO:0003677\|GO:0046872\|GO:0045449 | THC2473486 | Hs.646614 |
| A_33_P3330683 | | | | | | | chr2:137086701-137086952 | | | | |
| A_33_P3312802 | RPL13AP17 | Homo sapiens ribosomal protein L13a pseudogene 17 | NR_003680 | ENST00000450028 | 399670 | ribosomal protein L13a pseudogene 17 | chr7:77988714-77988773 | | NR_003680 | | Hs.568045 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3274080 | | (RPL13AP17), non-coding RNA [NR_003680] | | | | | chrY:02445063 4-024450575 | | | | |
| A_23_P154488 | PNPT1 | Homo sapiens polyribonucleotide nucleotidyltransferase 1 (PNPT1), mRNA [NM_033109] | NM_033109 | ENST00000402246 | 87178 | polyribo-nucleotide nucleo-tidyltrans-ferase 1 | chr2:55864694-55863476 | GO:0005739\|GO:0006396\|NM_033109\| GO:0005758\|GO:0004684\| GO:0000175\|GO:0003723\| GO:0006402\|GO:0016740 | NM_033109 | THC2463838 | Hs.388733 |
| A_23_P74609 | G0S2 | Homo sapiens G0/G1switch 2 (G0S2), mRNA [NM_015714] | NM_015714 | ENST00000367029 | 50486 | G0/G1switch 2 | chr1:20984959 7-209849656 | GO:0003674\|GO:0007049\|NM_015714\| GO:0005575 | NM_015714 | THC2463882 | Hs.432132 |
| A_33_P3280099 | CACNA1B | calcium channel, voltage-dependent, N type, alpha 1B subunit [Source: HGNC Symbol; Acc: 1389] [ENST00000371367] | | ENST00000371367 | 774 | calcium channel, voltage-dependent, N type, alpha 1B subunit | chr9:14092716 3-140927222 | | | NP238281 | |
| A_23_P106069 | | T cell receptor alpha variable 6 [Source: HGNC Symbol; Acc: 12144] [ENST00000390428] | X58747 | ENST00000390428 | | | chr14:2223716 5-22237224 | | | NP1171923 | Hs.455888 |
| A_23_P400 | KRTAP4-11 | keratin associated protein 4-11 (KRTAP4-11), mRNA [NM_033059] | NM_033059 | ENST00000391413 | 653240 | keratin associated protein 4-11 | chr17:3927383 8-39273779 | GO:0045095 | NM_033059 | THC2488192 | Hs.30701 |
| A_23_P12526 | TP53BP2 | Homo sapiens [NM_005426\|NM_005426] tumor protein p53 binding protein, 2 (TP53BP2), transcript variant 2, mRNA | NM_005426\|NM_005426 | ENST00000391878 | 7159 | tumor protein p53 binding protein, 2 | chr1:22396829 0-223968231 | GO:0005515\|GO:0007165\|NM_005426\| GO:0048471\|GO:0017124\| GO:0005737\|GO:0051059\| GO:0005070\|GO:0006915\| GO:0005634\|GO:0006917\| GO:0045786 | NM_005426 | THC2485922 | Hs.523968 |
| A_33_P3286157 | TNFRSF4 | Homo sapiens tumor necrosis factor receptor superfamily, member 4 (TNFRSF4), mRNA [NM_003327] | NM_003327 | ENST00000497869 | 7293 | tumor necrosis factor receptor superfamily, member 4 | chr1:1146781-1146722 | GO:0045859\|GO:0005515\|NM_003327\| GO:0005886\|GO:0030890\| GO:0042981\|GO:0050710\| GO:0043433\|GO:0006955\| GO:0006968\|GO:0005031\| GO:0006954\|GO:0032582\| GO:0042098\|GO:0005887\| GO:0051024\|GO:0004872\| GO:0009897 | NM_003327 | THC2619418 | Hs.129780 |
| A_33_P3408877 A_23_P217079 | DPM2 | Homo sapiens dolichyl-phosphate mannosyltransferase | NM_003863 | ENST00000495270 | 8818 | dolichyl-phosphate mannosyl- | chr9:13069765 5-130697596 | GO:0005515\|GO:0004582\|NM_003863\| GO:0005783\|GO:0009059\| GO:0016254\|GO:0018406 | NM_003863 | THC2532187 | Hs.108973 |

APPENDIX C-continued

FEMALES: Technology: AgilentSingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P94533 | | polypeptide 2, regulatory subunit (DPM2), mRNA [NM_003863] | | | | transferase polypeptide 2, regulatory subunit | | GO:0031501\|GO:0030176\|GO:0000506\|GO:0035269\|GO:0016020\|GO:0005789\|GO:0016021 | | THC2576582 | Hs.418123 |
| A_23_P94533 | CTSL1 | Homo sapiens cathepsin L1 (CTSL1), transcript variant 1, mRNA [NM_001912] | NM_001912 | ENST00000375894 | 1514 | cathepsin L1 | chr9:90345326-90345385 | GO:0004197\|GO:0042277\|NM_001912\|GO:0030984\|GO:0004177\|GO:0006508\|GO:0008233\|GO:0005625\|GO:0005576\|GO:0005764 | | | |
| A_33_P3409765 | MGAM | maltase-glucoamylase (alpha-glucosidase) [Source: HGNC Symbol; Acc: 7043] [ENST00000312952] | | ENST00000312952 | 8972 | maltase-glucoamylase (alpha-glucosidase) | chr7:141773913-141773972 | | | | |
| A_23_P50872 | NDUFB7 | Homo sapiens NADH dehydrogenase (ubiquinone) 1 beta subcomplex, 7, 18 kDa (NDUFB7), nuclear gene encoding mitochondrial protein, mRNA [NM_004146] | NM_004146 | ENST00000215565 | 4713 | NADH dehydrogenase (ubiquinone) 1 beta subcomplex, 7, 18 kDa | chr19:1468275-14677745 | GO:0005739\|GO:0003954\|NM_004146\|GO:0005747\|GO:0016020\|GO:0070469\|GO:0006810\|GO:0006120\|GO:0005743\|GO:0022900\|GO:0008137 | | THC2467693 | Hs.532853 |
| A_23_P254702 | DEK | Homo sapiens DEK oncogene (DEK), transcript variant 1, mRNA [NM_003472] | NM_003472 | ENST00000397239 | 7913 | DEK oncogene | chr6:18225006-18224948 | GO:0042393\|GO:0007165\|NM_003472\|GO:0051789\|GO:0006357\|GO:0003704\|GO:0005634\|GO:0019079\|GO:0003677 | | THC2556705 | Hs.484813 |
| A_23_P160751 | FCRL2 | Homo sapiens Fc receptor-like 2 (FCRL2), mRNA [NM_030764] | NM_030764 | ENST00000368181 | 79368 | Fc receptor-like 2 | chr1:157716511-157716460 | GO:0005886\|GO:0005070\|NM_030764\|GO:0007267\|GO:0005625\|GO:0004872\|GO:0016021 | | NP1165213 | Hs.437393 |
| A_33_P3285715 | GLI4 | GLI family zinc finger 4 [Source: HGNC Symbol; Acc: 4320] [ENST00000523812] | AB209654 | ENST00000523812 | 2738 | GLI family zinc finger 4 | chr8:144357115-144357174 | | | NP1473078 | Hs.400533 |
| A_33_P3294177 | LOC100131043 | Homo sapiens cDNA FLJ42228 fis, Clone THYMU2041252. [AK124222] | AK124222 | | 100131043 | hypothetical LOC100131043 | chr6:36723389-36723330 | | | THC2479958 | Hs.372129 |
| A_33_P3222852 | | Homo sapiens LP3317 mRNA, complete cds. [AY203941] | AY203941 | | | | chr19:3560292-35602988 | | | NP1212925 | Hs.404342 |
| A_23_P74330 | MGC4473 | Homo sapiens hypothetical LOC79100(MGC4473), non-coding RNA [NR_024160] | NR_024160 | ENST00000420691 | 79100 | hypothetical LOC79100 | chr1:168761917-168761978 | | NR_024160 | THC2618569 | Hs.250624 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P448360 | C17orf65 | *Homo sapiens* chromosome 17 open reading frame 65 (C17orf65), mRNA [NM_178542] | NM_178542 | ENST00000303061 | 339201 | chromosome 17 open reading frame 65 | chr17:42254031-42253972 | | NM_178542 | THC2473822 | Hs.656564 |
| A_33_P3251322 | MTMR14 | *Homo sapiens* cDNA FLJ46453 fis, clone THYMU3019916. [AK128312] | AK128312 | | 64419 | myotubularin related protein 14 | chr3:9742908-9742967 | | | THC2484657 | |
| A_33_P3421867 | MDGA1 | MAM domain containing glycosyl-phosphatidylinositol anchor 1 [Source: HGNC Symbol; Acc: 19267] [ENST00000373401] | AK126965 | ENST00000373401 | 266727 | MAM domain containing glycosyl-phosphat idylinositol anchor 1 | chr6:37606891-37606832 | GO:0003674\|GO:0005886\|GO:0007420\|GO:0007275\|GO:0001764\|GO:0046658\|GO:0030154\|GO:0021527\|GO:0007399 | | THC2632760 | Hs.437993 |
| A_33_P3350202 | MOCS3 | *Homo sapiens* molybdenum cofactor synthesis 3 (MOCS3), mRNA [NM_014484] | NM_014484 | ENST00000244051 | 27304 | molybdenum cofactor synthesis 3 | chr20:49577728-49577787 | GO:0005515\|GO:0016779\|GO:0034227\|GO:0005524\|GO:0008033\|GO:0005829\|GO:0002098\|GO:0005737\|GO:0001666\|GO:0018192\|GO:0006777\|GO:0008152\|GO:0004792\|GO:0042292\|GO:0016740 | NM_014484 | THC2472488 | Hs.159410 |
| A_33_P3226395 | LOC389634 | *Homo sapiens* hypothetical LOC389634 (LOC389634), non-coding RNA [NR_024420] | NR_024420 | ENST00000420040 | 389634 | hypothetical LOC389634 | chr12:8509640-8509581 | | NR_024420 | THC2545092 | Hs.434403 |
| A_23_P146654 | BAG1 | *Homo sapiens* mRNA BCL2-associated athanogene (BAG1), transcript variant 1, [NM_004323] | NM_004323 | ENST00000379707 | 573 | BCL2-associated athanogene | chr9:33255124-33255065 | GO:0005515\|GO:0005737\|NM_004323 GO:0030182\|GO:0006915\|GO:0006916\|GO:0005634\|GO:0005057\|GO:0005856\|GO:0007166\|GO:0005829 | | THC2494891 | Hs.377484 |
| A_33_P3883912 | ZCCHC10 | *Homo sapiens* zinc finger, CCHC domain containing 10 (ZCCHC10), mRNA [NM_017665] | NM_017665 | ENST00000324170 | 54819 | zinc finger, CCHC domain containing 10 | chr5:132333275-132332697 | GO:0008270\|GO:0003676\|NM_017665 GO:0046872 | | THC2522779 | Hs.29700 |
| A_24_P818268 | | | | | | | chr15:0743575 34-074357593 | | | | |
| A_23_P362893 | TEAD1 | *Homo sapiens* TEA domain family member 1 (SV40 transcriptional enhancer factor) (TEAD1), mRNA [NM_021961] | NM_021961 | ENST00000361985 | 7003 | TEA domain family member 1 (SV40 transcriptional enhancer factor) | chr11:1296522 5-12965284 | GO:0007507\|GO:0005515\|NM_021961 GO:0005667\|GO:0006355\|GO:0003700\|GO:0045944\|GO:0016563\|GO:0005634 | | THC2462665 | Hs.655331 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3284854 | FLJ25694 | Homo sapiens cDNA FLJ46084 fis, clone TESTI2006543. [AK127969] | AK127969 | | 100128202 | hypothetical protein FLJ25694 | chr13:64414947-64414888 | | | THC2479781 | |
| A_33_P3245183 | HRH1 | Homo sapiens histamine receptor H1 (HRH1), transcript variant 1, mRNA [NM_001098213] | NM_001098213 | ENST00000431010 | 3269 | histamine receptor H1 | chr3:11304879-11304938 | GO:0007165|GO:0006954|NM_001098213|GO:0005886|GO:0005887|GO:0004930|GO:0007268|GO:0007200|GO:0004872|GO:0004969|GO:0045429 | NM_001098213 | THC2706949 | Hs.1570 |
| A_33_P3211238 | VWCE | Homo sapiens von Willebrand factor C and EGF domains (VWCE), mRNA [NM_152718] | NM_152718 | ENST00000301770 | 220001 | von Willebrand factor C and EGF domains | chr11:61026206-61026147 | GO:0005509|GO:0005576 | NM_152718 | THC2474163 | Hs.60640 |
| A_24_P209171 | SH3BGRL2 | Homo sapiens SH3 domain binding glutamic acid-rich protein like 2 (SH3BGRL2), mRNA [NM_031469] | NM_031469 | ENST00000369838 | 83699 | SH3 domain binding glutamic acid-rich protein like 2 | chr6:80412808-80412867 | GO:0017124|GO:0005634 | NM_031469 | THC2780746 | Hs.302772 |
| A_33_P3235987 | PIN4 | Homo sapiens protein (peptidylprolyl cis/trans isomerase) NIMA-interacting, 4 (parvulin) (PIN4), nuclear gene encoding mitochondrial protein, transcript variant 1, mRNA [NM_006223] | NM_006223 | ENST00000373662 | 5303 | protein (peptidyl-prolyl cis/trans isomerase) NIMA interacting,4 (parvulin) | chrX:71416695-71416754 | GO:0005739|GO:0005737|NM_006223|GO:0006457|GO:0005759|GO:0005819|GO:0005730|GO:0003755|GO:0005634|GO:0016853|GO:0003677 | NM_006223 | THC2548393 | Hs.655623 |
| A_33_P3342235 | CDC42EP5 | Homo sapiens CDC42 effector protein (Rho GTPase binding) 5 (CDC42EP5), mRNA [NM_145057] | NM_145057 | ENST00000301200 | 148170 | CDC42 effector protein (Rho GTPase binding) 5 | chr19:5497627-54976211 | GO:0005515|GO:0005737|NM_145057|GO:0030838|GO:0005886|GO:0008360|GO:0007254|GO:0031274|GO:0017049|GO:0007266|GO:0005856|GO:0019898 | NM_145057 | THC2470448 | Hs.415791 |
| A_33_P3417086 | NIPAL1 | Homo sapiens NIPA like domain containing 1 (NIPAL1), mRNA [NM_207330] | NM_207330 | ENST00000295461 | 152519 | NIPA-like domain containing 1 | chr4:48039016-48039075 | GO:0016020|GO:0016021 | NM_207330 | THC2479335 | Hs.134190 |
| A_33_P3422654 | LOC100133985 | Homo sapiens hypothetical LOC100133985 (LOC100133985), non-coding RNA [NR_024444] | NR_024444 | ENST00000414141 | 100133985 | hypothetical LOC100133985 | chr2:70351510-70351451 | | NR_024444 | THC2658593 | Hs.135528 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3273534 | KRT81 | Homo sapiens keratin 81 (KRT81), mRNA [NM_002281] | NM_002281 | ENST00000327741 | 3887 | keratin 81 | chr12:52679758-52679699 | GO:0005515 GO:0005198 GO:0045095 | NM_002281 | THC2466812 | Hs.658118 |
| A_33_P3281018 | | Homo sapiens cDNA clone TEST4017688 5', mRNA sequence [DB074148] | DB074148 | | | | chr7:158799418-158799477 | | | | Hs.722879 |
| A_33_P3361513 | NLE1 | Homo sapiens notchless homolog 1 (Drosophila) (NLE1), transcript variant 2, mRNA [NM_001014445] | NM_001014445 | ENST00000360831 | 54475 | notchless homolog 1 (Drosophila) | chr17:33462341-33462282 | GO:0007219 GO:0005730 GO:0001826 GO:0005634 | NM_001014445 | NP1176229 | Hs.85570 |
| A_33_P3412847 | | | | ENST00000450152 | | | chr10:3975104-3975163 | | | THC2765998 | |
| A_33_P43034 | CCDC117 | Homo sapiens coiled-coil domain containing 117 (CCDC117), mRNA [NM_173510] | NM_173510 | ENST00000249064 | 150275 | coiled-coil domain containing 117 | chr22:29184752-29184811 | | NM_173510 | THC2496139 | Hs.406460 |
| A_33_P3376365 | HES2 | hairy and enhancer of split 2 (Drosophila) [Source: HGNC Symbol; Acc: 16005] [ENST00000377836] | BC012091 | ENST00000377836 | 54626 | hairy and enhancer of split 2 (Drosophila) | chr1:6473312-6473253 | | | THC2485116 | Hs.118727 |
| A_33_P3887888 | FLJ44511 | Homo sapiens hypothetical LOC441307 (FLJ44511), non-coding RNA [NR_033963] | NR_033963 | | 441307 | hypothetical LOC441307 | chr7:563781-563840 | | NR_033963 | THC2627801 | Hs.521334 |
| A_23_P111092 | OR2H1 | Homo sapiens olfactory receptor, family 2, subfamily H, member 1 (OR2H1), mRNA [NM_030883] | NM_030883 | ENST00000461453 | 26716 | olfactory receptor, family 2, subfamily H, member 1 | chr6:29430022-29430081 | GO:0007608 GO:0007165 GO:0004984 GO:0007186 GO:0005886 GO:0004872 GO:0016021 GO:0050896 | NM_030883 | THC2734737 | Hs.434715 |
| A_23_P89601 | KRT32 | Homo sapiens keratin 32 (KRT32), mRNA [NM_002278] | NM_002278 | ENST00000225899 | 3882 | keratin 32 | chr17:39616163-39616104 | GO:0005882 GO:0005515 GO:0008544 GO:0005198 | NM_002278 | THC2482607 | Hs.41752 |
| A_33_P3304878 | WDFY4 | Homo sapiens WDFY family member 4 (WDFY4), mRNA [NM_020945] | NM_020945 | ENST00000374161 | 57705 | WDFY family member 4 | chr10:50030522-50030581 | GO:0016020 GO:0005488 GO:0016021 | NM_020945 | THC2481073 | Hs.287379 |
| A_33_P3347099 | FLJ36000 | Homo sapiens hypothetical FLJ36000 (FLJ36000), | NR_027084 | | 284124 | hypothetical FLJ36000 | chr17:21909868-21909927 | | NR_027084 | THC2503236 | Hs.310247 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3318861 | DYTN | non-coding RNA [NR_027084] Homo sapiens dystrotelin (DYTN), mRNA [NM_001093730] | NM_001093730 | ENST00000452335 | 391475 | dystrotelin | chr2:207516408-207516349 | GO:0005886|GO:0005509|GO:0008270 | NM_001093730 | | Hs.640667 |
| A_33_P3263902 | MXI1 | Homo sapiens MAX interactor 1 (MXI1), transcript variant 1, mRNA [NM_005962] | NM_005962 | ENST00000393134 | 4601 | MAX interactor 1 | chr10:111985981-111986040 | GO:0008285|GO:0003714|GO:0030528|GO:0042994|GO:0005634|GO:0003677|GO:0045449 | NM_005962 | THC2526907 | Hs.501023 |
| A_33_P3350413 | SVIL | supervillin [Source: HGNC Symbol; Acc: 11480] [ENST00000538146] | AK310272 | ENST00000538146 | 6840 | supervillin | chr10:29769151-29769092 | | | | Hs.499209 |
| A_23_P218793 | XPNPEP3 | Homo sapiens X-prolyl aminopeptidase (aminopeptidase P) 3, putative (XPNPEP3), nuclear gene encoding mitochondrial protein, transcript variant 1, mRNA [NM_022098] | NM_022098 | ENST00000428799 | 63929 | X-prolyl aminopeptidase (aminopeptidase P) 3, putative | chr22:41322769-41322828 | GO:0005739|GO:0030145|GO:0009987|GO:0004177|GO:0008233|GO:0046872|GO:0008237 | NM_022098 | THC2473423 | Hs.529163 |
| A_23_P101084 | SPATA22 | Homo sapiens spermatogenesis associated 22 (SPATA22), transcript variant 2, mRNA [NM_032598] | NM_032598 | ENST00000541913 | 84690 | spermatogenesis associated 22 | chr17:3346555-3346496 | | NM_032598 | THC2485663 | Hs.351068 |
| A_23_P250245 | CD72 | Homo sapiens CD72 molecule (CD72), mRNA [NM_001782] | NM_001782 | ENST00000490239 | 971 | CD72 molecule | chr9:35610744-35610685 | GO:0016020|GO:0005887|GO:0005529|GO:0005102|GO:0007155|GO:0004888 | NM_001782 | THC2472427 | Hs.116481 |
| A_33_P3334843 | | Homo sapiens ppl3439 mRNA, complete cds. [AF318333] | AF318333 | ENST00000331659 | | | chr3:171510199-171510140 | | | THC2482830 | Hs.684469 |
| A_24_P753476 | LOC340508 | Homo sapiens growth arrest-specific 2 like 1 pseudogene (LOC340508), non-coding RNA [NR_002942] | NR_002942 | | 340508 | growth arrest-specific 2 like 1 pseudogene | chr9:99838292-99838233 | | NR_002942 | THC2627745 | Hs.680438 |
| A_23_P215751 | NDUFA5 | Homo sapiens NADH dehydrogenase (ubiquinone) 1 alpha subcomplex, 5, 13 kDa (NDUFA5), nuclear gene encoding | NM_005000 | ENST00000355749 | 4698 | NADH dehydrogenase (ubiquinone) 1 alpha subcomplex, 5, 13 kDa | chr7:123181228-123181169 | GO:0005739|GO:0005747|GO:0016020|GO:0070469|GO:0016651|GO:0006810|GO:0006120|GO:0005743|GO:0008137 | NM_005000 | THC2605956 | Hs.651219 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P218505 | LHB | mitochondrial protein, mRNA [NM_005000] Homo sapiens luteinizing hormone beta polypeptide (LHB), mRNA [NM_000894] | NM_000894 | ENST00000391870 | 3972 | luteinizing hormone beta polypeptide | chr19:49519464-49519405 | GO:0007165|GO:0007186|GO:0006701|GO:0005179|GO:0007267|GO:0005625|GO:0005576|GO:0008584 | NM_000894 | THC2475008 | Hs.154704 |
| A_33_P3361398 | C19orf26 | chromosome 19 open reading frame 26 [Source: HGNC Symbol; Acc: 28617] [ENST00000382477] | | ENST00000382477 | 255057 | chromosome 19 open reading frame 26 | chr19:1229297-1229238 | | | THC2671154 | |
| A_23_P72697 | GPIHBP1 | Homo sapiens glycosylphosphatidylinositol anchored high density lipoprotein binding protein 1 (GPIHBP1), mRNA [NM_178172] | NM_178172 | ENST00000330824 | 338328 | glycosyl-phosphat idylinositol anchored high density lipo-protein binding protein 1 | chr8:144298966-144299025 | GO:0008035|GO:0009986|GO:0005886|GO:00343641|GO:0006869|GO:0016021|GO:0046658|GO:0008289 | NM_178172 | THC2475436 | Hs.426410 |
| A_33_P3336262 | KIAA1751 | chromosome 1 open reading frame 222 [Source: HGNC Symbol; Acc: 27917] [ENST00000412120] | XM_003119800 | ENST00000412120 | 85452 | KIAA1751 | chr1:1853767-1853708 | | XM_003119800 | THC2488615 | Hs.259619 |
| A_33_P3770642 | LOC503519 | Homo sapiens hypothetical LOC503519 (LOC503519), non-coding RNA [NR_038851] | NR_038851 | | 503519 | hypothetical LOC503519 | chr15:26371437-26371496 | | NR_038851 | THC2605757 | Hs.371380 |
| A_32_P200237 | LOC157740 | Homo sapiens mRNA for chromosome 8 open reading frame 9 (c8ORF9). [AJ291676] | AJ291676 | | 157740 | hypothetical protein C8orf9 | chr8:11141291-11141232 | | | THC2480673 | Hs.591395 |
| A_23_P372834 | AQP1 | Homo sapiens aquaporin 1 (Colton blood group) (AQP1), transcript variant 1, mRNA [NM_198098] | NM_198098 | ENST00000311813 | 358 | aquaporin 1 (Colton blood group) | chr7:30965057-30965115 | GO:0005515|GO:0043005|GO:0005215|GO:0007588|GO:0043627|GO:0015696|GO:0015670|GO:0055085|GO:0032809|GO:0016323|GO:0016324|GO:0016020|GO:0005887|GO:0015250|GO:0051739|GO:0043679|GO:0006833|GO:0009725 | NM_198098 | NP1203192 | Hs.76152 |
| A_23_P46627 | ADIPOR1 | Homo sapiens adiponectin receptor 1 | NM_015999 | ENST00000436244 | 51094 | adiponectin receptor 1 | chr1:202910325-202910266 | GO:0006629|GO:0030308|GO:0019395|GO:0009755 | NM_015999 | NP1189273 | Hs.5298 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (ADIPOR1), transcript variant 1, mRNA [NM_015999] | | | | | | GO:0046982\|GO:0016020\|GO:0042562\|GO:0004872\|GO:0016021\|GO:0042802 | | | |
| A_23_P58407 | UGT2B15 | Homo sapiens UDP glucuronosyltransferase 2 family, polypeptide B15 (UGT2B15), mRNA [NM_001076] | NM_001076 | ENST00000338206 | 7366 | UDP glucuronosyl-transferase 2 family, poly-peptide B15 | chr4:69512817-69512758 | GO:0005792\|GO:0006805\|GO:0016020\|GO:0005783\|GO:0008152\|GO:0015020\|GO:0016021\|GO:0008202 | NM_001076 | NP095455 | Hs.150207 |
| A_33_P3373329 | TDRD1 | Homo sapiens tudor domain containing 1 (TDRD1), mRNA [NM_198795] | NM_198795 | ENST00000369280 | 56155 | tudor domain containing 1 | chr10:115985909-115985968 | GO:0005515\|GO:0007275\|GO:0007283\|GO:0031047\|GO:0003676\|GO:0007281\|GO:0046872\|GO:0030154\|GO:0033391\|GO:0005737\|GO:0007126\|GO:0034587\|GO:0008270\|GO:0043186\|GO:0043046 | NM_198795 | NP336945 | Hs.333132 |
| A_33_P3414789 | FSD1 | Homo sapiens fibronectin type III and SPRY domain containing 1 (FSD1), mRNA [NM_024333] | NM_024333 | ENST00000221856 | 79187 | fibronectin type III and SPRY domain containing 1 | chr19:4323373-4323432 | GO:0005622\|GO:0007067\|GO:0007049\|GO:0005813\|GO:0005737\|GO:0005874\|GO:0005634\|GO:0051301 | NM_024333 | THC2693421 | Hs.28144 |
| A_33_P3663142 | FLJ12334 | Homo sapiens hypothetical LOC400946(FLJ12334), non-coding RNA [NR_033875] | NR_033875 | | 400946 | hypothetical LOC400946 | chr2:20084652-20084711 | | NR_033875 | THC2507883 | Hs.289062 |
| A_23_P315991 | OR10A5 | Homo sapiens olfactory receptor, family 10, subfamily A, member 5 (OR10A5), mRNA [NM_178168] | NM_178168 | ENST00000379831 | 144124 | olfactory receptor, family 10, subfamily A, member 5 | chr11:6866954-6867013 | GO:0007608\|GO:0007165\|GO:0004984\|GO:0007186\|GO:0005886\|GO:0004872\|GO:0016021\|GO:0050896 | NM_178168 | THC2482026 | Hs.447478 |
| A_32_P77102 | LOC100128420 | Homo sapiens hypothetical LOC100128420 (LOC100128420), transcript variant 1, non-coding RNA [NR_038461] | NR_038461 | ENST00000454385 | 100128420 | hypothetical LOC100128420 | chrX:135724494-135724553 | | NR_038461 | THC2660884 | Hs.152595 |
| A_33_P3335576 | | | | | | | chr7:07675162-4-076751683 | | | | |
| A_23_P29655 | C3orf14 | Homo sapiens chromosome 3 open reading frame 14 (C3orf14), mRNA [NM_020685] | NM_020685 | ENST00000542214 | 57415 | chromosome 3 open reading frame 14 | chr3:62319086-62319145 | | NM_020685 | THC2464841 | Hs.47166 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P209055 | CD22 | Homo sapiens CD22 molecule (CD22), transcript variant 1, mRNA [NM_001771] | NM_001771 | ENST00000419549 | 933 | CD22 molecule | chr19:3583755 5-35837614 | GO:0005515\|GO:0005886\|NM_001771 GO:0005887\|GO:0005529\| GO:0007155\|GO:0009897 | THC2486527 | Hs.579691 |
| A_33_P3261097 | | | | | | | chr16:0780797 75-078079716 | | | | |
| A_23_P217917 | GSTM4 | Homo sapiens glutathione S-transferase mu 4 (GSTM4), transcript variant 2, mRNA [NM_147148] | NM_147148 | ENST00000493171 | 2948 | glutathione S-transferase mu 4 | chr1:11020162 8-110201686 | GO:0005737\|GO:0008152\|NM_147148 GO:0004364\|GO:0016740 | NP1456583 | Hs.348387 |
| A_24_P350228 | SLC22A23 | Homo sapiens solute carrier family 22, member 23 (SLC22A23), transcript variant 2, mRNA[NM_021945] | NM_021945 | ENST00000380298 | 63027 | solute carrier family 22, member 23 | chr6:3410447-3324203 | GO:0005215\|GO:0016020\|NM_021945 GO:0016021\|GO:0055085\| GO:0006811 | THC2504541 | Hs.713588 |
| A_23_P140290 | RTN1 | Homo sapiens reticulon 1 (RTN1), transcript variant 1, mRNA [NM_021136] | NM_021136 | ENST00000433623 | 6252 | reticulon 1 | chr14:6006995 5-60069808 | GO:0007165\|GO:0016020\|NM_021136 GO:0005783\|GO:0030182\| GO:0005783\|GO:0016021\| GO:0004871 | NP1212773 | Hs.368626 |
| A_33_P3300267 | VIT | Homo sapiens vitrin (VIT), transcript variant 1, mRNA [NM_053276] | NM_053276 | ENST00000389975 | 5212 | vitrin | chr2:37041517-37041576 | GO:0005578\|GO:0005576\|NM_053276 | NP481077 | Hs.137415 |
| A_33_P3410650 | SPAG8 | Homo sapiens sperm associated antigen 8 (SPAG8), transcript variant 1, mRNA [NM_001039592] | NM_001039592 | ENST00000471631 | 26206 | sperm associated antigen 8 | chr9:35810496-35810437 | GO:0008150\|GO:0003674\|NM_001039592 GO:0016020\|GO:0001669 | THC2690029 | Hs.256747 |
| A_33_P3287716 | LOC100129292 | Homo sapiens cDNA FLJ46168 fis, clone TESTI4003279, [AK128048] | AK128048 | | 100129292 | hypothetical protein LOC100129292 | chr20:4309499 5-43095054 | | THC2624161 | Hs.635587 |
| A_23_P328545 | GABRP | Homo sapiens gamma-aminobutyric acid (GABA) A receptor, pi (GABRP), mRNA [NM_014211] | NM_014211 | ENST00000539175 | 2568 | gamma-aminobutyric acid (GABA) A receptor, pi | chr5:17024045 3-170240512 | GO:0031404\|GO:0005230\|NM_014211 GO:0030054\|GO:0005886\| GO:0004890\|GO:00452111\| GO:0034707\|GO:0045202\| GO:0016021\|GO:0005254\| GO:0005216\|GO:0006811 | THC2463912 | Hs.26225 |
| A_33_P3295415 | ZBTB3 | Homo sapiens zinc finger and BTB domain containing 3 (ZBTB3), mRNA [NM_024784] | NM_024784 | ENST00000394807 | 79842 | zinc finger and BTB domain containing 3 | chr11:6251948 8-62519429 | GO:0005622\|GO:0005515\|NM_024784 GO:0008270\|GO:0005634\| GO:0003677\|GO:0046872\| GO:0045449 | THC2477256 | Hs.147554 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3221761 | MLL4 | Homo sapiens myeloid/lymphoid or mixed-lineage leukemia 4 (MLL4), mRNA [NM_014727] | NM_014727 | ENST00000341701 | 9757 | myeloid/ lymphoid or mixed-lineage leukemia 4 | chr19:36211178 2-36211841 | GO:0005515\|GO:0035097\|GO:0006355\|GO:0003700\| GO:0008168\|GO:0008270\| GO:0005634\|GO:0048096\| GO:0042800\|GO:0046872\| GO:0016740\|GO:0016568 | NM_014727 | THC2491229 | Hs.92236 |
| A_33_P3377380 | | peptidylprolyl isomerase E-like pseudogene (PPIEL), non-coding RNA [Source: RefSeq DNA; Acc: NR_003929] [ENST00000450157] | AK093659 | ENST00000450157 | | | chr1:39990685- 39990626 | | | THC2586785 | Hs.472508 |
| A_23_P76983 | C14orf45 | Homo sapiens chromosome 14 open reading frame 45 (C14orf45), mRNA [NM_025057] | NM_025057 | ENST00000394009 | 80127 | chromosome 14 open reading frame 45 | chr14:7453231 7-74532376 | | NM_025057 | THC2475241 | Hs.644621 |
| A_33_P3268174 | KBTBD6 | Homo sapiens kelch repeat and BTB (POZ) domain containing 6 (KBTBD6), mRNA [NM_152903] | NM_152903 | ENST00000379485 | 89890 | kelch repeat and BTB (POZ) domain containing 6 | chr13:4170194 0-41701881 | GO:0005515\|GO:0008150\|NM_152903 GO:0003674\|GO:0005575 | | THC2492106 | Hs.534040 |
| A_33_P3333677 | | | | | | | chr15:0227062 20-022706161 | | | | |
| A_24_P182281 | HHLA3 | Homo sapiens HERV-H LTR-associating 3 (HHLA3), transcript variant 3, mRNA [NM_001036646] | NM_001036646 | ENST00000531950 | 11147 | HERV-H LTR-associating 3 | chr1:70820653 70820712 | GO:0005515 | NM_001036646 | THC2694482 | Hs.142245 |
| A_23_P68601 | CST7 | Homo sapiens cystatin F (leukocystatin) (CST7), mRNA [NM_003650] | NM_003650 | ENST00000376835 | 8530 | cystatin F (leukocystatin) | chr20:2493807 4-24939601 | GO:0006955\|GO:0005737\|NM_003650 GO:0004869\|GO:0005576 | | THC2772477 | Hs.143212 |
| A_33_P3242136 | FGF1 | Homo sapiens fibroblast growth factor 1 (acidic) (FGF1), transcript variant 8, non-coding RNA [NR_026696] | NR_026696 | ENST00000489937 | 2246 | fibroblast growth factor 1 (acidic) | chr5:14207733 6-142077277 | GO:0050679\|GO:0005515\|NR_026696 GO:0030324\|GO:0005578\| GO:0005730\|GO:0005576\| GO:0005634\|GO:0007275\| GO:0001525\|GO:0001759\| GO:0009653\|GO:0005615\| GO:0030154\|GO:0007243\| GO:0045785\|GO:0007399\| GO:0007165\|GO:0005737\| GO:0008543\|GO:0051781\| GO:0008201\|GO:00080 83 | | THC2662054 | Hs.483635 |
| A_23_P89380 | SLC4A1 | Homo sapiens solute carrier family | NM_000342 | ENST00000399246 | 6521 | solute carrier family 4, anion | chr17:4232661 6-42326557 | GO:0006820\|GO:0005215\|NM_000342 GO:0008509\|GO:0030018 | | THC2474785 | Hs.443948 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | 4, anion exchanger, member 1 (erythrocyte membrane protein band 3, Diego blood group) (SLC4A1), mRNA [NM_000342] | | | | exchanger, member 1 (erythrocyte membrane protein band 3, Diego blood group) | | GO:0030506\|GO:0006873\|GO:0003779\|GO:0008022\|GO:0042803\|GO:0016323\|GO:0005452\|GO:0016020\|GO:0005887\|GO:0030863\|GO:0043495 | | | |
| A_24_P945293 | VPS24 | Homo sapiens vacuolar protein sorting 24 homolog (S. cerevisiae) (VPS24), transcript variant 1, mRNA [NM_016079] | NM_016079 | ENST00000263856 | 51652 | vacuolar protein sorting 24 homolog (S. cerevisiae) | chr2:86730587-86730551 | GO:0005515\|GO:0007049\|GO:0005737\|GO:0016020\|GO:0031902\|GO:0031225\|GO:0015031\|GO:0051301\|GO:0005829\|GO:0005768 | NM_016079 | THC2493800 | Hs.591582 |
| A_33_P3288649 | HOXA10 | Homo sapiens homeobox A10 (HOXA10), transcript variant 1, mRNA [NM_018951] | NM_018951 | ENST00000381834 | 3206 | homeobox A10 | chr7:27213023-27211789 | GO:0043565\|GO:0005515\|GO:0005667\|GO:0006355\|GO:0009954\|GO:0007275\|GO:0001501\|GO:0003700\|GO:0005634\|GO:0030326\|GO:0007283\|GO:0019952 | NM_018951 | NP1400322 | Hs.110637 |
| A_24_P64344 | BLNK | Homo sapiens B-cell linker (BLNK), transcript variant 1, mRNA [NM_013314] | NM_013314 | ENST00000393898 | 29760 | B-cell linker | chr10:9795674 5-97956686 | GO:0005622\|GO:0005515\|GO:0007242\|GO:0005737\|GO:0006954\|GO:0005886\|GO:0006959\|GO:0005070\|GO:0031083\|GO:0005068 | NM_013314 | NP1463979 | Hs.665244 |
| A_33_P3422822 | GJC2 | Homo sapiens gap junction protein, gamma 2, 47 kDa (GJC2), mRNA [NM_020435] | NM_20435 | ENST00000366714 | 57165 | gap junction protein, gamma 2, 47 kDa | chr1:22834746 4-228347523 | GO:0005243\|GO:0030054\|GO:0005886\|GO:0007267\|GO:0005922\|GO:0016021 | NM_020435 | | Hs.100072 |
| A_23_P90911 | RDH14 | Homo sapiens retinol dehydrogenase 14 (all-trans/9-cis/11-cis) (RDH14), mRNA [NM_020905] | NM_020905 | ENST00000381249 | 57665 | retinol de-hydrogenase 14 (all-trans/9-cis/11-cis) | chr2:18736163-18736104 | GO:0005783\|GO:0005488\|GO:0016491\|GO:0055114 | NM_020905 | THC2606653 | Hs.708385 |
| A_33_P3277805 | | | | | | | chr15:0207868 79-020786820 | | | | |
| A_23_P107051 | TCAP | Homo sapiens titin-cap (telethonin) (TCAP), mRNA [NM_003673] | NM_003673 | ENST00000309889 | 8557 | titin-cap (telethonin) | chr17:3782274 0-37822799 | GO:0030240\|GO:0030018\|GO:0001756\|GO:0030916\|GO:0045214\|GO:0006950\|GO:0060048\|GO:0030017\|GO:0007512\|GO:0031432\|GO:0048739\|GO:0005737\|GO:0047485\|GO:0006461\|GO:0050982\|GO:0003009\|GO:0008307\|GO:0030241\|GO:0055008\|GO:0070080 | NM_003673 | THC2512009 | Hs.77628 |
| A_33_P3417222 | CD72 | CD72 molecule [Source: HGNC | AK309268 | ENST00000378430 | 971 | CD72 molecule | chr9:35616995-35616936 | | | THC2629213 | Hs.116481 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3210848 | ELFN1 | Symbol; Acc: 1696] [ENST00000378430] Homo sapiens extracellular leucine-rich repeat and fibronectin type III domain containing 1 (ELFN1), mRNA [NM_001128636] | NM_001128636 | | 392617 | extracellular leucine-rich repeat and fibronectin type III domain containing 1 | chr7:1787400-1787459 | GO:0005515\|GO:0016020\|GO:0016021 | NM_001128636 | THC2649267 | Hs.42896 |
| A_33_P3395384 | RPH3A | Homo sapiens rabphilin 3A homolog (mouse) (RPH3A), transcript variant 1, mRNA [NM_001143854] | NM_001143854 | ENST00000389385 | 22895 | rabphilin 3A homolog (mouse) | chr12:113334902-113334961 | GO:0005515\|GO:0005215\|GO:0017137\|GO:0030054\|GO:0016020\|GO:0045202\|GO:0030672\|GO:0008270\|GO:0006886\|GO:0046872\|GO:0019898 | NM_001143854 | THC2472425 | Hs.21239 |
| A_33_P3315258 | CHD1L | Homo sapiens chromodomain helicase DNA binding protein 1-like (CHD1L), mRNA [NM_004284] | NM_004284 | ENST00000254086 | 9557 | chromodomain helicase DNA binding protein 1-like | chr1:146736128-146736187 | GO:0005515\|GO:0006281\|GO:0004003\|GO:0016787\|GO:0000166\|GO:0004386\|GO:0006338\|GO:0005634\|GO:0016887\|GO:0005524\|GO:0003677\|GO:0006974 | NM_004284 | NP1075670 | Hs.191164 |
| A_33_P3288135 | CPLX2 | complexin 2 [Source: HGNC Symbol; Acc: 2310] [ENST00000506642] | | ENST00000506642 | 10814 | complexin 2 | chr5:175264792-175264851 | | | | |
| A_23_P39251 | PLIN5 | Homo sapiens perilipin 5 (PLIN5), mRNA [NM_001013706] | NM_001013706 | ENST00000381848 | 440503 | perilipin 5 | chr19:4523409-4523350 | GO:0012511 | NM_001013706 | THC2604749 | Hs.131034 |
| A_33_P3412295 | LOC645645 | Homo sapiens cDNA FLJ44102 fis, clone TESTI4044035. [AK126090] | AK126090 | | 645645 | hypothetical protein LOC645645 | chr1:235752062-235752121 | | | THC2626252 | Hs.159711 |
| A_33_P3294603 | SLC22A31 | Homo sapiens solute carrier family 22, member 31 (SLC22A31), mRNA [NM_001242757] | NM_001242757 | | 146429 | solute carrier family 22, member 31 | chr16:89262615-89262556 | GO:0016020\|GO:0016021\|GO:0055085\|GO:0006811 | NM_001242757 | THC2667705 | Hs.447544 |
| A_32_P157927 | | immunoglobulin kappa variable 4-1 [Source: HGNC Symbol; Acc: 5834] [ENST00000390243] | S62210 | ENST00000390243 | | | chr2:89185420-89185479 | | | NP836564 | Hs.592929 |
| A_23_P12858 | C10orf27 | Homo sapiens chromosome 10 open reading frame 27 (C10orf27), mRNA [NM_152710] | NM_152710 | ENST00000536955 | 219793 | chromosome 10 open reading frame 27 | chr10:72534060-72534001 | GO:0005515\|GO:0005737\|GO:0007275\|GO:0005634\|GO:0007283\|GO:0030154\|GO:0005829 | NM_152710 | THC2619930 | Hs.386698 |
| A_33_P3244640 | GRK5 | Homo sapiens FP2025 mRNA, complete cds. [AF370369] | AF370369 | | 2869 | G protein-coupled receptor kinase 5 | chr10:121217016-121217075 | | | NP1212828 | Hs.524625 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3293524 | NEURL | Homo sapiens neuralized homolog (Drosophila) (NEURL), mRNA [NM_004210] | NM_004210 | ENST00000369780 | 9148 | neuralized homolog (Drosophila) | chr10:105352243-105352302 | GO:0005515\|GO:0048471\|GO:0009605\|GO:0005737\|GO:0007595\|GO:0005886\|GO:0007288\|GO:0008270\|GO:0030317\|GO:0046872\|GO:0007399 | NM_004210 | THC2463576 | Hs.730611 |
| A_33_P3368830 | LY9 | Homo sapiens lymphocyte antigen 9 (LY9), transcript variant 2, mRNA [NM_001033667] | NM_001033667 | ENST00000368039 | 4063 | lymphocyte antigen 9 | chr1:160772422-160772481 | GO:0005515\|GO:0003674\|GO:0016064\|GO:0016020\|GO:0016021\|GO:0007155 | NM_001033667 | THC2602337 | Hs.403857 |
| A_24_P226069 | FGFBP2 | Homo sapiens fibroblast growth factor binding protein 2 (FGFBP2), mRNA [NM_031950] | NM_031950 | ENST00000259989 | 83888 | fibroblast growth factor binding protein 2 | chr4:15964292-15964233 | GO:0019838\|GO:0005576\|GO:0005615 | NM_031950 | THC2473947 | Hs.98785 |
| A_23_P329870 | RHBDF2 | Homo sapiens rhomboid 5 homolog 2 (Drosophila) (RHBDF2), transcript variant 1, mRNA [NM_024599] | NM_024599 | ENST00000313080 | 79651 | rhomboid 5 homolog 2 (Drosophila) | chr17:74446703-74466978 | GO:0016020\|GO:0005783\|GO:0016021 | NM_024599 | NP434208 | Hs.464157 |
| A_33_P3629678 | COL5A1 | Homo sapiens collagen, type V, alpha 1 (COL5A1), mRNA [NM_000093] | NM_000093 | ENST00000371817 | 1289 | collagen, type V, alpha 1 | chr9:137736327-137736386 | GO:0005515\|GO:0005881\|GO:0035313\|GO:0001568\|GO:0048407\|GO:0043394\|GO:0048592\|GO:0005576\|GO:0005588\|GO:0005604\|GO:0003007\|GO:0005178\|GO:0051128\|GO:0030199\|GO:0045112\|GO:0043588\|GO:0043206\|GO:0032964\|GO:0007155\|GO:0008201\|GO:0005201 | NM_000093 | THC2469461 | Hs.210283 |
| A_33_P3218741 | | | | | | | chr15:089346503-089346562 | | | | |
| A_32_P170444 | SUB1 | Homo sapiens SUB1 homolog (S. cerevisiae) (SUB1), mRNA [NM_006713] | NM_006713 | ENST00000265073 | 10923 | SUB1 homolog (S. cerevisiae) | chr5:32603930-32603989 | GO:0005515\|GO:0005667\|GO:0006357\|GO:0003697\|GO:0003713\|GO:0005730\|GO:0005634\|GO:0003677 | NM_006713 | THC2526142 | Hs.229641 |
| A_33_P3382709 | LEMD3 | Homo sapiens LEM domain containing 3 (LEMD3), transcript variant 1, mRNA [NM_014319] | NM_014319 | ENST00000308330 | 23592 | LEM domain containing 3 | chr12:65641987-65642046 | GO:0030514\|GO:0005515\|GO:0016020\|GO:0000166\|GO:0005637\|GO:0005624\|GO:0032926\|GO:0005634\|GO:0016021\|GO:0005635\|GO:0003677\|GO:0005639 | NM_014319 | THC2462620 | Hs.728281 |
| A_23_P149368 | FCRL1 | Homo sapiens Fc receptor-like 1 (FCRL1), transcript variant 1, mRNA[NM_052938] | NM_052938 | ENST00000495126 | 115350 | Fc receptor-like 1 | chr1:157765602-157765543 | GO:0005886\|GO:0004872\|GO:0016021 | NM_052938 | THC2478058 | Hs.656112 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P321525 | RERG | Homo sapiens RAS-like, estrogen-regulated, growth inhibitor (RERG), transcript variant 1, mRNA [NM_032918] | NM_032918 | ENST00000536465 | 85004 | RAS-like, estrogen-regulated, growth inhibitor | chr12:1526097 0-1526097 | GO:0030308\|GO:0008285\|NM_032918 GO:0007264\|GO:0030331\| GO:0003924\|GO:0005634\| GO:0005525\|GO:0005829\| GO:0005622\|GO:0007165\| GO:0005737\|GO:0000166\| GO:0016020\|GO:0009725\| GO:0019003 | | THC2462986 | Hs.199487 |
| A_33_P3420446 | LRRD1 | Homo sapiens leucine-rich repeats and death domain containing 1 (LRRD1), mRNA [NM_001161528] | NM_001161528 | ENST00000430130 | 401387 | leucine-rich repeats and death domain containing 1 | chr7:91774317-91774258 | GO:0005515\|GO:0007165 | NM_001161528 | | Hs.71729 |
| A_33_P3372563 | ABCC10 | Homo sapiens ATP-binding cassette, subfamily C (CFTR/MRP), member 10 (ABCC10), transcript variant MRP7A, mRNA [NM_033450] | NM_033450 | ENST00000372512 | 89845 | ATP-binding cassette, subfamily C (CFTR/MRP), member 10 | chr6:43412934-43412993 | GO:0005886\|GO:0000166\|NM_033450 GO:0042626\|GO:0016021\| GO:0055085\|GO:0016887\| GO:0005524 | | THC2678120 | Hs.55879 |
| A_33_P3396746 | KIF26B | kinesin family member 26B [Source: HGNC Symbol; Acc: 25484] [ENST00000479506] | BC042481 | ENST00000479506 | 55083 | kinesin family member 26B | chr1:24553495 8-245535017 | | | THC2488603 | Hs.368096 |
| A_33_P3248900 | FLJ45445 | Homo sapiens hypothetical LOC399844 (FLJ45445), non-coding RNA [NR_028324] | NR_028324 | ENST00000425496 | 399844 | hypothetical LOC399844 | chr19:197281-197222 | | NR_028324 | THC2466370 | Hs.638866 |
| A_33_P3261353 | BCORP1 | Homo sapiens BCL6 corepressor pseudogene 1 (BCORP1), transcript variant 1, non-coding RNA [NR_033732] | NR_033732 | ENST00000400605 | 286554 | BCL6 corepressor pseudogene 1 | chrY:21621987-21621928 | | NR_033732 | NP1134333 | Hs.211713 |
| A_33_P3365501 | | | | | | | chr2:00019420 5-000194146 | | | | |
| A_23_P58390 | C4orf32 | Homo sapiens chromosome 4 open reading frame 32 (C4orf32), mRNA [NM_152400] | NM_152400 | ENST00000309733 | 132720 | chromosome 4 open reading frame 32 | chr4:11310996 9-113110028 | GO:0016020\|GO:0016021 | NM_152400 | THC2471790 | Hs.23439 |
| A_24_P374962 | STAG3L1 | Homo sapiens stromal antigen 3-like 1 (STAG3L1), transcript variant 1, mRNA [NM_018991] | NM_018991 | ENST00000457631 | 54441 | stromal antigen 3 like 1 | chr7:74996711-74996770 | | NM_018991 | THC2475336 | Hs.632310 |
| A_33_P3237270 | | | | ENST00000446887 | | | chr6:15948586 9-159485810 | | | | |
| A_33_P3264404 | LOC100132593 | Homo sapiens cDNA FLJ40951 fis, clone | AK098270 | | 100132593 | hypothetical LOC100132593 | chr7:10181866 5-101187244 | | | THC2486891 | Hs.661011 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3345614 | | UTERU2010124. [AK098270] | | | | | chr19:0128117 57-012811816 chr7:13561463 7-135614696 | | | | |
| A_33_P3316671 | | | | | | | | | | | |
| A_24_P234792 | CSNK1G3 | Homo sapiens casein kinase 1, gamma 3 (CSNK1G3), transcript variant 4, mRNA [NM_001044723] | NM_001044723 | ENST00000395412 | 1456 | casein kinase 1, gamma 3 | chr5:12295207 2-122952131 | GO:0007165\|GO:0005737\|NM_001044723\| GO:0000166\|GO:0004674\| GO:0006468\|GO:0016055\| GO:0005524\|GO:0016740\| GO:0006464 | | THC2610386 | Hs.129206 |
| A_33_P3258320 | | | | | | | | | | THC2659926 | Hs.470892 |
| A_23_P131139 | DIRC1 | Homo sapiens disrupted in renal carcinoma 1 (DIRC1), mRNA [NM_052952] | NM_052952 | ENST00000308100 | 116093 | disrupted in renal carcinoma 1 | chr19:0097854 02-009785343 chr2:18959933 1-189599277 | | NM_052952 | THC2479514 | Hs.631655 |
| A_33_P3507542 | LEPREL2 | Homo sapiens leprecan-like 2 (LEPREL2), mRNA [NM_014262] | NM_014262 | ENST00000536140 | 10536 | leprecan-like 2 | chr12:6948951-6949010 | GO:0031418\|GO:0005506\|NM_014262\| GO:0019797\|GO:0005783\| GO:0016705\|GO:0016702\| GO:0046872\|GO:0055114 | | THC2484662 | Hs.288164 |
| A_23_P92035 | SETD5 | Homo sapiens SET domain containing 5 (SETD5), mRNA [NM_001080517] | NM_001080517 | ENST00000466826 | 55209 | SET domain containing 5 | chr3:9517207-9517266 | | NM_001080517 | THC2521629 | Hs.510327 |
| A_23_P205370 | ASB2 | Homo sapiens ankyrin repeat and SOCS box containing 2 (ASB2), transcript variant 2, mRNA [NM_016150] | NM_016150 | ENST00000315988 | 51676 | ankyrin repeat and SOCS box containing 2 | chr14:9440066 0-94400601 | GO:0007242\|GO:0019941 | NM_016150 | THC2471932 | Hs.130988 |
| A_23_P0296 | DYRK1B | Homo sapiens dual-specificity tyrosine-(Y)-phosphorylation regulated kinase 1B (DYRK1B), transcript variant␣a, mRNA [NM_004714] | NM_004714 | ENST00000323039 | 9149 | dual-specificity tyrosine-(Y)-phosphorylation regulated kinase 1B | chr19:4031640 4-40316345 | GO:0005515\|GO:0000166\|NM_004714\| GO:0004674\|GO:0003713\| GO:0007520\|GO:0006468\| GO:0005634\|GO:0004713\| GO:0045893\|GO:0005524\| GO:0016740 | | THC2463639 | Hs.469280 |
| A_23_P115331 | AHDC1 | Homo sapiens AT hook, DNA binding motif, containing 1 (AHDC1), mRNA [NM_001029882] | NM_001029882 | ENST00000374011 | 27245 | AT hook, DNA binding motif, containing 1 | chr1:27861300-27861242 | GO:0003677 | NM_001029882 | THC2470530 | Hs.721460 |
| A_32_P122240 | ASCL5 | PREDICTED: Homo sapiens achaete-scute complex homolog 5 (Drosophila) (ASCL5), mRNA [XM_940966] | XM_940966 | | 647219 | achaete-scute complex homolog 5 (Drosophila) | chr1:20108393 0-201083871 | | XM_940966 | THC2659820 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P87013 | TAGLN | Homo sapiens transgelin (TAGLN), transcript variant 1, mRNA [NM_001001522] | NM_001001522 | ENST00000392951 | 6876 | transgelin | chr11:117074574-117074963 | GO:0005515\|GO:0005737\|GO:0007517\|GO:0003779 | NM_001001522 | THC2537883 | Hs.410977 |
| A_23_P318943 | NCRNA00311 | Homo sapiens non-protein coding RNA 311 (NCRNA00311), non-coding RNA [NR_038859] | NR_038859 | ENST00000366314 | 197196 | non-protein coding RNA 311 | chr16:85319477-85319536 | | NR_038859 | | Hs.679002 |
| A_23_P16523 | GDF15 | Homo sapiens growth differentiation factor 15 (GDF15), mRNA [NM_004864] | NM_004864 | ENST00000252809 | 9518 | growth differentiation factor 15 | chr19:18499890-18499949 | GO:0007165\|GO:0007267\|GO:0007179\|GO:0005576\|GO:0008083\|GO:0005615\|GO:0005125 | NM_004864 | THC2532749 | Hs.616962 |
| A_23_P208293 | PVRL2 | Homo sapiens polio-virus receptor-related 2 (herpesvirus entry mediator B) (PVRL2), transcript variant delta, mRNA [NM_001042724] | NM_001042724 | ENST00000252483 | 5819 | poliovirus receptor-related 2 (herpesvirus entry mediator B) | chr19:45392321-45392380 | GO:0005886\|GO:0009986\|GO:0019064\|GO:0007286\|GO:0051856\|GO:0015026\|GO:0033005\|GO:0042803\|GO:0060370\|GO:0005915\|GO:0005911\|GO:0042271\|GO:0002860\|GO:0016021\|GO:0046814\|GO:0007155\|GO:0050839\|GO:0002891\|GO:0007156 | NM_001042724 | THC2582406 | Hs.655455 |
| A_33_P3310588 | | | | | | | chr22:02437074 3-024370802 chr22:2271255 0-22712608 | | NP1471093 | | Hs.655198 |
| A_33_P3424754 | | immunoglobulin lambda variable 1-47 [Source: HGNC Symbol; Acc: 5880] [ENST00000390294] | AY685380 | ENST00000390294 | | | | | | | |
| A_24_P52293 | OR2A25 | Homo sapiens olfactory receptor, family 2, subfamily A, member 25 (OR2A25), mRNA [NM_001004488] | NM_001004488 | ENST00000408898 | 392138 | olfactory receptor, family 2, subfamily A, member 25 | chr7:143771732-143771791 | GO:0007608\|GO:0007165\|GO:0004984\|GO:0007186\|GO:0005886\|GO:0004872\|GO:0016021\|GO:0050896 | NM_001004488 | THC2741807 | Hs.553787 |
| A_33_P3364308 | OTOA | Homo sapiens otoancorin, mRNA (cDNA clone IMAGE: 5298475), with apparent retained intron. [BC040551] | BC040551 | | 146183 | otoancorin | chr16:21758641-21758700 | GO:0016324\|GO:0005886\|GO:0007605\|GO:0005578\|GO:0005576\|GO:0031225 | | THC2608175 | |
| A_32_P15706 | LOC100510012 | PREDICTED: Homo sapiens hypothetical protein LOC100510012 (LOC100510012), mRNA [XM_003119034] | XM_003119034 | | 100510012 | hypothetical protein LOC100510012 | chr7:45849739-45849798 | | XM_003119034 | | |
| A_33_P3344504 | APBA2 | Homo sapiens amyloid beta (A4) precursor protein-binding, family A, member 2 | AK124794 | ENST00000382938 | 321 | amyloid beta (A4) precursor protein-binding, | chr15:29394617-29394676 | | | THC2479001 | Hs.618112 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P26008 | MGLL | Homo sapiens monoglyceride lipase (MGLL), transcript variant 1, mRNA [NM_007283] [Source: HGNC Symbol; Acc: 579] [ENST00000382938] | NM_007283 | ENST00000536024 | 11343 | monoglyceride lipase, family A, member 2 | chr3:127413832-127411122 | GO:0006629\|GO:0006954\|NM_007283 GO:0016787\|GO:0004622\| GO:0047372 | | THC2534201 | Hs.277035 |
| A_33_P3402211 | LOC100506220 | Homo sapiens hypothetical LOC100506220 (LOC100506220), partial miscRNA [XR_110895] | XR_110895 | ENST00000534168 | 100506220 | hypothetical LOC100506220 | chr11:78154949-78155008 | | XR_110895 | THC2652947 | Hs.666398 |
| A_33_P3364661 | RHOA | ras homolog gene family, member A [Source: HGNC Symbol; Acc: 667] [ENST00000265538] | DC392227 | ENST00000265538 | 387 | ras homolog gene family, member A | chr3:49449897-49449838 | | | | Hs.714276 |
| A_33_P3815064 | LOC283575 | Homo sapiens cDNA FLJ35003 fis, clone OCBBF2011960. [AK092322] | AK092322 | | 283575 | hypothetical protein LOC283575 | chr14:77535783-77535842 | | | | Hs.651736 |
| A_33_P3213288 | AIF1 | Homo sapiens allograft inflammatory factor 1 (AIF1), transcript variant 2, mRNA [NM_004847] | NM_004847 | | 199 | allograft inflammatory factor 1 | chr6:31584267-31584326 | GO:0051015\|GO:0008285\|NM_004847 GO:0006954\|GO:0005884 GO:0005509\|GO:0006950 GO:0032587\|GO:0007050 GO:0005634\|GO:0051017 | | THC2484669 | Hs.76364 |
| A_23_P218892 | EIF4G1 | Homo sapiens eukaryotic translation initiation factor 4 gamma, 1 (EIF4G1), transcript variant 1, mRNA [NM_182917] | NM_182917 | ENST00000422614 | 1981 | eukaryotic translation initiation factor 4 gamma, 1 | chr3:184049566-184049761 | GO:0005515\|GO:0016281\|NM_182917 GO:0005737\|GO:0016070 GO:0044419\|GO:0003723 GO:0006446\|GO:0003743 GO:0005829 | | THC2545784 | Hs.433750 |
| A_23_P316612 | GLIS1 | Homo sapiens GLIS family zinc finger 1 (GLIS1), mRNA [NM_147193] | NM_147193 | ENST00000312233 | 148979 | GLIS family zinc finger 1 | chr1:53971989-53971930 | GO:0005622\|GO:0005737\|NM_147193 GO:0045941\|GO:0045944 GO:0003704\|GO:0005730 GO:0008270\|GO:0005634 GO:0000122\|GO:0003677 GO:0046872 | | THC2478516 | Hs.306691 |
| A_24_P293114 | SPTBN4 | Homo sapiens spectrin, beta, non-erythrocytic 4 (SPTBN4), transcript variant sigma 1, mRNA [NM_020971] | NM_020971 | ENST00000352632 | 57731 | spectrin, beta, non-erythrocytic 4 | chr19:4108202-41082085 | GO:0005515\|GO:0030424\|NM_020971 GO:0008091\|GO:0007605 GO:0030506\|GO:0003779 GO:0007409\|GO:0019226 GO:0016363\|GO:0051693 GO:0005829\|GO:0009566 GO:0005737\|GO:0016605 GO:0043203\|GO:0005200 | | THC2487198 | Hs.32706 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3842770 | LOC644450 | *Homo sapiens* hypothetical protein LOC644450, mRNA (cDNA clone IMAGE: 4606942), partial cds. [BC022881] | BC022881 | | 644450 | hypothetical LOC644450 | chrUn_gl000221:61093-61034 | GO:0007628\|GO:0030534\|GO:0040018\|GO:0016192\|GO:0005856\|GO:0005938\|GO:0007016 | | | Hs.652926 |
| A_33_P3259017 | CSNK1G2 | *Homo sapiens* casein kinase 1, gamma 2 (CSNK1G2), mRNA [NM_001319] | NM_001319 | ENST00000313975 | 1455 | casein kinase 1, gamma 2 | chr19:1980390-1980449 | GO:0051219\|GO:0042277\|GO:0000287\|GO:0005625\|GO:0005524\|GO:0005829\|GO:0007165\|GO:0005737\|GO:0001948\|GO:0046777\|GO:0000166\|GO:0004674\|GO:0016055\|GO:0016740 | NM_001319 | THC2641108 | Hs.651905 |
| A_33_P3397323 | ZNF441 | *Homo sapiens* zinc finger protein 441 (ZNF441), mRNA [NM_152355] | NM_152355 | ENST00000357901 | 126068 | zinc finger protein 441 | chr19:11894786-11894845 | GO:0005622\|GO:0008270\|GO:0005634\|GO:0003677\|GO:0046872\|GO:0045449 | NM_152355 | THC2601626 | Hs.675132 |
| A_33_P3222218 | NEURL1B | *Homo sapiens* neuralized homolog 1B (*Drosophila*) (NEURL1B), mRNA [NM_001142651] | NM_001142651 | ENST00000369800 | 54492 | neuralized homolog 1B (*Drosophila*) | chr5:172113239-172113298 | GO:0005515\|GO:0019941\|GO:0016874\|GO:0008270\|GO:0046872 | NM_001142651 | | Hs.91521 |
| A_33_P3325935 | PQBP1 | *Homo sapiens* polyglutamine binding protein 1 (PQBP1), transcript variant 8, mRNA [NM_001167989] | NM_001167989 | ENST00000376566 | 10084 | polyglutamine binding protein 1 | chrX:48760354-48760413 | GO:0005515\|GO:0006355\|GO:0005737\|GO:0003713\|GO:0005730\|GO:0005634\|GO:0003677 | NM_001167989 | THC2468728 | Hs.534384 |
| A_33_P3325349 | TSPAN5 | *Homo sapiens* tetraspanin 5 (TSPAN5), mRNA [NM_005723] | NM_005723 | ENST00000305798 | 10098 | tetraspanin 5 | chr4:99393471-99393412 | GO:0016020\|GO:0016021 | NM_005723 | THC2462540 | Hs.118118 |
| A_23_P897 | C1orf116 | *Homo sapiens* chromosome 1 open reading frame 116 (C1orf116), transcript variant 1, mRNA [NM_023938] | NM_023938 | ENST00000359470 | 79098 | chromosome 1 open reading frame 116 | chr1:207192288-207192229 | GO:0005737\|GO:0004872 | NM_023938 | THC2603168 | Hs.32417 |
| A_24_P411121 | TNFRSF18 | *Homo sapiens* tumor necrosis factor receptor superfamily, member 18 (TNFRSF18), transcript variant 2, mRNA [NM_148901] | NM_148901 | ENST00000379265 | 8784 | tumor necrosis factor receptor superfamily, member 18 | chr1:1140761-1139819 | GO:0007165\|GO:0005031\|GO:0005886\|GO:0006915\|GO:0006916\|GO:0005576\|GO:0004872\|GO:0016021 | NM_148901 | THC2640940 | Hs.212680 |
| A_33_P331345 | | Uncharacterized protein [Source: UniProtKB/ | XR_110308 | ENST00000383146 | | | chr22:16157365-16157306 | | XR_110308 | THC2474682 | Hs.729828 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3353941 | PIK3CD | TrEMBL; Acc: B5MBW5 [ENST00000383146] Homo sapiens phosphoinositide-3-kinase, catalytic, delta polypeptide (PIK3CD), mRNA [NM_005026] | NM_005026 | ENST00000361110 | 5293 | phosphoinositide-3-kinase, catalytic, delta polypeptide | chr1:9787045-9787104 | GO:0005515\|GO:0048015\|NM_005026\|GO:0005524\|GO:0007165\|GO:0046854\|GO:0000166\|GO:0046934\|GO:0016303\|GO:0016773\|GO:0006468\|GO:0005942\|GO:0004428\|GO:0016740 | NM_005026 | THC2485816 | Hs.518451 |
| A_24_P113131 | BZRAP1 | Homo sapiens benzodiazapine receptor (peripheral) associated protein 1 (BZRAP1), transcript variant 1, mRNA [NM_004758] | NM_004758 | ENST00000343736 | 9256 | benzodiazapine receptor (peripheral) associated protein 1 | chr17:56378659-56378600 | GO:0005739\|GO:0008150\|NM_004758\|GO:0005737\|GO:0030156 | | THC2615957 | Hs.112499 |
| A_23_P65466 | RAB2B | Homo sapiens RAB2B, member RAS oncogene family (RAB2B), transcript variant 1, mRNA [NM_032846] | NM_032846 | ENST00000304034 | 84932 | RAB2B, member RAS oncogene family | chr14:2192798-21927928 | GO:0005794\|GO:0005886\|NM_032846\|GO:0000166\|GO:0000139\|GO:0007264\|GO:0005783\|GO:0005789\|GO:0016192\|GO:0015031\|GO:0005525 | | THC2462467 | Hs.22399 |
| A_24_P357468 | | T cell receptor alpha variable 8-2 [Source: HGNC Symbol; Acc: 12147] | D13077 | ENST00000390434 | | | chr14:22315300-22315359 | | | NP089255 | Hs.697099 |
| A_24_P321511 | GOLT1B | Homo sapiens golgi transport 1B (GOLT1B), mRNA [NM_016072] | NM_016072 | ENbT00000229314 | 51026 | golgi transport 1B | chr12:21670468-21670527 | GO:0005794\|GO:0016020\|NM_016072\|GO:0005783\|GO:0016021\|GO:0004871\|GO:0043123\|GO:0016192\|GO:0015031 | | THC2466175 | Hs.62275 |
| A_33_P3415663 | MBLAC2 | Homo sapiens metallo-beta-lactamase domain containing 2 (MBLAC2), mRNA [NM_203406] | NM_203406 | ENST00000546270 | 153364 | metallo-beta-lactamase domain containing 2 | chr5:89754201-89754142 | GO:0016787\|GO:0008270\|NM_203406\|GO:0046872 | | THC2736661 | Hs.64004 |
| A_23_P334173 | LY75 | Homo sapiens lymphocyte antigen 75 (LY75), mRNA [NM_002349] | NM_002349 | ENST00000263636 | 4065 | lymphocyte antigen 75 | chr2:160660247-160660188 | GO:0006955\|GO:0006954\|NM_002349\|GO:0016020\|GO:0005887\|GO:0005488\|GO:0005529\|GO:0004872\|GO:0006897 | | THC2470974 | Hs.153563 |
| A_33_P3357163 | PPIEL | Homo sapiens peptidyl-prolyl isomerase E-like pseudogene (PPIEL), non-coding RNA [NR_003929] | NR_003929 | | 728448 | peptidyl-prolyl isomerase E-like pseudogene | chr1:40013341-40013282 | | NR_003929 | THC2553158 | Hs.472508 |
| A_33_P3302325 | | CR737729 Soares_NFL_T_GBC_S1 Homo sapiens cDNA clone IMAGp971D0264; IMAGE: 1578179 5', mRNA sequence [CR737729] | CR737729 | | | | chr1:20740205-20740264 | | | | Hs.679084 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P313822 | PAK4 | Homo sapiens p21 protein (Cdc42/Rac)-activated kinase 4 (PAK4), transcript variant 1, mRNA [NM_005884] | NM_005884 | ENST00000358801 | 10298 | p21 protein (Cdc42/Rac)-activated kinase 4 | chr19:39668337-39668396 | GO:0005515\|GO:0007165\|NM_005884 GO:0005794\|GO:0000166\| GO:0004674\|GO:0006928\| GO:0006468\|GO:0005524\| GO:0016740 | THC2739290 | Hs.20447 |
| A_33_P3259740 | | PREDICTED: Homo sapiens FLJ44881 (FLJ44881), misc RNA [XR_110159] | XR_110159 | ENST00000415242 | | | chr18:74440240-74402460 | | XR_110159 | THC2490934 | Hs.514963 |
| A_33_P3341259 | LEAP2 | liver expressed anti-microbial peptide 2 [Source: HGNC Symbol; Acc: 29571] [ENST00000483190] | AJ409065 | ENST00000483190 | 116842 | liver expressed antimicrobial peptide 2 | chr5:132209315-132209374 | | | THC2510296 | Hs.337588 |
| A_33_P3247057 | C17orf109 | Homo sapiens chromosome 17 open reading frame 109 (C17orf109), transcript variant 1, mRNA [NM_001162995] | NM_001162995 | ENST00000375215 | 643008 | chromosome 17 open reading frame 109 | chr17:7363742-73637484 | | NM_001162995 | THC2532809 | Hs.528605 |
| A_23_P252236 | KLKB1 | Homo sapiens kallikrein B, plasma (Fletcher factor) 1 (KLKB1), mRNA [NM_000892] | NM_000892 | ENST00000511406 | 3818 | kallikrein B, plasma (Fletcher factor) 1 | chr4:18717844-187178504 | GO:0005737\|GO:0006954\|NM_000892 GO:0004252\|GO:0007596\| GO:0002542\|GO:0051919\| GO:0006508\|GO:0031639\| GO:0008233\|GO:0005576\| GO:0005615 | | THC2474351 | Hs.237642 |
| A_24_P84781 | | Homo sapiens cDNA FLJ11871 fis, clone HEMBA1007052. [AK021933] | AK021933 | | | | chr7_gl000195_random:31018-30959 | | | THC2473856 | Hs.636816 |
| A_23_P258944 | DNAJB9 | Homo sapiens DnaJ (Hsp40) homolog, subfamily B, member 9 (DNAJB9), mRNA [NM_012328] | NM_012328 | ENST00000249356 | 4189 | DnaJ (Hsp40) homolog, subfamily B, member 9 | chr7:108821451-108214574 | GO:0005737\|GO:0006457\|NM_012328 GO:0005783\|GO:0031072\| GO:0005730\|GO:0005634\| GO:0051082 | | THC2665858 | Hs.6790 |
| A_24_P142495 | KRTAP1-3 | Homo sapiens keratin associated protein 1-3 (KRTAP1-3), mRNA [NM_030966] | NM_030966 | ENST00000344363 | 81850 | keratin associated protein 1-3 | chr17:39190648-39190589 | GO:0008150\|GO:0005576\|NM_030966 GO:0045095\|GO:0030280 | | NP367289 | Hs.534495 |
| A_33_P3411388 | UNCX | Homo sapiens UNC homeobox (UNCX), mRNA [NM_001080461] | NM_001080461 | ENST00000316333 | 340260 | UNC homeobox | chr7:12764341276493 | GO:0043565\|GO:0007389\|NM_001080461 GO:0006355\|GO:0003700\| GO:0001502\|GO:0045595\| GO:0005634\|GO:0021516\| GO:0007399 | | | Hs.232272 |
| A_23_P25155 | GPR84 | Homo sapiens G protein-coupled receptor 84 (GPR84), mRNA [NM_020370] | NM_020370 | ENST00000551809 | 53831 | G protein-coupled receptor 84 | chr12:54756423-54756364 | GO:0008150\|GO:0007165\|NM_020370 GO:0007186\|GO:0005886\| GO:0004930\|GO:0004872\| GO:0016021 | | THC2475172 | Hs.306199 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P259955 | GDF5 | Homo sapiens growth differentiation factor 5 (GDF5), mRNA [NM_000557] | NM_000557 | ENST00000374372 | 8200 | growth differentiation factor 5 | chr20:34022206-34022147 | GO:0005515\|GO:0035136\|NM_000557\|GO:0035129\|GO:0007267\|GO:0042981\|GO:0005576\|GO:0030326\|GO:0005125\|GO:0005615\|GO:0040014\|GO:0007179\|GO:0032332\|GO:0008083\|GO:0040007 | THC2483977 | Hs.1573 |
| A_23_P14708 | ZNF280D | Homo sapiens zinc finger protein 280D (ZNF280D), transcript variant 1, mRNA [NM_017661] | NM_017661 | ENST00000267807 | 54816 | zinc finger protein 280D | chr15:56923017-56923018 | GO:0005622\|GO:0008270\|NM_017661\|GO:0005634\|GO:0003677\|GO:0046872\|GO:0045449 | THC2464733 | Hs.511477 |
| A_23_P209652 | INO80D | Homo sapiens INO80 complex subunit D (INO80D), mRNA [NM_017759] | NM_017759 | ENST00000233270 | 54891 | INO80 complex subunit D | chr2:206869668-206869609 | | NM_017759 | THC2699199 | Hs.445036 |
| A_24_P399500 | PCP2 | Homo sapiens Purkinje cell protein 2 (PCP2), mRNA [NM_174895] | NM_174895 | ENST00000311069 | 126006 | Purkinje cell protein 2 | chr19:7696581-7696522 | GO:0007165\|GO:0005096 | NM_174895 | THC2476340 | Hs.591400 |
| A_33_P3270639 | | | | | | | chr15:0201935 28-020193469 | | | | |
| A_33_P3321369 | LOC145757 | PREDICTED: Homo sapiens hypothetical LOC145757 (LOC145757), miscRNA [XR_109231] | XR_109231 | | 145757 | hypothetical LOC145757 | chr15:1014141 36-101414195 | | XR_109231 | THC2646184 | Hs.730396 |
| A_23_P120435 | WFDC3 | Homo sapiens WAP four-disulfide core domain 3 (WFDC3), mRNA [NM_080614] | NM_080614 | ENST00000467679 | 140686 | WAP four-disulfide core domain 3 | chr20:4440412 0-44404061 | GO:0004867\|GO:0005576\|NM_080614\|GO:0030414 | NP819189 | Hs.419126 |
| A_23_P129629 | MT3 | Homo sapiens metallothionein 3 (MT3), mRNA [NM_005954] | NM_005954 | ENST00000200691 | 4504 | metallothionein 3 | chr16:5662493 3-56624991 | GO:0001666\|GO:0016209\|NM_005954\|GO:0050768\|GO:0008283\|GO:0005507\|GO:0019430\|GO:0008270\|GO:0006875\|GO:0046872\|GO:0008021 | THC2602129 | Hs.73133 |
| A_23_P319557 | | chromosome 21 open reading frame 89 [Source: HGNC Symbol; Acc: 16425] [ENST00000328344] | AF426268 | ENST00000328344 | | | chr21:4666346 8-46663527 | | | THC2484291 | Hs.375832 |
| A_23_P154330 | TXNDC9 | Homo sapiens thioredoxin domain containing 9 (TXNDC9), mRNA [NM_005783] | NM_005783 | ENST00000264255 | 10190 | thioredoxin domain containing 9 | chr2:99935957-99935898 | GO:0005515\|GO:0008150\|NM_005783\|GO:0005575 | THC2468294 | Hs.536122 |
| A_33_P3741678 | LOC284926 | full-length cDNA clone CS0DB004YM09 of Neuroblastoma Cot 10- | CR624447 | | 284926 | hypothetical protein LOC284926 | chr22:4664907 5-46649134 | | | THC2492227 | Hs.594938 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3283669 | ATP1A3 | normalized of *Homo sapiens* (human). [CR624447] *Homo sapiens* ATPase, Na+/K+ transporting, alpha 3 polypeptide (ATP1A3), mRNA [NM_152296] | NM_152296 | ENST00000545399 | 478 | ATPase, Na+/K+ transporting, alpha 3 polypeptide | chr19:4247080 5-42470746 | GO:0000287\|GO:0005794\|NM_152296 GO:0005886\|GO:0005783\| GO:0015077\|GO:0030955\| GO:0031402\|GO:0005890\| GO:0005524\|GO:0006754\| GO:0016787\|GO:0000166\| GO:0008152\|GO:0016820\| GO:0016021\|GO:0006814\| GO:0006813\|GO:0005391 | | THC2493019 | Hs.515427 |
| A_23_P17430 | RBM38 | *Homo sapiens* RNA binding motif protein 38 (RBM38), transcript variant 1, mRNA [NM_017495] | NM_017495 | ENST00000356208 | 55544 | RNA binding motif protein 38 | chr20:5598362 2-55983681 | GO:0006397\|GO:0007049\|NM_017495 GO:0005737\|GO:0000166\| GO:0003723\|GO:0043484\| GO:0005634\|GO:0005829 | | THC2469261 | Hs.236361 |
| A_33_P3303729 | | | | | | | chr7:05655983 7-056559896 | | | THC2715632 | |
| A_23_P76364 | CD9 | *Homo sapiens* CD9 molecule (CD9), mRNA [NM_001769] | NM_001769 | ENST0000540891 | 928 | CD9 molecule | chr12:6342625-6344426 | GO:0005515\|GO:0030913\|NM_001769 GO:0005886\|GO:0007342\| GO:0005887\|GO:0031092\| GO:0030168\|GO:0006928\| GO:0007155 | | THC2511652 | Hs.114286 |
| A_23_P164773 | FCER2 | *Homo sapiens* Fc fragment of IgE, low affinity II, receptor for (CD23) (FCER2), transcript variant 1, mRNA [NM_002002] | NM_002002 | ENST00000346664 | 2208 | Fc fragment of IgE, low affinity II, receptor for (CD23) | chr19:7761956-7761799 | GO:0005886\|GO:0051712\|NM_002002 GO:0005529\|GO:0005576\| GO:0002925\|GO:0019863\| GO:0005178\|GO:0005488\| GO:0005887\|GO:0051000\| GO:0004872\|GO:0051773\| GO:0009897 | | THC2607080 | Hs.465778 |
| A_33_P3309999 | DCAF12L2 | *Homo sapiens* DDB1 and CUL4 associated factor 12-like 2 (DCAF12L2), mRNA [NM_001013628] | NM_001013628 | ENST00000360028 | 340578 | DCB1 and CUL4 associated factor 12-like 2 | chrX:12529862 9-125298570 | | NM_001013628 | THC2635368 | Hs.181867 |
| A_23_P94647 | OR1L3 | *Homo sapiens* olfactory receptor, family 1, subfamily L, member 3 (OR1L3), mRNA [NM_001005234] | NM_001005234 | ENST00000304820 | 26735 | olfactory receptor, family 1, subfamily L, member 3 | chr9:12543770 8-125437767 | GO:0007608\|GO:0007165\|NM_001005234 GO:0004984\|GO:0007186\| GO:0005886\|GO:0004872\| GO:0016021\|GO:0050896 | | NP1461799 | Hs.626839 |
| A_33_P3359724 | C1orf194 | *Homo sapiens* chromosome 1 open reading frame 194 [Source: HGNC Symbol: Acc: 32331] [ENST00000369942] | BG717688 | ENST00000369942 | 127003 | chromosome 1 open reading frame 194 | chr1:10964937 9-109649320 | | | THC2719823 | Hs.446962 |
| A_33_P3386062 | LOC283585 | *Homo sapiens* hypothetical LOC283585 | NR_038445 | | 283585 | hypothetical LOC283585 | chr14:8738870 0-87388759 | | NR_038445 | THC2608384 | Hs.381998 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P116435 | IGF2AS | (LOC283585), non-coding RNA [NR_038445] Homo sapiens insulin-like growth factor 2 antisense (IGF2AS), transcript variant 1, non-coding RNA [NR_028044] | NR_028044 | ENST00000445504 | 51214 | insulin-like growth factor 2 antisense | chr11:2169765-2169824 | | NR_028044 | THC2478168 | Hs.716962 |
| A_33_P3321906 | | GB | | | | | chr7:14814305 9-148143118 | | | NP1252190 | |
| A_33_P3236310 | NOBOX | Homo sapiens NOBOX oogenesis homeobox (NOBOX), mRNA [NM_001080413] | NM_001080413 | ENST00000467773 | 135935 | NOBOX oogenesis homeobox | chr7:14440969l 0-144096851 | GO:0043565\|GO:0006355\|GO:0001541\|GO:0003700\|GO:0048477\|GO:0045944\|GO:0007275\|GO:0005634\|GO:0030154 | NM_001080413 | THC2602516 | Hs.558628 |
| A_24_P370172 | LILRA5 | Homo sapiens leukocyte immunoglobulin-like receptor, subfamily A (with TM domain), member 5 (LILRA5), transcript variant 3, mRNA [NM_181879] | NM_181879 | ENST00000432233 | 353514 | leukocyte immunoglobulin-like receptor, subfamily A (with TM domain), member 5 | chr19:5482277 7-54822718 | GO:0006955\|GO:0016020\|GO:0005576\|GO:0004872\|GO:0016021 | NM_181879 | THC2490917 | Hs.710986 |
| A_23_P10156 | CHMP6 | Homo sapiens chromatin modifying protein 6 (CHMP6), mRNA [NM_024591] | NM_024591 | ENST00000325167 | 79643 | chromatin modifying protein 6 | chr17:7897350 8-78973567 | GO:0047485\|GO:0016020\|GO:0031902\|GO:0031225\|GO:0015031\|GO:0012505\|GO:0005768 | NM_024591 | THC2467426 | Hs.514560 |
| A_23_P48109 | NINJ2 | Homo sapiens ninjurin 2 (NINJ2), mRNA [NM_016533] | NM_016533 | ENST00000305108 | 4815 | ninjurin 2 | chr12:674505-674446 | GO:0005515\|GO:0016020\|GO:0016533\|GO:0005887\|GO:0042246\|GO:0007155\|GO:0007399 | NM_016533 | THC2613843 | Hs.656450 |
| A_33_P3246203 | LOC148696 | Homo sapiens hypothetical LOC148696 (LOC148696), non-coding RNA [NR_026817] | NR_026817 | ENST00000320399 | 148696 | hypothetical LOC148696 | chr1:20799588 7-20795946 | GO:0007158 | NR_026817 | NP1167943 | Hs.125511 |
| A_24_P186943 | ELN | Homo sapiens elastin (ELN), transcript variant 1, mRNA [NM_000501] | NM_000501 | | 2006 | elastin | chr7:73474764-73474823 | GO:0007585\|GO:0008283\|GO:0008015\|GO:0005578\|GO:0009887\|GO:0030023\|GO:0005576 | NM_000501 | NP414382 | Hs.647061 |
| A_33_P3341731 | | | | | | | chr11:0677228 14-067722755 | | | | |
| A_32_P170397 | | HCG1998685 [Source: UniProtKB/TrEMBL; Acc: Q8TCB4] [ENST00000309874]eb;normal | AK057625 | ENST00000309874 | | | chr15:4218802 5-42188084 | | | THC2627263 | Hs.650238 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3237704 | | | | | | | | | | | |
| A_23_P17130 | C2orf88 | Homo sapiens chromosome 2 open reading frame 88 (C2orf88), transcript variant 1, mRNA [NM_001042519] | NM_001042519 | ENST00000450357 | 84281 | chromosome 2 open reading frame 88 | chr9:06648933 9-066489280 chr2:19106449 5-191064554 | GO:0005576 | NM_001042519 | THC2740834 | Hs.389311 |
| A_33_P3325068 | SIRT3 | Homo sapiens sirtuin 3 [Source: HGNC Symbol; Acc: 14931] [ENST00000529937] | AK074992 | ENST00000529937 | 23410 | sirtuin 3 | chr11:224126-224067 | | | THC2482940 | Hs.716456 |
| A_33_P3222069 | SPHK1 | Homo sapiens sphingosine kinase 1 (SPHK1), transcript variant 2, mRNA [NM_182965] | NM_182965 | ENST00000545180 | 8877 | sphingosine kinase 1 | chr17:7438386 7-74383926 | GO:0005516\|GO:0007242\|NM_182965 GO:0019722\|GO:0030307 GO:0006670\|GO:0048146 GO:0007205\|GO:0008481 GO:0005829\|GO:0005737 GO:0017050\|GO:0000166 GO:0045987\|GO:0004143 GO:0000287\|GO:0030335 GO:0005624\|GO:0006916 GO:0005625\|GO:0005524 GO:0003677\|GO:0045766 GO:0045931\|GO:0046521 GO:0016740 | | THC2474958 | Hs.68061 |
| A_24_P46953 | SGK3 | Homo sapiens serum/glucocorticoid regulated kinase family, member 3 (SGK3), transcript variant 1, mRNA [NM_013257] | NM_013257 | ENST00000262211 | 23678 | serum/glucocorticoid regulated kinase family, member 3 | chr8:67773851-67773910 | GO:0005515\|GO:0007154\|NM_013257 GO:0000166\|GO:0004674 GO:0006950\|GO:0016023 GO:0006916\|GO:0006468 GO:0035091\|GO:0005524 GO:0016740\|GO:0005769 | | THC2464125 | Hs.613417 |
| A_23_P79587 | ALPP | Homo sapiens alkaline phosphatase, placental (ALPP), mRNA [NM_001632] | NM_001632 | ENST00000485563 | 250 | alkaline phosphatase, placental | chr2:23324719 8-233247257 | GO:0000287\|GO:0016787\|NM_001632 GO:0009986\|GO:0005886 GO:0004035\|GO:0008152 GO:0008270\|GO:0031225 GO:0016021 | | THC2470635 | Hs.284255 |
| A_33_P3375476 | KLHDC4 | Homo sapiens kelch domain containing 4 (KLHDC4), transcript variant 1, mRNA [NM_017566] | NM_017566 | FNST00000270583 | 54758 | kelch domain containing 4 | chr16:8774147 8-87741419 | | NM_017566 | NP163336 | Hs.123450 |
| A_33_P3368560 | AHSA2 | Homo sapiens AHA1, activator of heat shock 90 kDa protein ATPase homolog 2 (yeast), mRNA (cDNA clone IMAGE: 5735095), partial cds. [BC050395] | BC050395 | | 130872 | AHA1, activator of heat shock 90 kDa protein ATPase homolog 2 (yeast) | chr2:61416001-61416060 | | | THC2533385 | Hs.655602 |
| A_33_P3713357 | ALCAM | Homo sapiens activated leukocyte cell adhesion | NM_001627 | ENST00000491388 | 214 | activated leukocyte | chr3:10529461 3-105294672 | GO:0030424\|GO:0007165\|NM_001627 GO:0008045\|GO:0016020 | | THC2462127 | Hs.591293 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3277178 | | molecule (ALCAM), mRNA [NM_001627] SCO-spondin homolog (Bos taurus) [Source: HGNC Symbol; Acc: 21998] [ENST00000472850] | AK093431 | ENST00000472850 | | cell adhesion molecule | chr7:149524038-149524097 | GO:0043025\|GO:0005102\|GO:0016021\|GO:0007155\|GO:0009897 | | THC2488338 | Hs.632022 |
| A_23_P382488 | LRRC16B | Homo sapiens leucine rich repeat containing 16B (LRRC16B), RNA [NM_138360] | NM_138360 | ENST00000342740 | 90668 | leucine rich repeat containing 163 | chr14:24538399-24538589 | | NM_138360 | THC2679710 | Hs.26135 |
| A_23_P23839 | LGR6 | Homo sapiens leucine-rich repeat containing G protein-coupled receptor 6 (LGR6), transcript variant 1, mRNA [NM_001017403] | NM_001017403 | ENST00000367277 | 59352 | leucine-rich repeat containing G protein-coupled receptor 6 | chr1:202288529-202288588 | GO:0005515\|GO:0007165\|GO:0007186\|GO:0005886\|GO:0004872\|GO:0016021\|GO:0016500 | NM_001017403 | NP704842 | Hs.497402 |
| A_33_P3641714 | C19orf66 | Homo sapiens chromosome 19 open reading frame 66 (C19orf66), mRNA [NM_018381] | NM_018381 | ENST00000397881 | 55337 | chromosome 19 open reading frame 66 | chr19:10203524-10203583 | | NM_018381 | THC2489089 | Hs.655613 |
| A_33_P3294826 | CRABP2 | Homo sapiens cellular retinoic acid binding protein 2 (CRABP2), transcript variant 2, mRNA [NM_001199723] | NM_001199723 | ENST00000368220 | 1382 | cellular retinoic acid binding protein 2 | chr1:156675605-156675546 | | NM_001199723 | | Hs.405662 |
| A_33_P3235517 | LOC100133286 | Homo sapiens hypothetical LOC100133286 (LOC100133286), non-coding RNA [NR_040084] | NR_040084 | ENST00000535199 | 100133286 | hypothetical LOC100133286 | chr21:37447245-37447186 | | NR_040084 | | Hs.728809 |
| A_32_P219942 | ZIC5 | Homo sapiens Zic family member 5 (ZIC5), mRNA [NM_033132] | NM_033132 | ENST00000397451 | 85416 | Zic family member 5 | chr13:100615740-100615681 | GO:0005622\|GO:0001843\|GO:0008270\|GO:0007275\|GO:0005634\|GO:0030900\|GO:0003677\|GO:0046872\|GO:0030154\|GO:0007399 | NM_033132 | THC2666554 | Hs.508570 |
| A_33_P3364964 | LOC100129596 | PREDICTED: Homo sapiens hypothetical LOC100129596 (LOC100129596), misc RNA [XR_110585] | XNR_110585 | | 100129596 | hypothetical LOC100129596 | chr8:146044575-146045697 | | XR_110585 | THC2489577 | Hs.639990 |
| A_33_P3323486 | | Synthetic construct DNA, clone: PF1KE0827, Homo sapiens OR4A13P gene for Putative olfactory receptor, family 4, | AB529256 | | | | chr11:5523513-55235191 | | | NP511198 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | subfamily A, member 13, without stop codon, in Flexi system. [AB529256] | | | | | | | | | |
| A_23_P18017 | CPA3 | Homo sapiens carboxypeptidase A3 (mast cell) (CPA3), mRNA [NM_001870] | NM_001870 | ENST00000290046 | 1359 | carboxy-peptidase A3 (mast cell) | chr3:148614465-148614524 | GO:0006508\|GO:0008270\|NM_001870<br>GO:0008233\|GO:0005634\|<br>GO:0030141\|GO:0046872\|<br>GO:0042629\|GO:0008237\|<br>GO:0004181 | NM_001870 | THC2472745 | Hs.646 |
| A_32_P206899 | DNAH2 | Homo sapiens dynein, axonemal, heavy chain 2 (DNAH2), mRNA [NM_020877] | NM_020877 | ENST00000389173 | 146754 | dynein, axonemal, heavy chain 2 | chr17:7736930-7736989 | GO:0005929\|GO:0001539\|NM_020877<br>GO:0000166\|GO:0005874\|<br>GO:0005858\|GO:0035085\|<br>GO:0003777\|GO:0016887\|<br>GO:0005524\|GO:0007018 | NM_020877 | THC2524546 | Hs.367649 |
| A_33_P3338152 | HIF3A | hypoxia inducible factor 3, alpha subunit [Source: HGNC Symbol; Acc: 15825] [ENST00000457865] | AB118749 | ENST00000457865 | 64344 | hypoxia inducible factor 3, alpha subunit | chr19:4681568 0-46815739 | GO:0007165\|GO:0001666<br>GO:0006355\|GO:0005737\|<br>GO:0003700\|GO:0006366\|<br>GO:0005634\|GO:0004871 | | THC2485400 | Hs.420830 |
| A_32_P195401 | FAM117B | Homo sapiens family with sequence similarity 117, member B (FAM117B), mRNA [NM_173511] | NM_173511 | ENST00000303116 | 150864 | family with sequence similarity 117, member B | chr2:20363437 5-203634434 | | NM_173511 | THC2629531 | Hs.471130 |
| A_33_P3394175 | | T cell receptor beta variable 9 [Source: HGNC Symbol; Acc: 12246] [ENST00000390363] | AB306151 | ENST00000390363 | | | chr7:14223965 1-142239592 | | | NP285403 | Hs.511735 |
| A_33_P3337742<br>A_33_P3327491 | | | | | | | chr19:0194789 29-019478988 | | | | |
| A_33_P3231670 | RNF208 | Homo sapiens ring finger protein 208 (RNF208), mRNA [NM_031297] | NM_031297 | ENST00000496613 | 727800 | ring finger protein 208 | chr9:14011475 8-140114699 | | NM_031297 | THC2601539 | Hs.512767 |
| A_23_P257583 | DENND2A | Homo sapiens DENN/MADD domain containing 2A (DENND2A), mRNA [NM_015689] | NM_015689 | ENST00000366839 | 27147 | DENN/MADD domain containing 2A | chr7:14021851 8-140218459 | | NM_015689 | | Hs.6385 |
| A_33_P3339173 | SRP9 | Homo sapiens signal recognition particle 9 kDa (SRP9), transcript variant 1, mRNA [NM_001130440] | NM_001130440 | ENST00000549634 | 6726 | signal recognition particle 9 kDa | chr1:22597724 3-225977302 | GO:0005786\|GO:0005515\|NM_001130440<br>GO:0005737\|GO:0005785\|<br>GO:0006614\|GO:0008312\|<br>GO:0005047\|GO:0045900 | | THC2561622 | Hs.706900 |
| A_24_P409595 | MAPK8IP1 | Homo sapiens mitogen-activated protein kinase | NM_005456 | | 9479 | mitogen-activated | chr11:4592720 3-45927262 | GO:0005515\|GO:0043005\|NM_005456<br>GO:0048471\|GO:0006355 | | THC2467596 | Hs.234249 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | 8 interacting protein 1 (MAPK8IP1), mRNA [NM_005456] | | | | protein kinase 8 interacting protein 1 | | GO:0031434\|GO:0031435\|GO:0005634\|GO:0006916\|GO:0007258\|GO:0005829\|GO:0007165\|GO:0005737\|GO:0046329\|GO:0016020\|GO:0004860\|GO:0019894\|GO:0043508\|GO:0008432\|GO:0016192\|GO:0005078 | | | |
| A_33_P3818959 | SAMD11 | Homo sapiens sterile alpha motif domain containing 11 (SAMD11), mRNA [NM_152486] | NM_152486 | ENST00000342066 | 148398 | sterile alpha motif domain containing 11 | chr1:879580-879639 | GO:0005634 | NM_152486 | THC2480231 | Hs.335293 |
| A_23_P47410 | ESAM | Homo sapiens endothelial cell adhesion molecule (ESAM), mRNA [NM_138961] | NM_138961 | ENST00000464067 | 90952 | endothelial cell adhesion molecule | chr11:124623564-124623505 | GO:0005515\|GO:0030054\|GO:0005912\|GO:0005886\|GO:0016021\|GO:0005923\|GO:0007156 | NM_138961 | THC2481228 | Hs.173840 |
| A_33_P3238623 | LOC729723 | Homo sapiens hypothetical LOC729723 (LOC729723), non-coding RNA [NR_034113] | NR_034113 | | 729723 | hypothetical LOC729723 | chr2:25258973-25259032 | | NR_034113 | THC2491470 | Hs.436366 |
| A_33_P3278187 | SLC35D2 | Homo sapiens solute carrier family 35, member D2 (SLC35D2), mRNA [NM_007001] | NM_007001 | ENST00000375259 | 11046 | solute carrier family 35, member D2 | chr9:99122496-99122437 | GO:0008150\|GO:0005794\|GO:0005338\|GO:0016020\|GO:0005338\|GO:0008643\|GO:0016021\|GO:0005575 | NM_007001 | NP1465624 | Hs.494556 |
| A_33_P3224710 | TFEC | Homo sapiens transcription factor EC (TFEC), transcript variant 1, mRNA [NM_012252] | NM_012252 | ENST00000393485 | 22797 | transcription factor EC | chr7:115580160-115580101 | GO:0034605\|GO:0003700\|NM_012252\|GO:0003714\|GO:0003713\|GO:0005634\|GO:0045449 | | THC2474951 | Hs.125962 |
| A_33_P3372647 | | immunoglobulin lambda variable 1-36 [Source: HGNC Symbol; Acc: 5876] [ENST00000390301] | DQ098690 | ENST00000390301 | | | chr22:2278659 7-22786656 | | | THC2560012 | Hs.474325 |
| A_23_P85783 | PHGDH | Homo sapiens phosphoglycerate dehydrogenase (PHGDH), mRNA [NM_006623] | NM_006623 | ENST00000369407 | 26227 | phosphoglycerate dehydrogenase | chr1:12028552 9-120285588 | GO:0010468\|GO:0048037\|NM_006623\|GO:0021510\|GO:0019530\|GO:0008652\|GO:0009055\|GO:0022402\|GO:0031175\|GO:0004617\|GO:0051287\|GO:0021782\|GO:0007420\|GO:0021915\|GO:0006544\|GO:0016491\|GO:0006564\|GO:0006566\|GO:0055114\|GO:0022008\|GO:0006541\|GO:0009448 | | THC2565900 | Hs.487296 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P98532 | ZDHHC5 | Homo sapiens zinc finger, DHHC-type containing 5 (ZDHHC5), mRNA[NM_015457] | NM_015457 | ENST00000529480 | 25921 | zinc finger, DHHC type containing 5 | chr11:57746834 0-57468399 | GO:0016020\|GO:0008270\|NM_015457 GO:0016021\|GO:0046872 GO:0016740\|GO:0008415 | NM_015457 | THC2616547 | Hs.27239 |
| A_33_P3250767 | | | | | | | chr17:0001814 12-000181353 | | | | |
| A_23_P215900 | SCARA3 | Homo sapiens scavenger receptor class A, member 3 (SCARA3), transcript variant 1, mRNA [NM_016240] | NM_016240 | ENST00000301904 | 51435 | scavenger receptor class A, member 3 | chr8:27530383-27530442 | GO:0009650\|GO:0005794\|NM_016240 GO:0016020\|GO:0005783\| GO:0016021\|GO:0006979 GO:0005044 | | THC2471428 | Hs.128856 |
| A_33_P3405754 | CEP104 | centrosomal protein 104 kDa [Source: HGNC Symbol; Acc: 24866] [ENST00000378223] | BC050721 | ENST00000378223 | 9731 | centrosomal protein 104 kDa | chr1:3759797-3759738 | | | THC2489059 | Hs.509017 |
| A_33_P3366431 | LCN1 | Homo sapiens lipocalin 1 (tear prealbumin) (LCN1), mRNA [NM_002297] | NM_002297 | ENST00000540044 | 3933 | lipocalin 1 (tear prealbumin) | chr9:13841576 5-138415823 | GO:0005515\|GO:0005215\|NM_002297 GO:0004869\|GO:0050909\| GO:0006810\|GO:0006508 GO:0005576\|GO:0050896 | | THC2508562 | Hs.530311 |
| A_33_P3279861 | | Homo sapiens clone 1120 immunoglobulin lambda light chain variable region mRNA, partial cds. [AF194718] | AF194718 | | | | chr22:2306358 1-23241800 | | | NP079543 | Hs.728758 |
| A_33_P3240200 | DPCD | Homo sapiens deleted in primary ciliary dyskinesia homolog (mouse) (DPCD), mRNA [NM_015448] | NM_015448 | ENST00000370149 | 25911 | deleted in primary ciliary dyskinesia homolog (mouse) | chr10:1033693 50-103369409 | GO:0005515 | NM_015448 | THC2757023 | Hs.658128 |
| A_23_P123164 | OR6W1P | Homo sapiens olfactory receptor, family 6, subfamily W, member 1 pseudogene (OR6W1P), non-coding RNA [NR_002140] | NR_002140 | ENST00000496192 | 89883 | olfactory receptor, family 6, subfamily W, member 1 pseudogene | Chr7:14275972 0-142759661 | | NR_002140 | THC2484218 | Hs.339818 |
| A_33_P3296181 | CCL3L3 | Homo sapiens chemokine (C-C motif) ligand 3-like 3 (CCL3L3), mRNA [NM_001001437] | NM_001001437 | ENST00000394484 | 414062 | chemokine (C-C motif) ligand 3-Mke 3 | chr17:3452413 9-34524080 | GO:0008009\|GO:0006955\|NM_001001437 GO:0008285\|GO:0006954 GO:0006935\|GO:0005576 GO:0005615 | | THC2605779 | Hs.512304 |
| A_23_P152066 | UBR1 | Homo sapiens ubiquitin protein ligase E3 component n-recognin 1 (UBR1), mRNA [NM_174916] | NM_174916 | ENST00000382177 | 197131 | ubiquitin protein ligase E3 component n-recognin 1 | chr15:4323534 0-43235281 | GO:0005515\|GO:0030163\|NM_174916 GO:0006511\|GO:0005737\| GO:0004842\|GO:0000502 GO:0016874\|GO:0000151 GO:0008270\|GO:0046872 GO:0005829 | | THC2461626 | Hs.591121 |
| A_33_P3274105 | C2orf63 | chromosome 2 open reading frame 63 | | ENST00000403506 | 130162 | chromosome 2 open reading | chr2:55451395-55451336 | | | THC2573429 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | [Source: HGNC Symbol; Acc: 26453] [ENST00000403506] | | | | frame 63 | | | | | |
| A_33_P3238310 | C21orf7 | Homo sapiens chromosome 21 open reading frame 7 (C21orf7), mRNA [NM_020152] | NM_020152 | ENST00000492930 | 56911 | chromosome 21 open reading frame 7 | chr21:30464842-30464901 | GO:0005515\|GO:0005634\|GO:0005829 | NM_020152 | THC2521637 | Hs.222802 |
| A_33_P3226560 | | HSU07000 breakpoint cluster protein {Homo sapiens}region (exp = -1; wgp = 0; cg = 0), partial (11%) [THC2481061] | | | | | chr22:0188444-018844410 | | | THC2481061 | |
| A_33_P3394405 | LOC727721 | DB238770 TRACH3 Homo sapiens cDNA clone TRACH3034794 5′, mRNA sequence [DB238770] | DB238770 | | 727721 | hypothetical LOC727721 | chr1:9241884-9241825 | | | THC2652642 | Hs.699065 |
| A_33_P3242693 | SLC22A11 | Homo sapiens solute carrier family 22 (organic anion/urate transporter), member 11 (SLC22A11), mRNA [NM_018484] | NM_018484 | ENST00000428570 | 55867 | solute carrier family 22 (organic anion/urate transporter), member 11 | chr11:64338937-64338996 | GO:0005515\|GO:0016324\|GO:0005886\|GO:0005452\|GO:0015347\|GO:0005887\|GO:0015711\|GO:0055085\|GO:0009897\|GO:0006811 | NM_018484 | NP852739 | Hs.220844 |
| A_33_P3230788 | MUSK | Homo sapiens muscle, skeletal, receptor tyrosine kinase [Source :HGNC Symbol; Acc: 7525] [ENST00000374440] | | ENST00000374440 | 4593 | muscle, skeletal, receptor tyrosine kinase | chr9:113468373-113468432 | | | THC2697013 | |
| A_23_P103532 | GPR161 | Homo sapiens G protein-coupled receptor G 161 (GPR161), transcript variant 2, mRNA [NM_153832] | NM_153832 | ENST00000493800 | 23432 | G protein-coupled receptor 161 | chr1:168065891-168065832 | GO:0007165\|GO:0007186\|GO:0005886\|GO:0004930\|GO:0007275\|GO:0004872\|GO:0016021 | NM_153832 | THC2628589 | Hs.632453 |
| A_33_P3234317 | RRAS2 | Homo sapiens related RAS viral (r-ras) oncogene homolog 2 (RRAS2), transcript variant 1, mRNA [NM_012250] | NM_012250 | ENST00000545643 | 22800 | related RAS viral (r-ras) oncogene homolog, 2 | chr11:14299538-14299479 | GO:0005622\|GO:0005515\|GO:0007165\|GO:0030335\|GO:0005886\|GO:0000166\|GO:0009987\|GO:0005783\|GO:0003924\|GO:0007265\|GO:0005525 | NM_012250 | THC2603796 | Hs.502004 |
| A_32_P511713 | C11orf42 | Homo sapiens chromosome 11 open reading frame 42 (C11orf42), mRNA [NM_173525] | NM_173525 | ENST00000316375 | 160298 | chromosome 11 open reading frame 42 | chr11:6231561-6231620 | | NM_173525 | THC2484466 | Hs.278221 |
| A_23_P164999 | CDC34 | Homo sapiens cell division cycle 34 homolog (S. cerevisiae) (CDC34), mRNA | NM_004359 | ENST00000215574 | 997 | cell division cycle 34 homolog (S. cerevisiae) | chr19:541675-541734 | GO:0005515\|GO:0051246\|GO:0004842\|GO:0000082\|GO:0016567\|GO:0000166\|GO:0006270\|GO:0019941 | NM_004359 | THC2746781 | Hs.514997 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3284686 | SSBP3 | Homo sapiens single stranded DNA binding protein 3 (SSBP3), transcript variant 3, mRNA [NM_001009955] [NM_004359] | NM_001009955 | ENST00000357475 | 23648 | single stranded DNA binding protein 3 | chr1:54693957-54692804 | GO:0016874\|GO:0005634\|GO:0005524 GO:0003697\|GO:0030528\|NM_001009955\|GO:0005634\|GO:0003677\|GO:0045449 | NM_001009955 | THC2482506 | Hs.658676 |
| A_32_P89827 | LOC374491 | Homo sapiens TPTE and PTEN homologous inositol lipid phosphatase pseudogene (LOC374491), non-coding RNA [NR_002815] | NR_002815 | ENST00000453498 | 374491 | TPTE and PTEN homologous inositol lipid phosphatase pseudogene | chr13:25171688-25171747 | | NR_002815 | THC2498037 | Hs.406779 |
| A_23_P90679 | STRAD B | Homo sapiens STE20-related kinase adaptor beta (STRADB), transcript variant 1, mRNA [NM_018571] | NM_018571 | ENST00000466770 | 55437 | STE20-related kinase adaptor beta | chr2:202344823-202344882 | GO:0005515\|GO:0007254\|NM_018571\|GO:0005634\|GO:0006916\|GO:0046320\|GO:0005524\|GO:0032147\|GO:0000902\|GO:0005737\|GO:0007049\|GO:0004672\|GO:0000166\|GO:0006611\|GO:0006468 | NM_018571 | NP1466986 | Hs.652338 |
| A_32_P191004 | ATAD2B | Homo sapiens ATPase family, AAA domain containing 2B (ATAD2B), transcript variant 1, mRNA [NM_017552] | NM_017552 | ENST00000238789 | 54454 | ATPase family, AAA domain containing 2B | chr2:239719683-23971909 | GO:0017111\|GO:0000166\|NM_017552\|GO:0005524 | NM_017552 | THC2606751 | Hs.467862 |
| A_24_P22939 | ADAMTSL5 | Homo sapiens ADAMTS-like 5 (ADAMTSL5), mRNA [NM_213604] | NM_213604 | ENST00000395467 | 339366 | ADAMTS-like 5 | chr19:1506006-1505947 | GO:0005515\|GO:0005578\|NM_213604\|GO:0008270\|GO:0005576\|GO:0004222 | NM_213604 | THC2477262 | Hs.371674 |
| A_33_P3315704 | | full-length cDNA clone CSODI009YC01 of Placenta Cot 25-normalized of Homo sapiens (human). [CR604707] | CR604707 | | | | chr9:03561747-4-035617533 chr10:48952880-48952939 | | | | Hs.661155 |
| A_32_P2634 | | | | | | | | | | | |
| A_33_P3221898 | LOC339240 | Homo sapiens keratin pseudogene (LOC339240), non-coding RNA [NR_001443] | NR_001443 | ENST00000445433 | 339240 | keratin pseudogene | chr17:20424303-20424244 | GO:0005576 | NM_001443 | THC2773065 | Hs.420616 |
| A_23_P21747 | CABP5 | Homo sapiens calcium binding protein 5 (CABP5), mRNA [NM_019855] | NM_019855 | ENST00000293255 | 56344 | calcium binding protein 5 | chr19:48533434-48533375 | GO:0007165\|GO:0005737\|NM_019855\|GO:0005509\|GO:0005575 | NM_019855 | NP186400 | Hs.117694 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3236259 | | BX398892 *Homo sapiens* PLACENTA COT 25-NORMALIZED *Homo sapiens* cDNA clone CS0DI066YG03 5-PRIME, mRNA sequence [BX398892] | BX398892 | ENST00000452342 | | | chr2:20254198-20254257 | | | | Hs.224673 |
| A_33_P3210443 | LOC145216 | *Homo sapiens* hypothetical LOC145216 (LOC145216), non-coding RNA [NR_038436] | NR_038436 | | 145216 | hypothetical LOC145216 | chr14:1043227 81-104322840 | | NR_038436 | NP1154465 | Hs.578091 |
| A_33_P3265359 | HES6 | *Homo sapiens* hairy and enhancer of split6 (*Drosophila*) (HES6), transcript variant 1, mRNA[NM_018645] | NM_018645 | ENST00000409160 | 55502 | hairy and enhancer of split 6 (*Drosophila*) | chr2:23914700 6-239146947 | GO:0003712 GO:0005667 GO:0003700 GO:0006357 GO:0007275 GO:0005634 GO:0030154 GO:0007399 | NM_018645 | THC2489573 | Hs.42949 |
| A_33_P3321657 | HSPG2 | *Homo sapiens* heparan sulfate proteoglycan 2 (HSPG2), mRNA [NM_005529] | NM_005529 | ENST00000374695 | 3339 | heparan sulfate proteoglycan 2 | chr1:22148799-22148740 | GO:0048738 GO:0005515 GO:0001958 GO:0008104 GO:0030198 GO:0007420 GO:0022062 GO:0060351 GO:0005605 GO:0048704 GO:0005576 GO:0007155 | NM_005529 | THC2571330 | Hs.562227 |
| A_33_P3257817 | | *Homo sapiens* cDNA FLJ34378 fis, clone FEBRA2018051. [AK091697] | AK091697 | ENST00000330539 | | | chr8:37592362-37592303 | | | THC2485861 | Hs.588388 |
| A_24_P925314 | GM2A | *Homo sapiens* GM2 ganglioside activator (GM2A), transcript variant 1, mRNA [NM_000405] | NM_000405 | ENST00000357164 | 2760 | GM2 ganglioside activator | chr5:15064966 2-150649721 | GO:0006629 GO:0032428 GO:0009313 GO:0051345 GO:0019915 GO:0006689 GO:0030149 GO:0019377 GO:0005764 GO:0030290 GO:0005739 GO:0005737 GO:0016004 GO:0045179 GO:0005889 GO:0006869 GO:0050885 GO:0007611 GO:0050877 GO:0009898 GO:0005319 | NM_000405 | THC2504387 | Hs.483873 |
| A_24_P239177 | MUC4 | *Homo sapiens* mucin 4, cell surface associated (MUC4), transcript variant 1, mRNA [NM_018406] | NM_018406 | ENST00000479406 | 4585 | mucin 4, cell surface associated | chr3:19551483 9-195514780 | GO:0005515 GO:0008150 GO:0016020 GO:0007160 GO:0005887 GO:0005578 GO:0005576 GO:0007155 | NM_018406 | THC2583776 | Hs.369646 |
| A_24_P334640 | PAQR8 | *Homo sapiens* progestin and adipoQ receptor family member VIII | NM_133367 | ENST00000360726 | 85315 | progestin and adipoQ receptor family | chr6:52271880-52271939 | GO:0048477 GO:0005886 GO:0007275 GO:0004872 GO:0016021 GO:0005496 | NM_133367 | THC2495245 | Hs.239388 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (PAQR8), mRNA [NM_133367] | | | | member VIII | | GO:0030154 | | | |
| A_24_P139901 | GYPC | Homo sapiens glycophorin C (Gerbich blood group) (GYPC), transcript variant 1, mRNA [NM_002101] | NM_002101 | ENST00000409836 | 2995 | glycophorin C (Gerbich blood group) | chr2:127453654-127453713 | GO:0005515\|GO:0006493\|NM_002101 GO:0005886\|GO:0005887\| GO:0009887\|GO:0030863 GO:0006487 | THC2523220 | Hs.59138 |
| A_33_P3333488 | HAGH | Homo sapiens hydroxyacylglutathione hydrolase (HAGH), transcript variant 2, mRNA [NM_001040427] | NM_001040427 | ENST0000397356 | 3029 | hydroxyacyl-glutathione hydrolase | chr16:1859176-1859117 | GO:0005739\|GO:0005737\|NM_001040427 GO:0016787\|GO:0005975\| GO:0006750\|GO:0005759\| GO:0008270\|GO:0004416\| GO:0046872 | THC2503851 | Hs.157394 |
| A_33_P3235841 | SLC22A20 | Homo sapiens solute carrier family 22, member 20 (SLC22A20), transcript variant 2, non-coding RNA [NR_033396] | NR_033396 | ENST00000529062 | 440044 | solute carrier family 22, member 20 | chr11:65009498-65009557 | GO:0016020\|GO:0016021\|NR_033396 GO:0055085\|GO:0006811 | THC2502028 | Hs.532372 |
| A_33_P3283300 | FAM204A | chromosome 10 open reading frame 84 [Source: HGNC Symbol; Acc: 25794] [ENST00000469758] | | ENST00000469758 | 63877 | family with sequence similarity 204, member A | chr10:120081877-120081818 | | | THC2631812 | |
| A_33_P3397520 | KRTAP10-12 | Homo sapiens keratin associated protein 10-12 (KRTAP10-12), mRNA [NM_198699] | NM_198699 | ENST00000400365 | 386685 | keratin associated protein 10-12 | chr21:46117448-46117507 | GO:0045095 | NM_198699 | THC2483182 | Hs.297526 |
| A_33_P3262555 | MEX3D | Homo sapiens mex-3 homolog D (C. elegans) (MEX3D), transcript variant 2, mRNA [NM_001174118] | NM_001174118 | ENST00000388824 | 399664 | mex-3 homolog D (C. elegans) | chr19:1555636-1555577 | GO:0005515\|GO:0005737\|NM_001174118 GO:0003723\|GO:0008270\| GO:0005634\|GO:0046872 | | THC2473313 | Hs.436495 |
| A_33_P3423825 | | Q4AIS5_9CHLB (Q4AIS5) Zymogen granule protein 16 precursor, partial (8%) [THC2681947] | | | | | chr6:033291182-033291123 | | | THC2681947 | |
| A_33_P3418194 | LYNX1 | Homo sapiens Ly6/neurotoxin 1 (LYNX1), transcript variant 1, mRNA [NM_023946] | NM_023946 | ENST00000335822 | 66004 | Ly6/neurotoxin 1 | chr8:143845815-143845756 | GO:0005886\|GO:0005576\|NM_023946 GO:0031225 | | THC2479368 | Hs.158665 |
| A_33_P3289034 | PKD2L1 | Homo sapiens polycystic kidney disease 2-like 1 (PKD2L1), mRNA [NM_016112] | NM_016112 | ENST00000355274 | 9033 | polycystic kidney disease 2-like 1 | chr10:102049840-102049781 | GO:0008092\|GO:0007165\|NM_016112 GO:0005886\|GO:0005783\| GO:0005509\|GO:0016021\| GO:0005227\|GO:0016812 | | THC2480195 | Hs.159241 |
| A_24_P390833 | MPPE1 | Homo sapiens metallophosphoesterase 1 | NM_023075 | ENST00000399978 | 65258 | metallo-phosphoe sterase | chr18:11888697-11886995 | GO:0016787\|GO:0016020\|NM_023075 GO:0016021\|GO:0046872 | | NP1162383 | Hs.712666 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P494620 | LHFPL5 | (MPPE1), transcript variant 1, mRNA [NM_023075] Homo sapiens lipoma-HMGIC fusion partner-like 5 (LHFPL5), mRNA[NM_182548] | NM_182548 | ENST00000373853 | 222662 | lipoma HMGIC fusion partnerlike 5 | chr6:35782332-35782391 | GO:0016324\|GO:0016020\|GO:0007605\|GO:0060088\|GO:0016021 | NM_182548 | THC2483295 | Hs.367947 |
| A_32_P399187 | LOC146336 | Homo sapiens hypothetical LOC146336 (LOC146336), non-coding RNA [NR_027242] | NR_027242 | | 146336 | hypothetical LOC146336 | chr16:1115380-1115321 | | NR_027242 | THC2478752 | Hs.250557 |
| A_33_P3279124 | FAM21C | Homo sapiens family with sequence similarity 21, member C (FAM21C), transcript variant 3, mRNA [NM_001169107] | NM_001169107 | ENST00000434114 | 253725 | family with sequence similarity 21, member C | chr10:46250458-46250517 | | NM_001169107 | THC2572798 | Hs.365286 |
| A_33_P3554318 | TRIM3 | Homo sapiens tripartite motif containing 3 (TRIM3), transcript variant 1, mRNA [NM_006458] | NM_006458 | ENST00000532542 | 10612 | tripartite motif containing 3 | chr11:6470292-6470233 | GO:0005622\|GO:0005737\|GO:0008270\|GO:0015031\|GO:0008022\|GO:0046872\|GO:0005769\|GO:0007399 | NM_006458 | THC2622264 | Hs.591992 |
| A_32_P79434 | PTPRN2 | Homo sapiens protein tyrosine phosphatase, receptor type, N polypeptide 2 (PTPRN2), transcript variant 1, mRNA [NM_002847] | NM_002847 | ENST00000389418 | 5799 | protein tyrosine phosphatase, receptor type, N polypeptide 2 | chr7:15733197-157331913 | GO:0005515\|GO:0006470\|GO:0016787\|GO:0016020\|GO:0005887\|GO:0005001\|GO:0004872 | NM_002847 | THC2484697 | Hs.490789 |
| A_33_P3352085 | | Q6IMN1_HUMAN (Q6IMN1) Growth arrest-specific 6, partial (13%) [THC2591638] | | | | | chr13:114523345-114523286 | | | THC2591638 | |
| A_33_P3239587 | MXRA7 | Homo sapiens matrix-remodelling associated 7 (MXRA7), transcript variant 2, mRNA [NM_001008529] | NM_001008529 | ENST00000375036 | 439921 | matrix-remodelling associated 7 | chr17:7467571-74675653 | GO:0016020\|GO:0016021 | NM_001008529 | THC2468893 | Hs.250723 |
| A_33_P3371270 | TUG1 | Homo sapiens taurine upregulated 1 (non-protein coding) (TUG1), non-coding RNA [NR_002323] | NR_002323 | | 55000 | taurine upregulated 1 (non-protein coding) | chr22:31375241-31375300 | | NR_002323 | THC2533843 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3311285 | LMNA | Homo sapiens lamin A/C (LMNA), transcript variant 1, mRNA [NM_170707] | NM_170707 | ENST00000347559 | 4000 | lamin A/C | chr1:156109774-156109833 | GO:0005515\|GO:0005737\|NM_170707 GO:0005886\|GO:0005198\| GO:0007283\|GO:0005634\| GO:0016363\|GO:0005626\| GO:0005638 | THC2495163 | Hs.594444 |
| A_24_P204727 | | immunoglobulin+ heavy variable 3-48 [Source: HGNC Symbol; Acc: 5606] | Z18824 | ENST00000390624 | | | chr14:106993989-106993930 | | NP120643 | Hs.703936 |
| A_33_P3293785 | KRTAP10-3 | Homo sapiens keratin associated protein 10-3 (KRTAP10-3), mRNA [NM_198696] | NM_198696 | ENST00000391620 | 386682 | keratin associated protein 10-3 | chr21:45977965-45977906 | GO:0045095 | NM_198696 | NP815036 | Hs.688630 |
| A_23_P31984 | ACTL7A | Homo sapiens actin-like 7A (ACTL7A), mRNA [NM_006687] | NM_006687 | ENST00000333999 | 10881 | actin-like 7A | chr9:111625848-111625907 | GO:0005515\|GO:0005737\|NM_006687 GO:0005200\|GO:0009434\| GO:0005856\|GO:0001673 | | THC2472182 | Hs.123530 |
| A_33_P3396129 | KATNB1 | Homo sapiens mRNA for katanin p80 subunit B 1 variant protein. [AB209250] | AB209250 | | 10300 | katanin p80 (WD repeat containing) subunit B 1 | chr16:57790219-57790278 | | | THC2603047 | Hs.275675 |
| A_33_P3336720 | HAMP | Homo sapiens hepcidin antimicrobial peptide (HAMP), mRNA [NM_021175] | NM_021175 | ENST00000222304 | 57817 | hepcidin antimicrobial peptide | chr19:35775986-35776045 | GO:0006879\|GO:0006955\|NM_021175 GO:0005737\|GO:0045179\| GO:0005179\|GO:0050832\| GO:0031640\|GO:0005576\| GO:0042742 | | THC2478089 | Hs.8821 |
| A_33_P3343305 | | | | | | | chr19:040391999-040391940 | | | | |
| A_23_P67127 | TMEM145 | Homo sapiens transmembrane protein 145 (TMEM145), mRNA [NM_173633] | NM_173633 | ENST00000301204 | 284339 | transmembrane protein 145 | chr19:42829141-42829200 | GO:0016020\|GO:0016021 | NM_173633 | THC2483750 | Hs.382075 |
| A_33_P3415859 | NLRC3 | Homo sapiens NLR family, CARD domain containing 3 [Source: HGNC Symbol; Acc: 29889] [ENST00000324659] | AK090476 | ENST00000324659 | 197358 | NLR family, CARD domain containing 3 | chr16:3612970-3612911 | | | THC2563500 | Hs.728268 |
| A_33_P3321293 | IQGAP3 | Homo sapiens IQ motif containing GTPase activating protein 3 (IQGAP3), mRNA [NM_178229] | NM_178229 | ENST00000361170 | 128239 | IQ motif containing GTPase activating protein 3 | chr1:156495257-156495198 | GO:0005622\|GO:0005099\|NM_178229 GO:0051056\|GO:0007165\| GO:0005516 | | THC2464087 | Hs.591495 |
| A_33_P3213392 | | HCG2045795Novel protein [Source: UniProtKB/TrEMBL; Acc: Q5T400] [ENST00000375713] | | ENST00000375713 | | | chr13:112278396-112278455 | | | THC2752485 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3275435 | LOC100216545 | Homo sapiens hypothetical LOC100216545 (LOC100216545), non-coding RNA [NR_024586] | NR_024586 | | 100216545 | hypothetical LOC100216545 | chr7:104651052-104650993 | | NR_024586 | | Hs.631150 |
| A_33_P3408244 | SPRNP1 | Homo sapiens shadow of prion protein homolog (zebrafish) pseudogene 1 (SPRNP1), non-coding RNA [NR_033789] | NR_033789 | ENST00000450958 | 399833 | shadow of prion protein homolog (zebrafish) pseudogene 1 | chr10:135381393-135381334 | | NR_033789 | THC2482646 | Hs.660426 |
| A_24_P312692 | API5 | Homo sapiens apoptosis inhibitor 5 (API5), transcript variant 2, mRNA [NM_006595] | NM_006595 | ENST00000378852 | 8539 | apoptosis inhibitor 5 | chr11:43365367-43365426 | GO:0005737|GO:0017134|NM_006595 GO:0005488|GO:0006915| GO:0006916|GO:0005681| GO:0005634 | | THC2656401 | Hs.435771 |
| A_23_P253791 | CAMP | Homo sapiens cathelicidin antimicrobial peptide (CAMP), mRNA [NM_004345] | NM_004345 | ENST00000296435 | 820 | cathelicidin antimicrobial peptide | chr3:48266856-48266915 | GO:0050829|GO:0042581|NM_004345 GO:0005576 | | THC2473094 | Hs.51120 |
| A_24_P413941 | C2orf69 | Homo sapiens chromosome 2 open reading frame 69 (C2orf69), mRNA [NM_153689] | NM_153689 | ENST00000319974 | 205327 | chromosome 2 open reading frame 69 | chr2:200792670-200792729 | GO:0005576 | NM_153689 | THC2462315 | Hs.471040 |
| A_24_P413941 | C14orf45 | Homo sapiens chromosome 14 open reading frame 45 (C14orf45), mRNA [NM_025057] | NM_025057 | ENST00000492247 | 80127 | chromosome 14 open reading frame 45 | chr14:74523896-74523955 | | NM_025057 | THC2620212 | Hs.644621 |
| A_23_P61050 | MLKL | Homo sapiens mixed lineage kinase domain-like (MLKL), transcript variant 1, mRNA [NM_152649] | NM_152649 | ENST00000308807 | 197259 | mixed lineage kinase domain-like | chr16:74705988-74705979 | GO:0005515|GO:0006468|NM_152649 GO:0004713|GO:0005524 | | THC2471524 | Hs.119878 |
| A_33_P3327818 | | | AL157466 | ENST00000366116 | | | chr9:34523644-3452305 | | | THC2612300 | Hs.664105 |
| A_33_P3338793 | KCNC3 | Homo sapiens potassium voltage-gated channel, Shaw-related subfamily, member 3 (KCNC3), mRNA [NM_004977] | NM_004977 | ENST00000477616 | 3748 | potassium voltage-gated channel, Shaw-related subfamily, member 3 | chr19:50819050-50818991 | GO:0005515|GO:0008219|NM_004977 GO:0005244|GO:0016020| GO:0008076|GO:0005249| GO:0030955|GO:0016021| GO:0055085|GO:0006813| GO:0006811 | | THC2481537 | Hs.467146 |
| A_33_P3292739 | USP17L2 | Homo sapiens ubiquitin specific peptidase 17-like 2 (USP17L2), mRNA [NM_201402] | NM_201402 | ENST00000333796 | 377630 | ubiquitin specific peptidase 17-like 2 | chr8:11994918-11994859 | GO:0006511|GO:0006915|NM_201402 GO:0008233|GO:0005634| GO:0008234|GO:0004221 | | THC2525229 | Hs.531448 |
| A_23_P81103 | SFRP2 | Homo sapiens secreted frizzled-related protein 2 (SFRP2), mRNA [NM_003013] | NM_003013 | ENST00000274063 | 6423 | secreted frizzled-related protein 2 | chr4:154702884-154702825 | GO:0005515|GO:0031668|NM_003013 GO:0001756|GO:0007275| GO:0005576|GO:0016055| GO:0030154 | | THC2621036 | Hs.481022 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P278192 | AK1 | Homo sapiens adenylate kinase 1 (AK1), mRNA [NM_000476] | NM_000476 | ENST00000373176 | 203 | adenylate kinase 1 | chr9:130629235-130629176 | GO:0005515\|GO:0006139\|NM_000476\|GO:0005737\|GO:0046034\|GO:0001166\|GO:0005634\|GO:0004017\|GO:0019206\|GO:0005524\|GO:0016740\|GO:0005829 | THC2468589 | Hs.175473 |
| A_33_P3395675 | | immunoglobulin lambda constant 2 (Kern-Oz-marker) [Source: HGNC Symbol; Acc: 5856] [ENST00000390323] | EU937523 | ENST00000390323 | | | chr22:23243336-23243395 | | NP093469 | | Hs.625768 |
| A_23_P141863 | ZNF544 | Homo sapiens zinc finger protein 544 (ZNF544), mRNA [NM_014480] | NM_014480 | ENST00000415203 | 27300 | zinc finger protein 544 | chr19:5877419-58774259 | GO:0005622\|GO:0006355\|NM_014480\|GO:0008270\|GO:0005634\|GO:0003677\|GO:0046872 | THC2464356 | Hs.438994 |
| A_23_P87082 | ROBO3 | Homo sapiens round-about, axon guidance receptor, homolog 3 (Drosophila) (ROBO3), mRNA [NM_022370] | NM_022370 | ENST00000524971 | 64221 | roundabout, axon guidance receptor, homolog 3 (Drosophila) | chr11:124749824-124750352 | GO:0016020\|GO:0006935\|NM_022370\|GO:0007411\|GO:0007275\|GO:0004872\|GO:0016021\|GO:0030154\|GO:0007399 | THC2480495 | Hs.435621 |
| A_23_P28707 | OGFR | Homo sapiens opioid growth factor receptor (OGFR), mRNA [NM_007346] | NM_007346 | ENST00000370461 | 11054 | opioid growth factor receptor | chr20:61445213-61445272 | GO:0005737\|GO:0016020\|NM_007346\|GO:0005634\|GO:0004872\|GO:0005575\|GO:0001558\|GO:0004985 | NP208924 | Hs.67896 |
| A_33_P3393245 | FTSJD2 | Homo sapiens FtsJ methyltransferase domain containing 2 (FTSJD2), mRNA [NM_015050] | NM_015050 | ENST00000373420 | 23070 | FtsJ methyltransferase domain containing 2 | chr6:37446962-37447021 | GO:0005622\|GO:0005515\|NM_015050\|GO:0008168\|GO:0005634\|GO:0003676\|GO:0032259\|GO:0016740 | THC2670365 | HvS20102 |
| A_23_P305140 | C10orf32 | Homo sapiens chromosome 10 open reading frame 32 (C10orf32), transcript variant 2, mRNA[NM_144591] | NM_144591 | ENST00000369883 | 110012 | chromosome 10 open reading frame 32 | chr10:104623852-104623911 | | NM_144591 | THC2472913 | Hs.34492 |
| A_33_P3404759 | | | | | | | chr1:243327622-243327563 | | | | |
| A_23_P157628 | DEFB4A | Homo sapiens defensin, beta 4A (DEFB4A), mRNA [NM_004942] | NM_004942 | ENST00000302247 | 1673 | defensin, beta 4A | chr8:7754081-7754140 | GO:0006955\|GO:0007186\|NM_004942\|GO:0006935\|GO:0005576\|GO:0042742 | THC2478963 | Hs.105924 |
| A_33_P3325952 | | Homo sapiens cDNA FLJ12151 fis, clone MAMMA1000431. [AK022213] | AK022213 | | | | chr12:123887812-123887753 | | | | |
| A_33_P3384133 | C17orf99 | Homo sapiens chromosome 17 open reading frame 99 (C17orf99), mRNA [NM_001163075] | NM_001163075 | ENST00000340363 | 100141515 | chromosome 17 open reading frame 99 | chr17:76162175-76162234 | GO:0005576 | NM_001163075 | THC2479539 | Hs.63034 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P231546 | FAM178B | Homo sapiens family with sequence similarity 178, member B (FAM178B), transcript variant B, mRNA [NM_016490] | NM_016490 | ENST00000490605 | 51252 | family with sequence similarity 178, member B | chr2:97541686-97541627 | | NM_016490 | | Hs.107922 |
| A_32_P29954 | NCRNA00168 | Homo sapiens non-protein coding RNA 168 (NCRNA00168), non-coding RNA [NR033387] | NR_033387 | ENST00000421697 | 642394 | non-protein coding RNA 168 | chr10:1599022-1599081 | | NR_033387 | THC2689654 | Hs.568831 |
| A_33_P3279362 | GRIK1-AS1 | Homo sapiens GRIK1 antisense RNA 1 (non-protein coding) (GRIK1-AS1), non-coding RNA [NR_027021] | NR_027021 | ENST00000455392 | 642976 | GRIK1 antisense RNA 1 (non-protein coding) | chr21:31121174-31121233 | | NR_027021 | | |
| A_33_P3629131 | CDRT3 | DKFZp686P15240_r1 686 (synonym:hlcc3) Homo sapiens cDNA clone DKFZp686P15240 5′, mRNA sequence [BX484257] | BX484257 | | 94145 | CMT1A duplicated region transcript 3 | chr17:15374090-15374149 | | | | Hs.697356 |
| A_33_P3331282 | LOC648987 | Homo sapiens hypothetical LOC648987 (LOC648987), transcript variant 1, non-coding RNA [NR_034085] | NR_034085 | ENST00000408890 | 648987 | hypothetical LOC648987 | chr5:43016241-43016182 | | NR_034085 | THC2492334 | Hs.649468 |
| A_33_P3301346 | RBM44 | RNA binding motif protein 44 [Source: HGNC Symbol; Acc: 24756] [ENST00000491996] | | ENST00000491996 | 375316 | RNA binding motif protein 44 | chr2:238743452-238743511 | | | | |
| A_33_P3272990 | FKBP8 | Homo sapiens FK506 binding protein 8, 38 kDa (FKBP8), mRNA [NM_012181] | NM_012181 | ENST00000453489 | 23770 | FK506 binding protein 8, 38 kDa | chr19:18642801-18642742 | GO:0005739\|GO:0007242\|GO:0016020\|GO:0006457\|GO:0005488\|GO:0044419\|GO:0005509\|GO:0003755\|GO:0006915\|GO:0016021\|GO:0016853 | NM_012181 | THC2783704 | Hs.173464 |
| A_33_P3220422 | POM121L12 | Homo sapiens POM121 membrane glycoprotein-like 12 (POM121L12), mRNA [NM_182595] | NM_182595 | ENST00000408890 | 285877 | POM121 membrane glyco protein-like 12 | chr7:53104196-53104255 | | NM_182595 | THC2480958 | Hs.381970 |
| A_24_P322771 | TFF1 | Homo sapiens trefoil factor 1 (TFF1), mRNA [NM_003225] | NM_003225 | ENST00000291527 | 7031 | trefoil factor 1 | chr21:43783499-43783440 | GO:0030277\|GO:0005975\|GO:0010039\|GO:0007586\|GO:0006950\|GO:0043434 | NM_003225 | THC2463848 | Hs.162807 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P120364 | PPDPF | *Homo sapiens* pancreatic progenitor cell differentiation and proliferation factor homolog (zebrafish) (PPDPF), mRNA [NM_024299] | NM_024299 | ENST00000370178 | 79144 | pancreatic progenitor cell differentiation and proliferation factor homolog (zebrafish) | chr20:62153440-62153499 | GO:0005576\|GO:0032355\|GO:0008083\|GO:0005615\|GO:0007275\|GO:0030154 | NM_024299 | THC2580274 | Hs.79625 |
| A_23_P140848 | MPHOSPH6 | *Homo sapiens* M-phase phosphoprotein 6 (MPHOSPH6), mRNA [NM_005792] | NM_005792 | ENST00000258169 | 10200 | M-phase phosphoprotein 6 | chr16:82182215-82182156 | GO:0005515\|GO:0005737\|GO:0000087\|GO:0005730\|GO:0005634 | NM_005792 | THC2461936 | Hs.344400 |
| A_33_P3261505 | EPG5 | *Homo sapiens* ectopic P-granules autophagy protein 5 homolog (*C. elegans*) (EPG5), mRNA [NM_020964] | NM_020964 | ENST00000540322 | 57724 | ectopic P-granules autophagy protein 5 homolog (*C. elegans*) | chr18:43427781-43427722 | | NM_020964 | THC2604384 | Hs.514843 |
| A_33_P2421108 | | OPAP_DROME (P23488) Male-specific opa-containing protein precursor (Protein dromsopa), partial (23%) [THC2680858] | | ENST00000507296 | | | chr4:158558926-158558984 | | | THC2680858 | |
| A_23_P250164 | HGD | *Homo sapiens* homogentisate 1,2-dioxygenase (HGD), mRNA [NM_000187] | NM_000187 | ENST00000283871 | 3081 | homogentisate 1,2-dioxygenase | chr3:120347262-120347203 | GO:0006559\|GO:0006520\|GO:0004411\|GO:0005506\|GO:0016491\|GO:0006572\|GO:0046872\|GO:0055114 | NM_000187 | THC2691554 | Hs.368254 |
| A_33_P3275835 | TOR2A | *Homo sapiens* torsin family 2, member A (TOR2A), transcript variant 3, mRNA [NM_001134430] | NM_001134430 | ENST00000336067 | 27433 | torsin family 2, member A | chr9:130496638-130496579 | GO:0017111\|GO:0005179\|GO:0000166\|GO:0005783\|GO:0051085\|GO:0005576\|GO:0005524 | NM_001134430 | THC2485391 | Hs.444106 |
| A_33_P3306948 | LRP6 | *Homo sapiens* low density lipoprotein receptor-related protein 6 (LRP6), mRNA [NM_002336] | NM_002336 | ENST00000538239 | 4040 | low density lipoprotein receptor-related protein 6 | chr12:12269123-12269064 | GO:0005515\|GO:0005886\|GO:0030178\|GO:0005624\|GO:0007275\|GO:0009952\|GO:0001702\|GO:0006897\|GO:0005041\|GO:0042074\|GO:0035116\|GO:0004872\|GO:0016021\|GO:0035115\|GO:0060070\|GO:0042733 | NM_002336 | THC2652456 | Hs.584775 |
| A_33_P3289167 | 2BTB32 | *Homo sapiens* zinc finger and BTB domain containing 32 (ZBTB32), mRNA [NM_014383] | NM_014383 | ENST00000392197 | 27033 | zinc finger and BTB domain containing 32 | chr19:36206667-36206726 | GO:0005515\|GO:0030097\|GO:0003714\|GO:0003704\|GO:0005634\|GO:0000122\|GO:0000228\|GO:0001817\|GO:0003677\|GO:0046872\|GO:0005622\|GO:0042098 | NM_014383 | THC2475057 | Hs.99430 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3326553 | TMEM82 | Homo sapiens transmembrane protein 82 (TMEM82), mRNA [NM_001013641] | NM_001013641 | ENST00000375782 | 388595 | transmembrane protein 82 | chr1:16074418-16074477 | GO:0005654\|GO:0008270\|GO:0045449 | NM_001013641 | THC2477712 | Hs.454828 |
| A_23_P130169 | TBKBP1 | Homo sapiens TBK1 binding protein 1 (TBKBP1), mRNA [NM_014726] | NM_014726 | ENST00000361722 | 9755 | TBK1 binding protein 1 | chr17:45788549-45788608 | GO:0045087 | NM_014726 | THC2618682 | Hs.94790 |
| A_33_P3232945 | F2RL1 | Homo sapiens coagulation factor II (thrombin) receptor-like 1 (F2RL1), mRNA [NM_005242] | NM_005242 | ENST00000296677 | 2150 | coagulation factor II (thrombin) receptor-like 1 | chr5:76130985-76131044 | GO:0005794\|GO:0005886\|GO:0004930\|GO:0015057\|GO:0005102\|GO:0007204\|GO:0002690\|GO:0050927\|GO:0007165\|GO:0007186\|GO:0030193\|GO:0005887\|GO:0004872 | NM_005242 | THC2464357 | Hs.154299 |
| A_33_P3381870 | EPB49 | Homo sapiens erythrocyte membrane protein band 4.9 (dematin) (EPB49), transcript variant 1, mRNA [NM_001978] | NM_001978 | ENST00000358242 | 2039 | erythrocyte membrane protein band 4.9 (dematin) | chr8:21939976-21940035 | GO:0005737\|GO:0007010\|GO:0003779\|GO:0015629\|GO:0051017\|GO:0051693 | NM_001978 | THC2463142 | Hs.106124 |
| A_33_P3404889 | LPHN2 | latrophilin 2 [Source: HGNC Symbol; Acc:18582] | AB018329 | ENST00000370725 | 23266 | latrophilin 2 | chr1:82452653-82452712 | | | NP1249049 | Hs.24212 |
| A_33_P3789693 | MGC24103 | PREDICTED: Homo sapiens hypothetical MGC24103 (MGC24103), miscRNA [XR_108934] | XR_108934 | | 158295 | hypothetical MGC24103 | chr9:16526545-16526486 | | XR_108934 | NP1159657 | Hs.664877 |
| A_24_P253723 | C17orf91 | Homo sapiens chromosome 17 open reading frame 91 (C17orf91), transcript variant 1, non-coding RNA [NR_028502] | NR_028502 | | 84981 | chromosome 17 open reading frame 91 | chr17:1615641-1615582 | | NR_028502 | THC2662960 | Hs.597755 |
| A_33_P3282181 | ARHGAP4 | Homo sapiens Rho GTPase activating protein 4 (ARHGAP4), transcript variant 1, mRNA [NM_001164741] | NM_001164741 | ENST00000404127 | 393 | Rho GTPase activating protein 4 | chrX:153173028-153172969 | GO:0008624\|GO:0006915\|GO:0005634\|GO:0007266\|GO:0005100\|GO:0005829\|GO:0005085\|GO:0005622\|GO:0007165\|GO:0005737\|GO:0005070\|GO:0007010\|GO:0005925\|GO:0005096 | NM_001164741 | THC2528773 | Hs.701324 |
| A_32_P150876 | LOC339290 | Homo sapiens hypothetical LOC339290 (LOC339290), non- | NR_015389 | | 339290 | hypothetical LOC339290 | chr18:5245815-5245874 | | NR_015389 | THC2499959 | Hs.643553 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P148151 | TSNAX | Homo sapiens translin-associated factor X (TSNAX), mRNA [NM_005999] coding RNA [NR_015389] | NM_005999 | ENST00000475168 | 7257 | translin-associated factor X | chr1:231701692-231701751 | GO:0043565|GO:0048471|NM_005999 GO:0005737|GO:0008565| GO:0007275|GO:0005634| GO:0007283|GO:0030154 | NM_005999 | THC2467018 | Hs.13318 |
| A_23_P52986 | VWCE | Homo sapiens von Willebrand factor C and EGF domains (VWCE), mRNA [NM_152718] | NM_152718 | ENST00000335613 | 220001 | von Willebrand factor C and EGF domains | chr11:61025840-61025781 | GO:0005509|GO:0005576|NM_152718 | NM_152718 | THC2474163 | Hs.60640 |
| A_23_P200741 | DPT | Homo sapiens dermatopontin (DPT), mRNA [NM_001937] | NM_001937 | ENST00000367817 | 1805 | dermatopontin | chr1:168664807-168664748 | GO:0005515|GO:0008285|NM_001937 GO:0030199|GO:0005578| GO:0005576|GO:0007155 | NM_001937 | THC2466283 | Hs.80552 |
| A_33_P3339865 | CALML5 | Homo sapiens calmodulin-like 5 (CALML5), mRNA [NM_017422] | NM_017422 | ENST00000380332 | 51806 | calmodulin-like 5 | chr10:5540719-5540660 | GO:0005515|GO:0007165|NM_017422 GO:0008544|GO:0005509 | NM_017422 | THC2476793 | Hs.180142 |
| A_33_P3349591 | LOC100129461 | Homo sapiens cDNA clone IMAGE: 40108878. [BC133670] | BC133670 | | 100129461 | hypothetical LOC100129461 | chr6:5043050-5043109 | | | THC2497217 | Hs.131700 |
| A_33_P3396275 | C15orf62 | Homo sapiens chromosome 15 open reading frame 62 (C15orf62), mRNA [NM_001130448] | NM_001130448 | ENST00000344320 | 643338 | chromosome 15 open reading frame 62 | chr15:41063123-41063182 | GO:0005739 | NM_001130448 | THC2606201 | Hs.631715 |
| A_23_P301995 | LIN9 | Homo sapiens lin-9 (LIN9), homolog (C. elegans) mRNA [NM_173083] | NM_173083 | ENST00000366807 | 286826 | lin-9 homolog (C. elegans) | chr1:226453937-226453300 | GO:0006260|GO:0007049|NM_173083 GO:0005654|GO:0005634 | NM_173083 | THC2484578 | Hs.120817 |
| A_33_P3245660 | | | | | | | chr10:083262391-083262450 | | | | |
| A_33_P3238543 | LOC92659 | Homo sapiens hypothetical LOC92659 (LOC92659), non-coding RNA [NR_015454] | NR_015454 | | 92659 | hypothetical LOC92659 | chr17:79888548-79888607 | | NR_015454 | THC2602138 | Hs.336958 |
| A_33_P3243652 | LOC100131831 | Homo sapiens cDNA FLJ26174 fis, clone ADG03920. [AK129685] | AK129685 | | 100131831 | hypothetical LOC100131831 | chr19:13950921-13950862 | | | THC2704187 | Hs.625909 |
| A_33_P3277970 | LOC285299 | PREDICTED: Homo sapiens FSHD region gene 2 family, member C-like, transcript variant 2 (LOC285299), mRNA [XM_003119204] | XM_003119204 | | 285299 | FSHD region gene 2 family, member C-like | chrUn_gl000222:84037-83978 | | XM_003119204 | | Hs.722640 |
| A_23_P25445 | FAM186B | Homo sapiens family with sequence similarity | NM_032130 | ENST00000257894 | 84070 | family with sequence | chr12:49998152-49981468 | GO:0043234 | NM_032130 | THC2706486 | Hs.524406 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P30264 | | 186, member B (FAM186B), transcript variant 1, mRNA [NM_032130] | | | | similarity 186, member B | | | | | |
| A_33_P3302070 | IPO11 | Homo sapiens importin 11 (IPO11), transcript variant 2, mRNA [NM_016338] GB | NM_016338 | ENST00000512177 | 51194 | importin 11 | chr5:61897649-61923013 chr22:040965968 | GO:0005515|GO:0005737|NM_016338 GO:0008565|GO:0005634| GO:0006886 | NM_016338 | THC2757834 NP1243929 | Hs.482269 |
| A_33_P3252141 | TMX3 | Homo sapiens thioredoxin-related transmembrane protein 3 (TMX3), mRNA [NM_019022] | NM_019022 | ENST00000299608 | 54495 | thioredoxin-related transmembrane protein 3 | chr18:6634102 0-66340961 | GO:0016020|GO:0005783|NM_019022 GO:0003756|GO:0045454| GO:0016021|GO:0016853 | NM_019022 | THC2491286 | Hs.440534 |
| A_33_P3351524 | | | | | | | chr4:00958855 2-009588493 | | | | |
| A_33_P3324675 | | | | | | | chr19:0002987 01-000298642 | | | | |
| A_33_P3326235 | HBM | Homo sapiens hemoglobin, mu (HBM), mRNA [NM_001003938] | NM_001003938 | ENST00000472539 | 3042 | hemoglobin, mu | chr16:216693-216752 | GO:0019825|GO:0005833|NM_001003938 GO:0006810|GO:0005344| GO:0046872|GO:0020037| GO:0015671 | NM_001003938 | THC2477716 | Hs.647389 |
| A_33_P2270636 | SHISA5 | Homo sapiens shisa homolog 5 (Xenopus laevis) (SHISA5), mRNA [NM_016479] | NM_016479 | ENST00000417841 | 51246 | shisa homolog 5 (Xenopus laevis) | chr3:48511187-48511128 | GO:0031965|GO:0016020|NM_016479 GO:0005783|GO:0006915| GO:0005634|GO:0016021| GO:0004871|GO:0043123 | NM_016479 | NP1190817 | Hs.414579 |
| A_23_P207507 | ABCC3 | Homo sapiens ATP-binding cassette, sub-family C (CFTR/MRP), member 3 (ABCC3), transcript variant 1, mRNA [NM_003786] | NM_003786 | ENST00000503337 | 8714 | ATP-binding cassette, sub-family C (CFTR/MRP), member 3 | chr17:4876870 1-48768760 | GO:0005215|GO:0016020|NM_003786 GO:0000166|GO:0005887| GO:0042626|GO:0005624| GO:0008514|GO:0055085| GO:0016887|GO:0005524 | NM_003786 | THC2482842 | Hs.463421 |
| A_33_P3394868 | LOC388588 | Homo sapiens hypothetical protein LOC388588 (LOC388588), mRNA [NM_001163724] | NM_001163724 | ENST00000444870 | 388588 | hypothetical protein LOC388588 | chr1:3692432-3692491 | GO:0016020|GO:0016021|NM_001163724 | NM_001163724 | THC2729239 | Hs.22047 |
| A_24_P171182 | ACBD3 | Homo sapiens acyl-CoA binding domain containing 3 (ACBD3), mRNA [NM_022735] | NM_022735 | ENST00000366812 | 64746 | acyl-CoA binding domain containing 3 | chr1:22633333 2-226333273 | GO:0005739|GO:0005515|NM_022735 GO:0006694|GO:0005794| GO:0016020|GO:0000062 | NM_022735 | THC2610270 | Hs.520207 |
| A_33_P3423270 | TMEM40 | Homo sapiens transmembrane protein 40 (TMEM40), mRNA [NM_018306] | NM_018306 | ENST00000435218 | 55287 | transmembrane protein 40 | chr3:12775584-12775525 | GO:0016020|GO:0016021|NM_018306 | NM_018306 | THC2474070 | Hs.475502 |
| A_33_P3691615 | | Homo sapiens cDNA FLJ37626 fis, clone | AK094945 | ENST00000507023 | | | chr4:17859814 7-178598206 | | | THC2609012 | Hs.435077 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P166306 | CBS | BRCOC2014748. [AK094945] Homo sapiens cysta-thionine-beta-synthase (CBS), transcript variant 1, mRNA [NM_000071] | NM_000071 | ENST00000398168 | 875 | cystathionine-beta-synthase | chr21:44473378-44473319 | GO:0019343|GO:0070814|GO:0006535|GO:0005730|GO:0008652|GO:0005634|GO:0046872|GO:0042803|GO:0016829|GO:0005829|GO:0005737|GO:0043418|GO:0030170|GO:0008152|GO:0004122|GO:0006565|GO:0019448|GO:0031625|GO:0020037 | NM_000071 | THC2468454 | Hs.533013 |
| A_32_P58407 | KCND3 | potassium voltage-gated channel, Shal-related sub-family, member 3 [Source: HGNC Symbol; Acc: 6239] [ENST00000369697] | AF070632 | ENST00000369697 | 3752 | potassium voltage-gated channel, Shal-related sub-family, member 3 | chr1:112313618-112313559 | GO:0005515|GO:0005250|GO:0043005|GO:0005244|GO:0030955|GO:0055085|GO:0046872|GO:0042383|GO:0005249|GO:0008076|GO:0043025|GO:0008270|GO:0016021|GO:0006813|GO:0006811 | | THC2610807 | Hs.23729 |
| A_23_P118693 | FOXN1 | Homo sapiens forkhead box N1 (FOXN1), mRNA [NM_003593] | NM_003593 | ENST00000226247 | 8456 | forkhead box N1 | chr17:26865006-26865065 | GO:0043565|GO:0003700|GO:0008544|GO:0006357|GO:0030216|GO:0003704|GO:0009887|GO:0007275|GO:0006952|GO:0005634|GO:0050673 | NMJID03593 | THC2485086 | Hs.663679 |
| A_23_P54217 | TMEM151A | Homo sapiens trans-membrane protein 151A (TMEM151A), mRNA [NM_153266] | NM_153266 | ENST00000327259 | 256472 | transmembrane protein 151A | chr11:66063843-66063902 | GO:0016020|GO:0016021 | NM_153266 | THC2474571 | Hs.399779 |
| A_23_P138541 | AKR1C3 | Homo sapiens aldo-keto reductase family 1, member C3 (3-alpha hydroxysteroid dehydrogenase, type II) (AKR1C3), mRNA [NM_003739] | NM_003739 | ENST00000439082 | 8644 | aldo-keto reductase family 1, member C3 (3-alpha hydroxysteroid de-hydrogenase, type II) | chr10:5147789-5147848 | GO:0005622|GO:0047718|GO:0005737|GO:0004033|GO:0006693|GO:0047026|GO:0050327|GO:0047115|GO:0016491|GO:0047017|GO:0047045|GO:0055114 | NM_003739 | THC2463182 | Hs.78183 |
| A_23_P87011 | TAGLN | Homo sapiens trans-gelin (TAGLN), trans-cript variant 1, mRNA [NM_001001522] | NM_001001522 | ENST00000392951 | 6876 | transgelin | chr11:117075155-117075214 | GO:0005515|GO:0005737|GO:0007517|GO:0003779 | NM_001001522 | THC2499202 | Hs.410977 |
| A_23_P68851 | KREMEN1 | Homo sapiens kringle containing transmembrane protein 1 (KREMEN1), transcript variant 3, mRNA [NM_001039570] | NM_001039570 | ENST00000440338 | 83999 | kringle containing transmembrane protein 1 | chr22:29542505-29542564 | GO:0003674|GO:0007154|GO:0016020|GO:0005624|GO:0016021|GO:0016055 | NM_001039570 | THC2471664 | Hs.229335 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P256155 | NKX1-2 | Homo sapiens NK1 homeobox 2 (NKX1-2), mRNA [NM_001146340] | NM_001146340 | | 390010 | NK1 homeobox 2 | chr10:126136173-126136114 | GO:0043565\|GO:0006355\|GO:0003700\|GO:0007275\|GO:0005634 | NM_001146340 | | Hs.712041 |
| A_33_P3235204 | ELMOD3 | Homo sapiens ELMO/CED-12 domain containing 3 (ELMOD3), transcript variant 1, mRNA [NM_032213] | NM_032213 | ENST00000486908 | 84173 | ELMO/CED-12 domain containing 3 | chr2:85617562-85617621 | GO:0006909\|GO:0005856 | NM_032213 | THC2741273 | Hs.269990 |
| A_33_P3353365 | SLC17A4 | Homo sapiens solute carrier family 17 (sodium phosphate), member 4[Source: HGNC Symbol; Acc: 10932] [ENST00000397076] | BC109207 | ENST00000397076 | 10050 | solute carrier family 17 (sodium phosphate), member 4 | chr6:25776995-25777054 | | | THC2487373 | Hs.282931 |
| A_33_P3318267 | LOC100131193 | Homo sapiens hypothetical LOC100131193 (LOC100131193), non-coding RNA [NR_024580] | NR_024580 | ENST00000414656 | 100131193 | hypothetical LOC100131193 | chr9:139698673-139698614 | | NR_024580 | THC2481660 | Hs.668138 |
| A_23_P98350 | BIRC3 | Homo sapiens baculoviral IAP repeat containing 3 (BIRC3), transcript variant 1, mRNA [NM_001165] | NM_001165 | ENST00000263464 | 330 | baculoviral IAP repeat containing 3 | chr11:102208356-102208415 | GO:0005515\|GO:0004842\|GO:0006916\|GO:0042981\|GO:0007283\|GO:0051291\|GO:0046872\|GO:0005622\|GO:0043234\|GO:0005737\|GO:0008270\|GO:0045121\|GO:0007166 | NM_001165 | THC2463921 | Hs.127799 |
| A_23_P104509 | FAM53B | Homo sapiens family with sequence similarity 53, member B (FAM53B), mRNA [NM_014661] | NM_014661 | ENST00000280780 | 9679 | family with sequence similarity 53, member B | chr10:126370389-126370330 | GO:0008150\|GO:0003674\|GO:0005575 | NM_014661 | THC2475876 | Hs.129195 |
| A_33_P3243248 | ZNFX1 | Homo sapiens zinc finger, NFX1-type containing 1 [Source: HGNC Symbol; Acc: 29271] [ENST00000469991] | | ENST00000469991 | 57169 | zinc finger, NFX1-type containing 1 | Chr20:47861201-47861142 | | | | Hs.30977 |
| A_33_P3378047 | SESTD1 | Homo sapiens SEC14 and spectrin domains 1 (SESTD1), mRNA [NM_178123] | NM_178123 | ENST00000428443 | 91404 | SEC14 and spectrin domains 1 | chr2:179973718-179973659 | GO:0005515 | NM_178123 | | |
| A_23_P38168 | FBXL19 | Homo sapiens F-box and leucine-rich repeat protein 19 (FBXL19), mRNA [NM_001099784] | NM_001099784 | ENST00000338343 | 54620 | F-box and leucine rich repeat protein 19 | chr16:30959177-30959236 | GO:0005515\|GO:0019941\|GO:0008270\|GO:0003677\|GO:0046872 | NM_001099784 | THC2686436 | Hs.152149 |
| A_33_P3362068 | LOC100129149 | LOC100129149 full-length cDNA clone CS0DI084YD11 of Placenta Cot 25-normal- | CR595361 | | 100129149 | hypothetical protein LOC100129149 | chr2:37899733-37899792 | | | THC2688744 | Hs.369574 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3233834 | IL6ST | ized of *Homo sapiens* (human). [CR595361] *Homo sapiens* interleukin 6 signal transducer (gp130, oncostatin M receptor) (IL6ST), transcript variant 3, mRNA [NM_00119C981] | NM_001190981 | ENST00000542298 | 3572 | interleukin 6 signal transducer (gp130, oncostatin M receptor) | chr5:55260096-55260037 | GO:0005138\|GO:0004921\|GO:0005886\|GO:0008284\|GO:0005886\|GO:0004924\|GO:0004923\|GO:0042803\|GO:0070110\|GO:0014911\|GO:0002675\|GO:0042102\|GO:0004872\|GO:0004897\|GO:0034097\|GO:0002821\|GO:0008593\|GO:0010613\|GO:0070106\|GO:0007584\|GO:0042517\|GO:0004915\|GO:0051481\|GO:0005977\|GO:0042511\|GO:0005896\|GO:0005576\|GO:0070120\|GO:0045768\|GO:0007259\|GO:0010575\|GO:0005127\|GO:0045669\|GO:0007165\|GO:0048861\|GO:0045509\|GO:0016021\|GO:0045509\|GO:0006642\|GO:0009897 | NM_001190981 | NP1400573 | Hs.532082 |
| A_23_P54576 | KIFC3 | *Homo sapiens* kinesin family member C3 (KIFC3), transcript variant 1, mRNA [NM_005550] | NM_005550 | ENST00000539578 | 3801 | kinesin family member C3 | chr16:57794465-57794283 | GO:0005871\|GO:0005794\|NM_005550\|GO:0001666\|GO:0005874\|GO:0007030\|GO:0003777\|GO:0007601\|GO:0005524\|GO:0007018 | NM_005550 | NP1473422 | Hs.23131 |
| A_23_P435407 | GPC4 | *Homo sapiens* glypican 4 (GPC4), mRNA [NM_001448] | NM_001448 | ENST00000536418 | 2239 | glypican 4 | chrX:132435488-132435429 | GO:0005886\|GO:0008283\|NM_001448\|GO:0005887\|GO:0005578\|GO:0043395\|GO:0005576\|GO:0031225\|GO:0009653\|GO:0005615 | NM_001448 | THC2475418 | Hs.58367 |
| A_24_P649747 | BMS1 | *Homo sapiens* BMS1 homolog, ribosome assembly protein (yeast) (BMS1), mRNA [NM_014753] | NM_014753 | ENST00000374518 | 9790 | BMS1 homolog, ribosome assembly protein (yeast) | chr10:43317522-43317581 | GO:0000166\|GO:0042255\|NM_014753\|GO:0005730\|GO:0005634\|GO:0005524 | NM_014753 | THC2585704 | Hs.10848 |
| A_24_P510357 | | immunoglobulin lambda variable 2-14 [Source: HGNC Symbol; Acc: 5888] [ENST00000390312] | S76132 | ENST00000390312 | | | chr22:23101631-23101690 | | | NP1087720 | Hs.625768 |
| A_23_P156620 | ZNF184 | *Homo sapiens* zinc finger protein 184 (ZNF184), mRNA [NM_007149] | NM_007149 | ENST00000377419 | 7738 | zinc finger protein 184 | chr6:27419044-27418985 | GO:0005622\|GO:0006355\|NM_007149\|GO:0005737\|GO:0008270\|GO:0005634\|GO:0003677\|GO:0046872 | NM_007149 | THC2489060 | Hs.158174 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3290672 | SELT | Homo sapiens seleno-protein T (SELT), mRNA [NM_016275] | NM_016275 | | 51714 | seleno-protein T | chr3:150348174-150348233 | GO:0008430\|GO:0001514\|GO:0045454 | NM_016275 | THC2731852 | Hs.369052 |
| A_33_P3325275 | NRSN2 | Homo sapiens neurensin 2 (NRSN2), mRNA [NM_024958] | NM_024958 | ENST00000382285 | 80023 | neurensin 2 | chr20:334382-334441 | GO:0030133\|GO:0008150\|GO:0003674\|GO:0005886\|GO:0043025\|GO:0016021 | NM_024958 | THC2605727 | Hs.416024 |
| A_33_P3313411 | ARHGAP33 | Homo sapiens Rho GTPase activating protein 33 (ARHGAP33), transcript variant 2, mRNA [NM_001172630] | NM_001172630 | ENST00000007510 | 115703 | Rho GTPase activating protein 33 | chr19:36278925-36278984 | GO:0005622\|GO:0005515\|GO:0007165\|GO:0005737\|GO:0005886\|GO:0035091\|GO:0015031\|GO:0030675\|GO:0005096 | NM_001172630 | NP107616 | Hs.515364 |
| A_33_P3248749 | RSPH9 | radial spoke head 9 homolog (Chlamydomonas) [Source: HGNC Symbol; Acc: 21057] [ENST00000372154] | AK055407 | ENST00000372154 | 221421 | radial spoke head 9 homolog (Chlamydomonas) | chr6:43640091-43640150 | | | THC2478697 | |
| A_23_P258912 | MYOM2 | Homo sapiens myo-mesin (M-protein) 2, 165 kDa (MYOM2), mRNA [NM_003970] | NM_003970 | ENST00000520298 | 9172 | myomesin (M-protein) 2, 165 kDa | chr8:2093070-2093129 | GO:0032982\|GO:0006936\|GO:0008307 | NM_003970 | THC2644431 | Hs.443683 |
| A_23_P3245908 | C10orf128 | Homo sapiens chromosome 10 open reading frame 128 (C10orf128), mRNA [NM_001010863] | NM_001010863 | ENST00000453436 | 170371 | chromosome 10 open reading frame 128 | chr10:50363949-50363890 | GO:0016020\|GO:0016021 | NM_001010863 | NP1203955 | Hs.385493 |
| A_33_P3252146 | HMX3 | Homo sapiens H6 family homeobox 3 (HMX3), mRNA [NM_001105574] | NM_001105574 | ENST00000357878 | 340784 | H6 family homeobox 3 | chr10:124897188-124897247 | GO:0043565\|GO:0006355\|GO:0042472\|GO:0003700\|GO:0007566\|GO:0007420\|GO:0060135\|GO:0050885\|GO:0005634\|GO:0030154\|GO:0007399 | NM_001105574 | | Hs.531194 |
| A_23_P43157 | MYBL1 | Homo sapiens v-myb myeloblastosis viral oncogene homolog (avian)-like 1 (MYBL1), transcript variant 1, mRNA [NM_001080416] | NM_001080416 | ENST00000522677 | 4603 | v-myb myeloblastosis viral oncogene homolog (avian)-like 1 | chr8:67474765-67474706 | GO:0006355\|GO:0016563\|GO:0005730\|GO:0005634\|GO:0003677 | NM_001080416 | THC2621930 | Hs.445898 |
| A_33_P3252441 | | | | ENST00000440582 | | | chr17:39258066-39258007 | | | | |
| A_33_P3387901 | SLC25A19 | Homo sapiens solute carrier family 25 (mitochondrial thiamine pyrophosphate carrier), member 19 | NM_001126121 | ENST00000402418 | 60386 | solute carrier family 25 (mitochondrial thiamine pyrophosphate | chr17:73279612-73279553 | GO:0005739\|GO:0005215\|GO:0016020\|GO:0005488\|GO:0030302\|GO:0005743\|GO:0016021\|GO:0055085\|GO:0030233 | NM_001126121 | THC2634425 | Hs.514470 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (SLC25A19), nuclear gene encoding mitochondrial protein, transcript variant 1, mRNA [NM_001126121] | | | | carrier), member 19 | | | | | |
| A_23_P326319 | C16orf45 | Homo sapiens chromosome 16 open reading frame 45 (C16orf45), transcript variant 1, mRNA [NM_033201] | NM_033201 | ENST00000300006 | 89927 | chromosome 16 open reading frame 45 | chr16:15681608-15681667 | GO:0005515 | NM_033201 | THC2497958 | Hs.401798 |
| A_33_P3281795 | MGLL | Homo sapiens monoglyceride lipase (MGLL), transcript variant 1, mRNA [NM_007283] | NM_007283 | ENST00000265052 | 11343 | monoglyceride lipase | chr3:127407970-127407911 | GO:0006629\|GO:0006954\|GO:0016787\|GO:0004622\|GO:0047372 | NM_007283 | THC2532122 | Hs.277035 |
| A_23_P43490 | CDKN2A | Homo sapiens cyclin-dependent kinase inhibitor 2A (melanoma, p16, inhibits CDK4) (CDKN2A), transcript variant 3, mRNA [NM_058197] | NM_058197 | ENST00000530628 | 1029 | cyclin-dependent kinase inhibitor 2A (melanoma, p16, inhibits CDK4) | chr9:21968098-21968039 | GO:0033088\|GO:0005515\|GO:0048103\|GO:0030308\|GO:0003700\|GO:0008285\|GO:0001652\|GO:0045736\|GO:0006364\|GO:0009303\|GO:0005634\|GO:0005737\|GO:0000082\|GO:0031647\|GO:0008637\|GO:0051444\|GO:0007050\|GO:0055105\|GO:0046822\|GO:0006355\|GO:0051059\|GO:0019901\|GO:0006919\|GO:0007569\|GO:0010389\|GO:0005730\|GO:0030889\|GO:0032088\|GO:0006917\|GO:0042326\|GO:0010149\|GO:0007049\|GO:0008544\|GO:0006309\|GO:0004861\|GO:0000075\|GO:0005654\|GO:0001953 | NM_058197 | THC2696182 | Hs.512599 |
| A_23_P19291 | TUBB2A | Homo sapiens tubulin, beta 2A (TUBB2A), mRNA [NM_001069] | NM_001069 | ENST00000333628 | 7280 | tubulin, beta 2A | chr6:3154094-3154035 | GO:0005515\|GO:0051258\|GO:0007067\|GO:0000166\|GO:0005198\|GO:0030182\|GO:0005874\|GO:0003924\|GO:0005525\|GO:0007018 | NM_001069 | THC2495718 | Hs.654543 |
| A_33_P3213006 | KRTAP1-3 | Homo sapiens keratin associated protein 1-3 (KRTAP1-3), mRNA [NM_030966] | NM_030966 | ENST00000377747 | 81850 | keratin associated protein 1-3 | chr17:039186024-039185965 | GO:0008150\|GO:0005576\|GO:0045095\|GO:0030280 | NM_030966 | THC2487206 | Hs.534495 |
| A_23_P84929 | SLC38A5 | Homo sapiens solute carrier family 38, member 5 (SLC38A5), mRNA [NM_033518] | NM_033518 | ENST00000462359 | 92745 | solute carrier family 38, member 5 | chrX:48317923-48317363 | GO:0015816\|GO:0015171\|GO:0005886\|GO:0006865\|GO:0015187\|GO:0016021 | NM_033518 | THC2461839 | Hs.195155 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P500410 | ATP6V1G2 | Homo sapiens ATPase, H+ transporting, lysosomal 13 kDa, V1 subunit G2 (ATP6V1G2), transcript variant 1, mRNA [NM_130463] | NM_130463 | ENST00000303892 | 534 | ATPase, H+ transporting, lysosomal 13 kDa, V1 subunit G2 | chr6:31512332-31512273 | GO:0005515\|GO:0042470\|GO:0016820\|GO:0016471\|GO:0015992\|GO:0006811 | NM_130463 | THC2504847 | Hs.249227 |
| A_33_P3363305 | | | | | | | chr11:0712797 48-071279807 | | | | |
| A_24_P366787 | FLJ42875 | Homo sapiens hypothetical LOC440556 (FLJ42875), transcript variant 2, non-coding RNA [NR_024371] | NR_024371 | ENST00000321336 | 440556 | hypothetical LOC440556 | chr1:2983914-2980821 | | NR_024371 | THC2478677 | Hs.531041 |
| A_23_P392470 | NR3C2 | Homo sapiens nuclear receptor subfamily 3, group C, member 2 (NR3C2), transcript variant 1, mRNA [NM_000901] | NM_000901 | ENST00000358102 | 4306 | nuclear receptor subfamily 3, group C, member 2 | chr4:14900042 3-149000364 | GO:0005515\|GO:0006355\|GO:0003700\|GO:0005783\|GO:0003707\|GO:0005634\|GO:0046872\|GO:0043565\|GO:0007165\|GO:0005737\|GO:0016020\|GO:0004872\|GO:0008270\|GO:0005496\|GO:0019898 | NM_000901 | THC2640620 | Hs.163924 |
| A_32_P834166 | LOC100128843 | Homo sapiens DNA polymerase epsilon catalytic subunit isoform a (POLE1) mRNA, partial cds. [AF128541] | AF128541 | | 100128843 | hypothetical LOC100128843 | chr12:1334135 70-133413511 | | | THC2641609 | Hs.657680 |
| A_33_P3335506 | FCRL5 | Fc receptor-like 5 [Source: HGNC Symbol; Acc: 18508] [ENST00000368190] | AF343662 | ENST00000368190 | 83416 | Fc receptor-like 5 | chr1:15749367 3-157493614 | | | THC2478268 | Hs.415950 |
| A_33_P3332396 | TMEM53 | Homo sapiens transmembrane protein 53 (TMEM53), mRNA [NM_024587] | NM_024587 | ENST00000372243 | 79639 | transmembrane protein 53 | chr1:45125906-45125847 | GO:0005794\|GO:0005886\|GO:0016021\|GO:0005925 | NM_024587 | THC2507947 | Hs.22157 |
| A_33_P3421611 | | Q96I88 HUMAN Q96I88) THADA protein (Fragment), partial (8%) [THC2552587] | | ENST00000423354 | | | chr2:43460474-43460533 | | | THC2552587 | |
| A_23_P255663 | MANEA | Homo sapiens mannosidase, endo alpha (MANEA), mRNA [NM_024641] | NM_024641 | ENST00000358812 | 79694 | mannosidase, endo-alpha | chr6:96056776-96056835 | GO:0005794\|GO:0016787\|GO:0016020\|GO:0016021\|GO:0004569 | NM_024641 | THC2492910 | Hs.730770 |
| A_33_P3339109 | POLR1C | polymerase (RNA) 1 polypeptide C, 30 kDa (Source: HGNC | CA416988 | ENST00000512472 | 9533 | polymerase (RNA) 1 polypeptide | chr6:43487252-43487311 | | | THC2626465 | Hs.73098 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P316019 | | Symbol; Acc: 201941 [ENST00000512472] Putative golgin subfamily A member 6-like protein 11 [Source: UniProtKB/Swiss-Prot; Acc: A6NCC3] [ENST00000333156] | XM_003118656 | ENST00000333156 | | C, 30 kDa | chr15:30851124-30851438 | | XM_003118656 | THC2557844 | Hs.568189 |
| A_33_P3257279 | TMEM145 | Homo sapiens transmembrane protein 145 (TMEM145), mRNA [NM_173633] | NM_173633 | ENST00000301204 | 284339 | transmembrane protein 145 | chr19:42829137-42829196 | GO:0016020|GO:0016021 | NM_173633 | THC2483750 | Hs.382075 |
| A_23_P4494 | DSC2 | Homo sapiens desmocollin 2 (DSC2), transcript variant Dsc2a, mRNA [NM_024422] | NM_024422 | ENST00000399347 | 1824 | desmocollin 2 | chr18:28651609-28650796 | GO:0030057|GO:0005515|GO:0024422|GO:0030054|GO:0005886|GO:0005509|GO:0016021|GO:0007155|GO:0007156 | NM_024422 | THC2462770 | Hs.95612 |
| A_33_P3358213 | PADI6 | Homo sapiens peptidyl arginine deiminase, type VI (PADI6), mRNA [NM_207421] | NM_207421 | ENST00000434762 | 353238 | peptidyl arginine deiminase, type VI | chr1:17728136-17728195 | GO:0018101|GO:0005737|NM_207421|GO:0016787|GO:0005509|GO:0005634|GO:0045111|GO:0004668|GO:0006464 | NM_207421 | THC2448002 | Hs.531598 |
| A_33_P3369761 | PDP1 | Homo sapiens pyruvate dehyrogenase phosphatase catalytic subunit 1 (PDP1), nuclear gene encoding mitochondrial protein, transcript variant 2, mRNA [NM_001161779] | NM_001161779 | ENST0000396200 | 54704 | pyruvate dehydrogenase phosphatase catalytic subunit 1 | chr8:94938235-94938294 | GO:0005739|GO:0008287|NM_001161779|GO:0006470|GO:0004741|GO:0000287|GO:0016787|GO:0005759|GO:0005509|GO:0004724|GO:0032403 | NM_001161779 | THC2466932 | Hs.22265 |
| A_33_P3244828 | | | | | | | chr14:102231782-102231841 | | | THC2779931 | |
| A_33_P3272352 | | HCG1988162 Uncharacterized protein [Source: UniProtKB/TrEMBL; Acc: A8MTT3] [ENST00000397064] | | ENST00000397064 | | | chr2:37440789-37440848 | | | | |
| A_33_P3257678 | HIST2H3A | Homo sapiens histone cluster 2, H3a (HIST2H3A), mRNA [NM_001005464] | NM_001005464 | ENST00000369158 | 333932 | histone cluster 2, H3a | chr1:149824626-149824685 | | NM_001005464 | THC2479197 | Hs.706618 |
| A_33_P3354322 | GPX1 | Homo sapiens glutathione peroxidase 1 (GPX1), transcript variant 2, mRNA [NM_201397] | NM_201397 | ENST00000419783 | 2876 | glutathione peroxidase 1 | chr3:49394667-49394608 | GO:0006629|GO:0051897|NM_201397|GO:0042542|GO:0060047|GO:0017124|GO:0009650|GO:0001659|GO:0002862|GO:0007605|GO:0006749|GO:0001836|GO:0005829|GO:0005739|GO:0004602|GO:0045523|GO:0005737 | NM_201397 | | Hs.76686 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | | | | | | | GO:0008430|GO:0042311| GO:0018158|GO:0045444| GO:0043403|GO:0043154| GO:0042744|GO:0009410| GO:0033194|GO:0010332| GO:0014902|GO:0051702| GO:0060055|GO:0008631| GO:0009611|GO:0009636| GO:0010269|GO:0006916| GO:0006917|GO:0008539| GO:0033599|GO:0043534| GO:0001885|GO:0009609| GO:0016491|GO:0040029| GO:0006641|GO:0045454| GO:0051450|GO:0055114 | | | |
| A_33_P3379463 | LYPLA2 | Homo sapiens lyso-phospholipase II (LYPLA2), mRNA [NM_007260] | NM_007260 | ENST00000374506 | 11313 | lysophos-pholipase II | chr1:24121848-24121907 | GO:0006629|GO:0005737|NM_007260 GO:0016787|GO:0006631 | | THC2602100 | Hs.533479 |
| A_23_P500206 | IL17RE | Homo sapiens interleukin 17 receptor E (IL17RE), transcript variant 5, mRNA [NM_153483] | NM_153483 | ENST00000295980 | 132014 | interleukin 17 receptor E | chr3:9957731-9957790 | GO:0005737|GO:0016020|NM_153483 GO:0005576|GO:0004872| GO:0016021 | | THC2478460 | Hs.390823 |
| A_33_P3256785 | CARM1 | Homo sapiens coacti-vator-associated arginine methyltransferase 1 (CARM1), mRNA [NM_199141] | NM_199141 | ENST00000344150 | 10498 | coactivator-associated arginine methyl transferase 1 | chr19:1103328 0-11033339 | GO:0005515|GO:0006355|NM_199141 GO:0005737|GO:0044419| GO:0016571|GO:0003713| GO:0005634|GO:0008276| GO:0008469|GO:0016740| GO:0034970|GO:0016568 | | THC2493442 | Hs.323213 |
| A_33_P3319331 | PRDM2 | Homo sapiens cDNA FLJ41611 fis, clone CTONG3002020. [AK123605] | AK123605 | | 7799 | PR domain containing 2, with ZNF domain | chr1:14146910-14146969 | GO:0005622|GO:0006355| GO:0005794|GO:0003700| GO:0008168|GO:0008270| GO:0005634|GO:0046872| GO:0016740|GO:0018024 | | THC2632509 | |
| A_33_P3221960 | IL18RAP | Homo sapiens interleukin 18 receptor accessory protein (IL18RAP), mRNA [NM_003853] | NM_003853 | ENST00000264260 | 8807 | interleukin 18 receptor accessory protein | chr2:10306869 5-103068754 | GO:0006954|GO:0016020|NM_003853 GO:0045087|GO:0016021| GO:0007166|GO:0004888 | | THC2489002 | Hs.158315 |
| A_33_P3233125 | PSD | Homo sapiens pleckstrin and Sec7 domain con-taining (PSD), mRNA [NM_002779] | NM_002779 | ENST00000020673 | 5662 | pleckstrin and Sec7 domain containing | chr10:1041624 36-104162377 | GO:0005622|GO:0007165|NM_002779 GO:0005086|GO:0030182| GO:0032012|GO:0016021| GO:0005575|GO:0004871 | | THC2491352 | Hs.154658 |
| A_33_P3388883 | | | | | | | chr1:14487327 3-144873214 | | | | |
| A_23_P39453 | MEX3D | Homo sapiens mex-3 homolog D (C. elegans) (MEX3D), transcript | NM_203304 | ENST00000402693 | 399664 | mex-3 homolog D (C. elegans) | chr19:1555264-1555205 | GO:0005515|GO:0005737|NM_203304 GO:0003723|GO:0008270| GO:0005634|GO:0046872 | | THC2473313 | Hs.436495 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3420862 | PAGE2B | variant 1, mRNA [NM_203304] *Homo sapiens* P antigen family, member 2B (PAGE2B), mRNA [NM_001015038] | NM_001015038 | ENST00000453343 | 389860 | P antigen family, member 2B | chrX:55103897-55103956 | | NM_001015038 | THC2476714 | Hs.293317 |
| A_33_P3424861 | FAM118A | *Homo sapiens* family with sequence similarity 118, member A (FAM118A), transcript variant 1, mRNA [NM_001104595] | NM_001104595 | ENST00000216214 | 55007 | family with sequence similarity 118, member A | chr22:45736795-45736854 | GO:0016020|GO:0016021 | NM_001104595 | THC2595955 | Hs.265018 |
| A_33_P3408665 | | | | | | | chr11n_gl000217:000049977-000050036 | | | | |
| A_24_P188800 | 1-Mar | *Homo sapiens* membrane-associated ring finger (C3HC4) 1 (MARCH1), transcript variant 2, mRNA [NM_017923] | NM_017923 | ENST00000339875 | 55016 | membrane-associated ring finger(C3HC4) 1 | chr4:164449262-164449203 | GO:0016020|GO:0019941|GO:0016874|GO:0008270|GO:0031410|GO:0016021|GO:0046872 | NM_017923 | THC2483811 | HS.S92804 |
| A_23_P2077 | OR4C3 | *Homo sapiens* olfactory receptor, family 4, subfamily C, member 3 (OR4C3), mRNA [NM_001004702] | NM_001004702 | ENST00000395239 | 256144 | olfactory receptor, family 4, subfamily C, member 3 | chr11:4834713-48347196 | GO:0007608|GO:0007165|GO:0004984|GO:0007186|GO:0005886|GO:0004872|GO:0016021|GO:0050896 | NM_001004702 | NP1461863 | Hs.553656 |
| A_23_P414308 | FLCN | *Homo sapiens* folliculin 2, (FLCN) transcript variant mRNA [NM_144606] | NM_144606 | ENST00000389169 | 201163 | folliculin | chr17:1712472-17124668 | GO:0005515|GO:0005737 | NM_144606 | THC2629147 | Hs.31652 |
| A_23_P303891 | LCE1C | *Homo sapiens* late cornified envelope 1C (LCE1C), mRNA [NM_178351] | NM_178351 | ENST00000368768 | 353133 | late cornified envelope 1C | chr1:152777789-152777835 | GO:0031424 | NM_17835] | NP1250118 | Hs.516429 |
| A_32_P116556 | ZNF469 | *Homo sapiens* zinc finger protein 469 (ZNF469), mRNA [NM_001127464] | NM_001127464 | ENST00000437464 | 84627 | zinc finger protein 469 | chr16:8850708-88507146 | GO:0005622|GO:0008270|GO:0005634|GO:0003677|GO:0046872|GO:0045449 | NM_001127464 | THC2497481 | Hs.54925 |
| A_33_P3366780 | | Q9UQ53_HUMAN (Q9UQ53) UDP-N-acetylglucosamine:alpha-1,3-D-mannoside beta-1,4-N-acetylglucosaminyltransferase IV (Aminyltransferase), | | | | | chr5:17922434-2-179224283 | GO:0005794|GO:0016758|GO:0016020|GO:0005975|GO:0006491|GO:0016021|GO:0046872|GO:0008454 | | THC2478738 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P413788 | FUT11 | partial (94%) [THC2478738] Homo sapiens fucosyl transferase 11 (alpha (1,3) fucosyltransferase) (FUT11), mRNA [NM_173540] | NM_173540 | ENST00000372841 | 170384 | fucosyl-transferase 11 (alpha (1,3) fucosyl-transferase) | chr10:7553558 6-75535645 | GO:0046920\|GO:0005794\|NM_173540 GO:0016020\|GO:0000139\| GO:0016757\|GO:0006486\| GO:0016027 | THC2473454 | Hs.588854 |
| A_33_P3311907 | TBC1D7 | Homo sapiens TBC1 domain family, member 7 (TBC1D7), transcript variant 3, mRNA [NM_001143965] | NM_001143965 | ENST00000379291 | 51256 | TBC1 domain family, member 7 | chr6:13325400-13325341 | GO:0005622\|GO:0032313\|NM_001143965 GO:0005097\|GO:0005096 | THC2546522 | Hs.484678 |
| A_23_P56328 | PLVAP | Homo sapiens plasma-lemma vesicle associated protein (PLVAP), mRNA [NM_031310] | NM_031310 | ENST00000252590 | 83483 | plasmalemma vesicle associated protein | chr19:1746270 1-17462642 | GO:0048471\|GO:0005737\|NM_031310 GO:0005886\|GO:0005901\| GO:0016021\|GO:0042803 | NP499212 | Hs.107125 |
| A_23_P20248 | MAP2K1 | Homo sapiens mitogen-activated protein kinase kinase 1 (MAP2K1), mRNA [NM_002755] | NM_002755 | ENST00000307102 | 5604 | mitogen-activated protein kinase kinase 1 | chr15:6678322 4-66783283 | GO:0005515\|GO:0048471\|NM_002755 GO:0005886\|GO:0008283 GO:0045597\|GO:0006928 GO:0032839\|GO:0007265 GO:0051291\|GO:0048678 GO:0032402\|GO:0005829 GO:0000187\|GO:0000166 GO:0030182\|GO:0043204 GO:0006935\|GO:0047496 GO:0004728\|GO:0005938 GO:0006979\|GO:0017016 GO:0004708\|GO:0048313 GO:0005874\|GO:0051384 GO:0034111\|GO:0031435 GO:0005625\|GO:0005524 GO:0033267\|GO:0007067 GO:0032320\|GO:0004674 GO:0030216\|GO:0048812 GO:0003056\|GO:0032968 GO:0004713\|GO:0016740 | THC2560714 | Hs.145442 |
| A_24_P366566 | OR5H1 | Homo sapiens olfactory receptor, family 5, subfamily H, member 1 (OR5H1), mRNA [NM_001005338] | NM_001005338 | ENST00000354565 | 26341 | olfactory receptor, family 5, subfamily H, member 1 | chr3:97852262-97852321 | GO:0007608\|GO:0007165\|NM_001005338 GO:0004984\|GO:0007186\| GO:0005886\|GO:0004872\| GO:0016021\|GO:0050896 | THC2603706 | Hs.537383 |
| A_33_P3337318 | HNRNPA2B1 | heterogeneous nuclear ribonucleoprotein A2/B1 [Source: HGNC Symbol; Acc: 5033] [ENST00000490912] | BX641084 | ENST00000490912 | 3181 | heterogeneous nuclear ribo-nucleoprotein A2/B1 | chr7:26241033-26240974 | | | THC2503695 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P247273 | | chromosome 11 open reading frame 89 [Source: HGNC Symbol; Acc: 35118] [ENST00000391480] | | ENST00000391480 | | | chr11:1910450-1910391 | | | | |
| A_23_P142631 | FKBP1B | Homo sapiens FK506 binding protein 1B, 12.6 kDa (FKBP1B), transcript variant 2, mRNA [NM_054033] | NM_054033 | ENST00000496149 | 2281 | FK506 binding protein 1B, 12.6 kDa | chr2:24286286-24286345 | GO:0010459\|GO:0003755\|GO:0005102\|GO:0033017\|GO:0005528\|GO:0010881\|GO:0014808\|GO:0034704\|GO:0019227\|GO:0022417\|GO:0005829\|GO:0009749\|GO:0006939\|GO:0042026\|GO:0005737\|GO:0042098\|GO:0006458\|GO:0032234\|GO:0060314\|GO:0032513\|GO:0051775\|GO:0016853\|GO:0030073\|GO:0005219 | NM_054033 | NP090150 | Hs.709461 |
| A_24_P169073 | FAM131C | Homo sapiens family with sequence similarity 131, member C (FAM131C), mRNA [NM_182623] | NM_182623 | ENST00000375662 | 348487 | family with sequence similarity 131, member C | chr1:16384334-16384275 | | NM_182623 | THC2475284 | Hs.126825 |
| A_23_P37623 | GOLGA8A | Homo sapiens golgin A8 family, member A (GOLGA8A), transcript variant 1, mRNA [NM_181077] | NM_181077 | ENST00000543376 | 23015 | golgin A8 family, member A | chr15:34672222-34672165 | GO:0005794\|GO:0016020\|GO:0019898 | NM_181077 | THC2473197 | Hs.720151 |
| A_33_P3347976 | MIB1 | Homo sapiens mindbomb homolog 1 (Drosophila) (MIB1), mRNA [NM_020774] | NM_020774 | ENST00000261537 | 57534 | mindbomb homolog 1 (Drosophila) | chr18:19450664-19450723 | GO:0005515\|GO:0004842\|GO:0001568\|GO:0016567\|GO:0005886\|GO:0016874\|GO:0001756\|GO:0031410\|GO:0001701\|GO:0046872\|GO:0001841\|GO:0045807\|GO:0001947\|GO:0007507\|GO:0005737\|GO:0045665\|GO:0007219\|GO:0019941\|GO:0008270 | NM_020774 | THC2512091 | Hs.140903 |
| A_33_P3262069 | OR2AG2 | Homo sapiens olfactory receptor, family 2, subfamily AG, member 2 (OR2AG2), mRNA [NM_001004490] | NM_001004490 | ENST00000338569 | 338755 | olfactory receptor, family 2, subfamily AG, member 2 | chr11:6789602-6789543 | GO:0007608\|GO:0007165\|GO:0004984\|GO:0007186\|GO:0005886\|GO:0004872\|GO:0016021\|GO:0050896 | NM_001004490 | NP1461805 | Hs.534614 |
| A_33_P3354975 | MTMR9LP | Homo sapiens myotubularin related protein 9-like, pseudogene (MTMR9LP), non- | NR_026850 | ENST00000403496 | 339483 | myotubularin related protein 9-like, | chr1:32697727-32697668 | | NR_026850 | THC2547854 | Hs.471067 |

APPENDIX C-continued

FEMALES: Technology: AgilentSingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P205031 | COL4A2 | coding RNA [NR_026850] Homo sapiens collagen, type IV, alpha 2 (COL4A2), mRNA [NM_001846] | NM_001846 | ENST00000360467 | 1284 | pseudogene collagen, type IV, alpha 2 | chr13:111165261-111165320 | GO:0005515\|GO:0005811\|NM_001846 GO:0030198\|GO:0016525\| GO:0005587\|GO:0005576\| GO:0005201 | | THC2549560 | Hs.508716 |
| A_33_P3296567 | PRRC2B | Homo sapiens proline-rich coiled-coil 2B (PRRC2B), mRNA [NM_013318] | NM_013318 | ENST00000422467 | 84726 | proline-rich coiled coil 2B | chr9:134343084-134346175 | | NM_013318 | THC2515770 | Hs.495349 |
| A_33_P3306163 | LGALS3 | Homo sapiens lectin, galactoside-binding, soluble, 3 (LGALS3), transcript variant 3, mRNA [NM_001177388] | NM_001177388 | ENST00000254301 | 3958 | lectin, galactoside-binding, soluble, 3 | chr14:55605026-55605085 | GO:0005515\|GO:0019863\|NM_001177388 GO:0005737\|GO:0001501\| GO:0005886\|GO:0030198\| GO:0005578\|GO:0005529\| GO:0005634\|GO:0030154 | | THC2788354 | Hs.531081 |
| A_23_P112774 | PTP4A3 | Homo sapiens protein tyrosine phosphatase type IVA, member 3 (PTP4A3), transcript variant 1, mRNA [NM_032611] | NM_032611 | ENST00000520105 | 11156 | protein tyrosine phosphatase type IVA, member 3 | chr8:142441433-142441492 | GO:0006470\|GO:0016787\|NM_032611 GO:0005886\|GO:0004727\| GO:0005769\|GO:0042802 | | THC2463792 | Hs.43666 |
| A_33_P3299047 | | | | | | | chr1:016569360-016569301 | | | | |
| A_24_P229871 | | chromosome 17 open reading frame 54 [Source: HGNC Symbol; Acc: 26863] [ENST00000321800] | BC101214 | ENST00000321800 | | | chr17:71746683-71746624 | | | NP1465661 | Hs.464079 |
| A_33_P3385656 | FNDC9 | Homo sapiens fibronectin type III domain containing 9 (FNDC9), mRNA [NM_001001343] | NM_001001343 | ENST00000312349 | 408263 | fibronectin type III domain containing 9 | chr5:156768667-156768608 | GO:0016020\|GO:0016021 | NM_001001343 | THC2644705 | Hs.437066 |
| A_33_P3348151 | | | | | | | chr9:043848640-043848699 | | | | |
| A_23_P1473 | PRF1 | Homo sapiens perforin 1 (pore forming protein) (PRF1), transcript variant 1, mRNA [NM_005041] | NM_005041 | ENST00000441259 | 5551 | perforin 1 (pore forming protein) | chr10:72357988-72357929 | GO:0006968\|GO:0005886\|NM_005041 GO:0045471\|GO:0019835\| GO:0005509\|GO:0016023\| GO:0007623\|GO:0006915\| GO:0005576\|GO:0016021 | | THC2462167 | Hs.2200 |
| A_33_P3277378 | OSM | Homo sapiens oncostatin M [Source: HGNC Symbol; Acc: 8506] [ENST00000403389] | | ENST00000403389 | 5008 | oncostatin M | chr22:30661669-30661610 | | | | |
| A_32_P176911 | NCRNA00239 | Homo sapiens non-protein coding RNA 239 (NCRNA00239), non-coding RNA [NR_026774] | NR_026774 | | 145200 | non-protein coding RNA 239 | chr14:102198716-102198775 | | NR_026774 | THC2704597 | Hs.150840 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P371765 | C21orf56 | Homo sapiens chromosome 21 open reading frame 56 (C21orf56), transcript variant 2, mRNA [NM_032261] | NM_032261 | ENST00000291672 | 84221 | chromosome 21 open reading frame 56 | chr21:47581854-47581585 | GO:0005515\|GO:0008150\|NM_032261 GO:0003674\|GO:0005575 | THC2602807 | Hs.381214 |
| A_24_P295963 | SLC38A2 | Homo sapiens solute carrier family 38, member 2 (SLC38A2), mRNA [NM_018976] | NM_018976 | ENST00000549258 | 54407 | solute carrier family 38, member 2 | chr12:46752769-46752710 | GO:0015171\|GO:0005886\|NM_018976 GO:0006865\|GO:0016021 GO:0031402\|GO:0006814 GO:0015293\|GO:0006811 | THC2461149 | Hs.221847 |
| A_33_P3275801 | DES | Homo sapiens desmin (DES), mRNA [NM_001927] | NM_001927 | ENST00000373960 | 1674 | desmin | chr2:220291400-220291459 | GO:0005515\|GO:0030018\|NM_001927 GO:0008016\|GO:0045202 GO:0005626\|GO:0005622 GO:0042383\|GO:0005737 GO:0006936\|GO:0043292 GO:0007010\|GO:0005200 GO:0045098\|GO:0005856 | THC2525325 | Hs.594952 |
| A_23_P131785 | BPI | Homo sapiens bactericidal/permeability-increasing protein (BPI), mRNA [NM_001725] | NM_001725 | ENST00000262865 | 671 | bactericidal/permeability-increasing protein | chr20:36969570-36965768 | GO:0032717\|GO:0032715\|NM_001725 GO:0043031\|GO:0032720 GO:0005576\|GO:0008368 GO:0008289\|GO:0001530 GO:0005737\|GO:0006955 GO:0016020\|GO:0005887 GO:0042742 | THC2470545 | Hs.529019 |
| A_23_P211680 | MLC1 | Homo sapiens megalencephalic leukoencephalopathy with subcortical cysts 1 (MLC1), transcript variant 1, mRNA [NM_015166] | NM_015166 | ENST00000311597 | 23209 | megalencephalic leukoencephalopathy with subcortical cysts 1 | chr22:50498007-50497948 | GO:0008150\|GO:0003674\|NM_015166 GO:0016020\|GO:0000299 GO:0016021\|GO:0005216 GO:0006811 | NP1141647 | Hs.517729 |
| A_23_P27424 | ZNF418 | Homo sapiens zinc finger protein 418 (ZNF418), mRNA [NM_133460] | NM_133460 | ENST00000425570 | 147686 | zinc finger protein 418 | chr19:58433735-58433676 | GO:0005622\|GO:0006355\|NM_133460 GO:0008270\|GO:0005634 GO:0003677\|GO:0046872 | THC2658428 | Hs.660728 |
| A_23_P142403 | TM6SF2 | Homo sapiens transmembrane 6 superfamily member 2 (TM6SF2), mRNA [NM_001001524] | NM_001001524 | ENST00000269990 | 53345 | transmembrane 6 superfamily member 2 | chr19:19378895-19378836 | GO:0008150\|GO:0003674\|NM_001001524 GO:0016020\|GO:0016021 | THC2675957 | Hs.531624 |
| A_24_P820037 | SLC6A17 | Homo sapiens solute carrier family 6, member 17 (SLC6A17), mRNA [NM_001010898] | NM_001010898 | ENST00000450985 | 388662 | solute carrier family 6, member 17 | chr1:110743689-110743748 | GO:0016020\|GO:0005887\|NM_001010898 GO:0005328\|GO:0006836 GO:0015293 | THC2473133 | Hs.128382 |
| A_33_P3246613 | CCDC78 | Homo sapiens coiled-coil domain containing 78 (CCDC78), mRNA [NM_001031737] | NM_001031737 | ENST00000478979 | 124093 | coiled-coil domain containing 78 | chr16:772645-772586 | | NM_001031737 | NP708886 | Hs.381943 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3283061 | LOC100128348 | Homo sapiens cDNA FLJ46249 fis, clone TESTI4021377. [AK128128] | AK12K12K | | 100128348 | hypothetical protein LOC100128348 | chr16:33347435-33347376 | | | THC2723408 | Hs.637572 |
| A_23_P430670 | CHST5 | Homo sapiens carbohydrate (N-acetylglucosamine 6-O) sulfotransferase 5 (CHST5), mRNA [NM_024533] | NM_024533 | ENST00000336257 | 23563 | carbohydrate (N-acetylglucosamine 6-O) sulfotransferase 5 | chr16:75562808-75562749 | GO:0006790\|GO:0005794\|NM_024533 GO:0016020\|GO:0005975\| GO:0031228\|GO:0006044\| GO:0000477\|GO:0016021\| GO:0001517\|GO:0016740 | NM_024533 | NP175264 | Hs.710689 |
| A_33_P3352827 | SLAMF1 | Homo sapiens signaling lymphocytic activation molecule family member 1 (SLAMF1), mRNA [NM_003037] | NM_003037 | ENST00000355199 | 6504 | signaling lymphocytic activation molecule family member 1 | chr1:160607126-160607067 | GO:0005515\|GO:0046649\|NM_003037 GO:0008284\|GO:0005886\| GO:0044419\|GO:0016021\| GO:0004823\|GO:0009897\| GO:0004888 | NM_003037 | THC2478679 | Hs.523660 |
| A_33_P3330125 | DIABLO | Homo sapiens diablo, IAP-binding mitochondrial protein (DIABLO), nuclear gene encoding mitochondrial protein, transcript variant 3, mRNA [NM_138929] | NM_138929 | ENST00000413918 | 56616 | diablo, IAP-binding mitochondrial protein | chr12:122710882-122710823 | GO:0008625\|GO:0005739\|NM_138929 GO:0005515\|GO:0005737\| GO:0008635\|GO:0008631\| GO:0006917\|GO:0005829 | NM_138929 | THC2640072 | Hs.169611 |
| A_23_P356122 | ZNF451 | Homo sapiens zinc finger protein 451 (ZNF451), transcript variant 1, mRNA [NM_001031623] | NM_001031623 | ENST00000357489 | 26036 | zinc finger protein 451 | chr6:57033933-57033992 | GO:0005622\|GO:0008270\|NM_001031623 GO:0005634\|GO:0003677\| GO:0046872\|GO:0045449 | NM_001031623 | THC2466864 | Hs.485628 |
| A_33_P3471466 | C14orf166B | Homo sapiens chromosome 14 open reading frame 166B (C14orf166B), mRNA [NM_194287] | NM_194287 | ENST00000460005 | 145497 | chromosome 14 open reading frame 166B | chr14:77304254-77304313 | GO:0005515 | NM_194287 | NP101062 | Hs.147276 |
| A_33_P3382493 | SIGLEC14 | Homo sapiens sialic acid binding Ig-like lectin 14 (SIGLEC14), mRNA [NM_001098612] | NM_001098612 | ENST00000360844 | 100049587 | sialic acid binding Ig-like lectin 14 | chr19:52146915-52146856 | GO:0005515\|GO:0016020\|NM_001098612 GO:0005529\|GO:0016021\| GO:0007155 | NM_001098612 | THC2508498 | Hs.707374 |
| A_23_P138805 | CHORDC1 | Homo sapiens cysteine and histidine-rich domain (CHORD) containing 1 (CHORDC1), transcript variant 1, mRNA [NM_012124] | NM_012124 | ENST00000533724 | 26973 | cysteine and histidine-rich domain (CHORD) containing 1 | chr11:89935104-89935045 | GO:0008150\|GO:0003674\|NM_012124 GO:0008270\|GO:0005575\| GO:0046872 | NM_012124 | THC2466458 | Hs.22857 |
| A_23_P431346 | PRR15 | Homo sapiens proline rich 15 (PRR15), mRNA [NM_175887] | NM_175887 | ENST00000319694 | 222171 | proline rich 15 | chr7:29606158-29606217 | GO:0007275 | NM_175887 | THC2464800 | Hs.728338 |
| A_23_P330908 | DERL1 | Homo sapiens Der1-like domain family, member 1 (DERL1), transcript variant 1, mRNA [NM_024295] | NM_024295 | ENST00000524119 | 79139 | Der1-like domain family, member 1 | chr8:124026717-124026658 | GO:0005515\|GO:0006986\|NM_024295 GO:0019060\|GO:0042288\| GO:0005783\|GO:0030970\| GO:0030176\|GO:0015031\| GO:0030433\|GO:0030968 | NM_024295 | THC2497250 | Hs.241576 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P116235 | MDK | Homo sapiens midkine (neurite growth-promoting factor 2) (MDK), transcript variant 1, mRNA [NM_001012334] | NM_001012334 | ENST00000407067 | 4192 | midkine (neurite growth-promoting factor 2) | chr11:46405231-46405290 | GO:0016020\|GO:0044419\|GO:0004872\|GO:0016021\|GO:0007165\|GO:0030325\|GO:0009611\|GO:0051781\|GO:0007275\|GO:0005576\|GO:0008201\|GO:0008083\|GO:0030154\|GO:0007399 | NP1464770 | Hs.82045 |
| A_33_P3337026 | SLC6A8 | solute carrier family 6 (neurotransmitter transporter, creatine), member 8 [Source: HGNC Symbol; Acc: 11055] [ENST00000328897] | U17986 | ENST00000328897 | 6535 | solute carrier family 6 (neurotransmitter transporter, creatine), member 8 | chrX:152959440-152959499 | | THC2489031 | Hs.540696 |
| A_33_P3295814 | | | | | | | chr7:073245261-073245202 | | | | |
| A_33_P3247095 | | | | ENST00000447610 | | | chr11:1076431 95-107643254 | | | | |
| A_24_P225719 | MOBKL3 | Homo sapiens MOB1, Mps One Binder kinase activator-like 3 (yeast) (MOBKL3), transcript variant 1, mRNA [NM_015387] | NM_015387 | ENST00000323303 | 25843 | MOB1, Mps One Binder kinase activator-like 3 (yeast) | chr2:198417148-198417207 | GO:0005515\|GO:0048471\|GO:0005737\|GO:0005794\|GO:0016020\|GO:0006810\|GO:0005624\|GO:0008270\|GO:0046872\|GO:0019898 | NM_015387 | Hs.63165 |
| A_33_P3256095 | | | | | | | chr1:222647359-222647300 | | | THC2572285 | |
| A_23_P51117 | ETAA1 | Homo sapiens Ewing tumor-associated antigen 1 (ETAA1), mRNA [NM_019002] | NM_019002 | ENST00000272342 | 54465 | Ewing tumor-associated antigen 1 | chr2:67637076-67637135 | GO:0005737 | NM_019002 | THC2671527 | Hs.353022 |
| A_24_P208045 | EDEM3 | Homo sapiens ER degradation enhancer, mannosidase alpha like 3 (EDEM3), mRNA [NM_025191] | NM_025191 | ENST00000318130 | 80267 | ER degradation enhancer, mannosidase alpha-like 3 | chr1:184660017-184659958 | GO:0006986\|GO:0016020\|GO:0005783\|GO:0005509\|GO:0004571\|GO:0006516\|GO:0005788\|GO:0043161\|GO:0004569 | NM_025191 | THC2493079 | Hs.523811 |
| A_33_P3308586 | DUXA | Homo sapiens double homeobox A (DUXA), mRNA [NM_001012729] | NM_001012729 | ENST00000376239 | 503835 | double homeobox A | chr19:57663153-57663094 | GO:0043565\|GO:0006355\|GO:0003700\|GO:0005634 | NM_001012729 | | Hs.585857 |
| A_33_P3264444 | PFDN6 | prefoldin subunit 6 [Source: HGNC Symbol; Acc: 4926] [ENST00000482292] | CR609151 | ENST00000482292 | 10471 | prefoldin subunit 6 | chr6:332658753-33265934 | | | THC2557117 | Hs.446374 |
| A_33_P3379669 | RNF208 | Homo sapiens ring finger protein 208 (RNF208), mRNA [NM_031297] | NM_031297 | ENST00000392827 | 727800 | ring finger protein 208 | chr9:140115164-140115105 | GO:0005515\|GO:0008270\|GO:0046872 | NM_031297 | THC2473148 | Hs.512767 |
| A_23_P87329 | NAT10 | Homo sapiens N-acetyltransferase 10 | NM_024662 | ENST00000531159 | 55226 | N-acetyltransferase 10 | chr11:34167990-34168049 | GO:0005515\|GO:0003674\|GO:0008080\|GO:0000166 | NM_024662 | NP1154163 | Hs.577281 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P212126 | | (GCN5-related) (NAT 10), transcript variant 1, mRNA [NM_024662] | | | | (GCN5-related) | | GO:0008152\|GO:0005730\|GO:0005634\|GO:0005524\|GO:0016740\|GO:0008415 | | | |
| A_33_P3378360 | COLQ | Homo sapiens collagen-like tail subunit (single strand of homotrimer) of asymmetric acetylcholinesterase (COLQ), transcript variant II, mRNA [NM_080538] | NM_080538 | ENST00000383788 | 8292 | collagen like tail subunit (single strand of homotrimer) of asymmetric acetylcholinesterase | chr3:15492044-15491985 | GO:0030054\|GO:0008105\|GO:0005605\|GO:0001507\|GO:0045202\|GO:0042135\|GO:0005615 | NM_080538 | NP423138 | Hs.146735 |
| A_33_P3340862 | PRELID1 | Homo sapiens PRELI domain containing 1 (PRELID1), mRNA [NM_013237] | NM_013237 | ENST00000504594 | 27166 | PRELI domain containing 1 | chr17:17673360-5-176733664 | GO:0005739\|GO:0006955\|GO:0007275 | NM_013237 | NP1177384 | Hs.279529 |
| A_23_P142125 | TMEM88B | Homo sapiens transmembrane protein 88B (TMEM88B), mRNA [NM_001146685] | NM_001146685 | | 643965 | transmembrane protein 88B | chr1:1363048-1363107 | GO:0016020\|GO:0016021 | NM_001146685 | | Hs.729765 |
| A_33_P3209386 | HRC | Homo sapiens histidine rich calcium binding protein (HRC), mRNA [NM_002152] | NM_002152 | ENST00000225825 | 3270 | histidine rich calcium binding protein | chr19:4965530-1-49654792 | GO:0006936\|GO:0008016\|GO:0005509\|GO:0033018\|GO:0033017\|GO:0055074 | NM_002152 | NP852745 | Hs.436885 |
| A_23_P372848 | TXNDC17 | Homo sapiens thioredoxin domain containing 17 (TXNDC17), mRNA [NM_032731] | NM_032731 | ENST00000250101 | 84817 | thioredoxin domain containing 17 | chr17:6547783-6547842 | GO:0005515\|GO:0005737\|GO:0004601\|GO:0009055\|GO:0047134\|GO:0033209\|GO:0005829 | NM_032731 | THC2602739 | Hs.408236 |
| A_24_P125283 | P2RX1 | Homo sapiens purinergic receptor P2X, ligand-gated ion channel, 1 (P2RX1), mRNA [NM_002558] | NM_002558 | ENST00000225538 | 5023 | purinergic receptor P2X, ligand-gated ion channel, 1 | chr17:3800243-3800184 | GO:0005515\|GO:0005886\|GO:0016265\|GO:0002554\|GO:0051291\|GO:0019228\|GO:0042803\|GO:0043270\|GO:0045211\|GO:00081144\|GO:0051924\|GO:0001614\|GO:0033198\|GO:0051260\|GO:0004872\|GO:0046513\|GO:0019717\|GO:0046982\|GO:0004931\|GO:0006919\|GO:0035249\|GO:0030168\|GO:0005524\|GO:0007320\|GO:0007165\|GO:0043234\|GO:0031240\|GO:0005887\|GO:0033056\|GO:0008217\|GO:0045121\|GO:0008270\|GO:0050896 | NM_002558 | THC2488665 | Hs.41735 |
| | HDAC5 | Homo sapiens histone deacetylase 5 (HDAC5), transcript variant 3, mRNA [NM_001015053] | NM_001015053 | ENST00000225983 | 10014 | histone deacetylase 5 | chr17:4215422-3-42154164 | GO:0032869\|GO:0016575\|GO:0016666\|GO:0006342\|GO:0043393\|GO:0010553\|GO:0010843\|GO:0005634 | NM_001015053 | THC2465832 | Hs.438782 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3337259 | WASH5P | Homo sapiens WAS protein family homolog 5 pseudogene (WASH5P), non-coding RNA [NR_033266] | NR_033266 | | 375690 | WAS protein family homolog 5 pseudogene | chr19:61457-61398 | GO:0010552│GO:0010832│ GO:0051091│GO:0005737│ GO:0000118│GO:0006954│ GO:0016787│GO:0070491│ GO:0030183│GO:0014898│ GO:0090051│GO:0006338│ GO:0004407│GO:0045449│ GO:0008134 | NR_033266 | THC2492043 | Hs.521961 |
| A_33_P3226105 | | | | | | | chr22:0204752 80-020475221 | | | | |
| A_23_P421526 | ODF4 | Homo sapiens outer dense fiber of sperm tails 4 (ODF4), mRNA [NM_153007] | NM_153007 | ENST00000328248 | 146852 | outer dense fiber of sperm tails 4 | chr17:8248725-8248784 | GO:0016020│GO:0009434│ GO:0007275│GO:0016021│ GO:0007283│GO:0030154│ GO:0001520 | NM_153007 | THC2483718 | Hs.186045 |
| A_33_P3362153 | LOC388564 | Homo sapiens hypothetical protein LOC388564 (LOC388564), mRNA[NM_001190764] | NM_001190764 | ENST00000444469 | 388564 | hypothetical protein LOC388564 | chr19:5589067 2-55890613 | | NM_001190764 | THC2582711 | Hs.534672 |
| A_23_P136413 | MMP17 | Homo sapiens matrix metallopeptidase 17 (membrane-inserted) (MMP17), mRNA [NM_016155] | NM_016155 | ENST00000360564 | 4326 | matrix metallopeptidase 17 (membrane-inserted) | chr12:1323362 44-132336301 | GO:0005886│GO:0005887│ GO:0008152│GO:0005509│ GO:0006508│GO:0005578│ GO:0008270│GO:0008233│ GO:0005576│GO:0031225│ GO:0008047│GO:0004222 | NM_016155 | THC2473946 | Hs.709245 |
| A_23_P307310 | ACAN | Homo sapiens aggrecan (ACAN), transcript variant 2, mRNA [NM_013227] | NM_013227 | ENST00000439576 | 176 | aggrecan | chr15:8941777 1-89417830 | GO:0005515│GO:0001501│ GO:0005540│GO:0006508│ GO:0005578│GO:0005529│ GO:0005576│GO:0007155│ GO:0005201 | NM_013227 | THC2764092 | Hs.2159 |
| A_33_P3374398 | | Homo sapiens cDNA FLJ39784 fis, clone SPLEN2002314. [AK097103] | AK097103 | | | | chr17:7260016 7-72600226 | | | THC2605561 | Hs.93825 |
| A_24_P358321 | | immunoglobulin kappa variable 2D-29 [Source: HGNC Symbol; Acc: 5800] [ENST00000491977] | U21012 | ENST00000491977 | | | chr2:89986891-89986950 | | | NP1132773 | Hs.731091 |
| A_33_P3381235 | LOC100127888 | Homo sapiens hypothetical LOC100127888 (LOC100127888), | NR_024470 | ENST00000411824 | 1001127888 | hypothetical LOC100127888 | chr20:6129443 9-61294380 | | NR_024470 | THC2620832 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3333560 | | non-coding RNA [NR_024470] | | | | | | | | | |
| A_33_P3645888 | SNORA71C | ax39a01.x1 Proliferating Human Erythroid Cells (LCB: ax library) Homo sapiens cDNA clone ax39a01 random, mRNA sequence [BG943532] | BG943532 | | 677839 | small nucleolar RNA, H/ACA box 71C | chr1:20749553-20749547 chr20:37058196-37058196 | | | THC2500898 | Hs.711516 |
| A_33_P3291459 | LOC100507547 | Homo sapiens hypothetical LOC100507547 (LOC100507547), transcript variant 1, non-coding RNA [NR_037169] | NR_037169 | ENST00000487140 | 100507547 | hypothetical LOC100507547 | chr6:32120638-32120579 | | NR_037169 | NP1168591 | Hs.549204 |
| A_33_P3366614 | | | | | | | chr2:147021801-147021860 | | | | |
| A_33_P3228609 | LOC151009 | Homo sapiens hypothetical LOC151009 (LOC151009), non-coding RNA [NR_027244] | NR_027244 | | 151009 | hypothetical LOC151009 | chr2:111134462-111134561 | | NR_027244 | THC2497499 | Hs.516403 |
| A_33_P3302373 | SZT2 | Homo sapiens seizure threshold 2 homolog (mouse) (SZT2), mRNA [NM_015284] | NM_015284 | ENST00000372442 | 23334 | seizure threshold 2 homolog (mouse) | chr1:43918245-43918304 | | NM_015284 | THC2522911 | Hs.643560 |
| A_24_P39076 | IGLL1 | Homo sapiens immunoglobulin lambda-like polypeptide 1 (IGLL1), transcript variant 1, mRNA [NM_020070] | NM_020070 | ENST00000330377 | 3543 | immunoglobulin lambda-like polypeptide 1 | chr22:23915710-23915651 | GO:0006955 GO:0016020 GO:0005576 | NM_020070 | THC2471192 | Hs.348935 |
| A_24_P12435 | NCOA7 | Homo sapiens nuclear receptor coactivator 7 (NCOA7), transcript variant 1, mRNA [NM_181782] | NM_181782 | ENST00000368357 | 135112 | nuclear receptor coactivator 7 | chr6:126251879-126251938 | GO:0005622 GO:0005515 GO:0016998 GO:0005634 GO:0045449 | NM_181782 | THC2461012 | Hs.171426 |
| A_23_P348208 | SPRR1A | Homo sapiens small proline-rich protein 1A (SPRR1A), transcript variant 2, mRNA [NM_005987] | NM_005987 | ENST00000368762 | 6698 | small proline-rich protein 1A | chr1:152957897-152957956 | GO:0005737 GO:0018149 GO:0005198 GO:0008544 GO:0005198 GO:0031424 GO:0030674 GO:0001533 | NM_005987 | NP1464433 | Hs.46320 |
| A_33_P3366456 | HDGFL1 | Homo sapiens hepatoma derived growth factor-like 1 (HDGFL1), mRNA [NM_138574] | NM_138574 | ENST00000230012 | 154150 | hepatoma derived growth factor-like 1 | chr6:22570614-22570673 | | NM_138574 | THC2474651 | Hs.629246 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3386297 | | *Homo sapiens* MST159 (MST159) mRNA, complete cds. [AF190162] | AF190162 | | | | chrX:135240238-135240297 | | | THC2488126 | Hs.689084 |
| A_33_P3309468 | PTPRS | *Homo sapiens* protein tyrosine phosphatase, receptor type, S (PTPRS), transcript variant 1, mRNA [NM_002850] | NM_002850 | ENST00000372412 | 5802 | protein tyrosine phosphatase, receptor type, S | chr19:5205578-5205519 | GO:0005515\|GO:0006470\|GO:0016787\|GO:0016020\|GO:0005887\|GO:0005001\|GO:0004872\|GO:0007155 | NM_002850 | THC2517908 | Hs.644384 |
| A_23_P16096 | PPAN | *Homo sapiens* peter pan homolog (*Drosophila*) (PPAN), mRNA [NM_020230] | NM_020230 | ENST00000466025 | 56342 | peter pan homolog (*Drosophila*) | chr19:10218744-10218803 | GO:0008380\|GO:0005515\|GO:0005730\|GO:0005634 | NM_020230 | THC2534071 | Hs.14468 |
| A_33_P3302245 | TMEM59L | *Homo sapiens* transmembrane protein 59-like (TMEM59L), mRNA [NM_012109] | NM_012109 | ENST00000262817 | 25789 | transmembrane protein 59-like | chr19:1873160-18731661 | GO:0016020\|GO:0005624\|GO:0016021 | NM_012109 | THC2601975 | Hs.329850 |
| A_24_P208345 | SLC45A3 | *Homo sapiens* solute carrier family 45, member 3 (SLC45A3), mRNA [NM_033102] | NM_033102 | ENST00000367145 | 85414 | solute carrier family 45, member 3 | chr1:205627096-205627037 | GO:0016020\|GO:0016021\|GO:0055085 | NM_033102 | NP1165434 | Hs.278695 |
| A_33_P3391517 | SNX22 | sorting nexin 22 [Source: HGNC Symbol; Acc: 16315] [ENST00000380278] | BC030225 | ENST00000380278 | 79856 | sorting nexin 22 | chr15:64446169-64446228 | | | THC2621916 | Hs.708268 |
| A_33_P3328289 A_23_P85693 | GBP2 | *Homo sapiens* guanylate binding protein 2, interferon-inducible (GBP2), mRNA [NM_004120] | NM_004120 | ENST00000463660 | 2634 | guanylate binding protein 2, interferon-inducible | chr1:89578160-89575896 | GO:0006955\|GO:0005886\|GO:0000166\|GO:0003924\|GO:0005525 | NM_004120 | THC2660155 | Hs.386567 |
| A_33_P3294159 | CALY | *Homo sapiens* calcyon neuron-specific vesicular protein (CALY), mRNA [NM_015722] | NM_015722 | ENST00000368556 | 50632 | calcyon neuron-specific vesicular protein | chr10:135141509-135141450 | GO:0045807\|GO:0005886\|GO:0032051\|GO:0005887\|GO:0031410\|GO:0007212\|GO:0050780\|GO:0048268 | NM_015722 | THC2605646 | Hs.148680 |
| A_24_P287756 | NUDT21 | *Homo sapiens* nudix (nucleoside diphosphate linked moiety X)-type motif 21 (NUDT21), mRNA [NM_007006] | NM_007006 | ENST00000533563 | 11051 | nudix (nucleoside diphosphate linked moiety X)-type motif 21 | chr16:56463585-56463526 | GO:0005515\|GO:0005813\|GO:0042382\|GO:0042826\|GO:0016787\|GO:0000398\|GO:0003723\|GO:0005634 | NM_007006 | THC2532864 | Hs.528834 |
| A_33_P3336822 | | immunoglobulin lambda variable 1-44 [Source: HGNC Symbol; Acc: 5879] [ENST00000390297] | U09907 | ENST00000390297 | | | chr22:22735478-22735537 | | | NP426024 | Hs.561078 |
| A_23_P361654 | | immunoglobulin kappa variable 10-16 [Source: | BC073764 | ENST00000492446 | | | chr2:90139373-90139432 | | | THC2551789 | Hs.449621 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P115558 | | HGNC Symbol; Acc: 5748] [ENST00000492446] y885d04.s1 Stratagene liver (#937224) Homo sapiens cDNA clone IMAGE:779959 3' similar to similar to gb:M26880 UBIQUITIN (HUMAN), mRNA sequence [T53825] | T53825 | | | | chr17:0162859 23-016285864 | | | THC2576794 | Hs.702098 |
| A_33_P3344574 | SFTPA2 | Homo sapiens surfactant protein A2(SFTPA2), mRNA [NM_001098668] | NM_001098668 | ENST00000372325 | 729238 | surfactant protein A2 | chr10:8131568 2-81315623 | GO:0007585\|GO:0005488\|NM_001098668 GO:0005509\|GO:0005578\| GO:0005529\|GO:0005576\| GO:0005615 | | | Hs.523084 |
| A_23_P432056 | RTN4RL1 | Homo sapiens reticulon 4 receptor like 1 (RTN4RL1), mRNA [NM_178568] | NM_178568 | ENST00000331238 | 146760 | reticulon 4 receptor-like 1 | chr17:1840616-1840557 | GO:0005515\|GO:0031103\|NM_178568 GO:0005886\|GO:0045121\| GO:0004872\|GO:0046658\| GO:0009897 | | THC2602362 | Hs.22917 |
| A_23_P19243 | AKIRIN2-AS1 | Homo sapiens AKIRIN2 antisense RNA 1 (non-protein coding) (AKIRIN2-AS1), non-coding RNA [NR_002767] | NR_002767 | | 55389 | AKIRIN2 antisense RNA 1 (non-protein coding) | chr6:88410191-88410132 | | NR_002767 | THC2539344 | Hs.662132 |
| A_33_P3417502 | WNT3A | Homo sapiens wingless-type MMTV integration site family, member 3A (WNT3A), mRNA [NM_033131] | NM_033131 | ENST00000366753 | 89780 | wingless-type MMTV integration site family, member 3A | chr1:22824794 6-228248005 | GO:0030097\|GO:0005515\|NM_033131 GO:0048103\|GO:0007368\| GO:0042472\|GO:0001756\| GO:0005578\|GO:0007267\| GO:0030879\|GO:0021874\| GO:0005576\|GO:0007275\| GO:0007409\|GO:0001701\| GO:0005615\|GO:0007223\| GO:0001947\|GO:0021766\| GO:0045595\|GO:0004871\| GO:0048343\|GO:0005201 | | NP1459415 | Hs.336930 |
| A_33_P3331326 | | | | | | | chr13:0281946 69-028194728 | | | | |
| A_33_P3229863 | LOC100128714 | Homo sapiens hypothetical LOC100128714 (LOC100128714), non-coding RNA [NR_040082] | NR_040082 | ENST00000383019 | 100128714 | hypothetical LOC100128714 | chr15:2629819 7-26298256 | | NR_040082 | THC2487359 | |
| A_33_P3309501 | LOC100507184 | PREDICTED: Homo sapiens hypothetical protein LOC100507184 (LOC100507184), mRNA [XM_003118917] | XM_003118917 | | 100507184 | hypothetical protein LOC100507184 | chr14:1013250 72-101325131 | | XM_003118917 | THC2474208 | Hs.728839 |
| A_33_P3275422 | C14orf70 | Homo sapiens chromosome 14 open reading frame 70 (C14orf70), | NR_024096 | ENST00000360899 | 283601 | chromosome 14 open reading frame 70 | chr14:1011389 94-101139053 | | NR_024096 | THC2483476 | Hs.379802 |

APPENDIX C-continued

FEMALES: Technology: Agilent.SingleColor.26652
Created On: Tue Jan 31 14:14:22 EST 2012

| ProbeName | Gene | Description | Gb_Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P3914 | WIPF3 | non-coding RNA [NR_024096] Homo sapiens WAS/WASL interacting protein family, member 3 (WIPF3), mRNA [NM_001080529] | NM_001080529 | ENST00000409290 | 644150 | WAS/WASL interacting protein family, member 3 | chr7:29955838-29955897 | | NM_001080529 | | Hs.709280 |
| A_33_P3290443 | SCARNA9 | Homo sapiens small Cajal body-specific RNA 9 (SCARNA9), guide RNA [NR_002569] | NR_002569 | ENST00000530422 | 619383 | small Cajal body-specific RNA 9 | chr11:93454973-93455032 | | NR_002569 | THC2562327 | |
| A_33_P3322388 | SPRR2D | Homo sapiens small proline-rich protein 2D (SPRR2D), mRNA [NM_006945] | NM_006945 | ENST00000439437 | 6703 | small proline-rich protein 2D | chr1:153012663-153012604 | GO:0005737 GO:0008544 GO:0031424 GO:0001533 | NM_006945 | THC2480904 | Hs.505327 |
| A_33_P3234472 | LOC284751 | Homo sapiens hypothetical LOC284751 (LOC284751), non-coding RNA [NR_034124] | NR_034124 | | 284751 | hypothetical LOC284751 | chr20:489313397-48931456 | | NR_034124 | | Hs.282325 |
| A_23_P128598 | TUBA3C | Homo sapiens tubulin, alpha 3c (TUBA3C), mRNA [NM_006001] | NM_006001 | ENST00000360801 | 7278 | tubulin, alpha 3c | chr13:19751197-19751138 | | NM_006001 | THC2490161 | Hs.349695 |
| A_33_P3416231 | HOXA9 | Homo sapiens homeobox A9 (HOXA9), mRNA [NM_152739] | NM_152739 | ENST00000242050 | 3205 | homeobox A9 | chr7:27203204-27203145 | GO:0005515 GO:0005667 GO:0006355 GO:0003700 GO:0016563 GO:0048706 GO:0060216 GO:0005634 GO:0007275 GO:0009954 GO:0030879 GO:0009952 GO:0043565 GO:0005737 GO:0035115 | NM_152739 | THC2746857 | Hs.659350 |
| A_23_P70095 | CD74 | Homo sapiens CD74 molecule, major histocompatibility complex, class II invariant chain (CD74), transcript variant 3, mRNA [NM_001025158] | NM_001025158 | ENST00000523813 | 972 | CD74 molecule, major histocompatibility complex, class II invariant chain | chr5:149792281-149792222 | GO:0042289 GO:0016064 GO:0005886 GO:0005783 GO:0008283 GO:0043030 GO:0006886 GO:0005764 GO:0042802 GO:0005622 GO:0000187 GO:0019886 GO:0006955 GO:0001516 GO:0019883 GO:0045581 GO:0045582 GO:0043066 GO:0005794 GO:0005771 GO:0006952 GO:0045059 GO:0045058 GO:0007165 GO:0006461 GO:0019955 GO:0051085 GO:0045060 GO:0016021 GO:0009897 | NM_001025158 | THC2590686 | Hs.436568 |
| A_33_P3297978 | MYO1E | Homo sapiens myosin IE (MYO1E), mRNA [NM_004998] | NM_004998 | ENST00000288235 | 4643 | myosin IE | chr15:59428708-59428649 | GO:0030048 GO:0055516 GO:0006807 GO:0042623 GO:0001822 GO:0003779 | NM_004998 | THC2468472 | Hs.654506 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3251462 | C20orf141 | *Homo sapiens* chromosome 20 open reading frame 141 (C20orf141), mRNA [NM_080739] | NM_080739 | ENST00000380589 | 128653 | chromosome 20 open reading frame 141 | chr20:2796282-2796341 | GO:0016459\|GO:0001701\|GO:0005524\|GO:0000146\|GO:0000166\|GO:0035166\|GO:0048008\|GO:0001570\|GO:0016020\|GO:0016021 | NM_080739 | THC2476421 | Hs.352187 |
| A_33_P3223592 | APOE | *Homo sapiens* apolipoprotein E (APOE), mRNA [NM_000041] | NM_000041 | ENST00000252486 | 348 | apolipoprotein E | chr19:45412590-45412649 | GO:0010468\|GO:0006707\|GO:0046911\|GO:0048844\|GO:0002021\|GO:0005615\|GO:0042803\|GO:0034361\|GO:0048168\|GO:0034364\|GO:0034363\|GO:0034362\|GO:0043025\|GO:0034447\|GO:0042632\|GO:0005794\|GO:0016209\|GO:0046982\|GO:0043691\|GO:0031232\|GO:0007271\|GO:0006898\|GO:0051651\|GO:0034372\|GO:0007186\|GO:0051000\|GO:0034375\|GO:0006641\|GO:0000302\|GO:0043537\|GO:0042159\|GO:0005319\|GO:0042158\|GO:0006629\|GO:0010544\|GO:0051044\|GO:0007263\|GO:0005886\|GO:0045541\|GO:0045471\|GO:0017127\|GO:0042627\|GO:0010873\|GO:0019934\|GO:0010875\|GO:0030425\|GO:0008034\|GO:0005737\|GO:0030516\|GO:0001540\|GO:0005543\|GO:0034384\|GO:0034382\|GO:0043407\|GO:0042311\|GO:0007010\|GO:0034380\|GO:0008201\|GO:0005770\|GO:0032488\|GO:0055088\|GO:0048156\|GO:0006874\|GO:0046907\|GO:0006916\|GO:0005576\|GO:0006917\|GO:0033700\|GO:0032805\|GO:0001937\|GO:0050728\|GO:0006869\|GO:0030828\|GO:0050750 | NM_000041 | THC2465276 | Hs.654439 |
| A_23_P202769 | DNAJC4 | *Homo sapiens* DnaJ (Hsp40) homolog, sub- | NM_005528 | ENST00000543791 | 3338 | DnaJ (Hsp40) homolog, | chr11:64000251-64000310 | GO:0006986\|GO:0016020\|GO:0006457\|GO:0031072 | NM_005528 | THC2583429 | Hs.172847 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P46222 | | family C, member 4 (DNAJC4), mRNA [NM_005528] | BC069416 | ENST0000368385 | | subfamily C, member 4 | chr1:155152361-155152920 | GO:0005624\|GO:0051082\|GO:0016021 | | THC2472412 | Hs.287735 |
| A_23_P33607 | TRIM46 | tripartite motif containing 46 [Source: HGNC Symbol; Acc: 19019] [ENST0000368385] | | ENST0000306049 | 80128 | tripartite motif containing 46 | | | | THC2470414 | Hs.317340 |
| A_33_P3257714 | C17orf42 | Homo sapiens chromosome 17 open reading frame 42 (C17orf42), mRNA [NM_024683] | NM_024683 | ENST0000296674 | 79736 | chromosome 17 open reading frame 42 | chr17:29227565-29227506 | GO:0003676 | NM_024683 | THC2494905 | Hs.527193 |
| A_24_P203072 | RPS23 | Homo sapiens ribosomal protein S23 (RPS23), mRNA [NM_001025] | NM_001025 | ENST0000218343 | 6228 | ribosomal protein S23 | chr5:81569349-81569290 | GO:0005622\|GO:0003674\|GO:0003735\|GO:0022627\|GO:0005840\|GO:0006414\|GO:0005829 | NM_001025 | THC2464683 | Hs.371977 |
| A_33_P3369128 | PHF16 | Homo sapiens PHD finger protein 16 (PHF16), transcript variant 1, mRNA [NM_014735] | NM_014735 | | 9767 | PHD finger protein 16 | chrX:46919911-46919970 | GO:0043981\|GO:0005515\|GO:0043983\|GO:0043982\|GO:0043966\|GO:0043984\|GO:0000123\|GO:0008270\|GO:0046872 | NM_014735 | THC2585044 | Hs.730332 |
| | LOC100132966 | Homo sapiens cDNA FLJ42565 fis, clone BRACE3007472. [AK124556] | AK124556 | | 100132966 | hypothetical LOC100132966 | chr1:143914671-143914730 | | | | |
| A_23_P8167 | GPRC5C | Homo sapiens G protein-coupled receptor, family C, group 5, member C (GPRC5C), transcript variant 1, mRNA [NM_022036] | NM_022036 | ENST0000342648 | 55890 | G protein-coupled receptor, family C, group 5, member C | chr17:72443413-72443472 | GO:0005515\|GO:0007165\|GO:0005886\|GO:0005887\|GO:0004930\|GO:0004872\|GO:0031410 | NM_022036 | THC2493229 | Hs.446438 |
| A_23_P26294 | TPSG1 | Homo sapiens tryptase gamma 1 (TPSG1), mRNA [NM_012467] | NM_012467 | ENST0000234798 | 25823 | tryptase gamma 1 | chr16:1271739-1271680 | GO:0016020\|GO:0004252\|GO:0005887\|GO:0006508 | NM_012467 | THC2478934 | Hs.592076 |
| A_33_P3304707 | | immunoglobulin lambda variable 2-8 [Source: HGNC Symbol; Acc: 5895] | Z46314 | ENST0000390317 | | | chr22:23165574-23165633 | | | NP165804 | Hs.625768 |
| A_33_P3382944 | YJEFN3 | Homo sapiens YjeF N-terminal domain containing 3 (YJEFN3), nuclear gene encoding mitochondrial protein, transcript variant 1, mRNA [NM_198537] | NM_198537 | ENST0000397179 | 374887 | YjeF N-terminal domain containing 3 | chr19:1964833-19648393 | | NM_198537 | THC2501471 | Hs.729508 |
| A_23_P78289 | FAM104A | Homo sapiens family with sequence similarity | NM_032837 | ENST0000405159 | 84923 | family with sequence | chr17:71203606-71203547 | | NM_032837 | THC2468706 | Hs.103555 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P75917 | | 104, member A (FAM104A), transcript variant 2, mRNA [NM_032837] | | | | similarity 104, member A | | | | | |
| A_24_P75917 | CCDC144A | Homo sapiens coiled-coil domain containing 144A (CCDC144A), mRNA [NM_014695] | NM_014695 | ENST00000420937 | 9720 | coiled-coil domain containing 144A | chr17:1661285 2-16612911 | | NM_014695 | THC2483620 | Hs.721149 |
| A_32_P356316 | HLA-DOA | Homo sapiens major histocompatibility complex, class II, DO alpha (HLA-DOA), mRNA [NM_002119] | NM_002119 | ENST00000229829 | 3111 | major histocompatibility complex, class II, DO alpha | chr6:32972029-32971970 | GO:0019886|GO:0006955|NM_002119 GO:0005886|GO:0002504| GO:0045580|GO:0042613| GO:0016021|GO:0032395 | | THC2653816 | Hs.631991 |
| A_23_P257815 | CD180 | Homo sapiens CD180 molecule (CD180), mRNA [NM_005582] | NM_005582 | ENST00000256447 | 4064 | CD180 molecule | chr5:664787 52 66478693 | GO:0005515|GO:0006954|NM_005582 GO:0005886|GO:0045087| GO:0004872|GO:0016021 | | THC2471609 | Hs.87205 |
| A_33_P3328284 | | | | | | | chr12:1046808 91-104680832 | | | | |
| A_33_P3210379 | SCGB3A1 | Homo sapiens secretoglobin, family 3A, member 1 (SCGB3A1), mRNA[NM_052863] | NM_052863 | ENST00000512120 | 92304 | secretoglobin, family 3A, member 1 | chr5:18001716 5-180017106 | GO:0030308|GO:0042127|NM_052863 GO:0005576|GO:0005615| GO:0005125 | | THC2608654 | Hs.62492 |
| A_33_P3271635 | HLA-DPB1 | Homo sapiens major histocompatibility complex, class II, DP beta 1 (HLA-DPB1), mRNA [NM_002121] | NM_002121 | ENST00000402095 | 3115 | major histocompatibility complex, class II, DP beta 1 | chr6:33048489-33048537 | GO:0006955|GO:0016020|NM_002121 GO:0005886|GO:0002504| GO:0042613|GO:0016021 | | THC2541762 | Hs.485130 |
| A_33_P3237125 | ANKRD54 | Homo sapiens ankyrin repeat domain 54 (ANKRD54), transcript variant 1, mRNA [NM_138797] | NM_138797 | ENST00000498417 | 129138 | ankyrin repeat domain 54 | chr22:3822800 2-38227943 | | NM_138797 | THC2555662 | Hs.135259 |
| A_33_P3378384 | DNM1P46 | Homo sapiens DNM1 pseudogene 46 (DNM1P46), non-coding RNA [NR_003260] | NR_003260 | ENST00000341853 | 196968 | DNM1 pseudogene 46 | chr1 5:1003400 36-100339983 | | NR_003260 | THC2485999 | Hs.585319 |
| A_33_P3550894 | GATA2 | Homo sapiens GATA binding protein 2 (GATA2), transcript variant 1, mRNA [NM_001145661] | NM_001145661 | ENST00000430265 | 2624 | GATA binding protein 2 | chr3:12819960 6-128199547 | GO:0006355|GO:0003700|NM_001145661 GO:0001709|GO:0021983| GO:0005730|GO:0001892| GO:0005634|GO:0010552| GO:0043565|GO:0045766| GO:0046872|GO:0050766| GO:0030182|GO:0048469| GO:0008270|GO:0008134 | | NP099465 | Hs.367725 |
| A_33_P3370364 | PRLHR | Homo sapiens prolactin releasing hormone receptor (PRLHR), mRNA | NM_004248 | ENST00000369169 | 2834 | prolactin releasing hormone receptor | chr10:1203530 20-120352961 | GO:0007631|GO:0007165|NM_004248 GO:0007565|GO:0004983| GO:0007186|GO:0005886 | | THC2605922 | Hs.248119 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | [NM_004248] | | | | | | GO:0005887\|GO:0004930\|<br>GO:0042445\|GO:0004872\|<br>GO:0017046 | | | |
| A_24_P412734 | PRSS36 | Homo sapiens protease, serine, 36 (PRSS36), mRNA [NM_173502] | NM_173502 | ENST00000268281 | 146547 | protease, serine, 36 | chr16:3115173 0-31151671 | GO:0005737\|GO:0004252\|<br>GO:0006508\|GO:0005578\|<br>GO:0008233\|GO:0005576 | NM_173502 | THC2477817 | Hs.256632 |
| A_23_P397238 | FKBP1A | Homo sapiens FK506 binding protein 1A, 12 kDa (FKBP1A), transcript variant 2, mRNA [NM_054014] | NM_054014 | ENST00000381715 | 2280 | FK506 binding protein 1A, 12 kDa | chr20:135258 1352530 | GO:0055010\|GO:0046332\|<br>GO:0022417\|GO:0005829\|<br>GO:0032092\|GO:0042026\|<br>GO:0005737\|GO:0006458\|<br>GO:0048185\|GO:0060314\|<br>GO:0031398\|GO:0005024\|<br>GO:0004871\|GO:0043206\|<br>GO:0043123\|GO:0014802\|<br>GO:0003755\|GO:0005528\|<br>GO:0003925\|GO:0034205\|<br>GO:0060347\|GO:0007183\|<br>GO:0042110\|GO:0034713\|<br>GO:0032513\|GO:0050776\|<br>GO:0016853\|GO:0005219 | NM_054014 | THC2472790 | Hs.471933 |
| A_33_P3269844 | LRRC26 | Homo sapiens leucine rich repeat containing 26 (LRRC26), mRNA [NM_001013653] | NM_001013653 | ENST00000371542 | 389816 | leucine rich repeat containing 26 | chr9:14006328 0-140063221 | GO:0005515\|GO:0005737\|<br>GO:0016020\|GO:0016021\|<br>GO:0005856 | NM_001013653 | THC2675561 | Hs.669977 |
| A_23_P161769 | FXYD2 | Homo sapiens FXYD domain containing ion transport regulator 2 (FXYD2), transcript variant b, mRNA [NM_021603] | NM_021603 | ENST00000532984 | 486 | FXYD domain containing ion transport regulator 2 | chr11:1176910 03-117690944 | GO:0005215\|GO:0016020\|<br>GO:0030955\|GO:0016021\|<br>GO:0031402\|GO:0006814\|<br>GO:0005890\|GO:0006813\|<br>GO:0005216\|GO:0006811\|<br>GO:0005391 | NM_021603 | THC2718763 | Hs.413137 |
| A_33_P3219850 | | Q4RKH8_TETNG (Q4RKH8) Chromosome 21 SCAF15029, whole genome shotgun sequence, partial (4%) [THC2702109] | | | | | chr17:0752538 78-075253819 | | | THC2702109 | |
| A_33_P3271395 | LOC100129534 | Homo sapiens small nuclear ribonucleo-protein polypeptide N pseudogene (LOC100129534), non-coding RNA [NR_024489] | NR_024489 | | 100129534 | small nuclear ribonucleoprotein polypeptide N pseudogene | chr1:2281912-2281853 | | NR_024489 | THC2481166 | Hs.655313 |
| A_23_P45099 | HLA-DRB5 | Homo sapiens major histocompatibility complex, class II, DR | NM_002125 | ENST00000374975 | 3127 | major histo-compatibility complex, class | chr6:32485465-32485406 | GO:0006955\|GO:0016020\|NM_002125<br>GO:0005886\|GO:0002504\|<br>GO:0042613\|GO:0016021 | | THC2478372 | Hs.534322 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3242039 | | beta 5 (HLA-DRB5), mRNA [NM_002125] | | | | II, DR beta 5 | | | | | |
| A_33_P3351606 | LOC100130155 | Homo sapiens hypothetical LOC100130155 (LOC100130155), non-coding RNA [NR_034102] | NR_034102 | ENST00000524060 | 100130155 | hypothetical LOC100130155 | chr12:106633792-106633851 chr8:65290622-65290681 | | NR_034102 | THC2738263 | Hs.7023 |
| A_33_P3282614 | C9orf173 | Homo sapiens chromosome 9 open reading frame 173 (C9orf173), mRNA [NM_001004353] | NM_001004353 | ENST00000388931 | 441476 | chromosome 9 open reading frame 173 | chr9:140147856-140147915 | | NM_001004353 | THC2488587 | Hs.372640 |
| A_33_P3236902 | | mucin 3A, cell surface associated [Source: HGNC Symbol; Acc: 7513] [ENST00000483366] | XM_001716644 | ENST00000483366 | | | chr7:100550075-100550134 | | XM_001716644 | NP853252 | Hs.489354 |
| A_23_P4474 | IER3IP1 | Homo sapiens immediate early response 3 interacting protein 1 (IER3IP1), mRNA [NM_016097] | NM_016097 | ENST00000256433 | 51124 | immediate early response 3 interacting protein 1 | chr18:44681930-44681874 | GO:0005794 GO:0016020 GO:0005783 GO:0016021 | NM_016097 | THC2468751 | Hs.130917 |
| A_33_P3258061 | PALM3 | Homo sapiens paralemmin 3 (PALM3), mRNA [NM_001145028] | NM_001145028 | ENST00000340790 | 342979 | paralemmin 3 | chr19:14164238-14164179 | GO:0005737 GO:0005886 GO:0000166 GO:0031225 GO:0005524 | NM_001145028 | THC2610963 | Hs.444298 |
| A_33_P3236858 | TGFB1I1 | Homo sapiens transforming growth factor beta 1 induced transcript 1 (TGFB1I1), transcript variant 1, mRNA [NM_001042454] | NM_001042454 | ENST00000394858 | 7041 | transforming growth factor beta 1 induced transcript 1 | chr16:31489205-31489264 | GO:0005515 GO:0008285 GO:0030054 GO:0006366 GO:0045599 GO:0010718 GO:0005634 GO:0050681 GO:0016363 GO:0046872 GO:0005622 GO:0005737 GO:0030855 GO:0016055 GO:0007155 GO:0005856 GO:0030579 GO:0030512 GO:0030511 GO:0003713 GO:0070411 GO:0045165 GO:0016331 GO:0008270 GO:0045893 GO:0005925 GO:0030521 | NM_001042454 | THC2609995 | Hs.513530 |
| A_33_P3227761 | | | | | | | chr4:071008210-071008151 | | | | |
| A_23_P47004 | DHX32 | Homo sapiens DEAH (Asp-Glu-Ala-His) box polypeptide 32 (DHX32), mRNA [NM_018180] | NM_018180 | ENST00000284690 | 55760 | DEAH (Asp-Glu-Ala-His) box polypeptide 32 | chr10:127527612-127526940 | GO:0005739 GO:0016787 GO:0000166 GO:0004386 GO:0005634 GO:0005524 | NM_018180 | THC2461938 | Hs.370292 |
| A_33_P3280575 | | Synthetic construct Homo sapiens gateway clone | CU691877 | | | | chr13:024895873-024895814 | | | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P140190 | | IMAGE: 100021124 3' read C1QTNF9 mRNA. [CU691877] | | | | | | | | THC2483256 | Hs.649259 |
| A_23_P3320782 | KIAA0125 | Homo sapiens KIAA0125 (KIAA0125), non-coding RNA [NR_026800] | NR_026800 | ENST00000484511 | 9834 | KIAA0125 | chr14:106388126-106388185 | | NR_026800 | | |
| A_33_P3320782 | ATXN7 | Homo sapiens ataxin 7 (ATXN7), transcript variant SCA7a, mRNA [NM_000333] | NM_000333 | ENST00000398590 | 6314 | ataxin 7 | chr3:63986252-63986311 | GO:0005622|GO:0005515|NM_000333 GO:0016578|GO:0008219 GO:0006997|GO:0005737 GO:0005730|GO:0008270 GO:0005634|GO:0007601 GO:0045449|GO:0016363 | NM_000333 | THC2471545 | Hs.729041 |
| A_33_P3233871 | F12 | Homo sapiens coagulation factor XII (Hageman factor) (F12), mRNA [NM_000505] | NM_000505 | ENST00000253496 | 2161 | coagulation factor XII (Hageman factor) | chr5:176829201-176829142 | GO:0016540|GO:0004252|NM_000505 GO:0051919|GO:0005576 GO:0005615|GO:0051787 GO:0051605|GO:0051788 GO:0005488|GO:0010756 GO:0030194|GO:0002542 GO:0007597|GO:0045087 GO:0006508|GO:0008233 GO:0070009|GO:0031638 | NM_000505 | THC2473799 | Hs.1321 |
| A_32_P47701 | EEF1A1 | Homo sapiens eukaryotic translation elongation factor 1 alpha 1(EEF1A1), mRNA [NM_001402] | NM_001402 | ENST00000488500 | 1915 | eukaryotic translation elongation factor 1 alpha 1 | chr6:74228782-74228723 | GO:0005515|GO:0005853|NM_001402 GO:0005737|GO:0000166 GO:0003924|GO:0005525 GO:0003746|GO:0006414 GO:0005829 | NM_001402 | NP1154415 | Hs.535192 |
| A_23_P435444 | PCDHGA7 | Homo sapiens protocadherin gamma subfamily A, 7 (PCDHGA7), transcript variant 2, mRNA [NM_032087] | NM_032087 | ENST00000368223 | 56108 | protocadherin gamma subfamily A, 7 | chr5:140764880-140764939 | GO:0005515|GO:0005886|NM_032087 GO:0005509|GO:0016021 GO:0007155|GO:0007156 | NM_032087 | THC2601387 | Hs.368160 |
| A_33_P3358233 | NES | Homo sapiens nestin (NES), mRNA [NM_006617] | NM_006617 | ENST00000417327 | 10763 | nestin | chr1:156639481-156639422 | GO:0005882|GO:0005622|NM_006617 GO:0005737|GO:0005198 GO:0042493|GO:0010212 GO:0031667|GO:0007417 GO:0005856 | NM_006617 | NP286942 | Hs.527971 |
| A_33_P3440264 | LOC100132273 | Homo sapiens hypothetical LOC100132273 (LOC100132273), non-coding RNA [NR_034118] | NR_034118 | ENST00000504477 | 100132273 | hypothetical LOC100132273 | chr22:42520486-42520545 | | NR_034118 | THC2492791 | Hs.709677 |
| A_33_P3216372 | IQGAP2 | Homo sapiens IQ motif containing GTPase activating protein 2 (IQGAP2), mRNA [NM_006633] | NM_006633 | | 10788 | IQ motif containing GTPase activating protein 2 | chr5:76003795-76003854 | GO:0005622|GO:0005099|NM_006633 GO:0051056|GO:0007165 GO:0005516|GO:0003779 GO:0015629|GO:0005095 | NM_006633 | THC2461535 | Hs.291030 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3308101 | | *Homo sapiens* cDNA FLJ46348 fis, clone TESTI4047569. [AK128836] | AK128836 | ENST00000434161 | | | chr7:56879807-56879748 | | | THC2481823 | Hs.520384 |
| A_33_P3355783 | LOC100507482 | Uncharacterized protein [Source: UniProtKB/TrEMBL; Acc: E7ES44] [ENST00000398976] | XM_003119184 | ENST00000398976 | 100507482 | hypothetical protein LOC100507482 | chr11:6153478 7-61534846 | | XM_003119184 | NP852509 | Hs.676126 |
| A_33_P3235189 | ANKRD13B | *Homo sapiens* ankyrin repeat domain 13B (ANKRD13B), mRNA [NM_152345] | NM_152345 | ENST00000493506 | 124930 | ankyrin repeat domain 13B | chr17:2793923 1-27939290 | | NM_152345 | NP1146859 | Hs.662164 |
| A_33_P3216232 | ITGB1BP1 | *Homo sapiens* integrin beta 1 binding protein 1 (ITGB1BP1), transcript variant 1, mRNA [NM_004763] | NM_004763 | ENST00000483795 | 9270 | integrin beta 1 binding protein 1 | chr2:9545927-9545868 | GO:0005515\|GO:0005737\|NM_004763 GO:0016477\|GO:0016020\| GO:0007160\|GO:0001726\| GO:0030027\|GO:0007243\| GO:0005829 | | THC2501038 | Hs.467662 |
| A_33_P3262969 | COL4A6 | collagen, type IV, alpha 6 [Source: HGNC Symbol; Acc: 2208] [ENST00000461897] | BT007228 | ENST00000461897 | 1288 | collagen, type IV, alpha 6 | chrX:10751236 9-107512310 | | | THC2480759 | Hs.145586 |
| A_33_P3411477 | NCCRP1 | *Homo sapiens* non-specific cytotoxic cell receptor protein 1 homolog (zebrafish) (NCCRP1), mRNA [NM_001001414] | NM_001001414 | ENST00000339852 | 342897 | non-specific cytotoxic cell receptor protein 1 homolog (zebra fish) | chr19:3969246 1-39692520 | GO:0005515\|GO:0030163 | NM_001001414 | NP1155945 | Hs 726934 |
| A_23_P108294 | PPAP2C | *Homo sapiens* phosphatidic acid phosphatase type 2C (PPAP2C), transcript variant 3, mRNA [NM_177543] | NM_177543 | ENST00000327790 | 8612 | phosphatidic acid phosphatase type 2C | chr19:282253-282194 | GO:0043392\|GO:0016787\|NM_177543 GO:0005886\|GO:0004721\| GO:0016021\|GO:0008195 | | THC2554424 | Hs.465506 |
| A_24_P305570 | RIN2 | *Homo sapiens* Ras and Rab interactor 2 (RIN2), transcript variant 2, mRNA [NM_018993] | NM_018993 | ENST00000255006 | 54453 | Ras and Rab interactor 2 | chr20:1998254 1-19982600 | GO:0005515\|GO:0017112\|NM_018993 GO:0007165\|GO:0005737\| GO:0005083\|GO:0007264\| GO:0005575\|GO:0006897\| GO:0005096 | | THC2463477 | Hs.472270 |
| A_33_P3226154 | | *Homo sapiens* immunoglobulin kappa constant [Source: HGNC Symbol; Acc: 5716] [ENST00000390237] | AY538254 | ENST00000390237 | | | chr2:89156970-89156911 | | | NP1073961 | Hs.449621 |
| A_33_P3416707 | PTK2 | PTK2 protein tyrosine kinase 2 [Source: HGNC Symbol; Acc: 9611] [ENST00000342207] | | ENST00000342207 | 5747 | PTK2 protein tyrosine kinase 2 | chr8:14174485 5-141744796 | | | | |
| A_33_P3231076 | LOC100132707 | *Homo sapiens* hypothetical LOC100132707 | NR_024477 | ENST00000411526 | 100132707 | hypothetical LOC100132707 | chr7:15473842 9-154738488 | | NR_024477 | THC2512332 | Hs.586358 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq Accession | TIGRID | UniGene ID |
|---|---|---|---|---|---|---|---|---|---|---|---|
| | | (LOC100132707), transcript variant 2, non-coding RNA [NR_024477] | | | | | | | | | |
| A_23_P411723 | PLAG1 | Homo sapiens pleiomorphic adenoma gene 1 (PLAG1), transcript variant 1, mRNA [NM_002655] | NM_002655 | ENST00000316981 | 5324 | pleiomorphic adenoma gene 1 | chr8:57074013-57073954 | GO:0005622\|GO:0003700\|NM_002655\|GO:0008270\|GO:0005634\|GO:0046872\|GO:0045449 | | THC2649104 | Hs.14968 |
| A_32_P63848 | OXCT1 | Homo sapiens 3-oxoacid CoA transferase 1 (OXCT1), nuclear gene encoding mitochondrial protein, mRNA [NM_000436] | NM_000436 | ENST00000546045 | 5019 | 3-oxoacid CoA transferase 1 | chr5:41730530-41730471 | GO:0005739\|GO:0046952\|NM_000436\|GO:0005759\|GO:0008152\|GO:0008260\|GO:0042803\|GO:0016740 | | THC2620135 | Hs.278277 |
| A_33_P3324805 | LOC100130345 | PREDICTED: Homo sapiens cadherin-related family member 3 like (LOC100130345), mRNA [XM_001716484] | XM_001716484 | | 100130345 | cadherin-related family member 3-like | chr3:63738330-63738271 | | XM_001716484 | | Hs.534738 |
| A_24_P305467 | GATAD2A | Homo sapiens GATA zinc finger domain containing 2A (GATAD2A), mRNA [NM_017660] | NM_017660 | ENST00000358713 | 54815 | GATA zinc finger domain containing 2A | chr19:19619473-19619532 | GO:0043565\|GO:0016564\|NM_017660\|GO:0006306\|GO:0003700\|GO:0016607\|GO:0016581\|GO:0005730\|GO:0008270\|GO:0005634\|GO:0030674\|GO:0045892\|GO:0046872 | | THC2496807 | Hs.118964 |
| A_23_P312920 | POU2AF1 | Homo sapiens POU class 2 associating factor 1 (POU2AF1), mRNA [NM_006235] | NM_006235 | ENST00000393067 | 5450 | POU class 2 associating factor 1 | chr11:111223063-111223004 | GO:0005515\|GO:0006366\|NM_006235\|GO:0006959\|GO:0003713\|GO:0005634\|GO:0003677\|GO:0045449 | | THC2464202 | Hs.654525 |
| A_23_P118516 | FAM18B1 | Homo sapiens family with sequence similarity 18, member B1 (FAM18B1), mRNA [NM_016078] | NM_016078 | ENST00000428082 | 51030 | family with sequence similarity 18, member B1 | chr17:18709283-18709342 | GO:0016020\|GO:0016021 | NM_016078 | THC2557159 | Hs.87295 |
| A_33_P3424467 | CNST | Homo sapiens consortin, connexin sorting protein (CNST), transcript variant 1, mRNA [NM_152609] | NM_152609 | ENST00000366513 | 163882 | consortin, connexin sorting protein | chr1:246831802-246831861 | GO:0043234\|GO:0016020\|NM_152609\|GO:0016021 | | THC2600974 | Hs.368353 |
| A_33_P3370521 | | | XM_001721393 | ENST00000427872 | | | chr1:120876554-120876495 | | XM_001721393 | THC2698492 | Hs.568526 |
| A_33_P3330663 | | GB | | | | | chr8:048114175-048114116 | | | NP109356 | |
| A_24_P67421 | | TCAAP1Q12860HGSC Pediatric acute myelogenous leukemia cell (FAB M1) Baylor- | BM147583 | | | | chr15:0327920225-032791965 | | | THC2535859 | Hs.730231 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | project = TCAA Homo sapiens cDNA clone TCAAP1286, mRNA sequence [BM147583] | | | | | | | | | |
| A_23_P311010 | SPRY3 | Homo sapiens sprouty homolog 3 (Drosophila) (SPRY3), mRNA [NM_005840] | NM_005840 | ENST00000302805 | 10251 | sprouty homolog 3 (Drosophila) | chrX:155012033 8-155012097 | GO:0005515\|GO:0003674\|GO:0005737\|GO:0016020\|GO:0007275\|GO:0009966\|GO:0019898 | NM_005840 | THC2615136 | Hs.381912 |
| A_23_P326080 | DEFA4 | Homo sapiens defensin, alpha 4, corticostatin (DEFA4), mRNA [NM_001925] | NM_001925 | ENST00000297435 | 1669 | defensin, alpha 4, corticostatin | chr8:6793424-6793365 | GO:0050832\|GO:0031640\|GO:0005576\|GO:0005615\|GO:0042742 | NM_001925 | THC2478179 | Hs.591391 |
| A_33_P3300975 | HOXC4 | Homo sapiens home-obox C4 (HOXC4), transcript variant 1, mRNA [NM_014620] | NM_014620 | ENST00000430889 | 3221 | homeobox C4 | chr12:5444975 5-54449814 | GO:0043565\|GO:0006355\|GO:0003700\|GO:0051216\|GO:0007275\|GO:0005634\|GO:0009952\|GO:0048562 | NM_014620 | THC2474518 | Hs.549040 |
| A_33_P3299739 | CLDN19 | Homo sapiens claudin 19 (CLDN19), transcript variant 2, mRNA [NM_001123395] | NM_001123395 | ENST00000372539 | 149461 | claudin 19 | chr1:43200754-43200695 | GO:0000287\|GO:0030054\|GO:0005886\|GO:0005634\|GO:0019227\|GO:0042802\|GO:0043297\|GO:0016323\|GO:0005737\|GO:0016338\|GO:0005198\|GO:0005923\|GO:0016021\|GO:0007601\|GO:0050896 | NM_001123395 | THC2482498 | Hs.496270 |
| A_23_P502808 | PRIMA1 | Homo sapiens proline rich membrane anchor 1 (PRIMA1), mRNA [NM_178013] | NM_178013 | ENST00000477603 | 145270 | proline rich membrane anchor 1 | chr14:9420365 0-94203591 | GO:0030054\|GO:0005886\|GO:0045202\|GO:0016021\|GO:0042135 | NM_178013 | THC2489283 | Hs.432401 |
| A_33_P3327888 | | chromosome 8 open reading frame 17 [Source: HGNC Symbol; Acc: 17737] [ENST00000507535] | XM_002346128 | ENST00000507535 | | | chr8:14094467 0-140944729 | | XM_002346128 | NP1462426 | Hs.283098 |
| A_33_P3309365 | FLJ40434 | Homo sapiens hypo-thetical FLJ40434 (FLJ40434), non-coding RNA [NR_002314] | NR_002314 | | 163742 | hypothetical FLJ40434 | chr1:53904127-53904068 | | NR_002314 | THC2482167 | Hs.722531 |
| A_24_P342591 | RERE | Homo sapiens arginine-glutamic acid dipeptide (RE) repeats (RERE), transcript variant 1, mRNA [NM_012102] | NM_012102 | ENST00000467350 | 473 | arginine-glutamic acid dipeptide (RE) repeats | chr1:8413045-8412986 | GO:0043565\|GO:0008267\|GO:0006355\|GO:0003700\|GO:0000118\|GO:0008270\|GO:0007275\|GO:0006338\|GO:0005634\|GO:0006607\|GO:0046872 | NM_012102 | | Hs.463041 |
| A_33_P3281468 | STARD9 | Homo sapiens StAR-related lipid transfer (START) domain con- | NM_020759 | ENST00000290607 | 57519 | StAR-related lipid transfer (START) | chr15:4297934 0-42979399 | GO:0001166\|GO:0003777\|GO:0005524\|GO:0007018 | NM_020759 | THC2602580 | Hs.122061 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3213888 | C17orf109 | taining 9 (STARD9), mRNA [NM_020759] Homo sapiens chromosome 17 open reading frame 109 (C17orf109), transcript variant 1, mRNA [NM_001162995] | NM_001162995 | ENST00000375215 | 643008 | chromosome 17 open reading frame 109 | chr17:73630124-73630183 | | NM_001162995 | THC2532809 | Hs.528605 |
| A_33_P3403082 | NCRNA00176 | Homo sapiens non-protein coding RNA 176 (NCRNA00176), transcript variant 1, non-coding RNA [NR_027686] | NR_027686 | | 284739 | non-protein coding RNA 176 | chr20:62671072-62671131 | | NR_027686 | | Hs.97840 |
| A_23_P210274 | MOBKL3 | Homo sapiens MOB1, Mps One Binder kinase activator-like 3 (yeast) (MOBKL3), transcript variant 1, mRNA [NM_015387] | NM_015387 | ENST00000497443 | 25843 | MOB1, Mps One Binder kinase activator-like 3 (yeast) | chr2:198415033-198415092 | GO:0005515 GO:0048471 GO:0005737 GO:0005794 GO:0016020 GO:0006810 GO:0005624 GO:0008270 GO:0046872 GO:0019898 | NM_015387 | THC2499735 | Hs.633165 |
| A_24_P933794 | LOC646513 | Homo sapiens clone DNA96880 VLGN1945 (UNQ1945) mRNA, complete cds. [AY358802] | AY358802 | | 646513 | VLGN1945 | chr22:30831574-30831633 | | | NP862031 | Hs.565803 |
| A_33_P3377760 | | DA946325 SPLEN2 Homo sapiens cDNA clone SPLEN2022065 5′, mRNA sequence [DA946325] | DA946325 | | | | chr6:170773783-170773842 | | | | Hs.583059 |
| A_33_P3313625 | | | | | | | chr13:050194775-050194716 | | | | |
| A_24_P84898 | FEN1 | Homo sapiens flap structure-specific endanuclease 1 (FEN1), mRNA [NM_004111] | NM_004111 | ENST00000305885 | 2237 | flap structure-specific endonuclease 1 | chr11:61564029-61564087 | GO:0005515 GO:0009650 GO:0030145 GO:0000287 GO:0008409 GO:0048015 GO:0005634 GO:0006302 GO:0003684 GO:0005739 GO:0006260 GO:0003690 GO:0004519 GO:0016787 GO:0004523 GO:0043137 GO:0017108 GO:0008309 | NM_004111 | THC2469346 | Hs.409065 |
| A_32_P14843 | | nuclear pore complex interacting protein-like 2 [Source: HGNC Symbol; Acc: 34409] [ENST00000429990] | XM_003118720 | ENST00000429990 | | | chr16:74425519-74425578 | | XM_003118720 | THC2556353 | Hs.448833 |
| A_23_P395954 | SSH2 | slingshot homolog 2 (Drosophila) [Source: HGNC Symbol; | AB072358 | ENST00000394848 | 85464 | slingshot homolog 2 (Drosophila) | chr17:27975135-27975076 | | | THC2543332 | Hs.654754 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P376556 | CYCS | Acc: 30580] [ENST00000394848] Homo sapiens cytochrome c, somatic (CYCS), nuclear gene encoding mitochondrial protein, mRNA [NM_018947] | NM_018947 | ENST00000409764 | 54205 | cytochrome c, somatic | chr7:25158296-25158264 | GO:0005515\|GO:0008635\|NM_018947 GO:0070469\|GO:0000159\| GO:0006915\|GO:0005634\| GO:0046872\|GO:0005829\| GO:0005739\|GO:0005758\| GO:0043333\|GO:0045155\| GO:0006309\|GO:0005759\| GO:0006810\|GO:0004722\| GO:0022900\|GO:002037 | | THC2535070 | Hs.437060 |
| A_33_P3244274 | RNF208 | Homo sapiens ring finger protein 208, mRNA (cDNA clone MGC21544 IMAGE: 4151712), complete cds. [BC016958] | BC016958 | | 727800 | ring finger protein 208 | chr9:14011476 0-140114701 | GO:0005515\|GO:0008270 GO:0046872 | | THC2473148 | Hs.512767 |
| A_23_P40192 | CDH22 | Homo sapiens cadherin 22, type 2 (CDH22), mRNA [NM_021248] | NM_021248 | ENST00000372262 | 64405 | cadherin 22, type 2 | chr20:4480279 4-44802735 | GO:0005515\|GO:0005886\|NM_021248 GO:0005509\|GO:0016021\| GO:0007155\|GO:0007156 | | THC2477489 | Hs.472861 |
| A_24_P131580 | ALPPL2 | Homo sapiens alkaline phosphatase, placental-like 2 (ALPPL2), mRNA [NM_031313] | NM_031313 | ENST00000295453 | 251 | alkaline phosphatase, placental-like 2 | chr2:23327534 7-233275406 | GO:0016310\|GO:0000287\|NM_031313 GO:0016787\|GO:0005886\| GO:0004035\|GO:0008152\| GO:0008270\|GO:0031225 | | THC2603490 | Hs.333509 |
| A_23_P78092 | EVI2A | Homo sapiens ecotropic viral integration site 2A (EVI2A), transcript variant 1, mRNA [NM_001003927] | NM_001003927 | ENST00000247270 | 2123 | ecotropic viral integration site 2A | chr17:2964546 1-29645402 | GO:0016020\|GO:0016021\|NM_001003927 GO:0004888 | | THC2462437 | Hs.591198 |
| A_33_P3367171 | SLC22A8 | Homo sapiens solute carrier family 22 (organic anion transporter), member 8 [Source: HGNC Symbol; Acc: 10972] [ENST00000451262] | AK123243 | ENST00000451262 | 9376 | solute carrier family 22 (organic anion transporter), member 8 | chr11:6276092 0-62760861 | | | THC2602662 | Hs.266223 |
| A_33_P3264533 | | | | | | | chr10:0927207 34-092720675 | | | | |
| A_23_P200138 | SLAMF8 | Homo sapiens SLAM family member 8 (SLAMF8), mRNA [NM_020125] | NM_020125 | ENST00000289707 | 56833 | SLAM family member 8 | chr1:15980698 0-154807039 | GO:0016020\|GO:0016021 NM_020125 | | THC2465098 | Hs.438683 |
| A_24_P148796 | MST1 | Homo sapiens macrophage stimulating 1 | NM_020998 | ENST00000493836 | 4485 | macrophage stimulating 1 | chr3:49721610 49721551 | GO:0008150\|GO:0004252\|NM_020998 GO:0007596\|GO:0005509 | | NP299055 | Hs.512587 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3395876 | | (hepatocyte growth factor-like) (MST1), mRNA [NM_020998] | | | | (hepatocyte growth factorlike) | | GO:0006508\|GO:0005576\|GO:0003824 | | | |
| | PDE4A | Homo sapiens phosphodiesterase 4A, cAMP-specific (PDE4A), transcript variant 1, mRNA [NM_001111307] | NM_001111307 | ENST00000380702 | 5141 | phosphodiesterase 4A, cAMP-specific | chr19:10572615-10572674 | GO:0005515\|GO:0048471\|GO:0004115\|GO:0042493\|GO:0005624\|GO:0005625\|GO:0005634\|GO:0032587\|GO:0005829\|GO:0007165\|GO:0005737\|GO:0016020\|GO:0016787\|GO:0019898 | NM_001111307 | THC2603099 | Hs.89901 |
| A_23_P200222 | LRP8 | Homo sapiens low density lipoprotein receptor-related protein 8, apolipoprotein e receptor (LRP8), transcript variant 2, mRNA [NM_033300] | NM_033300 | ENST00000306052 | 7804 | low density lipoprotein receptor-related protein 8, apolipoprotein e receptor | chr1:53711278-53711219 | GO:0005515\|GO:0006629\|GO:0005886\|GO:0005509\|GO:0019221\|GO:0005576\|GO:0021819\|GO:0005615\|GO:0006897\|GO:0021766\|GO:0007165\|GO:0030229\|GO:0005901\|GO:0045860\|GO:0006508\|GO:0016021\|GO:0034187\|GO:0004888 | NM_033300 | THC2470553 | Hs.726256 |
| A_33_P3303066 | BTBD2 | Homo sapiens BTB2 (POZ) domain containing (BTBD2), mRNA [NM_017797] | NM_017797 | ENST00000255608 | 55643 | BTB (POZ) domain containing 2 | chr19:1986041-1985982 | GO:0005515\|GO:0005737\|GO:0000932 | NM_017797 | THC2466054 | Hs.465543 |
| A_33_P3864861 | LOC339505 | Homo sapiens hypothetical LOC339505 (LOC339505), non-coding RNA [NR_033887] | NR_033887 | ENST00000426428 | 339505 | hypothetical LOC339505 | chr1:20687133-20687074 | | NR_033887 | THC2606901 | Hs.633269 |
| A_32_P148122 | | immunoglobulin kappa variable 1D-33 [Source: HGNC Symbol; Acc: 5753] [ENST00000390265] | BC095489 | ENST00000390265 | | | chr2:89953072-89953131 | | | NP093301 | Hs.449621 |
| A_23_P142096 | GPR32 | Homo sapiens G protein-coupled receptor 32 (GPR32), mRNA [NM_001506] | NM_001506 | ENST00000270590 | 2854 | G protein-coupled receptor 32 | chr19:5127466-51274723 | GO:0004982\|GO:0007165\|GO:0007186\|GO:0005886\|GO:0005887\|GO:0004930\|GO:0004872 | NM_001506 | THC2480357 | Hs.515555 |
| A_33_P3365963 | | | | | | | chr4:04136316-8-041363109 | | | | |
| A_23_P143885 | ARHGEF3 | Homo sapiens Rho guanine nucleotide exchange factor (GEF) 3 (ARHGEF3), transcript variant 3, mRNA [NM_019555] | NM_019555 | ENST00000413728 | 50650 | Rho guanine nucleotide exchange factor (GEF) 3 | chr3:56762170-56762111 | GO:0005622\|GO:0005085\|GO:0008624\|GO:0007242\|GO:0005737\|GO:0035023\|GO:0006915\|GO:0005089\|GO:0005829 | NM_019555 | THC2466586 | Hs.476402 |
| A_33_P3316903 | | PREDICTED: Homo sapiens hypo- | XR_110873 | ENST00000519753 | | | chr8:30240735-30240676 | | XR_110873 | THC2524368 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P75680 | | thetical LOC100128750 (LOC100128750), partial miscRNA [XR_110873] | | | | | | | | THC2617779 | Hs.370636 |
| A_23_P107735 | SLC4A8 | Homo sapiens solute carrier family 4, sodium bicarbonate cotransporter, member 8 (SLC4A8), transcript variant 2, mRNA [NM_004858] | NM_004858 | ENST00000546663 | 9498 | solute carrier family 4, sodium bicarbonate cotransporter, member 8 | chr12:51865202-51865261 | GO:0006820|GO:0008509|GO:0005215|GO:0015297|GO:0016020|GO:0005452|GO:0016021|GO:0031402|GO:0006814 | NM_004858 | THC2467444 | Hs.631567 |
| A_32_P32413 | CD79A | Homo sapiens CD79a molecule, immunoglobulin-associated alpha (CD79A), transcript variant 1, mRNA [NM_001783] | NM_001783 | ENST00000221972 | 973 | CD79a molecule, immunoglobulin-associated alpha | chr19:42385156-42385415 | GO:0005515|GO:0050853|GO:0005886|GO:0005771|GO:0019815|GO:0006955|GO:0042100|GO:0030183|GO:0045121|GO:0016021|GO:0007166|GO:0009897|GO:0004888 | NM_001783 | | |
| A_23_P202117 | SETBP1 | Homo sapiens SET binding protein 1 (SETBP1), transcript variant 1, mRNA [NM_015559] | NM_015559 | ENST00000282030 | 26040 | SET binding protein 1 | chr18:42647824-42648306 | GO:0005515|GO:0005634|GO:0003677 | NM_015559 | THC2755509 | Hs.435458 |
| A_23_P348911 | PCGF5 | polycomb group ring finger 5 [Source: HGNC Symbol; Acc: 28264] [ENST00000490164] | BC007377 | ENST00000490164 | 84333 | polycomb group ring finger 5 | chr10:92987458-92987517 | GO:0005515|GO:0005813|GO:0008270|GO:0046872|GO:0045449 | | THC2536515 | Hs.500512 |
| A_33_P3338491 | LOC100129726 | Homo sapiens hypothetical LOC100129726 (LOC100129726), non-coding RNA [NR_027251] | NR_027251 | | 100129726 | hypothetical LOC100129726 | chr2:43455024-43455083 | | NR_027251 | THC2481238 | Hs.194480 |
| A_24_P354715 | LOC392196 | Homo sapiens ubiquitin specific peptidase 17-like 2 pseudogene (LOC392196), non-coding RNA [NR_003275] | NR_003275 | | 392196 | ubiquitin specific peptidase 17-like 2 pseudogene | chr8:7200733-7200792 | | NR_003275 | | Hs.646768 |
| | NT5E | Homo sapiens 5' nucleotidase, ecto (CD73) (NT5E), transcript variant 1, mRNA [NM_002526] | NM_002526 | ENST00000257770 | 4907 | 5'-nucleotidase, ecto (CD73) | chr6:86204891-86204950 | GO:0005886|GO:0016788|GO:0005624|GO:0046086|GO:0006259|GO:0031225|GO:0009166|GO:0046872|GO:0008198|GO:0006196|GO:0005737|GO:0000166 | NM_002526 | THC2468393 | Hs.153952 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3381851 | KRTAP10-10 | Homo sapiens keratin associated protein 10-10 (KRTAP10-10), mRNA [NM_181688] | NM_181688 | ENST00000380095 | 353333 | keratin associated protein 10-10 | chr21:46058134-46058193 | GO:0050728\|GO:0008253\|GO:0008270\|GO:0006164\|GO:0045095 | NM_181688 | NP134181 | Hs.474001 |
| A_23_P139965 | SERP2 | Homo sapiens stress-associated endoplasmic reticulum protein family member 2 (SERP2), mRNA [NM_001010897] | NM_001010897 | ENST00000493476 | 387923 | stress-associated endoplasmic reticulum protein family member 2 | chr13:44971760-44971820 | GO:0016020\|GO:0005783\|GO:0016021\|GO:0015031\|GO:0055085 | NM_001010897 | THC2475127 | Hs.377972 |
| A_24_P184445 | MMP19 | Homo sapiens matrix metallopeptidase 19 (MMP19), transcript variant 1, mRNA [NM_002429] | NM_002429 | ENST00000394182 | 4327 | matrix metallopeptidase 19 | chr12:56229481-56229422 | GO:0030574\|GO:0008152\|GO:0005509\|GO:0006508\|GO:0005578\|GO:0008270\|GO:0008233\|GO:0007275\|GO:0005576\|GO:0001525\|GO:0004222\|GO:0030154 | NM_002429 | THC2488331 | Hs.591033 |
| A_23_P88234 | FAM158A | Homo sapiens family with sequence similarity 158, member A (FAM158A), mRNA [NM_016049] | NM_016049 | ENST00000419198 | 51016 | family with sequence similarity 158, member A | chr14:24608579-24608357 | | NM_016049 | THC2502204 | Hs.271614 |
| A_33_P3329078 | HBG1 | Homo sapiens hemoglobin, gamma A (HBG1), mRNA [NM_000559] | NM_000559 | ENST00000380256 | 3047 | hemoglobin, gamma A | chr11:5269613-5269554 | GO:0005515\|GO:0019825\|GO:0005833\|GO:0006810\|GO:0005344\|GO:0046872\|GO:0020037\|GO:0015671 | NM_000559 | NP094052 | Hs.712539 |
| A_33_P3257460 | DPM3 | Homo sapiens dolichyl-phosphate mannosyltransferase polypeptide 3 (DPM3), transcript variant 1, mRNA [NM_018973] | NM_018973 | ENST00000368399 | 54344 | dolichyl-phosphate mannosyltransferase polypeptide 3 | chr1:155112428-155112369 | GO:0005515\|GO:0004582\|GO:0033185\|GO:0016020\|GO:0005975\|GO:0005783\|GO:0005789\|GO:0018406\|GO:0030176\|GO:0016021\|GO:0035269\|GO:0006506 | NM_018973 | THC2471966 | Hs.110477 |
| A_33_P3368675 | C6orf120 | Homo sapiens chromosome 6 open reading frame 120 (C6orf120), mRNA [NM_001029863] | NM_001029863 | ENST00000332290 | 387263 | chromosome 6 open reading frame 120 | chr6:170106141-170106200 | GO:0005576 | NM_001029863 | | Hs.591375 |
| A_23_P215461 | LIMK1 | Homo sapiens LIM domain kinase 1 (LIMK1), transcript variant 1, mRNA [NM_002314] | NM_002314 | ENST00000336180 | 3984 | LIM domain kinase 1 | chr7:73536663-73536722 | GO:0005515\|GO:0030036\|GO:0007266\|GO:0005524\|GO:0046872\|GO:0007399\|GO:0007165\|GO:0005737\|GO:0000166\|GO:0004674\|GO:0006468\|GO:0008270\|GO:0016740 | NM_002314 | THC2489637 | Hs.647035 |
| A_33_P3287862 | | Homo sapiens cDNA FLJ59054 complete cds, | AK301306 | | | | Chr2:91873675-91873616 | | | NP511251 | Hs.694621 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | highly similar to D(1B) dopamine receptor. [AK301306] | | | | | | | | | |
| A_23_P206228 | VPS13C | Homo sapiens vacuolar protein sorting 13 homolog C (S. cerevisiae) (VPS13C), transcript variant 2A, mRNA [NM_020821] | NM_020821 | ENST00000261517 | 54832 | vacuolar protein sorting 13 homologC (S. cerevisiae) | chr15:62144891-62144832 | GO:0008104 | NM_020821 | NP1403881 | Hs.511668 |
| A_23_P167328 | CD38 | Homo sapiens CD38 molecule (CD38), mRNA [NM_001775] | NM_001775 | ENST00000540195 | 952 | CD38 molecule | chr4:15850185-15850244 | GO:0008624|GO:0005886|NM_001775|GO:0030307|GO:0030890|GO:0005634|GO:0060292|GO:0007204|GO:0045779|GO:0045907|GO:0016798|GO:0004872|GO:0032024|GO:0009725|GO:0032526|GO:0032355|GO:0033194|GO:0070555|GO:0005792|GO:0001666|GO:0007565|GO:0009986|GO:0016849|GO:0005624|GO:0007165|GO:0003953|GO:0005488|GO:0008152|GO:0032570|GO:0016021 | | NP088570 | Hs.479214 |
| A_33_P3372501 | PPP1R13B | Homo sapiens protein phosphatase 1, regulatory (inhibitor) subunit 13B (PPP1R13B), mRNA [NM_015316] | NM_015316 | ENST00000380023 | 23368 | protein phosphatase 1, regulatory (inhibitor) subunit 13B | chr14:104206483-104206424 | GO:0005515|GO:0005737|NM_015316|GO:0006915|GO:0005634|GO:0006917|GO:0045786 | | NP1151875 | Hs.709297 |
| A_33_P3349259 | FAM115A | Homo sapiens family with sequence similarity 115, member A (FAM115A), transcript variant 1, mRNA [NM_014719] | NM_014719 | ENST00000392900 | 9747 | family with sequence similarity 115, member A | chr7:143557466-143557407 | | NM_014719 | THC2787549 | Hs.406492 |
| A_23_P24784 | TNNI2 | Homo sapiens troponin 1 type 2 (skeletal, fast) (TNNI2), transcript variant 1, mRNA [NM_003282] | NM_003282 | ENST00000381906 | 7136 | troponin 1 type 2 (skeletal, fast) | chr11:1862437-1862744 | GO:0005515|GO:0031014|NM_003282|GO:0045941|GO:0005861|GO:0003009|GO:0005634|GO:0003779 | | THC2467502 | Hs.523403 |
| A_33_P3261433 | LOC100131473 | PREDICTED: Homo sapiens hypothetical protein LOC100131473 (LOC100131473), mRNA [XM_001720331] | XM_001720331 | | 100131473 | hypothetical protein LOC100131473 | chr2:74212866-74212807 | | XM_001720331 | THC2660992 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P390744 | FOPNL | Homo sapiens FGFR1OP N-terminal like (FOPNL), mRNA [NM_144600C] | NM_144600 | ENST00000255759 | 123811 | FGFR1OP N-terminal like | chr16:15959688-15959629 | | NM_144600 | THC2468681 | Hs.514179 |
| A_23_P150609 | IGF2 | Homo sapiens insulin-like growth factor 2 (somatomedin A) (IGF2), transcript variant 1, mRNA [NM_000612] | NM_000612 | ENST00000381319 | 3481 | insulin-like growth factor 2 (somatomedin A) | chr11:2150453-2150394 | GO:0005515|GO:0051897|NM_000612 GO:0008284|GO:0005159| GO:0005975|GO:0005158| GO:0046628|GO:0045840| GO:0005576|GO:0007275| GO:0005615|GO:0001649| GO:0001501|GO:0005179| GO:0032583|GO:0006349| GO:0009887|GO:0006006| GO:0051781|GO:0043410| GO:0008083 | | THC2465311 | Hs.272259 |
| A_33_P3299487 | AIM1L | Homo sapiens absent in melanoma 1-like (AIM1L), mRNA [NM_001039775] | NM_001039775 | ENST00000374207 | 55057 | absent in melanoma 1-like | chr1:26671913-26671854 | | NM_001039775 | THC2773713 | Hs.128738 |
| A_24_P453544 | | Homo sapiens clone FLB5634 PRO1477 mRNA, complete cds. [AF130059] | AY239294 | ENST00000541658 | | | chr9:13621792-136217864 | | | THC2476915 | |
| A_33_P3256585 | MUC8 | Homo sapiens mucin (MUC8) mRNA, partial cds. [U14383] | U14383 | | 4590 | mucin 8 | chr12:1330493-133049334 | | | THC2488232 | Hs.592357 |
| A_33_P3292896 | SFXN5 | Homo sapiens sidero-flexin 5 (SFXN5), nucleargene encoding mitochondrial protein, mRNA [NM_144579] | NM_144579 | ENST00000403277 | 94097 | sideroflexin 5 | chr2:73215461-73215402 | GO:0005739|GO:0016020|NM_144579 GO:0005506|GO:0008324| GO:0005743|GO:0006826| GO:0016021|GO:0055085| GO:0006812 | | THC2774255 | Hs.368171 |
| A_23_P127721 | P2RX3 | Homo sapiens purinergic receptor P2X, ligand-gated ion channel, 3 (P2RX3), mRNA [NM_002559] | NM_002559 | ENST00000534820 | 5024 | purinergic receptor P2X, ligand-gated ion channel, 3 | chr11:5711615-57117269 | GO:0030424|GO:0009408|NM_002559 GO:0010524|GO:0009409| GO:0042803|GO:0050850| GO:0009743|GO:0050909| GO:0048167|GO:0001614| GO:0033198|GO:0004872| GO:0014832|GO:0006812| GO:0001666|GO:0004931| GO:0046982|GO:0007274| GO:0005524|GO:0030432| GO:0007165|GO:0016020| GO:0005887|GO:0044424| GO:0005216|GO:0048266| GO:0050896 | | THC2480784 | Hs.146738 |
| A_23_P53018 | HRASLS5 | Homo sapiens HRAS-like suppressor family, | NM_054108 | ENST00000301790 | 117245 | HRAS-like suppressor | chr11:6323092-63230861 | | NM_054108 | THC2485151 | Hs.410316 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P103837 | FAM60A | member 5 (HRASLS5), transcript variant 1, mRNA [NM_054108] *Homo sapiens* family with sequence similarity 60, member A (FAM60A), transcript variant 2, mRNA [NM_021238] | NM_021238 | ENST00000337682 | 58516 | family, member 5 family with sequence similarity 60, member A | chr12:31433650-31433591 | | NM_021238 | THC2472594 | Hs.505154 |
| A_23_P74668 | C1orf158 | *Homo sapiens* chromosome 1 open reading frame 158 (C1orf158), mRNA [NM_152290] | NM_152290 | ENST00000376210 | 93190 | chromosome 1 open reading frame 158 | chr1:12821032-12821091 | | NM_152290 | NP1155029 | Hs.98095 |
| A_33_P3305438 | LOC100129827 | *Homo sapiens* hypothetical LOC100129827 (LOC100129827), non-coding RNA [NR_034094] | NR_034094 | ENST00000529979 | 100129827 | hypothetical LOC100129827 | chr7:155684885-155684944 chr11:10615670-10615729 | | NR_034094 | THC2480303 | Hs.246769 |
| A_23_P396299 | | | | | | | | | | | |
| A_33_P3239659 | DERL3 | *Homo sapiens* Der1-like domain family, member 3 (DERL3), transcript variant 3, mRNA [NM_198440] | NM_198440 | ENST00000290730 | 91319 | Der1-like domain family, member 3 | chr3:113950263-113950204 chr22:24176774-24176715 | GO:0005515|GO:0016020|GO:0030176| GO:0005783|GO:0030433| GO:0016021|GO:0030968 | NM_198440 | THC2488725 | Hs.593679 |
| A_33_P3724155 | PRKAG3 | *Homo sapiens* protein kinase, AMP-activated, gamma 3 non-catalytic subunit (PRKAG3), mRNA [NM_017431] | NM_017431 | ENST00000545803 | 53632 | protein kinase, AMP-activated, gamma 3 non-catalytic subunit | chr2:219688436-219688377 | GO:0019901|GO:0015758|NM_017431| GO:0004679|GO:0005978| GO:0006633|GO:0046320| GO:0007243 | | NP164557 | Hs.591634 |
| A_33_P3244843 | | | | | | | | | | | |
| A_33_P3251412 | C5orf15 | *Homo sapiens* chromosome 5 open reading frame 15 (C5orf15), mRNA[NM_020199] | NM_020199 | ENST00000231512 | 56951 | chromosome 5 open reading frame 15 | chr22:023055633-023055692 chr5:133291476-133291417 | GO:0016020|GO:0016021 NM_020199 | | THC2469485 | Hs.730670 |
| A_23_P81650 | MZT2A | *Homo sapiens* mitotic spindle organizing protein 2A [Source: HGNC Symbol; Acc: 33187] [ENST00000445782] | | ENST00000445782 | 653784 | mitotic spindle organizing protein 2A | chr2:132227819-132227760 | | | THC2544251 | |
| A_33_P3359856 | TFE3 | *Homo sapiens* transcription factor binding | NM_006521 | ENST00000315869 | 7030 | transcription factor binding | chrX:48887788-48887729 | GO:0005515|GO:0003700|NM_006521| GO:0006959|GO:0010843| | THC2524136 | Hs.730740 |
| A_33_P3370076 | | | | | | | | | | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3419691 | | to IGHM enhancer 3 (IFE3), mRNA [NM_006521] | | | | to IGHM enhancer 3 | | GO:0010552 GO:0005634 GO:0045449 | | | |
| A_33_P3340649 | GATS | Homo sapiens GATS, stromal antigen 3 opposite strand (GATS), transcript variant 2, non-coding RNA [NR_028038] | NR_028038 | | 352954 | GATS, stromal antigen 3 opposite strand | chr7:9980662 0-99806561 | | NR_028038 | THC2463982 | Hs.556063 |
| A_33_P3340649 | KRTAP19-8 | Homo sapiens keratin associated protein 19-8 (KRTAP19-8), mRNA [NM_001099219] | NM_001099219 | ENST00000382822 | 728299 | keratin associated protein 19-8 | chr21:3241053 7-32410478 | GO:0005882 | NM_001099219 | NP1460239 | Hs.580875 |
| A_33_P3291821 | ANKRD26P1 | Homo sapiens ankyrin repeat domain 26 pseudogene 1 (ANKRD26P1), non-coding RNA [NR_026556] | NR_026556 | ENST00000329373 | 124149 | ankyrin repeat domain 26 pseudogene 1 | chr16:4650572 7-46505668 | | NR_026556 | THC2621756 | Hs.97414 |
| A_33_P3305102 | GPR97 | Homo sapiens G protein-coupled receptor 97 (GPR97), mRNA [NM_170776] | NM_170776 | ENST00000327655 | 222487 | G protein-coupled receptor 97 | chr16:5771961 4-57719673 | GO:0005886 GO:0007218 GO:0004930 GO:0016021 | NM_170776 | NP587669 | Hs.383403 |
| A_33_P3362048 | SHMT1 | Homo sapiens serine hydroxymethyltransferase 1 (soluble) [Source: HGNC Symbol; Acc: 10850] [ENST00000395682] | | ENST00000395682 | 6470 | serine hydroxymethyltransferase 1 (soluble) | chr17:1825689 0-18256831 | | | | |
| A_24_P385190 | SLC4A1 | Homo sapiens solute carrier family 4, anion exchanger, member 1 (erythrocyte membrane protein band 3, Diego blood group) (SLC4A1), mRNA [NM_000342] | NM_000342 | ENST00000471005 | 6521 | solute carrier family 4, anion exchanger, member 1 (erythrocyte membrane protein band 3, Diego blood group) | chr17:4233785 8-42337799 | GO:0006820 GO:0052215 GO:0008509 GO:0030018 GO:0030506 GO:0006873 GO:0003779 GO:0008022 GO:0042803 GO:0016323 GO:0005452 GO:0016020 GO:0005887 GO:0030863 GO:0043495 | NM_000342 | THC2474664 | Hs.443948 |
| A_23_P49546 | GRIN2C | Homo sapiens glutamate receptor, ionotropic, N-methyl D-aspartate 2C (GRIN2C), mRNA [NM_000835] | NM_000835 | ENST00000293190 | 2905 | glutamate receptor, ionotropic, N-methyl D-aspartate 2C | chr17:7283826 3-72838204 | GO:0030054 GO:0005886 GO:0045234 GO:0017146 GO:0045202 GO:0008104 GO:0004972 GO:0048167 GO:0045211 GO:0042391 GO:0050885 GO:0004872 GO:0006811 GO:0005261 GO:0000287 GO:0033058 | NM_000835 | THC2476723 | Hs.436980 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3324454 | TPP1 | Homo sapiens tri-peptidyl peptidase I (TPP1), mRNA [NM_000391] | NM_000391 | ENST00000453338 | 1200 | tripeptidyl peptidase I | chr11:6636189-6636130 | GO:0042177\|GO:0005509\|GO:0009611\|GO:0060079\|GO:0014069\|GO:0072215\|GO:0030165\|GO:0047485\|GO:0005887 | NM_000391 | THC2533577 | Hs.523454 |
| A_23_P30929 | C12orf51 | Homo sapiens chromosome 12 open reading frame 51 (C12orf51), mRNA [NM_001109662] | NM_001109662 | ENST00000311694 | 283450 | chromosome 12 open reading frame 51 | chr12:112688911-112688852 | GO:0005515\|GO:0006629\|NM_000391\|GO:0042470\|GO:0008219\|GO:0042277\|GO:0004252\|GO:0045453\|GO:0005625\|GO:0005764\|GO:0007399\|GO:0005739\|GO:0050885\|GO:0006508\|GO:0008240\|GO:0008233\|GO:0043171\|GO:0007040 | NM_001109662 | THC2560894 | Hs.530943 |
| A_33_P3293336 | GFRA1 | Homo sapiens GDNF family receptor alpha 1 (GFRA1), transcript variant 1, mRNA [NM_005264] | NM_005264 | | 2674 | GDNF family receptor alpha 1 | chr10:117816498-117816439 | GO:0005622\|GO:0016881\|NM_001109662\|GO:0016020\|GO:0019941\|GO:0016874\|GO:0016021\|GO:0006464 | | THC2537666 | Hs.388347 |
| A_33_P3246715 | LOC441495 | Homo sapiens centromere protein V pseudogene (LOC441495), non-coding RNA [NR_033773] | NR_033773 | | 441495 | centromere protein V pseudogene | chrX:51454417-51454476 | GO:0016167\|GO:0005886\|NM_005264\|GO:0005102\|GO:0004872\|GO:0031225\|GO:0007166\|GO:0019898\|GO:0007399 | NR_033773 | THC2627621 | Hs.730388 |
| A_33_P3424057 | PEG3 | Homo sapiens paternally expressed 3 (PEG3), transcript variant 1, mRNA [NM_006210] | NM_006210 | ENST00000326441 | 5178 | paternally expressed 3 | chr19:57325766-57325707 | GO:0005622\|GO:0006355\|NM_006210\|GO:0005737\|GO:0003700\|GO:0006915\|GO:0008270\|GO:0005634\|GO:0003676\|GO:0046872 | | THC2462814 | Hs.201776 |
| A_33_P3714341 | | Homo sapiens IGK mRNA for immunoglobulin kappa light chain, partial cds, clone: F010-014L [AB363267] | A11363267 | | | | | | | | Hs.694269 |
| A_33_P3252134 | | | | | | | chr16:030309263-030309322 | | | | |
| A_33_P3401138 | | | | | | | chr17:019043002-019042943 | | | | |
| A_23_P97990 | HTRA1 | Homo sapiens HtrA serine peptidase 1 | NM_002775 | ENST00000435263 | 5654 | HtrA serine peptidase 1 | chr10:124274338-124274397 | GO:0030514\|GO:0004252\|NM_002775\|GO:0006508\|GO:0008233 | | NP710487 | Hs.501280 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P44768 | TBK1 | (HTRA1), mRNA [NM_002775] Homo sapiens TANK-binding kinase 1 (TBK1), mRNA [NM_013254] | NM_013254 | ENST00000331710 | 29110 | TANK-binding kinase 1 | chr12:64895443-64895502 | GO:0005576\|GO:0005615\| GO:0001558\|GO:0005520 GO:0005515\|GO:0005737\|NM_013254 GO:0000166\|GO:0004674\| GO:0045087\|GO:0044419 GO:0006468\|GO:0043123\| GO:0009615\|GO:0005524 GO:0016740\|GO:0005829 | THC2467484 | Hs.505874 |
| A_23_P200936 | MTU | Homo sapiens 5-methyltetrahydrofolate-homocysteine methyl-transferase (MTR), mRNA [NM_000254] | NM_000254 | ENST00000470570 | 4548 | 5-methyl-tetrahydrofolate-homocysteine methyl-transferase | chr1:237063523-237063582 | GO:0005515\|GO:0031419\|NM_000254 GO:0008168\|GO:0009086 GO:0008652\|GO:0005625 GO:0008705\|GO:0050667 GO:0046872\|GO:0005829 GO:0007399\|GO:0005622 GO:0005542\|GO:0005737 GO:0046653\|GO:0006479 GO:0008270\|GO:0009396 GO:0004156\|GO:0008898 GO:0044237\|GO:0016740 GO:0050897 | THC2473394 | Hs.498187 |
| A_33_P3258092 | LOC100129763 | Homo sapiens cDNA FLJ44135 fis, clone THYMU2009134. [AK126123] | AK126123 | | 100129763 | hypothetical protein LOC100129763 | chr4:8243806-8243865 | | THC2486333 | Hs.636684 |
| A_33_P3258546 | PCDHA5 | Homo sapiens proto-cadherin alpha 5 (PCDHA5), transcript variant 2, mRNA [NM_031501] | NM_031501 | ENST00000378126 | 56143 | protocadherin alpha 5 | chr5:140203700-140203759 | GO:0005515\|GO:0005886\|NM_031501 GO:0005887\|GO:0005509 GO:0007155\|GO:0007156 GO:0007399 | | Hs.199343 |
| A_24_P227211 | KLC2 | Homo sapiens kinesin light chain 2 (KLC2), transcript variant 1, mRNA [NM_022822] | NM_022822 | ENST00000394067 | 64837 | kinesin light chain 2 | chr11:66034526-66034585 | GO:0005515\|GO:0043005\|NM_022822 GO:0005871\|GO:0005737 GO:0035253\|GO:0005874 GO:0008088\|GO:0003777 GO:0005829 | THC2462083 | Hs.280792 |
| A_24_P416997 | APOL3 | Homo sapiens apoli-poprotein L, 3 (APOL3), transcript variant beta/a, mRNA [NM_145641] | NM_145641 | ENST00000397287 | 80833 | apolipo-protein L, 3 | chr22:36536995-36536936 | GO:0005737\|GO:0006954\|NM_145641 GO:0006869\|GO:0042157 GO:0005576\|GO:0004871 GO:0043123\|GO:0005319 GO:0008289 | THC2494358 | Hs.474737 |
| A_32_P98298 | DUSP8 | Homo sapiens dual specificity phospha-tase 8 (DUSP8), mRNA [NM_004420] | NM_004420 | ENST00000528778 | 1850 | dual specif-icity phos-phatase 8 | chr11:1579394-1579141 | GO:0000188\|GO:0005737\|NM_004420 GO:0006470\|GO:0016787 GO:0005634\|GO:0017017 GO:0004725 | THC2476346 | Hs.41688 |
| A_33_P3390637 | SLC23A3 | Homo sapiens solute carrier family 23 (nu-cleobase transporters), member 3 (SLC23A3), | NM_144712 | ENST00000421779 | 151295 | solute carrier family 23 (nucleobase transporters), | chr2:22003411-220034058 | GO:0005215\|GO:0016020\|NM_144712 GO:0016021\|GO:0055085 | THC2741672 | Hs.124565 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P85963 | OR6Y1 | Homo sapiens olfactory receptor, family 6, subfamily Y, member 1 (OR6Y1), mRNA [NM_001005189] | NM_001005189 | ENST00000302617 | 391112 | olfactory receptor, family 6, subfamily Y, member 1 | chr1:158517370-158517311 | GO:0007608\|GO:0007165\|GO:0004984\|GO:0007186\|GO:0005886\|GO:0004872\|GO:0016021\|GO:0050896 | NM_001005189 | NP1461830 | Hs.553780 |
| A_33_P3378514 | PDE5A | Homo sapiens phosphodiesterase 5A, cGMP-specific (PDE5A), transcript variant 1, mRNA [NM_001083] | NM_001083 | ENST00000394439 | 8654 | phosphodiesterase 5A, cGMP-specific | chr4:120415615-120415556 | GO:0001666\|GO:0000287\|GO:0009187\|GO:0047555\|GO:0046069\|GO:0005575\|GO:0007399\|GO:0007165\|GO:0000166\|GO:0016787\|GO:0030553\|GO:0042311\|GO:0008270 | NM_001083 | THC2501404 | Hs.647971 |
| A_23_P406227 | MGC23284 | Homo sapiens hypothetical LOC197187 (MGC23284), transcript variant 2, non-coding RNA [NR_024399] | NR_024399 | | 197187 | hypothetical LOC197187 | chr16:88753499-88753558 | | NR_024399 | THC2480970 | Hs.499548 |
| A_33_P3407062 | | Homo sapiens mRNA for T cell receptor alpha variable 41, partial cds, clone: un 278. [AB306126] | AB306126 | ENST00000390468 | | | chr14:22789024-22789083 | | | NP1172335 | Hs.74647 |
| A_23_P130961 | ELANE | Homo sapiens elastase, neutrophil expressed (ELANE), mRNA [NM_001972] | NM_001972 | ENST00000263621 | 1991 | elastase, neutrophil expressed | chr19:853356-855575 | GO:0006909\|GO:0004252\|GO:0009986\|GO:0045415\|GO:0045416\|GO:0006874\|GO:0005576\|GO:0050900\|GO:0048661\|GO:0008367\|GO:0050922\|GO:0019955\|GO:0043406\|GO:0050728\|GO:0045079\|GO:0006508\|GO:0008233\|GO:0009411 | NM_001972 | THC2472602 | Hs.99863 |
| A_33_P3401990 | VPREB3 | Homo sapiens pre-B lymphocyte 3 (VPREB3), mRNA [NM_013378] | NM_013378 | ENST00000248948 | 29802 | pre-B lymphocyte 3 | chr22:24095142-24095083 | GO:0005783 | NM_013378 | THC2476292 | Hs.136713 |
| A_23_P400147 | CCDC61 | Homo sapiens coiled-coil domain containing 61 (CCDC61), mRNA [NM_001080402] | NM_001080402 | ENST00000002&3284 | 729440 | coiled-coil domain containing 61 | chr19:46520544-46521376 | | NM_001080402 | THC2619849 | Hs.515479 |
| A_24_P400832 | LOC100130950 | Homo sapiens hypothetical LOC100130950 (LOC100130950), non-coding RNA [NR_034082] | NR_034082 | | 100130950 | hypothetical LOC100130950 | chr17:5118521-5118580 | | NR_034082 | THC2632507 | Hs.668646 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3332302 | MTVR2 | Homo sapiens mouse mammary tumor virus receptor homolog 2 (MTVR2), non-coding RNA [NR_027025] | NR_027025 | | 246754 | mouse mammary tumor virus receptor homolog 2 | chr17:54962202-54962143 | | NR_027025 | | |
| A_24_P131392 | FAM82A1 | Homo sapiens family with sequence similarity 82, member A1 (FAM82A1), transcript variant 1, mRNA [NM_144713] | NM_144713 | ENST00000442857 | 151393 | family with sequence similarity 82, member A1 | chr2:38231143-38231293 | GO:0005737\|GO:0016020\|NM_144713\|GO:0005488\|GO:0005874\|GO:0005819\|GO:0016021 | | THC2480570 | Hs.591566 |
| A_33_P3341970 | NEGR1 | Homo sapiens neuronal growth regulator 1 (NEGR1), mRNA [NM_173808] | NM_173808 | ENST00000306821 | 257194 | neuronal growth regulator 1 | chr1:71868720-71868661 | GO:0005515\|GO:0005886\|NM_173808\|GO:0043025\|GO:0031225\|GO:0007155\|GO:0030425 | | THC2606710 | Hs.146542 |
| A_33_P3296024 | SALL3 | Homo sapiens sal-like 3 (Drosophila) (SALL3), mRNA [NM_171999] | NM_171999 | ENST00000537592 | 27164 | sal-like 3 (Drosophila) | chr18:7675731-76757372 | GO:0005622\|GO:0021891\|NM_171999\|GO:0005737\|GO:0008270\|GO:0005634\|GO:0003677\|GO:0046872\|GO:0045449 | | THC2601042 | Hs.700557 |
| A_32_P191860 | SCGBL | Homo sapiens secretoglobin-like (SCGBL), mRNA [NM_001025591] | NM_001025591 | ENST00000379204 | 284402 | secretoglobin-like | chr19:3508440-35084346 | GO:0005488\|GO:0005576\|NM_001025591 | | THC2615333 | Hs.656990 |
| A_33_P3305725 | LOC730102 | Homo sapiens oxidoreductase-like protein 2 pseudo-quinonegene (LOC730102), non-coding RNA [NR_037167] | NR_037167 | ENST00000512906 | 730102 | quinone oxidoreductase-like protein 2 pseudogene | chr1:17800390-2-178003843 | | NR_037167 | THC2644945 | Hs.149540 |
| A_23_P151506 | PLEK2 | Homo sapiens pleckstrin 2 (PLEK2), mRNA [NM_016445] | NM_016445 | ENST00000216446 | 26499 | pleckstrin 2 | chr14:6785387-67853811 | GO:0007242\|GO:0005737\|NM_016445\|GO:0030036\|GO:0005886\|GO:0042995\|GO:0005856\|GO:0019898 | | THC2462892 | Hs.170473 |
| A_33_P3321682 | | | | | | | chr2:23667334-2-236673283 | | | | |
| A_33_P3275668 | BAG6 | Homo sapiens BCL2-associated athanogene 6 (BAG6), transcript variant 1, mRNA [NM_004639] | NM_004639 | ENST00000404765 | 7917 | BCL2-associated athanogene 6 | chr6:31606925-31606866 | GO:0005515\|GO:0005634 | NM_004639 | THC2469828 | Hs.440900 |
| A_33_P3269570 | CD160 | CD160 molecule [Source: HGNC Symbol; Acc: 170131] [ENST00000369290] | EU016100 | ENST00000369290 | 11126 | CD160 molecule | chr1:14569884-5-145698786 | | | THC2631630 | Hs.488237 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P108662 | MOGS | Homo sapiens mannosyl-oligosaccharide glucosidase (MOGS), transcript variant 1, mRNA [NM_006302] | NM_006302 | ENST00000462189 | 7841 | mannosyl-oligosaccharide glucosidase | chr2:74688343-74688284 | GO:0009311\|GO:0016020\|NM_006302 GO:0005783\|GO:0004573\| GO:0016798\|GO:0008152\| GO:0005624\|GO:0016021\| GO:0006487 | NM_006302 | THC2681968 | Hs.516119 |
| A_33_P3346635 | LOC100508554 | Homo sapiens hypothetical LOC100508554 (LOC100508554), partial miscRNA [XR_112953] | XR_112953 | | 100508554 | hypothetical LOC100508554 | chr7:197863-197922 | | XR_112953 | THC2477098 | Hs.134742 |
| A_23_P111981 | LYNX1 | Homo sapiens Ly6/neurotoxin 1 (LYNX1), transcript variant 3, mRNA [NM_177457] | NM_177457 | ENST00000398906 | 66004 | Ly6/neurotoxin 1 | chr8:143852799-143852740 | GO:0005886\|GO:0005576\|NM_177457 GO:0031225 | NM_177457 | THC2464267 | Hs.158665 |
| A_23_P95640 | C1orf86 | Homo sapiens chromosome 1 open reading frame 186 (C1orf186), mRNA [NM_001007544] | NM_001007544 | ENST00000331555 | 440712 | chromosome 1 open reading frame 186 | chr1:206239073-206239014 | GO:0016020\|GO:0016021 NM_001007544 | NM_001007544 | THC2475722 | Hs.662248 |
| A_33_P3307490 | SYNRG | synergin, gamma [Source: HGNC Symbol; Acc: 557] [ENST00000378189] | AK126988 | ENST00000378189 | 11276 | synergin, gamma | chr17:3592703-35926980 | | | THC2482261 | Hs.594647 |
| A_33_P3245734 | ZNF680 | Homo sapiens zinc finger protein 680 (ZNF680), transcript variant 2, mRNA [NM_001130022] | NM_001130022 | ENST00000447137 | 340252 | zinc finger protein 680 | chr7:63986836-63986777 | GO:0005622\|GO:0006355\|NM_001130022 GO:0005730\|GO:0008270\| GO:0005634\|GO:0003677\| GO:0046872 | NM_001130022 | THC2478527 | Hs.520886 |
| A_23_P18246 | XCR1 | Homo sapiens chemokine (C motif) receptor 1 (XCR1), transcript variant 1, mRNA [NM_005283] | NM_005283 | ENST00000542109 | 2829 | chemokine (C motif) receptor 1 | chr3:46062985-46062926 | GO:0007165\|GO:0051209\|NM_005283 GO:0006954\|GO:0006935\| GO:0005886\|GO:0007187\| GO:0005887\|GO:0004930\| GO:0004950\|GO:0004872\| GO:0034097\|GO:0007204 | NM_005283 | THC2481211 | Hs.24816 |
| A_23_P258381 | SPSB4 | Homo sapiens splA/ryanodine receptor domain and SOCS box containing 4 (SPSB4), mRNA [NM_080862] | NM_080862 | ENST00000508126 | 92369 | splA/ryanodine receptor domain and SOCS box containing 4 | chr3:140867372-140867431 | GO:0007242\|GO:0005737\|NM_080862 GO:0019941 | NM_080862 | THC2632742 | Hs.655112 |
| A_23_P350451 | PRDM1 | Homo sapiens PR domain containing 1, with ZNF domain (PRDM1), transcript variant 1, mRNA [NM_001198] | NM_001198 | ENST00000456278 | 639 | PR domain containing 1, with ZNF domain | chr6:106555123-106555182 | GO:0010628\|GO:0005622\|NM_001198 GO:0045165\|GO:0003700\| GO:0001893\|GO:0001892\| GO:0008270\|GO:0005634\| GO:0000122\|GO:0046872\| GO:0045449 | NM_001198 | THC2470627 | Hs.436023 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3370930 | LAMB1 | laminin, beta 1 [Source: HGNC Symbol; Acc: 6486] [ENST00000393559] | | ENST00000393559 | 3912 | laminin, beta 1 | chr7:107643457-107643398 | | | THC2637518 | |
| A_23_P160438 | MYOG | Homo sapiens myogenin (myogenic factor 4) (MYOG), mRNA [NM_002479] | NM_002479 | ENST00000241651 | 4656 | myogenin (myogenic factor 4) | chr1:203052930-203052871 | GO:0006355|GO:0007517|GO:0003700|GO:0045944|GO:0016563|GO:0048741|GO:0007275|GO:0005634|GO:0030154 | NM_002479 | THC2479983 | Hs.2830 |
| A_23_P57110 | C20orf54 | Homo sapiens chromosome 20 open reading frame 54 (C20orf54), mRNA [NM_033409] | NM_033409 | ENST00000381944 | 113278 | chromosome 20 open reading frame 54 | chr20:741069-741010 | GO:0034605|GO:0005515|GO:0016020|GO:0016021 | NM_033409 | THC2472248 | Hs.283865 |
| A_33_P3209321 | LOC729558 | Homo sapiens cDNA FLJ39676 fis, clone SMINT2009832. [AK096995] | AK096995 | | 729558 | hypothetical protein LOC729558 | chr4:151500399-151500458 | | | THC2616799 | Hs.647978 |
| A_23_P202345 | ADO | Homo sapiens 2-aminoethanethiol (cysteamine) dioxygenase (ADO), mRNA [NM_032804] | NM_032804 | ENST00000373783 | 84890 | 2-aminoethanethio 1 (cysteamine) dioxygenase | chr10:64567804-64567863 | GO:0005506|GO:0016491|GO:0047800|GO:0046872|GO:0055114 | NM_032804 | THC2493611 | Hs.99821 |
| A_23_P20298 | AGL | Homo sapiens amylo-alpha-1, 6-glucosidase, 4-alpha-glucano-transferase (AGL), transcript variants mRNA [NM_000028] | NM_000028 | ENST00000294724 | 178 | amylo-alpha-1, 6-glucosidase, 4-alpha-glucano-transferase | chr1:100389229-100389288 | GO:0005515|GO:0043033|GO:0043169|GO:0005975|GO:0016234|GO:0016757|GO:0005978|GO:0005634|GO:0005829|GO:0005737|GO:0016798|GO:0008152|GO:0004134|GO:0004135|GO:0030247|GO:0031593 | NM_000028 | THC2461565 | Hs.904 |
| A_33_P3297545 | | T cell receptor beta variable 6-8 [Source: HGNC Symbol; Acc: 12233] [ENST00000390376] | | ENST00000390376 | | | chr7:142124310-142124251 | | | THC2589734 | |
| A_33_P3410372 | NUDT10 | Homo sapiens nudix (nucleoside diphosphate linked moiety X)-type motif 10 (NUDT10), mRNA [NM_153183] | NM_153183 | ENST00000376006 | 170685 | nudix (nucleoside diphosphate linked moiety X)-type motif 10 | chrX:51076242-51076301 | GO:0005737|GO:0030145|GO:0000287|GO:0016787|GO:0008486 | NM_153183 | THC2476742 | Hs.375178 |
| A_24_P318990 | | Homo sapiens immunoglobulin lambda variable 1-50 (non-functional) [Source: HGNC Symbol; Acc: 5881] [ENST00000390291] | BC012876 | ENST00000390291 | | | chr22:22682080-22682139 | | NP1457207 | | Hs.449585 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3235721 | C11orf87 | Homo sapiens chromosome 11 open reading frame 87 (C11orf87), mRNA [NM_207645] | NM_207645 | ENST00000327419 | 399947 | chromosome 11 open reading frame 87 | chr11:109296246-109296305 | GO:0016020\|GO:0016021 | NM_207645 | THC2475112 | Hs.172982 |
| A_33_P3409249 | LOC729424 | PREDICTED: Homo sapiens hypothetical protein LOC729424 (LOC729424), mRNA [XM_001714320] | XM_001714320 | | 729424 | hypothetical protein LOC729424 | chr4:128544676-128544735 | | XM_001714320 | | |
| A_33_P3424489 | | | S73129 | | | immunoglobulin lambda variable 3-25 | chr22:23029555-23029614 | | | NP084490 | Hs.449585 |
| A_33_P3230259 | NCAPH | Homo sapiens non-SMC condensin I complex, subunit H (NCAPH), mRNA [NM_015341] | NM_015341 | ENST00000390305 [Source: HGNC Symbol; Acc: 5908] [ENST00000390305] | 23397 | non-SMC condensin I complex, subunit H | chr2:97041160-97041219 | GO:0000796\|GO:0007076\|GO:0007067\|GO:0005737\|GO:0005634\|GO:0000278\|GO:0051301 | NM_015341 | THC2461132 | Hs.308045 |
| A_33_P3380331 | NKIRAS2 | Homo sapiens NFKB inhibitor interacting Ras-like 2 (NKIRAS2), transcript variant 3, mRNA [NM_001144927] | NM_001144927 | ENST00000316082 | 28511 | NFKB inhibitor interacting Ras-like 2 | chr17:40175899-40175958 | GO:0005622\|GO:0005737\|GO:0000166\|GO:0007264\|GO:0007249\|GO:0003924\|GO:0005575\|GO:0005525 | NM_001144927 | THC2623577 | Hs.632252 |
| A_33_P3298057 | ABCC5 | Homo sapiens ATP-binding cassette, sub-family C (CFTR/MRP), member 5 (ABCC5), transcript variant 2, mRNA [NM_001023587] | NM_001023587 | ENST00000438979 | 10057 | ATP-binding cassette, subfamily C (CFTR/MRP), member 5 | chr3:183705645-183705586 | GO:0032868\|GO:0048471\|GO:0016020\|GO:0000166\|GO:0005887\|GO:0032496\|GO:0042626\|GO:0005624\|GO:0008514\|GO:0055085\|GO:0016887\|GO:0005524 | NM_001023587 | THC2525236 | Hs.728765 |
| A_23_P30175 | ERBB2IP | Homo sapiens erbb2 interacting protein (ERBB2IP), transcript variant 2, mRNA [NM_018695] | NM_018695 | | 55914 | erbb2 interacting protein | chr5:65375840-65375899 | GO:0005515\|GO:0030056\|GO:0030054\|GO:0045104\|GO:0005634\|GO:0045175\|GO:0006605\|GO:0045197\|GO:0005604\|GO:0005176\|GO:0007165\|GO:0005737\|GO:0007049\|GO:0005178\|GO:0007173\|GO:0007229\|GO:0005200\|GO:0016049\|GO:0007155 | NM_018695 | THC2670825 | Hs.591774 |
| A_23_P204087 | OAS2 | Homo sapiens 2'-5'-oligoadenylate synthetase 2, 69/71 kDa (OAS2), | NM_016817 | ENST00000392583 | 4939 | 2'-5'-oligoadenylate synthetase | chr12:113448601-113448660 | GO:0005792\|GO:0005783\|GO:0001730\|GO:0003723\|GO:0016779\|GO:0005634 | NM_016817 | THC2461916 | Hs.414332 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | transcript variant 1, mRNA [NM_016817] | | | | 2, 69/71 kDa | | GO:0005524\|GO:0006401\|GO:0005739\|GO:0006139\|GO:0006955\|GO:0000166\|GO:0016020\|GO:0016740 | | | |
| A_33_P3251283 | CTAGE4 | Homo sapiens CTAGE family, member 4 (CTAGE4), mRNA [NM_198495] | NM_198495 | ENST00000486333 | 100128553 | CTAGE family, member 4 | chr7:14388255-143882618 | GO:0008150\|GO:0016020\|NM_198495\|GO:0016021\|GO:0005575 | | THC2477975 | Hs.720693 |
| A_33_P3251932 | BCL2L11 | Homo sapiens BCL2-like 11 (apoptosis facilitator) (BCL2L11), transcript variant 9, mRNA [NM_207002] | NM_207002 | ENST00000337565 | 10018 | BCL2-like 11 (apoptosis facilitator) | chr2:111886352-111886411 | GO:0005515\|GO:0008017\|NM_207002\|GO:0008624\|GO:0001783\|GO:0001782\|GO:0005886\|GO:0048538\|GO:0005741\|GO:0030879\|GO:0007283\|GO:0048536\|GO:0009791\|GO:0005829\|GO:0043583\|GO:0005739\|GO:0005737\|GO:0042475\|GO:0002262\|GO:0043029\|GO:0046620\|GO:0008633\|GO:0001822\|GO:0035148\|GO:0048563\|GO:0001701\|GO:0048070\|GO:0007160\|GO:0008584\|GO:0000300\|GO:0019898 | | THC2695067 | Hs.469658 |
| A_33_P3308553 | | | | | | | chr2:19414226-19414226 | | | | |
| A_23_P6066 | CPXM1 | Homo sapiens carboxypeptidase X (M14 family), member 1 (CPXM1), transcript variant 1, mRNA [NM_019609] | NM_019609 | ENST00000421947 | 56265 | carboxypeptidase X (M14 family), member 1 | chr20:2776406-2776347 | GO:0006508\|GO:0008270\|NM_019609\|GO:0008233\|GO:0005576\|GO:0007155\|GO:0005615\|GO:0046872\|GO:0008237\|GO:0004181 | | THC2769779 | Hs.659346 |
| A_33_P3250840 | NIPA1 | Homo sapiens non imprinted in Prader-Willi/Angelman syndrome 1 (NIPA1), transcript variant 1, mRNA [NM_144599] | NM_144599 | ENST00000437912 | 123606 | non imprinted in Prader-Willi/Angelman syndrome 1 | chr15:2304342-23043362 | GO:0008219\|GO:0016020\|NM_144599\|GO:0016021 | | THC2492604 | Hs.511797 |
| A_33_P3308434 | MORN1 | Homo sapiens MORN repeat containing 1 (MORN1), mRNA [NM_024848] | NM_024848 | ENST00000378525 | 79906 | MORN repeat containing 1 | chr1:2317328-2317269 | | NM_024848 | THC2519762 | Hs.642701 |
| A_23_P73150 | TTC25 | Homo sapiens tetratricopeptide repeat domain 25 (TTC25), mRNA [NM_031421] | NM_031421 | ENST00000377540 | 83538 | tetratricopeptide repeat domain 25 | chr17:4011752-40117583 | GO:0005515\|GO:0005737\|fV M_031421 | | NP1178351 | Hs.201134 |
| A_23_P29067 | TMPRSS2 | Homo sapiens transmembrane protease, | NM_005656 | ENST00000398585 | 7113 | transmembrane pro- | chr21:4283696-42836904 | GO:0005737\|GO:0005886\|NM_005656\|GO:0004252\|GO:0005887 | | THC2485211 | Hs.439309 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq- Accession | TIGRID | UniGene ID |
|---|---|---|---|---|---|---|---|---|---|---|---|
| | | serine 2 (TMPRSS2), transcript variant 2, mRNA [NM_005656] | | | | tease, serine 2 | | GO:0006508\|GO:0008233\| GO:0005576\|GO:0005044 | | | |
| A_33_P3361891 | TMPRSS7 | Homo sapiens trans-membrane protease, serine 7 (TMPRSS7), transcript variant 1, mRNA [NM_001042575] | NM_001042575 | ENST00000419127 | 344805 | transmembrane protease, serine 7 | chr3:111799988-111799944 | GO:0005515\|GO:0005886\|NM_001042575 GO:0004252\|GO:0006508\| GO:0008233\|GO:0016021 | | THC2487758 | Hs.435490 |
| A_33_P3369631 | EIF3J | Homo sapiens eukaryotic translation initiation factor 3, subunit J (EIF3J), mRNA [NM_003758] | NM_003758 | ENST00000261868 | 8669 | eukaryotic translation initiation factor 3, subunit J | chr15:44854849-44854908 | GO:0005515\|GO:0005737\|NM_003758 GO:0005852\|GO:0003743\| GO:0006413\|GO:0005829 | | THC2473241 | Hs.404056 |
| A_24_P141707 | INHBE | Homo sapiens inhibin, beta E (INHBE), mRNA [NM_031479] | NM_031479 | ENST00000266646 | 83729 | inhibin, beta E | chr12:5785086 4-57850923 | GO:0005179\|GO:0005576\|NM_031479 GO:0008083 | | THC2472179 | Hs.632713 |
| A_32_P140139 | F13A1 | Homo sapiens coagulation factor XIII, A1 polypeptide (F13A1), mRNA [NM_000129] | NM_000129 | ENST00000264870 | 2162 | coagulation factor XIII, A1 polypeptide | chr6:6144484-6144425 | GO:0005737\|GO:0018149\|NM_000129 GO:0007596\|GO:0003810\| GO:0005509\|GO:0031093\| GO:0005576\|GO:0016740\| GO:0008415 | | THC2468237 | Hs.335513 |
| A_23_P143817 | MYLK | Homo sapiens myosin light chain kinase (MYLK), transcript variant 1, mRNA [NM_053025] | NM_053025 | ENST00000475616 | 4638 | myosin light chain kinase | chr3:12333313 3-123333074 | GO:0005516\|GO:0000287\|NM_053025 GO:0000166\|GO:0005509\| GO:0004687\|GO:0006468\| GO:0003779\|GO:0005524\| GO:0016740 | | THC2514570 | Hs.477375 |
| A_33_P3387170 | LOC100129196 | Homo sapiens hypothetical LOC100129196 (LOC100129196), non-coding RNA [NR_034182] | NR_034182 | ENST00000414532 | 100129196 | hypothetical LOC100129196 | chr1:31192359-31194140 | | NR_034182 | THC2624896 | Hs.659751 |
| A_33_P3424217 | | major histocompatibility complex, class II, DQ beta 1 [Source: HGNC Symbol; Acc:4944] [ENST00000399670] | XM_003119092 | ENST00000399670 | | | | | XM_003119092 | THC2560922 | |
| A_33_P3218120 | LOC402036 | PREDICTED: Homo sapiens hCG1646661-like (LOC402036), mRNA[XM_001719325] | XM_001719325 | | 402036 | hCG1646661-like | chr22:1901959 3-19019534 | | XM_001719325 | | Hs.646437 |
| A_33_P3413394 | ZACN | zinc activated ligand-gated ion channel [Source: HGNC Symbol; Acc: 29504] [ENST00000392503] | BC110596 | ENST00000392503 | 353174 | zinc activated ligand-gated ion channel | chr17:7407692 0-74076979 | | | THC2485792 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3259705 | SIGIRR | single immunoglobulin and toll-interleukin 1 receptor (TIR) domain [Source: HGNC Symbol; Acc: 30575] [ENST00000382520] | AY358342 | ENST00000382520 | 59307 | single immunoglobulin and toll-interleukin 1 receptor (TIR) domain | chr11:406142-406083 | | | THC2485349 | Hs.501624 |
| A_23_P50508 | PLA2G4C | Homo sapiens phospholipase A2, group IVC (cytosolic, calcium-independent) (PLA2G4C), transcript variant 1, mRNA [NM_003706] | NM_003706 | ENST00000354276 | 8605 | phospholipase A2, group IVC (cytosolic, calcium-independent) | chr19:4855130-7-48551248 | GO:0019369|GO:0007242|GO:0007567|GO:0031225|GO:0005829|GO:0016042|GO:0005543|GO:0006954|GO:0016020|GO:0016787|GO:0047499|GO:0008152|GO:0046475 | NM_003706 | NI1152204 | Hs.631562 |
| A_23_P40453 | CBR3 | Homo sapiens carbonyl reductase 3 (CBR3), mRNA [NM_001236] | NM_001236 | ENST00000290354 | 874 | carbonyl reductase 3 | chr21:3751837-9-37518438 | GO:0005737|GO:0004090|GO:0005488|GO:0016491|GO:0070402|GO:0055114|GO:0005829 | NM_001236 | THC2472161 | Hs.154510 |
| A_23_P160460 | UAP1 | Homo sapiens UDP-N-acetylglucosamine pyrophosphorylase 1 (UAP1), mRNA [NM_003115] | NM_003115 | ENST00000367926 | 6675 | UDP-N-acetylglucosamine pyrophosphorylase 1 | chr1:16256016-2-162560221 | GO:0005737|GO:0003977|GO:0008152|GO:0016779|GO:0005730|GO:0005634|GO:0006048|GO:0016740 | NM_003115 | THC2602097 | Hs.492859 |
| A_33_P3294946 | LOC100506173 | PREDICTED: Homo sapiens putative killer cell immunoglobulin like receptor like protein KIR3DP1-like (LOC100506173), mRNA [XM_003119122] | XM_003119122 | | 100506173 | putative killer cell immunoglobulin-like receptor like protein KIR3DP1-like | chr19_gl00020 9_random: 51823-51882 | | XM_003119122 | | Hs.730948 |
| A_23_P348063 | SYNGR1 | Homo sapiens synaptogyrin 1 (SYNGR1), transcript variant 1a, mRNA [NM_004711] | NM_004711 | ENST00000328933 | 9145 | synaptogyrin 1 | chr22:3978099-5-39781054 | GO:0042470|GO:0030054|GO:0016020|GO:0005887|GO:0048169|GO:0045202|GO:0030672|GO:0006605|GO:0048172 | NM_004711 | THC2618835 | Hs.216226 |
| A_23_P7342 | UGT2B10 | Homo sapiens UDP glucuronosyltransferase 2 family, polypeptide B10 (UGT2B10), transcript variant 1, mRNA [NM_001075] | NM_001075 | ENST00000425704 | 7365 | UDP glucuronosyltransferase 2 family, polypeptide B10 | chr4:69696473-69696532 | GO:0006629|GO:0005792|GO:0016020|GO:0005783|GO:0008152|GO:0015020|GO:0016021 | NM_001075 | THC2703933 | Hs.201634 |
| A_33_P3226135 | | Q13401_HUMAN (Q13401) HPMSR3, partial (51%) [THC2571723] | | | | | chr7:07510390-7-07510848 | | | THC2571723 | |
| A_23_P76951 | TMX1 | Homo sapiens thioredoxin-related transmembrane protein | NM_030755 | ENST00000457354 | 81542 | thioredoxin-related transmem- | chr14:5172255-9-51722618 | GO:0005783|GO:0008283|GO:0030612|GO:0006950|GO:0005624|GO:0015036 | NM_030755 | THC2466402 | Hs.125221 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | 1 (TMX1), mRNA [NM_030755] | | | | brane protein 1 | | GO:0005634\|GO:0006916\| GO:0006260\|GO:0006888\| GO:0007165\|GO:0045321\| GO:0016020\|GO:0005789\| GO:0006810\|GO:0045454\| GO:0016021\|GO:0045893\| GO:0022900\|GO:0045927 | | |
| A_33_P3254191 | OSBPL8 | *Homo sapiens* oxysterol binding protein-like 8 (OSBPL8), transcript variant 1, mRNA [NM_020841] | NM_020841 | ENST00000446075 | 114882 | oxysterol binding protein-like 8 | chr12:76748399-76748340 | GO:0006869\|GO:0008202\|NM_020841 | | THC2462486 | Hs.430849 |
| A_23_P50508 | PLA2G4C | *Homo sapiens* phospholipase A2, group IVC (cytosolic, calcium-independent) (PLA2G4C), transcript variant 1, mRNA [NM_003706] | NM_003706 | ENST00000354276 | 8605 | phospholipase A2, group IVC (cytosolic, calcium-independent) | chr19:48551307-48551248 | GO:0019369\|GO:0007242\|NM_003706 GO:0007567\|GO:0031225\| GO:0005829\|GO:0016042\| GO:0005543\|GO:0006954\| GO:0016020\|GO:0016787\| GO:0047499\|GO:0008152\| GO:0046475 | | NM_1152204 | Hs.631562 |
| A_23_P40453 | CBR3 | *Homo sapiens* carbonyl reductase 3 (CBR3), mRNA [NM_001236] | NM_001236 | ENST00000290354 | 874 | carbonyl reductase 3 | chr21:37518379-37518438 | GO:0005737\|GO:0004090\|NM_001236 GO:0005488\|GO:0016491\| GO:0070402\|GO:0055114\| GO:0005829 | | THC2472161 | Hs.154510 |
| A_23_P160460 | UAP1 | *Homo sapiens* UDP-N-acteylglucosamine pyrophosphorylase 1 (UAP1), mRNA [NM_003115] | NM_003115 | ENST00000367926 | 6675 | UDP-N-acteylglucosamine pyrophos-phorylase 1 | chr1:162560162-162560221 | GO:0005737\|GO:0003977\|NM_003115 GO:0008152\|GO:0016779\| GO:0005730\|GO:0005634\| GO:0006048\|GO:0016740 | | THC2602097 | Hs.492859 |
| A_33_P3294946 | LOC100506173 | *Homo sapiens* PREDICTED: putative killer cell immunoglobulin like receptor like protein KIR3DP1-like (LOC100506173), mRNA [XM_003119122] | XM_003119122 | | 100506173 | putative killer cell immunoglobulin-like receptor like protein KIR3DP1-like | chr19_gl000209_random: 51823-51882 | | XM_003119122 | | Hs.730948 |
| A_23_P348063 | SYNGR1 | *Homo sapiens* synaptogyrin 1 (SYNGR1), transcript variant 1a, mRNA [NM_004711] | NM_004711 | ENST00000328933 | 9145 | synaptogyrin 1 | chr22:39780995-39781054 | GO:0042470\|GO:0030054\|NM_004711 GO:0016020\|GO:0005887\| GO:0048169\|GO:0045202\| GO:0030672\|GO:0006605\| GO:0048172 | | THC2618835 | Hs.216226 |
| A_23_P7342 | UGT2B10 | *Homo sapiens* UDP glucuronosyltransferase 2 family, polypeptide B10 (UGT2B10), transcript variant 1, mRNA [NM_001075] | NM_001075 | ENST00000425704 | 7365 | UDP glucuronosyltransferase 2 family, polypeptide B10 | chr4:69696473-69696532 | GO:0006629\|GO:0005792\|NM_001075 GO:0016020\|GO:0005783\| GO:0008152\|GO:0015020\| GO:0016021 | | THC2703933 | Hs.201634 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P326135 | | Q13401_HUMAN (Q13401) HPMSR3, partial (51%) [THC2571723] | | | | | chr7:07510390 7-075103848 | | | THC2571723 | |
| A_23_P76951 | TMX1 | Homo sapiens thio-redoxin-related transmembrane protein 1 (TMX1), mRNA [NM_030755] | NM_030755 | ENST00000457354 | 81542 | thioredoxin-related transmembrane protein 1 | chr14:5172255 9-51722618 | GO:0005783\|GO:0008283\|NM_030755 GO:0030612\|GO:0006950\| GO:0005624\|GO:0015036\| GO:0006634\|GO:0006916\| GO:0006260\|GO:0006888\| GO:0007165\|GO:0045321\| GO:0016020\|GO:0005789\| GO:0006810\|GO:0045454\| GO:0016021\|GO:0045893\| GO:0022900\|GO:0045927 | | THC2466402 | Hs.125221 |
| A_33_P3254191 | OSBPL8 | Homo sapiens oxy-sterol binding protein-like 8 (OSBPL8), transcript variant 1, mRNA [NM_020841] | NM_020841 | ENST00000446075 | 114882 | oxysterol binding protein like 8 | chr12:7674839 9-76748340 | GO:0006869\|GO:0008202 | NM_020841 | THC2462486 | Hs.430849 |
| A_23_P1206 | RPS24 | Homo sapiens riboso-mal protein S24 (RPS24), transcript variant c, mRNA [NM_001026] | NM_001026 | ENST00000467106 | 6229 | ribosomal protein S24 | chr10:7979537 1-79795430 | GO:0005622\|GO:0003735\|NM_001026 GO:0000166\|GO:0022627\| GO:0006364\|GO:0034101\| GO:0005840\|GO:0031369\| GO:0042274\|GO:0006414\| GO:0005829 | | THC2572247 | Hs.280130 |
| A_33_P3320217 | ADCY2 | Homo sapiens adenylate cyclase 2 (brain) (ADCY2), mRNA [NM_020546] | NM_020546 | ENST00000382532 | 108 | adenylate cyclase 2 (brain) | chr5:7828412-7828471 | GO:0009755\|GO:0004016\|NM_020546 GO:0000287\|GO:0005886\| GO:0001166\|GO:0006171\| GO:0016021\|GO:0007189\| GO:0034199\|GO:0007193\| GO:0005524\|GO:0030425 | | THC2463084 | Hs.481545 |
| A_32_P133840 | TMCC2 | Homo sapiens trans-membrane and coiled-coil domain family 2 (TMCC2), transcript variant 1, mRNA [NM_014858] | NM_014858 | ENST00000358024 | 9911 | transmembrane and coiled-coil domain family 2 | chr1:20524211 7-205242176 | GO:0016020\|GO:0016021 | NM_014858 | THC2489531 | Hs.6360 |
| A_33_P3280531 | CRAT | Homo sapiens carni-tine O-acetyltransferase (CRAT), nuclear gene encoding mitochondrial protein, transcript variant 1, mRNA [NM_000755] | NM_000755 | ENST00000351352 | 1384 | carnitine O-acetyltrans-ferase | chr9:13185713 4-131857075 | GO:0006629\|GO:0004092\|NM_000755 GO:0005783\|GO:0005743\| GO:0005739\|GO:0016020\| GO:0033540\|GO:0006810\| GO:0016740\|GO:0005777\| GO:0008415 | | THC2467214 | Hs.12068 |
| A_33_P3228739 | LRRC3C | Homo sapiens leucine rich repeat containing | NM_001195545 | ENST00000377924 | 100505591 | leucine rich repeat | chr17:3810086 9-38100928 | GO:0005515\|GO:0016020\|NM_001195545 GO:0016021 | | | Hs.145136 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3250148 | SP8 | 3C (LRRC3C), mRNA [NM_001195545] Homo sapiens Sp8 transcription factor (SP8), transcript variant 2, mRNA [NM_198956] | NM_198956 | ENST00000297210 | 221833 | containing 3C Sp8 transcription factor | chr7:20823968-20823909 | GO:0005622\|GO:0009954\|NM_198956 GO:0008270\|GO:0005634\| GO:0030326\|GO:0009953\| GO:0003677\|GO:0046872 | | THC2481338 | Hs.195922 |
| A_33_P3287661 | LOC100130430 | Homo sapiens cDNA FLJ45052 fis, Clone BRAWH3022542. [AK126997] | AK126997 | | 100130430 | hypothetical LOC100130430 | chr16:1358800-1358741 | | | THC2488009 | |
| A_33_P3399438 | C9orf29 | Homo sapiens chromosome 9 open reading frame 29 (C9orf29), non-coding RNA [NR_034087] | NR_034087 | ENST00000536054 | 652972 | chromosome 9 open reading frame 29 | chr9:114365175-114365116 | | NR_034087 | THC2609605 | Hs.551134 |
| A_33_P3343473 | ATRNL1 | Homo sapiens attractin-like 1 (ATRNL1), mRNA [NM_207303] | NM_207303 | ENST00000303745 | 26033 | attractin-like 1 | chr10:117308976-117309035 | GO:0005515\|GO:0016020\|NM_207303 GO:0007186\|GO:0005529\| GO:0016021 | | THC2543996 | Hs.501127 |
| A_33_P3353948 | | Q8NCT2_HUMAN (Q8NCT2) CDC14C protein (Fragment), complete [THC2526367] | | | | | chr7:04888627-4-048886333 | | | THC2526367 | |
| A_33_P3851788 | C19orf23 | Homo sapiens chromosome 19 open reading frame 23 (C19orf23), non-coding RNA [NR_027271] | NR_027271 | ENST00000431491 | 148046 | chromosome 19 open reading frame 23 | chr19:1267531-1267472 | | NR_027271 | THC2485522 | Hs.438829 |
| A_23_P16415 | LRP3 | Homo sapiens low density lipoprotein receptor-related protein 3 (LRP3), mRNA [NM_002333] | NM_002333 | | 4037 | low density lipoprotein receptor-related protein 3 | chr19:3369833 6-33698395 | GO:0005905\|GO:0016020\|NM_002333 GO:0004872\|GO:0016021\| GO:0006898 | | THC2461289 | Hs.515340 |
| A_23_P21800 | | Homo sapiens immunoglobulin kappa variable 3-20 [Source: HGNC Symbol; Acc: 5817] [ENST00000492167] | DQ187531 | ENST00000492167 | | | chr2:89442284-89442225 | | | NP511624 | Hs.449621 |
| A_23_P4382 | CLCA3P | Homo sapiens chloride channel accessory 3, pseudogene (CLCA3P), non-coding RNA [NR_024604] | NR_024604 | ENST00000466454 | 9629 | chloride channel accessory 3, pseudogene | chr1:87120974-87121033 | GO:0005215\|GO:0031404\|NR_024604 GO:0005262\|GO:0005244\| GO:0005509\|GO:0034707\| GO:0006816\|GO:0005576\| GO:0005615\|GO:0005254\| GO:0006811 | | | |
| A_33_P3373185 | LOC399744 | Homo sapiens hypothetical LOC399744 (LOC399744), non- | NR_024497 | ENST00000438516 | 399744 | hypothetical LOC399744 | chr10:3873784 0-38737899 | | NR_024497 | THC2594684 | Hs.730469 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3220994 | | coding RNA [NR_024497] | | | | | chr6:02686997 9-026870038 | | | | |
| A_24_P813550 | | immunoglobulin heavy variable 4-59 [Source: HGNC Symbol; Acc: 5654] [ENST00000390629] | XM_003119589 | ENST00000390629 | | | chr14:1070833 60-107083301 | | XM_003119589 | NP1077996 | Hs.631647 |
| A_33_P3273624 | HYAL3 | Homo sapiens hyaluronoglucosaminidase 3 (HYAL3), transcript variant 1, mRNA [NM_003549] | NM_003549 | ENST00000359051 | 8372 | hyaluronoglucosaminidase 3 | chr3:50330627-50330568 | GO:0005975\|GO:0016798\|NM_003549 GO:0008152\|GO:0005576\| GO:0004415\|GO:0005764 | | THC2486407 | Hs.729310 |
| A_33_P3310226 | LOC100129115 | Homo sapiens cDNA FLJ37894 fis, clone BRTHA2004639. [AK095213] | AK095213 | | 100129115 | hypothetical protein LOC100129115 | chr17:4320558 0-43205521 | | | THC2484758 | Hs.683858 |
| A_24_P182947 | GCET2 | Homo sapiens germinal center expressed transcript 2 (GCET2), transcript variant 3, mRNA [NM_001190259] | NM_001190259 | ENST00000308910 | 257144 | germinal center expressed transcript 2 | chr3:11184002 8-111839969 | GO:0005739\|GO:0005737 | NM_001190259 | THC2517803 | Hs.49614 |
| A_33_P3409580 | LOC100129722 | Homo sapiens hypothetical LOC100129722 (LOC100129722), non-coding RNA [NR_038389] | NR_038389 | | 100129722 | hypothetical LOC100129722 | chr9:14014474 6-140144687 | | NR_038389 | THC2619216 | Hs.656347 |
| A_33_P3263666 | ANKRD9 | Homo sapiens ankyrin repeat domain 9 (ANKRD9), mRNA [NM_152326] | NM_152326 | ENST00000286918 | 122416 | ankyrin repeat domain 9 | chr14:1029732 57-102973198 | | NM_152326 | THC2480472 | Hs.432945 |
| A_33_P3343260 | | ALU1_HUMAN (P39188) Alu subfamily J sequence contamination warning entry, partial (16%) [THC2541287] | | | | | chr16:0031228 24-003122765 | | | THC2541287 | |
| A_33_P3266998 | FAM106CP | Homo sapiens family with sequence similarity 106, member C, pseudogene (FAM106CP), non-coding RNA [NR_026810] | NR_026810 | ENST00000379228 | 100129396 | family with sequence similarity 106, member C pseudogene | chr17:1669322 4-16693282 | | NR_026810 | | Hs.712114 |
| A_33_P3374253 | | PREDICTED: Homo sapiens similar to | XM_001717762 | | | | chr18:7731928 4-77319225 | | XM_001717762 | | Hs.336526 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3311830 | OTOR | hCG1645807 (LOC100127987), mRNA [XM_001717762] Homo sapiens otoraplin (OTOR), mRNA [NM_020157] | NM_020157 | ENST00000246081 | 56914 | otoraplin | chr20:16732674-16732733 | GO:0001502\|GO:0007605\|GO:0005576 | NM_020157 | THC2602987 | Hs.41119 |
| A_23_P75800 | RAB3IL1 | Homo sapiens RAB3A interacting protein (rabin3)-like 1 (RAB3IL1), mRNA [NM_013401] | NM_013401 | ENST00000394836 | 5866 | RAB3A interacting protein (rabin3)-like 1 | chr11:61665038-61664979 | GO:0005515\|GO:0005085 | NM_013401 | THC2472895 | Hs.13759 |
| A_24_P38572 | NOL6 | Homo sapiens nucleolar protein family 6 (RNA-associated) (NOL6), transcript variant alpha, mRNA [NM_022917] | NM_022917 | ENST00000325914 | 65083 | nucleolar protein family 6 (RNA-associated) | chr9:33464935-33464159 | GO:0000794\|GO:0003723\|GO:0005730\|GO:0005732\|GO:0005634 | NM_022917 | NP287178 | H_493709 |
| A_33_P3331882 | CRTC1 | Homo sapiens CREB regulated transcription coactivator 1 (CRTC1), transcript variant 3, mRNA [NM_001098482] | NM_001098482 | ENST00000262813 | 23373 | CREB regulated transcription coactivator 1 | chr19:18888231-18888290 | GO:0005515\|GO:0008140\|GO:0005737\|GO:0045944\|GO:0044419\|GO:0005634\|GO:0045449 | NM_001098482 | THC2472431 | Hs.371096 |
| A_33_P3261428 | | | | | | | chr14:07502738-075027397 | | | | |
| A_33_P3219870 | PNPLA2 | Homo sapiens patatin-like phospholipase domain containing 2 (PNPLA2), mRNA [NM_020376] | NM_020376 | ENST00000529255 | 57104 | patatin-like phospholipase domain containing 2 | chr11:824764-824823 | GO:0016042\|GO:0004806\|GO:0016787\|GO:0005886\|GO:0010891\|GO:0008152\|GO:0010898\|GO:0016021\|GO:0012511\|GO:0005829 | NM_020376 | THC2466068 | Hs.654697 |
| A_33_P3262833 | GOLGA8E | Homo sapiens golgin A8 family, member E (GOLGA8E), non-coding RNA [NR_033350] | NR_033350 | ENST00000341390 | 390535 | golgin A8 family, member E | chr15:23447789-23447848 | | NR_033350 | THC2493346 | Hs.454647 |
| A_24_P401990 | ERCC2 | Homo sapiens excision repair cross-complementing rodent repair deficiency, complementation group 2 (ERCC2), transcript variant 1, mRNA[NM_000400] | NM_000400 | ENST00000391940 | 2068 | excision repair cross-complementing rodent repair deficiency, complementation group 2 | chr19:45864874-45864815 | GO:0009650\|GO:0006368\|GO:0006367\|GO:0009791\|GO:0016818\|GO:0000166\|GO:0030198\|GO:0044419\|GO:0006979\|GO:0045449\|GO:0019907\|GO:0000287\|GO:0005506\|GO:0007568\|GO:0001701\|GO:0006283\|GO:0043388\|GO:0000075\|GO:0043139\|GO:0005654\|GO:0043588\|GO:0035315\|GO:0021510\|GO:0008283\|GO:0016563\|GO:0005634 | NM_000400 | NP1457049 | Hs.487294 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P323072 | GNRH2 | Homo sapiens gonadotropin-releasing hormone 2 (GNRH2), transcript variant 2, mRNA [NM_178332] | NM_178332 | ENST00000359987 | 2797 | gonadotropin-releasing hormone 2 | chr20:3025110-3025169 | GO:0030282\|GO:0004003\| GO:0043249\|GO:0035264\| GO:0040016\|GO:0045944\| GO:0048820\|GO:0043066\| GO:0051536\|GO:0044386\| GO:0006917\|GO:0060218\| GO:0008022\|GO:0032289\| GO:0008353\|GO:0003677\| GO:0005524\|GO:0006974\| GO:0004672\|GO:0047485\| GO:0016787\|GO:0000718\| GO:0005675\|GO:0033683 | | | |
| | | | | | | | | GO:0007165\|GO:0005179 | NM_178332 | THC2484054 | Hs.129715 |
| A_33_P3361991 | OR9A2 | Homo sapiens olfactory receptor, family 9, subfamily A, member 2 (OR9A2), mRNA [NM_001001658] | NM_001001658 | ENST00000350513 | 135924 | olfactory receptor, family 9, subfamily A, member 2 | chr7:142723371-142723312 | GO:0007275\|GO:0005625\| GO:0005576 | | | |
| | | | | | | | | GO:0007608\|GO:0007165 | NM_001001658 | THC2603293 | Hs.553594 |
| A_24_P343095 | DHFR | Homo sapiens dihydrofolate reductase (DHFR), mRNA [NM_000791] | NM_000791 | ENST00000513048 | 1719 | dihydrofolate reductase | chr5:79924927-79924848 | GO:0004984\|GO:0007186\| GO:0005886\|GO:0004872\| GO:0016021\|GO:0050896 | | | |
| | | | | | | | | GO:0050661\|GO:0016491 | NM_000791 | NP098266 | Hs.648635 |
| A_24_P2361 | CLCNKA | Homo sapiens chloride channel Ka (CLCNKA), transcript variant 1, mRNA [NM_004070] | NM_004070 | ENST00000439316 | 1187 | chloride channel Ka | chr1:16358986-16359688 | GO:0006545\|GO:0005575\| GO:0006730\|GO:0091165\| GO:0055114\|GO:0004146 | | | |
| | | | | | | | | GO:0007588\|GO:0006821 | NM_004070 | THC2607488 | Hs.591533 |
| A_33_P3346937 | MON2 | Homo sapiens MON2 homolog (S. cerevisiae) (MON2), mRNA [NM_015026] | NM_015026 | ENST00000393630 | 23041 | MON2 homolog (S. cerevisiae) | chr12:6290215-62902215 | GO:0031404\|GO:0005244\| GO:0016020\|GO:0005887\| GO:0005247\|GO:0034707\| GO:0055085\|GO:0006811 | | | |
| | | | | | | | | GO:0005488\|GO:0015031 | NM_015026 | NP796518 | Hs.389378 |
| A_33_P3716128 | SMC4 | Homo sapiens structural maintenance of chromosomes 4 (SMC4), transcript variant 1, mRNA [NM_005496] | NM_005496 | ENST00000462787 | 10051 | structural maintenance of chromosomes 4 | chr3:160151158-160151640 | GO:0006895 | | | |
| | | | | | | | | GO:0005515\|GO:0000796 | NM_005496 | THC2478358 | Hs.58992 |
| A_23_P115519 | LCE3D | Homo sapiens late cornified envelope 3D (LCE3D), mRNA [NM_032563] | NM_032563 | ENST00000368787 | 84648 | late cornified envelope 3D | chr1:152552017-152551958 | GO:0005737\|GO:0007049\| GO:0000166\|GO:0046982\| GO:0005634\|GO:0005694\| GO:0051301 | | | |
| | | | | | | | | GO:0031424 | NM_032563 | THC2481277 | Hs.244349 |
| A_33_P3681776 | LOC255512 | Homo sapiens hypothetical LOC255512 | NR_029409 | ENST00000530897 | 255512 | hypothetical LOC255512 | chr11:1331801-1331860 | | NR_029409 | THC2603843 | Hs.588291 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P388703 | | (LOC255512), non-coding RNA [NR_029409] | | | | | | | | | |
| | MGC42157 | Homo sapiens cDNA clone IMAGE: 4799398. [BC030111] | BC030111 | | 439933 | hypothetical locus MGC42157 | chr4:36258205-36258264 | | | THC2485423 | Hs.591071 |
| A_32_P209230 | CITED4 | Homo sapiens Cbp/p300-interacting transactivator, with Glu/Asp-rich carboxy-terminal domain, 4 (CITED4), mRNA [NM_133467] | NM_133467 | ENST00000372638 | 163732 | Cbp/p300-interacting transactivator, with Glu/Asp-rich carboxy-terminal domain, 4 | chr1:41326794-41326735 | GO:0005737\|GO:0045941\|NM_133467\|GO:0030528\|GO:0003713\|GO:0005634 | | THC2473039 | Hs.355820 |
| A_23_P161968 | SLC22A10 | Homo sapiens solute carrier family 22, member 10 (SLC22A10), mRNA [NM_001039752] | NM_001039752 | ENST00000332793 | 387775 | solute carrier family 22, member 10 | chr11:6307221-63072270 | GO:0016020\|GO:0016021\|NM_001039752\|GO:0055085 | | THC2480380 | Hs.188982 |
| A_33_P3325102 | LOC644173 | full-length cDNA clone CSODC007YI01 of Neuroblastoma Cot 25-normalized of Homo sapiens (human). [CR604878] | CR604878 | | 644173 | hypothetical LOC644173 | chr4:56814185-56814126 | | | THC2739440 | Hs.646314 |
| A_33_P3304883 | LOC100131372 | PREDICTED: Homo sapiens hypothetical LOC100131372 (LOC100131372), miscRNA [XR_113971] | XR_113971 | | 100131372 | hypothetical LOC100131372 | chr7:469712-469653 | | XR_113971 | THC2632533 | Hs.704272 |
| A_33_P3332135 | PHOSPHO1 | Homo sapiens phosphatase, orphan 1 (PHOSPHO1), transcript variant 1, mRNA [NM_001143804] | NM_001143804 | ENST00000413580 | 162466 | phosphatase, orphan 1 | chr17:47300802-47300743 | GO:0000287\|GO:0016787\|NM_001143804\|GO:0008152\|GO:0033884 | | THC2478263 | Hs.405607 |
| A_24_P286054 | ZFYVE16 | Homo sapiens zinc finger, FYVE domain containing 16 (ZFYVE16), transcript variant 2, mRNA [NM_001105251] | NM_001105251 | ENST00000512907 | 9765 | zinc finger, FYVE domain containing 16 | chr5:79774799-79774858 | GO:0005515\|GO:0030509\|NM_001105251\|GO:0046872\|GO:0005545\|GO:0007165\|GO:0016050\|GO:0005737\|GO:0016020\|GO:0030100\|GO:0031901\|GO:0008565\|GO:0016197\|GO:0006622\|GO:0008270\|GO:0019898 | | THC2502523 | HS.482660 |
| A_23_P43412 | HEMGN | Homo sapiens hemogen (HEMGN), transcript variant 1, mRNA [NM_018437] | NM_018437 | ENST00000259456 | 55363 | hemogen | chr9:100692550-100692491 | GO:0045667\|GO:0007275\|NM_018437\|GO:0005654\|GO:0005634\|GO:0030154 | | THC2464628 | Hs.176626 |
| A_33_P3347522 | | | | | | | chr16:0298876 96-029887637 | | | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3390539 | GYLTL1B | Homo sapiens glyco-syltransferase-like 1B (GYLTL1B), mRNA [NM_152312] | NM_152312 | ENST00000389968 | 120071 | glycosyltrans-ferase-like 1B | chr11:45948027-45948086 | GO:0005794\|GO:0016020\|GO:0016757\|GO:0016021\|GO:0046716 | NM_152312 | THC2742187 | Hs.86543 |
| A_23_P166848 | LTF | Homo sapiens lacto-transferrin (LTF), transcript variant 1, mRNA [NM_002343] | NM_002343 | ENST00000426532 | 4057 | lactotransferrin | chr3:46479489-46477720 | GO:0006879\|GO:0005515\|GO:0005737\|GO:0004252\|GO:0006959\|GO:0006826\|GO:0008233\|GO:0005576\|GO:0046872\|GO:0042742\|GO:0008199\|GO:0006811 | NM_002343 | THC2485813 | Hs.529517 |
| A_33_P3306352 | C20orf108 | chromosome 20 open reading frame 108 [Source: HGNC Symbol; Acc: 16102] [ENST00000437418] | | ENST00000437418 | 116151 | chromosome 20 open reading frame 108 | chr20:5493524-54935301 | | | THC2691510 | |
| A_23_P137689 | OLFML2B | Homo sapiens olfacto-medin-like 2B (OLFML2B), mRNA [NM_015441] | NM_015441 | ENST00000294794 | 25903 | olfactomedin-like 2B | chr1:161953276-161953217 | GO:0016020\|GO:0005576 | NM_015441 | THC2464089 | Hs.507515 |
| A_32_P41604 | F5 | Homo sapiens co-agulation factor V (proaccelerin, labile factor) (F5), mRNA [NM_000130] | NM_000130 | | 2153 | coagulation factor V (proaccelerin, labile factor) | chr1:169481302-169481243 | GO:0005886\|GO:0007596\|GO:0005507\|GO:0005509\|GO:0016491\|GO:0031093\|GO:0005576\|GO:0007155\|GO:0055114 | NM_000130 | THC2654286 | Hs.30054 |
| A_33_P3386487 | | | | | | | chr7:031402201-031402142 | | | | |
| A_23_P409438 | IL28A | Homo sapiens inter-leukin 28A (interferon, lambda 2) (IL28A), mRNA [NM_172138] | NM_172138 | ENST00000331982 | 282616 | interleukin 28A (interferon, lambda 2) | chr19:39760635-39760694 | GO:0005576\|GO:0009615\|GO:0005615\|GO:0005125 | NM_172138 | THC2481798 | Hs.567792 |
| A_33_P3253723 | AQP1 | Homo sapiens aqua-porin 1 (Colton blood group) (AQP1), transcript variant 1, mRNA [NM_198098] | NM_198098 | ENST00000265298 | 358 | aquaporin 1 (Colton blood group) | chr7:30963485-30963544 | GO:0005515\|GO:0043005\|GO:0005215\|GO:0007588\|GO:0043627\|GO:0015696\|GO:0015670\|GO:0055085\|GO:0032809\|GO:0016323\|GO:0016324\|GO:0016020\|GO:0005887\|GO:0015250\|GO:0051739\|GO:0043679\|GO:0006833\|GO:0009725 | NM_198098 | NP1203192 | Hs.76152 |
| A_23_P352950 | PNMA5 | Homo sapiens para-neoplastic antigen like 5 (PNMA5), transcript variant 3, mRNA [NM_052926] | NM_052926 | ENST00000439251 | 114824 | paraneoplastic antigen like 5 | chrX:152157755-152157696 | | NM_052926 | THC2481798 | Hs.573567 |
| A_33_P3240996 | LOC100134240 | PREDICTED: Homo sapiens hypo-thetical protein LOC100134240 | XM_001718062 | | 100134240 | hypothetical protein LOC100134240 | chr2:133110835-133110894 | | XM_001718062 | THC2492745 | Hs.98178 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P161144 | | LOC100134240 (LOC100134240), mRNA[XM_001718062] | | | | | | | | | |
| A_33_P3361741 | ZNF843 | Homo sapiens zinc finger protein 843 (ZNF843), mRNA [NM_001136509] | NM_001136509 | | 283933 | zinc finger protein 843 | chr16:3144705 1-31446992 | GO:0005622\|GO:0008270\|NM_001136509 GO:0003676\|GO:0046872 | | THC2483860 | Hs.722243 |
| A_33_P3263387 | DNAJC15 | Homo sapiens DnaJ (Hsp40) homolog, subfamily C, member 15 (DNAJC15), mRNA [NM_013238] | NM_013238 | | 29103 | DnaJ (Hsp40) homology subfamily C, member 15 | chr13:4368324 5-43683304 | GO:0005737\|GO:0005886\|NM_013238 GO:0031072\|GO:0005634\| GO:0016021\|GO:0005925 | | | Hs.438830 |
| A_33_P3258593 | TTLL4 | Homo sapiens tubulin tyrosine ligase like family, member 4 (TTLL4), mRNA [NM_014640] | NM_014640 | ENST00000392102 | 9654 | tubulin tyrosine ligase like family, member 4 | chr2:21962007 7-219620136 | GO:0005929\|GO:0004835\|NM_014640 GO:0016874\|GO:0005932\| GO:0006464 | | THC2661456 | Hs.471405 |
| A_33_P425073 | PRB1 | Homo sapiens proline-rich protein BstNI subfamily 1(PRB1), transcript variant 1, mRNA [NM_005039] | NM_005039 | ENST00000240636 | 5542 | proline-rich protein BstNI subfamily 1 | chr12:1150629 1-11506232 | GO:0008150\|GO:0003674\|NM_005039 GO:0005576 | | THC2476439 | Hs.631726 |
| A_23_P425073 | RBMS2 | Homo sapiens RNA binding motif, single stranded interacting protein 2 (RBMS2), mRNA [NM_002898] | NM_002898 | ENST00000552916 | 5939 | RNA binding motif, single stranded interacting protein 2 | chr12:5698276 5-56982945 | GO:0006396\|GO:0000166\|NM_002898 GO:0003723\|GO:0005634 | | THC2470737 | Hs.505729 |
| A_33_P3290235 | LOC149950 | Homo sapiens hypothetical LOC149950 (LOC149950), non-coding RNA [NR_034152] | NR_034152 | ENST00000375673 | 149950 | hypothetical LOC149950 | chr20:3119644 7-31196506 | | NR_034152 | THC2488463 | Hs.516980 |
| A_33_P3288924 | | PREDICTED: Homo sapiens hypothetical protein LOC100506005 (LOC100506005), mRNA[XM_003118609] | XM_003118609 | | | | chr9:130318386 5-13031832 | | XM_003118609 | NP498580 | Hs.683792 |
| A_32_P204218 | FAM180A | Homo sapiens family with sequence similarity 180, member A (FAM180A), mRNA [NM_205855] | NM_205855 | ENST00000415751 | 389558 | family with sequence similarity 180, member A | Chr7:13541888 6-135418827 | GO:0005576 | NM_205855 | THC2478197 | Hs.55200 |
| A_23_P92196 | RETNLB | Homo sapiens resistin like beta (RETNLB), mRNA [NM_032579] | NM_032579 | ENST00000295755 | 84666 | resistin like beta | chr3:10847593 6-108475407 | GO:0003674\|GO:0005179\|NM_032579 GO:0008283\|GO:0005576 | | THC2479326 | Hs.307047 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3216448 | COL11A2 | Homo sapiens collagen, type XI, alpha 2 (COL11A2), transcript variant 4, mRNA [NM_001163771] | NM_001163771 | ENST00000383088 | 1302 | collagen, type XI, alpha 2 | chr6:33154291-33154232 | GO:0005581\|GO:0030020\|GO:0001894\|GO:0005592\|GO:0002062\|GO:0030199\|GO:0007605\|GO:0048705\|GO:0005576\|GO:0030674\|GO:0007155\|GO:0060023 | NM_001163771 | THC2481257 | Hs.390171 |
| A_33_P3308132 | FLJ39632 | PREDICTED: Homo sapiens hypothetical LOC642477 (FLJ39632), miscRNA [XR_110291] | XR_110291 | | 642477 | hypothetical LOC642477 | chr14:19887513-19887514 | | XR_110291 | Hs.474095 | |
| A_33_P3396635 | SSX3 | Homo sapiens synovial sarcoma, X breakpoint 3 (SSX3), transcript variant 1, mRNA [NM_021014] | NM_021014 | ENST00000376895 | 10214 | synovial sarcoma, X breakpoint 3 | chrX:48206180-48206121 | GO:0005622\|GO:0006355\|GO:0005634\|GO:0003676 | NM_021014 | THC2484853 | Hs.558445 |
| A_23_P103690 | FAM189B | Homo sapiens family with sequence similarity 189, member B (FAM189B), transcript variant 1, mRNA [NM_006589] | NM_006589 | ENST00000487649 | 10712 | family with sequence similarity 189, member B | chr1:155217344-155217285 | GO:0008150\|GO:0003674\|GO:0016020\|GO:0050699\|GO:0016021 | NM_006589 | NP1167666 | Hs.348308 |
| A_23_P80068 | BTG3 | Homo sapiens BTG family, member 3 (BTG3), transcript variant 2, mRNA [NM_006806] | NM_006806 | ENST00000339775 | 10950 | BTG family, member 3 | chr21:18966119-18966060 | GO:0005737\|GO:0008285\|GO:0045930 | NM_006806 | THC2526595 | Hs.473420 |
| A_23_P65370 | GLRX5 | Homo sapiens glutaredoxin 5 (GLRX5), nuclear gene encoding mitochondrial protein, mRNA [NM_016417] | NM_016417 | ENST00000331334 | 51218 | glutaredoxin 5 | chr14:96010787-96010846 | GO:0005739\|GO:0015035\|GO:0009055\|GO:0045454 | NM_016417 | THC2463309 | Hs.728210 |
| A_33_P3282693 | OR3A4 | Homo sapiens olfactory receptor, family 3, subfamily A, member 4 (OR3A4), non-coding RNA [NR_024128] | NR_024128 | | 390756 | olfactory receptor, family 3, subfamily A, member A | chr17:3214592-3214651 | | NR_024128 | THC2612119 | Hs.632245 |
| A_33_P3362933 | GYPA | Homo sapiens glycophorin A (MNS blood group) (GYPA), mRNA [NM_002099] | NM_002099 | ENST00000508337 | 2993 | glycophorin A (MNS blood group) | chr4:145035902-145035843 | GO:0005886\|GO:0005624\|GO:0016021\|GO:0042802 | NM_002099 | NP082322 | Hs.434973 |
| A_24_P339869 | ZNF295 | Homo sapiens zinc finger protein 295 (ZNF295), transcript variant 2, mRNA [NM_020727] | NM_020727 | ENST00000310826 | 49854 | zinc finger protein 295 | chr21:43407139-43407080 | GO:0005622\|GO:0005515\|GO:0008270\|GO:0005634\|GO:0003677\|GO:0046872\|GO:0045449 | NM_020727 | THC2755459 | Hs.434947 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P431933 | CAMKK1 | Homo sapiens calcium/calmodulin dependent protein kinase kinase 1, alpha (CAMKK1), transcript variant 1, mRNA [NM_032294] | NM_032294 | ENST00000381771 | 84254 | calcium/calmodulin-dependent protein kinase kinase 1, alpha | chr17:3763939-3763880 | GO:0005516\|GO:0005737\|NM_032294 GO:0000166\|GO:0006468\| GO:0005634\|GO:0004683\| GO:0005524\|GO:0016740 | | THC2464408 | Hs.8417 |
| A_33_P3284919 | SEMA6C | Homo sapiens sema domain, transmembrane domain (TM), and cytoplasmic domain, (semaphorin) 6C (SEMA6C), transcript variant 1, mRNA [NM_001178061] | NM_001178061 | ENST00000341697 | 10500 | sema domain, transmembrane domain (TM), and cytoplasmic domain, (semaphorin) 6C | chr1:151104255-151104196 | GO:0016020\|GO:0007275\|NM_001178061 GO:0004872\|GO:0016021\| GO:0030154\|GO:0007399 | | THC2541643 | Hs.516316 |
| A_33_P3327663 | SUSD4 | sushi domain containing 4 [Source: HGNC Symbol; Acc: 25470] [ENST00000366877] | | ENST00000366877 | 55061 | sushi domain containing 4 | chr1:223533605-223533546 | | | THC2679732 | |
| A_23_P24586 | ACCS | Homo sapiens 1-aminocyclopropane-1-carboxylate synthase homolog (Arabidopsis) (non-functional) (ACCS), transcript variant 1, mRNA [NM_032592] | NM_032592 | ENST00000263776 | 84680 | 1-aminocyclopropane-1-carboxylate synthase homolog (Arabidopsis) (no n-functional) | chr11:44105056-44105115 | GO:0009058\|GO:0016847\|NM_032592 GO:0016769\|GO:0030170\| GO:0003824\|GO:0042803 | | THC2470602 | Hs.126706 |
| A_33_P3403733 | | UPF0627 protein ENSP00000341061/ ENSP00000339743 [Source: UniProtKB/Swiss-Prot; Acc: A6NEA5] [ENST00000434336] | XM_001721533 | ENST00000434336 | | | chr1:16999939-16999998 | | XM_001721533 | | |
| A_24_P13716 | B3GNT7 | Homo sapiens UDP-GlcNAc:betaGal beta-1,3-N-acetylglucosaminyltransferase 7 (B3GNT7), mRNA [NM_145236] | NM_145236 | ENST00000287590 | 93010 | UDP-GlcNAc:betaGal beta-1,3-N-acetylglucosaminyltransferase 7 | chr2:232265452-232265511 | GO:0005794\|GO:0016020\|NM_145236 GO:0016757\|GO:0006486\| GO:0016021\|GO:0008378 | | THC2672480 | Hs.299329 |
| A_33_P3351052 | POU3F1 | Homo sapiens POU class 3 homeobox 1 (POU3F1), mRNA [NM_002699] | NM_002699 | (-NST00000373012 | 5453 | POU class 3 homeobox 1 | chr1:38509710-38509651 | GO:0043565\|GO:0010628\|NM_002699 GO:0005667\|GO:0006355\| GO:0003700\|GO:0008544\| GO:0030216\|GO:0022011\| GO:0016563\|GO:0005634 | | THC2498352 | Hs.1837 |
| A_23_P20804 | C9orf25 | Homo sapiens chromosome 9 open reading frame 25 (C9orf25), transcript variant 4, mRNA [NM_147202] | NM_147202 | ENST00000297620 | 203259 | chromosome 9 open reading frame 25 | chr9:34398447-34398388 | | NM_147202 | THC2495188 | Hs.493771 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P114740 | CFH | Homo sapiens complement factor H (CFH), transcript variant 1, mRNA [NM_000186] | NM_000186 | ENST00000466229 | 3075 | complement factor H | chr1:196716550-196716609 | GO:0006957\|GO:0005576\|GO:0005615 | NM_000186 | THC2469545 | Hs.363396 |
| A_33_P3237874 | TROAP | Homo sapiens trophinin associated protein (tastin) (TROAP), transcript variant 2, mRNA [NM_001100620] | NM_001100620 | ENST00000380327 | 10024 | trophinin associated protein (tastin) | chr12:49717948-49718007 | GO:0005515\|GO:0005737\|GO:0007155 | NM_001100620 | THC2481969 | Hs.524399 |
| A_23_P202602 | SEC23IP | Homo sapiens SEC23 interacting protein (SEC23IP), transcript variant 1, mRNA [NM_007190] | NM_007190 | ENST00000369075 | 11196 | SEC23 interacting protein | chr10:121700786-121700845 | GO:0005515\|GO:0005793\|GO:0016020\|GO:0005737\|GO:0007030\|GO:0005783\|GO:0031410\|GO:0006886\|GO:0046872 | NM_007190 | THC2469270 | Hs.435004 |
| A_23_P210465 | PI3 | Homo sapiens peptidase inhibitor 3, skin-derived (PI3), mRNA [NM_002638] | NM_002638 | ENST00000243924 | 5266 | peptidase inhibitor 3, skin-derived | chr20:43804645-43804704 | GO:0005515\|GO:0004867\|GO:0005578\|GO:0005576\|GO:0007620 | NM_002638 | THC2461616 | Hs.112341 |
| A_33_P3279720 | ARFRP1 | ADP-ribosylation factor related protein 1 [Source: HGNC Symbol; Acc: 662] [ENST00000217224] | | ENST00000217224 | 10139 | ADP-ribosylation factor related protein 1 | chr20:62332602-62332543 | | | THC2679434 | |
| A_23_P57379 | CDC45 | Homo sapiens cell division cycle 45 homolog (S. cerevisiae) (CDC45), transcript variant 2, mRNA [NM_003504] | NM_003504 | ENST00000493724 | 8318 | cell division cycle 45 homolog (S. cerevisiae) | chr22:19508635-19508015 | GO:0006260\|GO:0005515\|GO:0007049\|GO:0005813\|GO:0005737\|GO:0006270\|GO:0000076\|GO:0005654\|GO:0005634 | NM_003504 | THC2492552 | Hs.474217 |
| A_33_P3271711 | | Uncharacterized protein [Source: UniProtKB/TrEMBL; Acc: C 9JFK8] [ENST00000449914] | | ENST00000449914 | | | chr3:4856040-4855981 | | | THC2706532 | |
| A_24_P237389 | EIF1AX | Homo sapiens eukaryotic translation initiation factor 1A, X linked (EIF1AX), mRNA [NM_001412] | NM_001412 | ENST00000379607 | 1964 | eukaryotic translation initiation factor 1A, X-linked | chrX:20143018-20142959 | GO:0005737\|GO:0003723\|GO:0006413\|GO:0005829 | NM_001412 | THC2559655 | Hs.522590 |
| A_33_P3399618 | KLHL33 | Homo sapiens kelch-like 33 (Drosophila) (KLHL33), mRNA [NM_001109997] | NM_001109997 | ENST00000344581 | 123103 | kelch-like 33 (Drosophila) | chr14:20897205-20897146 | GO:0005515 | NM_001109997 | THC2663623 | Hs.556014 |
| A_23_P142031 | SBK2 | Homo sapiens SH3-binding domain kinase family, member 2 | NM_001101401 | ENST00000344158 | 646643 | SH3-binding domain kinase family, | chr19:56041653-56041594 | GO:0000166\|GO:0004674\|GO:0006468\|GO:0005524\|GO:0016740 | NM_001101401 | THC2663623 | Hs.532676 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (SBK2), mRNA [NM_001101401] | | | | member 2 | | | | | |
| A_33_P3209706 | ARGFX | Homo sapiens arginine-fifty homeobox (ARGFX), mRNA [NM_001012659] | NM_001012659 | | 503582 | arginine-fifty homeobox | chr3:121309243-121309302 | GO:0043565\|GO:0006355\|GO:0003700\|GO:0005634 | NM_001012659 | | Hs.224976 |
| A_32_P175349 | | Homo sapiens cDNA FLJ46600 fis, clone THYMU3047144 [Source: UniProtKB/TrEMBL; Acc: Q6ZR66] [ENST00000374945] | AK128457 | ENST00000374945 | | | chr17:76259455-76259396 | | | THC2485217 | Hs.594042 |
| A_33_P3210363 | LOC100128191 | Homo sapiens hypothetical LOC100128191 (LOC100128191), non-coding RNA [NR_027157] | NR_027157 | | 100128191 | hypothetical LOC100128191 | chr12:98906810-98906751 | | NR_027157 | | Hs.594042 |
| A_23_P170901 | PACRG | Homo sapiens PARK2 co-regulated (PACRG), transcript variant 1, mRNA [NM_152410] | NM_152410 | ENST00000545186 | 135138 | PARK2 co-regulated | chr6:163510375-163510434 | | NM_152410 | THC2492437 | Hs.25791 |
| A_33_P3570228 | LOC644962 | Homo sapiens cDNA FLJ46065 fis, clone TBAES2007862. [AK127954] | AK127954 | | 644962 | trinucleotide repeat containing 18 pseudogene | chr4:141562411-141562355 | | | THC2691532 | Hs.676500 |
| A_33_P3294377 | | DA880232 PROST2 Homo sapiens cDNA clone PROST2019563 5′, mRNA sequence [DA880232] | DA880232 | ENST00000550687 | | | chr12:94288901-94288842 | | | THC2485964 | Hs.577495 |
| A_23_P69383 | PARP9 | Homo sapiens poly (ADP-ribose) polymerase family, member 9 (PARP9), transcript variant 1, mRNA [NM_031458] | NM_031458 | ENST00000452457 | 83666 | poly (ADP-ribose) polymerase family, member 9 | chr3:122247356-122247297 | GO:0003674\|GO:0016477\|GO:0005634\|GO:0016740\|GO:0003950 | NM_031458 | NP1159658 | Hs.518200 |
| A_23_P3406873 | NFASC | Homo sapiens neurofascin (NFASC), transcript variant 5, mRNA [NM_001005389] | NM_001005389 | ENST00000403080 | 23114 | neurofascin | chr1:204944486-204944545 | GO:0005515\|GO:0030424\|GO:0005886\|GO:0007411\|GO:0016021\|GO:0007155 | NM_001005389 | NP1247431 | Hs.13349 |
| A_33_P3742500 | LOC642947 | Homo sapiens hypothetical protein LOC642947, mRNA (cDNA clone IMAGE:40146909). [BC132887] | BC132887 | | 642947 | hypothetical protein LOC642947 | chr9:79809627-79809686 | | | NP1472442 | Hs.689418 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P209954 | GNLY | Homo sapiens granulysin (GNLY), transcript variant NKG5, mRNA [NM_006433] | NM_006433 | ENST00000489980 | 10578 | granulysin | chr2:85924656-85924715 | GO:0006968\|GO:0050832\|GO:0031640\|GO:0005576\|GO:0005615\|GO:0042742 | NM_006433 | THC2641793 | Hs.105806 |
| A_33_P3291484 | ST8SIA4 | Homo sapiens ST8 alpha-N-acetyl-neuraminide alpha-2,8-sialyltransferase 4 (ST8SIA4), transcript variant 1, mRNA [NM_005668] | NM_005668 | | 7903 | ST8 alpha-N-acetyl-neuraminide alpha-2,8-sialyltransferase 4 | chr5:10014301 6-100142957 | GO:0003828\|GO:0030173\|GO:0009311\|GO:0005794\|GO:0016020\|GO:0006491\|GO:0006486\|GO:0016021\|GO:0007399 | NM_005668 | THC2531659 | Hs.308628 |
| A_33_P3355208 | CROT | Homo sapiens carnitine O-octanoyltransferase (CROT), transcript variant 3, non-coding RNA [NR_026585] | NR_026585 | ENST00000412227 | 54677 | carnitine O-octanoyl-transferase | chr7:86989366-86989425 | GO:0006629\|GO:0005782\|GO:0006810\|GO:0006631\|GO:0008458\|GO:0006091\|GO:0016740\|GO:0008415\|GO:0005777 | NR_026585 | | Hs.125039 |
| A_32_P135517 | LOC100506105 | PREDICTED: Homo sapiens hypothetical LOC100506105 (LOC100506105), partial miscRNA [XR_109318] | XR_109318 | | 100506105 | hypothetical LOC100506105 | chr16:7149789 6-71497955 | | XR_109318 | THC2568448 | Hs.647355 |
| A_33_P3403851 | | O52K2_HUMAN (Q8NGK3) Olfactory receptor 52K2, partial (29%) [THC2647746] | | | | | chr11:0044970 21-004497080 | | | THC2647746 | |
| A_23_P343411 | AGRN | Homo sapiens agrin (AGRN), mRNA [NM_198576] | NM_198576 | ENST00000461111 | 375790 | agrin | chr1:991186-991245 | GO:0007009\|GO:0009986\|GO:0005605\|GO:0045202\|GO:0005576\|GO:0045213\|GO:0007213\|GO:0007416\|GO:0007165\|GO:0045162\|GO:0007528\|GO:0030348\|GO:0045944\|GO:0043236\|GO:0005200\|GO:0043113\|GO:0008582 | NM_198576 | NP1152870 | Hs.273330 |
| A_23_P61042 | | immunoglobulin heavy constant alpha 2 (A2m marker) [Source: HGNC Symbol; Acc: 5479] [ENST00000390539] | XR_111480 | ENST00000390539 | | | chr14:1060539 30-106053649 | | XR_111480 | NP1154471 | Hs.699841 |
| A_23_P127279 | FAM35A | Homo sapiens family with sequence similarity 35, member A (FAM35A), mRNA [NM_019054] | NM_019054 | ENST00000298786 | 54537 | family with sequence similarity 35, member A | chr10:8895074 1-88950800 | | NM_019054 | THC2462523 | Hs.500419 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P42768 | SRRM3 | Homo sapiens serine/arginine repetitive matrix 3 (SRRM3), mRNA [NM_001110199] | NM_001110199 | ENST00000326382 | 222183 | serine/arginine repetitive matrix 3 | chr7:75890675-75890731 | | NM_001110199 | THC2614609 | Hs.511025 |
| A_33_P3260605 | CTNNAL1 | Homo sapiens catenin (cadherin-associated protein), alpha-like 1 (CTNNAL1), mRNA [NM_003798] | NM_003798 | ENST00000374593 | 8727 | catenin (cadherin associated protein), alphalike 1 | chr9:111754973-111754914 | GO:0005737 GO:0045296 GO:0005886 GO:0005198 GO:0015629 GO:0007155 GO:0019898 | NM_003798 | NP1195581 | Hs.58488 |
| A_33_P3316248 | | | | | | | chrX:000515186-000515127 | | | | |
| A_23_P132139 | C21orf58 | Homo sapiens chromosome 21 open reading frame 58 (C21orf58), mRNA [NM_058180] | NM_058180 | ENST00000417060 | 54058 | chromosome 21 open reading frame 58 | chr21:47731417-47722479 | | NM_058180 | THC2482412 | Hs.236572 |
| A_33_P3305790 | NOS3 | Homo sapiens nitric oxide synthase 3 (endothelial cell) (NOS3), transcript variant 1, mRNA [NM_000603] | NM_000603 | ENST00000461406 | 4846 | nitric oxide synthase 3 (endothelial cell) | chr7:150711495-150711554 | GO:0005516 GO:0014070 GO:0009408 GO:0010181 GO:0034405 GO:0043267 GO:0006809 GO:0050880 GO:0032496 GO:0051926 GO:0005856 GO:0031663 GO:0032355 GO:0003100 GO:0010288 GO:0005794 GO:0051346 GO:0007568 GO:0005509 GO:0014806 GO:0001542 GO:0004517 GO:0043542 GO:0055094 GO:0055093 GO:0002028 GO:0016491 GO:0008270 GO:0031284 GO:0007005 GO:0051114 GO:0020037 GO:0050661 GO:0010544 GO:0005886 GO:0030324 GO:0045471 GO:0050660 GO:0043434 GO:0005634 GO:0046870 GO:0005829 GO:0006527 GO:0034097 GO:0043200 GO:0001666 GO:0042493 GO:0005730 GO:0045177 GO:0048662 GO:0006916 GO:0005625 GO:0045766 GO:0003785 GO:0007165 GO:0000139 GO:0014740 GO:0034618 GO:0001974 GO:0005901 GO:0034617 GO:0008217 | NM_000603 | THC2520376 | Hs.647092 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P352291 | SRSF10 | Homo sapiens serine/arginine-rich splicing factor 10 (SRSF10), transcript variant 2, mRNA [NM_054016] | NM_054016 | ENST00000374449 | 10772 | serine/arginine-rich splicing factor 10 | chr1:24296306-24296247 | GO:0000244\|GO:0008380\|NM_054016\|GO:0048025\|GO:0003723\|GO:0006376\|GO:0005634\|GO:0050733\|GO:0005737\|GO:0006406\|GO:0000166\|GO:0016607\|GO:0016482\|GO:0005654\|GO:0051082\|GO:0045440 | | THC2468077 | Hs.3530 |
| A_33_P3389342 | ARID5A | Homo sapiens AT rich interactive domain 5A (MRF1-like) (ARID5A), mRNA [NM_212481] | NM_212481 | ENST00000359765 | 10865 | AT rich interactive domain 5A (MRF1-like) | chr2:97216361-97216420 | GO:0016564\|GO:0005622\|NM_212481\|GO:0005634\|GO:0045892\|GO:0003677\|GO:0045449 | | THC2627646 | Hs.920 |
| A_33_P3285371 | | | | | | | chr1:20446213 5-20446207 6 | | | | |
| A_33_P3386132 | C2orf49 | chromosome 2 open reading frame 49 [Source: HGNC Symbol; Acc: 28772] [ENST00000437250] | AK304268 | ENST00000437250 | 79074 | chromosome 2 open reading frame 49 | chr2:10596199 2-105962051 | | | THC2507880 | Hs.549577 |
| A_33_P3252181 | | cDNA FLJ40032 fis, clone STOMA2009256 [Source: UniProtKB/TrEMBL; Acc: Q8N843] [ENST00000358234] | AK097351 | ENST00000358234 | | | chr19:4983156 3-49831504 | | | THC2482392 | Hs.660609 |
| A_23_P28334 | IL18RAP | Homo sapiens interleukin 18 receptor accessory protein (IL18RAP), mRNA [NM_003853] | NM_003853 | ENST00000264260 | 8807 | interleukin 18 receptor accessory protein | chr2:10306888 5-103068944 | GO:0006954\|GO:0016020\|NM_003853\|GO:0045087\|GO:0016021\|GO:0007166\|GO:0004888 | | THC2478417 | Hs.158315 |
| A_33_P3363100 | | | | | | | chr6:02994291 1-029942852 | | | | |
| A_33_P3261074 | | | | | | | chr22:018666 07-018666848 | | | | |
| A_23_P129829 | ORMDL3 | Homo sapiens ORM1-like 3 (S. cerevisiae) (ORMDL3), mRNA [NM_139280] | NM_139280 | ENST00000304046 | 94103 | ORM1-like 3 (S. cerevisiae) | chr17:3807755 8-38077499 | GO:0016020\|GO:0005783\|NM_139280\|GO:0016021 | | THC2461115 | Hs.514151 |
| A_32_P163533 | ZNF322A | Homo sapiens zinc finger protein 322A (ZNF322A), transcript variant 1, mRNA [NM_001242797] | NM_001242797 | ENST00000375210 | 79692 | zinc finger protein 322A | chr6:26637056-26636997 | GO:0005622\|GO:0008270\|NM_001242797\|GO:0005634\|GO:0003677\|GO:0046872\|GO:0045449 | | THC2470822 | Hs.126280 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3423721 | JPH3 | junctophilin 3 [Source: HGNC Symbol; Acc: 14203] [ENST00000301008] | AB593088 | ENST00000301008 | 57338 | junctophilin 3 | chr16:87637922-87637981 | | | THC2485118 | Hs.592068 |
| A_23_P10194 | SEZ6L2 | Homo sapiens seizure related 6 homolog (mouse)-like 2 (SEZ6L2), transcript variant 2, mRNA [NM_201575] | NM_201575 | ENST00000537485 | 26470 | seizure related 6 homolog (mouse)-like 2 | chr16:29882918-29882859 | GO:0005886\|GO:0005783\|NM_201575 GO:0016021 | | NP160855 | Hs.6314 |
| A_33_P3363254 | | | | | | | chr2:131449816-131449757 | | | | |
| A_33_P3284888 | DLEU7 | Homo sapiens deleted in lymphocytic leukemia, 7 (DLEU7), mRNA [NM_198989] | NM_198989 | ENST00000335465 | 220107 | deleted in lymphocytic leukemia, 7 | chr13:51417384-51417325 | | NM_198989 | THC2485203 | Hs.710878 |
| A_33_P3263747 A_33_P3219303 | CEL | Homo sapiens carboxyl ester lipase (bile salt-stimulated lipase) (CEL), mRNA [NM_001807] | NM_001807 | ENST00000303626 | 1056 | carboxyl ester lipase (bile salt-stimulated lipase) | chr9:135947092-135947151 | GO:0006707\|GO:0004806\|NM_001807 GO:0005576\|GO:0030157 GO:0018350\|GO:0009062 GO:0016042\|GO:0030299 GO:0005737\|GO:0016787 GO:0047372\|GO:0006641 GO:0046514\|GO:0044258 GO:0008201\|GO:0004771 | | THC2462969 | Hs.533258 |
| A_33_P3289860 | | Homo sapiens mRNA; cDNA DKFZp686G10213 (from clone DKFZp686G10213). [BX648603] | BX648603 | | | | chr18:48087024-48087083 | | | THC2652919 | Hs.433728 |
| A_23_P360804 | CPNE5 | Homo sapiens copine V (CPNE5), mRNA [NM_020939] | NM_020939 | ENST00000244751 | 57699 | copine V | chr6:36708629-36708570 | GO:0043005\|GO:0043025 | NM_020939 | THC2464138 | Hs.657869 |
| A_33_P3301306 | MLL3 | Homo sapiens myeloid/lymphoid or mixed-lineage leukemia 3 (MLL3), mRNA [NM_170606] | NM_170606 | ENST00000355193 | 58508 | myeloid/lymphoid or mixed-lineage leukemia 3 | chr7:151832089-151832030 | GO:0005515\|GO:0007242\|NM_170606 GO:0006355\|GO:0008168 GO:0008270\|GO:0005634 GO:0003677\|GO:0046872 GO:0016740\|GO:0018024 GO:0016568 | | THC2469247 | Hs.647120 |
| A_33_P3333107 | | | | | | | chr16:08561372-085613663 | | | THC2764040 | |
| A_24_P191013 | CYP4A11 | Homo sapiens cytochrome P450, family 4, subfamily A, polypeptide 11 (CYP4A11), mRNA | NM_000778 | ENST00000371905 | 1579 | cytochrome P450, family 4, subfamily A, polypeptide 11 | chr1:47398708-47398504 | GO:0008393\|GO:0005792\|NM_000778 GO:0005783\|GO:0018685 GO:0009055\|GO:0046872 GO:0016020\|GO:0019825 GO:0005789\|GO:0006631 | | NP175000 | Hs.1645 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P89780 | LAMA3 | Homo sapiens laminin, alpha 3 (LAMA3), transcript variant 1, mRNA [NM_198129] | NM_198129 | ENST00000416669 | 3909 | laminin, alpha 3 | chr18:21534735-21534794 | GO:0019898\|GO:0020037\|GO:0055114\|GO:0045995\|GO:0030334\|GO:0005198\|GO:0008544\|GO:0005102\|GO:0005606\|GO:0005576\|GO:0030155 | NM_198129 | THC2461199 | Hs.436367 |
| A_33_P3283400 | LOC100507747 | Homo sapiens hypothetical protein LOC100507747 (LOC100507747), mRNA [XM_003119562] | XM_003119562 | | 100507747 | hypothetical protein LOC100507747 | | GO:0005604 | XM_003119562 | THC2482547 | Hs.704267 |
| A_33_P3214012 | HMGCLL1 | Homo sapiens 3-hydroxymethyl-3-methylglutaryl-CoA lyase-like 1 (HMGCLL1), transcript variant 1, mRNA [NM_019036] | NM_019036 | ENST00000370852 | 54511 | 3-hydroxy-methyl-3-methylglutaryl-CoA lyase-like 1 | chr6:55360319-55360260 | GO:0008152\|GO:0046872\|GO:0016829\|GO:0004419 | NM_019036 | THC2474902 | Hs.147054 |
| A_24_P104512 | EVPL | Homo sapiens envoplakin (EVPL), mRNA [NM_001988] | NM_001988 | ENST00000301607 | 2125 | envoplakin | chr17:7400306-74003008 | GO:0030057\|GO:0005737\|GO:0030054\|GO:0018149\|GO:0008544\|GO:0005198\|GO:0031424\|GO:0030674\|GO:0001533 | NM_001988 | THC2471184 | Hs.500635 |
| A_23_P143713 | APOBEC3G | Homo sapiens apolipoprotein B mRNA editing enzyme, catalytic polypeptide-like 3G (APOBEC3G), mRNA [NM_021822] | NM_021822 | ENST00000480000 | 60489 | apolipoprotein B mRNA editing enzyme, catalytic polypeptide-like 3G | chr22:39477481-39477540 | GO:0030895\|GO:0005515\|GO:0003723\|GO:0016553\|GO:0045869\|GO:0005730\|GO:0048525\|GO:0005634\|GO:0006410\|GO:0009615\|GO:0046872\|GO:0042803\|GO:0005829\|GO:0005739\|GO:0005737\|GO:0016787\|GO:0045087\|GO:0044419\|GO:0002230\|GO:0004126\|GO:0008270 | NM_021822 | THC2677649 | Hs.660143 |
| A_33_P3396891 | AVPI1 | Homo sapiens arginine vasopressin-induced 1 (AVPI1), mRNA [NM_021732] | NM_021732 | ENST00000370626 | 60370 | arginine vasopressin-induced 1 | chr10:99437521-99437462 | GO:0007049 | NM_021732 | THC2602356 | Hs.23918 |
| A_23_P202034 | GUCY2GP | Homo sapiens guanylate cyclase 2G homolog (mouse), pseudogene (GUCY2GP), non-coding RNA [NR_028134] | NR_028134 | ENST00000490269 | 390003 | guanylate cyclase 2G homolog (mouse), pseudogene | chr10:114074088-114074029 | | NR_028134 | THC2662526 | |
| A_33_P3589819 | LOC100507637 | Homo sapiens cDNA: FLJ22849 fis, clone | AK026502 | | 100507637 | hypothetical LOC100507637 | chr22:27117555-27117614 | | | THC2515177 | Hs.730728 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3495962 | SNORA71A | KAIA987. [AK026502] AGENCOURT NIH_MGC_106 Homo sapiens cDNA clone IMAGE: 6611325485440 5', mRNA sequence [BM918074] | BM918074 | | 26777 | small nucleolar RNA, H/ACA box 71A | chr20:37054976-37054917 | | | | Hs.681779 |
| A_33_P3416622 | NCRNA00322 | PREDICTED: Homo sapiens chromosome 21 open reading frame 136 (C21orf136), miscRNA [XR_109689] | XR_109689 | | 100126693 | non-protein coding RNA 322 | chr21:44748637-44748578 | | XR_109689 | THC2482602 | Hs.473952 |
| A_23_P8351 | ATL1 | Homo sapiens atlastin GTPase 1 (ATL1), transcript variant 2, mRNA [NM_181598] | NM_181598 | ENST00000441560 | 51062 | atlastin GTPase 1 | chr14:51095050-51095109 | GO:0030424|GO:0005792|NM_181598 GO:0008219|GO:0005794 GO:0005783|GO:0003924 GO:0007409|GO:0005525 GO:0042802|GO:0000137 GO:0000166|GO:0016020 GO:0005789|GO:0051260 GO:0016021|GO:0007029 | | THC2609154 | Hs.584905 |
| A_23_P368484 | C17orf76 | Homo sapiens chromosome 17 open reading frame 76 (C17orf76), transcript variant 2, mRNA [NM_207387] | NM_207387 | ENST00000409887 | 388341 | chromosome 17 open reading frame 76 | chr17:16345428-16345369 | | NM_207387 | THC2473528 | Hs.25425 |
| A_24_P151032 | MYL4 | Homo sapiens myosin, light chain 4, alkali; atrial, embryonic (MYL4), transcript variant 2, mRNA [NM_002476] | NM_002476 | ENST00000354968 | 4635 | myosin, light chain 4, alkali; atrial, embryonic | chr17:45286758-45286817 | GO:0005509|GO:0016459|NM_002476 GO:0032781|GO:0060048 GO:0003785|GO:0003774 GO:0007517|GO:0051015 GO:0002026|GO:0032038 GO:0005859|GO:0008307 GO:0031672 | | NP093155 | Hs.463300 |
| A_33_P3241786 | ADD2 | Homo sapiens adducin 2 (beta) (ADD2), transcript variant 2, mRNA [NM_017482] | NM_017482 | ENST00000413157 | 119 | adducin 2 (beta) | chr2:70902283-70902224 | GO:0030097|GO:0005516|NM_017482 GO:0030036|GO:0046982 GO:0005886|GO:0030507 GO:0042803|GO:0046872 GO:0032092|GO:0051016 GO:0005737|GO:0051015 GO:0005198|GO:0008290 GO:0005856|GO:0051017 GO:0006811 | | NP1475291 | Hs.188528 |
| A_33_P3342862 | ZNF664-FAM101A | Homo sapiens ZNF664-FAM101A readthrough | NM_001204299 | ENST00000324038 | 100533183 | ZNF664-FAM101A readthrough | chr12:124799228-124799287 | | NM_001204299 | THC2471258 | Hs.432901 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3380982 | TMEM30A | (ZNF664-FAM101A), mRNA [NM_001204299] Homo sapiens trans-membrane protein 30A (TMEM30A), transcript variant 1, mRNA [NM_018247] | NM_018247 | ENST00000545449 | 55754 | transmembrane protein 30A | chr6:75962725-75962666 | GO:0016020\|GO:0016021 | NM_018247 | THC2654263 | Hs.108530 |
| A_33_P3289246 | | immunoglobulin heavy variable 3-9 [Source: HGNC Symbol; Acc: 5628] [ENST00000390600] | GQ233935 | ENST00000390600 | | | chr14:106552343-106552285 | | | NP104532 | Hs.720841 |
| A_24_P393611 | GNAO1 | Homo sapiens guanine nucleotide binding protein (G protein), alpha activating activity polypeptide O (GNAO1), transcript variant 2, mRNA [NM_138736] | NM_138736 | ENST00000262494 | 2775 | guanine nucleotide binding | chr16:56374823-56374882 | GO:0014070\|GO:0042542\|GO:0005886\|GO:0031852\|GO:0003924\|GO:0032403\|GO:0031175\|GO:0006936\|GO:0000166\|GO:0051926\|GO:0004871\|GO:0019717\|GO:0034097\|GO:0042493\|GO:0007568\|GO:0010243\|GO:0043278\|GO:0005525\|GO:0043547\|GO:0007165\|GO:0043234\|GO:0019001\|GO:0007186\|GO:0031821\|GO:0030900 | NM_138736 | THC2495079 | Hs.644524 |
| A_33_P3391536 | | | | | | | chr7:02647020-1-026470260 | | | | |
| A_33_P3292164 | KRTAP9-7 | keratin associated protein 9-7 [Source: HGNC Symbol; Acc: 18915] [ENST00000391354] | XM_003120879 | ENST00000391354 | 100505724 | keratin associated protein 9-7 | chr17:3943226-4-39432323 | GO:0045095 | XM_003120879 | | |
| A_23_P72668 | SDPR | Homo sapiens serum deprivation response (SDPR), mRNA [NM_004657] | NM_004657 | ENST00000304141 | 8436 | serum deprivation response | chr2:19270016-1-192700102 | GO:0005515\|GO:0005737\|GO:0016020\|GO:0005901\|GO:0001786\|GO:0005829 | NM_004657 | THC2461139 | Hs.26530 |
| A_33_P3362301 | HSP90AASP | Homo sapiens heat shock protein 90Ae (HSP90Ae) mRNA, complete cds. [AY956761] | AY956761 | | 730211 | heat shock protein 90 kDa alpha (cytosolic), class A member 5, pseudogene | chr3:18383559-5-183835654 | | | NP1455480 | Hs.581644 |
| A_33_P3323559 | CRYAA | Homo sapiens crystallin, alpha A (CRYAA), mRNA [NM_000394] | NM_000394 | ENST00000291554 | 1409 | crystallin, alpha A | chr21:4458928-5-44589344 | GO:0005212\|GO:0032387\|GO:0009408\|GO:0006916\|GO:0042026\|GO:0005737\|GO:0070309\|GO:0051260\|GO:0007015\|GO:0043010\|GO:0007005\|GO:0051082 | NM_000394 | THC2468650 | Hs.184085 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3286929 | | | | | | | chr15:0327813 87-032781328 | GO:0000072|GO:0007601| GO:0050896 | | | |
| A_33_P3292241 | | | | | | | chr8:02784745 6-027847515 | | | | |
| A_33_P1227467 | BNIP2 | *Homo sapiens* BCL2/ adenovirus E1B 19 kDa interacting protein 2 (BNIP2), mRNA [NM_004330] | NM_004330 | ENST00000267859 | 663 | BCL2/ adenovirus E1B 19 kDa interacting protein 2 | chr15:5995515 4-59955095 | GO:0005515|GO:0048471|GO:0005509| GO:0005737|GO:0005509| GO:0006915|GO:0006916| GO:0005635|GO:0043231| GO:0005096 | NM_004330 | THC2496581 | Hs.646490 |
| A_33_P3382489 | | | BC033982 | ENST00000429878 | | | chr2:12006351- 12006410 | | | THC2657735 | |
| A_33_P3224020 | ARAF2P | *Homo sapiens* v-raf murine sarcoma 3611 viral oncogene homolog pseudogene, mRNA (cDNA clone IMAGE: 5295529). [BC033982] | | | 644000 | v-raf murine sarcoma 3611 viral oncogene homolog 2, pseudogene | chr7:62865027- 62864968 | | | THC2605425 | |
| A_23_P58482 | MGAT1 | *Homo sapiens* man- nosyl (alpha-1,3-)- glycoprotein beta-1,2-N- acetylglucosaminyl- transferase (MGAT1), transcript variant 2, mRNA [NM_002406] | NM_002406 | ENST00000446023 | 4245 | mannosyl (alpha-1,3-)- glycoprotein beta 1,2-N- acetylglucosa- minyltransferase | chr5:18021807 8-180218019 | GO:0003827|GO:0005794|NM_002406 GO:0016020|GO:0000139| GO:0016757|GO:0005975| GO:0016021|GO:0006487 | | THC2470078 | Hs.519818 |
| A_23_P214026 | FBN2 | *Homo sapiens* fibrillin 2 (FBN2), mRNA [NM_001999] | NM_001999 | ENST00000508053 | 2201 | Fibrillin 2 | chr5:12759423 2-127594173 | GO:0005488|GO:0005509|NM_001999 GO:0005578|GO:0005576| GO:0030326|GO:0009653| GO:0005201 | | THC2749486 | Hs.519294 |
| A_33_P3387696 | TMBIM4 | *Homo sapiens* trans- membrane BAX inhibitor motif con- taining 4 (TMBIM4), mRNA [NM_016056] | NM_016056 | ENST00000358230 | 51643 | transmem- brane BAX inhibitor motif con- taining 4 | chr12:6653079 2-66530733 | GO:0005515|GO:0016020|NM_016056 GO:0016021 | | THC2544517 | Hs.505934 |
| A_24_P943472 | NR1D2 | *Homo sapiens* nuclear receptor subfamily 1, group D, member 2 (NR1D2), transcript variant 1, mRNA [NM_005126] | NM_005126 | | 9975 | nuclear receptor subfamily 1, group D, member 2 | chr3:24021460- 24021519 | GO:0043565|GO:0006355|NM_005126 GO:0003700|GO:0003707| GO:0008270|GO:0005634| GO:0046872 | | THC2601359 | Hs.37288 |
| A_33_P3303463 | LOC100128348 | *Homo sapiens* cDNA FLJ46249 fis, clone TESTI4021377. [AK128128] | AK128128 | | 100128348 | hypothetical protein LOC100128348 | chr16:3334756 6-33347507 | | | | Hs.637572 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P145501 | MED23 | Homo sapiens mediator complex subunit 23 (MED23), transcript variant 1, mRNA [NM_004830] | NM_004830 | ENST00000545957 | 9439 | mediator complex subunit 23 | chr6:131190790-131907873 | GO:0005515\|GO:0005667\|NM_004830 GO:0006367\|GO:0006357\| GO:0030528\|GO:0003713\| GO:0005634 | THC2620147 | Hs.29679 |
| A_33_P3325336 | | | | | | | chrX:097644673-097644732 | | | | |
| A_23_P13294 | OR1S2 | Homo sapiens olfactory receptor, family 1, subfamily S, member 2 (OR1S2), mRNA [NM_001004459] | NM_001004459 | ENST00000302592 | 219958 | olfactory receptor, family 1, subfamily S, member 2 | chr11:5797156 9-57971510 | GO:0007608\|GO:0007165\|NM_001004459 GO:0004984\|GO:0007186\| GO:0005886\|GO:0004872\| GO:0016021\|GO:0050896 | THC2603194 | Hs.553644 |
| A_23_P163025 | RNASE3 | Homo sapiens ribonuclease, RNase A family, 3 (RNASE3), mRNA [NM_002935] | NM_002935 | ENST00000304639 | 6037 | ribonuclease, RNase A family, 3 | chr14:2135959 1-21359880 | GO:0004519\|GO:0016787\|NM_002935 GO:0005625\|GO:0005576\| GO:0004540\|GO:0004522\| GO:0003676\|GO:0042742\| GO:0006401 | THC2477182 | Hs.73839 |
| A_24_P33993 | OR2W3 | Homo sapiens olfactory receptor, family 2, subfamily W, member 3 (OR2W3), mRNA [NM_001001957] | NM_001001957 | ENST00000360358 | 343171 | olfactory receptor, family 2, subfamily W, member 3 | chr1:24805952 0-248059579 | GO:0007608\|GO:0007165\|NM_001001957 GO:0004984\|GO:0007186\| GO:0005886\|GO:0004872\| GO:0016021\|GO:0050896 | THC2480700 | Hs.269151 |
| A_23_P51679 | MEF2D | Homo sapiens myocyte enhancer factor 2D (MEF2D), mRNA [NM_005920] | NM_005920 | ENST00000464356 | 4209 | myocyte enhancer factor 2D | chr1:15643664 4-156436585 | GO:0005515\|GO:0006355\|NM_005920 GO:0003700\|GO:0016563 GO:0005730\|GO:0006915 GO:0005634\|GO:0007275 GO:0001649\|GO:0007399 GO:0043565\|GO:0001958 GO:0005737\|GO:0007517\| GO:0002062 | THC2462787 | Hs.314327 |
| A_24_P173566 | | immunoglobulin lambda variable 3-1 [Source: HGNC Symbol; Acc: 5896] [ENST00000390319] | X57818 | ENST00000390319 | | | chr22:2322330 8-23223367 | | NP1458222 | Hs.449585 |
| A_24_P11436 | TTC22 | Homo sapiens tetratricopeptide repeat domain 22 (TTC22), transcript variant 2, mRNA [NM_017904] | NM_017904 | ENST00000488771 | 55001 | tetratricopeptide repeat domain 22 | chr1:55251801-55251742 | GO:0005488 | NM_017904 | THC2655240 | Hs.16230 |
| A_32_P66881 | TLR4 | Homo sapiens toll-like receptor 4 (TLR4), transcript variant 1, mRNA [NM_138554] | NM_138554 | | 7099 | toll-like receptor 4 | chr9:12047923 6-120479295 | GO:0005515\|GO:0032755\|NM_138554 GO:0048471\|GO:0005886 GO:0045471\|GO:0046330 GO:0001875\|GO:0050731 GO:0032874\|GO:0042088 GO:0002237\|GO:0005737 GO:0051092\|GO:0010572 GO:0032497\|GO:0002282 | THC2629156 | Hs.174312 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | | | | | | | GO:0070374\|GO:0032609\|GO:0043123\|GO:0006979\|GO:0046696\|GO:0043065\|GO:0032760\|GO:0070434\|GO:0045416\|GO:0042535\|GO:0045671\|GO:0070430\|GO:0002224\|GO:0050829\|GO:0007165\|GO:0045084\|GO:0042116\|GO:0005887\|GO:0052033\|GO:0045087\|GO:0050729\|GO:0045121\|GO:0016046\|GO:0009897\|GO:0004888\|GO:0043548 | | | |
| A_33_P3253672 | KCNH3 | Homo sapiens potassium voltage-gated channel, subfamily H (eag-related), member 3 (KCNH3), mRNA [NM_012284] | NM_012284 | ENST00000257981 | 23416 | potassium voltage-gated channel, subfamily H (eag-related), member 3 | chr12:49952000-49952059 | GO:0006355\|GO:0001160\|GO:0005244\|GO:0016020\|GO:0015249\|GO:0030955\|GO:0016021\|GO:0055085\|GO:0006813\|GO:0000155\|GO:0006811 | NM_012284 | | Hs.64064 |
| A_23_P309701 | PTPN2 | Homo sapiens protein tyrosine phosphatase, non-receptor type 2 (PTPN2), transcript variant 1, mRNA [NM_00282R] | NM_002828 | ENST00000309660 | 5771 | protein tyrosine phosphatase, non-receptor type 2 | chr18:12794039-12793980 | GO:0008286\|GO:0005515\|GO:0005737\|GO:0006470\|GO:0016787\|GO:0004726 | NM_002828 | THC2475995 | Hs.654527 |
| A_33_P3410206 | C16orf7 | Homo sapiens chromosome 16 open reading frame 7 (C16orf7), mRNA [NM_004913] | NM_004913 | ENST00000261625 | 9605 | chromosome 16 open reading frame 7 | chr16:89777241-89777182 | GO:0005215\|GO:0015986 | NM_004913 | THC2472575 | Hs.164410 |
| A_33_P3261953 | | | | | | | chr19:022791181-022791240 | | | | |
| A_23_P63379 | CA14 | Homo sapiens carbonic anhydrase XIV (CA14), mRNA [NM_012113] | NM_012113 | ENST00000369160H | 23632 | carbonic anhydrase XIV | chr1:150237369-150237428 | GO:0016020\|GO:0008270\|GO:0016021\|GO:0004089\|GO:0046872\|GO:0016829 | NM_012113 | THC2471240 | Hs.528988 |
| A_33_P3287348 | CHN2 | Homo sapiens chimerin (chimaerin) 2 (CHN2), transcript variant 2, mRNA [NM_004067] | NM_004067 | ENST00000409041 | 1124 | chimerin (chimaerin) 2 | chr7:29553778-29553837 | GO:0005622\|GO:0005515\|GO:0007242\|GO:0016020\|GO:0005070\|GO:0008270\|GO:0046872\|GO:0019898\|GO:0005096 | NM_004067 | THC2463843 | Hs.654611 |
| A_33_P3364293 | LOC389834 | Homo sapiens ankyrin repeat domain 57 pseudogene (LOC389834), non-coding RNA [NR_027420] | NR_027420 | | 389834 | ankyrin repeat domain 57 pseudogene | chr21:9921746-9921687 | | NR_027420 | THC2474667 | Hs.720653 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P390734 | FGFR1OP2 | Homo sapiens FGFR1 oncogene partner 2 (FGFR1OP2), transcript variant 1, mRNA [NM_015633] | NM_015633 | ENST00000229395 | 26127 | FGFR1 oncogene partner 2 | chr12:27118788-27118847 | GO:0005737 | NM_015633 | THC2462507 | Hs.591162 |
| A_33_P3267640 | HGFAC | Homo sapiens HGF activator (HGFAC), mRNA [NM_001528] | NM_001528 | ENST00000382774 | 3083 | HGF activator | chr4:3451154-3451213 | GO:0005515\|GO:0004252\|GO:0006508\|GO:0008233\|GO:0005576\|GO:0005615 | NM_001528 | THC2478808 | Hs.104 |
| A_33_P3362249 | | Homo sapiens cDNA FLJ46348 fis, clone TEST4047569. [AK128836] | AK128836 | ENST00000434161 | | | chr7:56877663-56877604 | | | THC2481823 | Hs.520384 |
| A_23_P158880 | STARD5 | Homo sapiens StAR-related lipid transfer (START) domain containing 5 (STARD5), mRNA [NM_181900] | NM_181900 | ENST00000325346 | 80765 | StAR-related lipid transfer (START) domain containing 5 | chr15:81605262-81605203 | GO:0006694\|GO:0006869\|GO:0008289\|GO:0005829 | NM_181900 | THC2474209 | Hs.513075 |
| A_33_P3262156 | SLC8A1 | Homo sapiens solute carrier family 8 (sodium/calcium exchanger), member 1 (SLC8A1), transcript variant A, mRNA [NM_021097] | NM_021097 | ENST00000403092 | 6546 | solute carrier family 8 (sodium/calcium exchanger), member 1 | chr2:40342452-40342393 | GO:0060401\|GO:0005516\|GO:0042542\|GO:0031402\|GO:0005432\|GO:0007204\|GO:0007154\|GO:0006936\|GO:0015297\|GO:0031072\|GO:0051924\|GO:0033198\|GO:0006811\|GO:0001666\|GO:0007584\|GO:0042493\|GO:0005509\|GO:0006874\|GO:0015085\|GO:0005624\|GO:0030315\|GO:0015081\|GO:0055085\|GO:0009749\|GO:0005887\|GO:0002026\|GO:0005901\|GO:0002028 | NM_021097 | THC2483436 | Hs.468274 |
| A_32_P44394 | AIM2 | Homo sapiens absent in melanoma 2 (AIM2), mRNA [NM_004833] | NM_004833 | ENST00000368130 | 9447 | absent in melanoma 2 | chr1:159033365-159033306 | GO:0005515\|GO:0006955\|GO:0005634 | NM_004833 | THC2474709 | Hs.281898 |
| A_33_P3402257 | LOC100508241 | PREDICTED: Homo sapiens membrane-spanning 4-domains subfamily A member 18-like (LOC100508241), mRNA [XM_003119499] | XM_003119499 | ENST00000529108 | 100508241 | membrane-spanning 4-domains subfamily A member 18 like | chr11:60511408-60511467 | | XM_003119499 | THC2717961 | Hs.326275 |
| A_33_P3344618 | TFEB | Homo sapiens transcription factor EB (TFEB), transcript | NM_007162 | ENST00000373033 | 7942 | transcription factor EB | chr6:41651777-41651718 | GO:0005667\|GO:0005737\|GO:0003700\|GO:0006959\|GO:0010843\|GO:0001892 | NM_007162 | THC2463798 | Hs.48536 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3331237 | G3BP1 | GTPase activating protein (SH3 domain) binding protein 1 variant 1, mRNA [NM_007162] [Source: HGNC Symbol; Acc: 30292] [ENST00000394123] | | ENST00000394123 | 10146 | GTPase activating protein (SH3 domain) binding protein 1 | chr5:151192282-151192341 | GO:0010552\|GO:0005634\|GO:0045893\|GO:0005515\|GO:0005886\|GO:0003723\|GO:0004386\|GO:0007265\|GO:0005634\|GO:0003677\|GO:0005524\|GO:0005829\|GO:0004004\|GO:0005622\|GO:0005737\|GO:0004003\|GO:0004519\|GO:0016787\|GO:0000166\|GO:0006810 | | THC2711864 | Hs.534032 |
| A_33_P3370029 | | T cell receptor gamma variable 11 (non-functional) [Source: HGNC Symbol; Acc: 12286] [ENST00000390340] | S60780 | ENST00000390340 | | | chr7:38331276-38331217 | | | THC2547979 | Hs.657843 |
| A_33_P3321678 | RNF180 | ring finger protein 180 [Source: HGNC Symbol; Acc: 27752] [ENST00000381081] | AK090756 | ENST00000381081 | 285671 | ring finger protein 180 | chr5:63513485-63513544 | | | THC2478341 | Hs.104825 |
| A_33_P3265504 | EIF5AL1 | Homo sapiens eukaryotic translation initiation factor 5A-like 1 (EIF5AL1), mRNA [NM_001099692] | NM_001099692 | ENST00000520547 | 143244 | eukaryotic translation initiation factor 5A-like 1 | chr10:8200371-82003653 | GO:0008612\|GO:0005783\|NM_001099692\|GO:0003723\|GO:0005634\|GO:0003746\|GO:0015031\|GO:0055085\|GO:0006412\|GO:0045905\|GO:0005737\|GO:0006452\|GO:0016020\|GO:0005643\|GO:0043022\|GO:0051028\|GO:0045901 | THC2684242 | Hs.198072 |
| A_33_P3422499 | PDE4B | Homo sapiens phosphodiesterase 4B, cAMP-specific (PDE4B), transcript variant d, mRNA [NM_001037341] | NM_001037341 | ENST00000329654 | 5142 | phosphodiesterase 4B, cAMP-specific | chr1:66839789-66839848 | GO:0007165\|GO:0016787\|NM_001037341\|GO:0004115\|GO:0005625\|GO:0005626\|GO:0005829 | | THC2477454 | Hs.437008 |
| A_23_P74278 | EPHB4 | Homo sapiens EPH receptor B4 (EPHB4), mRNA [NM_004444] | NM_004444 | ENST00000487222 | 2050 | EPH receptor B4 | chr7:10040059-0-100400531 | GO:0005515\|GO:0009986\|NM_004444\|GO:0008283\|GO:0045765\|GO:0005524\|GO:0005003\|GO:0000166\|GO:0016020\|GO:0005887\|GO:0009887\|GO:0004872\|GO:0006468\|GO:0007169\|GO:0016740 | NP1473086 | |
| A_23_P20075 | NPC1L1 | Homo sapiens NPC1 (Niemann-Pick disease, type C1, gene) like 1 (NPC1L1), transcript | NM_013389 | ENST00000289547 | 29881 | NPC1 (Niemann-Pick disease, type C1, | chr1:04690206-6-046902125 chr7:44552449-44552390 | GO:0042632\|GO:0030299\|NM_013389\|GO:0006629\|GO:0006695\|GO:0005886\|GO:0042157\|GO:0008158\|GO:0031410 | | THC2704282 THC2474926 | Hs.567486 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P38952 | ACER1 | *Homo sapiens* alkaline ceramidase 1 (ACER1), mRNA [NM_133492] | NM_133492 | ENST00000301452 | 125981 | alkaline ceramidase 1 | chr19:6312480-6312421 | GO:0016021|GO:0008202 GO:0006665|GO:0017040|GO:0016020 GO:0016787|GO:0005783 GO:0000139|GO:0005789|GO:0046514 GO:0016021|GO:0019216 | NM_133492 | THC2490357 | Hs.352609 |
| A_33_P3241250 | | *Homo sapiens* cDNA FLJ46348 fis, clone TEST4047569. [AK128836] | AK128836 | ENST00000434161 | | | chr7:56876826-56876817 | | | THC2481823 | Hs.520384 |
| A_23_P394605 | SEC24A | *Homo sapiens* SEC24 family, member A (S. cerevisiae) (SEC24A), mRNA [NM_021982] | NM_021982 | ENST00000398844 | 10802 | SEC24 family, member A (S. cerevisiae) | chr5:134063223-134063282 | GO:0005515|GO:0048471|NM_021982 GO:0030127|GO:0005794 GO:0005783|GO:0006886 GO:0006888|GO:0003674 GO:0005737|GO:0000139 GO:0016020|GO:0005789 GO:0008270|GO:0016192 GO:0016044 | | THC2493017 | Hs.595540 |
| A_32_P112910 | UBL4B | *Homo sapiens* ubiquitin-like 4B (UBL4B), mRNA [NM_203412] | NM_203412 | ENST00000334179 | 164153 | ubiquitin-like 4B | chr11:110655660-110655719 | GO:0005737 | NM_203412 | THC2477239 | Hs.374027 |
| A_23_P201951 | ARID4B | *Homo sapiens* AT rich interactive domain 4B (RBP1-like) (ARID4B), transcript variant 1, mRNA [NM_016374] | NM_016374 | ENST00000264183 | 51742 | AT rich interactive domain 4B (RBP1-like) | chr1:235331255-235331196 | GO:0005622|GO:0008150|NM_016374 GO:0003674|GO:0005737 GO:0003682|GO:0005634 GO:0005575|GO:0003677 GO:0000785|GO:0045449 GO:0006333 | | THC2490824 | Hs.575782 |
| A_33_P3306287 | METTL16 | *Homo sapiens* methyl-transferase like 16 (METTL16), mRNA [NM_024086] | NM_024086 | ENST00000399834 | 79066 | methyl-transferase like 16 | chr17:23711152371056 | GO:0008168|GO:0016740 | NM_024086 | THC2487575 | Hs.632237 |
| A_32_P40547 | MEG3 | *Homo sapiens* maternally expressed 3 (non-protein coding) (MEG3), transcript variant 1, non-coding RNA [NR_002766] | NR_002766 | ENST00000452514 | 55384 | maternally expressed 3 (nonprotein coding) | chr14:101295974-101296033 | | NR_002766 | THC2722032 | Hs.728839 |
| A_33_P3291772 | | | | | | | chr18:0611640 87-061164146 | | | | |
| A_33_P3356816 | LCE1B | *Homo sapiens* late cornified envelope 1B (LCE1B), mRNA [NM_178349] | NM_178349 | ENST00000360090 | 353132 | late cornified envelope 1B | chr1:15278528 0-152785339 | GO:0031424 | NM_178349 | | Hs.375103 |
| A_23_P167599 | FAM134B | *Homo sapiens* family with sequence similarity 134, member B | NM_001034850 | ENST00000306320 | 54463 | family with sequence similarity 134, | chr5:16473404 16473345 | GO:0016020|GO:0016021 | NM_001034850 | THC2461507 | Hs.662367 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (FAM134B), transcript variant 1, mRNA [NM_001034850] | | | | member B | | | | | |
| A_23_P122439 | BTN2A2 | Homo sapiens butyrophilin, subfamily 2, member A2 (BTN2A2), transcript variant 2, mRNA [NM_181531] | NM_181531 | ENST00000416795 | 10385 | butyrophilin, subfamily 2, member A2 | chr6:26394026-26394085 | GO:0016020\|GO:0016021 | NM_181531 | THC2612342 | Hs.373938 |
| A_33_P3306802 | LOC100130916 | Homo sapiens clone DNA131652 HSAL5836 (UNQ5836) mRNA, complete cds. [AY358791] | AY358791 | | 100130916 | HSAL5836 | chr9:99840523-99840464 | | | THC2486676 | Hs.655523 |
| A_33_P3340868 | LOC643719 | Homo sapiens hypothetical LOC643719 (LOC643719), non-coding RNA [NR_027620] | NR_027620 | | 643719 | hypothetical LOC643719 | chr19:3506786 9-35067810 | | NR_027620 | THC2622807 | Hs.686754 |
| A_23_P169934 | RILPL1 | Homo sapiens Rab interacting lysosomal protein-like 1 (RILPL1), mRNA [NM_178314] | NM_178314 | ENST00000376874 | 353116 | Rab interacting lysosomal protein-like 1 | chr12:1239569 85-123956926 | GO:0005737\|GO:0005829 | NM_178314 | THC2488648 | Hs.530315 |
| A_33_P3272663 | | PREDICTED: Homo sapiens hypothetical protein LOC100506093 (LOC100506093), mRNA [XM_003118587] | XM_003118587 | | | | chr7:95778898-95778839 | | XM_003118587 | THC2486345 | Hs.665212 |
| A_23_P485 | ORM2 | Homo sapiens orosomucoid 2 (ORM2), mRNA [NM_000608] | NM_000608 | ENST00000412657 | 5005 | orosomucoid 2 | chr9:11709390 5-117094115 | GO:0005488\|GO:0002682\|GO:0005576\|GO:0006953\|GO:0005615 | NM_000608 | THC2562815 | Hs.719954 |
| A_33_P3350892 | LOC651337 | PREDICTED: Homo sapiens hypothetical protein LOC100506062 (LOC100506062), mRNA [XM_003118884] | XM_003118884 | | 651337 | hypothetical protein LOC651337 | chr9:14067970 1-140679642 | | XM_003118884 | THC2482301 | Hs.603195 |
| A_23_P129413 | DPEP3 | Homo sapiens dipeptidase 3 (DPEP3), transcript variant 1, mRNA [NM_022357] | NM_022357 | ENST00000268793 | 64180 | dipeptidase 3 | chr16:6800964 0-68009581 | GO:0016020\|GO:0008235\|GO:0006508\|GO:0005624\|GO:0008270\|GO:0008233\|GO:0031225\|GO:0008239\|GO:0016805\|GO:0046872 | NM_022357 | THC2472083 | Hs.302028 |
| A_33_P3414202 | MBNL3 | Homo sapiens muscleblind-like 3 (Drosophila) (MBNL3), transcript | NM_001170704 | ENST00000465964 | 55796 | muscleblind like 3 (Drosophila) | chrX:13151629 5-131516236 | GO:0005737\|GO:0005794\|GO:0005730\|GO:0008270\|GO:0007275\|GO:0005634 | NM_001170704 | THC2608812 | Hs.105134 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3356792 | GGT7 | Homo sapiens gamma-glutamyltransferase 7 (GGT7), mRNA variant 6, mRNA [NM_001170704] | NM_178026 | ENST00000470952 | 2686 | gamma-glutamyl-transferase 7 | chr20:3343917 0-33439111 | GO:0003676\|GO:0046872\| GO:0045662 GO:0016020\|GO:0003840\|NM_178026 GO:0006750\|GO:0016021\| GO:0016740\|GO:0008415 | NP325734 | Hs.433738 |
| A_33_P3223243 | ST7L | Homo sapiens suppression of tumorigenicity 7 like [Source: HGNC Symbol; Acc: 18441] [ENST00000369664] | AK301869 | ENST00000369664 | 54879 | suppression of tumorigenicity 7 like | chr1:11316068 9-113160630 | | | THC2508274 | Hs.201921 |
| A_32_P72341 | TRIM59 | Homo sapiens tripartite motif containing 59 (TRIM59), mRNA [NM_173084] | NM_173084 | ENST00000309784 | 286827 | tripartite motif containing 59 | chr3:16015358 5-160153526 | GO:0005622\|GO:0005515\|NM_173084 GO:0016020\|GO:0008270 GO:0016021\|GO:0046872 | THC2525484 | Hs.212957 |
| A_23_P168916 | CA1 | Homo sapiens carbonic anhydrase 1 (CA1), transcript variant 2, mRNA [NM_001738] | NM_001738 | ENST00000523022 | 759 | carbonic antydrase 1 | chr8:86240793-86240734 | GO:0005737\|GO:0008270\|NM_001738 GO:0004089\|GO:0006730\| GO:0046872\|GO:0016829 | THC2667429 | Hs.23118 |
| A_24_P189739 | DUSP16 | Homo sapiens dual specificity phosphatase 16 (DUSP16), mRNA [NM_030640] | NM_030640 | ENST00000228862 | 80824 | dual specificity phosphatase 16 | chr12:1262942 9-12629370 | GO:0045209\|GO:0005515\|NM_030640 GO:0000188\|GO:0005737\| GO:0006470\|GO:0016787\| GO:0005634\|GO:0045204\| GO:0017017\|GO:0004725 | THC2463749 | Hs.536535 |
| A_33_P3301075 | | immunoglobulin heavy variable 3-33 [Source: HGNC Symbol; Acc: 5596] [ENST00000390615] | XM_003120441 | ENST00000390615 | | | chr14:1068158 14-106815755 | | XM_003120441 | NP240776 | Hs.703889 |
| A_32_P41553 | C1orf182 | Homo sapiens chromosome 1 open reading frame 182 (C1orf182), mRNA [NM_144627] | NM_144627 | ENST00000466306 | 128229 | chromosome 1 open reading frame 182 | chr1:15631671 1-156316770 | | NM_144627 | NP397546 | Hs.534539 |
| A_24_P119685 | OBSCN | Homo sapiens obscurin, cytoskeletal calmodulin and titin-interacting RhoGEF (OBSCN), transcript variant 1, mRNA [NM_052843] | NM_052843 | ENST00000284548 | 84033 | obscurin, cytoskeletal calmodulin and titin-interacting RhoGEF | chr1:22854857 6-228548635 | GO:0005515\|GO:0008624\|NM_052843 GO:0030018\|GO:0005886 GO:0035023\|GO:0005634 GO:0030016\|GO:0030154 GO:0005829\|GO:0005622 GO:0005085\|GO:0005737 GO:0000166\|GO:0005089 GO:0008307\|GO:0000287 GO:0006915\|GO:0007275 GO:0005524\|GO:0031430 GO:0031432\|GO:0004674 GO:0006468\|GO:0004713 GO:0016740 | NP1165096 | Hs.656999 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P90997 | OTOS | Homo sapiens otospiralin (OTOS), mRNA [NM_148961] | NM_148961 | ENST00000391989 | 150677 | otospiralin | chr2:241078673-241078614 | GO:0007605\|GO:0005576 | NM_148961 | THC2481051 | Hs.148586 |
| A_33_P3417281 | MUC4 | Homo sapiens mucin 4, cell surface associated (MUC4), transcript variant 1, mRNA [NM_018406] | NM_018406 | ENST00000479406 | 4585 | mucin 4, cell surface associated | chr3:195506369-195506310 | GO:0005515\|GO:0008150\|GO:0005176\|GO:0030197\|GO:0016020\|GO:0007160\|GO:0005887\|GO:0005578\|GO:0005576\|GO:0005155 | NM_018406 | THC2584230 | Hs.369646 |
| A_23_P18692 | ADH5 | Homo sapiens alcohol dehydrogenase 5 (class III), chi polypeptide (ADH5), mRNA [NM_000671] | NM_000671 | ENST00000296412 | 128 | alcohol dehydrogenase 5 (class III), chi polypeptide | chr4:99992455-99992396 | GO:0051409\|GO:0045777\|GO:0042803\|GO:0046872\|GO:0005739\|GO:0004022\|GO:0005737\|GO:0003016\|GO:0051287\|GO:0051903\|GO:0032496\|GO:0005504\|GO:0006069\|GO:0009055\|GO:0005625\|GO:0018119\|GO:0001523\|GO:0035276\|GO:0046294\|GO:0005488\|GO:0016491\|GO:0051775\|GO:0008270\|GO:0018467\|GO:0055114 | NM_000671 | THC2465499 | Hs.78989 |
| A_33_P3274691 | LOC619207 | Homo sapiens scavenger receptor protein family member (LOC619207), non-coding RNA [NR_002934] | NR_002934 | ENST00000356567 | 619207 | scavenger receptor protein family member | chr10:135278188-135278247 | GO:0016020\|GO:0005576\|GO:0005044 | NR_002934 | NP1076594 | Hs.659384 |
| A_33_P3259423 | WDR55 | Homo sapiens WD repeat domain 55 (WDR55), mRNA [NM_017706] | NM_017706 | ENST00000358337 | 54853 | WD repeat domain 55 | chr5:140050494-140050553 | GO:0008150\|GO:0003674\|GO:0005737\|GO:0006364\|GO:0005730\|GO:0005634\|GO:0005575 | NM_017706 | THC2464522 | Hs.286261 |
| A_33_P3380567 | SHARPIN | Homo sapiens SHANK-associated RH domain interactor (SHARPIN), transcript variant 1, mRNA [NM_030974] | NM_030974 | ENST00000532536 | 81858 | SHANK-associated RH domain interactor | chr8:145153595-145153536 | GO:0005622\|GO:0005737\|GO:0030262\|GO:0008544\|GO:0031424\|GO:0008270\|GO:0007005\|GO:0046872\|GO:0042802 | NM_030974 | THC2488562 | Hs.529755 |
| A_33_P3406281 | SAMHD1 | Homo sapiens SAM domain and HD domain 1 (SAMHD1), mRNA [NM_015474] | NM_015474 | ENST00000262878 | 25939 | SAM domain and HD domain 1 | chr20:35520818-35520759 | GO:0005622\|GO:0051607\|GO:0016787\|GO:0045088\|GO:0005634 | NM_015474 | NP166373 | Hs.580681 |
| A_23_P87279 | TRPM5 | Homo sapiens transient receptor potential cation channel, subfamily M, member 5 (TRPM5), mRNA [NM_014555] | NM_014555 | ENST00000452833 | 29850 | transient receptor potential cation channel, subfamily M, member 5 | chr11:2427270-2426786 | GO:0005244\|GO:0005886\|GO:0004872\|GO:0016021\|GO:0055085\|GO:0006811 | NM_014555 | NP166373 | Hs.272287 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P52921 | BCAT1 | Homo sapiens branched chain amino-acid transaminase 1, cytosolic (BCAT1), transcript variant 1, mRNA [NM_005504] | NM_005504 | ENST00000544418 | 586 | branched chain amino-acid trans aminase 1, cytosolic | chr12:24995040-24989496 | GO:0005737\|GO:0000082\|GO:0008283\| GO:0009082\|GO:0008152\| GO:0004084\|GO:0016740\| GO:0009083\|GO:0005829\| GO:0042802 | NM_005504 | THC2739017 | Hs.438993 |
| A_33_P3441583 | SRGAP2P1 | AGENCOURT_6387596 NIH_MGC_71 Homo sapiens cDNA clone IMAGE: 5529651 5', mRNA sequence [BM453041] | BM453041 | | 653464 | SLIT-ROBO Rho GTPase activating protein 2 pseudogene 1 | | | | | Hs.69027 |
| A_23_P80240 | CEACAM8 | Homo sapiens carcinoembryonic antigen-related cell adhesion molecule 8 (CEACAM8), mRNA [NM_001816] | NM_001816 | ENST00000244336 | 1088 | carcinoembryonic antigen-related cell adhesion molecule 8 | chr19:4308456 5-43084506 | GO:0006955\|GO:0005886\| GO:0005887\|GO:0031225\| GO:0005615 | NM_001816 | THC2475392 | Hs.41 |
| A_33_P3265941 | LOC100510004 | PREDICTED: Homo sapiens hypothetical protein LOC100510004 (LOC100510004), mRNA [XM_003119032] | XM_003119032 | | 100510004 | hypothetical protein LOC100510004 | chr5:01279430 1-01279242 chr7:47093109-47093168 | | XM_003119032 | | |
| A_33_P3291329 | | | | | | | | | | | |
| A_33_P3347772 | 2-Sep | septin 2 [Source: HGNC Symbol; Acc: 7729] [ENST00000473479] | AK025163 | ENST00000473479 | | septin 2 | chr2:2422755 16-242275575 | | | THC2514366 | Hs.335057 |
| A_23_P16110 | OR7E24 | Homo sapiens olfactory receptor, family 7, subfamily E, member 24 (OR7E24), mRNA [NM_001079935] | NM_001079935 | ENST00000456448 | 26648 | olfactory receptor, family 7, subfamily E, member 24 | chr19:9362278-9362337 | GO:0007608\|GO:0007165\| GO:0004984\|GO:0007186\| GO:0005886\|GO:0004872\| GO:0016021\|GO:0050896 | NM_001079935 | THC2533847 | Hs.129832 |
| A_33_P3378383 | DNM1P46 | Homo sapiens DNM1 pseudogene 46 (DNM1P46), non-coding RNA [NR_003260] | NR_003260 | ENST00000455423 | 196968 | DNM1 pseudogene 46 | chr15:1003403 50-100340291 | | NR_003260 | THC2485999 | Hs.585319 |
| A_24_P944458 | INSIG2 | Homo sapiens insulin induced gene 2 (INSIG2), mRNA [NM_016133] | NM_016133 | ENST00000471186 | 51141 | insulin induced gene 2 | chr2:11886696 4-118867023 | GO:0006629\|GO:0005515\| GO:0016020\|GO:0005783\| GO:0032937\|GO:0030967\| GO:0016021\|GO:0008202\| GO:0008203 | NM_016133 | THC2461710 | Hs.7089 |
| A_33_P3326892 | | cDNA FLJ26718 fis, clone PNC03325 [Source: UniProtKB/TrEMBL; Acc: Q6ZP17] [ENST00000398957] | AK130228 | ENST00000398957 | | | chr3:47645495-47645436 | | | NP852683 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P651948 | NEO1 | Homo sapiens neogenin 1 (NEO1), transcript variant 1, mRNA [NM_002499] | NM_002499 | ENST00000261908 | 4756 | neogenin 1 | chr15:73596015-73596074 | GO:0005515\|GO:0045296\|NM_002499 GO:0005886\|GO:0005887\| GO:0030528\|GO:0007520\| GO:0004872\|GO:0007155\| GO:0045449 | THC2492572 | Hs.388613 |
| A_33_P302312 | IER5L | Homo sapiens immediate early response 5-like (IER5L), mRNA [NM_203434] | NM_203434 | ENST00000372491 | 389792 | immediate early response 5-like | chr9:131939832-131939773 | | NM_203434 | THC2464402 | Hs.529857 |
| A_33_P334828 | INSL3 | Homo sapiens insulin-like 3 (Leydig cell) (INSL3), mRNA [NM_005543] | NM_005543 | ENST00000379695 | 3640 | insulin-like 3 (Leydig cell) | chr19:17927383-17927324 | GO:0005179\|GO:0005158\|NM_005543 GO:0007267\|GO:0005625\| GO:0005576\|GO:0007283\| GO:0004871 | NP881609 | Hs.37062 |
| A_33_P399788 | SERPINA3 | Homo sapiens serpin peptidase inhibitor, clade A (alpha-1 antiproteinase, antitrypsin), member 3 (SERPINA3), mRNA [NM_001085] | NM_001085 | ENST00000380354 | 12 | serpin peptidase inhibitor, clade A (alpha-1 antiproteinase, antitrypsin), member 3 | chr14:95090330-95090389 | GO:0005622\|GO:0005515\|NM_001085 GO:0006954\|GO:0030277\| GO:0004867\|GO:0005634\| GO:0005576\|GO:0006953\| GO:0030414\|GO:0003677\| GO:0019216 | THC2509353 | Hs.534293 |
| A_24_P132633 | C9orf71 | Homo sapiens chromosome 9 open reading frame 71 (C9orf71), mRNA [NM_153237] | NM_153237 | ENST00000377311 | 169693 | chromosome 9 open reading frame 71 | chr9:71152330-71152271 | GO:0016020\|GO:0016021 NM_153237 | THC2484013 | Hs.663056 |
| A_33_P396010 | AGER | Homo sapiens advanced glycosylation end product-specific receptor (AGER), transcript variant 9, mRNA [NM_001206966] | NM_001206966 | ENST00000438221 | 177 | advanced glycosylation end product-specific receptor | chr6:32149366-32149307 | | NM_001206966 | NP868672 | Hs.534342 |
| A_24_P21831 | ZNF26 | Homo sapiens zinc finger protein 26 (ZNF26), mRNA [NM_019591] | NM_019591 | ENST00000391574 | 7574 | zinc finger protein 26 | chr12:133588011-133588060 | GO:0005622\|GO:0006355\|NM_019591 GO:0008270\|GO:0005634\| GO:0003677\|GO:0046872 | THC2477768 | Hs.489608 |
| A_33_P3247540 | LOC389834 | Homo sapiens ankyrin repeat domain 57 pseudogene (LOC389834), non-coding RNA [NR_027420] | NR_027420 | | 389834 | ankyrin repeat domain 57 pseudogene | chr21:9921687-9921628 | | NR_027420 | THC2499620 | Hs.720653 |
| A_33_P3294252 | ATF1 | Homo sapiens activating transcription factor 1 (ATF1), mRNA [NM_005171] | NM_005171 | ENST00000262053 | 466 | activating transcription factor 1 | chr12:51214846-51214905 | GO:0043565\|GO:0005667\|NM_005171 GO:0006355\|GO:0003700\| GO:0046983\|GO:0005634 | THC2552669 | Hs.648565 |
| A_32_P86150 | CTRB2 | Homo sapiens chymotrypsinogen B2 (CTRB2), mRNA [NM_001025200] | NM_001025200 | ENST00000303037 | 440387 | chymotrypsinogen B2 | chr16:75238059-75238000 | GO:0004252\|GO:0007586\|NM_001025200 GO:0006508\|GO:0008233\| GO:0005576\|GO:0005615 | THC2562346 | Hs.632211 |
| A_33_P3314401 | CLDN16 | Homo sapiens claudin 16 (CLDN16), mRNA | NM_006580 | ENST00000264734 | 10686 | claudin 16 | chr3:190128216-190128275 | GO:0007588\|GO:0030054\|NM_006580 GO:0016338\|GO:0000287 | THC2475714 | Hs.251391 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3220415 | GALT | galactose-1-phosphate uridylyltransferase [Source: HGNC Symbol; Acc: 4135] [ENST00000487381] [NM_006580] | AK096026 | ENST00000487381 | 2592 | galactose-1-phosphate uridylyl-transferase | chr9:34648451-34648510 | GO:0005886\|GO:0005198\| GO:0015095\|GO:0016021\| GO:0006875\|GO:0005923\| GO:0042802\|GO:0006811 | | THC2504909 | |
| A_33_P3401571 | MUC2 | Homo sapiens mucin 2, oligomeric mucus/gel-forming (MUC2), mRNA [NM_002457] | NM_002457 | ENST00000359061 | 4583 | mucin 2, oligomeric mucus/gel-forming | chr11:1092337-1092396 | GO:0005515\|GO:0070703\|NM_002457 GO:0070702\|GO:0005576 | | THC2461569 | Hs.315 |
| A_24_P322353 | PSTPIP2 | Homo sapiens proline-serine-threonine phosphatase interacting protein 2 (PSTPIP2), mRNA [NM_024430] | NM_024430 | ENST00000495213 | 9050 | proline-serine-threonine phosphatase interacting protein 2 | chr18:43564417-43564358 | GO:0005737\|GO:0016020\|NM_024430 GO:0005624\|GO:0005856\| GO:0019898\|GO:0005829 | | THC2472686 | Hs.567384 |
| A_33_P3270346 | KIR2DL5A | Homo sapiens killer cell immunoglobulin-like receptor, two domains, long cytoplasmic tail, 5A (KIR2DL5A), mRNA [NM_020535] | NM_020535 | ENST00000391731 | 57292 | killer cell immunoglobulin like receptor, two domains, long cytoplasmic tail, 5A | chr19_gl000209_random:89704-89763 | GO:0005886\|GO:0004872\|NM_020535 GO:0016021 | | THC2489091 | Hs.676464 |
| A_23_P395911 | FBXO17 | Homo sapiens cDNA FLJ11798 fis, clone HEMBA1006198. [AK021860] | AK021860 | | 115290 | F-box protein 17 | chr19:39436636-39436577 | | | THC2483169 | Hs.531770 |
| A_24_P38702 | NKX2-3 | Homo sapiens NK2 homeobox 3 (NKX2-3), mRNA [NM_145285] | NM_145285 | ENST00000344586 | 159296 | NK2 homeobox 3 | chr10:101292909-101292968 | GO:0003700\|GO:0016563\|NM_145285 GO:0005634\|GO:0009791\| GO:0048536\|GO:0050900\| GO:0048535\|GO:0006955\| GO:0048541\|GO:0042127\| GO:0045944\|GO:0030183\| GO:0030225\|GO:0022612\| GO:0001776\|GO:0048621\| GO:0048565\|GO:0043367\| GO:0043565\|GO:0008150\| GO:0016333\|GO:0002317\| GO:0006641 | | NP1246719 | Hs.243272 |
| A_33_P3416503 | NUDT8 | Homo sapiens nudix (nucleoside diphosphate linked moiety X)-type motif 8 (NUDT8), mRNA [NM_181843] | NM_181843 | ENST00000534054 | 254552 | nudix (nucleoside diphosphate linked moiety X)-type motif 8 | chr11:6739576 4-67395705 | GO:0005739\|GO:0030145\|NM_181843 GO:0000287\|GO:0016787 | | THC2604113 | Hs.433329 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P58606 | CCNG1 | Homo sapiens cyclin G1 (CCNG1), transcript variant 1, mRNA [NM_004060] | NM_004060 | ENST00000393929 | 900 | cyclin G1 | chr5:162871009-162871068 | GO:0007067\|GO:0007049\|GO:0016049\|GO:0005634\|GO:0000079\|GO:0051301 | NM_004060 | THC2516963 | Hs.79101 |
| A_33_P3222769 | PRR25 | Homo sapiens proline rich 25 (PRR25), mRNA [NM_001013638] | NM_001013638 | ENST00000301698 | 388199 | proline rich 25 | chr16:863802-863861 | | NM_001013638 | NP366233 | Hs.528461 |
| A_33_P3405004 | NFXL1 | Homo sapiens nuclear transcription factor, X-box binding-like 1 (NFXL1), mRNA [NM_152995] | NM_152995 | ENST00000464756 | 152518 | nuclear transcription factor, X-box binding-like 1 | chr4:47849447-47849388 | GO:0005515\|GO:0006355\|GO:0003700\|GO:0016020\|GO:0008270\|GO:0005634\|GO:0016021\|GO:0046872 | NM_152995 | THC2471778 | Hs.646325 |
| A_23_P346302 | ZMAT2 | Homo sapiens zinc finger, matrin-type 2 (ZMAT2), mRNA [NM_144723] | NM_144723 | ENST00000274712 | 153527 | zinc finger, matrin-type 2 | chr5:140086002-140086061 | GO:0005622\|GO:0008270\|GO:0005634\|GO:0003677\|GO:0046872 | NM_144723 | THC2468624 | Hs.350194 |
| A_33_P3221111 | PGA3 | Homo sapiens mRNA; cDNA DKFZp666I2410 (from clone DKFZp666I2410). [AL832946] | AL832946 | ENST00000538258 | 643834 | pepsinogen 3, group 1 (pepsinogen A) | chr11:60978471-60978530 | | | THC2558400 | Hs.601055 |
| A_33_P3351062 | | | | | | | chr17:03911147040-39114645 | | | | |
| A_24_P167642 | GCH1 | Homo sapiens GTP cyclohydrolase 1 (GCH1), transcript variant 1, mRNA [NM_000161] | NM_000161 | ENST00000491895 | 2643 | GTP cyclohydrolase 1 | chr14:55309447-55309388 | GO:0050662\|GO:0014916\|GO:0051066\|GO:0006729\|GO:0005634\|GO:0045776\|GO:0051291\|GO:0042803\|GO:0006809\|GO:0005829\|GO:0042416\|GO:0005737\|GO:0000166\|GO:0042311\|GO:0050884\|GO:0032496\|GO:0046654\|GO:0051260\|GO:0034341\|GO:0005509\|GO:0003934\|GO:0005625\|GO:0006917\|GO:0031410\|GO:0005525\|GO:0006184\|GO:0043234\|GO:0030742\|GO:0006461\|GO:0016787\|GO:0051000\|GO:0048265\|GO:0008270\|GO:0034612 | NM_000161 | THC2463290 | Hs.86724 |
| A_23_P124760 | MED24 | Homo sapiens mediator complex subunit 24 (MED24), transcript variant 1, mRNA [NM_014815] | NM_014815 | ENST00000422942 | 9862 | mediator complex subunit 24 | chr17:38178296-38178237 | GO:0046966\|GO:0037712\|GO:0006355\|GO:0030374\|GO:0006367\|GO:0042809\|GO:0016592\|GO:0016563\|GO:0005634\|GO:0004872\|GO:0016455\|GO:0030521 | NM_014815 | THC2578251 | Hs.462983 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3395743 | VWA1 | Homo sapiens von Willebrand factor A domain containing 1 (VWA1), transcript variant 1, mRNA [NM_022834] | NM_022834 | ENST00000476993 | 64856 | von Willebrand factor A domain containing 1 | chr1:1376086-1376145 | GO:0030198\|GO:0005576\|NM_022834 GO:0005614\|GO:0005604 | | THC2469429 | Hs.449009 |
| A_33_P3275722 | LY6G6D | Homo sapiens lymphocyte antigen 6 complex, locus G6D (LY6G6D), mRNA [NM_021246] | NM_021246 | ENST00000383415 | 58530 | lymphocyte antigen 6 complex, locus G6D | chr6:31685522-31685581 | GO:0005886\|GO:0031225 | NM_021246 | NP510943 | Hs.591792 |
| A_24_P40417 | FMR1 | Homo sapiens fragile X mental retardation 1 (FMR1), transcript variant ISO1, mRNA [NM_002024] | NM_002024 | ENST00000370477 | 2332 | fragile X mental retardation 1 | chrX:14703175 2-147031811 | GO:0005515\|GO:0005737\|NM_002024 GO:0042788\|GO:0006810\| GO:0005730\|GO:0005654\| GO:0051028\|GO:0003729 | | THC2661856 | Hs.103183 |
| A_33_P3358228 | VWA2 | Homo sapiens von Willebrand factor A domain containing 2 (VWA2), mRNA [NM_198496] | NM_198496 | ENST00000298715 | 340706 | von Willebrand factor A domain containing 2 | chr10:1160496 14-116049673 | GO:0005576\|GO:0042802 | NM_198496 | THC2480326 | Hs.19741 |
| A_U_P3263359 | DGKA | diacylglycerol kinase, alpha 80 kDa [Source: HGNC Symbol; Acc: 2849] [ENST00000546995] | BC08292 | ENST00000546995 | 1606 | diacylglycerol kinase, alpha 80 kDa | chr12:5632204 1-56322100 | | | THC2510364 | Hs.524488 |
| A_24_P148907 | MAB21L2 | Homo sapiens mab-21-like 2 (C. elegans) (MAB21L2), mRNA [NM_006439] | NM_006439 | ENST00000317605 | 10586 | mab-21-like 2 (C. elegans) | chr4:15150499 1-151505050 | GO:0010172\|GO:0008284\|NM_006439 GO:0043010\|GO:0007275\| GO:0005634\|GO:0007399 | | THC2472779 | Hs.584852 |
| A_33_P3401711 | USH1G | Homo sapiens Usher syndrome 1G (autosomal recessive) (USH1G), mRNA [NM_173477] | NM_173477 | ENST00000319642 | 124590 | Usher syndrome 1G (autosomal recessive) | chr17:7291223 5-72912176 | GO:0005515\|GO:0005737\|NM_173477 GO:0060113\|GO:0042472\| GO:0007605\|GO:0050957\| GO:0045494\|GO:0015629\| GO:0050896\|GO:0042803 | | | Hs.376688 |
| A_33_P3401169 | | T cell receptor beta variable 21/OR9-2 (non-functional) [Source: HGNC Symbol; Acc: 12199] [ENST00000331828] | | ENST00000331828 | | | chr9:33629473-33629532 | | | THC2565247 | |
| A_33_P3260969 | PRAP1 | Homo sapiens proline-rich acidic protein 1 (PRAP1), transcript variant 1, mRNA [NM_145202] | NM_145202 | ENST00000463201 | 118471 | proline-rich acidic protein 1 | chr10:1351659 87-135166046 | GO:0005576 | NM_145202 | NP587643 | Hs.15951 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P202859 | H1FNT | Homo sapiens H1 histone family, member N, testis-specific (H1FNT), mRNA [NM_181788] | NM_181788 | ENST00000335017 | 341567 | H1 histone family, member N, testis specific | chr12:48723983-48724042 | GO:0000790\|GO:0000166\|GO:0030261\|GO:0005694\|GO:0007290\|GO:0007275\|GO:0005634\|GO:0007283\|GO:0035092\|GO:0005524\|GO:0003677\|GO:0030154 | NM_181788 | THC2475276 | Hs.155833 |
| A_33_P3260373 | ISY1-RAB43 | Homo sapiens ISY1-RAB43 readthrough (ISY1-RAB43), mRNA [NM_001204890] | NM_001204890 | ENST00000315150 | 100534599 | ISY1-RAB43 readthrough | chr3:128810123-128810064 | GO:0005886\|GO:0000166\|NM_001204890\|GO:0007264\|GO:0015031\|GO:0005525 | NM_001204890 | THC2604277 | Hs.512661 |
| A_33_P3378291 | IL17REL | Homo sapiens interleukin 17 receptor E-like (IL17REL), mRNA [NM_001001694] | NM_001001694 | ENST00000341280 | 400935 | interleukin 17 receptor E-like | chr22:50433061-50433002 | | NM_001001694 | THC2486439 | Hs.526712 |
| A_23_P50646 | LOC390940 | Homo sapiens hypothetical protein LOC390940 (LOC390940), transcript variant 1, mRNA [NM_001193621] | NM_001193621 | | 390940 | hypothetical protein LOC390940 | chr19:4408613-44086198 | GO:0004859\|GO:0005576 | NM_001193621 | THC2515604 | Hs.22049 |
| A_33_P3235282 | LOC401561 | PREDICTED: Homo sapiens FP7915 protein (LOC401561), miscRNA [XR_110095] | XR_110095 | | 401561 | FP7915 protein | chr9:139511203-139511144 | | XR_110095 | NP924771 | Hs.609301 |
| A_23_P387552 | RARG | Homo sapiens retinoic acid receptor, gamma (RARG), transcript variant 1, mRNA [NM_000966] | NM_000966 | ENST00000425354 | 5916 | retinoic acid receptor, gamma | chr12:53604624-53604565 | GO:0005515\|GO:0005667\|GO:0008361\|GO:0006355\|GO:0043065\|GO:0003700\|GO:0008285\|GO:0003707\|GO:0005634\|GO:0000122\|GO:0003708\|GO:0046872\|GO:0048384\|GO:0043565\|GO:0046965\|GO:0045944\|GO:0035116\|GO:0008270\|GO:0016021\|GO:0032526\|GO:0060070\|GO:0048048 | NM_000966 | THC2465083 | Hs.1497 |
| A_23_P168229 | TXNDC5 | Homo sapiens thioredoxin domain containing 5 (endoplasmic reticulum) (TXNDC5), transcript variant 1, mRNA [NM_030810] | NM_030810 | ENST00000439343 | 81567 | thioredoxin domain containing 5 (endoplasmic reticulum) | chr6:7882079-7882020 | GO:0005783\|GO:0006892\|GO:0005788\|GO:0045454\|GO:0006916\|GO:0016853\|GO:0016044 | NM_030810 | THC2483613 | Hs.150837 |
| A_33_P3382887 | | | | | | | chr18:05846204-67-058462008 | | | | |
| A_23_P377882 | KCNH2 | Homo sapiens potassium voltage-gated channel, subfamily H (eag related), member 2 | NM_172056 | ENST00000430723 | 3757 | potassium voltage-gated channel, subfamily H | chr7:150647043-150646984 | GO:0005251\|GO:0005242\|GO:0006355\|GO:0005244\|GO:0005886\|GO:0008015\|GO:0008016\|GO:0030955 | NM_172056 | THC2730451 | Hs.647099 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (KCNH2), transcript variant 2, mRNA [NM_172056] | | | | (eag-related), member 2 | | GO:0005635|GO:0055085| GO:0000155|GO:0000160| GO:0005737|GO:0006936| GO:0008076|GO:0042391| GO:0006813|GO:0006811 | | |
| A_33_P3383856 | TREX2 | *Homo sapiens* three prime repair exonuclease 2 (TREX2), mRNA [NM_080701] | NM_080701 | ENST00000330912 | 11219 | three prime repair exonuclease 2 | chrX:15271055 4-152710495 | GO:0005622|GO:0008296|NM_080701 GO:0004527|GO:0006281| GO:0000287|GO:0016787| GO:0008853|GO:0005634| GO:0003676|GO:0006974 | NP1214668 | Hs.644635 |
| A_23_P148015 | AXIN2 | *Homo sapiens* axin 2 (AXIN2), mRNA [NM_004655] | NM_004655 | ENST00000307078 | 8313 | axin 2 | chr17:6352544 8-63525389 | GO:0008219|GO:0008285|NM_004655 GO:0008013|GO:0019901| GO:0001756|GO:0030178| GO:0005634|GO:0007275| GO:0005622|GO:0007165| GO:0005737|GO:0045668| GO:0001957|GO:0004871 | THC2461858 | Hs.156527 |
| A_33_P3374258 | NHLH2 | nescient helix loop helix 2 [Source: HGNC Symbol; Acc: 7818] [ENST00000369506] | AK056621 | ENST00000369506 | 4808 | nescient helix loop helix 2 | chr1:11638108 0-116381021 | GO:0007617|GO:0030528| GO:0042698|GO:0007275| GO:0005634|GO:0007417| GO:0003677|GO:0045449| GO:0030154 | THC2601021 | |
| A_24_P341019 | C20orf30 | *Homo sapiens* chromosome 20 open reading frame 30 (C20orf30), transcript variant 2, mRNA [NM_001009924] | NM_001009924 | ENST00000379276 | 29058 | chromosome 20 open reading frame 30 | chr20:5089998-5086918 | GO:0016020|GO:0016021 NM_001009924 | THC2529296 | Hs.472024 |
| A_23_P154849 | OLIG1 | *Homo sapiens* oligodendrocyte transcription factor 1 (OLIG1), mRNA [NM_138983] | NM_138983 | ENST00000426947 | 116448 | oligodendrocyte transcription factor 1 | chr21:3444453 7-34444596 | GO:0005515|GO:0030528|NM_138983 GO:0007275|GO:0005634| GO:0048663|GO:0003677| GO:0045449 | THC2464968 | Hs.56663 |
| A_23_P207842 | RARA | *Homo sapiens* retinoic acid receptor, alpha (RARA), transcript variant 2, mRNA [NM_001024809] | NM_001024809 | ENST00000394089 | 5914 | retinoic acid receptor, alpha | chr17:3851317 4-38513233 | GO:0005515|GO:0032753|NM_001024809 GO:0006355|GO:0032754| GO:0003700|GO:0009986| GO:0003713|GO:0003707| GO:0032720|GO:0005634| GO:0046872|GO:0048384| GO:0043565|GO:0007165| GO:0001972|GO:0008270| GO:0032526|GO:0045630| GO:0032689|GO:0032355| GO:0030520 | THC2473007 | Hs.654583 |
| A_33_P3399468 | | *Homo sapiens* cDNA, FLJ18157. [AK311115] | AK311115 | | | | chr16:9023543 5-90235494 | | | | Hs.661255 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P4039 | FCRLA | Homo sapiens Fc receptor-like A (FCRLA), transcript variant 2, mRNA [NM_032738] | NM_032738 | ENST00000236938 | 84824 | Fc receptor-like A | chr1:161683792-161683851 | GO:0005737\|GO:0005576\|NM_032738\|GO:0030154 | | THC2463353 | Hs.266331 |
| A_33_P3301025 | CPOX | Homo sapiens coproporphyrinogen oxidase (CPOX), mRNA [NM_000097] | NM_000097 | ENST00000264193 | 1371 | coproporphyrinogen oxidase | chr3:98298372-98298313 | GO:0005739\|GO:0005758\|NM_000097\|GO:0046685\|GO:0005737\|GO:0042493\|GO:0016491\|GO:0046689\|GO:0004109\|GO:0055114\|GO:0042802\|GO:0006783 | | THC2463467 | Hs.476982 |
| A_33_P3363637 | BLNK | Homo sapiens B cell linker (BLNK), transcript variant 1, mRNA [NM_013314] | NM_013314 | ENST00000393898 | 29760 | B-cell linker | chr10:97951697-97951638 | GO:0005622\|GO:0005515\|NM_013314\|GO:0007242\|GO:0005737\|GO:0006954\|GO:0005886\|GO:0006959\|GO:0005070\|GO:0030183\|GO:0005068 | | THC2479443 | Hs.665244 |
| A_33_P3214072 | LOC729175 | PREDICTED: Homo sapiens hypothetical protein LOC729175 (LOC729175), mRNA [XM_001129558] | XM_001129558 | | 729175 | hypothetical protein LOC729175 | chr4:24474070-24474011 | | XM_001129558 | | Hs.627177 |
| A_24_P22079 | FOXO1 | Homo sapiens forkhead box O1 (FOXO1), mRNA [NM_002015] | NM_002015 | ENST00000379561 | 2308 | forkhead box O1 | chr13:41130768-41130709 | GO:0005515\|GO:0008286\|NM_002015\|GO:0006355\|GO:0001568\|GO:0003700\|GO:0016563\|GO:0005634\|GO:0006916\|GO:0005829\|GO:0043565\|GO:0005737\|GO:0045941\|GO:0045944\|GO:0042127\|GO:0005654 | | THC2606078 | Hs.370666 |
| A_33_P3245674 | ZNF329 | zinc finger protein 329 [Source: HGNC Symbol; Acc: 14209] [ENST00000500161] | AK090893 | ENST00000500161 | 79673 | zinc finger protein 329 | chr19:58666162-58666103 | | | THC2550377 | Hs.458377 |
| A_33_P3562537 | RET | Homo sapiens ret proto-oncogene (RET), transcript variant 4, mRNA [NM_020630] | NM_020630 | ENST00000340058 | 5979 | ret proto-oncogene | chr10:43622213-43622272 | GO:0005515\|GO:0001657\|NM_020630\|GO:0042551\|GO:0001755\|GO:0005509\|GO:0001838\|GO:0005524\|GO:0048484\|GO:0007399\|GO:0007165\|GO:0016020\|GO:0000166\|GO:0000165\|GO:0007497\|GO:0004872\|GO:0006468\|GO:0016021\|GO:0004714\|GO:0007169\|GO:0007156\|GO:0016740 | | NP838836 | Hs.350321 |
| A_33_P3334398 | CA6 | Homo sapiens carbonic anhydrase VI (CA6), mRNA [NM_001215] | NM_001215 | ENST00000475703 | 765 | carbonic anhydrase VI | chr1:9030977-9031036 | GO:0008270\|GO:0005576\|NM_001215\|GO:0004089\|GO:0006730\|GO:0046872\|GO:0016829 | | NP1400569 | Hs.100322 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P81441 | C5orf20 | Homo sapiens chromosome 5 open reading frame 20 (C5orf20), mRNA [NM_130848] | NM_130848 | ENST00000537858 | 140947 | chromosome 5 open reading frame 20 | chr5:13478003 3-134779974 | GO:0005634 | NM_130848 | THC2480949 | Hs.152477 |
| A_24_P227450 | ACAD10 | Homo sapiens acyl-CoA dehydrogenase family, member 10 (ACAD10), transcript variant 2, mRNA [NM_025247] | NM_025247 | ENST00000547491 | 80724 | acyl-CoA dehydrogenase family, member 10 | chr12:1121934 89-112193548 | GO:0016787\|GO:0050660\|GO:0003995\|GO:0055114 | NM_025247 | NP1163233 | Hs.331141 |
| A_32_P6180 | | chromosome 6 open reading frame 220 [Source: HGNC Symbol; Acc: 21553] [ENST00000369123] | BF223582 | ENST00000369123 | | | chr6:10538838 7-105388328 | | | | Hs.649249 |
| A_33_P3268954 | FBLL1 | Homo sapiens fibrillarin-like 1 (FBLL1), non-coding RNA [NR_024356] | NR_024356 | | 345630 | fibrillarin-like 1 | chr5:16795739 5-167957454 | GO:0030529\|GO:0006364\|GO:0003723\|GO:0008168\|GO:0005730\|GO:0005634\|GO:0016740\|GO:0008033 | NR_024356 | THC2623630 | Hs.554581 |
| A_33_P3225378 | OR10G3 | Homo sapiens olfactory receptor, family 10, subfamily G, member 3 (OR10G3), mRNA [NM_001005465] | NM_001005465 | ENST00000303532 | 26533 | olfactory receptor, family 10, subfamily G, member 3 | chr14:2203799 3-22037934 | GO:0007608\|GO:0007165\|GO:0004984\|GO:0007186\|GO:0005886\|GO:0004872\|GO:0016021\|GO:0050896 | NM_001005465 | THC2612456 | Hs.683873 |
| A_33_P3417123 | LOC652119 | PREDICTED: Homo sapiens double homeobox protein 4-like (LOC652119), mRNA [XM_001720798] | XM_001720798 | | 652119 | double homeobox protein 4-like | chrUn_gl00023 5:000001907-0000001848 | | XM_001720798 | | |
| A_23_P211326 | CECR2 | Homo sapiens cat eye syndrome chromosome region, candidate 2 (CECR2), mRNA [NM_031413] | NM_031413 | ENST00000355219 | 27443 | cat eye syndrome chromosome region, candidate 2 | chr22:1803338 7-18033446 | GO:0000910\|GO:0006309\|GO:0007010\|GO:0006915\|GO:0005634\|GO:0016192\|GO:0016568 | NM_031413 | NP500153 | Hs.658723 |
| A_24_P170726 | LOC645427 | Homo sapiens cDNA FLJ37088 fis, clone BRACE2017124. [AK094407] | AK094407 | | 645427 | hypothetical LOC645427 | chr17:2131732 7-21317386 | | | THC2487445 | Hs.683873 |
| A_33_P3382111 | | | | | | | | | | | |
| A_23_P20181 | PTPN22 | Homo sapiens protein tyrosine phosphatase, non-receptor type 22 (lymphoid) (PTPN22), transcript variant 2, mRNA [NM_012411] | NM_012411 | ENST00000354605 | 26191 | protein tyrosine phosphatase, non-receptor type 22 (lymphoid) | chr1:11437699 0-114376931 | GO:0005515\|GO:0050852\|GO:0007165\|GO:0005737\|GO:0006470\|GO:0030217\|GO:0016787\|GO:0004725 | NM_012411 | NP079320 | Hs.535276 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P218126 | | immunoglobulin heavy constant gamma 1 (G1m marker) [Source: HGNC Symbol; Acc: 5525] [ENST00000390549] | BC024289 | ENST00000390549 | | | chr14:106208310-106208251 | | | NP852618 | Hs.510635 |
| A_23_P150053 | ACTA2 | Homo sapiens actin, alpha 2, smooth muscle, aorta (ACTA2), transcript variant 2, mRNA [NM_001613] | NM_001613 | ENST00000458208 | 59 | actin, alpha 2, smooth muscle, aorta | chr10:90697958-90697899 | GO:0005515\|GO:0005737\|NM_001613 GO:0000166\|GO:0008217\| GO:0015629\|GO:0005524\| GO:0030485\|GO:0014829 | | THC2573035 | Hs.500483 |
| A_23_P38190 | ORMDL3 | Homo sapiens ORM1-like 3 (S. cerevisiae) (ORMDL3), mRNA [NM_139280] | NM_139280 | HNST00000394169 | 94103 | ORM1-like 3 (S. cerevisiae) | chr17:38079397-38078912 | GO:0016020\|GO:0005783\|NM_139280 GO:0016021 | | NP842990 | Hs.514151 |
| A_33_P3789056 | C1orf200 | Homo sapiens chromosome 1 open reading frame 200 (C1orf200), non-coding RNA [NR_027045] | NR_027045 | ENST00000377320 | 644997 | chromosome 1 open reading frame 200 | chr1:9712762-9712703 | | NR_027045 | THC2482521 | Hs.568595 |
| A_33_P3271925 | ARFGEF2 | Homo sapiens ADP-ribosylation factor guanine nucleotide exchange factor 2 (brefeldin A-inhibited) (ARFGEF2), mRNA [NM_006420] | NM_006420 | ENST00000371917 | 10564 | ADP-ribosylation factor guanine nucleotide exchange factor 2 (brefeldin A-inhibited) | chr20:47652817-47652876 | GO:0005802\|GO:0007242\|NM_006420 GO:0050811\|GO:0006887\| GO:0005829\|GO:0005622\| GO:0005086\|GO:0005737\| GO:0000139\|GO:0016020\| GO:0005488\|GO:0032012\| GO:0017022 | | THC2533999 | Hs.62578 |
| A_23_P1602 | CDC42EP2 | Homo sapiens CDC42 effector protein (Rho GTPase binding) 2 (CDC42EP2), mRNA [NM_006779] | NM_006779 | ENST00000544348 | 10435 | CDC42 effector protein (Rho GTPase binding) 2 | chr11:65089746-65089805 | GO:0005515\|GO:0005886\|NM_006779 GO:0008360\|GO:0005100\| GO:0005737\|GO:0031334\| GO:0030838\|GO:0001515\| GO:0031274\|GO:0007015\| GO:0017049\|GO:0005856\| GO:0019898 | | THC2461993 | Hs.343380 |
| A_33_P3289491 | LOC100129069 | Homo sapiens cDNA FLJ45433 fis, clone BRHIP3040878. [AK127359] | AK127359 | | 100129069 | hypothetical protein LOC100129069 | chr11:124630128-124630069 | | | THC2482533 | Hs.675422 |
| A_33_P3367701 | TMEM164 | Homo sapiens transmembrane protein 164 (TMEM164), transcript variant 2, mRNA [NM_032227] | NM_032227 | ENST00000288381 | 84187 | transmembrane protein 164 | chrX:109416711-109416770 | GO:0016020\|GO:0016021 NM_032227 | | THC2483947 | Hs.496572 |
| A_33_P3377294 | TCF7L2 | Homo sapiens transcription factor 7-like 2 (T-cell specific, HMG-box) [Source: | | ENST00000349937 | 6934 | transcription factor 7-like 2 (T-cell specific, | chr10:114905803-114905862 | | | THC2504286 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | HGNC Symbol; Acc: 11641] [ENST00000349937] | | | | HMG-box) | | | | | |
| A_32_P353072 | TMEM106B | Homo sapiens transmembrane protein 106B (TMEM106B), transcript variant 1, mRNA [NM_018374] | NM_018374 | ENST00000396667 | 54664 | transmembrane protein 106B | chr7:12276527-12276586 | GO:0008150\|GO:0003674\|NM_018374 GO:0016020\|GO:0016021\| GO:0005575 | | THC2714339 | Hs.396358 |
| A_33_P3275574 | HLA-A | Homo sapiens major histocompatibility complex, class I, A (HLA-A), transcript variant 2, mRNA [NM_001242758] | NM_001242758 | ENST00000355767 | 3105 | major histocompatibility complex, class I, A | chr6:29910343-29910402 | GO:0005515\|GO:0002474\|NM_001242758 GO:0006955\|GO:0016020\| GO:0000139\|GO:0019882\| GO:0005887\|GO:0044419\| GO:0042612\|GO:0031901\| GO:0016021\|GO:0032393 | | NP1275975 | Hs.181244 |
| A_33_P3250857 | | axin interactor, dorsalization associated [Source: HGNC Symbol; Acc: 25761] [ENST00000474863] | BC043142 | ENST00000474863 | | | chr1:22288599 7-222885938 | GO:0043496\|GO:0005515 GO:0046329\|GO:0007275\| GO:0009953\|GO:0005575 | | THC2507656 | Hs.534965 |
| A_33_P3399598 | ABCD4 | Homo sapiens cDNA FLJ43119 fis, clone CTONG3003179, [AK125109] | AK125109 | | 5826 | ATP-binding cassette, sub-family D (ALD), member 4 | chr14:7476628 5-74766344 | | | THC2523786 | Hs.94395 |
| A_33_P3381292 | | | | | | | chr11:0699243 28-06992438 7 | | | | |
| A_32_P385587 | ALAS2 | Homo sapiens aminolevulinate, delta-, synthase 2 (ALAS2), nuclear gene encoding mitochondrial protein, transcript variant 1, mRNA [NM_000032] | NM_000032 | ENST00000330807 | 212 | amino levulinate, delta-, synthase 2 | chrX:55035564-55035505 | GO:0042541\|GO:0005515\|NM_000032 GO:0050662\|GO:0001666\| GO:0009058\|GO:0016769\| GO:0005743\|GO:0033014\| GO:0006783\|GO:0005739\| GO:0006879\|GO:0006778\| GO:0005759\|GO:0030218\| GO:0030170\|GO:0016594\| GO:0032364\|GO:0003870\| GO:0008415 | | THC2470945 | Hs.522666 |
| A_33_P3322553 | MED25 | Homo sapiens mediator complex subunit 25 (MED25), mRNA [NM_030973] | NM_030973 | ENST00000377077 | 81857 | mediator complex subunit 25 | chr19:5033830 3-50338362 | GO:0005634\|GO:0045449 NM_030973 | | NP1193880 | Hs.656639 |
| A_32_P49668 | LOC100510697 | PREDICTED: Homo sapiens putative POM 121-like protein 1-like (LOC100510697), mRNA [XM_003118465] | XM_003118465 | | 100510697 | putative POM121-like protein 1-like | chr5:69826390-69826449 | | XM_003118465 | | Hs.634013 |
| A_33_P3321070 | WNT4 | Homo sapiens wingless-type MMTV integration site family, member 4 [Source: | | ENST00000374655 | 54361 | wingless-type MMTV integration | chr1:22453872-22453813 | | | THC2680884 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | HGNC Symbol; Acc: 12783 [ENST00000374655] | | | | site family, member 4 | | | | | |
| A_33_P3342653 | ADAM33 | Homo sapiens ADAM metallopeptidase domain 33 (ADAM33), transcript variant 2, mRNA [NM_153202] | NM_153202 | ENST00000358035 | 80332 | ADAM metallopeptidase domain 33 | chr20:3637774-3657715 | GO:0016020|GO:0006508|NM_153202|GO:0008270|GO:0008233|GO:0016021|GO:0004222|GO:0046872 | | NP805663 | Hs.173716 |
| A_33_P3322103 A_33_P3375398 | TBL3 | Homo sapiens transducin (beta)-like 3 (TBL3), mRNA [NM_006453] | NM_006453 | ENST00000332704 | 10607 | transducin (beta)-like 3 | chr16:2028684-2028743 | GO:0006364|GO:0032040|NM_006453 GO:0007199|GO:0005730|GO:0005634|GO:0005057 | | THC2468480 | Hs.513267 |
| A_33_P3358799 | SLC35C2 | Homo sapiens solute carrier family 35, member C2 (SLC35C2), transcript variant 1, mRNA [NM_173179] | NM_173179 | ENST00000372223 | 51006 | solute carrier family 35, member C2 | chr20:4497843 7-44978378 | GO:0016020|GO:0006810|NM_173179 GO:0016021 | | THC2481513 | Hs.593344 |
| A_33_P3364637 | | PREDICTED: Homo sapiens hypothetical LOC100132272 (LOC100132272), miscRNA [XR_109540] | XR_109540 | ENST00000378108 | | | chr19:4274735 7-42747416 | | XR_109540 | THC2484875 | Hs.711405 |
| A_24_P95723 | KIAA0125 | Homo sapiens KIAA0125 (KIAA0125), non-coding RNA [NR_026800] | NR_026800 | | 9834 | KIAA0125 | chr14:1063983 26-106398385 | | NR_026800 | THC2657912 | Hs.649259 |
| A_23_P27571 | MCOLN1 | Homo sapiens mucolipin 1 (MCOLN1), mRNA [NM_020533] | NM_020533 | ENST00000394321 | 57192 | mucolipin 1 | chr19:7593764 7593823 | GO:0005261|GO:0005886|NM_020533 GO:0005887|GO:0005509| GO:0006816|GO:0055085| GO:0005764|GO:0006812| GO:0005768 | | THC2467038 | Hs.631858 |
| A_23_P405282 | MGC45922 | Homo sapiens hypothetical LOC284365 (MGC45922), non-coding RNA [NR_038359] | NR_038359 | ENST00000326989 | 284365 | hypothetical LOC284365 | chr19:5132167 4-51321733 | | NR_038359 | THC2485442 | Hs.161397 |
| A_33_P3313532 | ANKRD20A1 | Homo sapiens ankyrin repeat domain 20 family, member A1 (ANKRD20A1), mRNA [NM_032250] | NM_032250 | ENST00000485255 | 84210 | ankyrin repeat domain 20 family, member A1 | chr9:67927016-67927074 | GO:0005886 | NM_032250 | | Hs.632671 |
| A_23_P500130 | KANK1 | Homo sapiens KN motif and ankyrin repeat domains 1 (KANK1), transcript | NM_153186 | ENST00000382289 | 23189 | KN motif and ankyrin repeat domains 1 | chr9:746006-746065 | GO:0005737 | NM_153186 | NP1165352 | Hs.306764 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3360886 | | variant 2, mRNA [NM_153186] GRP33_ARTSA (P13230) Glycine-rich protein GRP33, partial (8%) [THC2642603] | | | | | chr13:0443602 75-044360216 | | | THC2642603 | |
| A_33_P3270593 | | | | | | | chr1:02852779 2-028527851 | | | | |
| A_33_P3228732 | LOC100131551 | Homo sapiens hypothetical LOC100131551 (LOC100131551), non-coding RNA [NR_024480] | NR_024480 | ENST00000397644 | 100131551 | hypothetical LOC100131551 | chr3:19402362 1-194023562 | | NR_024480 | THC2519857 | Hs.128066 |
| A_23_P139600 | RASAL1 | Homo sapiens RAS protein activator like 1 (GAP1 like) (RASAL1), transcript variant 2, mRNA [NM_004658] | NM_004658 | ENST00000446861 | 8437 | RAS protein activator like 1 (GAP1 like) | chr12:1135376 35-113537576 | GO:0005622 GO:0005099 GO:0051056 GO:0007242 GO:0005543 GO:0008270 GO:0046872 | NM_004658 | THC2483187 | Hs.528693 |
| A_23_P14627 | PCDHB13 | Homo sapiens protocadherin beta 13 (PCDHB13), mRNA [NM_018933] | NM_018933 | ENST00000419217 | 56123 | protocadherin beta 13 | chr5:14059597 8-140596037 | GO:0016339 GO:0005515 GO:0005886 GO:0005509 GO:0007268 GO:0016021 GO:0007155 GO:0007416 GO:0007156 | NM_018933 | NP285722 | Hs.283803 |
| A_33_P3390546 | | PREDICTED:thetical), Homo sapiens hypoprotein LOC100506590 (LOC100506590 mRNA [XM_003118499] | XM_003118499 | | | | chr1:20147485 2-201474793 | | XM_003118499 | NP852258 | Hs.689295 |
| A_33_P3382924 | SPARC | Homo sapiens secreted protein, acidic, cysteine-rich (osteonectin) (SPARC), mRNA [NM_003118] | NM_003118 | ENST00000231061 | 6678 | secreted protein, acidic, cysteine-rich (osteonectin) | chr5:15104109 9-151041040 | GO:0007165 GO:0001503 GO:0005507 GO:0042127 GO:0005518 GO:0005509 GO:0050840 GO:0031093 GO:0005576 GO:0005604 | NM_003118 | THC2465583 | Hs.111779 |
| A_33_P3323136 | ENKUR | Homo sapiens enkurin, TRPC channel interacting protein (ENKUR), mRNA [NM_145010] | NM_145010 | ENST00000376363 | 219670 | enkurin, TRPC channel interacting protein | chr10:2530486 5-25304806 | GO:0019861 GO:0005929 GO:0005516 GO:0017124 | NM_145010 | NP841402 | Hs.534486 |
| A_33_P3349495 | TTTY16 | Homo sapiens testis-specific transcript, Y-linked 16 (nonprotein coding) (TTTY16), non-coding RNA [NR_001552] | NR_001552 | ENST00000437686 | 252948 | testis-specific transcript, Y-linked 16 (nonprotein coding) | chrY:7569288-7569229 | | NR_001552 | NP1161733 | Hs.522848 |
| A_23_P215931 | LEPROTL1 | Homo sapiens leptin receptor overlapping transcript-like 1 | NM_015344 | ENST00000321250 | 23484 | leptin receptor overlapping transcript- | chr8:29965452-29965511 | GO:0016020 GO:0016021 | NM_015344 | THC2469608 | Hs.146585 |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3382648 | RBMY1B | Homo sapiens RNA binding motif protein, Y-linked, family 1, member B (RBMY1B), mRNA [NM_001006121] | NM_001006121 | ENST0000382658 | 378948 | RNA binding motif protein, Y-linked, family 1, member B | chrY:23681093-23681152 | GO:0008380\|GO:0006397\|GO:0005515\|GO:0000166\|GO:0003723\|GO:0005634\|GO:0007283\|GO:0008584 | NM_001006121 | THC2487576 | Hs.725744 |
| A_33_P3291891 | LOC100130825 | PREDICTED: Homo sapiens hypothetical protein LOC100130825 (LOC100130825), mRNA [XM_001720026] | XM_001720026 | | 100130825 | hypothetical protein LOC100130825 | chr12:1321483 78-132148319 | | XM_001720026 | | Hs.538511 |
| A_33_P104413 | DUX4 | Homo sapiens double homeobox 4 (DUX4), mRNA[NM_033178] | NM_033178 | ENST0000507734 | 22947 | double homeobox 4 | chrUn_gl00022 8:77218-77276 | GO:0043565\|GO:0006355\|GO:0003700\|GO:0005634 | NM_033178 | THC2493180 | Hs.553518 |
| A_33_P3268313 | PGAM2 | Homo sapiens phosphoglycerate mutase 2 (muscle) (PGAM2), mRNA [NM_000290] | NM_000290 | ENST0000297283 | 5224 | phosphoglycerate mutase 2 (muscle) | chr7:44102471-44102412 | GO:0048037\|GO:0004082\|GO:0004083\|GO:0046538\|GO:0006094\|GO:0006941\|GO:0005625\|GO:0005634\|GO:0005575\|GO:0007283\|GO:0006096\|GO:0005829\|GO:0010035\|GO:0016787\|GO:0008152\|GO:0016853\|GO:0046689 | NM_000290 | THC2472046 | Hs.632642 |
| A_23_P67367 | DHDH | Homo sapiens dihydrodiol dehydrogenase (dimeric) (DHDH), mRNA [NM_014475] | NM_014475 | ENST0000520557 | 27294 | dihydrodiol dehydrogenase (dimeric) | chr19:4944811 2-49448171 | GO:0005975\|GO:0005488\|GO:0047837\|GO:0047115\|GO:0016491\|GO:0008746\|GO:0009055\|GO:0055114 | NM_014475 | THC2478626 | Hs.631555 |
| A_23_P150428 | OR6M1 | Homo sapiens olfactory receptor, family 6, subfamily M, member 1 (OR6M1), mRNA [NM_001005325] | NM_001005325 | ENST0000309154 | 390261 | olfactory receptor, family 6, subfamily M, member 1 | chr11:1236765 31-123676472 | GO:0007608\|GO:0007165\|GO:0004984\|GO:0007186\|GO:0005886\|GO:0004872\|GO:0016021\|GO:0050896 | NM_001005325 | THC2612208 | Hs.557924 |
| A_33_P3375576 | MAP7 | Homo sapiens microtubule-associated protein 7 (MAP7), transcript variant 4, mRNA [NM_003980] | NM_003980 | ENST0000345567 | 9053 | microtubule-associated protein 7 | chr6:13666709 5-136667036 | GO:0016323\|GO:0048471\|GO:0005737\|GO:0007163\|GO:0005886\|GO:0005198\|GO:0005875\|GO:0005874\|GO:0000226 | NM_003980 | NP208771 | Hs.486548 |
| A_23_P25626 | C13orf34 | Homo sapiens chromosome 13 open reading frame 34 (C13orf34), mRNA [NM_024808] | NM_024808 | ENST0000377815 | 79866 | chromosome 13 open reading frame 34 | chr13:7332935 6-73329415 | GO:0007067\|GO:0007049\|GO:0051301 | NM_024808 | THC2464290 | Hs.643464 |
| A_24_P382579 | OXT | Homo sapiens oxytocin, prepropeptide (OXT), mRNA [NM_000915] | NM_000915 | ENST0000217386 | 5020 | oxytocin, prepropeptide | chr20:3053096-3053155 | GO:0005515\|GO:0014070\|GO:0060406\|GO:0042220\|GO:0001696\|GO:0005615 | NM_000915 | THC2480057 | Hs.113216 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3348884 | CCDC141 | Homo sapiens coiled-coil domain containing 141 (CCDC141), mRNA [NM_173648] | NM_173648 | ENST00000480419 | 285025 | coiled-coil domain containing 141 | chr2:179698959-179698900 | | NM_173648 | THC2485672 | Hs.324341 |
| A_33_P3214042 | | | | | | | chr11:064645811-064645940 | | | THC2598321 | |
| A_33_P3263512 | | | | | | | chr12:122206835-122206776 | | | | |
| A_33_P3347452 | RPS6KA2 | Homo sapiens ribosomal protein S6 kinase, 90 kDa, polypeptide 2 (RPS6KA2), transcript variant 1, mRNA [NM_021135] | NM_021135 | ENST00000510118 | 6196 | ribosomal protein S6 kinase, 90 kDa, polypeptide 2 | chr6:166822961-166822902 | GO:0000287|GO:0000166|GO:0004674|GO:0006468|GO:0005654|GO:0005634|GO:0005524|GO:0016740|GO:0007243 | NM_021135 | THC2635208 | Hs.655277 |
| A_23_P3963 | CDR2L | Homo sapiens cerebellar degeneration-related protein 2-like (CDR2L), mRNA [NM_014603] | NM_014603 | ENST00000337231 | 30850 | cerebellar degeneration-related protein 2-like | chr17:73001557-73001616 | | NM_014603 | THC2784175 | Hs.78358 |
| A_33_PWW18 | TUBBP5 | Homo sapiens tubulin, beta pseudogene 5 (TUBBP5), non- | NR_027156 | | 643224 | tubulin, beta pseudogene 5 | chr9:141071820-141071879 | GO:0051258|GO:0000166|NR_027156|GO:0005198|GO:0005874|GO:0003924|GO:0005525 | | THC2493332 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P50972 | GOLGA6L6 | coding RNA [NR_027156] Homo sapiens golgin A6 family-like 6 (GOLGA6L6), mRNA [NM_001145004] | NM_001145004 | ENST00000454724 | 727832 | golgin A6 family-like 6 | chr15:20738771-20738712 | GO:0007018 GO:0016020 GO:0016021 | NM_001145004 | THC2481492 | Hs.125917 |
| A_33_P3274009 | LOC100132966 | Homo sapiens cDNA FLJ42565 fis, clone BRACE3007472. [AK124556] | AK124556 | | 100132966 | hypothetical LOC100132966 | chr1:143914523-143914582 | | | THC2585044 | Hs.730332 |
| A_33_P3222932 | SHISA8 | Homo sapiens shisa homolog 8 (Xenopus laevis) (SHISA8), mRNA [NM_001207020] | NM_001207020 | | 440829 | shisa homolog 8 (Xenopus laevis) | chr22:42305884-42305825 | | NM_001207020 | THC2683228 | Hs.526704 |
| A_23_P85703 | SOX13 | Homo sapiens SRY (sex determining region Y)-box 13 (SOX13), mRNA [NM_005686] | NM_005686 | ENST00000367204 | 9580 | SRY (sex determining region Y)-box 13 | chr1:204096551-20406610 | GO:0043565 GO:0003700 GO:0005634 GO:0009653 GO:0045449 | NM_005686 | THC2462481 | Hs.201671 |
| A_33_P3303469 | | | | | | | chr16:08600767 78-086007737 | | | THC2646038 | Hs.106070 |
| A_23_P428129 | CDKN1C | Homo sapiens cyclin-dependent kinase inhibitor 1C (p57, Kip2) (CDKN1C), transcript variant 1, mRNA [NM_000076] | NM_000076 | ENST00000313407 | 1028 | cyclin-dependent kinase inhibitor 1C (p57, Kip2) | chr11:2904962-2904903 | GO:0033673 GO:0005515 GO:0016564 GO:0042551 GO:0045735 GO:0016563 GO:0050680 GO:0005730 GO:0005634 GO:0000079 GO:0001122 GO:0042326 GO:0005737 GO:0007049 GO:0032582 GO:0004861 GO:0048460 GO:0007050 GO:0000080 GO:0030511 | NM_000076 | | |
| A_23_P434518 | LFNG | Homo sapiens LFNG O-fucosylpeptide 3-beta-N-acetylglucosaminyl-transferase (LFNG), transcript variant 2, mRNA [NM_001040168] | NM_001040168 | ENST00000359574 | 3955 | LFNG O-fucosylpeptide 3-beta-N-acetylglucosaminyl-transferase | chr7:2568740-2568799 | GO:0007389 GO:0033829 GO:0007386 GO:0005794 GO:0016757 GO:0005576 GO:0003674 GO:0001541 GO:0030173 GO:0016020 GO:0009887 GO:0016021 GO:0007143 | NM_001040168 | THC2486300 | Hs.159142 |
| A_33_P3290567 | WEE1 | Homo sapiens WEE1 homolog (S. pombe) (WEE1), transcript variant 1, mRNA [NM_003390] | NM_003390 | ENST00000299613 | 7465 | WEE1 homolog (S. pombe) | chr11:9611073-9611132 | GO:0005515 GO:0000287 GO:0005634 GO:0005524 GO:0007049 GO:0007067 GO:0001666 GO:0004674 GO:0005654 GO:0006468 GO:0004715 GO:0016740 | NM_003390 | THC2616575 | Hs.249441 |
| A_23_P431981 | HMGXB4 | Homo sapiens HMG box domain containing 4 (HMGXB4), trans- | NM_001003681 | ENST00000216106 | 10042 | HMG box domain containing 4 | chr22:3569138 4-35691443 | GO:0008333 GO:0030178 GO:0005634 GO:0003677 GO:0051301 | NM_001003681 | THC2461089 | Hs.588815 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_32_P168349 | C6orf25 | Homo sapiens chromosome 6 open reading frame 25 (C6orf25), transcript variant 7, mRNA [NM_138277] | NM_138277 | ENST00000466799 | 80739 | chromosome 6 open reading frame 25 | chr6:31694319-31694378 | GO:0005794\|GO:0005886\|NM_138277\|GO:0005783\|GO:0004872\|GO:0016021\|GO:0008201 | | THC2534407 | Hs.247879 |
| A_33_P3273732 | | cript variant 1, mRNA [NM_001003681] | | | | | chr9:13700036 8-137000309 | | | | |
| A_24_P323084 | C17orf55 | Homo sapiens chromosome 17 open reading frame 55 (C17orf55), non-coding RNA [NR_038080] | NR_038080 | ENST00000332012 | 284185 | chromosome 17 open reading frame 55 | chr17:7927669 6-79276637 | | NR_038080 | THC2478525 | Hs.631762 |
| A_23_P379630 | SLC38A10 | Homo sapiens solute carrier family 38, member 10 (SLC38A10), transcript variant 2, mRNA [NM_138570] | NM_138570 | ENST00000288439 | 124565 | solute carrier family 38, member 10 | chr17:7922512 4-79225065 | GO:0016020\|GO:0006865\|NM_138570\|GO:0016021\|GO:0031402\|GO:0006814\|GO:0006811 | | THC2464913 | Hs.352240 |
| A_24_P128727 | | Homo sapiens olfactory receptor-like (PJCG9) pseudogene mRNA, partial sequence. [AF359419] | AF359419 | | | | chr2:71282963-71283022 | | | THC2529021 | Hs.382969 |
| A_33_P3701139 | LOC440525 | 60293979OF1 NIH_MGC_12 Homo sapiens cDNA clone IMAGE: 5102926 5, mRNA sequence [BI224516] | BI224516 | | 440525 | proline rich 13 pseudogene | | | | | Hs.631599 |
| A_33_P3222761 | | T cell receptor alpha variable 9-1 [Source: HGNC Symbol; Acc: 12153] [ENST00000390431] | | ENST00000390431 | | | chr14:2227988 3-22279942 | | | | |
| A_23_P302018 | TXK | Homo sapiens TXK tyrosine kinase (TXK), mRNA [NM_003328] | NM_003328 | ENST00000514937 | 7294 | TXK tyrosine kinase | chr4:48069318-48069259 | GO:0005515\|GO:0005737\|NM_003328\|GO:0000166\|GO:0006468\|GO:0005524\|GO:0004715\|GO:0016740\|GO:0007243 | | THC2476508 | Hs.479669 |
| A_33_P3219596 | LOC254559 | Homo sapiens hypothetical LOC254559 (LOC254559), non-coding RNA [NR_015411] | NR_015411 | | 254559 | hypothetical LOC254559 | chr15:8994165 8-899441717 | | NR_015411 | THC2601829 | Hs.136313 |
| A_32_P67060 | CTDSPL2 | Homo sapiens CTD 2 (carboxy-terminal domain, RNA polymerase | NM_016396 | ENST00000396780 | 51496 | CTD (carboxy-terminal | chr15:4481936 6-44819425 | GO:0016787\|GO:0004721\|NM_016396 | | THC2532072 | Hs.497967 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3217619 | | II, polypeptide A) small phosphatase like (CTDSPL2), mRNA [NM_016396] | | ENST00000552290 | | domain, RNA polymerase II, polypeptide A) small phosphatase like 2 | chr12:76083366-76083307 | | | | |
| A_23_P69826 | DHX15 | Homo sapiens DEAH (Asp-Glu-Ala-His) box polypeptide 15 (DHX15), mRNA [NM_001358] | NM_001358 | ENST00000535946 | 1665 | DEAH (Asp-Glu-Ala-His) box polypeptide 15 | chr4:24531344-24531285 | GO:0003380\|GO:0008026\|NM_001358 GO:0006397\|GO:0003724\| GO:0016787\|GO:0000166\| GO:0005634\|GO:0003676\| GO:0005524\|GO:0005689 | | THC2549682 | Hs.696074 |
| A_24_P51683 | CDK5R2 | Homo sapiens cyclin-dependent kinase 5, regulatory subunit 2 (p39) (CDK5R2), mRNA [NM_003936] | NM_003936 | ENST00000302625 | 8941 | cyclin-dependent kinase 5, regulatory subunit 2 (p39) | chr2:219826143-219826142 | GO:0016534\|GO:0016533\|NM_003936 GO:0000079 | | THC2472201 | Hs.158460 |
| A_23_P258164 | CORT | Homo sapiens cortistatin (CORT), mRNA [NM_001302] | NM_001302 | ENST00000320498 | 1325 | cortistatin | chr1:10511688-10511747 | GO:0001664\|GO:0007268\|NM_001302 GO:0005625\|GO:0005576\| GO:0005184\|GO:0007193 | | THC2479856 | Hs.412311 |
| A_33_P3345354 | RRNAD1 | Homo sapiens ribosomal RNA adenine di-methylase domain containing 1 (RRNAD1), transcript variant 1, mRNA [NM_015997] | NM_015997 | ENST00000368216 | 51093 | ribosomal RNA adenine dimethylase domain containing 1 | chr1:156706714-156706665 | GO:0008649\|GO:0016020\|NM_015997 GO:0016021\|GO:0000154\| GO:0000179 | | THC2463346 | Hs.512597 |
| A_33_P3247858 | MPP1 | Homo sapiens membrane protein, palmitoylated 1, 55 kDa (MPP1), transcript variant 3, mRNA [NM_001166461] | NM_001166461 | ENST00000488694 | 4354 | membrane protein, palmitoylated 1, 55 kDa | chrX:154019318-154019259 | GO:0005622\|GO:0005515\|NM_001166461 GO:0007165\|GO:0016020\| GO:0005887\|GO:0032420\| GO:0005624\|GO:0004385\| GO:0030863\|GO:0042995\| GO:0019898 | | NP1465354 | Hs.496984 |
| A_32_P219148 | LOC497257 | Homo sapiens cDNA clone IMAGE: 5199989. [BC030211] | BC030211 | | 497257 | hypothetical LOC497257 | chr8:7917445-7917504 | | | THC2499286 | Hs.322761 |
| A_33_P3253239 | | | | | | | chr1:180922784-180922843 | | | THC2497493 | |
| A_24_P295999 | CD4 | Homo sapiens CD4 molecule (CD4), transcript variant 1, mRNA [NM_000616] | NM_000616 | ENST00000011653 | 920 | CD4 molecule | chr12:6929910-6929969 | GO:0042289\|GO:0005886\|NM_000616 GO:0050731\|GO:0019059\| GO:0001816\|GO:0042803\| GO:0050850\|GO:0051789\| GO:0006955\|GO:0001948\| GO:0042101\|GO:0044419\| GO:0045860\|GO:0007155\| GO:0019901\|GO:0015026\| GO:0045058\|GO:0006948\| GO:0045086\|GO:0050870\| GO:0005789\|GO:0005788 | | THC2470142 | Hs.631659 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3369245 | LOC100129826 | PREDICTED: Homo sapiens hypothetical LOC100129826 (LOC100129826), misc RNA [XR_114456] | XR_114456 | | 100129826 | hypothetical LOC100129826 | chr11:1997823-1997882 | GO:0045121\|GO:0008270\|GO:0006487\|GO:0016021\|GO:0007169\|GO:0005769\|GO:0009897\|GO:0005201\|GO:0048888\|GO:0005769 | XR_114456 | THC2479538 | Hs.3254 |
| A_24_P816384 | UBE2Q2P1 | Homo sapiens ubiquitin-conjugating enzyme E2Q family member 2 pseudogene 1 (UBE2Q2P1), non-coding RNA [NR_003661] | NR_003661 | ENST00000339094 | 388165 | ubiquitin-conjugating enzyme E2Q family member 2 pseudogene 1 | chr15:85098273-85098214 | | NR_003661 | THC2783302 | Hs.498348 |
| A_33_P3331992 | | Uncharacterized protein [Source: UniProtKB/TrEMBL; Acc: B5MCR4] | | ENST00000401694 | | | chr7:155404014-155403955 | | | THC2558637 | |
| A_23_P203475 | PRKCDBP | Homo sapiens protein kinase C, delta binding protein (PRKCDBP), mRNA [NM_145040] | NM_145040 | ENST00000303927 | 112464 | protein kinase C, delta binding protein | chr11:6340269-6340210 | GO:0005080 | NM_145040 | THC2467530 | Hs.434044 |
| A_33_P3268612 | IL28RA | Homo sapiens interleukin 28 receptor, alpha (interferon, lambda receptor) (IL28RA), transcript variant 1, mRNA [NM_170743] | NM_170743 | ENST00000374421 | 163702 | interleukin 28 receptor, alpha (interferon, lambda receptor) | chr1:24483896-24483837 | GO:0005515\|GO:0008285\|NM_170743\|GO:0004896\|GO:0016020\|GO:0032002\|GO:0004872\|GO:0016021\|GO:0050691 | | NP610669 | Hs.221375 |
| A_33_P3240340 | | | | | | | chr17:00086249 3-000862552 | | | | |
| A_33_P3261720 | LOC151009 | Homo sapiens hypothetical LOC151009 (LOC151009), non-coding RNA [NR_027244] | NR_027244 | | 151009 | hypothetical LOC151009 | chr2:11113460 3-111134544 | | NR_027244 | THC2497499 | Hs.516403 |
| A_32_P32739 | NAGS | Homo sapiens N-acetylglutamate synthase (NAGS), mRNA [NM_153006] | NM_153006 | ENST00000293404 | 162417 | N-acetylglutamate synthase | chr17:4208630 2-42086361 | GO:0005739\|GO:0006536\|NM_153006\|GO:0003991\|GO:0005759\|GO:0008152\|GO:0006526\|GO:0000050\|GO:0008652\|GO:0016740\|GO:0008415\|GO:0004042 | | THC2661443 | Hs.8876 |
| A_33_P3287815 | DDX21 | Homo sapiens DEAD (Asp-Glu-Ala-Asp) box | NM_004728 | ENST00000354185 | 9188 | DEAD (Asp-Glu-Ala-Asp) | chr10:7074418 6-70744245 | GO:0005515\|GO:0004004\|NM_004728\|GO:0016787\|GO:0000166 | | THC2469678 | Hs.223141 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3249872 | | polypeptide 21 (DDX21), mRNA [NM_004728] | | | | box polypeptide 21 | | GO:0003723\|GO:0004386\|GO:0005634\|GO:0005524 | | | |
| A_33_P3235132 | FBLN1 | Homo sapiens fibulin 1 (FBLN1), transcript variant C, mRNA [NM_001996] | NM_001996 | ENST00000262722 | 2192 | fibulin 1 | chr22:45959173-45959232 | GO:0005515\|GO:0044419\|GO:0005578\|GO:0005625\|GO:0005576\|GO:0005615\|GO:0005201 | NM_001996 | THC2513019 | Hs.24601 |
| A_33_P3235132 | LOC400968 | Homo sapiens cDNA FLJ45884 fis, clone OCBBF3021166. [AK127783] | AK127783 | ENST00000412149 | 400968 | hypothetical LOC400968 | chr15:21356589-21356648 | | | THC2481983 | Hs.592022 |
| A_24_P308029 | HSPB6 | Homo sapiens heat shock protein, alpha-crystallin-related, B6 (HSPB6), mRNA [NM_144617] | NM_144617 | ENST00000416180 | 126393 | heat shock protein, alpha-crystallin-related, B6 | chr19:36234607-36246020 | GO:0005515\|GO:0009408 | NM_144617 | THC2661563 | Hs.534538 |
| A_23_P139198 | LGALS12 | Homo sapiens lectin, galactoside-binding, soluble, 12 (LGALS12), transcript variant 2, mRNA [NM_033101] | NM_033101 | ENST00000394618 | 85329 | lectin, galactoside-binding, soluble, 12 | chr11:63283937-6283996 | GO:0005529\|GO:0006915\|GO:0005634\|GO:0030395\|GO:0008629 | NM_033101 | NP374307 | Hs.502774 |
| A_33_P3375859 | CXCR2P1 | Homo sapiens chemokine (C-X-C motif) receptor 2 pseudogene 1 (CXCR2P1), non-coding RNA [NR_002712] | NR_002712 | ENST00000439871 | 3580 | chemokine (C-X-C motif) receptor 2 pseudogene 1 | chr2:218923959-218923900 | | NR_002712 | THC2605732 | Hs.647858 |
| A_33_P3303507 | HSPA6 | Homo sapiens cDNA full-length cDNA clone CS0DI029YJ23 of Placenta Cot 25-normalized of Homo sapiens (human). [CR623806] | CR623806 | | 3310 | heat shock 70 kDa protein 6 (HSP70B1) | chr1:161493849-161493908 | | | THC2683968 | Hs.654614 |
| A_33_P3220160 | RAC2 | Homo sapiens cDNA FLJ39605 fis, clone SKNSH2005981, weakly similar to RAS-RELATED C3 BOTULINUM TOXIN SUB. STRATE 2. [AK09G924] | AK096924 | ENST00000401529 | 5880 | ras-related C3 botulinum toxin substrate 2 (rho family, small GTP binding protein Rac2) | chr22:37636907-37636848 | | | THC2510406 | Hs.517601 |
| A_33_P3424882 | CSPG4P6Y | PREDICTED: Homo sapiens chondroitin sulfate proteoglycan 4 pseudogene 6, Y linked | XM_002344203 | | 100287758 | chondroitin sulfate proteoglycan 4 pseudogene | chrY:27626260-27626319 | | XM_002344203 | | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (CSPG4P6Y), mRNA [XM_002344203] | | | | 6, Y-linked | | | | | Hs.658489 |
| A_33_P3224250 | CLCC1 | *Homo sapiens* chloride channel CLIC-like 1 (CLCC1), transcript variant 1, mRNA [NM_001048210] | NM_001048210 | ENST00000369971 | 23155 | chloride channel CLIC-like 1 | chr1:109472215-109472156 | GO:0006821\|GO:0005792\|NM_001048210\|GO:0005737\|GO:0005794\|GO:0016020\|GO:0005783\|GO:0005634\|GO:0016021\|GO:0005254 | | |
| A_33_P3333603 | SMOC1 | *Homo sapiens* SPARC related modular calcium binding 1 (SMOC1), transcript variant 2, mRNA [NM_022137] | NM_022137 | ENST00000381280 | 64093 | SPARC related modular calcium binding 1 | chr14:70490104-70490163 | GO:0005509\|GO:0005576\|NM_022137\|GO:0005604 | THC2461766 | Hs.497349 |
| A_23_P76386 | SLC6A12 | *Homo sapiens* solute carrier family 6 (neurotransmitter transporter, betaine/GABA), member 12 (SLC6A12), transcript variant 1, mRNA [NM_003044] | NM_003044 | ENST00000424061 | 6539 | solute carrier family 6 (neurotransmitter transporter, betaine/GABA), member 12 | chr12:299799-299740 | GO:0016020\|GO:0005887\|NM_003044\|GO:0005328\|GO:0006865\|GO:0006836\|GO:0005332\|GO:0015293 | THC2479328 | Hs.437174 |
| A_24_P233078 | PYY2 | *Homo sapiens* peptide YY, 2 (seminalplasmin) (PYY2), non-coding RNA [NR_003064] | NR_003064 | ENST00000441253 | 23615 | peptide YY, 2 (seminalplasmin) | chr17:2655490-26554967 | GO:0005179\|GO:0005576 | NR_003064 | THC2480408 | Hs.157195 |
| A_33_P3313476 | ZAR1L | *Homo sapiens* zygote arrest 1-like (ZAR1L), mRNA [NM_001136571] | NM_001136571 | ENST00000345108 | 646799 | zygote arrest 1-like | chr13:32877973-32877914 | | NM_001136571 | THC2759804 | Hs.569254 |
| A_33_P3303394 | | | | | | | chr17:05220885-055208836 | | | | |
| A_33_P3376958 | LOC96610 | *Homo sapiens* BMS1 homolog, ribosome assembly protein (LOC96610), pseudogene (LOC96610), non-coding RNA [NR_027293] | NR_027293 | ENST00000390290 | | BMS1 homolog, ribosome assembly protein (yeast) pseudogene | chr22:22677174-22677233 | | NR_027293 | NP162580 | Hs.449601 |
| A_32_P142700 | C22orf15 | *Homo sapiens* chromosome 22 open reading frame 15 (C22orf15), mRNA [NM_182520] | NM_182520 | ENST00000336186 | 150248 | chromosome 22 open reading frame 15 | chr22:24106835-24106894 | | NM_182520 | NP1077442 | Hs.116254 |
| A_33_P3210622 | ASB13 | *Homo sapiens* ankyrin repeat and SOCS box containing 13 (ASB13), transcript variant 1, mRNA [NM_024701] | NM_024701 | ENST00000482921 | 79754 | ankyrin repeat and SOCS box containing 13 | chr10:5693260-5693201 | GO:0005515\|GO:0007242\|NM_024701\|GO:0019941 | THC2490517 | Hs.445899 |
| A_33_P3240318 | PITX3 | *Homo sapiens* paired-like homeodomain 3 (PITX3), mRNA | NM_005029 | ENST00000370002 | 5309 | paired like homeo-domain 3 | chr10:10399006-103989947 | GO:0043565\|GO:0006355\|NM_005029\|GO:0003700\|GO:0048666\|GO:0009887\|GO:0030901 | NP083974 | Hs.137568 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | [NM_005029] | | | | | | GO:0007626\|GO:0007275\|GO:0005634 | | | |
| A_23_P73747 | ARMCX2 | Homo sapiens armadillo repeat containing, X-linked 2 (ARMCX2), mRNA [NM_014782] | NM_014782 | ENST00000328766 | 9823 | armadillo repeat containing, X-linked 2 | chrX:100910394-100910335 | GO:0016020\|GO:0005488\|GO:0016021 | NM_014782 | THC2467696 | Hs.48924 |
| A_23_P325726 | ACOT11 | Homo sapiens acyl-CoA thioesterase 11 (ACOT11), transcript variant 1, mRNA [NM_015547] | NM_015547 | ENST00000481208 | 26027 | acyl-CoA thioesterase 11 | chr1:55070090-55070795 | GO:0004091\|GO:0007242\|GO:0005737\|GO:0016787\|GO:0016291\|GO:0009409\|GO:0006631 | NM_015547 | THC2707621 | Hs.729424 |
| A_33_P3638471 | TRGV7 | Homo sapiens T cell receptor gamma variable 7 pseudogene, mRNA (cDNA clone IMAGE: 5210958). [BC027954] | BC027954 | | 6981 | T cell receptor gamma variable 7 (pseudogene) | chr7:38373063-38373004 | | | THC2480213 | Hs.534032 |
| A_24_P64167 | PTGS1 | Homo sapiens prostaglandin-endoperoxide synthase 1 (prostaglandin G/H synthase and cyclooxygenase) (PTGS1), transcript variant 1, mRNA [NM_000962] | NM_000962 | ENST00000362012 | 5742 | prostaglandin-endoperoxide synthase 1 (prostaglandin G/H synthase and cyclooxygenase) | chr9:125157536-125157595 | GO:0005886\|GO:0032811\|GO:0005783\|GO:0005634\|GO:0005635\|GO:0046872\|GO:0008289\|GO:0005737\|GO:0004601\|GO:0001516\|GO:0045907\|GO:0045987\|GO:0042127\|GO:0006633\|GO:0005792\|GO:0051412\|GO:0007568\|GO:0004666\|GO:0010243\|GO:0010700\|GO:0008217\|GO:0016491\|GO:0016702\|GO:0055114\|GO:0019898\|GO:0020037 | NM_000962 | THC2601958 | Hs.201978 |
| A_23_P118095 | RPL3L | Homo sapiens ribosomal protein L3-like (RPL3L), mRNA [NM_005061] | NM_005061 | ENST00000268661 | 6123 | ribosomal protein L3-like | chr16:1995873-1995598 | GO:0005622\|GO:0003735\|GO:0005840\|GO:0003723\|GO:0006414 | NM_005061 | THC2472677 | Hs.657266 |
| A_33_P3281283 | S1PR3 | Homo sapiens sphingosine-1-phosphate receptor 3 (S1PR3), mRNA [NM_005226] | NM_005226 | ENST00000375846 | 1903 | sphingosine-1-phosphate receptor 3 | chr9:91619814-91619873 | GO:0008284\|GO:0005886\|GO:0004930\|GO:0001816\|GO:0009653\|GO:0007193\|GO:0007204\|GO:0008289\|GO:0007165\|GO:0006954\|GO:0001619\|GO:0007186\|GO:0005887\|GO:0004872\|GO:0032651 | NM_005226 | THC2494541 | Hs.585118 |
| A_33_P3621701 | | Novel protein [Source: UniProtKB/TrEMBL; Acc: A6ZJ83] [ENST00000463107] | BC048428 | ENST00000463107 | | | chr22:4893919-48939134 | | | THC2609712 | Hs.159057 |
| A_33_P3220445 | SMAD5 | Homo sapiens SMAD family member 5 | NM_001001419 | ENST00000514641 | 4090 | SMAD family | chr5:135513109-135513168 | GO:0030618\|GO:0005515\|GO:0005667\|GO:0006355 | NM_001001419 | THC2462440 | Hs.167700 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | (SMAD5), transcript variant 2, mRNA [NM_001001419] | | | | member 5 | | GO:0003700\|GO:0016563\|GO:0002051\|GO:0005634\|GO:0030509\|GO:0060048\|GO:0007281\|GO:0005829\|GO:0045669\|GO:0099880\|GO:0005622\|GO:0007165\|GO:0005737\|GO:0045944\|GO:0030218\|GO:0001880\|GO:0007179\|GO:0005654\|GO:0016021\|GO:0005057 | | | |
| A_33_P3399634 | RASSF10 | *Homo sapiens* Ras association (RalGDS/AF-6) domain family (N-terminal) member 10 (RASSF10), mRNA [NM_001080521] | NM_001080521 | | 644943 | Ras association (RalGDS/AF-6) domain family (N terminal) member 10 | chr11:1303258 8-13032647 | GO:0007165 | NM_001080521 | | Hs.134650 |
| A_33_P3363355 | ICAM4 | *Homo sapiens* intercellular adhesion molecule 4 (Landsteiner-Wiener blood group) (ICAM4), transcript variant 2, mRNA [NM_022377] | NM_022377 | ENST00000393717 | 3386 | intercellular adhesion molecule 4 (Landsteiner-Wiener blood group) | chr19:1039913 9-10399198 | GO:0005515\|GO:0016337\|GO:0005178\|GO:0005886\|GO:0005576\|GO:0016021 | NM_022377 | THC2490784 | Hs.706750 |
| A_33_P3223397 | | DHH_HUMAN (O43323) Desert hedgehog protein precursor (DHH) (HHG-3) [Contains: Desert hedgehog protein N-product; Desert hedgehog protein C-product], partial (19%) [THC2641433] | | ENST00000553174 | | | chr12:4948675 2-49486811 | | | THC2641433 | |
| A_33_P3411985 | RABGAP1 | RAB GTPase activating protein 1 [Source: HGNC Symbol; Acc: 17155] [ENST00000402311] | | ENST00000402311 | 23637 | RAB GTPase activating protein 1 | chr9:12570765 1-125707710 | | | THC2679929 | |
| A_33_P3351180 | | immunoglobulin heavy constant alpha 1 [Source: HGNC Symbol; Acc: 5478] [ENST00000390547] | XR_114797 | ENST00000390547 | | | chr14:1061735 64-106173505 | | XR_114797 | NP852642 | Hs.699841 |
| A_33_P3298567 | ZNF692 | zinc finger protein 692 [Source: HGNC Symbol; Acc: 26049] | AK309421 | ENST00000391820 | 55657 | zinc finger protein 692 | chr1:24915224 7-249152188 | | | THC2523720 | Hs.377705 |
| A_23_P209129 | LAIR 2 | *Homo sapiens* leukocyte-associated immunoglobulin-like receptor 2 (LAIR2), transcript variant 1, mRNA [NM_002288] | NM_002288 | ENST00000301202 | 3904 | leukocyte-associated immunoglobulin-like receptor 2 | chr19:5502180 9-55021868 | GO:0005576\|GO:0004872 | NM_002288 | THC2480754 | Hs.43803 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3405038 | LOC100130264 | Homo sapiens hypothetical LOC100130264 (LOC100130264), non-coding RNA [NR_024564] | NR_024564 | ENST00000319682 | 100130264 | hypothetical LOC100130264 | chr20:19223005-19222946 | | NR_024564 | THC2487513 | Hs.683814 |
| A_23_P255257 | DCAF12 | Homo sapiens DDB1 and CUL4 associated factor 12 (DCAF12), mRNA [NM_015397] | NM_015397 | ENST00000361264 | 25853 | DDB1 and CUL4 associated factor 12 | chr9:34086957-34086898 | GO:0005813\|GO:0005737 | NM_015397 | THC2468846 | Hs.493750 |
| A_33_P3329128 | | Q96DD6_HUMAN (Q96DD6) LOC119710 protein (HEPIS), partial (10%) [THC2715547] | | | | | chr1:08975500-089754941 | | | THC2715547 | |
| A_33_P3430391 | LOC389273 | Homo sapiens cDNA FLJ27351 fis, clone TST05050. [AK130861] | AK130861 | ENST00000506021 | 389273 | hypothetical LOC389273 | chr5:10505167-10505108 | | | NP1157119 | Hs.519206 |
| A_33_P3214849 | KDELC2 | Homo sapiens KDEL (Lys-Asp-Glu-Leu) containing 2 (KDELC2), mRNA [NM_153705] | NM_153705 | ENST00000434945 | 143888 | KDEL (Lys-Asp-Glu-Leu) containing 2 | chr11:1083431 24-108343065 | GO:0005783\|GO:0005788 | NM_153705 | THC2499983 | Hs.83286 |
| A_23_P342709 | FBXO15 | Homo sapiens F-box protein 15 (FBXO15), transcript variant 1, mRNA [NM_152676] | NM_152676 | ENST00000269500 | 201456 | F-box protein 15 | chr18:7174079 7-71740738 | GO:0005515\|GO:0019941\|GO:0019005 | NM_152676 | THC2472376 | Hs.664011 |
| A_33_P3414228 | | | | | | | chr15:0227486 70-022748611 | | | | |
| A_33_P3356220 | STARD3 | Homo sapiens StAR-related lipid transfer (START) domain containing 3 (STARD3), transcript variant 2, mRNA [NM_001165937] | NM_001165937 | ENST00000471896 | 10948 | StAR-related lipid transfer (START) domain containing 3 | chr17:3781966 3-37819722 | GO:0006629\|GO:0006694\|GO:0005737\|GO:0016020\|GO:0015485\|GO:0017127\|GO:0006869\|GO:0016021\|GO:0006839\|GO:0008289\|GO:0008203\|GO:0005768 | NM_001165937 | THC2526791 | Hs.728838 |
| A_24_P4462 | TPM1 | Homo sapiens tropomyosin 1 (alpha) (TPM1), transcript variant 5, mRNA [NM_000366] | NM_000366 | ENST00000317516 | 7168 | tropomyosin 1 (alpha) | chr15:6335344 1-63354441 | GO:0005862\|GO:0055010\|GO:0008016\|GO:0006928\|GO:0060048\|GO:0030017\|GO:0031529\|GO:0006937\|GO:0005737\|GO:0003065\|GO:0007010\|GO:0008307\|GO:0005856\|GO:0001725\|GO:0030336\|GO:0030049\|GO:0045214\|GO:0003779\|GO:0032587\|GO:0032781\|GO:0045785\|GO:0032059\|GO:0042060\|GO:0051496\|GO:0005200\|GO:0034614 | NM_000366 | NP1470921 | Hs.133892 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P813147 | TUBB8 | Homo sapiens tubulin, beta 8 (TUBB8), transcript variant 1, mRNA [NM_177987] | NM_177987 | ENST00000328974 | 347688 | tubulin, beta 8 | chr10:93404-93345 | GO:0051258\|GO:0000166\|GO:0005198\|GO:0005874\|GO:0003924\|GO:0005525\|GO:0007018 | NM_177987 | NP1178315 | Hs.532659 |
| A_33_P3259522 | CDCP2 | Homo sapiens CUB domain containing protein 2 (CDCP2), mRNA [NM_201546] | NM_201546 | ENST00000371330 | 200008 | CUB domain containing protein 2 | chr1:54605389-54605330 | GO:0005576\|GO:0007018 | NM_201546 | THC2486749 | Hs.568555 |
| A_33_P3290124 | ASB10 | Homo sapiens ankyrin repeat and SOCS box containing 10 (ASB10), transcript variant 1, mRNA [NM_001142459] | NM_001142459 | ENST00000420175 | 136371 | ankyrin repeat and SOCS box containing 10 | chr7:150872789-150872789 | GO:0007242\|GO:0019941 | NM_001142459 | NP1150152 | Hs.647081 |
| A_33_P3414017 | | | | | | | chr7:00229924-2-002299301 | | | | |
| A_23_P138717 | RGS10 | Homo sapiens regulator of G-protein signaling 10 (RGS10), transcript variant 1, mRNA [NM_001005339] | NM_001005339 | ENST00000369103 | 6001 | regulator of G-protein signaling 10 | chr10:1212595 82-121259523 | GO:0005515\|GO:0009968\|GO:0004871 | NM_001005339 | THC2783455 | Hs.501200 |
| A_33_P3248586 | DUX4 | Homo sapiens double homeobox 4 (DUX4), mRNA [NM_033178] | NM_033178 | ENST00000507734 | 22947 | double homeobox 4 | chrUn_gl00022 8:77296-77355 | GO:0043565\|GO:0006355\|GO:0003700\|GO:0005634 | NM_033178 | THC2493180 | Hs.553518 |
| A_24_P6317 | MBNL2 | Homo sapiens muscleblind-like 2 (Drosophila) (MBNL2), transcript variant 1, mRNA [NM_144778] | NM_144778 | ENST00000343600 | 10150 | muscleblind-like 2 (Drosophila) | chr13:9804622 6-98046285 | GO:0005737\|GO:0003723\|GO:0008270\|GO:0005634\|GO:0046872 | NM_144778 | THC2468304 | Hs.657347 |
| A_23_P142389 | LSR | Homo sapiens lipolysis stimulated lipoprotein receptor (LSR), transcript variant 2, mRNA [NM_205834] | NM_205834 | ENST00000361790 | 51599 | lipolysis stimulated lipoprotein receptor | chr19:3575843 4-35758493 | GO:0005794\|GO:0005886\|GO:0005730\|GO:0042627\|GO:0005634\|GO:0009790\|GO:0019216\|GO:0001889\|GO:0034361\|GO:0005737\|GO:0034362\|GO:0004872\|GO:0016021 | NM_205834 | THC2519817 | Hs.466507 |
| A_33_P3354990 | SYNJ2 | synaptojanin 2[Source: HGNC Symbol; Acc: 11504] [ENST00000449320] | AK296242 | ENST00000449320 | 8871 | synaptojanin 2 | chr6:15843876 7-158438826 | | | THC2549364 | Hs.434494 |
| A_33_P3295803 | RAB2B | Homo sapiens RAB2B, member RAS oncogene family (RAB2B), transcript variant 1, mRNA [NM_032846] | NM_032846 | ENST00000304034 | 84932 | RAB2B, member RAS oncogene family | chr14:2192838 5-21928326 | GO:0005794\|GO:0005886\|NM_032846\|GO:0000166\|GO:0000139\|GO:0007264\|GO:0005783\|GO:0005789\|GO:0016192\|GO:0015031\|GO:0005525 | NM_032846 | THC2771975 | Hs.22399 |
| A_33_P3276329 | | Homo sapiens cDNA FLJ41115 fis, clone BRACE1000533. [AK123110] | AK123110 | | | | chr7:74803807-74803748 | | | THC2509132 | Hs.594823 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3303031 | FLJ40606 | Homo sapiens hypothetical protein LOC643549, mRNA (cDNA Clone IMAGE: 40147028). [BC133006] | BC133006 | | 643549 | hypothetical protein LOC643549 | chr20:44563229-44563170 | | | | Hs.472856 |
| A_23_P51487 | GBP3 | Homo sapiens guanylate binding protein 3 (GBP3), mRNA [NM_018284] | NM_018284 | ENST00000370481 | 2635 | guanylate binding protein 3 | chr1:89472608-89472549 | GO:0016020\|GO:0000166\|NM_018284\|GO:0003924\|GO:0016021\|GO:0005525 | | THC2491572 | Hs.720167 |
| A_33_P3219811 | PTGDS | prostaglandin D2 synthase 21 kDa (brain) [Source: HGNC Symbol; Acc: 9592] [ENST00000371623] | CR610092 | ENST00000371623 | 5730 | prostaglandin D2 synthase 21 kDa (brdin) | chr9:13987379-139873853 | | | THC2644569 | Hs.446429 |
| A_23_P14302 | C14orf139 | Homo sapiens chromosome 14 open reading frame 139 (C14orf139), non-coding RNA [NR_026779] | NR_026779 | ENST00000464767 | 79686 | chromosome 14 open reading frame 139 | chr14:95873748-95873689 | | NR_026779 | THC2472996 | Hs.41502 |
| A_33_P3373775 | BCL2L15 | Homo sapiens BCL2-like 15 (BCL2L15), mRNA [NM_001010922] | NM_001010922 | | 440603 | BCL2-like 15 | chr1:114419524-114419465 | GO:0006915\|GO:0005634\|NM_001010922\|GO:0005829 | | THC2651058 | Hs.123106 |
| A_33_P3357658 | HMGA2 | Homo sapiens high mobility group AT-hook 2 (HMGA2), transcript variant 2, mRNA [NM_003484] | NM_003484 | ENST00000354636 | 8091 | high mobility group AT-hook 2 | chr12:66309240-66309299 | GO:0005515\|GO:0006355\|NM_003484\|GO:0005694\|GO:0006325\|GO:0005634\|GO:0007275\|GO:0003677\|GO:0007049\|GO:0007067\|GO:0003680\|GO:0000785\|GO:0040008\|GO:0051301 | | THC2477434 | Hs.505924 |
| A_32_P206735 | | L22858 AcOrf-91 peptide {Autographa californica nucleopolyhedrovirus}(exp = -1; wgp = 0; cg = 1), partial (8%) [THC2483664] | | | | | chr3:114392012-114391953 | | | THC2483664 | |
| A_33_P3239744 | | PREDICTED: Homo sapiens hypothetical LOC150051 (LOC150051), misc RNA [XR_109661] | XR_109661 | ENST00000433071 | | | chr21:32932572-32932631 | | XR_109661 | THC2610508 | Hs.708976 |
| A_33_P3376925 | | | | | | | chrX:093574757-093574816 | | | | |
| A_23_P64070 | SLC25A45 | Homo sapiens solute carrier family 25, member 45 (SLC25A45), transcript variant 1, mRNA [NM_182556] | NM_182556 | ENST00000417511 | 283130 | solute carrier family 25, member 45 | chr11:65143810-65143751 | GO:0005739\|GO:0016020\|NM_182556\|GO:0005488\|GO:0005743\|GO:0016021\|GO:0055085 | | NP1076259 | Hs.661604 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3273906 | OR10G4 | Homo sapiens olfactory receptor, family 10, subfamily G, member 4 (OR10G4), mRNA [NM_001004462] | NM_001004462 | ENST00000320891 | 390264 | olfactory receptor, family 10, subfamily G, member 4 | chr11:123887013-123887072 | GO:0007608\|GO:0007165\|GO:0004984\|GO:0007186\|GO:0005886\|GO:0004872\|GO:0016021\|GO:0050896 | NM_001004462 | | Hs.553760 |
| A_33_P3333455 | EMILIN1 | Homo sapiens elastin microfibril interfacer 1 (EMILIN1), mRNA [NM_007046] | NM_007046 | ENST00000544143 | 11117 | elastin microfibril interfacer 1 | chr2:27309204-27309263 | GO:0030198\|GO:0010811\|GO:0005578\|GO:0030023\|GO:0005576\|GO:0007155\|GO:0042802 | NM_007046 | THC2601131 | Hs.63348 |
| A_33_P3279009 | HMX1 | Homo sapiens H6 family homeobox 1 (HMX1), mRNA [NM_018942] | NM_018942 | ENST00000400677 | 3166 | H6 family homeobox 1 | chr4:8869424-8869365 | GO:0043565\|GO:0016564\|GO:0003700\|GO:0007275\|GO:0005634\|GO:0045892 | NM_018942 | THC2476064 | Hs.104134 |
| A_33_P3257607 | PPP1R12B | Homo sapiens protein phosphatase 1, regulatory (inhibitor) subunit 12B (PPP1R12B), transcript variant 7, mRNA [NM_001197131] | NM_001197131 | | 4660 | protein phosphatase 1, regulatory (inhibitor) subunit 12B | chr1:202509288-202509347 | | NM_001197131 | | Hs.444403 |
| A_33_P3289204 | AAK1 | Homo sapiens AP2 associated kinase 1 (AAK1), mRNA [NM_014911] | NM_014911 | ENST00000409085 | 22848 | AP2 associated kinase 1 | chr2:69736579-69736520 | GO:0005905\|GO:0006355\|GO:0000166\|GO:0004674\|GO:0006468\|GO:0005524\|GO:0016740\|GO:0019898 | NM_014911 | THC2517701 | Hs.468878 |
| A_23_P63390 | FCGR1B | Homo sapiens Fc fragment of IgG, high affinity Ib, receptor (CD64) (FCGR1B), transcript variant 1, mRNA [NM_001017986] | NM_001017986 | ENST00000444948 | 2210 | Fc fragment of IgG, high affinity Ib, receptor (CD64) | chr1:120927353-120927294 | GO:0006955\|GO:0005886\|GO:0001017986\|GO:0019864\|GO:0004872\|GO:0016021\|GO:0019763 | NM_001017986 | THC2717837 | Hs.534956 |
| A_23_P5221 | ZNF333 | Homo sapiens zinc finger protein 333 (ZNF333), mRNA [NM_032433] | NM_032433 | ENST00000292530 | 84449 | zinc finger protein 333 | chr19:14831167-14831226 | GO:0005622\|GO:0006355\|GO:0008270\|GO:0005634\|GO:0003677\|GO:0046872 | NM_032433 | THC2515092 | Hs.515215 |
| A_33_P3274501 | KLRF1 | Homo sapiens killer cell lectin-like receptor subfamily F, member 1 (KLRF1), mRNA [NM_016523] | NM_016523 | ENST00000545196 | 51348 | killer cell lectin-like receptor subfamily F, member 1 | chr12:9984950-9985009 | GO:0016020\|GO:0005887\|GO:0005488\|GO:0005529\|GO:0007166\|GO:0032393 | NM_016523 | | Hs.183125 |
| A_33_P3219591 | RNF213 | Homo sapiens ring finger protein 213 (RNF213), transcript variant 2, mRNA [NM_020954] | NM_020954 | ENST00000319921 | 57674 | ring finger protein 213 | chr17:78295199-78295258 | GO:0005515\|GO:0017111\|GO:0000166\|GO:0008270\|GO:0046872 | NM_020954 | THC2470667 | Hs.195642 |
| A_33_P3376154 | LOC100130825 | PREDICTED: Homo sapiens hypothetical protein LOC100130825 | XM_001720026 | | 100130825 | hypothetical protein LOC100130825 | chr12:132148597-132148538 | | XM_001720026 | | |

APPENDIX C-continued

FEMALES: Technology: Agilent.SingleColor:26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P43106 | U2SURP | (LOC10013 0825), mRNA [XM_001720026] Homo sapiens U2 snRNP-associated SURP domain containing (U2SURP), mRNA [NM_001080415] | NM_001080415 | ENST00000473835 | 23350 | U2 snRNP-associated SURP domain containing | chr3:142778660-142778719 | GO:0006396\|GO:0000166\|GO:0003723 | NM_001080415 | THC2556970 | Hs.596572 |
| A_24_P37409 | DUSP2 | Homo sapiens dual specificity phosphatase 2 (DUSP2), mRNA [NM_004418] | NM_004418 | ENST00000488952 | 1844 | dual specificity phosphatase 2 | chr2:96809962-96809903 | GO:0000188\|GO:0006470\|GO:0016787\|GO:0008330\|GO:0005634\|GO:0017017\|GO:0004725\|GO:0051019 | NM_004418 | THC2687427 | Hs.1183 |
| A_23_P164927 | SYNGR4 | Homo sapiens synaptogyrin 4 (SYNGR4), mRNA [NM_012451] | NM_012451 | ENST00000344846 | 23546 | synaptogyrin 4 | chr19:48879538-48879597 | GO:0016020\|GO:0016021 | NM_012451 | THC2478295 | Hs.408333 |
| A_33_P3344291 | | CDNA FLJ46261 fis, clone TEST14025062 [Source: UniProtKB/TrEMBL; Acc: Q6ZRL6] [ENST00000356374] | XR_111092 | ENST00000356374 | | | chr10:82012926-82012985 | | XR_111092 | THC2484630 | Hs.447456 |
| A_23_P9772 | CLCN1 | Homo sapiens chloride channel 1, skeletal muscle (CLCN1), mRNA [NM_000083] | NM_000083 | ENST00000343257 | 1180 | chloride channel 1, skeletal muscle | chr7:143043683-143043742 | GO:0042383\|GO:0006821\|GO:0031404\|GO:0006036\|GO:0005244\|GO:0016020\|GO:0005887\|GO:0005247\|GO:0034707\|GO:0055085\|GO:0019227\|GO:0006811 | NM_000083 | THC2482326 | Hs.121483 |
| A_33_P3340065 | | | | | | | chr9:117416639-117416580 | | | | |
| A_33_P3329549 | FBRS | Homo sapiens fibrosin (FBRS), mRNA [NM_001105079] | NM_001105079 | ENST00000395073 | 64319 | fibrosin | chr16:30681443-30681503 | | NM_001105079 | THC2467136 | Hs.247186 |
| A_32_P159445 | IQSEC2 | Homo sapiens IQ 2 motif and Sec7 domain (IQSEC2), transcript variant 2, mRNA [NM_015075] | NM_015075 | ENST00000375365 | 23096 | IQ motif and Sec7 domain 2 | chrX:53263787-53263728 | GO:0005622\|GO:0005086\|GO:0005737\|GO:0032012 | NM_015075 | THC2715714 | Hs.496138 |
| A_23_P25069 | | | XM_003119523 | ENST00000542925 | | | chr12:3126780-31267369 | | XM_003119523 | THC2503104 | Hs.434604 |
| A_33_P3262089 | OR8G2 | Homo sapiens olfactory receptor, family 8, subfamily G, member 2 (OR8G2), mRNA [NM_001007249] | NM_001007249 | | 26492 | olfactory receptor, family 8, subfamily G, member 2 | chr11:124096044-124096103 | GO:0007608\|GO:0007165\|GO:0004984\|GO:0007186\|GO:0005886\|GO:0004872\|GO:0016021\|GO:0050896 | NM_001007249 | THC2605277 | Hs.381319 |
| A_32_P167471 | CLMN | Homo sapiens calmin (calponin-like, trans-membrane) (CLMN), mRNA [NM_024734] | NM_024734 | ENST00000298912 | 79789 | calmin (calponin-like, trans-membrane) | chr14:95648676-95648617 | GO:0005737\|GO:0016020\|GO:0003779\|GO:0016021 | NM_024734 | THC2496792 | Hs.301478 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3402010 | LOC100508141 | PREDICTED: *Homo sapiens* hypothetical protein LOC100508141 (LOC100508141), mRNA [XM_003119578] | XM_003119578 | | 100508141 | hypothetical protein LOC100508141 | chr14:71683095-71683036 | | XM_003119578 | THC2750828 | Hs.551210 |
| A_24_P272845 | DOCK3 | *Homo sapiens* dedicator of cytokinesis 3 (DOCK3), mRNA [NM_004947] | NM_004947 | ENST00000266037 | 1795 | dedicator of cytokinesis 3 | chr3:51399313-51399372 | GO:0005515\|GO:0005085\|GO:0017124\|GO:0005737\|GO:0051020\|GO:0005625\|GO:0005525 | NM_004947 | THC2472118 | Hs.476284 |
| A_23_P140675 | EPB42 | *Homo sapiens* erythrocyte membrane protein band 4.2 (EPB42), transcript variant 1, mRNA [NM_000119] | NM_000119 | ENST00000397027 | 2038 | erythrocyte membrane protein band 4.2 | chr15:43489566-43489506 | GO:0005515\|GO:0005737\|GO:0043249\|GO:0018149\|GO:0005886\|GO:0008360\|GO:0003810\|GO:0005200\|GO:0005856\|GO:0005524 | NM_000119 | NP1465858 | Hs.368642 |
| A_33_P3389773 | | EFCB_PAPAN (P61552) ERV-BabFcenv provirus ancestral Env polyprotein precursor (Envelope polyprotein) (BabFcenv) [Includes: Surface protein (SU); Transmembrane protein (TM)], partial (28%) [THC2739063] | | | | | chr7:064295759-064295700 | | | THC2739063 | |
| A_33_P3245623 | TSPY17P | PREDICTED: *Homo sapiens* testis specific protein, Y-linked 17 (pseudogene) (TSPY17P), mRNA [XM_003118834] | XM_003118834 | | 100132124 | testis specific protein, Y-linked 17, pseudogene | chrY:63889944-6389003 | | XM_003118834 | | |
| A_33_P3882264 | GRASP05 | *Homo sapiens* cDNA clone IMAGE: 5212507. [BC028005] | BC028005 | | 692159 | GRP1-associated scaffold protein opposite strand | chr12:52400087-52400028 | | | | Hs.621295 |
| A_33_P3419621 | LOC100289580 | *Homo sapiens* cDNA FLJ45121 fis, clone BRAWH3036077. [AK127064] | AK127064 | | 100289580 | hypothetical LOC100289580 | chr16:88807748-88807807 | | | THC2664787 | |
| A_33_P3285354 | C11orf95 | *Homo sapiens* chromosome 11 open reading frame 95 (C11orf95), mRNA [NM_001144936] | NM_001144936 | ENST00000445014 | 65998 | chromosome 11 open reading frame 95 | chr11:63533339-63533280 | | NM_001144936 | THC2632379 | Hs.101073 |
| A_33_P3220149 | MAML1 | *Homo sapiens* mastermind-like 1 (*Drosophila*) [Source: HGNC Symbol; | AB209135 | ENST00000503050 | 9794 | mastermind-like 1 (*Drosophila*) | chr5:179223213-179223272 | | | THC2776662 | Hs.63951 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P16252 | KLK1 | Acc: 13632] [FNST00000503050] Homo sapiens kallikrein 1 (KLK1), mRNA [NM_002257] | NM_002257 | ENST00000448701 | 3816 | kallikrein 1 | chr19:51322506-51322447 | GO:0004252\|GO:0006508\|GO:0008233 | NM_002257 | NP113453 | Hs.123107 |
| A_23_P354894 | ZNF567 | Homo sapiens zinc finger protein 567 (ZNF567), mRNA [NM_152603] | NM_152603 | ENST00000360729 | 163081 | zinc finger protein 567 | chr19:37211954-37212013 | GO:0005622\|GO:0006355\|GO:0008270\|GO:0003677\|GO:0046872 | NM_152603 | THC2628196 | Hs.412517 |
| A_23_P366812 | AQP5 | Homo sapiens aquaporin 5 (AQP5), mRNA [NM_001651] | NM_001651 | ENST00000553132 | 362 | aquaporin 5 | chr12:50358821-50358880 | GO:0005515\|GO:0005215\|GO:0007588\|GO:0005783\|GO:0015670\|GO:0055085\|GO:0005902\|GO:0016324\|GO:0009925\|GO:0016020\|GO:0005887\|GO:0015250\|GO:0006833 | NM_001651 | THC2616592 | Hs.298023 |
| A_24_P363548 | HIP1 | Homo sapiens huntingtin interacting protein 1 (HIP1), mRNA [NM_005338] | NM_005338 | ENST00000336926 | 3092 | huntingtin interacting protein 1 | chr7:75164311-75164252 | GO:0008219\|GO:0005794\|GO:0006919\|GO:0005624\|GO:0042981\|GO:0003779\|GO:0005634\|GO:0031410\|GO:0006917\|GO:0030154\|GO:0006897\|GO:0012505\|GO:0030665\|GO:0005737\|GO:0016020\|GO:0030276\|GO:0048260\|GO:0005200\|GO:0035091\|GO:0005856\|GO:0045449\|GO:0048268 | NM_005338 | THC2501285 | Hs.329266 |
| A_33_P3383029 | MXI1 | Homo sapiens MAX interactor 1 (MXI1), transcript variant 2, mRNA [NM_130439] | NM_130439 | ENST00000369613 | 4601 | MAX interactor 1 | chr10:11204 4747-112044806 | GO:0008285\|GO:0003714\|GO:0030528\|GO:0042994\|GO:0005634\|GO:0003677\|GO:0045449 | NM_130439 | THC2522010 | Hs.501023 |
| A_33_P3302210 | LOC100129129 | PREDICTED: Homo sapiens hypothetical LOC100129129 (LOC100129129), partial miscRNA [XR_113108] | XR_113108 | ENST00000525867 | 100129129 | hypothetical LOC100129129 | chr8:11203536-11203477 | | XR_113108 | THC2610893 | Hs.662094 |
| A_24_P346762 | KIAA1539 | Homo sapiens KIAA1539 (KIAA1539), mRNA [NM_025182] | NM_025182 | ENST00000479357 | 80256 | KIAA1539 | chr9:35105138-35105079 | GO:0005634 | NM_025182 | THC2653744 | Hs.301696 |
| A_24_P134392 | HSPA13 | Homo sapiens heat shock protein 70 kDa family, member 13 (HSPA13), mRNA [NM_006948] | NM_006948 | ENST00000285667 | 6782 | heat shock protein 70 kDa family, member 13 | chr21:15743635-15743576 | GO:0005792\|GO:0000166\|NM_006948\|GO:0005783\|GO:0005524 | | THC2469197 | Hs.352341 |
| A_33_P3374388 | LOC100131702 | Homo sapiens cDNA FLJ45037 fis, clone | AK126983 | | 100131702 | hypothetical protein | chr22:24247121-24247062 | | | | Hs.656723 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3344339 | KCNH5 | BRAWH3019820. [AK126983] Homo sapiens potassium voltage-gated channel, subfamily H (eag-related), member 5 (KCNH5), transcript variant 1, mRNA [NM_139318] | NM_139318 | ENST00000420622 | 27133 | potassium voltage-gated channel, subfamily H (eag-related), member 5 | chr14:6317408 4-63174025 | GO:0005516\|GO:0006355\|NM_139318 GO:0000160\|GO:0005244\| GO:0016020\|GO:0005249\| GO:0030955\|GO:0016021\| GO:0055085\|GO:0006813\| GO:0000155\|GO:0006811 | | THC2490856 | Hs.27043 |
| A_24_P312519 | PBLD | Homo sapiens phenazine biosynthesis-like protein domain containing (PBLD), transcript variant 2, mRNA [NM_001033083] | NM_001033083 | ENST00000468798 | 64081 | phenazine biosynthesis-like protein domain containing | chr10:7004871 9-70048391 | GO:0008150\|GO:0009058\|NM_001033083 GO:0005575\|GO:0016853 | | THC2576209 | Hs.198158 |
| A_23_P6285 | REEP1 | Homo sapiens receptor accessory protein 1 (REEP1), nuclear gene encoding mitochondrial protein, transcript variant 2, mRNA [NM_022912] | NM_022912 | ENST00000533845 | 65055 | receptor accessory protein 1 | chr2:86441557-86441498 | GO:0005739\|GO:0008219\|NM_022912 GO:0005737\|GO:0016020\| GO:0051205\|GO:0016021\| GO:0031849 | | THC2468332 | Hs.368884 |
| A_33_P3413795 | | | XM_001721393 | ENST00000427872 | | | chr1:12090512 8-120905069 | | XM_001721393 | THC2698492 | Hs.568526 |
| A_33_P3326447 | LOC100510506 | PREDICTED: Homo sapiens hypothetical protein LOC100510506 (LOC100510506), mRNA [XM_003120741] | XM_003120741 | | 100510506 | hypothetical protein LOC100510506 | chr12:1293281 17-129328058 | | XM_003120741 | THC2479151 | Hs.449723 |
| A_33_P3213747 | ZNHIT2 | Homo sapiens zinc finger, HIT-type containing 2 (ZNHIT2), mRNA [NM_014205] | NM_014205 | ENST00000310597 | 741 | zinc finger, HIT-type containing 2 | chr11:6488413 1-64884072 | GO:0008270\|GO:0046872 | NM_014205 | THC2467573 | Hs.121025 |
| A_33_P3271885 | | | | | | | chrY:01967126 1-01967202 | | | | |
| A_33_P3413759 | ACER2 | Homo sapiens alkaline ceramidase 2 (ACER2), mRNA [NM_001010887] | NM_001010887 | ENST00000380376 | 340485 | alkaline ceramidase 2 | chr9:19424730-19424789 | GO:0006629\|GO:0017040\|NM_001010887 GO:0005794\|GO:0016787\| GO:0016020\|GO:0000139\| GO:0006672\|GO:0005789\| GO:0016021 | | NP1212864 | Hs.41379 |
| A_32_P224850 | | | | | | | chr2:12048089 2-120480833 | | | THC2715283 | |
| A_33_P3410925 | KLF1 | Homo sapiens Kruppel-like factor 1 (erythroid) (KLF1), mRNA [NM_006563] | NM_006563 | ENST00000264834 | 10661 | Kruppel-like factor 1 (erythroid) | chr19:1299529 5-12995236 | GO:0005622\|GO:0001889\|NM_006563 GO:0043249\|GO:0003700\| GO:0008270\|GO:0006338\| GO:0005634\|GO:0035162 | | THC2478746 | Hs.37860 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P1682 | TMEM45B | Homo sapiens transmembrane protein 45B (TMEM45B), mRNA [NM_138788] | NM_138788 | ENST00000281441 | 120224 | transmembrane protein 45B | chr11:129728946-129729005 | GO:0001701\|GO:0046872\|GO:0045449\|GO:0016020\|GO:0016021 | NM_138788 | THC2463597 | Hs.504301 |
| A_23_P430161 | EXOC8 | Homo sapiens exocyst complex component 8 (EXOC8), mRNA [NM_175876] | NM_175876 | ENST00000366645 | 149371 | exocyst complex components | chr1:231469145-231469086 | GO:0005515\|GO:0005737\|GO:0000145\|GO:0042995\|GO:0015031\|GO:0006887\|GO:0030426 | NM_175876 | THC2474277 | Hs.356198 |
| A_33_P3276784 | | | | ENST00000454671 | | | chr16:23122843-23123443 | | | | |
| A_33_P3268234 | KRT39 | Homo sapiens keratin 39 (KRT39), mRNA [NM_213656] | NM_213656 | ENST00000355612 | 390792 | keratin 39 | chr17:39114740-39114681 | GO:0005882\|GO:0005198 | NM_213656 | THC2487370 | Hs.28467 |
| A_23_P134814 | THAP1 | Homo sapiens THAP domain containing, apoptosis associated protein 1 (THAP1), transcript variant 1, mRNA [NM_018105] | NM_018105 | ENST00000345117 | 55145 | THAP domain containing, apoptosis associated protein 1 | chr8:42692056-42691997 | GO:0043565\|GO:0007346\|GO:0007049\|GO:0006355\|GO:0030528\|GO:0001935\|GO:0008270\|GO:0005654\|GO:0005634\|GO:0046872 | NM_018105 | THC2605203 | Hs.7432 |
| A_33_P3355418 | AGBL1 | Homo sapiens ATP/GTP binding protein-like 1 (AGBL1), mRNA [NM_152336] | NM_152336 | ENST00000389298 | 123624 | ATP/GTP binding protein-like 1 | chr15:87217546-87217605 | GO:0005737\|GO:0005488\|GO:0006508\|GO:0008270\|GO:0008233\|GO:0046872\|GO:0008237\|GO:0004181 | NM_152336 | | Hs.679833 |
| A_24_P212024 | | | AY867113 | ENST00000498435 | | immunoglobulin kappa variable 1-27 [Source: HGNC Symbol; Acc: 5735] [ENST00000498435] | chr2:89513053-89512994 | | | NP1400333 | Hs.720289 |
| A_33_P3775281 | LOC644050 | Homo sapiens cDNA FLJ30698 fis, clone FCBBF2000825. [AK055260] | AK055260 | | 644050 | hypothetical LOC644050 | chr19:36279837-36279778 | | | THC2637220 | Hs.651888 |
| A_33_P3305320 | LOC100289383 | PREDICTED: Homo sapiens protein capicua homolog (LOC100289383), mRNA [XM_002344123] | XM_002344123 | | 100289383 | capicua homolog pseudogene | chr16:90238916-90238857 | | XM_002344123 | THC2481163 | Hs.625768 |
| A_33_P3305320 | | immunoglobulin lambda constant 2 (Kern-Oz- marker) [Source: HGNC Symbol; Acc: 5856] [ENST00000390323] | AY172962 | ENST00000390323 | | | chr22:23243286-23243345 | | | NP493030 | |
| A_33_P3346098 | TAOK2 | Homo sapiens TAO kinase 2 (TAOK2), | NM_016151 | ENST00000308893 | 9344 | TAO kinase 2 | chr16:29999515-29999574 | GO:0030036\|GO:0000287\|GO:0008360\|GO:0046330 | NM_016151 | NP797374 | Hs.291623 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| | | transcript variant 2, mRNA [NM_016151] | | | | | | GO:0006950\|GO:0006915\|GO:0001558\|GO:0005524\|GO:0000186\|GO:0016477\|GO:0000166\|GO:0016020\|GO:0004674\|GO:0048041\|GO:0006612\|GO:0016023\|GO:0016021\|GO:0016740 | | | |
| A_33_P3408711 | FLNA | Homo sapiens filamin A, alpha (FLNA), transcript variant 1, mRNA [NM_001456] | NM_001456 | ENST00000369852 | 2316 | filamin A, alpha | chrX:153589903-153589844 | GO:0005802\|GO:0005886\|GO:0031267\|GO:0005634\|GO:0007195\|GO:0015629\|GO:0045022\|GO:0042993\|GO:0042803\|GO:0043433\|GO:0045184\|GO:0005829\|GO:0005737\|GO:0051015\|GO:0001948\|GO:0005080\|GO:0051764\|GO:0004871\|GO:0043123\|GO:0005938\|GO:0034989\|GO:0034988\|GO:0031532\|GO:0042177\|GO:0051220\|GO:0050821\|GO:0005576\|GO:0048365\|GO:0034394\|GO:0043113\|GO:0008134 | NM_001456 | THC2728266 | Hs.195464 |
| A_33_P3316093 | | | | ENST00000415226 | | | chr2:237203493-237203552 | | | | |
| A_23_P128919 | LGALS3 | Homo sapiens lectin, galactoside-binding, soluble, 3 (LGALS3), transcript variant 1, mRNA [NM_002306] | NM_002306 | ENST00000254301 | 3958 | lectin, galactoside-binding, soluble, 3 | chr14:55609454-55611879 | GO:0005515\|GO:0019863\|GO:0005737\|GO:0001501\|GO:0005886\|GO:0030198\|GO:0005634\|GO:0030154 | NM_002306 | THC2745323 | Hs.531081 |
| A_24_P64918 | ZBTB1 | Homo sapiens zinc finger and BTB domain containing 1 (ZBTB1), transcript variant 1, mRNA [NM_014950] | NM_014950 | ENST00000394712 | 22890 | zinc finger and BTB domain containing 1 | chr14:64990003-64990062 | GO:0005622\|GO:0005515\|GO:0008270\|GO:0005634\|GO:0003677\|GO:0046872\|GO:0045449 | NM_014950 | THC2471109 | Hs.605143 |
| A_33_P3294217 | UTF1 | Homo sapiens undifferentiated embryonic cell transcription factor 1 (UTF1), mRNA [NM_003577] | NM_003577 | ENST00000304477 | 8433 | undifferentiated embryonic cell transcription factor 1 | chr10:135045003-135045062 | GO:0005515\|GO:0003702\|GO:0045944\|GO:0003713\|GO:0005634\|GO:0045449\|GO:0008584 | NM_003577 | THC2486743 | Hs.458406 |
| A_33_P3799692 | LOC338620 | Homo sapiens hypothetical protein LOC338620 mRNA (cDNA clone IMAGE:6023208), partial cds. [BC043009] | BC043009 | | 338620 | hypothetical protein LOC338620 | chr13:3317636-33176306 | | | THC2707863 | Hs.660499 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3228757 | ZNF814 | Homo sapiens zinc finger protein 814 (ZNF814), mRNA [NM_001144989] | NM_001144989 | ENST00000376205 | 730051 | zinc finger protein 814 | chr19:5838424 9-58384190 | GO:0005622\|GO:0006355\|GO:0008270\|GO:0005634\|GO:0003677\|GO:0046872 | NM_001144989 | | Hs.634143 |
| A_33_P3226070 | | | | | | | chr4:00154889 6-001548955 | | | | |
| A_33_P3216487 | | | | | | | chr11:1113290 97-111329156 | | | | |
| A_23_P124988 | KCNH4 | Homo sapiens potassium voltage-gated channel, subfamily H (eag-related), member 4 (KCNH4), mRNA [NM_012285] | NM_012285 | ENST00000264661 | 23415 | potassium voltage-gated channel, subfamily H (eag-related), member 4 | chr17:4031177 6-40309105 | GO:0006355\|GO:0000160\|GO:0005244\|GO:0016020\|GO:0008076\|GO:0005249\|GO:0030955\|GO:0016021\|GO:0055085\|GO:0006813\|GO:0000155\|GO:0006811 | NM_012285 | THC2488133 | Hs.304081 |
| A_33_P3366903 | CHST6 | Homo sapiens carbohydrate (N-acetylglucosamine 6-O) sulfotransferase 6 (CHST6), mRNA [NM_021615] | NM_021615 | ENST00000390664 | 4166 | carbohydrate (N-acetylglucosamine 6-O) sulfotransferase 6 | chr16:7551246 3-75512404 | GO:0006790\|GO:0005794\|GO:0018146\|GO:0016020\|GO:0000139\|GO:0005975\|GO:0006044\|GO:0016021\|GO:0001517\|GO:0016740 | NM_021615 | THC2483430 | Hs.655622 |
| A_24_P374244 | GATA1 | Homo sapiens GATA binding protein 1 (globin transcription factor 1) (GATA1), mRNA [NM_002049] | NM_002049 | ENST00000376665 | 2623 | GATA binding protein 1 (globin transcription factor 1) | chrX:48650853-48651615 | GO:0043565\|GO:0005515\|GO:0003700\|GO:0006357\|GO:0005730\|GO:0008270\|GO:0007275\|GO:0005634\|GO:0046872 | NM_002049 | NP370725 | Hs.765 |
| A_24_P686965 | SH2D5 | Homo sapiens SH2 domain containing 5 (SH2D5), transcript variant 1, mRNA [NM_001103161] | NM_001103161 | ENST00000375031 | 400745 | SH2 domain containing 5 | chr1:21046321-21046262 | GO:0005515 | NM_001103161 | THC2473200 | Hs.591522 |
| A_33_P3210671 | GPAT2 | Homo sapiens glycerol-3-phosphate acyltransferase 2, mitochondrial (GPAT2), nuclear gene encoding mitochondrial protein, mRNA [NM_207328] | NM_207328 | ENST00000458519 | 150763 | glycerol-3-phosphate acyltransferase 2, mitochondrial | chr2:96690381-96690322 | GO:0005739\|GO:0016020\|GO:0008152\|GO:0005741\|GO:0004366\|GO:0016021\|GO:0008654\|GO:0016740\|GO:0008415 | NM_207328 | THC2483887 | Hs.34629 |
| A_33_P3281465 | SLC5A6 | Homo sapiens solute carrier family 5 (sodium-dependent vitamin transporter), member 6 (SLC5A6), transcript variant 1, mRNA [NM_021095] | NM_021095 | ENST00000408041 | 8884 | solute carrier family 5 (sodium-dependent vitamin transporter), member 6 | chr2:27423946-27423887 | GO:0012506\|GO:0015887\|GO:0005215\|GO:0005624\|GO:0031526\|GO:0016020\|GO:0055085\|GO:0008523\|GO:0005887\|GO:0008523\|GO:0015878\|GO:0006814\|GO:0006811\|GO:0015293 | NM_021095 | THC2507513 | Hs.435735 |
| A_23_P8142 | CLPS | Homo sapiens colipase, pancreatic (CLPS), | NM_001832 | ENST00000541088 | 1208 | colipase, pancreatic | chr6:35762842-35762783 | GO:0016042\|GO:0007586\|GO:0005576\|GO:0043085 | NM_001832 | THC2601801 | Hs.1340 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3236327 | | Homo sapiens cDNA FLJ46124 fis, clone TESTI2040372. [AK128005] | AK128005 | ENST00000371169 | | | chr20:56532241-56532182 | GO:0009791\|GO:0008047\|GO:0032094 | | THC2484382 | Hs.525529 |
| A_23_P64792 | KCNMB4 | Homo sapiens potassium large conductance calcium-activated channel, subfamily M, beta member 4 (KCNMB4), mRNA [NM_014505] | NM_014505 | ENST00000258111 | 27345 | potassium large conductance calcium-activated channel, subfamily M, beta member 4 | chr12:70824623-70824682 | GO:0005515\|GO:0005513\|GO:0008076\|GO:0016020\|GO:0008076\|GO:0046928\|GO:0007268\|GO:0015269\|GO:0006813\|GO:0005216\|GO:0019228\|GO:0019229\|GO:0006811 | NM_014505 | THC2470841 | Hs.449585 |
| A_33_P3379039 | IGLL5 | Homo sapiens immunoglobulin lambda-like polypeptide 5 (IGLL5), transcript variant 1, mRNA [NM_001178126] | NM_001178126 | ENST00000390321 | 100423062 | immunoglobulin lambda-like polypeptide 5 | chr22:23237630-23237689 | | NM_001178126 | NP492959 | Hs.433492 |
| A_32_P516342 | ANKRD33 | Homo sapiens ankyrin repeat domain 33 (ANKRD33), transcript variant 2, mRNA [NM_182608] | NM_182608 | ENST00000548383 | 341405 | ankyrin repeat domain 33 | chr12:52284985-52285044 | | NM_182608 | NP1159358 | Hs.443428 |
| A_33_P3337161 | ADCY4 | Homo sapiens adenylate cyclase 4 (ADCY4), transcript variant 3, mRNA [NM_001198568] | NM_001198568 | ENST00000396747 | 196883 | adenylate cyclase 4 | chr14:24793331-24793272 | GO:0000287\|GO:0005886\|GO:0005524\|GO:0007193\|GO:0030425\|GO:0005622\|GO:0004016\|GO:0009755\|GO:0000166\|GO:0006171\|GO:0007189\|GO:0016021\|GO:0034199 | NM_001198568 | THC2471883 | Hs.22641 |
| A_33_P3321611 | PHACTR4 | Homo sapiens phosphatase and actin regulator 4 (PHACTR4), transcript variant 1, mRNA [NM_001048183] | NM_001048183 | ENST00000463428 | 65979 | phosphatase and actin regulator 4 | chr1:28792957-28793016 | GO:0004864\|GO:0003779\|GO:0005575 | NM_001048183 | THC2478475 | Hs.270851 |
| A_24_P402898 | OTUD4 | Homo sapiens OTU domain containing 4 (OTUD4), transcript variant 3, mRNA [NM_001102653] | NM_001102653 | ENST00000454497 | 54726 | OTU domain containing 4 | chr4:146055623-146055564 | GO:0005515\|GO:0008150\|GO:0003674\|GO:0005575 | NM_001102653 | THC2603393 | Hs.71912 |
| A_24_P18917 | LMF1 | Homo sapiens lipase maturation factor 1 (LMF1), transcript variant 1, mRNA [NM_022773] | NM_022773 | ENST00000543238 | 64788 | lipase maturation factor 1 | chr16:904229-904170 | GO:0009306\|GO:0016020\|GO:0005783\|GO:0016021 | NM_022773 | THC2628156 | |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3226008 | GCET2 | Homo sapiens germinal center expressed transcript 2 (GCET2), transcript variant 3, mRNA [NM_001190259] | NM_001190259 | ENST00000495418 | 257144 | germinal center expressed transcript 2 | chr3:111842406-111842347 | GO:0005739|GO:0005737 | NM_001190259 | THC2607167 | Hs.49614 |
| A_24_P288836 | HLA-DPB2 | Homo sapiens major histocompatibility complex, class II, DP beta 2 (pseudogene) (HLA-DPB2), non-coding RNA [NR_001435] | NR_001435 | | 3116 | major histocompatibility complex, class II, DP beta 2 (pseudogene) | chr6:33096422-33096481 | | NR_001435 | | |
| A_32_P158966 | KLRF1 | Homo sapiens killer cell lectin-like receptor subfamily F, member 1 (KLRF1), mRNA [NM_016523] | NM_016523 | ENST00000535631 | 51348 | killer cell lectin-like receptor subfamily F, member 1 | chr12:9997324-9997383 | GO:0016020|GO:0005887|GO:0005488|GO:0005529|GO:0007166|GO:0032393 | NM_016523 | NP183062 | Hs.183125 |
| A_33_P3360392 | NCRNA00092 | Homo sapiens non-protein coding RNA 92 (NCRNA00092), non-coding RNA [NR_024129] | NR_024129 | | 100188953 | non-protein coding RNA92 | chr9:98782134-98782075 | | NR_024129 | THC2497538 | Hs.434310 |
| A_32_P205110 | FOXC1 | Homo sapiens forkhead box C1 (FOXC1), mRNA [NM_001453] | NM_001453 | ENST00000380874 | 2296 | forkhead box C1 | chr6:1613858-1613917 | GO:0001657|GO:0055010|GO:0003705|GO:0016563|GO:0048844|GO:0005634|GO:0001541|GO:0050880|GO:0007219|GO:0014032|GO:0045944|GO:0030199|GO:0042475|GO:0043010|GO:0030203|GO:0001945|GO:0048010|GO:0046620|GO:0008354|GO:0001568|GO:0035050|GO:0001822|GO:0008301|GO:0048762|GO:0006916|GO:0001701|GO:0060038|GO:0043565|GO:0032808|GO:0005720|GO:0003007|GO:0001501|GO:0001503|GO:0045930|GO:0001974|GO:0007420|GO:0048341|GO:0008134 | NM_001453 | THC2495614 | Hs.348883 |
| A_23_P95594 | NAT1 | Homo sapiens N-acetyltransferase 1 (arylamine N-acetyltransferase) (NAT1), transcript variant 5, mRNA [NM_000662] | NM_000662 | ENST00000520546 | 9 | N-acetyltransferase 1 (arylamine N-acetyltransferase ) | chr8:18080376-18080435 | GO:0005737|GO:0008152|GO:0004060|GO:0016407|GO:0016740|GO:0005829 | NM_000662 | THC2490997 | Hs.591847 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3344451 | C16orf13 | Homo sapiens chromosome 16 open reading frame 13 (C16orf13), transcript variant 1, mRNA [NM_032366] | NM_032366 | ENST00000301686 | 84326 | chromosome 16 open reading frame 13 | chr16:684643-684584 | | NM_032366 | THC2653959 | Hs.239500 |
| A_32_P172864 | FAM102B | Homo sapiens family with sequence similarity 102, member B (FAM102B), mRNA [NM_001010883] | NM_001010883 | ENST00000483371 | 284611 | family with sequence similarity 102, member B | chr1:1091816 2-109181681 | | NM_001010883 | THC2601428 | Hs.200230 |
| A_23_P144126 | FETUB | Homo sapiens fetuin B (FETUB), mRNA [NM_014375] | NM_014375 | ENST00000420570 | 26998 | fetuin B | chr3:18637051 8-186370577 | GO:0008150|GO:0003674|NM_014375 GO:0004869|GO:0005576 | | THC2470628 | Hs.81073 |
| A_32_P133090 | | RST35951 Athersys RAGE Library Homo sapiens cDNA, mRNA sequence [BG216262] | BG216262 | | | | chr3:12551663 4-125516693 | | | THC2580853 | Hs.637431 |
| A_33_P3419808 | | immunoglobulin lambda variable 3-27[Source: HGNC Symbol; Acc: 5910] [ENST00000390304] | AF060129 | ENST00000390304 | | | chr22:2301121 9-23011276 | | | THC2523002 | Hs.729081 |
| A_24_P331150 | CYP4F22 | Homo sapiens cytochrome P450, family 4, subfamily F, polypeptide 22 (CYP4F22), mRNA [NM_173483] | NM_173483 | ENST00000269703 | 126410 | cytochrome P450, family 4, subfamily F, polypeptide 22 | chr19:1566272 0-15662779 | GO:0005792|GO:0004497|NM_173483 GO:0016020|GO:0005783 GO:0009055|GO:0046872 GO:0055114|GO:0020037 GO:0019898 | | THC2479532 | Hs.156452 |
| A_23_P141173 | MPO | Homo sapiens myeloperoxidase (MPO), nuclear gene encoding mitochondrial protein, mRNA [NM_000250] | NM_000250 | ENST00000340482 | 4353 | myeloperoxidase | chr17:5634792 7-56347868 | GO:0005509|GO:0005634|NM_000250 GO:0006916|GO:0006952 GO:0005615|GO:0005764 GO:0004601|GO:0034374 GO:0003682|GO:0016491 GO:0042744|GO:0006979 GO:0055114|GO:0020037 | | THC2776236 | Hs.458272 |
| A_33_P3320748 | FDX1L | Homo sapiens ferredoxin 1-like (FDX1L), nuclear gene encoding mitochondrial protein, mRNA [NM_001031734] | NM_001031734 | ENST00000343376 | 112812 | ferredoxin 1-like | chr19:1042158 9-10421530 | GO:0005739|GO:0005506|NM_001031734 GO:0051537|GO:0005759 GO:0006810|GO:0009055 GO:0022900|GO:0046872 | | THC2668248 | Hs.654865 |
| A_33_P3301620 | RNF32 | Homo sapiens ring finger protein 32 (RNF32), transcript variant 2, mRNA [NM_001184997] | NM_001184997 | ENST00000392740 | 140545 | ring finger protein 32 | chr7:15643739 1-156437450 | GO:0005515|GO:0005737|NM_001184997 GO:0016235|GO:0008270 GO:0046872|GO:0005768 | | THC2771893 | Hs.446194 |
| A_33_P3295738 | CNGB1 | Homo sapiens cyclic nucleotide gated channel beta 1 (CNGB1), transcript variant 2, | NM_001135639 | ENST00000311183 | 1258 | cyclic nucleotide gated channel beta 1 | chr16:5799480 4-57994745 | GO:0007608|GO:0005222|NM_001135639 GO:0005624|GO:0045494 GO:0055085|GO:0030552 GO:0000166|GO:0016020 | | NP087010 | Hs.147062 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P21485 | PID1 | Homo sapiens phosphotyrosine interaction domain containing 1 (PID1), transcript variant 1, mRNA [NM_017933] | NM_017933 | ENST00000392055 | 55022 | phosphotyrosine interaction domain containing 1 | chr2:229889030-229888971 | GO:0016021\|GO:0007602\|GO:0050896\|GO:0006811\|GO:0015276\|GO:0017071\|GO:0005737 | NM_017933 | THC2606128 | Hs.409352 |
| A_33_P3355306 | LYG2 | Homo sapiens LYG2 mRNA, complete cds. [AF323919] | AF323919 | ENST00000409679 | 254773 | lysozyme G-like 2 | chr2:99860310-99860251 | | | THC2487325 | Hs.436468 |
| A_33_P3320953 | CTXN1 | Homo sapiens cortexin 1 (CTXN1), mRNA [NM_206833] | NM_206833 | ENST00000318978 | 404217 | cortexin 1 | fhn9:7989441-7989382 | GO:0016020\|GO:0016021 | NM_206833 | THC2471562 | Hs.657978 |
| A_23_P3247890 | | T cell receptor alpha variable 1-2 [Source: HGNC Symbol; Acc: 12102] [ENST00000390423] | X58744 | ENST00000390423 | | | chr14:2211173-22111791 | | | NP096670 | Hs.455887 |
| A_23_P49559 | GPR142 | Homo sapiens G protein-coupled receptor 142 (GPR142), mRNA [NM_181790] | NM_181790 | ENST00000335666 | 350383 | G protein-coupled receptor 142 | chr17:7236829-72363357 | GO:0007165\|GO:0007186\|GO:0005886\|GO:0004930\|GO:0004872\|GO:0016021 | NM_181790 | THC2603174 | Hs.574368 |
| A_33_P3316273 | CCL3 | Homo sapiens chemokine (C-C motif) ligand 3 (CCL3), mRNA [NM_002983] | NM_002983 | ENST00000470334 | 6348 | chemokine (C-C motif) ligand 3 | chr17:3441566-4-34415605 | GO:0008009\|GO:0007267\|GO:0006874\|GO:0045069\|GO:0006928\|GO:0005576\|GO:0005625\|GO:0006887\|GO:0042056\|GO:0005615\|GO:0007165\|GO:0006955\|GO:0006954\|GO:0006935\|GO:0007186\|GO:0007010\|GO:0004871 | NM_002983 | THC2601998 | Hs.514107 |
| A_23_P78543 | AP1M2 | Homo sapiens adaptor-related protein complex 1, mu 2 subunit (AP1M2), mRNA[NM_005498] | NM_005498 | ENST00000250244 | 10053 | adaptor-related protein complex 1, mu 2 subunit | chr19:1068562-1-10685159 | GO:0005515\|GO:0030131\|GO:0005794\|GO:0016020\|GO:0006892\|GO:0031410\|GO:0006605\|GO:0016044\|GO:0006903\|GO:0005829 | NM_005498 | THC2780514 | Hs.18894 |
| A_33_P3321372 | CNTNAP3 | contactin associated protein-like 3 [Source: HGNC Symbol; Acc: 13834] [ENST00000377653] | AK024257 | ENST00000377653 | 79937 | contactin associated protein-like 3 | chr9:39174527-39174468 | | | THC2481668 | Hs.604441 |
| A_33_P3353979 | SYT15 | Homo sapiens synaptotagmin XV (SYT15), transcript variant b, mRNA [NM_181519] | NM_181519 | ENST00000374330 | 83849 | synaptotagmin XV | chr10:4696752-3-46967464 | GO:0005886\|GO:0016021 | NM_181519 | THC2665044 | Hs.696346 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3346680 | | GB | | | | | | | | NP105946 | |
| A_33_P3312682 | REXO1 | Homo sapiens REX1, RNA exonuclease 1 homolog (S. cerevisiae) (REXO1), mRNA [NM_020695] | NM_020695 | ENST00000170168 | 57455 | REX1, RNA exonuclease 1 homolog (S. cerevisiae) | chr16:0287115 89-028711530 chr19:1815304-1815245 | GO:0005622\|GO:0004527\|NM_020695 GO:0016787\|GO:0005634\| GO:0003676 | NM_020695 | THC2612197 | Hs.192477 |
| A_33_P3419594 | PDE9A | Homo sapiens cDNA FLJ90181 fis. Clone MAMMA1000706. [AK074662] | AK074662 | | 5152 | phospho-diesterase 9A | chr21:4419011 9-44190178 | | | THC2686196 | |
| A_23_P46238 | CELA2A | Homo sapiens chymo-trypsin-like elastase family, member 2A (CELA2A), mRNA [NM_033440] | NM_033440 | ENST00000375924 | 63036 | chymotryp-sin-like elas-tase family, member 2A | chr1:15793981-15798491 | GO:0004252\|GO:0006508\|NM_033440 GO:0008233\|GO:0005576 | NM_033440 | THC2472773 | Hs.631866 |
| A_23_P51936 | TNFRSF9 | Homo sapiens tumor necrosis factor receptor superfamily, member 9 (TNFRSF9), mRNA [NM_001561] | NM_001561 | ENST00000377507 | 3604 | tumor necrosis factor receptor superfamily, member 9 | chr1:7980782-7980723 | GO:0005515\|GO:0008285\|NM_001561 GO:0016020\|GO:0005887\| GO:0004872\|GO:0006917 | NM_001561 | THC2479062 | Hs.86447 |
| A_33_P3367073 | | | | | | | chr17:0026274 68-002627409 | | | | |
| A_33_P3261620 | GHSR | Homo sapiens growth hormone secretagogue receptor (GHSR), transcript variant 1b, mRNA [NM_004122] | NM_004122 | ENST00000427970 | 2693 | growth hormone secret-agogue receptor | chr3:17216554 3-172165484 | GO:0008343\|GO:0005515\|NM_004122 GO:0043005\|GO:0005886\| GO:0032691\|GO:0032100\| GO:0045409\|GO:0016520\| GO:0032094\|GO:0046697\| GO:0045923\|GO:0001616\| GO:0004872\|GO:0030252\| GO:0009725\|GO:0040018\| GO:0046676\|GO:0051963\| GO:0032869\|GO:0009986\| GO:0042536\|GO:0007165\| GO:0009755\|GO:0007186\| GO:0008154\|GO:0043568\| GO:0050728\|GO:0045121\| GO:0016021\|GO:0017046\| GO:0043134 | NM_004122 | THC2603925 | Hs.130212 |
| A_33_P3396473 | PPP6R2 | Homo sapiens protein phosphatase 6, regulatory subunit 2 (PPP6R2), transcript variant 1, mRNA [NM_001242898] | NM_001242898 | ENST00000395741 | 9701 | protein phosphatase 6, regulatory subunit 2 | chr22:5088269 9-50882758 | GO:0005515\|GO:0005737 NM_001242898 | NM_001242898 | THC2466888 | Hs.449098 |
| A_33_P3418597 | GAS2L1 | Homo sapiens growth arrest-specific 2 like 1 (GAS2L1), transcript | NM_152237 | ENST00000360113 | 10634 | growth arrest-specific 2 like 1 | chr22:2970842 7-29708486 | GO:0005737\|GO:0007050\|NM_152237 GO:0005856 | NM_152237 | THC2743842 | Hs.322852 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P347880 | ALOXE3 | variant 3, mRNA [NM_152237] Homo sapiens arachidonate lipoxygenase 3 (ALOXE3), transcript variant 2, mRNA [NM_021628] | NM_021628 | ENST00000318227 | 59344 | arachidonate lipoxygenase 3 like 1 | chr17:8006732-8006673 | GO:0019370\|GO:0005506\|GO:0016491\|GO:0046872\|GO:0055114 | NM_021628 | THC2477386 | Hs.232770 |
| A_33_P3353921 | GNLY | granulysin [Source: HGNC Symbol; Acc: 4414] [ENST00000489214] | AK310057 | ENST00000489214 | 10578 | granulysin | chr2:85923450-85923509 | | | THC2674183 | Hs.105806 |
| A_33_P3272527 | MAVS | Homo sapiens mitochondrial antiviral signaling protein (MAVS), nuclear gene encoding mitochondrial protein, transcript variant 3, mRNA [NM_001206491] | NM_001206491 | ENST00000356687 | 57506 | mitochondrial antiviral signaling protein | chr20:3835323-3835382 | GO:0005515\|GO:0032728\|GO:0032727\|GO:0005741\|GO:0009615\|GO:0005739\|GO:0016020\|GO:0045087\|GO:0002230\|GO:0044419\|GO:0004871\|GO:0016021\|GO:0043123\|GO:0042742 | NM_001206491 | THC2488008 | Hs.570362 |
| A_33_P3864411 | | ARP3 actin-related protein 3 homolog B (yeast) pseudogene 5 [Source: HGNC Symbol; Acc:38682] [ENST00000541147] | AY026352 | ENST00000541147 | | | chr22:1696902 1-16969080 | | | THC2487688 | |
| A_33_P3350748 | KRT7 | Homo sapiens keratin 7 (KRT7), mRNA [NM_005556] | NM_005556 | ENST00000422319 | 3855 | keratin 7 | chr12:5264259 0-52642649 | GO:0006260\|GO:0005515\|GO:0005737\|GO:0005198\|GO:0044419\|GO:0007010\|GO:0045095\|GO:0051325\|GO:0006417 | NM_005556 | THC2465320 | Hs.411501 |
| A_33_P3373810 | | Q5K675_HUMAN (Q5K675) Osteoligament factor, partial (23%) [THC2668752] | | | | | chr5:14848921 9-148489278 | | | THC2668752 | |
| A_23_P315286 | C19orf22 | Homo sapiens chromosome 19 open reading frame 22 (C19orf22), mRNA [NM_138774] | NM_138774 | ENST00000361574 | 91300 | chromosome 19 open reading frame 22 | chr19:897179-897120 | GO:0005634\|GO:0003676 | NM_138774 | THC2560561 | Hs.557655 |
| A_24_P259922 | LANCL1 | Homo sapiens LanC lantibiotic synthetase component C-like 1 (bacterial) (LANCL1), transcript variant 1, mRNA [NM_006055] | NM_006055 | ENST00000443314 | 10314 | LanC lantibiotic synthetase component C-like 1 (bacterial) | chr2:21129674 4-211296685 | GO:0005737\|GO:0016020\|GO:0007186\|GO:0005887\|GO:0004930\|GO:0003824\|GO:0050750\|GO:0019898 | NM_006055 | THC2734611 | Hs.13351 |
| A_33_P3223678 | LHX3 | Homo sapiens LIM homeobox 3 (LHX3), transcript variant 2, mRNA [NM_014564] | NM_014564 | ENST00000325195 | 8022 | LIM homeobox 3 | chr9:13908923 0-139089171 | GO:0043565\|GO:0006355\|GO:0003700\|GO:0003702\|GO:0009887\|GO:0008270\|GO:0005634\|GO:0046872 | NM_014564 | NP183253 | Hs.148427 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3381762 | | | | | | | | | | | |
| A_33_P3274245 | ENDOV | Homo sapiens endonuclease V (ENDOV), transcript variant 1, mRNA [NM_173627] | NM_173627 | ENST00000521565 | 284131 | endonuclease V | chr19:0047918 16-004791757 chr17:7839570 2-78395761 | GO:0006281\|GO:0004519\|NM_173627 GO:0016787\|GO:0006974 | | THC2526422 | Hs.728933 |
| A_33_P3256105 | DUX4 | Homo sapiens double homeobox 4 (DUX4), mRNA [NM_033178] | NM_033178 | ENST00000507734 | 22947 | double homeobox 4 | chrUn_gl00022 8:77296-77355 | GO:0043565\|GO:0006355\|NM_033178 GO:0003700\|GO:0005634 | | THC2493180 | Hs.553518 |
| A_23_P117363 | SERPINA6 | Homo sapiens serpin peptidase inhibitor, clade A (alpha-1 antiproteinase, antitrypsin), member 6 (SERPINA6), mRNA [NM_001756] | NM_001756 | ENST00000341584 | 866 | serpin peptidase inhibitor, clade A (alpha-1 antiproteinase, antitrypsin), member 6 | chr14:9477068 9-94770630 | GO:0004867\|GO:0006810\|NM_001756 GO:0005576\|GO:0005615\| GO:0005496\|GO:0008211 | | NP705151 | Hs.532635 |
| A_33_P3364959 | | Homo sapiens isolate N1408L immunoglobulin lambda light chain variable region (IGLV2) mRNA, IGLV2-23*02 allele, partial Cds. [DQ098707] | DQ098707 | | | | chr22:2304084 7-23040906 | | | THC2524123 | Hs.449585 |
| A_23_P3400217 | SLC4A1 | Homo sapiens solute carrier family 4, anion exchanger, member 1 (erythrocyte membrane protein band 3, Diego blood group) (SLC4A1), mRNA [NM_000342] | NM_000342 | ENST00000262418 | 6521 | solute carrier family 4, anion exchanger, member 1 (erythrocyte membrane protein band 3, Diego blood group) | chr17:4233062 8-42330569 | GO:0006820\|GO:0005215\|NM_000342 GO:0008509\|GO:0030018\| GO:0030506\|GO:0006873\| GO:0003779\|GO:0008022\| GO:0042803\|GO:0016323\| GO:0005452\|GO:0016020\| GO:0005887\|GO:0030863\| GO:0043495 | | THC2474664 | Hs.443948 |
| A_23_P142187 | HIF3A | Homo sapiens hypoxia inducible factor 3, alpha subunit (HIF3A), transcript variant 2, mRNA [NM_022462] | NM_022462 | ENST000OO33%13 | 64344 | hypoxia inducible factor 3, alpha subunit | chr19:4684638 1-46846440 | GO:0007165\|GO:0001666\|NM_022462 GO:0006355\|GO:0005737\| GO:0003700\|GO:0006366\| GO:0005634\|GO:0004871 | | THC2470601 | Hs.420830 |
| A_23_P1056 | GPR89B | Homo sapiens G protein-coupled receptor 89B (GPR89B), mRNA [NM_016334] | NM_016334 | ENST00000493684 | 51463 | G protein-coupled receptor 89B | chr1:14746517 3-147465232 | | NM_016334 | NP1454439 | Hs.645432 |
| A_33_P3262024 | ATMIN | Homo sapiens cDNA FLJ61620 complete cds. [AK302556] | AK302556 | | 23300 | ATM interactor | chr3:19567236 8-195672427 | | | THC2500773 | Hs.589959 |
| A_33_P3378354 | | guanylate cyclase 1, soluble, beta 2 [Source:HGNC | CR615161 | ENST00000389600 | | | chr13:5158961 4-51589554 | | | THC2603577 | Hs.411573 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3230037 | | Symbol; Acc: 4686] [ENST00000389600] Homo sapiens FKSG58 (FKSG58) mRNA, complete cds. [AF336885] | AF336885 | | | | chr11:64469434-64469375 | | | NP316843 | Hs.446021 |
| A_33_P3259293 | SLC37A3 | solute carrier family 37 (glycerol-3 phosphate transporter), member 3[Source: HGNC Symbol; Acc: 20651] [ENST00000493423] | AK131347 | ENST00000493423 | 84255 | solute carrier family 37 (glycerol-3-phosphate transporter), member 3 | chr7:140102392-140102333 | | | THC2487539 | Hs.446021 |
| A_23_P160159 | SLC2A5 | Homo sapiens solute carrier family 2 (facilitated glucose/fructose transporter), member 5 (SLC2A5), transcript variant 1, mRNA [NM_003039] | NM_003039 | ENST00000377424 | 6518 | solute carrier family 2 (facilitated glucose/fructose transporter), member 5 | chr1:9097229-9097170 | GO:0015755|GO:0005215|NM_003039| GO:0015758|GO:0005886| GO:0005975|GO:0022891| GO:0005353|GO:0008643| GO:0016021|GO:0055085| GO:0005355 | | THC2467315 | Hs.530003 |
| A_33_P3244258 | SLC41A3 | Homo sapiens solute carrier family 41, member 3 (SLC41A3), transcript variant 2, mRNA [NM_017836] | NM_017836 | ENST00000506102 | 54946 | solute carrier family 41, member 3 | chr3:125725888-125725829 | GO:0005515|GO:0005886|NM_017836| GO:0008324|GO:0016021| GO:0006812 | | THC2707275 | Hs.573007 |
| A_33_P3235400 | HDGF | Homo sapiens hepatoma-derived growth factor (HDGF), transcript variant 1, mRNA [NM_004494] | NM_004494 | ENST00000406805 | 3068 | hepatoma-derived growth factor | chr1:156713610-156713551 | GO:0007165|GO:0005737|NM_004494| GO:0001166|GO:0008483| GO:0005634|GO:0008201| GO:0008083|GO:0005615| GO:0003677|GO:0045449 | | NP417915 | Hs.506748 |
| A_33_P3354137 | MAP4 | Homo sapiens microtubule-associated protein 4 (MAP4), transcript variant 3, mRNA [NM_030885] | NM_030885 | ENST00000360240 | 4134 | microtubule-associated protein 4 | chr3:48130383-48130324 | GO:0005515|GO:0005198|NM_030885| GO:0005875|GO:0005874| GO:0007026 | | THC2519872 | Hs.517949 |
| A_24_P239176 | MUC4 | Homo sapiens mucin 4, cell surface associated (MUC4), transcript variant 1, mRNA [NM_018406] | NM_018406 | ENST00000479406 | 4585 | mucin 4, cell surface associated | chr3:195514819-195514760 | GO:0005515|GO:0008150|NM_018406| GO:0005176|GO:0030197| GO:0016020|GO:0007160| GO:0005887|GO:0005578| GO:0005576|GO:0007155 | | THC2575387 | Hs.369646 |
| A_33_P3267865 | | | GB | | | | chr6:029975243-029975302 | | | NP111779 | |
| A_33_P3351554 | ETNK2 | Homo sapiens ethanolamine kinase 2 (ETNK2), mRNA [NM_018208] | NM_018208 | ENST00000367199 | 55224 | ethanolamine kinase 2 | chr1:204100263-204100204 | GO:0004305|GO:0008150|NM_018208| GO:0006646|GO:0035264| GO:0000166|GO:0004103| GO:0005575|GO:0001890| GO:0009791|GO:0005524| GO:0001701|GO:0016740 | | THC2466750 | Hs.497469 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3247210 | | | | | | | chr2:01793526 8-017935209 | | | | |
| A_33_P3333683 | | AF039690 antigen NY-CO-8 {Homo sapiens} (exp = −1; wgp = 0; cg = 0; partial (10%) [THC2493232] | | | | | chr1:243646419 1-243646132 | | | THC2493232 | |
| A_24_P336853 | PNO1 | Homo sapiens partner of NOB1 homolog (S. cerevisiae) (PNO1), mRNA [NM_020143] | NM_020143 | ENST00000263657 | 56902 | partner of NOB1 homolog (S. cerevisiae) | chr2:68402335-68402394 | GO:0003723|GO:0005730 GO:0005634 | NM_020143 | THC2462538 | Hs.262858 |
| A_33_P3291176 | VMAC | Homo sapiens vimentin-type intermediate filament associated coiled-coil protein (VMAC), mRNA [NM_001017921] | NM_001017921 | ENST00000339485 | 400673 | vimentin-type intermediate filament associated coiled-coil protein | chr19:5910197-5910256 | GO:0005737 | NM_001017921 | NP1158993 | Hs.020821 |
| A_23_P5176 | FOLR1 | Homo sapiens folate receptor 1 (adult) (FOLR1), transcript variant 1, mRNA [NM_016725] | NM_016725 | ENST00000393679 | 2 348 | folate receptor 1 (adult) | chr11:7190726 8-71907327 | GO:0005903|GO:0005542|NM_016725 GO:0005886|GO:0005887| GO:0015884|GO:0005624| GO:0046655|GO:0005576| GO:0004872|GO:0046658 | | NP226704 | Hs.73769 |
| A_23_P3325429 | | Homo sapiens mRNA for T cell receptor beta variable 5, partial cds, clone: un 66. [AB306153] | AB306153 | | | | | GO:0006898 | | NP404580 | Hs.382212 |
| A_24_P277657 | GMPR | Homo sapiens guanosine monophosphate reductase (GMPR), mRNA [NM_006877] | NM_006877 | ENST00000540478 | 2766 | guanosine monophosphate reductase | chr6:16290766-16290825 | GO:0009409|GO:0016491|NM_006877 GO:0030955|GO:0003920| GO:0046872|GO:0009117| GO:0055114 | | THC2640768 | Hs.484741 |
| A_33_P3280346 | LOC100130857 | Homo sapiens cDNA FLJ39731 fis, clone SMINT2015745. [AK097050] | AK097050 | | 100130857 | hypothetical protein LOC100130857 | chr15:3226864 1-32268700 | | | THC2488237 | Hs.636752 |
| A_23_P254271 | TUBB6 | Homo sapiens tubulin, beta 6 (TUBB6), mRNA [NM_032525] | NM_032525 | ENST00000417736 | 84617 | tubulin, beta 6 | chr18:1232647 6-12326535 | GO:0051258|GO:0000166|NM_032525 GO:0005198|GO:0005874| GO:0003924|GO:0005525| GO:0007018 | | THC2493956 | Hs.193491 |
| A_33_P3383551 | SEC14L3 | SEC14-like 3 (S. cerevisiae) [Source: HGNC Symbol; Acc: 18655] [ENST00000415957] | AK131358 | ENST00000415957 | 266629 | SEC14-like 3 (S. cerevisiae) | chr22:3084400 5-30843946 | | | THC2508076 | Hs.505601 |
| A_33_P3256257 | KRTAP4-7 | Homo sapiens keratin associated protein 4-7 | NM_033061 | ENST00000391417 | 100132476 | keratin associated | chr17:3924083 1-39240890 | GO:0045095 | NM_033061 | THC2488799 | Hs.632746 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_24_P417007 | POLR2F | (KRTAP4-7), mRNA [NM_033061] *Homo sapiens* polymerase (RNA) II (DNA directed) polypeptide F (POLR2F), mRNA [NM_021974] | NM_021974 | ENST00000442738 | 5435 | protein 4-7 polymerase (RNA) II (DNA directed) polypeptide F | chr22:3836519 4-38365253 | GO:0030880|GO:0006368|NM_021974 GO:0006367|GO:0004672| GO:0003899|GO:0000398| GO:0005730|GO:0005665| GO:0005654|GO:0005634| GO:0003677 | | THC2612620 | Hs.436578 |
| A_33_P3485976 | | *Homo sapiens* CDNA FLJ37762 lis, clone BRHIP2024347, weakly similar to GALECTIN-3. [AK095081] | AK095081 | ENST00000528482 | | | chr11:1343577 50-134357809 | | | THC2629979 | Hs.504390 |
| A_33_P3374957 | KLF16 | *Homo sapiens* Kruppel-like factor 16 (KLF16), mRNA [NM_031918] | NM_031918 | ENST00000250916 | 83855 | Kruppel-like factor 16 | chr19:1852458-1852399 | GO:0005622|GO:0003700|NM_031918 GO:0006357|GO:0008270| GO:0005634|GO:0007212| GO:0046872|GO:0045449 | | THC2631959 | Hs.136280 |
| A_33_P3312799 | | Q9UMX8_HUMAN (Q9UMX8) Melanoma antigen, complete [THC2774746] | | | | | chr2:09545477 6-095454835 | | | THC2774746 | |
| A_33_P3331220 | | immunoglobulin heavy variable 3-35 (non-functional) [Source: HGNC Symbol ; Acc: 5598] [ENST00000390617] | Z46771 | ENST00000390617 | | | chr14:1068454 16-106845357 | | | NP1166158 | Hs.510635 |
| A_23_P406785 | C9orf50 | *Homo sapiens* chromosome 9 open reading frame 50 (C9orf50), mRNA[NM_199350] | NM_199350 | ENST00000372478 | 375759 | chromosome 9 open reading frame 50 | chr9:13237459 9-132374540 | | NM_199350 | THC2478134 | Hs.124223 |
| A_32_P107002 | RUNDC2A | *Homo sapiens* RUN domain containing 2A (RUNDC2A), mRNA [NM_032167] | NM_032167 | ENST00000502626 | 84127 | RUN domain containing 2A | chr16:1214597 8-12146037 | | NM_032167 | THC2476984 | Hs.458401 |
| A_33_P3279640 | HCN2 | *Homo sapiens* hyperpolarization activated cyclic nucleotide-gated potassium channel 2 (HCN2), mRNA [NM_001194] | NM_001194 | ENST00000251287 | 610 | hyperpolarization activated cyclic nucleotide-gated potassium channel 2 | chr19:617098-617157 | GO:0005515|GO:0005244|NM_001194 GO:0005272|GO:0007267| GO:0030955|GO:0031402| GO:0055085|GO:0030552| GO:0016020|GO:0000166| GO:0008076|GO:0005249| GO:0016021|GO:0006814| GO:0006813|GO:0006812 | | THC2473872 | Hs.124161 |
| A_23_P67952 | MYCNOS | *Homo sapiens* v-myc myelocytomatosis viral | NR_026766 | | 10408 | v-myc myelocytomatosis viral | chr2:16080141-16080082 | GO:0007275 | NR_026766 | THC2481543 | Hs.651453 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3371553 | FLJ32756 | related oncogene, neuro-blastoma derived (avian) opposite strand (MYCNOS), non-coding RNA [NR_026766] Homo sapiens cDNA FLJ32756 fis, clone TESTI2001758. [AK057318] | AK057318 | | 642757 | hypothetical LOC642757 | chr22:47310056-47309997 | | | THC2484067 | Hs.632786 |
| A_33_P33U267 | KRTAP19-2 | Homo sapiens keratin associated protein 19-2 (KRTAP19-2), mRNA [NM_181608] | NM_181608 | ENST00000334055 | 337969 | keratin associated protein 19-2 | chr21:31859568-31859509 | GO:0005882 | NM_181608 | THC2488580 | Hs.553692 |
| A_24_P41939 | | | | | | | chr9:081651996-081651936 | | | | |
| A_23_P74799 | SLC25A24 | Homo sapiens solute carrier family 25 (mitochondrial carrier; phosphate carrier), member 24 (SLC25A24), nuclear gene encoding mitochondrial protein, transcript variant 2, mRNA [NM_213651] | NM_213651 | ENST00000370041 | 29957 | solute carrier family 25 (mitochondrial carrier; phosphate carrier), member 24 | chr1:108677551-108677492 | GO:0005739\|GO:0016020\|NM_213651 GO:0005488\|GO:0005509 GO:0005743\|GO:0016021 GO:0055085 | | THC2477421 | Hs.656870 |
| A_23_P109133 | AVP | Homo sapiens arginine vasopressin (AVP), mRNA [NM_000490] | NM_000490 | ENST00000380293 | 551 | arginine vasopressin | chr20:3063624-3063391 | GO:0008284\|GO:0030307\|NM_000490 GO:0045471\|GO:0030819 GO:0007267\|GO:0031894 GO:0006091\|GO:0051970 GO:0031895\|GO:0007204 GO:0005615\|GO:0030425 GO:0014049\|GO:0003084 GO:0045907\|GO:0007626 GO:0006833\|GO:0007625 GO:0030141\|GO:0005185 GO:0042711\|GO:0030146 GO:0031394\|GO:0006950 GO:0032849\|GO:0042538 GO:0005625\|GO:0005576 GO:0043084\|GO:0002125 GO:0007165\|GO:0007186 GO:0050891\|GO:0035176 GO:0003078\|GO:0007621 GO:0035094 | | THC2480295 | Hs.89648 |
| A_33_P3368950 | LOC389333 | Homo sapiens hypo-thetical protein LOC389333 | NM_001161546 | ENST00000434752 | 389333 | hypothetical protein LOC389333 | chr5:138728725-138728666 | | NM_001161546 | THC2603790 | Hs.729482 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3322373 | GBGT1 | (LOC389333), mRNA [NM_001161546] Homo sapiens globoside alpha-1,3-N-acetylgalactosaminyltransferase 1 (GBGT1), mRNA [NM_021996] | NM_021996 | ENST00000372038 | 26301 | globoside alpha-1,3-N-acetylgalactosaminyltransferase 1 | chr9:13603691 4-136036855 | GO:0009247|GO:0030145|GO:0005794|GO:0016758|GO:0016020|GO:0005975|GO:0047277|GO:0016021|GO:0046872 | NM_021996 | THC2630024 | Hs.495419 |
| A_23_P214950 | PERP | Homo sapiens PERP, TP53 apoptosis effector (PERP), mRNA [NM_022121] | NM_022121 | ENST00000265603 | 64065 | PERP, TP53 apoptosis effector | chr6:13841211 5-138412056 | GO:0030057|GO:0005739|GO:0005515|GO:0030054|GO:0005794|GO:0005886|GO:0005887|GO:0006915|GO:0006917|GO:0007155 | NM_022121 | THC2545695 | Hs.201446 |
| A_33_P3250055 | MAPK12 | Homo sapiens cDNA, FLJ98809. [AK308768] | AK308768 | ENST00000395778 | 6300 | mitogen-activated protein kinase 12 | chr22:5069617 7-50696118 | | | THC2621046 | Hs.432642 |
| A_33_P3215797 | AHDC1 | Homo sapiens AT hook, DNA binding motif, containing 1 (AHDC1), mRNA[NM_001029882] | NM_001029882 | ENST00000482400 | 27245 | AT hook, DNA binding motif, containing 1 | chr1:27877922-27877863 | GO:0003677 | NM_001029882 | THC2470530 | Hs.469280 |
| A_33_P3333648 | OR51I2 | Homo sapiens olfactory receptor, family 51, subfamily I, member 2 (OR51I2), mRNA [NM_001004754] | NM_001004754 | ENST00000341449 | 390064 | olfactory receptor, family 51, subfamily I, member 2 | chr11:5475338-5475397 | GO:0007608|GO:0007165|GO:0004984|GO:0007186|GO:0005886|GO:0004872|GO:0016021|GO:0050896 | NM_001004754 | NP1461849 | Hs.553733 |
| A_33_P3345708 | CREB3L4 | Homo sapiens cAMP responsive element binding protein 3-like 4 (CREB3L4), mRNA [NM_130898] | NM_130898 | ENST00000368600 | 148327 | cAMP responsive element binding protein 3-like 4 | chr1:15394548 4-153945543 | GO:0043565|GO:0006986|GO:0006355|GO:0005794|GO:0003700|GO:0016020|GO:0005783|GO:0045944|GO:0046983|GO:0005634|GO:0016021|GO:0007283 | NM_130898 | THC2775729 | Hs.372924 |
| A_33_P3869455 | ATXN8 | Homo sapiens ataxin 8 (ATXN8) mRNA, partial cds. [DQ641254] | DQ641254 | | 724066 | ataxin 8 | chr13:7071208 9-70712030 | | | THC2561290 | Hs.645205 |
| A_33_P3281444 | | immunoglobulin kappa variable 10-43 [Source: HGNC Symbol; Acc: 5758] [ENST00000468879] | DQ100647 | ENST00000468879 | | | chr2:90249232-90249291 | | | | Hs.558199 |
| A_33_P3835524 | POU2F2 | Homo sapiens POU class 2 homeobox 2 (POU2F2), transcript variant 3, mRNA [NM_001207026] | NM_001207026 | ENST00000534559 | 5452 | POU class 2 homeobox 2 | chr19:4260000 0-42599941 | GO:0043565|GO:0006355|NM_001207026|GO:0005737|GO:0003700|GO:0006366|GO:0006959|GO:0005634 | NM_001207026 | THC2604353 | Hs.654420 |
| A_33_P3424507 | OR51F1 | Homo sapiens olfactory receptor, family 51, subfamily F, member 1 | NM_001004752 | ENST00000380383 | 256892 | olfactory receptor, family 51, subfamily F, | chr11:4790483-4790424 | GO:0007608|GO:0007165|NM_001004752|GO:0004984|GO:0007186|GO:0005886|GO:0004872 | NM_001004752 | NP1461808 | Hs.553659 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_23_P16225 | | (OR51F1), mRNA [NM_001004752] | | | | | | GO:0016021\|GO:0050896 | | | |
| | BEST2 | Homo sapiens bestrophin 2 (BEST2), mRNA [NM_017682] | NM_017682 | ENST00000549706 | 54831 | bestrophin 2 | chr19:1286898 1-12869040 | GO:0007608\|GO:0031404\|GO:0051899\|GO:0005886\|GO:0005509\|GO:0034707\|GO:0005254\|GO:0003674\|GO:0005929\|GO:0008150\|GO:0016021\|GO:0005216\|GO:0006811 | NM_017682 | THC2481764 | Hs.435611 |
| A_33_P3310976 | | | | | | member 1 | chr20:0605200 44-060520103 | | | | |
| A_23_P411113 | CNTNAP1 | Homo sapiens contactin associated protein 1 (CNTNAP1), mRNA [NM_003632] | NM_003632 | ENST00000264638 | 8506 | contactin associated protein 1 | chr17:4085161 1-40851671 | GO:0007165\|GO:0017124\|GO:0016020\|GO:0005887\|GO:0005070\|GO:0005102\|GO:0033270\|GO:0004872\|GO:0007155 | NM_003632 | THC2470788 | Hs.408730 |
| A_33_P3399005 | | | | | | | chr3:01160600 0-011605941 | | | THC2708197 | |
| A_33_P3316696 A_24_P353289 | C22orf13 | Homo sapiens chromosome 22 open reading frame 13 (C22orf13), mRNA [NM_031444] | NM_031444 | ENST00000490922 | 83606 | chromosome 22 open reading frame 13 | chr22:2493668 6-24936627 | | NM_031444 | THC2520972 | Hs.9850 |
| A_23_P47102 | ACY3 | Homo sapiens aspartoacylase (aminocyclase) 3 (ACY3), mRNA [NM_080658] | NM_080658 | ENST00000255082 | 91703 | aspartoacylase (aminocyclase) 3 | chr11:6741255 5-67412321 | GO:0016324\|GO:0005737\|GO:0019807\|GO:0016788\|GO:0005624\|GO:0008270\|GO:0004046\|GO:0046872\|GO:0042802 | NM_080658 | THC2491201 | Hs.126265 |
| A_24_P373885 | C19orf25 | Homo sapiens chromosome 19 open reading frame 25 (C19orf25), mRNA [NM_152482] | NM_152482 | ENST00000335104 | 148223 | chromosome 19 open reading frame 25 | chr19:1474952-1474893 | GO:0005515 | NM_152482 | THC2617463 | Hs.532840 |
| A_23_P135239 | TLE1 | Homo sapiens transducin-like enhancer of split 1 (E(sp1)homolog, Drosophila) (TLE1), mRNA [NM_005077] | NM_005077 | ENST00000355002 | 7088 | transducin-like enhancer of split 1 (E(spl) homolog, Drosophila) | chr9:84199177-84199118 | GO:0007165\|GO:0005667\|GO:0003714\|GO:0003682\|GO:0030178\|GO:0016481\|GO:0009887\|GO:0007275\|GO:0005634\|GO:0000122\|GO:0008134 | NM_005077 | THC2776653 | Hs.197320 |
| A_33_P3258316 | LOC100507269 | PREDICTED: Homo sapiens hypothetical protein LOC100507269 (LOC100507269), mRNA [XM_003118986] | XM_003118986 | | 100507269 | hypothetical protein LOC100507269 | chr7:55812467-55812408 | | XM_003118986 | THC2558116 | Hs.730469 |
| A_23_P259506 | C5orf32 | Homo sapiens chromosome 5 open reading frame 32 (C5orf32), mRNA [NM_032412] | NM_032412 | ENST00000261811 | 84418 | chromosome 5 open reading frame 32 | chr5:13962312 6-139623185 | | NM_032412 | THC2580943 | Hs.529798 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P370435 | HIGD2B | *Homo sapiens* HIG1 hypoxia inducible domain family, member 2B (pseudogene) (HIGD2B), non-coding RNA [NR_002780] | NR_002780 | ENST00000311755 | 123346 | HIG1 hypoxia inducible domain family, member 2B (pseudogene) | chr15:72968273-72968214 | GO:0016020|GO:0016021 | NR_002780 | THC2609380 | Hs.434111 |
| A_23_P106258 | SLC25A47 | *Homo sapiens* solute carrier family 25, member 47 (SLC25A47), mRNA [NM_207117] | NM_207117 | ENST00000361529 | 283600 | solute carrier family 25, member 47 | chr14:100796235-100796294 | GO:0005739|GO:0005215|GO:0016020|GO:0005488|GO:0005743|GO:0016021|GO:0055085 | NM_207117 | THC2624616 | Hs.108268 |
| A_33_P3408237 | | Q71V99_HUMAN (Q71V99) Cyclophilin, partial (12%) [THC2560329] | | | | | chr11:04348892-04348981 | | | THC2560329 | |
| A_33_P3297345 | TTC24 | *Homo sapiens* tetratricopeptide repeat domain 24 (TTC24), mRNA [NM_001105669] | NM_001105669 | ENST00000368236 | 164118 | tetratricopeptide repeat domain 24 | chr1:156556503-156556562 | GO:0005488 | NM_001105669 | THC2645990 | Hs.447851 |
| A_23_P85441 | IGSF9 | *Homo sapiens* immunoglobulin superfamily, member 9 (IGSF9), transcript variant 2, mRNA [NM_020789] | NM_020789 | ENST00000198587 | 57549 | immunoglobulin superfamily, member 9 | chr1:159896995-159896936 | GO:0030054|GO:0005886|GO:0045202|GO:0007275|GO:0016021|GO:0030425|GO:0030154|GO:0016358|GO:0007399 | NM_020789 | THC2473023 | Hs.591472 |
| A_23_P502350 | RFX2 | *Homo sapiens* regulatory factor X, 2 (influences HLA class II expression) (RFX2), transcript variant 1, mRNA [NM_000635] | NM_000635 | ENST00000303657 | 5990 | regulatory factor X, 2 (influences HLA class II expression) | chr19:5993250-5993191 | GO:0006355|GO:0030528|GO:0005634|GO:0003677 | NM_000635 | THC2466761 | Hs.465709 |
| A_33_P3355816 | ITGA4 | *Homo sapiens* integrin, alpha 4 (antigen CD49D, alpha 4 subunit of VLA-4 receptor) (ITGA4), mRNA [NM_000885] | NM_000885 | | 3676 | integrin, alpha 4 (antigen CD49D, alpha 4 subunit of VLA-4 receptor) | chr2:182402273-182402334 | GO:0008305|GO:0005886|GO:0005509|GO:0042802|GO:0007507|GO:0016477|GO:0001974|GO:0007229|GO:0030183|GO:0007159|GO:0004872|GO:0016021|GO:0001968|GO:0007155|GO:0007157|GO:0009897 | NM_000885 | THC2465069 | Hs.440955 |
| A_33_P3363645 | MGAT1 | *Homo sapiens* mannosyl (alpha-1,3-)-glycoprotein beta-1,2-N-acetylglucos-aminyltransferase (MGAT1), transcript variant 1, mRNA [NM_001114618] | NM_001114618 | ENST00000504385 | 4245 | mannosyl (alpha-1,3-)-glycoprotein beta 1,2-N-acetylglu-cosaminyl-transferase | chr5:180235948-180235889 | GO:0003827|GO:0005794|GO:0016020|GO:0000139|GO:0016757|GO:0005975|GO:0016021|GO:0006487 | NM_001114618 | THC2513235 | Hs.519818 |
| A_23_P93562 | SESN1 | *Homo sapiens* sestrin 1 (SESN1), transcript variant 1, mRNA [NM_014454] | NM_014454 | ENST00000302071 | 27244 | sestrin 1 | chr6:109308536-109308477 | GO:0008285|GO:0007050|GO:0005634|GO:0006974 | NM_014454 | THC2467659 | Hs.591336 |
| A_33_P3420852 | KIRREL2 | *Homo sapiens* kin of IRRE like 2 (*Drosophila*) | NM_199180 | ENST00000360202 | 84063 | kin of IRRE like 2 | chr19:36357335-36357394 | GO:0005886|GO:0016021|GO:0007155 | NM_199180 | THC2603242 | Hs.145729 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3227010 | | (KIRREL2), transcript variant 3, mRNA [NM_199180] | | | | (Drosophila) | chr2:07311423 4-073114175 | | | | |
| A_23_P162596 | ACTR6 | Homo sapiens ARP6 actin-related protein 6 homolog (yeast) (ACTR6), mRNA [NM_022496] | NM_022496 | ENST00000188312 | 64431 | ARP6 actin-related protein 6 homolog (yeast) | chr12:1006180 04-100618063 | GO:0005515|GO:0005737|NM_022496 GO:0005856 | | THC2519245 | Hs.115088 |
| A_24_P923251 | TGM2 | Homo sapiens transglutaminase 2 (C polypeptide, protein-glutamine-gamma-glutamyltransferase) (TGM2), transcript variant 2, mRNA [NM_198951] | NM_198951 | ENST00000468262 | 7052 | transglutaminase 2 (C polypeptide, protein-glutamine-gamma-glutamyl-transferase) | chr20:36766650 5-36766446 | GO:0005886|GO:0005509|NM_198951 GO:0019904|GO:0006917 GO:0005525|GO:0048661 GO:0045785|GO:0005739 GO:0018149|GO:0001974 GO:0051482|GO:0003810 GO:0050729|GO:0051260 GO:0018153|GO:0043123 GO:0016740|GO:0008415 | | THC2659478 | Hs.517033 |
| A_23_P211345 | TBX1 | Homo sapiens T-box 1 (TBX1), transcript variant C, mRNA [NM_080647] | NM_080647 | ENST00000332710 | 6899 | T-box 1 | chr22:1975478 8-19754847 | GO:0003700|GO:0006357|NM_080647 GO:0003702|GO:0005634 GO:0048538|GO:0048703 GO:0009653|GO:0042803 GO:0060037|GO:0007507 GO:0043565|GO:0060017 GO:0060023 | | THC2477322 | Hs.173984 |
| A_23_P344853 | WDR43 | Homo sapiens WD repeat domain 43 (WDR43), mRNA [NM_015131] | NM_015131 | ENST00000407426 | 23160 | WD repeat domain 43 | chr2:29170870-29170929 | GO:0005730|GO:0005634 NM_015131 | | THC2553340 | Hs.709228 |
| A_33_P3303086 | HNRPLL | Homo sapiens heterogeneous nuclear ribonucleoprotein L-like (HNRPLL), transcript variant 1, mRNA [NM_138394] | NM_138394 | ENST00000272249 | 92906 | heterogeneous nuclear ribonucleoprotein L-like | chr2:38790718-38790659 | GO:0006397|GO:0005515|NM_138394 GO:0000166|GO:0030529 GO:0005634|GO:0003729 GO:0033120 | | NP1156896 | Hs.445497 |
| A_23_P201211 | FCRL5 | Homo sapiens Fc receptor-like 5 (FCRL5), transcript variant 1, mRNA[NM_031281] | NM_031281 | ENST00000461387 | 83416 | Fc receptor-like 5 | chr1:15748329 7-157483238 | GO:0005886|GO:0004872|NM_031281 GO:0016021 | | THC2617135 | Hs.415950 |
| A_33_P3395823 | KCNQ2 | Homo sapiens potassium voltage-gated channel, KQT-like subfamily, member 2 (KCNQ2), transcript variant 5, mRNA [NM_172109] | NM_172109 | ENST00000344425 | 3785 | potassium voltage-gated channel, KQT-like subfamily, member 2 | chr20:6206515 7-62065098 | GO:0005244|GO:0016020|NM_172109 GO:0008076|GO:0005249 GO:0007268|GO:0030955 GO:0016021|GO:0055085 GO:0006813|GO:0007399 | | THC2474136 | Hs.161851 |
| A_33_P3314481 | | Homo sapiens mRNA for T cell receptor alpha variable 19, partial cds, | AB305728 | ENST00000390447 | | | chr14:2247631 1-22476370 | GO:0006811 | | NP1074392 | Hs.495021 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq-Accession | TIGRID | UniGene ID |
|---|---|---|---|---|---|---|---|---|---|---|---|
| A_33_P3300142 | ANKFY1 | clone: SEB 274. [AB305728] Homo sapiens ankyrin repeat and FYVE domain containing 1 (ANKFY1), transcript variant 1, mRNA [NM_016376] | NM_016376 | ENST00000341657 | 51479 | ankyrin repeat and FYVE domain containing 1 | chr17:4066776-4066717 | GO:0005515\|GO:0005737\|NM_016376\|GO:0016020\|GO:0008270\|GO:0046872\|GO:0010008\|GO:0019898\|GO:0005768 | | THC2638444 | Hs.696087 |
| A_33_P3375646 | | GTP binding protein 6 (putative) [Source: HGNC Symbol; Acc: 30189] [ENST00000485332] | XM_003120165 | ENST00000485332 | | | chrY:179213-179154 | | XM_003120165 | THC2551411 | Hs.437145 |
| A_23_P347632 | MTSS1 | Homo sapiens metastasis suppressor 1 (MTSS1), mRNA [NM_014751] | NM_014751 | ENST00000520771 | 9788 | metastasis suppressor 1 | chr8:12556331 4-125563255 | GO:0017124\|GO:0030036\|NM_014751\|GO:0005102\|GO:0006928\|GO:0030139\|GO:0015629\|GO:0001726\|GO:0003785\|GO:0007165\|GO:0005737\|GO:0046847\|GO:0007155\|GO:0007169\|GO:0008093 | | THC2487877 | Hs.336994 |
| A_24_P368544 | SLC25A26 | Homo sapiens solute carrier family 25, member 26 (SLC25A26), nuclear gene encoding mitochondrial protein, transcript variant 1, mRNA [NM_173471] | NM_173471 | ENST00000336733 | L15286 | solute carrier family 25, member 26 | chr3:66428767-66428826 | | NM_173471 | THC2463927 | Hs.379386 |
| A_33_P3546161 | C8orf67 | RC2-BT0841-021000-012-C08 BT0841 Homo sapiens cDNA, mRNA sequence [BF742660] | BF742660 | | 619338 | chromosome 8 open reading frame 67 | chr8:675800-675859 | | | THC2707252 | Hs.678836 |
| A_24_P174341 | CCNT2 | Homo sapiens cyclin 12 (CCNT2), transcript variant b, mRNA [NM_058241] | NM_058241 | ENST00000419781 | 905 | cyclin T2 | chr2:13571365 2-135713711 | GO:0005515\|GO:0007049\|NM_058241\|GO:0005737\|GO:0006366\|GO:0044419\|GO:0005730\|GO:0005654\|GO:0005634\|GO:0000079\|GO:0045449\|GO:0051301 | | THC2631629 | Hs.591241 |
| A_24_P3461 | LOC100507496 | chromosome 5 open reading frame 60 [Source: HGNC Symbol; Acc: 27753] [ENST00000511063] | AK093197 | ENST00000425471 | 100507496 | putative uncharacterized protein FLJ35723-like | chr5:17907890 2-179078961 | | | THC2510113 | Hs.631949 |
| A_33_P3291414 | | PREDICTED: Homo sapiens hypothetical protein LOC100507023 (LOC100507023), mRNA [XM_003118886] | XM_003118886 | | | | chr12:1331296 93-133129752 | | XM_003118886 | THC2626595 | Hs.678863 |
| A_23_P316381 | ACOX3 | Homo sapiens acyl-CoA oxidase 3, pristanoyl (ACOX3), transcript | NM_003501 | ENST00000356406 | 8310 | acyl-CoA oxidase 3, pristanoyl | chr4:8368669-8368610 | GO:0006629\|GO:0006635\|NM_003501\|GO:0050660\|GO:0006631\|GO:0003997\|GO:0008206 | | THC2463761 | Hs.479122 |

APPENDIX C-continued

FEMALES: Technology: Agilent.SingleColor.26652
Created On: Tue Jan 31 14:14:22 EST 2012

| ProbeName | Gene | Description | Gb Accession | EnsemblID | Entrez GeneID | Gene Name | Genomic Coordinates | Go | RefSeq- Accession | TIGRID | UniGene ID |
|---|---|---|---|---|---|---|---|---|---|---|---|
| | | variant 1, mRNA [NM_003501] | | | | | | GO:0003995|GO:0055114| GO:0005777 | | | |
| A_33_P3228564 | DOK3 | Homo sapiens docking protein 3 (DOK3), transcript variant 2, mRNA [NM_001144875] | NM_001144875 | ENST00000312943 | 79930 | docking protein 3 | chr5:17693022 3-176930164 | GO:0005515|GO:0005737|GO:0005886|GO:0005158| GO:0007265 | NM_001144875 | THC2482593 | Hs.720849 |
| A_33_P3388283 | HMGCL | 3-hydroxymethyl-3-methylglutaryl CoA lyase [Source: HGNC Symbol; Acc: 5005] [ENST00000496907] | | ENST00000496907 | 3155 | 3-hydroxymethyl-3-methylglutaryl-CoA lyase | chr1:24133704-24133645 | | | THC2522126 | |
| A_33_P3376273 | GK | glycerol kinase [Source: HGNC Symbol; Acc: 4289] [ENST00000378941] | | ENST00000378941 | 2710 | glycerol kinase | chrX:30696155-30696214 | | | | |

APPENDIX D

| Name | Accession | Comment |
|---|---|---|
| ACTB\|0 | NM_001101.2 | Normalizer |
| B2M\|0 | NM_004048.2 | Normalizer |
| ebv-miR-BART16\|0.008 | | MIMAT0003714 |
| ebv-miR-BART6-5p\|0 | | MIMAT0003414 |
| GAPDH\|0 | NM_002046.3 | Normalizer |
| hcmv-miR-UL112\|0 | | MIMAT0001577 |
| hcmv-miR-US5-2\|0 | | MIMAT0001580 |
| hiv1-miR-TAR-3p\|0 | | MIMAT0006017 |
| hsa-let-7b\|0 | | MIMAT0000063 |
| hsa-let-7c\|0 | | MIMAT0000064 |
| hsa-let-7d\|0 | | MIMAT0000065 |
| hsa-let-7e\|0.009 | | MIMAT0000066 |
| hsa-let-7g\|0 | | MIMAT0000414 |
| hsa-let-7i\|0 | | MIMAT0000415 |
| hsa-miR-101\|0 | | MIMAT0000099 |
| hsa-miR-103\|0 | | MIMAT0000101 |
| hsa-miR-106b\|0 | | MIMAT0000680 |
| hsa-miR-107\|0 | | MIMAT0000104 |
| hsa-miR-10a\|0 | | MIMAT0000253 |
| hsa-miR-10b\|0 | | MIMAT0000254 |
| hsa-miR-1180\|0 | | MIMAT0005825 |
| hsa-miR-1205\|0 | | MIMAT0005869 |
| hsa-miR-1206\|0 | | MIMAT0005870 |
| hsa-miR-122\|0 | | MIMAT0000421 |
| hsa-miR-1244\|0 | | MIMAT0005896 |
| hsa-miR-126\|0 | | MIMAT0000445 |
| hsa-miR-1266\|0 | | MIMAT0005920 |
| hsa-miR-1283\|0 | | MIMAT0005799 |
| hsa-miR-1297\|0 | | MIMAT0005886 |
| hsa-miR-1302\|0 | | MIMAT0005890 |
| hsa-miR-1307\|0 | | MIMAT0005951 |
| hsa-miR-130b\|0 | | MIMAT0000691 |
| hsa-miR-132\|0.009 | | MIMAT0000426 |
| hsa-miR-136\|0 | | MIMAT0000448 |
| hsa-miR-137\|0 | | MIMAT0000429 |
| hsa-miR-140-3p\|0 | | MIMAT0004597 |
| hsa-miR-142-3p\|0 | | MIMAT0000434 |
| hsa-miR-144\|0 | | MIMAT0000436 |
| hsa-miR-145\|0 | | MIMAT0000437 |
| hsa-miR-148a\|0 | | MIMAT0000243 |
| hsa-miR-151-3p\|0 | | MIMAT0000757 |
| hsa-miR-1537\|0 | | MIMAT0007399 |
| hsa-miR-154\|0 | | MIMAT0000452 |
| hsa-miR-15a\|0 | | MIMAT0000068 |
| hsa-miR-181b+ hsa-miR-181d\|0 | | MIMAT0000257 |
| hsa-miR-183\|0 | | MIMAT0000261 |
| hsa-miR-185\|0 | | MIMAT0000455 |
| hsa-miR-186\|0 | | MIMAT0000456 |
| hsa-miR-18a\|0 | | MIMAT0000072 |
| hsa-miR-1914\|0 | | MIMAT0007889 |
| hsa-miR-193a-3p\|0.02 | | MIMAT0000459 |
| hsa-miR-196a\|0.009 | | MIMAT0000226 |
| hsa-miR-199a-3p + hsa-miR-199b-3p\|0 | | MIMAT0000232 |
| hsa-miR-19a\|0 | | MIMAT0000073 |
| hsa-miR-19b\|0 | | MIMAT0000074 |
| hsa-miR-200b\|0 | | MIMAT0000318 |
| hsa-miR-206\|0 | | MIMAT0000462 |
| hsa-miR-208a\|0 | | MIMAT0000241 |
| hsa-miR-21\|0 | | MIMAT0000076 |
| hsa-miR-2114\|0 | | MIMAT0011156 |
| hsa-miR-215\|0 | | MIMAT0000272 |
| hsa-miR-221\|0 | | MIMAT0000278 |
| hsa-miR-222\|0 | | MIMAT0000279 |
| hsa-miR-223\|0 | | MIMAT0000280 |
| hsa-miR-23a\|0 | | MIMAT0000078 |
| hsa-miR-25\|0 | | MIMAT0000081 |
| hsa-miR-28-5p\|0 | | MIMAT0000085 |
| hsa-miR-29b\|0 | | MIMAT0000100 |
| hsa-miR-29c\|0 | | MIMAT0000681 |
| hsa-miR-300\|0 | | MIMAT0004903 |
| hsa-miR-30a\|0 | | MIMAT0000087 |
| hsa-miR-30b\|0 | | MIMAT0000420 |
| hsa-miR-30c\|0 | | MIMAT0000244 |
| hsa-miR-30d\|0 | | MIMAT0000245 |
| hsa-miR-30e\|0 | | MIMAT0000692 |
| hsa-miR-32\|0 | | MIMAT0000090 |
| hsa-miR-320a\|0 | | MIMAT0000510 |
| hsa-miR-320b\|0 | | MIMAT0005792 |
| hsa-miR-320c\|0.028 | | MIMAT0005793 |
| hsa-miR-320d\|0 | | MIMAT0006764 |
| hsa-miR-324-3p\|0 | | MIMAT0000762 |
| hsa-miR-324-5p\|0 | | MIMAT0000761 |
| hsa-miR-326\|0 | | MIMAT0000756 |
| hsa-miR-330-5p\|0 | | MIMAT0004693 |
| hsa-miR-331-3p\|0 | | MIMAT0000760 |
| hsa-miR-335\|0 | | MIMAT0000765 |
| hsa-miR-342-3p\|0 | | MIMAT0000753 |
| hsa-miR-34b\|0 | | MIMAT0004676 |
| hsa-miR-34c-5p\|0 | | MIMAT0000686 |
| hsa-miR-361-5p\|0 | | MIMAT0000703 |
| hsa-miR-362-3p\|0 | | MIMAT0004683 |
| hsa-miR-363\|0 | | MIMAT0000707 |
| hsa-miR-372\|0 | | MIMAT0000724 |
| hsa-miR-374a\|0 | | MIMAT0000727 |
| hsa-miR-377\|0 | | MIMAT0000730 |
| hsa-miR-378\|0 | | MIMAT0000732 |
| hsa-miR-379\|0 | | MIMAT0000733 |
| hsa-miR-381\|0 | | MIMAT0000736 |
| hsa-miR-383\|0 | | MIMAT0000738 |
| hsa-miR-409-3p\|0 | | MIMAT0001639 |
| hsa-miR-410\|0 | | MIMAT0002171 |
| hsa-miR-423-3p\|0 | | MIMAT0001340 |
| hsa-miR-425\|0 | | MIMAT0003393 |
| hsa-miR-431\|0 | | MIMAT0001625 |
| hsa-miR-450b-5p\|0 | | MIMAT0004909 |
| hsa-miR-453\|0 | | MIMAT0001630 |
| hsa-miR-455-3p\|0 | | MIMAT0004784 |
| hsa-miR-485-3p\|0.01 | | MIMAT0002176 |
| hsa-miR-486-3p\|0 | | MIMAT0004762 |
| hsa-miR-494\|0.025 | | MIMAT0002816 |
| hsa-miR-495\|0 | | MIMAT0002817 |
| hsa-miR-517c+hsa-miR-519a\|0 | | MIMAT0002866 |
| hsa-miR-518f\|0 | | MIMAT0002842 |
| hsa-miR-520d-5p + hsa-miR-527+hsa-miR-518a-5p\|0 | | MIMAT0002855 |
| hsa-miR-526a + hsa-miR-518d-5p+hsa-miR-520c-5p\|0 | | MIMAT0002845 |
| hsa-miR-532-5p\|0 | | MIMAT0002888 |
| hsa-miR-539\|0 | | MIMAT0003163 |
| hsa-miR-542-3p\|0 | | MIMAT0003389 |
| hsa-miR-542-5p\|0 | | MIMAT0003340 |
| hsa-miR-544\|0.049 | | MIMAT0003164 |
| hsa-miR-548a-3p\|0 | | MIMAT0003251 |
| hsa-miR-548a-5p\|0 | | MIMAT0004803 |
| hsa-miR-548b-3p\|0 | | MIMAT0003254 |
| hsa-miR-548f\|0 | | MIMAT0005895 |
| hsa-miR-548g\|0 | | MIMAT0005912 |
| hsa-miR-548h\|0 | | MIMAT0005928 |
| hsa-miR-551b\|0 | | MIMAT0003233 |
| hsa-miR-553\|0 | | MIMAT0003216 |
| hsa-miR-555\|0 | | MIMAT0003219 |
| hsa-miR-563\|0 | | MIMAT0003227 |
| hsa-miR-566\|0 | | MIMAT0003230 |
| hsa-miR-570\|0 | | MIMAT0003235 |
| hsa-miR-576-5p\|0 | | MIMAT0003241 |
| hsa-miR-589\|0 | | MIMAT0004799 |
| hsa-miR-590-5p\|0.029 | | MIMAT0003258 |
| hsa-miR-591\|0 | | MIMAT0003259 |
| hsa-miR-595\|0 | | MIMAT0003263 |
| hsa-miR-600\|0 | | MIMAT0003268 |
| hsa-miR-601\|0 | | MIMAT0003269 |
| hsa-miR-603\|0.016 | | MIMAT0003271 |
| hsa-miR-613\|0 | | MIMAT0003281 |
| hsa-miR-615-5p\|0 | | MIMAT0004804 |
| hsa-miR-619\|0 | | MIMAT0003288 |
| hsa-miR-648\|0 | | MIMAT0003318 |
| hsa-miR-651\|0 | | MIMAT0003321 |
| hsa-miR-655\|0 | | MIMAT0003331 |
| hsa-miR-656\|0 | | MIMAT0003332 |
| hsa-miR-659\|0 | | MIMAT0003337 |
| hsa-miR-660\|0 | | MIMAT0003338 |
| hsa-miR-664\|0.018 | | MIMAT0005949 |
| hsa-miR-759\|0 | | MIMAT0010497 |

APPENDIX D-continued

| Name | Accession | Comment |
|---|---|---|
| hsa-miR-764\|0 | | MIMAT0010367 |
| hsa-miR-767-5p\|0 | | MIMAT0003882 |
| hsa-miR-769-5p\|0 | | MIMAT0003886 |
| hsa-miR-875-5p\|0 | | MIMAT0004922 |
| hsa-miR-877\|0 | | MIMAT0004949 |
| hsa-miR-892b\|0 | | MIMAT0004918 |
| hsa-miR-92a\|0 | | MIMAT0000092 |
| hsa-miR-92b\|0 | | MIMAT0003218 |
| hsa-miR-934\|0 | | MIMAT0004977 |
| hsa-miR-96\|0 | | MIMAT0000095 |
| hsa-miR-99a\|0 | | MIMAT0000097 |
| hsv1-miR-H1\|0 | | MIMAT0003744 |
| kshv-miR-K12-4-5p\|0 | | MIMAT0002191 |
| kshv-miR-K12-7\|0 | | MIMAT0002187 |
| kshv-miR-K12-9\|0 | | MIMAT0002185 |
| RPL19\|0 | NM_000981.3 | Normalizer |

APPENDIX E

Sequence Description hsa-miR-142-3p
hsa-miR-150
hsa-miR-144
hsa-miR-720
hsa-miR-145
hsa-miR-23a
hsa-miR-191
hsa-miR-192
hsa-miR-30c
hsa-miR-223
hsa-miR-151-3p
hsa-miR-30b
hsa-miR-19b
hsa-miR-342-3p
hsa-miR-296-5p

APPENDIX E-continued

Sequence Description hsa-miR-423-3p
hsa-miR-425
hsa-miR-19a
hsa-miR-186
hsa-miR-146a
hsa-miR-26a
hsa-miR-151-5p
hsa-miR-194
hsa-miR-374b
hsa-miR-25
hsa-miR-320d
hsa-miR-142-5p
hsa-miR-532-3p
hsa-miR-328
hsa-miR-1307
hsa-miR-30a
hsa-miR-574-3p
hsa-miR-484
ebv-miR-BART9
hsa-miR-21
hsa-miR-26b
hsa-miR-103
hsa-miR-93
hsa-let-7d
hsa-let-7f
hsa-let-7g
hsa-miR-20a + hsa-miR-20b
hsa-miR-15a
hsa-miR-222
hsa-miR-30e
hsa-miR-106b
hsa-miR-148a
hsa-miR-490-3p
hsa-let-7i
hsa-let-7b
hsa-miR-126
hsa-miR425b

APPENDIX F

BULLET POINTS

By using a Support Vector Machine classification algorithm, patients and controls were stratified with an average success rate of roughly 90% using an N-Fold validation, Subjects were segragated into gender before classification attempts.

| | Females | | Males | |
|---|---|---|---|---|
| Total successful prediction rate | 91.0% | | 89.9% | |
| Successful control prediction rate | 93.5% | | 93.8% | |
| Successful patient prediction rate | 89.4% | | 85.8% | |
| Average confidence of false predictions | 78.0% | | 79.0% | |
| Average confidence of true predictions | 89.0% | | 94.0% | |
| | | range | | range |
| average age control | 48.90 | 29-67 | 48.30 | 31-67 |
| average age patient | 45.70 | 22-58 | 47.10 | 29-65 |
| SVM parameters | | | | |

Kernel; Linear
Iterations; 1,000,000
Cost; 200
Repeats; 100
Ratio; 1.0
Kernel parameter 1; 0.1
Kernel parameter 2; 1
Exponent; 2
Sigma; 1
N-Fold; 3

| Subject Identifier | Subject Value | Predicted Value | Confidence | Prediction Result | Age |
|---|---|---|---|---|---|
| C55 f50 1835_2 | [control female] | [control, female] | 1 | T | 50 |
| C55-3 f50 4157_4 | [control, female] | [control female] | 1 | T | 50 |
| CFP P3 f47 2536_1 | [patient, female] | [patient, female] | 1 | T | 47 |
| Shm EC f32 2528_2 | [patient, female] | [patient, female] | 1 | T | 32 |

APPENDIX F-continued

BULLET POINTS
By using a Support Vector Machine classification algorithm, patients and controls were stratified with an average success rate of roughly 90% using an N-Fold validation, Subjects were segragated into gender before classification attempts.

| | | | | | |
|---|---|---|---|---|---|
| Shm127 f44 2521_3 | [patient, female] | [patient, female] | 1 | T | 44 |
| Shm163 f47 2520_1 | [patient, female] | [patient, female] | 1 | T | 47 |
| Shm212-2 f35 2521_4 | [patient, female] | [patient, female] | 1 | T | 35 |
| Shm233 f53 2533_4 | [patient, female] | [patient, female] | 1 | T | 53 |
| Shm234 f56 2534_1 | [patient, female] | [patient, female] | 1 | T | 56 |
| Shm250 f44 2535_1 | [patient, female] | [patient, female] | 1 | T | 44 |
| Shm262 f50 4908_4 | [patient, female] | [patient, female] | 1 | T | 50 |
| Shm269 f45 4392_4 | [patient, female] | [patient, female] | 1 | T | 45 |
| Shm270 f54 4909_2 | [patient, female] | [patient, female] | 1 | T | 54 |
| Shm283 f42 2519_2 | [patient, female] | [patient, female] | 1 | T | 42 |
| Shm284 f30 4909_4 | [patient, female] | [patient, female] | 1 | T | 30 |
| Shm290 f52 4910_4 | [patient, female] | [patient, female] | 1 | T | 52 |
| Shm293 f53 4158_3 | [patient, female] | [patient, female] | 1 | T | 53 |
| Shm295 f33 2519_4 | [patient, female] | [patient, female] | 1 | T | 33 |
| Shm306 f58 2518_4 | [patient, female] | [patient, female] | 1 | T | 58 |
| Shm309 f52 4158_1 | [patient, female] | [patient, female] | 1 | T | 52 |
| Shm309 f52 4160_2 | [patient, female] | [patient, female] | 1 | T | 52 |
| Shm337 f50 4390_2 | [patient, female] | [patient, female] | 1 | T | 50 |
| Shm78 f42 2521_2 | [patient, female] | [patient, female] | 1 | T | 42 |
| Shm9 f40 2522_4 | [patient, female] | [patient, female] | 1 | T | 40 |
| ShmA17 f53 2525_2 | [patient, female] | [patient, female] | 1 | T | 53 |
| C46-1 f55 2542_3 | [control, female] | [control, female] | 0.99 | T | 55 |
| C62 f31 1839_4 | [control, female] | [control, female] | 0.99 | T | 31 |
| Shm319 f53 2520_2 | [patient, female] | [patient, female] | 0.99 | T | 53 |
| Shm319 f53 4157_3 | [patient, female] | [patient, female] | 0.99 | T | 53 |
| C46-3 f55 2534_2 | [control, female] | [control, female] | 0.98 | T | 55 |
| C62 f31 2541_3 | [control, female] | [control, female] | 0.98 | T | 31 |
| CCC799 f56 2523_4 | [control, female] | [control, female] | 0.98 | T | 56 |
| Shm258 f50 4393_2 | [patient, female] | [control, female] | 0.98 | F | 50 |
| PCC405 f55 2535_4 | [patient, female] | [patient, female] | 0.98 | T | 55 |
| C73-1 f38 4156_4 | [control, female] | [control, female] | 0.97 | T | 38 |
| CCC799 f56 2536_2 | [control, female] | [control, female] | 0.97 | T | 56 |
| ShmA10 f38 2522_1 | [patient, female] | [control, female] | 0.97 | F | 38 |
| Shm246-1 f52 1839_2 | [patient, female] | [patient, female] | 0.97 | T | 52 |
| C46-2 f55 2530_1 | [control, female] | [control, female] | 0.96 | T | 55 |
| Shm276 f35 4391_4 | [patient, female] | [patient, female] | 0.96 | T | 35 |
| C93-1 f67 4909_1 | [control, female] | [control, female] | 0.95 | T | 67 |
| Shm325-3 f52 4160_4 | [patient, female] | [patient, female] | 0.94 | T | 52 |
| Shm144 f56 2528_4 | [patient, female] | [control, female] | 0.92 | F | 56 |
| C47 f34 2528_1 | [control, female] | [control, female] | 0.90 | T | 34 |
| Shm349 f50 4389_2 | [patient, female] | [patient, female] | 0.90 | T | 50 |
| C93-2 f67 4389_3 | [control, female] | [control, female] | 0.88 | T | 67 |
| Shm212 f35 2542_2 | [patient, female] | [patient, female] | 0.88 | T | 35 |
| Shm246-2 f52 2542_4 | [patient, female] | [patient, female] | 0.88 | T | 52 |
| C73-2 f38 43923 | [control, female] | [control, female] | 0.87 | T | 38 |
| C45-2 f43 2531_3 | [control, female] | [control, female] | 0.86 | T | 43 |
| C105 f59 4909_3 | [control, female] | [control, female] | 0.85 | T | 59 |
| Shm151 f22 1836_3 | [patient, female] | [patient, female] | 0.85 | T | 22 |
| PCC405 f55 2524_4 | [patient, female] | [patient, female] | 0.84 | T | 55 |
| Shm271 f46 4392_2 | [patient, female] | [patient, female] | 0.84 | T | 46 |
| TW-1 f45 2531_4 | [patient, female] | [patient, female] | 0.82 | T | 45 |
| TW-2 f45 2533_2 | [patient, female] | [patient, female] | 0.82 | T | 45 |
| C51 f32 1837_4 | [control, female] | [patient, female] | 0.81 | F | 32 |
| C45-1 f43 2542_1 | [control, female] | [control, female] | 0.81 | T | 43 |
| CCC765 f52 2523_1 | [control, female] | [control, female] | 0.80 | T | 52 |
| C108 f64 4910_1 | [control, female] | [control, female] | 0.79 | T | 64 |
| C71-1 f53 2518_2 | [control, female] | [control, female] | 0.78 | T | 53 |
| Shm260 f45 4393_4 | [patient, female] | [patient, female] | 0.77 | T | 45 |
| CCC765 f52 2537_4 | [control, female] | [control, female] | 0.76 | T | 52 |
| C57 f45 2541_2 | [control, female] | [control, female] | 0.74 | T | 45 |
| C68-1 f29 2519_1 | [control, female] | [patient, female] | 0.73 | F | 29 |
| C57 f45 1838_4 | [control, female] | [control, female] | 0.72 | T | 45 |
| C71-2 f53 4159_4 | [control, female] | [control, female] | 0.70 | T | 53 |
| Shm187 f50 2541_1 | [patient, female] | [patient, female] | 0.70 | T | 50 |
| Shm286 f47 4391_2 | [patient, female] | [patient, female] | 0.69 | T | 47 |
| C36-1 f49 2528_3 | [control, female] | [control, female] | 0.67 | T | 49 |
| C36-2 l49 2533_3 | [control, female] | [control, female] | 0.67 | T | 49 |
| Shm352-2 f32 4160_1 | [patient, female] | [patient, female] | 0.65 | T | 32 |
| Shm3524 f32 4156_3 | [patient, female] | [patient, female] | 0.64 | T | 32 |
| C105-2 f59 4389_1 | [control, female] | [control, female] | 0.63 | T | 59 |
| C37-2 f61 4390_1 | [control, female] | [control, female] | 0.61 | T | 61 |
| C52 f30 1836_2 | [control, female] | [control, female] | 0.60 | T | 30 |
| Shm245 f52 2532_3 | [patient, female] | [control, female] | 0.56 | F | 52 |
| Shm204 f30 2541_4 | [patient, female] | [control, female] | 0.52 | F | 30 |
| total successful prediction rate | | 0.91 | | | |

APPENDIX F-continued

BULLET POINTS
By using a Support Vector Machine classification algorithm, patients and controls were stratified with an average success rate of roughly 90% using an N-Fold validation, Subjects were segragated into gender before classification attempts.

| | | |
|---|---|---|
| successful control prediction rate | 0.94 | |
| successful patient prediction rate | 0.89 | |
| average confidence of false predictions | 0.78 | |
| average confidence of true predictions | 0.89 | |
| | | range |
| average age control | 48.90 | 29-67 |
| average age patient | 45.70 | 22-58 |

| Subject identifier | Subject Value | Predicted Value | Confidence | Prediction Result | Age |
|---|---|---|---|---|---|
| C111 m41 4910_3 | [control, male] | [control, male] | 1 | T | 41 |
| C41-2 m36 4392_1 | [control, male] | [control, male] | 1 | T | 36 |
| C44-2 m31 4157_2 | [control, male] | [control, male] | 1 | T | 31 |
| C54 m48 2526_2 | [control, male] | [control, male] | 1 | T | 48 |
| C54-2 m48 2532_4 | [control, male] | [control, male] | 1 | T | 48 |
| C54-3 m48 2520_3 | [control, male] | [control, male] | 1 | T | 48 |
| C56-2 m40 4158_2 | [control, male] | [control, male] | 1 | T | 40 |
| C59-2 m61 4391_3 | [control, male] | [control, male] | 1 | T | 61 |
| C65-1 m40 2540_1 | [control, male] | [control, male] | 1 | T | 40 |
| C65-2 m40 2534_4 | [control, male] | [control, male] | 1 | T | 40 |
| C66-2 m59 2537_2 | [control, male] | [control, male] | 1 | T | 59 |
| C67-1 m35 2520_4 | [control, male] | [control, male] | 1 | T | 35 |
| C70-1 m51 2518_1 | [control, male] | [control, male] | 1 | T | 51 |
| CC211 m59 2524_1 | [control, male] | [control, male] | 1 | T | 59 |
| CC211 m59 2535_3 | [control, male] | [control, male] | 1 | T | 59 |
| CFP C4-2 m49 2526_4 | [control, male] | [control, male] | 1 | T | 49 |
| CFP P1-1 m60 2527_4 | [patient, male] | [patient, male] | 1 | T | 60 |
| CFP P1-2 m60 2539_2 | [patient, male] | [patient, male] | 1 | T | 60 |
| CFP P8-1 m46 2526_3 | [patient, male] | [patient, male] | 1 | T | 46 |
| CFP P8-1 m46 2532_1 | [patient, male] | [patient, male] | 1 | T | 46 |
| CFP P8-2 m46 2525_4 | [patient, male] | [patient, male] | 1 | T | 46 |
| PCC991 m65 2523_3 | [patient, male] | [patient, male] | 1 | T | 65 |
| Shm153 m29 1836_1 | [patient, male] | [patient, male] | 1 | T | 29 |
| Shm239 m49 2540_2 | [patient, male] | [patient, male] | 1 | T | 49 |
| Shm239-2 m49 2538_3 | [patient, male] | [patient, male] | 1 | T | 49 |
| 5hrn298 m43 4159_1 | [patient, male] | [patient, male] | 1 | T | 43 |
| Shm308 m55 4159_3 | [patient, male] | [patient, male] | 1 | T | 55 |
| Shm71-1 m33 1835_1 | [patient, male] | [patient, male] | 1 | T | 33 |
| Shm73 m41 1835_3 | [patient, male] | [patient, male] | 1 | T | 41 |
| C32-2 m46 2538_4 | [control, male] | [control, male] | 0.99 | T | 46 |
| C42-2 m36 2522_3 | [control, male] | [control, male] | 0.99 | T | 36 |
| C44-1 m31 2529_1 | [control, male] | [control, male] | 0.39 | T | 31 |
| C60-2 m64 4158_4 | [control, male] | [control, male] | 0.99 | T | 64 |
| C61-2 m29 4391_1 | [control, male] | [control, male] | 0.99 | T | 29 |
| C66-1 m59 2540_4 | [control, male] | [control, male] | 0.99 | T | 59 |
| C70-2 m51 4159_2 | [control, male] | [control, male] | 0.99 | T | 51 |
| PCC991 m65 2536_3 | [patient, male] | [patient, male] | 0.39 | T | 65 |
| Shm175-2 m29 2530_4 | [patient, male] | [patient, male] | 0.99 | T | 29 |
| Shm261 m54 4908_2 | [patient, male] | [patient, male] | 0.99 | T | 54 |
| Shm287 m49 4910_2 | [patient, male] | [patient, male] | 0.99 | T | 49 |
| Shm353 m44spc 4156_1 | [patient, male] | [control, male] | 0.98 | F | 44 |
| C32 m48 1837_2 | [control, male] | [control, male] | 0.98 | T | 48 |
| C59-1 m61 1839_3 | [control, male] | [control, male] | 0.98 | T | 61 |
| C72-2 m32 4390_3 | [control, male] | [control, male] | 0.98 | T | 32 |
| CCC505 m45 2536_4 | [control, male] | [control, male] | 0.98 | T | 45 |
| CCC505 m45 4160_3 | [control, male] | [control, male] | 0.98 | 1 | 45 |
| Shm186-2 m46 2540_3 | [patient, male] | [patient, male] | 0.98 | T | 46 |
| C81 m55 4393_1 | [control, male] | [control, male] | 0.97 | T | 55 |
| Shm132 m57 1837_8 | [patient, male] | [patient, male] | 0.97 | T | 57 |
| Shm186 m46 2538_1 | [patient, male] | [patie.nt, male] | 0.97 | T | 46 |
| Shm1864 m46 1838_2 | [patient, male] | [patient, male) | 0.97 | T | 46 |
| Shm175 m29 1838_1 | [patient, male] | [patient, male] | 0.96 | T | 29 |
| Shm241 m35 2534_3 | [patient, male] | [control, male] | 0.95 | F | 35 |
| C27 m33 1835_4 | [control, male] | [control, male] | 0.95 | T | 33 |
| C31-2 m52 2538_2 | [control.. male] | [control, male] | 0.95 | T | 52 |
| CFP C4-1 m49 2527_1 | [control, male] | [control, male] | 0.95 | T | 49 |
| PCC27 m34 2524_2 | [patient, male] | [patient, male] | 0.94 | T | 34 |
| Shm158 m34 2529_2 | [patient, male] | [patient, male] | 0.94 | T | 34 |
| CFP P7-1 m58 2526_1 | [patient, male] | [patient, male] | 0.93 | T | 58 |
| C35 m55 2532_2 | [control, male] | [control, male] | 0.92 | T | 55 |
| C56 m40 1836_4 | [control, male] | [control, male] | 0.92 | T | 40 |
| CFP C1-2 m60 2527_3 | [control, male] | [control, male] | 0.92 | T | 60 |
| PCC569 m47 2523_2 | [patient, male] | [patient, male] | 0.91 | T | 47 |
| ShmGW-1 m47 1837_1 | [patient, male] | [patient, male] | 0.91 | T | 47 |

APPENDIX F-continued

BULLET POINTS
By using a Support Vector Machine classification algorithm, patients and controls were
stratified with an average success rate of roughly 90% using an N-Fold validation,
Subjects were segragated into gender before classification attempts.

| | | | | | |
|---|---|---|---|---|---|
| ShmGW-3 m47 2537_3 | [patient, male] | [patient, male] | 0.91 | T | 47 |
| PCC27 m34 2537_1 | [patient, male] | [patient, male] | 0.9 | T | 34 |
| Shm191 m59 1839_1 | [patient, male] | [control, male] | 0.88 | F | 59 |
| Shm201 m53 2531_2 | [patient, male] | [control, male] | 0.88 | F | 53 |
| PCC569 m47 2535_2 | [patient, male] | [patient, male] | 0.88 | T | 47 |
| ShmGW m47 2539_3 | [patient, male] | [patient, male] | 0.88 | T | 47 |
| CFP P7-2 m58 2527_2 | [patient, male] | [patient, male] | 0.87 | T | 58 |
| C49-2 m49 2525_1 | [control, male] | [patient, male] | 0.85 | F | 49 |
| C92 m67 4908_3 | [control, male] | [control, male] | 0.85 | T | 67 |
| CFP C1-1 m60 2539_1 | [control, male] | [control, male] | 0.81 | T | 60 |
| C34-2 m55 2531_1 | [control, male] | [control, male] | 0.79 | T | 55 |
| C34-1 m55 1838_3 | [control, male] | [control, male] | 0.78 | T | 55 |
| C72-1 m32 4156_2 | [control, male] | (control, male] | 0.78 | T | 32 |
| C31-1 m52 2529_3 | [control, male] | [control, male] | 0.77 | T | 52 |
| ShmA14 m53 2525_3 | [patient, male] | [patient, male] | 0.74 | T | 53 |
| C43-2 m42 2533_1 | [control, male] | [patient, male] | 0.73 | F | 42 |
| C33 m49 2539_4 | [control, male] | [control, male] | 0.73 | T | 49 |
| C33-2 m49 2530_3 | [control, male] | [control, male] | 0.73 | T | 49 |
| Shm344 m45 4389_4 | [patient, male] | [patient, male] | 0.72 | T | 45 |
| C69-2 m63 2519_3 | [control, male] | [control, male] | 0.7 | T | 63 |
| Shm236 m47 2529_4 | [patient, male] | [patient, male] | 0.7 | T | 47 |
| ShmA18 m41 2522_2 | [patient, male] | [control, male] | 0.68 | F | 41 |
| Shm136 m59 2530_2 | [patient, male] | [control, male] | 0.6 | F | 59 |
| C88 m58 4908_1 | [control, male] | [control, male] | 0.57 | T | 58 |
| C82 m50 4393_3 | [control, male] | [patient, male] | 0.55 | F | 50 |
| total successful prediction rate | | 0.90 | | | |
| successful control prediction rate | | 0.94 | | | |
| successful patient prediction rate | | 0.85 | | | |
| average confidence of false predictions | | 0.79 | | | |
| average confidence of true predictions | | 0.94 | | | |
| | | | range | | |
| average age control | | 48.30 | 31-67 | | |
| average age patient | | 47.10 | 29-65 | | |

The invention claimed is:

1. A method of treating chronic inflammatory response syndrome (CIRS) in a subject, comprising administering a therapeutically effective amount of vasoactive intestinal peptide (VIP) to the subject.

2. The method of claim 1, wherein the therapeutically effective amount of VIP is 10 to 100 micrograms.

3. The method of claim 1, wherein the therapeutically effective amount of VIP is 25 to 75 micrograms.

4. The method of claim 1, wherein the therapeutically effective amount of VIP is 50 micrograms.

5. The method of claim 1, wherein the therapeutically effective amount is administered 1 to 4 times per day.

6. The method of claim 1, wherein the therapeutically effective amount is administered nasally or injected.

7. The method of claim 1, wherein the therapeutically effective amount is 10 to 100 micrograms, is administered 1 to 4 times per day, and is administered nasally.

8. The method of claim 1, wherein the therapeutically effective amount is 50 micrograms, is administered 1 to 4 times per day, and is administered nasally.

9. The method of claim 1, wherein the subject additionally exhibits an increase in forebrain parenchyma, an increase in cortical gray area, an increase in the volume of the hippocampus, a decrease in the volume of caudate, and/or an increase in the volume of palladium compared to a subject not having CIRS.

10. The method of claim 1, further comprising administering a therapeutically effective amount of cholestyramine to the subject; treating the subject to eliminate MARCoNS infection if the subject has MARCoNS infection; and correcting or restoring levels of antigliadin, androgens, ADH/osmolality, MMP9, VEGF, C3a, C4a, and TGF-β1 in the subject before administering said therapeutically effective amount of VIP.

11. The method of claim 7, further comprising administering a therapeutically effective amount of cholestyramine to the subject; treating the subject to eliminate MARCoNS infection if the subject has MARCoNS infection; and correcting or restoring levels of antigliadin, androgens, ADH/osmolality, MMP9, VEGF, C3a, C4a, and TGF-β1 in the subject before administering said therapeutically effective amount of VIP.

12. The method of claim 8, further comprising administering a therapeutically effective amount of cholestyramine to the subject; treating the subject to eliminate MARCoNS infection if the subject has MARCoNS infection; and correcting or restoring levels of antigliadin, androgens, ADH/osmolality, MMP9, VEGF, C3a, C4a, and TGF-β1 in the subject before administering said therapeutically effective amount of VIP.

* * * * *